US012533127B2

(12) United States Patent
Shelton, IV et al.

(10) Patent No.: US 12,533,127 B2
(45) Date of Patent: Jan. 27, 2026

(54) ARTICULATABLE SURGICAL INSTRUMENTS WITH MOVABLE JAWS LOCATED IN CLOSE PROXIMITY TO AN ARTICULATION AXIS

(71) Applicant: Cilag GmbH International, Zug (CH)

(72) Inventors: Frederick E. Shelton, IV, Hillsboro, OH (US); Jason L. Harris, Lebanon, OH (US)

(73) Assignee: Cilag GmbH International, Zug (CH)

( * ) Notice: Subject to any disclaimer, the term of this patent is extended or adjusted under 35 U.S.C. 154(b) by 1147 days.

(21) Appl. No.: 17/357,099

(22) Filed: Jun. 24, 2021

(65) Prior Publication Data

US 2021/0378669 A1 Dec. 9, 2021

Related U.S. Application Data

(63) Continuation of application No. 15/635,612, filed on Jun. 28, 2017, now Pat. No. 11,478,242.

(51) Int. Cl.

*A61B 17/072* (2006.01)
*A61B 34/30* (2016.01)
(Continued)

(52) U.S. Cl.

CPC ........ *A61B 17/07207* (2013.01); *A61B 34/30* (2016.02); *A61B 2017/00017* (2013.01);
(Continued)

(58) Field of Classification Search

CPC .... A61B 2017/2947; A61B 2017/2946; A61B 2017/2939; A61B 2017/2936;
(Continued)

(56) References Cited

U.S. PATENT DOCUMENTS

| | | | |
|---|---|---|---|
| 66,052 | A | 6/1867 | Smith |
| 662,587 | A | 11/1900 | Blake |

(Continued)

FOREIGN PATENT DOCUMENTS

| | | | |
|---|---|---|---|
| AU | 2012200594 | A1 | 2/2012 |
| AU | 2012203035 | A1 | 6/2012 |

(Continued)

OTHER PUBLICATIONS

ASTM procedure D2240-00, "Standard Test Method for Rubber Property-Durometer Hardness," (Published Aug. 2000).

(Continued)

*Primary Examiner* — Anna K Kinsaul
*Assistant Examiner* — Mary C Hibbert-Copeland
(74) *Attorney, Agent, or Firm* — Lempia Summerfield Katz LLC

(57) ABSTRACT

A surgical instrument that includes a first jaw that has a pair of laterally aligned vertical slots formed in a proximal end portion thereof. Each vertical slot includes an open upper end. A second jaw is movably supported for selective pivotal travel relative to the first jaw between a fully open and a fully closed position. Pivot members protrude laterally from the second jaw and are each received in a corresponding one of the vertical slots in the first jaw such that the pivot members may pivot therein. A retainer member is configured to operably engage the proximal end portion of the first jaw and retain the pivot members in the corresponding vertical slots as the second jaw moves between the fully open and the fully closed positions.

18 Claims, 59 Drawing Sheets

(51) Int. Cl.

| | |
|---|---|
| *A61B 17/00* | (2006.01) |
| *A61B 17/29* | (2006.01) |
| *A61B 90/00* | (2016.01) |

(52) U.S. Cl.
CPC ............... *A61B 2017/00022* (2013.01); *A61B 2017/00398* (2013.01); *A61B 2017/0046* (2013.01); *A61B 2017/00464* (2013.01); *A61B 2017/00473* (2013.01); *A61B 2017/00477* (2013.01); *A61B 2017/00734* (2013.01); *A61B 2017/00862* (2013.01); *A61B 2017/07214* (2013.01); *A61B 2017/07257* (2013.01); *A61B 2017/07264* (2013.01); *A61B 2017/07271* (2013.01); *A61B 2017/07278* (2013.01); *A61B 2017/07285* (2013.01); *A61B 2017/2925* (2013.01); *A61B 2017/2927* (2013.01); *A61B 2017/2929* (2013.01); *A61B 2017/2933* (2013.01); *A61B 2017/2934* (2013.01); *A61B 2017/2936* (2013.01); *A61B 2017/2939* (2013.01); *A61B 2017/2946* (2013.01); *A61B 2017/2947* (2013.01); *A61B 2090/0814* (2016.02)

(58) Field of Classification Search
CPC .... A61B 2017/2934; A61B 2017/2933; A61B 2017/2929; A61B 2017/2927; A61B 2017/2925; A61B 2017/07285; A61B 2017/07278; A61B 2017/07271; A61B 2017/07264; A61B 2017/07257; A61B 2017/07214; A61B 2017/00862; A61B 2017/00734; A61B 2017/00477; A61B 2017/00473; A61B 2017/00464; A61B 2017/0046; A61B 2017/00398; A61B 2017/00022; A61B 2017/00017; A61B 17/07207; A61B 34/30; A61B 2090/0814
USPC ...................................................... 227/175.1
See application file for complete search history.

(56) References Cited

U.S. PATENT DOCUMENTS

| | | | |
|---|---|---|---|
| 670,748 | A | 3/1901 | Weddeler |
| 719,487 | A | 2/1903 | Minor |
| 804,229 | A | 11/1905 | Hutchinson |
| 903,739 | A | 11/1908 | Lesemann |
| 951,393 | A | 3/1910 | Hahn |
| 1,075,556 | A | 10/1913 | Fenoughty |
| 1,082,105 | A | 12/1913 | Anderson |
| 1,188,721 | A | 6/1916 | Bittner |
| 1,306,107 | A | 6/1919 | Elliott |
| 1,314,601 | A | 9/1919 | McCaskey |
| 1,466,128 | A | 8/1923 | Hallenbeck |
| 1,677,337 | A | 7/1928 | Grove |
| 1,794,907 | A | 3/1931 | Kelly |
| 1,849,427 | A | 3/1932 | Hook |
| 1,912,783 | A | 6/1933 | Meyer |
| 1,944,116 | A | 1/1934 | Stratman |
| 1,954,048 | A | 4/1934 | Jeffrey et al. |
| 2,028,635 | A | 1/1936 | Wappler |
| 2,037,727 | A | 4/1936 | La Chapelle |
| 2,120,951 | A | 6/1938 | Hodgman |
| 2,132,295 | A | 10/1938 | Hawkins |
| 2,161,632 | A | 6/1939 | Nattenheimer |
| D120,434 | S | 5/1940 | Gold |
| 2,211,117 | A | 8/1940 | Hess |
| 2,214,870 | A | 9/1940 | West |
| 2,224,108 | A | 12/1940 | Ridgway |
| 2,224,882 | A | 12/1940 | Peck |
| 2,256,295 | A | 9/1941 | Schmid |
| 2,318,379 | A | 5/1943 | Davis et al. |
| 2,329,440 | A | 9/1943 | La Place |
| 2,377,581 | A | 6/1945 | Shaffrey |
| 2,406,389 | A | 8/1946 | Lee |
| 2,420,552 | A | 5/1947 | Morrill |
| 2,441,096 | A | 5/1948 | Happe |
| 2,448,741 | A | 9/1948 | Scott et al. |
| 2,450,527 | A | 10/1948 | Smith |
| 2,491,872 | A | 12/1949 | Neuman |
| 2,507,872 | A | 5/1950 | Unsinger |
| 2,526,902 | A | 10/1950 | Rublee |
| 2,527,256 | A | 10/1950 | Jackson |
| 2,578,686 | A | 12/1951 | Fish |
| 2,638,901 | A | 5/1953 | Sugarbaker |
| 2,674,149 | A | 4/1954 | Benson |
| 2,701,489 | A | 2/1955 | Osborn |
| 2,711,461 | A | 6/1955 | Happe |
| 2,724,289 | A | 11/1955 | Wight |
| 2,742,955 | A | 4/1956 | Dominguez |
| 2,804,848 | A | 9/1957 | O'Farrell et al. |
| 2,808,482 | A | 10/1957 | Zanichkowsky et al. |
| 2,825,178 | A | 3/1958 | Hawkins |
| 2,853,074 | A | 9/1958 | Olson |
| 2,856,192 | A | 10/1958 | Schuster |
| 2,887,004 | A | 5/1959 | Stewart |
| 2,957,353 | A | 10/1960 | Lewis |
| 2,959,974 | A | 11/1960 | Emrick |
| 3,026,744 | A | 3/1962 | Rouse |
| 3,032,769 | A | 5/1962 | Palmer |
| 3,035,256 | A | 5/1962 | Egbert |
| 3,060,972 | A | 10/1962 | Sheldon |
| 3,075,062 | A | 1/1963 | Iaccarino |
| 3,078,465 | A | 2/1963 | Bobrov |
| 3,079,606 | A | 3/1963 | Bobrov et al. |
| 3,080,564 | A | 3/1963 | Strekopitov et al. |
| 3,166,072 | A | 1/1965 | Sullivan, Jr. |
| 3,180,236 | A | 4/1965 | Beckett |
| 3,196,869 | A | 7/1965 | Scholl |
| 3,204,731 | A | 9/1965 | Bent et al. |
| 3,252,643 | A | 5/1966 | Strekopytov et al. |
| 3,266,494 | A | 8/1966 | Brownrigg et al. |
| 3,269,630 | A | 8/1966 | Fleischer |
| 3,269,631 | A | 8/1966 | Takaro |
| 3,275,211 | A | 9/1966 | Hirsch et al. |
| 3,315,863 | A | 4/1967 | O'Dea |
| 3,317,103 | A | 5/1967 | Cullen et al. |
| 3,317,105 | A | 5/1967 | Astafjev et al. |
| 3,357,296 | A | 12/1967 | Lefever |
| 3,359,978 | A | 12/1967 | Smith, Jr. |
| 3,377,893 | A | 4/1968 | Shorb |
| 3,480,193 | A | 11/1969 | Ralston |
| 3,490,675 | A | 1/1970 | Green et al. |
| 3,494,533 | A | 2/1970 | Green et al. |
| 3,499,591 | A | 3/1970 | Green |
| 3,503,396 | A | 3/1970 | Pierie et al. |
| 3,509,629 | A | 5/1970 | Kidokoro |
| 3,551,987 | A | 1/1971 | Wilkinson |
| 3,568,675 | A | 3/1971 | Harvey |
| 3,572,159 | A | 3/1971 | Tschanz |
| 3,583,393 | A | 6/1971 | Takahashi |
| 3,589,589 | A | 6/1971 | Akopov |
| 3,598,943 | A | 8/1971 | Barrett |
| 3,604,561 | A | 9/1971 | Mallina et al. |
| 3,608,549 | A | 9/1971 | Merrill |
| 3,618,842 | A | 11/1971 | Bryan |
| 3,635,394 | A | 1/1972 | Natelson |
| 3,638,652 | A | 2/1972 | Kelley |
| 3,640,317 | A | 2/1972 | Panfili |
| 3,643,851 | A | 2/1972 | Green et al. |
| 3,650,453 | A | 3/1972 | Smith, Jr. |
| 3,661,339 | A | 5/1972 | Shimizu |
| 3,661,666 | A | 5/1972 | Foster et al. |
| 3,662,939 | A | 5/1972 | Bryan |
| 3,685,250 | A | 8/1972 | Henry et al. |
| 3,688,966 | A | 9/1972 | Perkins et al. |
| 3,692,224 | A | 9/1972 | Astafiev et al. |
| 3,695,646 | A | 10/1972 | Mommsen |
| 3,709,221 | A | 1/1973 | Riely |
| 3,717,294 | A | 2/1973 | Green |
| 3,724,237 | A | 4/1973 | Wood |
| 3,726,755 | A | 4/1973 | Shannon |

(56) References Cited

U.S. PATENT DOCUMENTS

| | | | |
|---|---|---|---|
| 3,727,904 | A | 4/1973 | Gabbey |
| 3,734,207 | A | 5/1973 | Fishbein |
| 3,740,994 | A | 6/1973 | De Carlo, Jr. |
| 3,744,495 | A | 7/1973 | Johnson |
| 3,746,002 | A | 7/1973 | Haller |
| 3,747,603 | A | 7/1973 | Adler |
| 3,747,692 | A | 7/1973 | Davidson |
| 3,751,902 | A | 8/1973 | Kingsbury et al. |
| 3,752,161 | A | 8/1973 | Bent |
| 3,799,151 | A | 3/1974 | Fukaumi et al. |
| 3,808,452 | A | 4/1974 | Hutchinson |
| 3,815,476 | A | 6/1974 | Green et al. |
| 3,819,100 | A | 6/1974 | Noiles et al. |
| 3,821,919 | A | 7/1974 | Knohl |
| 3,822,818 | A | 7/1974 | Strekopytov et al. |
| 3,826,978 | A | 7/1974 | Kelly |
| 3,836,171 | A | 9/1974 | Hayashi et al. |
| 3,837,555 | A | 9/1974 | Green |
| 3,841,474 | A | 10/1974 | Maier |
| 3,851,196 | A | 11/1974 | Hinds |
| 3,863,639 | A | 2/1975 | Kleaveland |
| 3,863,940 | A | 2/1975 | Cummings |
| 3,883,624 | A | 5/1975 | McKenzie et al. |
| 3,885,491 | A | 5/1975 | Curtis |
| 3,887,393 | A | 6/1975 | La Rue, Jr. |
| 3,892,228 | A | 7/1975 | Mitsui |
| 3,894,174 | A | 7/1975 | Cartun |
| 3,899,829 | A | 8/1975 | Storm et al. |
| 3,902,247 | A | 9/1975 | Fleer et al. |
| 3,940,844 | A | 3/1976 | Colby et al. |
| 3,944,163 | A | 3/1976 | Hayashi et al. |
| 3,950,686 | A | 4/1976 | Randall |
| 3,952,747 | A | 4/1976 | Kimmell, Jr. |
| 3,955,581 | A | 5/1976 | Spasiano et al. |
| 3,959,879 | A | 6/1976 | Sellers |
| RE28,932 | E | 8/1976 | Noiles et al. |
| 3,972,734 | A | 8/1976 | King |
| 3,973,179 | A | 8/1976 | Weber et al. |
| 3,981,051 | A | 9/1976 | Brumlik |
| 3,999,110 | A | 12/1976 | Ramstrom et al. |
| 4,025,216 | A | 5/1977 | Hives |
| 4,027,746 | A | 6/1977 | Kine |
| 4,034,143 | A | 7/1977 | Sweet |
| 4,038,987 | A | 8/1977 | Komiya |
| 4,047,654 | A | 9/1977 | Alvarado |
| 4,054,108 | A | 10/1977 | Gill |
| 4,060,089 | A | 11/1977 | Noiles |
| 4,066,133 | A | 1/1978 | Voss |
| 4,085,337 | A | 4/1978 | Moeller |
| 4,100,820 | A | 7/1978 | Evett |
| 4,106,446 | A | 8/1978 | Yamada et al. |
| 4,106,620 | A | 8/1978 | Brimmer et al. |
| 4,108,211 | A | 8/1978 | Tanaka |
| 4,111,206 | A | 9/1978 | Vishnevsky et al. |
| 4,127,227 | A | 11/1978 | Green |
| 4,129,059 | A | 12/1978 | Van Eck |
| 4,132,146 | A | 1/1979 | Uhlig |
| 4,135,517 | A | 1/1979 | Reale |
| 4,149,461 | A | 4/1979 | Simeth |
| 4,154,122 | A | 5/1979 | Severin |
| 4,160,857 | A | 7/1979 | Nardella et al. |
| 4,169,990 | A | 10/1979 | Lerdman |
| 4,180,285 | A | 12/1979 | Reneau |
| 4,185,701 | A | 1/1980 | Boys |
| 4,190,042 | A | 2/1980 | Sinnreich |
| 4,198,734 | A | 4/1980 | Brumlik |
| 4,198,982 | A | 4/1980 | Fortner et al. |
| 4,203,444 | A | 5/1980 | Bonnell et al. |
| 4,207,898 | A | 6/1980 | Becht |
| 4,213,562 | A | 7/1980 | Garrett et al. |
| 4,226,242 | A | 10/1980 | Jarvik |
| 4,239,431 | A | 12/1980 | Davini |
| 4,241,861 | A | 12/1980 | Fleischer |
| 4,244,372 | A | 1/1981 | Kapitanov et al. |
| 4,250,436 | A | 2/1981 | Weissman |
| 4,250,817 | A | 2/1981 | Michel |
| 4,261,244 | A | 4/1981 | Becht et al. |
| 4,272,002 | A | 6/1981 | Moshofsky |
| 4,272,662 | A | 6/1981 | Simpson |
| 4,274,304 | A | 6/1981 | Curtiss |
| 4,274,398 | A | 6/1981 | Scott, Jr. |
| 4,275,813 | A | 6/1981 | Noiles |
| 4,278,091 | A | 7/1981 | Borzone |
| 4,282,573 | A | 8/1981 | Imai et al. |
| 4,289,131 | A | 9/1981 | Mueller |
| 4,289,133 | A | 9/1981 | Rothfuss |
| 4,290,542 | A | 9/1981 | Fedotov et al. |
| D261,356 | S | 10/1981 | Robinson |
| 4,293,604 | A | 10/1981 | Campbell |
| 4,296,654 | A | 10/1981 | Mercer |
| 4,296,881 | A | 10/1981 | Lee |
| 4,304,236 | A | 12/1981 | Conta et al. |
| 4,305,539 | A | 12/1981 | Korolkov et al. |
| 4,312,363 | A | 1/1982 | Rothfuss et al. |
| 4,312,685 | A | 1/1982 | Riedl |
| 4,317,451 | A | 3/1982 | Cerwin et al. |
| 4,319,576 | A | 3/1982 | Rothfuss |
| 4,321,002 | A | 3/1982 | Froehlich |
| 4,321,746 | A | 3/1982 | Grinage |
| 4,328,839 | A | 5/1982 | Lyons et al. |
| 4,331,277 | A | 5/1982 | Green |
| 4,340,331 | A | 7/1982 | Savino |
| 4,347,450 | A | 8/1982 | Colligan |
| 4,348,603 | A | 9/1982 | Huber |
| 4,349,028 | A | 9/1982 | Green |
| 4,350,151 | A | 9/1982 | Scott |
| 4,353,371 | A | 10/1982 | Cosman |
| 4,357,940 | A | 11/1982 | Muller |
| 4,361,057 | A | 11/1982 | Kochera |
| 4,366,544 | A | 12/1982 | Shima et al. |
| 4,369,013 | A | 1/1983 | Abildgaard et al. |
| 4,373,147 | A | 2/1983 | Carlson, Jr. |
| 4,376,380 | A | 3/1983 | Burgess |
| 4,379,457 | A | 4/1983 | Gravener et al. |
| 4,380,312 | A | 4/1983 | Landrus |
| 4,382,326 | A | 5/1983 | Rabuse |
| 4,383,634 | A | 5/1983 | Green |
| 4,389,963 | A | 6/1983 | Pearson |
| 4,393,728 | A | 7/1983 | Larson et al. |
| 4,394,613 | A | 7/1983 | Cole |
| 4,396,139 | A | 8/1983 | Hall et al. |
| 4,397,311 | A | 8/1983 | Kanshin et al. |
| 4,402,445 | A | 9/1983 | Green |
| 4,406,621 | A | 9/1983 | Bailey |
| 4,408,692 | A | 10/1983 | Sigel et al. |
| 4,409,057 | A | 10/1983 | Molenda et al. |
| 4,415,112 | A | 11/1983 | Green |
| 4,416,276 | A | 11/1983 | Newton et al. |
| 4,417,890 | A | 11/1983 | Dennehey et al. |
| 4,421,264 | A | 12/1983 | Arter et al. |
| 4,423,456 | A | 12/1983 | Zaidenweber |
| 4,425,915 | A | 1/1984 | Ivanov |
| 4,428,376 | A | 1/1984 | Mericle |
| 4,429,695 | A | 2/1984 | Green |
| 4,430,997 | A | 2/1984 | DiGiovanni et al. |
| 4,434,796 | A | 3/1984 | Karapetian et al. |
| 4,438,659 | A | 3/1984 | Desplats |
| 4,442,964 | A | 4/1984 | Becht |
| 4,448,194 | A | 5/1984 | DiGiovanni et al. |
| 4,451,743 | A | 5/1984 | Suzuki et al. |
| 4,452,376 | A | 6/1984 | Klieman et al. |
| 4,454,887 | A | 6/1984 | Kruger |
| 4,459,519 | A | 7/1984 | Erdman |
| 4,461,305 | A | 7/1984 | Cibley |
| 4,467,805 | A | 8/1984 | Fukuda |
| 4,468,597 | A | 8/1984 | Baumard et al. |
| 4,469,481 | A | 9/1984 | Kobayashi |
| 4,470,414 | A | 9/1984 | Imagawa et al. |
| 4,471,780 | A | 9/1984 | Menges et al. |
| 4,471,781 | A | 9/1984 | Di Giovanni et al. |
| 4,473,077 | A | 9/1984 | Noiles et al. |
| 4,475,679 | A | 10/1984 | Fleury, Jr. |
| 4,476,864 | A | 10/1984 | Tezel |
| 4,478,220 | A | 10/1984 | Di Giovanni et al. |

(56) References Cited

U.S. PATENT DOCUMENTS

| | | | |
|---|---|---|---|
| 4,480,641 | A | 11/1984 | Failla et al. |
| 4,481,458 | A | 11/1984 | Lane |
| 4,483,562 | A | 11/1984 | Schoolman |
| 4,485,816 | A | 12/1984 | Krumme |
| 4,485,817 | A | 12/1984 | Swiggett |
| 4,486,928 | A | 12/1984 | Tucker et al. |
| 4,488,523 | A | 12/1984 | Shichman |
| 4,489,875 | A | 12/1984 | Crawford et al. |
| 4,493,983 | A | 1/1985 | Taggert |
| 4,494,057 | A | 1/1985 | Hotta |
| 4,499,895 | A | 2/1985 | Takayama |
| 4,500,024 | A | 2/1985 | DiGiovanni et al. |
| D278,081 | S | 3/1985 | Green |
| 4,503,842 | A | 3/1985 | Takayama |
| 4,505,272 | A | 3/1985 | Utyamyshev et al. |
| 4,505,273 | A | 3/1985 | Braun et al. |
| 4,505,414 | A | 3/1985 | Filipi |
| 4,506,671 | A | 3/1985 | Green |
| 4,512,038 | A | 4/1985 | Alexander et al. |
| 4,514,477 | A | 4/1985 | Kobayashi |
| 4,520,817 | A | 6/1985 | Green |
| 4,522,327 | A | 6/1985 | Korthoff et al. |
| 4,526,174 | A | 7/1985 | Froehlich |
| 4,527,724 | A | 7/1985 | Chow et al. |
| 4,530,357 | A | 7/1985 | Pawloski et al. |
| 4,530,453 | A | 7/1985 | Green |
| 4,531,522 | A | 7/1985 | Bedi et al. |
| 4,532,927 | A | 8/1985 | Miksza, Jr. |
| 4,540,202 | A | 9/1985 | Amphoux et al. |
| 4,548,202 | A | 10/1985 | Duncan |
| 4,556,058 | A | 12/1985 | Green |
| 4,560,915 | A | 12/1985 | Soultanian |
| 4,565,109 | A | 1/1986 | Tsay |
| 4,565,189 | A | 1/1986 | Mabuchi |
| 4,566,620 | A | 1/1986 | Green et al. |
| 4,569,346 | A | 2/1986 | Poirier |
| 4,569,469 | A | 2/1986 | Mongeon et al. |
| 4,571,213 | A | 2/1986 | Ishimoto |
| 4,573,468 | A | 3/1986 | Conta et al. |
| 4,573,469 | A | 3/1986 | Golden et al. |
| 4,573,622 | A | 3/1986 | Green et al. |
| 4,576,165 | A | 3/1986 | Green et al. |
| 4,576,167 | A | 3/1986 | Noiles |
| 4,580,712 | A | 4/1986 | Green |
| 4,585,153 | A | 4/1986 | Failla et al. |
| 4,586,501 | A | 5/1986 | Claracq |
| 4,586,502 | A | 5/1986 | Bedi et al. |
| 4,589,416 | A | 5/1986 | Green |
| 4,589,582 | A | 5/1986 | Bilotti |
| 4,589,870 | A | 5/1986 | Citrin et al. |
| 4,591,085 | A | 5/1986 | Di Giovanni |
| RE32,214 | E | 7/1986 | Schramm |
| 4,597,753 | A | 7/1986 | Turley |
| 4,600,037 | A | 7/1986 | Hatten |
| 4,604,786 | A | 8/1986 | Howie, Jr. |
| 4,605,001 | A | 8/1986 | Rothfuss et al. |
| 4,605,004 | A | 8/1986 | Di Giovanni et al. |
| 4,606,343 | A | 8/1986 | Conta et al. |
| 4,607,636 | A | 8/1986 | Kula et al. |
| 4,607,638 | A | 8/1986 | Crainich |
| 4,608,980 | A | 9/1986 | Aihara |
| 4,608,981 | A | 9/1986 | Rothfuss et al. |
| 4,610,250 | A | 9/1986 | Green |
| 4,610,383 | A | 9/1986 | Rothfuss et al. |
| 4,612,933 | A | 9/1986 | Brinkerhoff et al. |
| D286,180 | S | 10/1986 | Korthoff |
| D286,442 | S | 10/1986 | Korthoff et al. |
| 4,617,893 | A | 10/1986 | Donner et al. |
| 4,617,914 | A | 10/1986 | Ueda |
| 4,619,262 | A | 10/1986 | Taylor |
| 4,619,391 | A | 10/1986 | Sharkany et al. |
| 4,624,401 | A | 11/1986 | Gassner et al. |
| D287,278 | S | 12/1986 | Spreckelmeier |
| 4,628,459 | A | 12/1986 | Shinohara et al. |
| 4,628,636 | A | 12/1986 | Folger |
| 4,629,107 | A | 12/1986 | Fedotov et al. |
| 4,632,290 | A | 12/1986 | Green et al. |
| 4,633,861 | A | 1/1987 | Chow et al. |
| 4,633,874 | A | 1/1987 | Chow et al. |
| 4,634,419 | A | 1/1987 | Kreizman et al. |
| 4,635,638 | A | 1/1987 | Weintraub et al. |
| 4,641,076 | A | 2/1987 | Linden |
| 4,642,618 | A | 2/1987 | Johnson et al. |
| 4,642,738 | A | 2/1987 | Meller |
| 4,643,173 | A | 2/1987 | Bell et al. |
| 4,643,731 | A | 2/1987 | Eckenhoff |
| 4,646,722 | A | 3/1987 | Silverstein et al. |
| 4,646,745 | A | 3/1987 | Noiles |
| 4,651,734 | A | 3/1987 | Doss et al. |
| 4,652,820 | A | 3/1987 | Maresca |
| 4,654,028 | A | 3/1987 | Suma |
| 4,655,222 | A | 4/1987 | Florez et al. |
| 4,662,555 | A | 5/1987 | Thornton |
| 4,663,874 | A | 5/1987 | Sano et al. |
| 4,664,305 | A | 5/1987 | Blake, III et al. |
| 4,665,916 | A | 5/1987 | Green |
| 4,667,674 | A | 5/1987 | Korthoff et al. |
| 4,669,647 | A | 6/1987 | Storace |
| 4,671,278 | A | 6/1987 | Chin |
| 4,671,280 | A | 6/1987 | Dorband et al. |
| 4,671,445 | A | 6/1987 | Barker et al. |
| 4,672,964 | A | 6/1987 | Dee et al. |
| 4,675,944 | A | 6/1987 | Wells |
| 4,676,245 | A | 6/1987 | Fukuda |
| 4,679,460 | A | 7/1987 | Yoshigai |
| 4,679,719 | A | 7/1987 | Kramer |
| 4,684,051 | A | 8/1987 | Akopov et al. |
| 4,688,555 | A | 8/1987 | Wardle |
| 4,691,703 | A | 9/1987 | Auth et al. |
| 4,693,248 | A | 9/1987 | Failla |
| 4,698,579 | A | 10/1987 | Richter et al. |
| 4,700,703 | A | 10/1987 | Resnick et al. |
| 4,705,038 | A | 11/1987 | Sjostrom et al. |
| 4,708,141 | A | 11/1987 | Inoue et al. |
| 4,709,120 | A | 11/1987 | Pearson |
| 4,715,520 | A | 12/1987 | Roehr, Jr. et al. |
| 4,719,917 | A | 1/1988 | Barrows et al. |
| 4,721,099 | A | 1/1988 | Chikama |
| 4,722,340 | A | 2/1988 | Takayama et al. |
| 4,724,840 | A | 2/1988 | McVay et al. |
| 4,727,308 | A | 2/1988 | Huljak et al. |
| 4,728,020 | A | 3/1988 | Green et al. |
| 4,728,876 | A | 3/1988 | Mongeon et al. |
| 4,729,260 | A | 3/1988 | Dudden |
| 4,730,726 | A | 3/1988 | Holzwarth |
| 4,741,336 | A | 5/1988 | Failla et al. |
| 4,743,214 | A | 5/1988 | Tai-Cheng |
| 4,744,363 | A | 5/1988 | Hasson |
| 4,747,820 | A | 5/1988 | Hornlein et al. |
| 4,750,902 | A | 6/1988 | Wuchinich et al. |
| 4,752,024 | A | 6/1988 | Green et al. |
| 4,754,909 | A | 7/1988 | Barker et al. |
| 4,755,070 | A | 7/1988 | Cerutti |
| 4,761,326 | A | 8/1988 | Barnes et al. |
| 4,763,669 | A | 8/1988 | Jaeger |
| 4,767,044 | A | 8/1988 | Green |
| D297,764 | S | 9/1988 | Hunt et al. |
| 4,773,420 | A | 9/1988 | Green |
| 4,777,780 | A | 10/1988 | Holzwarth |
| 4,781,186 | A | 11/1988 | Simpson et al. |
| 4,784,137 | A | 11/1988 | Kulik et al. |
| 4,787,387 | A | 11/1988 | Burbank, III et al. |
| 4,788,485 | A | 11/1988 | Kawagishi et al. |
| D298,967 | S | 12/1988 | Hunt |
| 4,788,978 | A | 12/1988 | Strekopytov et al. |
| 4,790,225 | A | 12/1988 | Moody et al. |
| 4,790,314 | A | 12/1988 | Weaver |
| 4,805,617 | A | 2/1989 | Bedi et al. |
| 4,805,823 | A | 2/1989 | Rothfuss |
| 4,807,628 | A | 2/1989 | Peters et al. |
| 4,809,695 | A | 3/1989 | Gwathmey et al. |
| 4,815,460 | A | 3/1989 | Porat et al. |
| 4,817,643 | A | 4/1989 | Olson |
| 4,817,847 | A | 4/1989 | Redtenbacher et al. |

(56) References Cited

U.S. PATENT DOCUMENTS

| | | | |
|---|---|---|---|
| 4,819,853 | A | 4/1989 | Green |
| 4,821,939 | A | 4/1989 | Green |
| 4,827,552 | A | 5/1989 | Bojar et al. |
| 4,827,911 | A | 5/1989 | Broadwin et al. |
| 4,828,542 | A | 5/1989 | Hermann |
| 4,828,944 | A | 5/1989 | Yabe et al. |
| 4,830,855 | A | 5/1989 | Stewart |
| 4,832,158 | A | 5/1989 | Farrar et al. |
| 4,833,937 | A | 5/1989 | Nagano |
| 4,834,096 | A | 5/1989 | Oh et al. |
| 4,834,720 | A | 5/1989 | Blinkhorn |
| 4,838,859 | A | 6/1989 | Strassmann |
| 4,844,068 | A | 7/1989 | Arata et al. |
| 4,848,637 | A | 7/1989 | Pruitt |
| 4,856,078 | A | 8/1989 | Konopka |
| 4,860,644 | A | 8/1989 | Kohl et al. |
| 4,862,891 | A | 9/1989 | Smith |
| 4,863,423 | A | 9/1989 | Wallace |
| 4,865,030 | A | 9/1989 | Polyak |
| 4,868,530 | A | 9/1989 | Ahs |
| 4,868,958 | A | 9/1989 | Suzuki et al. |
| 4,869,414 | A | 9/1989 | Green et al. |
| 4,869,415 | A | 9/1989 | Fox |
| 4,873,977 | A | 10/1989 | Avant et al. |
| 4,875,486 | A | 10/1989 | Rapoport et al. |
| 4,880,015 | A | 11/1989 | Nierman |
| 4,890,613 | A | 1/1990 | Golden et al. |
| 4,892,244 | A | 1/1990 | Fox et al. |
| 4,893,622 | A | 1/1990 | Green et al. |
| 4,894,051 | A | 1/1990 | Shiber |
| 4,896,584 | A | 1/1990 | Stoll et al. |
| 4,896,678 | A | 1/1990 | Ogawa |
| 4,900,303 | A | 2/1990 | Lemelson |
| 4,903,697 | A | 2/1990 | Resnick et al. |
| 4,909,789 | A | 3/1990 | Taguchi et al. |
| 4,915,100 | A | 4/1990 | Green |
| 4,919,679 | A | 4/1990 | Averill et al. |
| 4,921,479 | A | 5/1990 | Grayzel |
| 4,925,082 | A | 5/1990 | Kim |
| 4,928,699 | A | 5/1990 | Sasai |
| 4,930,503 | A | 6/1990 | Pruitt |
| 4,930,674 | A | 6/1990 | Barak |
| 4,931,047 | A | 6/1990 | Broadwin et al. |
| 4,931,737 | A | 6/1990 | Hishiki |
| 4,932,960 | A | 6/1990 | Green et al. |
| 4,933,800 | A | 6/1990 | Yang |
| 4,933,843 | A | 6/1990 | Scheller et al. |
| D309,350 | S | 7/1990 | Sutherland et al. |
| 4,938,408 | A | 7/1990 | Bedi et al. |
| 4,941,623 | A | 7/1990 | Pruitt |
| 4,943,182 | A | 7/1990 | Hoblingre |
| 4,944,443 | A | 7/1990 | Oddsen et al. |
| 4,946,067 | A | 8/1990 | Kelsall |
| 4,948,327 | A | 8/1990 | Crupi, Jr. |
| 4,949,707 | A | 8/1990 | LeVahn et al. |
| 4,950,268 | A | 8/1990 | Rink |
| 4,951,860 | A | 8/1990 | Peters et al. |
| 4,951,861 | A | 8/1990 | Schulze et al. |
| 4,954,960 | A | 9/1990 | Lo et al. |
| 4,955,959 | A | 9/1990 | Tompkins et al. |
| 4,957,212 | A | 9/1990 | Duck et al. |
| 4,962,681 | A | 10/1990 | Yang |
| 4,962,877 | A | 10/1990 | Hervas |
| 4,964,559 | A | 10/1990 | Deniega et al. |
| 4,964,863 | A | 10/1990 | Kanshin et al. |
| 4,965,709 | A | 10/1990 | Ngo |
| 4,970,656 | A | 11/1990 | Lo et al. |
| 4,973,274 | A | 11/1990 | Hirukawa |
| 4,973,302 | A | 11/1990 | Armour et al. |
| 4,976,173 | A | 12/1990 | Yang |
| 4,978,049 | A | 12/1990 | Green |
| 4,978,333 | A | 12/1990 | Broadwin et al. |
| 4,979,952 | A | 12/1990 | Kubota et al. |
| 4,984,564 | A | 1/1991 | Yuen |
| 4,986,808 | A | 1/1991 | Broadwin et al. |
| 4,987,049 | A | 1/1991 | Komamura et al. |
| 4,988,334 | A | 1/1991 | Hornlein et al. |
| 4,995,877 | A | 2/1991 | Ams et al. |
| 4,995,959 | A | 2/1991 | Metzner |
| 4,996,975 | A | 3/1991 | Nakamura |
| 5,001,649 | A | 3/1991 | Lo et al. |
| 5,002,543 | A | 3/1991 | Bradshaw et al. |
| 5,002,553 | A | 3/1991 | Shiber |
| 5,005,754 | A | 4/1991 | Van Overloop |
| 5,009,222 | A | 4/1991 | Her |
| 5,009,661 | A | 4/1991 | Michelson |
| 5,012,411 | A | 4/1991 | Policastro et al. |
| 5,014,898 | A | 5/1991 | Heidrich |
| 5,014,899 | A | 5/1991 | Presty et al. |
| 5,015,227 | A | 5/1991 | Broadwin et al. |
| 5,018,515 | A | 5/1991 | Gilman |
| 5,018,657 | A | 5/1991 | Pedlick et al. |
| 5,024,652 | A | 6/1991 | Dumenek et al. |
| 5,024,671 | A | 6/1991 | Tu et al. |
| 5,025,559 | A | 6/1991 | McCullough |
| 5,027,834 | A | 7/1991 | Pruitt |
| 5,030,226 | A | 7/1991 | Green et al. |
| 5,031,814 | A | 7/1991 | Tompkins et al. |
| 5,033,552 | A | 7/1991 | Hu |
| 5,035,040 | A | 7/1991 | Kerrigan et al. |
| 5,037,018 | A | 8/1991 | Matsuda et al. |
| 5,038,109 | A | 8/1991 | Goble et al. |
| 5,038,247 | A | 8/1991 | Kelley et al. |
| 5,040,715 | A | 8/1991 | Green et al. |
| 5,042,707 | A | 8/1991 | Taheri |
| 5,056,953 | A | 10/1991 | Marot et al. |
| 5,060,658 | A | 10/1991 | Dejter, Jr. et al. |
| 5,061,269 | A | 10/1991 | Muller |
| 5,062,491 | A | 11/1991 | Takeshima et al. |
| 5,062,563 | A | 11/1991 | Green et al. |
| 5,065,929 | A | 11/1991 | Schulze et al. |
| 5,071,052 | A | 12/1991 | Rodak et al. |
| 5,071,430 | A | 12/1991 | de Salis et al. |
| 5,074,454 | A | 12/1991 | Peters |
| 5,077,506 | A | 12/1991 | Krause |
| 5,079,006 | A | 1/1992 | Urquhart |
| 5,080,556 | A | 1/1992 | Carreno |
| 5,083,695 | A | 1/1992 | Foslien et al. |
| 5,084,057 | A | 1/1992 | Green et al. |
| 5,088,979 | A | 2/1992 | Filipi et al. |
| 5,088,997 | A | 2/1992 | Delahuerga et al. |
| 5,089,606 | A | 2/1992 | Cole et al. |
| 5,094,247 | A | 3/1992 | Hernandez et al. |
| 5,098,004 | A | 3/1992 | Kerrigan |
| 5,098,360 | A | 3/1992 | Hirota |
| 5,100,042 | A | 3/1992 | Gravener et al. |
| 5,100,420 | A | 3/1992 | Green et al. |
| 5,100,422 | A | 3/1992 | Berguer et al. |
| 5,104,025 | A | 4/1992 | Main et al. |
| 5,104,397 | A | 4/1992 | Vasconcelos et al. |
| 5,104,400 | A | 4/1992 | Berguer et al. |
| 5,106,008 | A | 4/1992 | Tompkins et al. |
| 5,108,368 | A | 4/1992 | Hammerslag et al. |
| 5,109,722 | A | 5/1992 | Hufnagle et al. |
| 5,111,987 | A | 5/1992 | Moeinzadeh et al. |
| 5,116,349 | A | 5/1992 | Aranyi |
| D327,323 | S | 6/1992 | Hunt |
| 5,119,009 | A | 6/1992 | McCaleb et al. |
| 5,122,156 | A | 6/1992 | Granger et al. |
| 5,124,990 | A | 6/1992 | Williamson |
| 5,129,570 | A | 7/1992 | Schulze et al. |
| 5,137,198 | A | 8/1992 | Nobis et al. |
| 5,139,513 | A | 8/1992 | Segato |
| 5,141,144 | A | 8/1992 | Foslien et al. |
| 5,142,932 | A | 9/1992 | Moya et al. |
| 5,151,102 | A | 9/1992 | Kamiyama et al. |
| 5,155,941 | A | 10/1992 | Takahashi et al. |
| 5,156,315 | A | 10/1992 | Green et al. |
| 5,156,609 | A | 10/1992 | Nakao et al. |
| 5,156,614 | A | 10/1992 | Green et al. |
| 5,158,222 | A | 10/1992 | Green et al. |
| 5,158,567 | A | 10/1992 | Green |
| D330,699 | S | 11/1992 | Gill |
| 5,163,598 | A | 11/1992 | Peters et al. |

(56) References Cited

U.S. PATENT DOCUMENTS

| | | | |
|---|---|---|---|
| 5,164,652 | A | 11/1992 | Johnson et al. |
| 5,168,605 | A | 12/1992 | Bartlett |
| 5,170,925 | A | 12/1992 | Madden et al. |
| 5,171,247 | A | 12/1992 | Hughett et al. |
| 5,171,249 | A | 12/1992 | Stefanchik et al. |
| 5,171,253 | A | 12/1992 | Klieman |
| 5,173,053 | A | 12/1992 | Swanson et al. |
| 5,173,133 | A | 12/1992 | Morin et al. |
| 5,176,677 | A | 1/1993 | Wuchinich |
| 5,176,688 | A | 1/1993 | Narayan et al. |
| 5,181,514 | A | 1/1993 | Solomon et al. |
| 5,187,422 | A | 2/1993 | Izenbaard et al. |
| 5,188,102 | A | 2/1993 | Idemoto et al. |
| 5,188,111 | A | 2/1993 | Yates et al. |
| 5,188,126 | A | 2/1993 | Fabian et al. |
| 5,190,517 | A | 3/1993 | Zieve et al. |
| 5,190,544 | A | 3/1993 | Chapman et al. |
| 5,190,560 | A | 3/1993 | Woods et al. |
| 5,190,657 | A | 3/1993 | Heagle et al. |
| 5,192,288 | A | 3/1993 | Thompson et al. |
| 5,193,731 | A | 3/1993 | Aranyi |
| 5,195,505 | A | 3/1993 | Josefsen |
| 5,195,968 | A | 3/1993 | Lundquist et al. |
| 5,197,648 | A | 3/1993 | Gingold |
| 5,197,649 | A | 3/1993 | Bessler et al. |
| 5,197,966 | A | 3/1993 | Sommerkamp |
| 5,197,970 | A | 3/1993 | Green et al. |
| 5,200,280 | A | 4/1993 | Karasa |
| 5,201,750 | A | 4/1993 | Hocherl et al. |
| 5,205,459 | A | 4/1993 | Brinkerhoff et al. |
| 5,207,672 | A | 5/1993 | Roth et al. |
| 5,207,697 | A | 5/1993 | Carusillo et al. |
| 5,209,747 | A | 5/1993 | Knoepfler |
| 5,209,756 | A | 5/1993 | Seedhom et al. |
| 5,211,649 | A | 5/1993 | Kohler et al. |
| 5,211,655 | A | 5/1993 | Hasson |
| 5,217,457 | A | 6/1993 | Delahuerga et al. |
| 5,217,478 | A | 6/1993 | Rexroth |
| 5,219,111 | A | 6/1993 | Bilotti et al. |
| 5,220,269 | A | 6/1993 | Chen et al. |
| 5,221,036 | A | 6/1993 | Takase |
| 5,221,281 | A | 6/1993 | Klicek |
| 5,222,945 | A | 6/1993 | Basnight |
| 5,222,963 | A | 6/1993 | Brinkerhoff et al. |
| 5,222,975 | A | 6/1993 | Crainich |
| 5,222,976 | A | 6/1993 | Yoon |
| 5,223,675 | A | 6/1993 | Taft |
| D338,729 | S | 8/1993 | Sprecklemeier et al. |
| 5,234,447 | A | 8/1993 | Kaster et al. |
| 5,236,269 | A | 8/1993 | Handy |
| 5,236,424 | A | 8/1993 | Imran |
| 5,236,440 | A | 8/1993 | Hlavacek |
| 5,236,629 | A | 8/1993 | Mahabadi et al. |
| 5,239,981 | A | 8/1993 | Anapliotis |
| 5,240,163 | A | 8/1993 | Stein et al. |
| 5,242,456 | A | 9/1993 | Nash et al. |
| 5,242,457 | A | 9/1993 | Akopov et al. |
| 5,244,462 | A | 9/1993 | Delahuerga et al. |
| 5,246,156 | A | 9/1993 | Rothfuss et al. |
| 5,246,443 | A | 9/1993 | Mai |
| 5,251,801 | A | 10/1993 | Ruckdeschel et al. |
| 5,253,793 | A | 10/1993 | Green et al. |
| 5,258,007 | A | 11/1993 | Spetzler et al. |
| 5,258,008 | A | 11/1993 | Wilk |
| 5,258,009 | A | 11/1993 | Conners |
| 5,258,010 | A | 11/1993 | Green et al. |
| 5,258,012 | A | 11/1993 | Luscombe et al. |
| 5,259,366 | A | 11/1993 | Reydel et al. |
| 5,259,835 | A | 11/1993 | Clark et al. |
| 5,260,637 | A | 11/1993 | Pizzi |
| 5,261,135 | A | 11/1993 | Mitchell |
| 5,261,877 | A | 11/1993 | Fine et al. |
| 5,261,922 | A | 11/1993 | Hood |
| 5,263,629 | A | 11/1993 | Trumbull et al. |
| 5,263,937 | A | 11/1993 | Shipp |
| 5,263,973 | A | 11/1993 | Cook |
| 5,264,218 | A | 11/1993 | Rogozinski |
| 5,268,622 | A | 12/1993 | Philipp |
| 5,269,794 | A | 12/1993 | Rexroth |
| 5,271,543 | A | 12/1993 | Grant et al. |
| 5,271,544 | A | 12/1993 | Fox et al. |
| RE34,519 | E | 1/1994 | Fox et al. |
| 5,275,322 | A | 1/1994 | Brinkerhoff et al. |
| 5,275,323 | A | 1/1994 | Schulze et al. |
| 5,275,608 | A | 1/1994 | Forman et al. |
| 5,279,416 | A | 1/1994 | Malec et al. |
| 5,281,216 | A | 1/1994 | Klicek |
| 5,281,400 | A | 1/1994 | Berry, Jr. |
| 5,282,806 | A | 2/1994 | Haber et al. |
| 5,282,826 | A | 2/1994 | Quadri |
| 5,282,829 | A | 2/1994 | Hermes |
| 5,284,128 | A | 2/1994 | Hart |
| 5,285,381 | A | 2/1994 | Iskarous et al. |
| 5,285,945 | A | 2/1994 | Brinkerhoff et al. |
| 5,286,253 | A | 2/1994 | Fucci |
| 5,289,963 | A | 3/1994 | McGarry et al. |
| 5,290,271 | A | 3/1994 | Jernberg |
| 5,290,310 | A | 3/1994 | Makower et al. |
| 5,291,133 | A | 3/1994 | Gokhale et al. |
| 5,292,053 | A | 3/1994 | Bilotti et al. |
| 5,293,024 | A | 3/1994 | Sugahara et al. |
| 5,297,714 | A | 3/1994 | Kramer |
| 5,302,148 | A | 4/1994 | Heinz |
| 5,303,606 | A | 4/1994 | Kokinda |
| 5,304,204 | A | 4/1994 | Bregen |
| D347,474 | S | 5/1994 | Olson |
| 5,307,976 | A | 5/1994 | Olson et al. |
| 5,308,353 | A | 5/1994 | Beurrier |
| 5,308,358 | A | 5/1994 | Bond et al. |
| 5,308,576 | A | 5/1994 | Green et al. |
| 5,309,387 | A | 5/1994 | Mori et al. |
| 5,309,927 | A | 5/1994 | Welch |
| 5,312,023 | A | 5/1994 | Green et al. |
| 5,312,024 | A | 5/1994 | Grant et al. |
| 5,312,329 | A | 5/1994 | Beaty et al. |
| 5,313,935 | A | 5/1994 | Kortenbach et al. |
| 5,313,967 | A | 5/1994 | Lieber et al. |
| 5,314,424 | A | 5/1994 | Nicholas |
| 5,314,445 | A | 5/1994 | Heidmueller nee Degwitz et al. |
| 5,314,466 | A | 5/1994 | Stern et al. |
| 5,318,221 | A | 6/1994 | Green et al. |
| 5,320,627 | A | 6/1994 | Sorensen et al. |
| D348,930 | S | 7/1994 | Olson |
| 5,326,013 | A | 7/1994 | Green et al. |
| 5,329,923 | A | 7/1994 | Lundquist |
| 5,330,486 | A | 7/1994 | Wilk |
| 5,330,487 | A | 7/1994 | Thornton et al. |
| 5,330,502 | A | 7/1994 | Hassler et al. |
| 5,331,971 | A | 7/1994 | Bales et al. |
| 5,332,142 | A | 7/1994 | Robinson et al. |
| 5,333,422 | A | 8/1994 | Warren et al. |
| 5,333,772 | A | 8/1994 | Rothfuss et al. |
| 5,333,773 | A | 8/1994 | Main et al. |
| 5,334,183 | A | 8/1994 | Wuchinich |
| 5,336,130 | A | 8/1994 | Ray |
| 5,336,229 | A | 8/1994 | Noda |
| 5,336,232 | A | 8/1994 | Green et al. |
| 5,338,317 | A | 8/1994 | Hasson et al. |
| 5,339,799 | A | 8/1994 | Kami et al. |
| 5,341,724 | A | 8/1994 | Vatel |
| 5,341,807 | A | 8/1994 | Nardella |
| 5,341,810 | A | 8/1994 | Dardel |
| 5,342,380 | A | 8/1994 | Hood |
| 5,342,381 | A | 8/1994 | Tidemand |
| 5,342,385 | A | 8/1994 | Norelli et al. |
| 5,342,395 | A | 8/1994 | Jarrett et al. |
| 5,342,396 | A | 8/1994 | Cook |
| 5,343,382 | A | 8/1994 | Hale et al. |
| 5,343,391 | A | 8/1994 | Mushabac |
| 5,344,059 | A | 9/1994 | Green et al. |
| 5,344,060 | A | 9/1994 | Gravener et al. |
| 5,344,454 | A | 9/1994 | Clarke et al. |
| 5,346,504 | A | 9/1994 | Ortiz et al. |
| 5,348,259 | A | 9/1994 | Blanco et al. |

(56) References Cited

U.S. PATENT DOCUMENTS 5,350,104 A 9/1994 Main et al.
5,350,355 A 9/1994 Sklar
5,350,388 A 9/1994 Epstein
5,350,391 A 9/1994 Iacovelli
5,350,400 A 9/1994 Esposito et al.
5,352,229 A 10/1994 Goble et al.
5,352,235 A 10/1994 Koros et al.
5,352,238 A 10/1994 Green et al.
5,353,798 A 10/1994 Sieben
5,354,250 A 10/1994 Christensen
5,354,303 A 10/1994 Spaeth et al.
5,355,897 A 10/1994 Pietrafitta et al.
5,356,006 A 10/1994 Alpern et al.
5,356,064 A 10/1994 Green et al.
5,358,506 A 10/1994 Green et al.
5,358,510 A 10/1994 Luscombe et al.
5,359,231 A 10/1994 Flowers et al.
D352,780 S 11/1994 Glaeser et al.
5,359,993 A 11/1994 Slater et al.
5,360,305 A 11/1994 Kerrigan
5,360,428 A 11/1994 Hutchinson, Jr.
5,361,902 A 11/1994 Abidin et al.
5,364,001 A 11/1994 Bryan
5,364,002 A 11/1994 Green et al.
5,364,003 A 11/1994 Williamson, IV
5,366,133 A 11/1994 Geiste
5,366,134 A 11/1994 Green et al.
5,366,479 A 11/1994 McGarry et al.
5,368,015 A 11/1994 Wilk
5,368,592 A 11/1994 Stern et al.
5,368,599 A 11/1994 Hirsch et al.
5,369,565 A 11/1994 Chen et al.
5,370,645 A 12/1994 Klicek et al.
5,372,124 A 12/1994 Takayama et al.
5,372,596 A 12/1994 Klicek et al.
5,372,602 A 12/1994 Burke
5,374,277 A 12/1994 Hassler
5,375,588 A 12/1994 Yoon
5,376,095 A 12/1994 Ortiz
5,379,933 A 1/1995 Green et al.
5,381,649 A 1/1995 Webb
5,381,782 A 1/1995 DeLaRama et al.
5,381,943 A 1/1995 Allen et al.
5,382,247 A 1/1995 Cimino et al.
5,383,460 A 1/1995 Jang et al.
5,383,874 A 1/1995 Jackson et al.
5,383,880 A 1/1995 Hooven
5,383,881 A 1/1995 Green et al.
5,383,882 A 1/1995 Buess et al.
5,383,888 A 1/1995 Zvenyatsky et al.
5,383,895 A 1/1995 Holmes et al.
5,388,568 A 2/1995 van der Heide
5,389,072 A 2/1995 Imran
5,389,098 A 2/1995 Tsuruta et al.
5,389,102 A 2/1995 Green et al.
5,389,104 A 2/1995 Hahnen et al.
5,391,180 A 2/1995 Tovey et al.
5,392,979 A 2/1995 Green et al.
5,395,030 A 3/1995 Kuramoto et al.
5,395,033 A 3/1995 Byrne et al.
5,395,034 A 3/1995 Allen et al.
5,395,312 A 3/1995 Desai
5,395,384 A 3/1995 Duthoit et al.
5,397,046 A 3/1995 Savage et al.
5,397,324 A 3/1995 Carroll et al.
5,400,267 A 3/1995 Denen et al.
5,403,276 A 4/1995 Schechter et al.
5,403,312 A 4/1995 Yates et al.
5,404,106 A 4/1995 Matsuda
5,404,870 A 4/1995 Brinkerhoff et al.
5,404,960 A 4/1995 Wada et al.
5,405,072 A 4/1995 Zlock et al.
5,405,073 A 4/1995 Porter
5,405,344 A 4/1995 Williamson et al.
5,405,360 A 4/1995 Tovey
5,407,293 A 4/1995 Crainich
5,408,409 A 4/1995 Glassman et al.
5,409,498 A 4/1995 Braddock et al.
5,409,703 A 4/1995 McAnalley et al.
D357,981 S 5/1995 Green et al.
5,411,481 A 5/1995 Allen et al.
5,411,508 A 5/1995 Bessler et al.
5,413,107 A 5/1995 Oakley et al.
5,413,267 A 5/1995 Solyntjes et al.
5,413,268 A 5/1995 Green et al.
5,413,272 A 5/1995 Green et al.
5,413,573 A 5/1995 Koivukangas
5,415,334 A 5/1995 Williamson et al.
5,415,335 A 5/1995 Knodell, Jr.
5,417,203 A 5/1995 Tovey et al.
5,417,361 A 5/1995 Williamson, IV
5,419,766 A 5/1995 Chang et al.
5,421,829 A 6/1995 Olichney et al.
5,422,567 A 6/1995 Matsunaga
5,423,471 A 6/1995 Mastri et al.
5,423,809 A 6/1995 Klicek
5,423,835 A 6/1995 Green et al.
5,425,355 A 6/1995 Kulick
5,425,745 A 6/1995 Green et al.
5,427,298 A 6/1995 Tegtmeier
5,431,322 A 7/1995 Green et al.
5,431,323 A 7/1995 Smith et al.
5,431,645 A 7/1995 Smith et al.
5,431,654 A 7/1995 Nic
5,431,666 A 7/1995 Sauer et al.
5,431,668 A 7/1995 Burbank, III et al.
5,433,721 A 7/1995 Hooven et al.
5,437,681 A 8/1995 Meade et al.
5,438,302 A 8/1995 Goble
5,438,997 A 8/1995 Sieben et al.
5,439,155 A 8/1995 Viola
5,439,156 A 8/1995 Grant et al.
5,439,479 A 8/1995 Shichman et al.
5,441,191 A 8/1995 Linden
5,441,193 A 8/1995 Gravener
5,441,483 A 8/1995 Avitall
5,441,494 A 8/1995 Ortiz
5,441,499 A 8/1995 Fritzsch
5,443,197 A 8/1995 Malis et al.
5,443,198 A 8/1995 Viola et al.
5,443,463 A 8/1995 Stern et al.
5,444,113 A 8/1995 Sinclair et al.
5,445,155 A 8/1995 Sieben
5,445,304 A 8/1995 Plyley et al.
5,445,604 A 8/1995 Lang
5,445,644 A 8/1995 Pietrafitta et al.
5,446,646 A 8/1995 Miyazaki
5,447,265 A 9/1995 Vidal et al.
5,447,417 A 9/1995 Kuhl et al.
5,447,513 A 9/1995 Davison et al.
5,449,355 A 9/1995 Rhum et al.
5,449,365 A 9/1995 Green et al.
5,449,370 A 9/1995 Vaitekunas
5,452,836 A 9/1995 Huitema et al.
5,452,837 A 9/1995 Williamson, IV et al.
5,454,378 A 10/1995 Palmer et al.
5,454,822 A 10/1995 Schob et al.
5,454,824 A 10/1995 Fontayne et al.
5,454,827 A 10/1995 Aust et al.
5,456,401 A 10/1995 Green et al.
5,456,917 A 10/1995 Wise et al.
5,458,279 A 10/1995 Plyley
5,458,579 A 10/1995 Chodorow et al.
5,462,215 A 10/1995 Viola et al.
5,464,013 A 11/1995 Lemelson
5,464,144 A 11/1995 Guy et al.
5,464,300 A 11/1995 Crainich
5,465,819 A 11/1995 Weilant et al.
5,465,894 A 11/1995 Clark et al.
5,465,895 A 11/1995 Knodel et al.
5,465,896 A 11/1995 Allen et al.
5,466,020 A 11/1995 Page et al.
5,467,911 A 11/1995 Tsuruta et al.
5,468,253 A 11/1995 Bezwada et al.

(56) References Cited

U.S. PATENT DOCUMENTS 5,470,006 A 11/1995 Rodak
5,470,007 A 11/1995 Plyley et al.
5,470,008 A 11/1995 Rodak
5,470,009 A 11/1995 Rodak
5,470,010 A 11/1995 Rothfuss et al.
5,471,129 A 11/1995 Mann
5,472,132 A 12/1995 Savage et al.
5,472,442 A 12/1995 Klicek
5,473,204 A 12/1995 Temple
5,474,057 A 12/1995 Makower et al.
5,474,223 A 12/1995 Viola et al.
5,474,566 A 12/1995 Alesi et al.
5,474,570 A 12/1995 Kockerling et al.
5,474,738 A 12/1995 Nichols et al.
5,476,206 A 12/1995 Green et al.
5,476,479 A 12/1995 Green et al.
5,476,481 A 12/1995 Schondorf
5,478,003 A 12/1995 Green et al.
5,478,308 A 12/1995 Cartmell et al.
5,478,354 A 12/1995 Tovey et al.
5,480,089 A 1/1996 Blewett
5,480,409 A 1/1996 Riza
5,482,197 A 1/1996 Green et al.
5,483,952 A 1/1996 Aranyi
5,484,095 A 1/1996 Green et al.
5,484,398 A 1/1996 Stoddard
5,484,451 A 1/1996 Akopov et al.
5,485,947 A 1/1996 Olson et al.
5,485,952 A 1/1996 Fontayne
5,487,377 A 1/1996 Smith et al.
5,487,499 A 1/1996 Sorrentino et al.
5,487,500 A 1/1996 Knodel et al.
5,489,058 A 2/1996 Plyley et al.
5,489,256 A 2/1996 Adair
5,489,290 A 2/1996 Furnish
5,490,819 A 2/1996 Nicholas et al.
5,492,671 A 2/1996 Krafft
5,496,312 A 3/1996 Klicek
5,496,317 A 3/1996 Goble et al.
5,497,933 A 3/1996 DeFonzo et al.
5,498,164 A 3/1996 Ward et al.
5,498,838 A 3/1996 Furman
5,501,654 A 3/1996 Failla et al.
5,503,320 A 4/1996 Webster et al.
5,503,635 A 4/1996 Sauer et al.
5,503,638 A 4/1996 Cooper et al.
5,505,363 A 4/1996 Green et al.
5,507,425 A 4/1996 Ziglioli
5,507,426 A 4/1996 Young et al.
5,507,773 A 4/1996 Huitema et al.
5,509,596 A 4/1996 Green et al.
5,509,916 A 4/1996 Taylor
5,509,918 A 4/1996 Romano
5,511,564 A 4/1996 Wilk
5,514,129 A 5/1996 Smith
5,514,149 A 5/1996 Green et al.
5,514,157 A 5/1996 Nicholas et al.
5,518,163 A 5/1996 Hooven
5,518,164 A 5/1996 Hooven
5,520,609 A 5/1996 Moll et al.
5,520,634 A 5/1996 Fox et al.
5,520,678 A 5/1996 Heckele et al.
5,520,700 A 5/1996 Beyar et al.
5,522,817 A 6/1996 Sander et al.
5,522,831 A 6/1996 Sleister et al.
5,527,264 A 6/1996 Moll et al.
5,527,320 A 6/1996 Carruthers et al.
5,529,235 A 6/1996 Boiarski et al.
D372,086 S 7/1996 Grasso et al.
5,531,305 A 7/1996 Roberts et al.
5,531,744 A 7/1996 Nardella et al.
5,531,856 A 7/1996 Moll et al.
5,533,521 A 7/1996 Granger
5,533,581 A 7/1996 Barth et al.
5,533,661 A 7/1996 Main et al.
5,535,934 A 7/1996 Boiarski et al.
5,535,935 A 7/1996 Vidal et al.
5,535,937 A 7/1996 Boiarski et al.
5,540,375 A 7/1996 Bolanos et al.
5,540,705 A 7/1996 Meade et al.
5,541,376 A 7/1996 Ladtkow et al.
5,541,489 A 7/1996 Dunstan
5,542,594 A 8/1996 McKean et al.
5,542,945 A 8/1996 Fritzsch
5,542,949 A 8/1996 Yoon
5,543,119 A 8/1996 Sutter et al.
5,543,695 A 8/1996 Culp et al.
5,544,802 A 8/1996 Crainich
5,547,117 A 8/1996 Hamblin et al.
5,549,583 A 8/1996 Sanford et al.
5,549,621 A 8/1996 Bessler et al.
5,549,627 A 8/1996 Kieturakis
5,549,628 A 8/1996 Cooper et al.
5,549,637 A 8/1996 Crainich
5,551,622 A 9/1996 Yoon
5,553,624 A 9/1996 Francese et al.
5,553,675 A 9/1996 Pitzen et al.
5,553,765 A 9/1996 Knodel et al.
5,554,148 A 9/1996 Aebischer et al.
5,554,169 A 9/1996 Green et al.
5,556,020 A 9/1996 Hou
5,556,416 A 9/1996 Clark et al.
5,558,533 A 9/1996 Hashizawa et al.
5,558,665 A 9/1996 Kieturakis
5,558,671 A 9/1996 Yates
5,560,530 A 10/1996 Bolanos et al.
5,560,532 A 10/1996 DeFonzo et al.
5,561,881 A 10/1996 Klinger et al.
5,562,239 A 10/1996 Boiarski et al.
5,562,241 A 10/1996 Knodel et al.
5,562,682 A 10/1996 Oberlin et al.
5,562,690 A 10/1996 Green et al.
5,562,694 A 10/1996 Sauer et al.
5,562,701 A 10/1996 Huitema et al.
5,562,702 A 10/1996 Huitema et al.
5,563,481 A 10/1996 Krause
5,564,615 A 10/1996 Bishop et al.
5,569,161 A 10/1996 Ebling et al.
5,569,270 A 10/1996 Weng
5,569,284 A 10/1996 Young et al.
5,571,090 A 11/1996 Sherts
5,571,100 A 11/1996 Goble et al.
5,571,116 A 11/1996 Bolanos et al.
5,571,285 A 11/1996 Chow et al.
5,571,488 A 11/1996 Beerstecher et al.
5,573,169 A 11/1996 Green et al.
5,573,543 A 11/1996 Akopov et al.
5,574,431 A 11/1996 McKeown et al.
5,575,054 A 11/1996 Klinzing et al.
5,575,789 A 11/1996 Bell et al.
5,575,799 A 11/1996 Bolanos et al.
5,575,803 A 11/1996 Cooper et al.
5,575,805 A 11/1996 Li
5,577,654 A 11/1996 Bishop
5,578,052 A 11/1996 Koros et al.
5,579,978 A 12/1996 Green et al.
5,580,067 A 12/1996 Hamblin et al.
5,582,611 A 12/1996 Tsuruta et al.
5,582,617 A 12/1996 Klieman et al.
5,582,907 A 12/1996 Pall
5,583,114 A 12/1996 Barrows et al.
5,584,425 A 12/1996 Savage et al.
5,586,711 A 12/1996 Plyley et al.
5,588,579 A 12/1996 Schnut et al.
5,588,580 A 12/1996 Paul et al.
5,588,581 A 12/1996 Conlon et al.
5,591,170 A 1/1997 Spievack et al.
5,591,187 A 1/1997 Dekel
5,597,107 A 1/1997 Knodel et al.
5,599,151 A 2/1997 Daum et al.
5,599,279 A 2/1997 Slotman et al.
5,599,344 A 2/1997 Paterson
5,599,350 A 2/1997 Schulze et al.
5,599,852 A 2/1997 Scopelianos et al.

(56) References Cited

U.S. PATENT DOCUMENTS 5,601,224 A 2/1997 Bishop et al.
5,601,573 A 2/1997 Fogelberg et al.
5,601,604 A 2/1997 Vincent
5,602,449 A 2/1997 Krause et al.
5,603,443 A 2/1997 Clark et al.
5,605,272 A 2/1997 Witt et al.
5,605,273 A 2/1997 Hamblin et al.
5,607,094 A 3/1997 Clark et al.
5,607,095 A 3/1997 Smith et al.
5,607,433 A 3/1997 Polla et al.
5,607,436 A 3/1997 Pratt et al.
5,607,450 A 3/1997 Zvenyatsky et al.
5,607,474 A 3/1997 Athanasiou et al.
5,609,285 A 3/1997 Grant et al.
5,609,601 A 3/1997 Kolesa et al.
5,611,709 A 3/1997 McAnulty
5,611,813 A 3/1997 Lichtman
5,613,499 A 3/1997 Palmer et al.
5,613,937 A 3/1997 Garrison et al.
5,613,966 A 3/1997 Makower et al.
5,614,887 A 3/1997 Buchbinder
5,615,820 A 4/1997 Viola
5,618,294 A 4/1997 Aust et al.
5,618,303 A 4/1997 Marlow et al.
5,618,307 A 4/1997 Donlon et al.
5,619,992 A 4/1997 Guthrie et al.
5,620,289 A 4/1997 Curry
5,620,326 A 4/1997 Younker
5,620,452 A 4/1997 Yoon
5,624,398 A 4/1997 Smith et al.
5,624,452 A 4/1997 Yates
5,626,587 A 5/1997 Bishop et al.
5,626,595 A 5/1997 Sklar et al.
5,626,979 A 5/1997 Mitsui et al.
5,628,446 A 5/1997 Geiste et al.
5,628,743 A 5/1997 Cimino
5,628,745 A 5/1997 Bek
5,630,539 A 5/1997 Plyley et al.
5,630,540 A 5/1997 Blewett
5,630,541 A 5/1997 Williamson, IV et al.
5,630,782 A 5/1997 Adair
5,631,973 A 5/1997 Green
5,632,432 A 5/1997 Schulze et al.
5,632,433 A 5/1997 Grant et al.
5,633,374 A 5/1997 Humphrey et al.
5,634,584 A 6/1997 Okorocha et al.
5,636,779 A 6/1997 Palmer
5,636,780 A 6/1997 Green et al.
5,637,110 A 6/1997 Pennybacker et al.
5,638,582 A 6/1997 Klatt et al.
5,639,008 A 6/1997 Gallagher et al.
D381,077 S 7/1997 Hunt
5,643,291 A 7/1997 Pier et al.
5,643,293 A 7/1997 Kogasaka et al.
5,643,294 A 7/1997 Tovey et al.
5,643,319 A 7/1997 Green et al.
5,645,209 A 7/1997 Green et al.
5,647,526 A 7/1997 Green et al.
5,647,869 A 7/1997 Goble et al.
5,649,937 A 7/1997 Bito et al.
5,649,956 A 7/1997 Jensen et al.
5,651,491 A 7/1997 Heaton et al.
5,651,762 A 7/1997 Bridges
5,651,821 A 7/1997 Uchida
5,653,373 A 8/1997 Green et al.
5,653,374 A 8/1997 Young et al.
5,653,677 A 8/1997 Okada et al.
5,653,721 A 8/1997 Knodel et al.
5,653,748 A 8/1997 Strecker
5,655,698 A 8/1997 Yoon
5,656,917 A 8/1997 Theobald
5,657,417 A 8/1997 Di Troia
5,657,429 A 8/1997 Wang et al.
5,657,921 A 8/1997 Young et al.
5,658,238 A 8/1997 Suzuki et al.
5,658,281 A 8/1997 Heard
5,658,298 A 8/1997 Vincent et al.
5,658,300 A 8/1997 Bito et al.
5,658,307 A 8/1997 Exconde
5,662,258 A 9/1997 Knodel et al.
5,662,260 A 9/1997 Yoon
5,662,662 A 9/1997 Bishop et al.
5,662,667 A 9/1997 Knodel
5,664,404 A 9/1997 Ivanov et al.
5,665,085 A 9/1997 Nardella
5,667,517 A 9/1997 Hooven
5,667,526 A 9/1997 Levin
5,667,527 A 9/1997 Cook
5,667,864 A 9/1997 Landoll
5,669,544 A 9/1997 Schulze et al.
5,669,904 A 9/1997 Platt, Jr. et al.
5,669,907 A 9/1997 Platt, Jr. et al.
5,669,918 A 9/1997 Balazs et al.
5,672,945 A 9/1997 Krause
5,673,840 A 10/1997 Schulze et al.
5,673,841 A 10/1997 Schulze et al.
5,673,842 A 10/1997 Bittner et al.
5,674,184 A 10/1997 Hassler, Jr.
5,674,286 A 10/1997 D'Alessio et al.
5,678,748 A 10/1997 Plyley et al.
5,680,981 A 10/1997 Mililli et al.
5,680,982 A 10/1997 Schulze et al.
5,680,983 A 10/1997 Plyley et al.
5,681,341 A 10/1997 Lunsford et al.
5,683,349 A 11/1997 Makower et al.
5,685,474 A 11/1997 Seeber
5,686,090 A 11/1997 Schilder et al.
5,688,270 A 11/1997 Yates et al.
5,690,269 A 11/1997 Bolanos et al.
5,690,675 A 11/1997 Sawyer et al.
5,692,668 A 12/1997 Schulze et al.
5,693,020 A 12/1997 Rauh
5,693,042 A 12/1997 Boiarski et al.
5,693,051 A 12/1997 Schulze et al.
5,695,494 A 12/1997 Becker
5,695,502 A 12/1997 Pier et al.
5,695,504 A 12/1997 Gifford, III et al.
5,695,524 A 12/1997 Kelley et al.
5,697,542 A 12/1997 Knodel et al.
5,697,543 A 12/1997 Burdorff
5,697,909 A 12/1997 Eggers et al.
5,697,943 A 12/1997 Sauer et al.
5,700,270 A 12/1997 Peyser et al.
5,700,276 A 12/1997 Benecke
5,702,387 A 12/1997 Arts et al.
5,702,408 A 12/1997 Wales et al.
5,702,409 A 12/1997 Rayburn et al.
5,704,087 A 1/1998 Strub
5,704,534 A 1/1998 Huitema et al.
5,704,792 A 1/1998 Sobhani
5,706,997 A 1/1998 Green et al.
5,706,998 A 1/1998 Plyley et al.
5,707,392 A 1/1998 Kortenbach
5,709,334 A 1/1998 Sorrentino et al.
5,709,335 A 1/1998 Heck
5,709,680 A 1/1998 Yates et al.
5,709,706 A 1/1998 Kienzle et al.
5,711,472 A 1/1998 Bryan
5,711,960 A 1/1998 Shikinami
5,712,460 A 1/1998 Carr et al.
5,713,128 A 2/1998 Schrenk et al.
5,713,505 A 2/1998 Huitema
5,713,895 A 2/1998 Lontine et al.
5,713,896 A 2/1998 Nardella
5,713,920 A 2/1998 Bezwada et al.
5,715,604 A 2/1998 Lanzoni
5,715,836 A 2/1998 Kliegis et al.
5,715,987 A 2/1998 Kelley et al.
5,715,988 A 2/1998 Palmer
5,716,352 A 2/1998 Viola et al.
5,716,366 A 2/1998 Yates
5,718,359 A 2/1998 Palmer et al.
5,718,360 A 2/1998 Green et al.
5,718,548 A 2/1998 Cotellessa

(56) References Cited

U.S. PATENT DOCUMENTS

| | | | |
|---|---|---|---|
| 5,718,714 | A | 2/1998 | Livneh |
| 5,720,744 | A | 2/1998 | Eggleston et al. |
| D393,067 | S | 3/1998 | Geary et al. |
| 5,724,025 | A | 3/1998 | Tavori |
| 5,725,536 | A | 3/1998 | Oberlin et al. |
| 5,725,554 | A | 3/1998 | Simon et al. |
| 5,728,110 | A | 3/1998 | Vidal et al. |
| 5,728,113 | A | 3/1998 | Sherts |
| 5,728,121 | A | 3/1998 | Bimbo et al. |
| 5,730,758 | A | 3/1998 | Allgeyer |
| 5,732,712 | A | 3/1998 | Adair |
| 5,732,821 | A | 3/1998 | Stone et al. |
| 5,732,871 | A | 3/1998 | Clark et al. |
| 5,732,872 | A | 3/1998 | Bolduc et al. |
| 5,733,308 | A | 3/1998 | Daugherty et al. |
| 5,735,445 | A | 4/1998 | Vidal et al. |
| 5,735,848 | A | 4/1998 | Yates et al. |
| 5,735,874 | A | 4/1998 | Measamer et al. |
| 5,736,271 | A | 4/1998 | Cisar et al. |
| 5,738,474 | A | 4/1998 | Blewett |
| 5,738,629 | A | 4/1998 | Moll et al. |
| 5,738,648 | A | 4/1998 | Lands et al. |
| 5,741,271 | A | 4/1998 | Nakao et al. |
| 5,743,456 | A | 4/1998 | Jones et al. |
| 5,746,770 | A | 5/1998 | Zeitels et al. |
| 5,747,953 | A | 5/1998 | Philipp |
| 5,749,889 | A | 5/1998 | Bacich et al. |
| 5,749,893 | A | 5/1998 | Vidal et al. |
| 5,749,896 | A | 5/1998 | Cook |
| 5,749,968 | A | 5/1998 | Melanson et al. |
| 5,752,644 | A | 5/1998 | Bolanos et al. |
| 5,752,965 | A | 5/1998 | Francis et al. |
| 5,752,970 | A | 5/1998 | Yoon |
| 5,752,973 | A | 5/1998 | Kieturakis |
| 5,755,717 | A | 5/1998 | Yates et al. |
| 5,755,726 | A | 5/1998 | Pratt et al. |
| 5,758,814 | A | 6/1998 | Gallagher et al. |
| 5,762,255 | A | 6/1998 | Chrisman et al. |
| 5,762,256 | A | 6/1998 | Mastri et al. |
| 5,762,458 | A | 6/1998 | Wang et al. |
| 5,765,565 | A | 6/1998 | Adair |
| 5,766,186 | A | 6/1998 | Faraz et al. |
| 5,766,188 | A | 6/1998 | Igaki |
| 5,766,205 | A | 6/1998 | Zvenyatsky et al. |
| 5,769,303 | A | 6/1998 | Knodel et al. |
| 5,769,640 | A | 6/1998 | Jacobus et al. |
| 5,769,748 | A | 6/1998 | Eyerly et al. |
| 5,769,791 | A | 6/1998 | Benaron et al. |
| 5,769,892 | A | 6/1998 | Kingwell |
| 5,772,099 | A | 6/1998 | Gravener |
| 5,772,379 | A | 6/1998 | Evensen |
| 5,772,578 | A | 6/1998 | Heimberger et al. |
| 5,772,659 | A | 6/1998 | Becker et al. |
| 5,773,991 | A | 6/1998 | Chen |
| 5,776,130 | A | 7/1998 | Buysse et al. |
| 5,778,939 | A | 7/1998 | Hok-Yin |
| 5,779,130 | A | 7/1998 | Alesi et al. |
| 5,779,131 | A | 7/1998 | Knodel et al. |
| 5,779,132 | A | 7/1998 | Knodel et al. |
| 5,782,396 | A | 7/1998 | Mastri et al. |
| 5,782,397 | A | 7/1998 | Koukline |
| 5,782,748 | A | 7/1998 | Palmer et al. |
| 5,782,749 | A | 7/1998 | Riza |
| 5,782,859 | A | 7/1998 | Nicholas et al. |
| 5,784,934 | A | 7/1998 | Izumisawa |
| 5,785,232 | A | 7/1998 | Vidal et al. |
| 5,785,647 | A | 7/1998 | Tompkins et al. |
| 5,787,897 | A | 8/1998 | Kieturakis |
| 5,791,231 | A | 8/1998 | Cohn et al. |
| 5,792,135 | A | 8/1998 | Madhani et al. |
| 5,792,162 | A | 8/1998 | Jolly et al. |
| 5,792,165 | A | 8/1998 | Klieman et al. |
| 5,792,573 | A | 8/1998 | Pitzen et al. |
| 5,794,834 | A | 8/1998 | Hamblin et al. |
| 5,796,188 | A | 8/1998 | Bays |
| 5,797,536 | A | 8/1998 | Smith et al. |
| 5,797,537 | A | 8/1998 | Oberlin et al. |
| 5,797,538 | A | 8/1998 | Heaton et al. |
| 5,797,637 | A | 8/1998 | Ervin |
| 5,797,900 | A | 8/1998 | Madhani et al. |
| 5,797,906 | A | 8/1998 | Rhum et al. |
| 5,797,927 | A | 8/1998 | Yoon |
| 5,797,941 | A | 8/1998 | Schulze et al. |
| 5,797,959 | A | 8/1998 | Castro et al. |
| 5,798,752 | A | 8/1998 | Buxton et al. |
| 5,799,857 | A | 9/1998 | Robertson et al. |
| 5,800,379 | A | 9/1998 | Edwards |
| 5,800,423 | A | 9/1998 | Jensen |
| 5,804,726 | A | 9/1998 | Geib et al. |
| 5,804,936 | A | 9/1998 | Brodsky et al. |
| 5,806,676 | A | 9/1998 | Wasgien |
| 5,807,241 | A | 9/1998 | Heimberger |
| 5,807,376 | A | 9/1998 | Viola et al. |
| 5,807,378 | A | 9/1998 | Jensen et al. |
| 5,807,393 | A | 9/1998 | Williamson, IV et al. |
| 5,809,441 | A | 9/1998 | McKee |
| 5,810,240 | A | 9/1998 | Robertson |
| 5,810,721 | A | 9/1998 | Mueller et al. |
| 5,810,811 | A | 9/1998 | Yates et al. |
| 5,810,846 | A | 9/1998 | Virnich et al. |
| 5,810,855 | A | 9/1998 | Rayburn et al. |
| 5,812,188 | A | 9/1998 | Adair |
| 5,813,813 | A | 9/1998 | Daum et al. |
| 5,814,055 | A | 9/1998 | Knodel et al. |
| 5,814,057 | A | 9/1998 | Oi et al. |
| 5,816,471 | A | 10/1998 | Plyley et al. |
| 5,817,084 | A | 10/1998 | Jensen |
| 5,817,091 | A | 10/1998 | Nardella et al. |
| 5,817,093 | A | 10/1998 | Williamson, IV et al. |
| 5,817,109 | A | 10/1998 | McGarry et al. |
| 5,817,119 | A | 10/1998 | Klieman et al. |
| 5,820,009 | A | 10/1998 | Melling et al. |
| 5,823,066 | A | 10/1998 | Huitema et al. |
| 5,824,333 | A | 10/1998 | Scopelianos et al. |
| 5,826,776 | A | 10/1998 | Schulze et al. |
| 5,827,271 | A | 10/1998 | Buysse et al. |
| 5,827,298 | A | 10/1998 | Hart et al. |
| 5,827,323 | A | 10/1998 | Klieman et al. |
| 5,829,662 | A | 11/1998 | Allen et al. |
| 5,830,598 | A | 11/1998 | Patterson |
| 5,833,690 | A | 11/1998 | Yates et al. |
| 5,833,695 | A | 11/1998 | Yoon |
| 5,833,696 | A | 11/1998 | Whitfield et al. |
| 5,836,503 | A | 11/1998 | Ehrenfels et al. |
| 5,836,960 | A | 11/1998 | Kolesa et al. |
| 5,839,369 | A | 11/1998 | Chatterjee et al. |
| 5,839,639 | A | 11/1998 | Sauer et al. |
| 5,841,284 | A | 11/1998 | Takahashi |
| 5,843,021 | A | 12/1998 | Edwards et al. |
| 5,843,096 | A | 12/1998 | Igaki et al. |
| 5,843,097 | A | 12/1998 | Mayenberger et al. |
| 5,843,122 | A | 12/1998 | Riza |
| 5,843,132 | A | 12/1998 | Ilvento |
| 5,843,169 | A | 12/1998 | Taheri |
| 5,846,254 | A | 12/1998 | Schulze et al. |
| 5,847,566 | A | 12/1998 | Marritt et al. |
| 5,849,011 | A | 12/1998 | Jones et al. |
| 5,849,020 | A | 12/1998 | Long et al. |
| 5,849,023 | A | 12/1998 | Mericle |
| 5,851,179 | A | 12/1998 | Ritson et al. |
| 5,851,212 | A | 12/1998 | Zirps et al. |
| 5,853,366 | A | 12/1998 | Dowlatshahi |
| 5,855,311 | A | 1/1999 | Hamblin et al. |
| 5,855,583 | A | 1/1999 | Wang et al. |
| 5,860,581 | A | 1/1999 | Robertson et al. |
| 5,860,975 | A | 1/1999 | Goble et al. |
| 5,865,361 | A | 2/1999 | Milliman et al. |
| 5,865,638 | A | 2/1999 | Trafton |
| 5,868,361 | A | 2/1999 | Rinderer |
| 5,868,664 | A | 2/1999 | Speier et al. |
| 5,868,760 | A | 2/1999 | McGuckin, Jr. |
| 5,868,790 | A | 2/1999 | Vincent et al. |
| 5,871,135 | A | 2/1999 | Williamson, IV et al. |
| 5,873,885 | A | 2/1999 | Weidenbenner |

(56) References Cited

U.S. PATENT DOCUMENTS

| | | | |
|---|---|---|---|
| 5,876,401 | A | 3/1999 | Schulze et al. |
| 5,878,193 | A | 3/1999 | Wang et al. |
| 5,878,607 | A | 3/1999 | Nunes et al. |
| 5,878,937 | A | 3/1999 | Green et al. |
| 5,878,938 | A | 3/1999 | Bittner et al. |
| 5,881,777 | A | 3/1999 | Bassi et al. |
| 5,881,943 | A | 3/1999 | Heck et al. |
| 5,891,094 | A | 4/1999 | Masterson et al. |
| 5,891,160 | A | 4/1999 | Williamson, IV et al. |
| 5,891,558 | A | 4/1999 | Bell et al. |
| 5,893,506 | A | 4/1999 | Powell |
| 5,893,835 | A | 4/1999 | Witt et al. |
| 5,893,878 | A | 4/1999 | Pierce |
| 5,894,979 | A | 4/1999 | Powell |
| 5,897,552 | A | 4/1999 | Edwards et al. |
| 5,897,562 | A | 4/1999 | Bolanos et al. |
| 5,899,824 | A | 5/1999 | Kurtz et al. |
| 5,899,914 | A | 5/1999 | Zirps et al. |
| 5,901,895 | A | 5/1999 | Heaton et al. |
| 5,902,312 | A | 5/1999 | Frater et al. |
| 5,903,117 | A | 5/1999 | Gregory |
| 5,904,647 | A | 5/1999 | Ouchi |
| 5,904,693 | A | 5/1999 | Dicesare et al. |
| 5,904,702 | A | 5/1999 | Ek et al. |
| 5,906,577 | A | 5/1999 | Beane et al. |
| 5,906,625 | A | 5/1999 | Bito et al. |
| 5,907,211 | A | 5/1999 | Hall et al. |
| 5,907,664 | A | 5/1999 | Wang et al. |
| 5,908,402 | A | 6/1999 | Blythe |
| 5,908,427 | A | 6/1999 | McKean et al. |
| 5,909,062 | A | 6/1999 | Krietzman |
| 5,911,353 | A | 6/1999 | Bolanos et al. |
| 5,915,616 | A | 6/1999 | Viola et al. |
| 5,916,225 | A | 6/1999 | Kugel |
| 5,918,791 | A | 7/1999 | Sorrentino et al. |
| 5,919,198 | A | 7/1999 | Graves, Jr. et al. |
| 5,921,956 | A | 7/1999 | Grinberg et al. |
| 5,922,001 | A | 7/1999 | Yoon |
| 5,922,003 | A | 7/1999 | Anctil et al. |
| 5,924,864 | A | 7/1999 | Loge et al. |
| 5,928,137 | A | 7/1999 | Green |
| 5,928,256 | A | 7/1999 | Riza |
| 5,931,847 | A | 8/1999 | Bittner et al. |
| 5,931,853 | A | 8/1999 | McEwen et al. |
| 5,937,951 | A | 8/1999 | Izuchukwu et al. |
| 5,938,667 | A | 8/1999 | Peyser et al. |
| 5,941,442 | A | 8/1999 | Geiste et al. |
| 5,941,890 | A | 8/1999 | Voegele et al. |
| 5,944,172 | A | 8/1999 | Hannula |
| 5,944,715 | A | 8/1999 | Goble et al. |
| 5,946,978 | A | 9/1999 | Yamashita |
| 5,947,984 | A | 9/1999 | Whipple |
| 5,947,996 | A | 9/1999 | Logeman |
| 5,948,030 | A | 9/1999 | Miller et al. |
| 5,948,429 | A | 9/1999 | Bell et al. |
| 5,951,301 | A | 9/1999 | Younker |
| 5,951,516 | A | 9/1999 | Bunyan |
| 5,951,552 | A | 9/1999 | Long et al. |
| 5,951,574 | A | 9/1999 | Stefanchik et al. |
| 5,951,575 | A | 9/1999 | Bolduc et al. |
| 5,951,581 | A | 9/1999 | Saadat et al. |
| 5,954,259 | A | 9/1999 | Viola et al. |
| 5,957,831 | A | 9/1999 | Adair |
| 5,964,394 | A | 10/1999 | Robertson |
| 5,964,774 | A | 10/1999 | McKean et al. |
| 5,966,126 | A | 10/1999 | Szabo |
| 5,971,916 | A | 10/1999 | Koren |
| 5,973,221 | A | 10/1999 | Collyer et al. |
| D416,089 | S | 11/1999 | Barton et al. |
| 5,976,122 | A | 11/1999 | Madhani et al. |
| 5,977,746 | A | 11/1999 | Hershberger et al. |
| 5,980,248 | A | 11/1999 | Kusakabe et al. |
| 5,984,949 | A | 11/1999 | Levin |
| 5,988,479 | A | 11/1999 | Palmer |
| 5,990,379 | A | 11/1999 | Gregory |
| 5,993,466 | A | 11/1999 | Yoon |
| 5,997,528 | A | 12/1999 | Bisch et al. |
| 5,997,552 | A | 12/1999 | Person et al. |
| 6,001,108 | A | 12/1999 | Wang et al. |
| 6,003,517 | A | 12/1999 | Sheffield et al. |
| 6,004,319 | A | 12/1999 | Goble et al. |
| 6,004,335 | A | 12/1999 | Vaitekunas et al. |
| 6,007,521 | A | 12/1999 | Bidwell et al. |
| 6,010,054 | A | 1/2000 | Johnson et al. |
| 6,010,513 | A | 1/2000 | Tormala et al. |
| 6,010,520 | A | 1/2000 | Pattison |
| 6,012,494 | A | 1/2000 | Balazs |
| 6,013,076 | A | 1/2000 | Goble et al. |
| 6,013,991 | A | 1/2000 | Philipp |
| 6,015,406 | A | 1/2000 | Goble et al. |
| 6,015,417 | A | 1/2000 | Reynolds, Jr. |
| 6,017,322 | A | 1/2000 | Snoke et al. |
| 6,017,354 | A | 1/2000 | Culp et al. |
| 6,017,356 | A | 1/2000 | Frederick et al. |
| 6,018,227 | A | 1/2000 | Kumar et al. |
| 6,019,745 | A | 2/2000 | Gray |
| 6,019,780 | A | 2/2000 | Lombardo et al. |
| 6,022,352 | A | 2/2000 | Vandewalle |
| 6,023,275 | A | 2/2000 | Horvitz et al. |
| 6,023,641 | A | 2/2000 | Thompson |
| 6,024,708 | A | 2/2000 | Bales et al. |
| 6,024,741 | A | 2/2000 | Williamson, IV et al. |
| 6,024,748 | A | 2/2000 | Manzo et al. |
| 6,024,750 | A | 2/2000 | Mastri et al. |
| 6,024,764 | A | 2/2000 | Schroeppel |
| 6,027,501 | A | 2/2000 | Goble et al. |
| 6,030,384 | A | 2/2000 | Nezhat |
| 6,032,849 | A | 3/2000 | Mastri et al. |
| 6,033,105 | A | 3/2000 | Barker et al. |
| 6,033,378 | A | 3/2000 | Lundquist et al. |
| 6,033,399 | A | 3/2000 | Gines |
| 6,033,427 | A | 3/2000 | Lee |
| 6,036,641 | A | 3/2000 | Taylor et al. |
| 6,036,667 | A | 3/2000 | Manna et al. |
| 6,037,724 | A | 3/2000 | Buss et al. |
| 6,037,927 | A | 3/2000 | Rosenberg |
| 6,039,126 | A | 3/2000 | Hsieh |
| 6,039,733 | A | 3/2000 | Buysse et al. |
| 6,039,734 | A | 3/2000 | Goble |
| 6,042,601 | A | 3/2000 | Smith |
| 6,042,607 | A | 3/2000 | Williamson, IV et al. |
| 6,043,626 | A | 3/2000 | Snyder et al. |
| 6,045,560 | A | 4/2000 | McKean et al. |
| 6,047,861 | A | 4/2000 | Vidal et al. |
| 6,049,145 | A | 4/2000 | Austin et al. |
| 6,050,172 | A | 4/2000 | Corves et al. |
| 6,050,472 | A | 4/2000 | Shibata |
| 6,050,989 | A | 4/2000 | Fox et al. |
| 6,050,990 | A | 4/2000 | Tankovich et al. |
| 6,050,996 | A | 4/2000 | Schmaltz et al. |
| 6,053,390 | A | 4/2000 | Green et al. |
| 6,053,899 | A | 4/2000 | Slanda et al. |
| 6,053,922 | A | 4/2000 | Krause et al. |
| 6,054,142 | A | 4/2000 | Li et al. |
| 6,055,062 | A | 4/2000 | Dina et al. |
| RE36,720 | E | 5/2000 | Green et al. |
| 6,056,735 | A | 5/2000 | Okada et al. |
| 6,056,746 | A | 5/2000 | Goble et al. |
| 6,059,806 | A | 5/2000 | Hoegerle |
| 6,062,360 | A | 5/2000 | Shields |
| 6,063,020 | A | 5/2000 | Jones et al. |
| 6,063,025 | A | 5/2000 | Bridges et al. |
| 6,063,050 | A | 5/2000 | Manna et al. |
| 6,063,095 | A | 5/2000 | Wang et al. |
| 6,063,097 | A | 5/2000 | Oi et al. |
| 6,063,098 | A | 5/2000 | Houser et al. |
| 6,065,679 | A | 5/2000 | Levie et al. |
| 6,065,919 | A | 5/2000 | Peck |
| 6,066,132 | A | 5/2000 | Chen et al. |
| 6,066,151 | A | 5/2000 | Miyawaki et al. |
| 6,068,627 | A | 5/2000 | Orszulak et al. |
| 6,071,233 | A | 6/2000 | Ishikawa et al. |
| 6,072,299 | A | 6/2000 | Kurle et al. |
| 6,074,386 | A | 6/2000 | Goble et al. |

(56) References Cited

U.S. PATENT DOCUMENTS

| | | | |
|---|---|---|---|
| 6,074,401 | A | 6/2000 | Gardiner et al. |
| 6,075,441 | A | 6/2000 | Maloney |
| 6,077,280 | A | 6/2000 | Fossum |
| 6,077,286 | A | 6/2000 | Cuschieri et al. |
| 6,077,290 | A | 6/2000 | Marini |
| 6,079,606 | A | 6/2000 | Milliman et al. |
| 6,080,181 | A | 6/2000 | Jensen et al. |
| 6,082,577 | A | 7/2000 | Coates et al. |
| 6,083,191 | A | 7/2000 | Rose |
| 6,083,223 | A | 7/2000 | Baker |
| 6,083,234 | A | 7/2000 | Nicholas et al. |
| 6,083,242 | A | 7/2000 | Cook |
| 6,086,544 | A | 7/2000 | Hibner et al. |
| 6,086,600 | A | 7/2000 | Kortenbach |
| 6,090,106 | A | 7/2000 | Goble et al. |
| 6,090,123 | A | 7/2000 | Culp et al. |
| 6,093,186 | A | 7/2000 | Goble |
| 6,094,021 | A | 7/2000 | Noro et al. |
| D429,252 | S | 8/2000 | Haitani et al. |
| 6,099,537 | A | 8/2000 | Sugai et al. |
| 6,099,551 | A | 8/2000 | Gabbay |
| 6,102,271 | A | 8/2000 | Longo et al. |
| 6,102,926 | A | 8/2000 | Tartaglia et al. |
| 6,104,162 | A | 8/2000 | Sainsbury et al. |
| 6,104,304 | A | 8/2000 | Clark et al. |
| 6,106,511 | A | 8/2000 | Jensen |
| 6,109,500 | A | 8/2000 | Alli et al. |
| 6,110,187 | A | 8/2000 | Donlon |
| 6,113,618 | A | 9/2000 | Nic |
| 6,117,148 | A | 9/2000 | Ravo et al. |
| 6,117,158 | A | 9/2000 | Measamer et al. |
| 6,119,913 | A | 9/2000 | Adams et al. |
| 6,120,433 | A | 9/2000 | Mizuno et al. |
| 6,120,462 | A | 9/2000 | Hibner et al. |
| 6,123,241 | A | 9/2000 | Walter et al. |
| 6,123,701 | A | 9/2000 | Nezhat |
| H1904 | H | 10/2000 | Yates et al. |
| RE36,923 | E | 10/2000 | Hiroi et al. |
| 6,126,058 | A | 10/2000 | Adams et al. |
| 6,126,359 | A | 10/2000 | Dittrich et al. |
| 6,126,670 | A | 10/2000 | Walker et al. |
| 6,131,789 | A | 10/2000 | Schulze et al. |
| 6,131,790 | A | 10/2000 | Piraka |
| 6,132,368 | A | 10/2000 | Cooper |
| 6,134,962 | A | 10/2000 | Sugitani |
| 6,139,546 | A | 10/2000 | Koenig et al. |
| 6,142,149 | A | 11/2000 | Steen |
| 6,142,933 | A | 11/2000 | Longo et al. |
| 6,147,135 | A | 11/2000 | Yuan et al. |
| 6,149,660 | A | 11/2000 | Laufer et al. |
| 6,151,323 | A | 11/2000 | O'Connell et al. |
| 6,152,935 | A | 11/2000 | Kammerer et al. |
| 6,155,473 | A | 12/2000 | Tompkins et al. |
| 6,156,056 | A | 12/2000 | Kearns et al. |
| 6,157,169 | A | 12/2000 | Lee |
| 6,159,146 | A | 12/2000 | El Gazayerli |
| 6,159,200 | A | 12/2000 | Verdura et al. |
| 6,159,224 | A | 12/2000 | Yoon |
| 6,162,208 | A | 12/2000 | Hipps |
| 6,162,220 | A | 12/2000 | Nezhat |
| 6,162,537 | A | 12/2000 | Martin et al. |
| 6,165,175 | A | 12/2000 | Wampler et al. |
| 6,165,184 | A | 12/2000 | Verdura et al. |
| 6,165,188 | A | 12/2000 | Saadat et al. |
| 6,167,185 | A | 12/2000 | Smiley et al. |
| 6,168,605 | B1 | 1/2001 | Measamer et al. |
| 6,171,305 | B1 | 1/2001 | Sherman |
| 6,171,316 | B1 | 1/2001 | Kovac et al. |
| 6,171,330 | B1 | 1/2001 | Benchetrit |
| 6,173,074 | B1 | 1/2001 | Russo |
| 6,174,308 | B1 | 1/2001 | Goble et al. |
| 6,174,309 | B1 | 1/2001 | Wrublewski et al. |
| 6,174,318 | B1 | 1/2001 | Bates et al. |
| 6,175,290 | B1 | 1/2001 | Forsythe et al. |
| 6,179,195 | B1 | 1/2001 | Adams et al. |
| 6,179,776 | B1 | 1/2001 | Adams et al. |
| 6,181,105 | B1 | 1/2001 | Cutolo et al. |
| 6,182,673 | B1 | 2/2001 | Kindermann et al. |
| 6,185,356 | B1 | 2/2001 | Parker et al. |
| 6,186,142 | B1 | 2/2001 | Schmidt et al. |
| 6,186,957 | B1 | 2/2001 | Milam |
| 6,187,003 | B1 | 2/2001 | Buysse et al. |
| 6,190,386 | B1 | 2/2001 | Rydell |
| 6,193,129 | B1 | 2/2001 | Bittner et al. |
| 6,197,042 | B1 | 3/2001 | Ginn et al. |
| 6,200,311 | B1 | 3/2001 | Danek et al. |
| 6,200,330 | B1 | 3/2001 | Benderev et al. |
| 6,202,914 | B1 | 3/2001 | Geiste et al. |
| 6,206,894 | B1 | 3/2001 | Thompson et al. |
| 6,206,897 | B1 | 3/2001 | Jamiolkowski et al. |
| 6,206,903 | B1 | 3/2001 | Ramans |
| 6,206,904 | B1 | 3/2001 | Ouchi |
| 6,209,414 | B1 | 4/2001 | Uneme |
| 6,210,403 | B1 | 4/2001 | Klicek |
| 6,211,626 | B1 | 4/2001 | Lys et al. |
| 6,213,999 | B1 | 4/2001 | Platt, Jr. et al. |
| 6,214,028 | B1 | 4/2001 | Yoon et al. |
| 6,220,368 | B1 | 4/2001 | Ark et al. |
| 6,221,007 | B1 | 4/2001 | Green |
| 6,221,023 | B1 | 4/2001 | Matsuba et al. |
| 6,223,100 | B1 | 4/2001 | Green |
| 6,223,835 | B1 | 5/2001 | Habedank et al. |
| 6,224,617 | B1 | 5/2001 | Saadat et al. |
| 6,228,080 | B1 | 5/2001 | Gines |
| 6,228,081 | B1 | 5/2001 | Goble |
| 6,228,083 | B1 | 5/2001 | Lands et al. |
| 6,228,084 | B1 | 5/2001 | Kirwan, Jr. |
| 6,228,089 | B1 | 5/2001 | Wahrburg |
| 6,228,098 | B1 | 5/2001 | Kayan et al. |
| 6,231,565 | B1 | 5/2001 | Tovey et al. |
| 6,234,178 | B1 | 5/2001 | Goble et al. |
| 6,235,036 | B1 | 5/2001 | Gardner et al. |
| 6,237,604 | B1 | 5/2001 | Burnside et al. |
| 6,238,384 | B1 | 5/2001 | Peer |
| 6,241,139 | B1 | 6/2001 | Milliman et al. |
| 6,241,140 | B1 | 6/2001 | Adams et al. |
| 6,241,723 | B1 | 6/2001 | Heim et al. |
| 6,245,084 | B1 | 6/2001 | Mark et al. |
| 6,248,116 | B1 | 6/2001 | Chevillon et al. |
| 6,248,117 | B1 | 6/2001 | Blatter |
| 6,249,076 | B1 | 6/2001 | Madden et al. |
| 6,249,105 | B1 | 6/2001 | Andrews et al. |
| 6,250,532 | B1 | 6/2001 | Green et al. |
| 6,251,485 | B1 | 6/2001 | Harris et al. |
| D445,745 | S | 7/2001 | Norman |
| 6,254,534 | B1 | 7/2001 | Butler et al. |
| 6,254,619 | B1 | 7/2001 | Garabet et al. |
| 6,254,642 | B1 | 7/2001 | Taylor |
| 6,258,107 | B1 | 7/2001 | Balazs et al. |
| 6,261,246 | B1 | 7/2001 | Pantages et al. |
| 6,261,286 | B1 | 7/2001 | Goble et al. |
| 6,261,679 | B1 | 7/2001 | Chen et al. |
| 6,264,086 | B1 | 7/2001 | McGuckin, Jr. |
| 6,264,087 | B1 | 7/2001 | Whitman |
| 6,264,617 | B1 | 7/2001 | Bales et al. |
| 6,269,997 | B1 | 8/2001 | Balazs et al. |
| 6,270,508 | B1 | 8/2001 | Klieman et al. |
| 6,270,916 | B1 | 8/2001 | Sink et al. |
| 6,273,252 | B1 | 8/2001 | Mitchell |
| 6,273,876 | B1 | 8/2001 | Klima et al. |
| 6,273,897 | B1 | 8/2001 | Dalessandro et al. |
| 6,277,114 | B1 | 8/2001 | Bullivant et al. |
| 6,280,407 | B1 | 8/2001 | Manna et al. |
| 6,283,981 | B1 | 9/2001 | Beaupre |
| 6,293,927 | B1 | 9/2001 | McGuckin, Jr. |
| 6,293,942 | B1 | 9/2001 | Goble et al. |
| 6,296,640 | B1 | 10/2001 | Wampler et al. |
| 6,302,311 | B1 | 10/2001 | Adams et al. |
| 6,302,743 | B1 | 10/2001 | Chiu et al. |
| 6,305,891 | B1 | 10/2001 | Burlingame |
| 6,306,134 | B1 | 10/2001 | Goble et al. |
| 6,306,149 | B1 | 10/2001 | Meade |
| 6,306,424 | B1 | 10/2001 | Vyakarnam et al. |
| 6,309,397 | B1 | 10/2001 | Julian et al. |

(56) References Cited

U.S. PATENT DOCUMENTS 6,309,400 B2 10/2001 Beaupre
6,309,403 B1 10/2001 Minor et al.
6,312,435 B1 11/2001 Wallace et al.
6,315,184 B1 11/2001 Whitman
6,317,616 B1 11/2001 Glossop
6,319,510 B1 11/2001 Yates
6,320,123 B1 11/2001 Reimers
6,322,494 B1 11/2001 Bullivant et al.
6,324,339 B1 11/2001 Hudson et al.
6,325,799 B1 12/2001 Goble
6,325,805 B1 12/2001 Ogilvie et al.
6,325,810 B1 12/2001 Hamilton et al.
6,328,498 B1 12/2001 Mersch
6,330,965 B1 12/2001 Milliman et al.
6,331,181 B1 12/2001 Tierney et al.
6,331,761 B1 12/2001 Kumar et al.
6,333,029 B1 12/2001 Vyakarnam et al.
6,334,860 B1 1/2002 Dorn
6,334,861 B1 1/2002 Chandler et al.
6,336,926 B1 1/2002 Goble
6,338,737 B1 1/2002 Toledano
6,343,731 B1 2/2002 Adams et al.
6,346,077 B1 2/2002 Taylor et al.
6,348,061 B1 2/2002 Whitman
6,349,868 B1 2/2002 Mattingly et al.
D454,951 S 3/2002 Bon
6,352,503 B1 3/2002 Matsui et al.
6,352,532 B1 3/2002 Kramer et al.
6,355,699 B1 3/2002 Vyakarnam et al.
6,356,072 B1 3/2002 Chass
6,358,224 B1 3/2002 Tims et al.
6,358,263 B2 3/2002 Mark et al.
6,358,459 B1 3/2002 Ziegler et al.
6,361,542 B1 3/2002 Dimitriu et al.
6,364,828 B1 4/2002 Yeung et al.
6,364,877 B1 4/2002 Goble et al.
6,364,888 B1 4/2002 Niemeyer et al.
6,366,441 B1 4/2002 Ozawa et al.
6,370,981 B2 4/2002 Watarai
6,371,114 B1 4/2002 Schmidt et al.
6,373,152 B1 4/2002 Wang et al.
6,377,011 B1 4/2002 Ben-Ur
6,383,201 B1 5/2002 Dong
6,387,092 B1 5/2002 Burnside et al.
6,387,113 B1 5/2002 Hawkins et al.
6,387,114 B2 5/2002 Adams
6,391,038 B2 5/2002 Vargas et al.
6,392,854 B1 5/2002 O'Gorman
6,394,998 B1 5/2002 Wallace et al.
6,398,779 B1 6/2002 Buysse et al.
6,398,781 B1 6/2002 Goble et al.
6,398,797 B2 6/2002 Bombard et al.
6,402,766 B2 6/2002 Bowman et al.
6,402,780 B2 6/2002 Williamson, IV et al.
6,406,440 B1 6/2002 Stefanchik
6,406,472 B1 6/2002 Jensen
6,409,724 B1 6/2002 Penny et al.
H2037 H 7/2002 Yates et al.
6,412,639 B1 7/2002 Hickey
6,413,274 B1 7/2002 Pedros
6,415,542 B1 7/2002 Bates et al.
6,416,486 B1 7/2002 Wampler
6,416,509 B1 7/2002 Goble et al.
6,419,695 B1 7/2002 Gabbay
6,423,079 B1 7/2002 Blake, III
6,424,885 B1 7/2002 Niemeyer et al.
RE37,814 E 8/2002 Allgeyer
6,428,070 B1 8/2002 Takanashi et al.
6,428,487 B1 8/2002 Burdorff et al.
6,429,611 B1 8/2002 Li
6,430,298 B1 8/2002 Kettl et al.
6,432,065 B1 8/2002 Burdorff et al.
6,436,097 B1 8/2002 Nardella
6,436,107 B1 8/2002 Wang et al.
6,436,110 B2 8/2002 Bowman et al.
6,436,115 B1 8/2002 Beaupre
6,436,122 B1 8/2002 Frank et al.
6,439,439 B1 8/2002 Rickard et al.
6,439,446 B1 8/2002 Perry et al.
6,440,146 B2 8/2002 Nicholas et al.
6,441,577 B2 8/2002 Blumenkranz et al.
D462,758 S 9/2002 Epstein et al.
6,443,973 B1 9/2002 Whitman
6,445,530 B1 9/2002 Baker
6,447,518 B1 9/2002 Krause et al.
6,447,523 B1 9/2002 Middleman et al.
6,447,799 B1 9/2002 Ullman
6,447,864 B2 9/2002 Johnson et al.
6,450,391 B1 9/2002 Kayan et al.
6,450,989 B2 9/2002 Dubrul et al.
6,454,656 B2 9/2002 Brissette et al.
6,454,781 B1 9/2002 Witt et al.
6,457,338 B1 10/2002 Frenken
6,457,625 B1 10/2002 Tormala et al.
6,458,077 B1 10/2002 Boebel et al.
6,458,142 B1 10/2002 Faller et al.
6,458,147 B1 10/2002 Cruise et al.
6,460,627 B1 10/2002 Below et al.
6,468,275 B1 10/2002 Wampler et al.
6,468,286 B2 10/2002 Mastri et al.
6,471,106 B1 10/2002 Reining
6,471,659 B2 10/2002 Eggers et al.
6,478,210 B2 11/2002 Adams et al.
6,482,063 B1 11/2002 Frigard
6,482,200 B2 11/2002 Shippert
6,482,217 B1 11/2002 Pintor et al.
6,485,490 B2 11/2002 Wampler et al.
6,485,503 B2 11/2002 Jacobs et al.
6,485,667 B1 11/2002 Tan
6,486,286 B1 11/2002 McGall et al.
6,488,196 B1 12/2002 Fenton, Jr.
6,488,197 B1 12/2002 Whitman
6,488,659 B1 12/2002 Rosenman
6,491,201 B1 12/2002 Whitman
6,491,690 B1 12/2002 Goble et al.
6,491,701 B2 12/2002 Tierney et al.
6,491,702 B2 12/2002 Heilbrun et al.
6,492,785 B1 12/2002 Kasten et al.
6,494,882 B1 12/2002 Lebouitz et al.
6,494,885 B1 12/2002 Dhindsa
6,494,888 B1 12/2002 Laufer et al.
6,494,896 B1 12/2002 D'Alessio et al.
6,498,480 B1 12/2002 Manara
6,500,176 B1 12/2002 Truckai et al.
6,500,189 B1 12/2002 Lang et al.
6,500,194 B2 12/2002 Benderev et al.
D468,749 S 1/2003 Friedman
6,503,139 B2 1/2003 Coral
6,503,257 B2 1/2003 Grant et al.
6,503,259 B2 1/2003 Huxel et al.
6,505,768 B2 1/2003 Whitman
6,506,197 B1 1/2003 Rollero et al.
6,506,399 B2 1/2003 Donovan
6,510,854 B2 1/2003 Goble
6,511,468 B1 1/2003 Cragg et al.
6,512,360 B1 1/2003 Goto et al.
6,514,252 B2 2/2003 Nezhat et al.
6,516,073 B1 2/2003 Schulz et al.
6,517,528 B1 2/2003 Pantages et al.
6,517,535 B2 2/2003 Edwards
6,517,565 B1 2/2003 Whitman et al.
6,517,566 B1 2/2003 Hovland et al.
6,520,971 B1 2/2003 Perry et al.
6,520,972 B2 2/2003 Peters
6,522,101 B2 2/2003 Malackowski
6,524,180 B1 2/2003 Simms et al.
6,525,499 B2 2/2003 Naganuma
D471,206 S 3/2003 Buzzard et al.
6,527,782 B2 3/2003 Hogg et al.
6,527,785 B2 3/2003 Sancoff et al.
6,530,942 B2 3/2003 Fogarty et al.
6,532,958 B1 3/2003 Buan et al.
6,533,157 B1 3/2003 Whitman
6,533,723 B1 3/2003 Lockery et al.

(56) References Cited

U.S. PATENT DOCUMENTS

| | | | |
|---|---|---|---|
| 6,533,784 | B2 | 3/2003 | Truckai et al. |
| 6,535,764 | B2 | 3/2003 | Imran et al. |
| 6,539,297 | B2 | 3/2003 | Weiberle et al. |
| D473,239 | S | 4/2003 | Cockerill |
| 6,539,816 | B2 | 4/2003 | Kogiso et al. |
| 6,540,737 | B2 | 4/2003 | Bacher et al. |
| 6,543,456 | B1 | 4/2003 | Freeman |
| 6,545,384 | B1 | 4/2003 | Pelrine et al. |
| 6,547,786 | B1 | 4/2003 | Goble |
| 6,550,546 | B2 | 4/2003 | Thurler et al. |
| 6,551,333 | B2 | 4/2003 | Kuhns et al. |
| 6,554,844 | B2 | 4/2003 | Lee et al. |
| 6,554,861 | B2 | 4/2003 | Knox et al. |
| 6,555,770 | B2 | 4/2003 | Kawase |
| 6,558,378 | B2 | 5/2003 | Sherman et al. |
| 6,558,379 | B1 | 5/2003 | Batchelor et al. |
| 6,558,429 | B2 | 5/2003 | Taylor |
| 6,561,187 | B2 | 5/2003 | Schmidt et al. |
| 6,565,560 | B1 | 5/2003 | Goble et al. |
| 6,566,619 | B2 | 5/2003 | Gillman et al. |
| 6,569,085 | B2 | 5/2003 | Kortenbach et al. |
| 6,569,171 | B2 | 5/2003 | DeGuillebon et al. |
| 6,569,173 | B1 | 5/2003 | Blatter et al. |
| 6,572,629 | B2 | 6/2003 | Kalloo et al. |
| 6,578,751 | B2 | 6/2003 | Hartwick |
| 6,582,364 | B2 | 6/2003 | Butler et al. |
| 6,582,427 | B1 | 6/2003 | Goble et al. |
| 6,582,441 | B1 | 6/2003 | He et al. |
| 6,583,533 | B2 | 6/2003 | Pelrine et al. |
| 6,585,144 | B2 | 7/2003 | Adams et al. |
| 6,585,664 | B2 | 7/2003 | Burdorff et al. |
| 6,586,898 | B2 | 7/2003 | King et al. |
| 6,587,750 | B2 | 7/2003 | Gerbi et al. |
| 6,588,277 | B2 | 7/2003 | Giordano et al. |
| 6,588,643 | B2 | 7/2003 | Bolduc et al. |
| 6,588,931 | B2 | 7/2003 | Betzner et al. |
| 6,589,118 | B1 | 7/2003 | Soma et al. |
| 6,589,164 | B1 | 7/2003 | Flaherty |
| 6,592,538 | B1 | 7/2003 | Hotchkiss et al. |
| 6,592,572 | B1 | 7/2003 | Suzuta |
| 6,592,597 | B2 | 7/2003 | Grant et al. |
| 6,594,552 | B1 | 7/2003 | Nowlin et al. |
| 6,595,914 | B2 | 7/2003 | Kato |
| 6,596,296 | B1 | 7/2003 | Nelson et al. |
| 6,596,304 | B1 | 7/2003 | Bayon et al. |
| 6,596,432 | B2 | 7/2003 | Kawakami et al. |
| 6,599,295 | B1 | 7/2003 | Tornier et al. |
| 6,599,323 | B2 | 7/2003 | Melican et al. |
| D478,665 | S | 8/2003 | Isaacs et al. |
| D478,986 | S | 8/2003 | Johnston et al. |
| 6,601,749 | B2 | 8/2003 | Sullivan et al. |
| 6,602,252 | B2 | 8/2003 | Mollenauer |
| 6,602,262 | B2 | 8/2003 | Griego et al. |
| 6,603,050 | B2 | 8/2003 | Heaton |
| 6,605,078 | B2 | 8/2003 | Adams |
| 6,605,669 | B2 | 8/2003 | Awokola et al. |
| 6,605,911 | B1 | 8/2003 | Klesing |
| 6,607,475 | B2 | 8/2003 | Doyle et al. |
| 6,611,793 | B1 | 8/2003 | Burnside et al. |
| 6,613,069 | B2 | 9/2003 | Boyd et al. |
| 6,616,686 | B2 | 9/2003 | Coleman et al. |
| 6,619,529 | B2 | 9/2003 | Green et al. |
| 6,620,111 | B2 | 9/2003 | Stephens et al. |
| 6,620,161 | B2 | 9/2003 | Schulze et al. |
| 6,620,166 | B1 | 9/2003 | Wenstrom, Jr. et al. |
| 6,625,517 | B1 | 9/2003 | Bogdanov et al. |
| 6,626,834 | B2 | 9/2003 | Dunne et al. |
| 6,626,938 | B1 | 9/2003 | Butaric et al. |
| H2086 | H | 10/2003 | Amsler |
| 6,629,630 | B2 | 10/2003 | Adams |
| 6,629,974 | B2 | 10/2003 | Penny et al. |
| 6,629,988 | B2 | 10/2003 | Weadock |
| 6,635,838 | B1 | 10/2003 | Kornelson |
| 6,636,412 | B2 | 10/2003 | Smith |
| 6,638,108 | B2 | 10/2003 | Tachi |
| 6,638,285 | B2 | 10/2003 | Gabbay |
| 6,638,297 | B1 | 10/2003 | Huitema |
| RE38,335 | E | 11/2003 | Aust et al. |
| 6,641,528 | B2 | 11/2003 | Torii |
| 6,644,532 | B2 | 11/2003 | Green et al. |
| 6,645,201 | B1 | 11/2003 | Utley et al. |
| 6,646,307 | B1 | 11/2003 | Yu et al. |
| 6,648,816 | B2 | 11/2003 | Irion et al. |
| 6,648,901 | B2 | 11/2003 | Fleischman et al. |
| 6,652,595 | B1 | 11/2003 | Nicolo |
| D484,243 | S | 12/2003 | Ryan et al. |
| D484,595 | S | 12/2003 | Ryan et al. |
| D484,596 | S | 12/2003 | Ryan et al. |
| 6,656,177 | B2 | 12/2003 | Truckai et al. |
| 6,656,193 | B2 | 12/2003 | Grant et al. |
| 6,659,940 | B2 | 12/2003 | Adler |
| 6,660,008 | B1 | 12/2003 | Foerster et al. |
| 6,663,623 | B1 | 12/2003 | Oyama et al. |
| 6,663,641 | B1 | 12/2003 | Kovac et al. |
| 6,666,854 | B1 | 12/2003 | Lange |
| 6,666,860 | B1 | 12/2003 | Takahashi |
| 6,666,875 | B1 | 12/2003 | Sakurai et al. |
| 6,667,825 | B2 | 12/2003 | Lu et al. |
| 6,669,073 | B2 | 12/2003 | Milliman et al. |
| 6,670,806 | B2 | 12/2003 | Wendt et al. |
| 6,671,185 | B2 | 12/2003 | Duval |
| D484,977 | S | 1/2004 | Ryan et al. |
| 6,676,660 | B2 | 1/2004 | Wampler et al. |
| 6,677,687 | B2 | 1/2004 | Ho et al. |
| 6,679,269 | B2 | 1/2004 | Swanson |
| 6,679,410 | B2 | 1/2004 | Wursch et al. |
| 6,681,978 | B2 | 1/2004 | Geiste et al. |
| 6,681,979 | B2 | 1/2004 | Whitman |
| 6,682,527 | B2 | 1/2004 | Strul |
| 6,682,528 | B2 | 1/2004 | Frazier et al. |
| 6,682,544 | B2 | 1/2004 | Mastri et al. |
| 6,685,698 | B2 | 2/2004 | Morley et al. |
| 6,685,727 | B2 | 2/2004 | Fisher et al. |
| 6,689,153 | B1 | 2/2004 | Skiba |
| 6,692,507 | B2 | 2/2004 | Pugsley et al. |
| 6,692,692 | B2 | 2/2004 | Stetzel |
| 6,695,198 | B2 | 2/2004 | Adams et al. |
| 6,695,199 | B2 | 2/2004 | Whitman |
| 6,695,774 | B2 | 2/2004 | Hale et al. |
| 6,695,849 | B2 | 2/2004 | Michelson |
| 6,696,814 | B2 | 2/2004 | Henderson et al. |
| 6,697,048 | B2 | 2/2004 | Rosenberg et al. |
| 6,698,643 | B2 | 3/2004 | Whitman |
| 6,699,177 | B1 | 3/2004 | Wang et al. |
| 6,699,214 | B2 | 3/2004 | Gellman |
| 6,699,235 | B2 | 3/2004 | Wallace et al. |
| 6,704,210 | B1 | 3/2004 | Myers |
| 6,705,503 | B1 | 3/2004 | Pedicini et al. |
| 6,709,445 | B2 | 3/2004 | Boebel et al. |
| 6,712,773 | B1 | 3/2004 | Viola |
| 6,716,215 | B1 | 4/2004 | David et al. |
| 6,716,223 | B2 | 4/2004 | Leopold et al. |
| 6,716,232 | B1 | 4/2004 | Vidal et al. |
| 6,716,233 | B1 | 4/2004 | Whitman |
| 6,720,734 | B2 | 4/2004 | Norris |
| 6,722,550 | B1 | 4/2004 | Ricordi et al. |
| 6,722,552 | B2 | 4/2004 | Fenton, Jr. |
| 6,723,087 | B2 | 4/2004 | O'Neill et al. |
| 6,723,091 | B2 | 4/2004 | Goble et al. |
| 6,723,106 | B1 | 4/2004 | Charles et al. |
| 6,723,109 | B2 | 4/2004 | Solingen |
| 6,726,651 | B1 | 4/2004 | Robinson et al. |
| 6,726,697 | B2 | 4/2004 | Nicholas et al. |
| 6,726,705 | B2 | 4/2004 | Peterson et al. |
| 6,726,706 | B2 | 4/2004 | Dominguez |
| 6,729,119 | B2 | 5/2004 | Schnipke et al. |
| 6,731,976 | B2 | 5/2004 | Penn et al. |
| 6,736,810 | B2 | 5/2004 | Hoey et al. |
| 6,736,825 | B2 | 5/2004 | Blatter et al. |
| 6,736,854 | B2 | 5/2004 | Vadurro et al. |
| 6,740,030 | B2 | 5/2004 | Martone et al. |
| 6,743,230 | B2 | 6/2004 | Lutze et al. |
| 6,744,385 | B2 | 6/2004 | Kazuya et al. |
| 6,747,121 | B2 | 6/2004 | Gogolewski |

(56) References Cited

U.S. PATENT DOCUMENTS 6,747,300 B2 6/2004 Nadd et al.
6,749,560 B1 6/2004 Konstorum et al.
6,749,600 B1 6/2004 Levy
6,752,768 B2 6/2004 Burdorff et al.
6,752,816 B2 6/2004 Culp et al.
6,754,959 B1 6/2004 Guiette, III et al.
6,755,195 B1 6/2004 Lemke et al.
6,755,338 B2 6/2004 Hahnen et al.
6,755,825 B2 6/2004 Shoenman et al.
6,755,843 B2 6/2004 Chung et al.
6,756,705 B2 6/2004 Pulford, Jr.
6,758,846 B2 7/2004 Goble et al.
6,761,685 B2 7/2004 Adams et al.
6,762,339 B1 7/2004 Klun et al.
6,763,307 B2 7/2004 Berg et al.
6,764,445 B2 7/2004 Ramans et al.
6,766,957 B2 7/2004 Matsuura et al.
6,767,352 B2 7/2004 Field et al.
6,767,356 B2 7/2004 Kanner et al.
6,769,590 B2 8/2004 Vresh et al.
6,769,594 B2 8/2004 Orban, III
6,770,027 B2 8/2004 Banik et al.
6,770,070 B1 8/2004 Balbierz
6,770,072 B1 8/2004 Truckai et al.
6,770,078 B2 8/2004 Bonutti
6,773,409 B2 8/2004 Truckai et al.
6,773,437 B2 8/2004 Ogilvie et al.
6,773,438 B1 8/2004 Knodel et al.
6,775,575 B2 8/2004 Bommannan et al.
6,777,838 B2 8/2004 Miekka et al.
6,778,846 B1 8/2004 Martinez et al.
6,780,151 B2 8/2004 Grabover et al.
6,780,180 B1 8/2004 Goble et al.
6,783,524 B2 8/2004 Anderson et al.
6,784,775 B2 8/2004 Mandell et al.
6,786,382 B1 9/2004 Hoffman
6,786,864 B2 9/2004 Matsuura et al.
6,786,896 B1 9/2004 Madhani et al.
6,788,018 B1 9/2004 Blumenkranz
6,790,173 B2 9/2004 Saadat et al.
6,793,652 B1 9/2004 Whitman et al.
6,793,661 B2 9/2004 Hamilton et al.
6,793,663 B2 9/2004 Kneifel et al.
6,793,669 B2 9/2004 Nakamura et al.
6,796,921 B1 9/2004 Buck et al.
6,799,669 B2 10/2004 Fukumura et al.
6,801,009 B2 10/2004 Makaran et al.
6,802,822 B1 10/2004 Dodge
6,802,843 B2 10/2004 Truckai et al.
6,802,844 B2 10/2004 Ferree
6,805,273 B2 10/2004 Bilotti et al.
6,806,808 B1 10/2004 Watters et al.
6,806,867 B1 10/2004 Arruda et al.
6,808,525 B2 10/2004 Latterell et al.
6,810,359 B2 10/2004 Sakaguchi
6,814,154 B2 11/2004 Chou
6,814,741 B2 11/2004 Bowman et al.
6,817,508 B1 11/2004 Racenet et al.
6,817,509 B2 11/2004 Geiste et al.
6,817,974 B2 11/2004 Cooper et al.
6,818,018 B1 11/2004 Sawhney
6,820,791 B2 11/2004 Adams
6,821,273 B2 11/2004 Mollenauer
6,821,282 B2 11/2004 Perry et al.
6,821,284 B2 11/2004 Sturtz et al.
6,827,246 B2 12/2004 Sullivan et al.
6,827,712 B2 12/2004 Tovey et al.
6,827,725 B2 12/2004 Batchelor et al.
6,828,902 B2 12/2004 Casden
6,830,174 B2 12/2004 Hillstead et al.
6,831,629 B2 12/2004 Nishino et al.
6,832,998 B2 12/2004 Goble
6,834,001 B2 12/2004 Myono
6,835,173 B2 12/2004 Couvillon, Jr.
6,835,199 B2 12/2004 McGuckin, Jr. et al.
6,835,336 B2 12/2004 Watt
6,836,611 B2 12/2004 Popovic et al.
6,837,846 B2 1/2005 Jaffe et al.
6,837,883 B2 1/2005 Moll et al.
6,838,493 B2 1/2005 Williams et al.
6,840,423 B2 1/2005 Adams et al.
6,840,938 B1 1/2005 Morley et al.
6,841,967 B2 1/2005 Kim et al.
6,843,403 B2 1/2005 Whitman
6,843,789 B2 1/2005 Goble
6,843,793 B2 1/2005 Brock et al.
6,846,307 B2 1/2005 Whitman et al.
6,846,308 B2 1/2005 Whitman et al.
6,846,309 B2 1/2005 Whitman et al.
6,847,190 B2 1/2005 Schaefer et al.
6,849,071 B2 2/2005 Whitman et al.
6,850,817 B1 2/2005 Green
6,852,122 B2 2/2005 Rush
6,852,330 B2 2/2005 Bowman et al.
6,853,879 B2 2/2005 Sunaoshi
6,858,005 B2 2/2005 Ohline et al.
6,859,882 B2 2/2005 Fung
RE38,708 E 3/2005 Bolanos et al.
D502,994 S 3/2005 Blake, III
6,860,169 B2 3/2005 Shinozaki
6,861,142 B1 3/2005 Wilkie et al.
6,861,954 B2 3/2005 Levin
6,863,668 B2 3/2005 Gillespie et al.
6,863,694 B1 3/2005 Boyce et al.
6,863,924 B2 3/2005 Ranganathan et al.
6,866,178 B2 3/2005 Adams et al.
6,866,668 B2 3/2005 Giannetti et al.
6,866,671 B2 3/2005 Tierney et al.
6,867,248 B1 3/2005 Martin et al.
6,869,430 B2 3/2005 Balbierz et al.
6,869,435 B2 3/2005 Blake, III
6,872,214 B2 3/2005 Sonnenschein et al.
6,874,669 B2 4/2005 Adams et al.
6,876,850 B2 4/2005 Maeshima et al.
6,877,647 B2 4/2005 Green et al.
6,878,106 B1 4/2005 Herrmann
6,882,127 B2 4/2005 Konigbauer
6,883,199 B1 4/2005 Lundell et al.
6,884,392 B2 4/2005 Malkin et al.
6,884,428 B2 4/2005 Binette et al.
6,886,730 B2 5/2005 Fujisawa et al.
6,887,244 B1 5/2005 Walker et al.
6,887,710 B2 5/2005 Call et al.
6,889,116 B2 5/2005 Jinno
6,893,435 B2 5/2005 Goble
6,894,140 B2 5/2005 Roby
6,895,176 B2 5/2005 Archer et al.
6,899,538 B2 5/2005 Matoba
6,899,593 B1 5/2005 Moeller et al.
6,899,705 B2 5/2005 Niemeyer
6,899,915 B2 5/2005 Yelick et al.
6,905,057 B2 6/2005 Swayze et al.
6,905,497 B2 6/2005 Truckai et al.
6,905,498 B2 6/2005 Hooven
6,908,472 B2 6/2005 Wiener et al.
6,911,033 B2 6/2005 de Guillebon et al.
6,911,916 B1 6/2005 Wang et al.
6,913,579 B2 7/2005 Truckai et al.
6,913,608 B2 7/2005 Liddicoat et al.
6,913,613 B2 7/2005 Schwarz et al.
6,921,397 B2 7/2005 Corcoran et al.
6,921,412 B1 7/2005 Black et al.
6,923,093 B2 8/2005 Ullah
6,923,803 B2 8/2005 Goble
6,923,819 B2 8/2005 Meade et al.
6,925,849 B2 8/2005 Jairam
6,926,716 B2 8/2005 Baker et al.
6,927,315 B1 8/2005 Heinecke et al.
6,928,902 B1 8/2005 Eyssallenne
6,929,641 B2 8/2005 Goble et al.
6,929,644 B2 8/2005 Truckai et al.
6,931,830 B2 8/2005 Liao
6,932,218 B2 8/2005 Kosann et al.
6,932,810 B2 8/2005 Ryan

(56) References Cited

U.S. PATENT DOCUMENTS

| | | | |
|---|---|---|---|
| 6,936,042 | B2 | 8/2005 | Wallace et al. |
| 6,936,948 | B2 | 8/2005 | Bell et al. |
| D509,297 | S | 9/2005 | Wells |
| D509,589 | S | 9/2005 | Wells |
| 6,938,706 | B2 | 9/2005 | Ng |
| 6,939,358 | B2 | 9/2005 | Palacios et al. |
| 6,942,662 | B2 | 9/2005 | Goble et al. |
| 6,942,674 | B2 | 9/2005 | Belef et al. |
| 6,945,444 | B2 | 9/2005 | Gresham et al. |
| 6,945,981 | B2 | 9/2005 | Donofrio et al. |
| 6,949,196 | B2 | 9/2005 | Schmitz et al. |
| 6,951,562 | B2 | 10/2005 | Zwirnmann |
| 6,953,138 | B1 | 10/2005 | Dworak et al. |
| 6,953,139 | B2 | 10/2005 | Milliman et al. |
| 6,953,461 | B2 | 10/2005 | McClurken et al. |
| 6,957,758 | B2 | 10/2005 | Aranyi |
| 6,958,035 | B2 | 10/2005 | Friedman et al. |
| D511,525 | S | 11/2005 | Hernandez et al. |
| 6,959,851 | B2 | 11/2005 | Heinrich |
| 6,959,852 | B2 | 11/2005 | Shelton, IV et al. |
| 6,960,107 | B1 | 11/2005 | Schaub et al. |
| 6,960,163 | B2 | 11/2005 | Ewers et al. |
| 6,960,220 | B2 | 11/2005 | Marino et al. |
| 6,962,587 | B2 | 11/2005 | Johnson et al. |
| 6,963,792 | B1 | 11/2005 | Green |
| 6,964,363 | B2 | 11/2005 | Wales et al. |
| 6,966,907 | B2 | 11/2005 | Goble |
| 6,966,909 | B2 | 11/2005 | Marshall et al. |
| 6,968,908 | B2 | 11/2005 | Tokunaga et al. |
| 6,969,385 | B2 | 11/2005 | Moreyra |
| 6,969,395 | B2 | 11/2005 | Eskuri |
| 6,971,988 | B2 | 12/2005 | Orban, III |
| 6,972,199 | B2 | 12/2005 | Lebouitz et al. |
| 6,974,435 | B2 | 12/2005 | Daw et al. |
| 6,974,462 | B2 | 12/2005 | Sater |
| 6,978,921 | B2 | 12/2005 | Shelton, IV et al. |
| 6,978,922 | B2 | 12/2005 | Bilotti et al. |
| 6,981,628 | B2 | 1/2006 | Wales |
| 6,981,941 | B2 | 1/2006 | Whitman et al. |
| 6,981,978 | B2 | 1/2006 | Gannoe |
| 6,984,203 | B2 | 1/2006 | Tartaglia et al. |
| 6,984,231 | B2 | 1/2006 | Goble et al. |
| 6,986,451 | B1 | 1/2006 | Mastri et al. |
| 6,988,649 | B2 | 1/2006 | Shelton, IV et al. |
| 6,988,650 | B2 | 1/2006 | Schwemberger et al. |
| 6,989,034 | B2 | 1/2006 | Hammer et al. |
| 6,990,731 | B2 | 1/2006 | Haytayan |
| 6,990,796 | B2 | 1/2006 | Schnipke et al. |
| 6,991,146 | B2 | 1/2006 | Sinisi et al. |
| 6,993,200 | B2 | 1/2006 | Tastl et al. |
| 6,993,413 | B2 | 1/2006 | Sunaoshi |
| 6,994,708 | B2 | 2/2006 | Manzo |
| 6,995,729 | B2 | 2/2006 | Govari et al. |
| 6,996,433 | B2 | 2/2006 | Burbank et al. |
| 6,997,931 | B2 | 2/2006 | Sauer et al. |
| 6,997,935 | B2 | 2/2006 | Anderson et al. |
| 6,998,736 | B2 | 2/2006 | Lee et al. |
| 6,998,816 | B2 | 2/2006 | Wieck et al. |
| 6,999,821 | B2 | 2/2006 | Jenney et al. |
| 7,000,818 | B2 | 2/2006 | Shelton, IV et al. |
| 7,000,819 | B2 | 2/2006 | Swayze et al. |
| 7,000,911 | B2 | 2/2006 | McCormick et al. |
| 7,001,380 | B2 | 2/2006 | Goble |
| 7,001,408 | B2 | 2/2006 | Knodel et al. |
| 7,004,174 | B2 | 2/2006 | Eggers et al. |
| 7,005,828 | B2 | 2/2006 | Karikomi |
| 7,007,176 | B2 | 2/2006 | Goodfellow et al. |
| 7,008,433 | B2 | 3/2006 | Voellmicke et al. |
| 7,008,435 | B2 | 3/2006 | Cummins |
| 7,009,039 | B2 | 3/2006 | Yayon et al. |
| 7,011,213 | B2 | 3/2006 | Clark et al. |
| 7,011,657 | B2 | 3/2006 | Truckai et al. |
| 7,014,640 | B2 | 3/2006 | Kemppainen et al. |
| 7,018,357 | B2 | 3/2006 | Emmons |
| 7,018,390 | B2 | 3/2006 | Turovskiy et al. |
| 7,021,399 | B2 | 4/2006 | Driessen |
| 7,021,669 | B1 | 4/2006 | Lindermeir et al. |
| 7,022,131 | B1 | 4/2006 | Derowe et al. |
| 7,023,159 | B2 | 4/2006 | Gorti et al. |
| 7,025,064 | B2 | 4/2006 | Wang et al. |
| 7,025,732 | B2 | 4/2006 | Thompson et al. |
| 7,025,743 | B2 | 4/2006 | Mann et al. |
| 7,025,774 | B2 | 4/2006 | Freeman et al. |
| 7,025,775 | B2 | 4/2006 | Gadberry et al. |
| 7,028,570 | B2 | 4/2006 | Ohta et al. |
| 7,029,435 | B2 | 4/2006 | Nakao |
| 7,029,439 | B2 | 4/2006 | Roberts et al. |
| 7,030,904 | B2 | 4/2006 | Adair et al. |
| 7,032,798 | B2 | 4/2006 | Whitman et al. |
| 7,032,799 | B2 | 4/2006 | Viola et al. |
| 7,033,356 | B2 | 4/2006 | Latterell et al. |
| 7,033,378 | B2 | 4/2006 | Smith et al. |
| 7,035,716 | B2 | 4/2006 | Harris et al. |
| 7,035,762 | B2 | 4/2006 | Menard et al. |
| 7,036,680 | B1 | 5/2006 | Flannery |
| 7,037,314 | B2 | 5/2006 | Armstrong |
| 7,037,344 | B2 | 5/2006 | Kagan et al. |
| 7,038,421 | B2 | 5/2006 | Trifilo |
| 7,041,088 | B2 | 5/2006 | Nawrocki et al. |
| 7,041,102 | B2 | 5/2006 | Truckai et al. |
| 7,041,868 | B2 | 5/2006 | Greene et al. |
| 7,043,852 | B2 | 5/2006 | Hayashida et al. |
| 7,044,350 | B2 | 5/2006 | Kameyama et al. |
| 7,044,352 | B2 | 5/2006 | Shelton, IV et al. |
| 7,044,353 | B2 | 5/2006 | Mastri et al. |
| 7,046,082 | B2 | 5/2006 | Komiya et al. |
| 7,048,165 | B2 | 5/2006 | Haramiishi |
| 7,048,687 | B1 | 5/2006 | Reuss et al. |
| 7,048,716 | B1 | 5/2006 | Kucharczyk et al. |
| 7,048,745 | B2 | 5/2006 | Tierney et al. |
| 7,052,454 | B2 | 5/2006 | Taylor |
| 7,052,494 | B2 | 5/2006 | Goble et al. |
| 7,052,499 | B2 | 5/2006 | Steger et al. |
| 7,055,730 | B2 | 6/2006 | Ehrenfels et al. |
| 7,055,731 | B2 | 6/2006 | Shelton, IV et al. |
| 7,056,123 | B2 | 6/2006 | Gregorio et al. |
| 7,056,284 | B2 | 6/2006 | Martone et al. |
| 7,056,330 | B2 | 6/2006 | Gayton |
| 7,059,331 | B2 | 6/2006 | Adams et al. |
| 7,059,508 | B2 | 6/2006 | Shelton, IV et al. |
| 7,063,671 | B2 | 6/2006 | Couvillon, Jr. |
| 7,063,712 | B2 | 6/2006 | Vargas et al. |
| 7,064,509 | B1 | 6/2006 | Fu et al. |
| 7,066,879 | B2 | 6/2006 | Fowler et al. |
| 7,066,944 | B2 | 6/2006 | Laufer et al. |
| 7,067,038 | B2 | 6/2006 | Trokhan et al. |
| 7,070,083 | B2 | 7/2006 | Jankowski |
| 7,070,559 | B2 | 7/2006 | Adams et al. |
| 7,070,597 | B2 | 7/2006 | Truckai et al. |
| 7,071,287 | B2 | 7/2006 | Rhine et al. |
| 7,075,412 | B1 | 7/2006 | Reynolds et al. |
| 7,075,770 | B1 | 7/2006 | Smith |
| 7,077,856 | B2 | 7/2006 | Whitman |
| 7,080,769 | B2 | 7/2006 | Vresh et al. |
| 7,081,114 | B2 | 7/2006 | Rashidi |
| 7,081,318 | B2 | 7/2006 | Lee et al. |
| 7,083,073 | B2 | 8/2006 | Yoshie et al. |
| 7,083,075 | B2 | 8/2006 | Swayze et al. |
| 7,083,571 | B2 | 8/2006 | Wang et al. |
| 7,083,615 | B2 | 8/2006 | Peterson et al. |
| 7,083,619 | B2 | 8/2006 | Truckai et al. |
| 7,083,620 | B2 | 8/2006 | Jahns et al. |
| 7,083,626 | B2 | 8/2006 | Hart et al. |
| 7,086,267 | B2 | 8/2006 | Dworak et al. |
| 7,087,049 | B2 | 8/2006 | Nowlin et al. |
| 7,087,054 | B2 | 8/2006 | Truckai et al. |
| 7,087,071 | B2 | 8/2006 | Nicholas et al. |
| 7,090,637 | B2 | 8/2006 | Danitz et al. |
| 7,090,673 | B2 | 8/2006 | Dycus et al. |
| 7,090,683 | B2 | 8/2006 | Brock et al. |
| 7,090,684 | B2 | 8/2006 | McGuckin, Jr. et al. |
| 7,091,191 | B2 | 8/2006 | Laredo et al. |
| 7,091,412 | B2 | 8/2006 | Wang et al. |
| 7,093,492 | B2 | 8/2006 | Treiber et al. |

(56) References Cited

U.S. PATENT DOCUMENTS

| | | | |
|---|---|---|---|
| 7,094,202 | B2 | 8/2006 | Nobis et al. |
| 7,094,247 | B2 | 8/2006 | Monassevitch et al. |
| 7,094,916 | B2 | 8/2006 | DeLuca et al. |
| 7,096,972 | B2 | 8/2006 | Orozco, Jr. |
| 7,097,089 | B2 | 8/2006 | Marczyk |
| 7,097,644 | B2 | 8/2006 | Long |
| 7,097,650 | B2 | 8/2006 | Weller et al. |
| 7,098,794 | B2 | 8/2006 | Lindsay et al. |
| 7,100,949 | B2 | 9/2006 | Williams et al. |
| 7,101,187 | B1 | 9/2006 | Deconinck et al. |
| 7,101,363 | B2 | 9/2006 | Nishizawa et al. |
| 7,101,371 | B2 | 9/2006 | Dycus et al. |
| 7,101,394 | B2 | 9/2006 | Hamm et al. |
| 7,104,741 | B2 | 9/2006 | Krohn |
| 7,108,695 | B2 | 9/2006 | Witt et al. |
| 7,108,701 | B2 | 9/2006 | Evens et al. |
| 7,108,709 | B2 | 9/2006 | Cummins |
| 7,111,768 | B2 | 9/2006 | Cummins et al. |
| 7,111,769 | B2 | 9/2006 | Wales et al. |
| 7,112,214 | B2 | 9/2006 | Peterson et al. |
| RE39,358 | E | 10/2006 | Goble |
| D530,339 | S | 10/2006 | Hernandez et al. |
| 7,114,642 | B2 | 10/2006 | Whitman |
| 7,116,100 | B1 | 10/2006 | Mock et al. |
| 7,118,020 | B2 | 10/2006 | Lee et al. |
| 7,118,528 | B1 | 10/2006 | Piskun |
| 7,118,563 | B2 | 10/2006 | Weckwerth et al. |
| 7,118,582 | B1 | 10/2006 | Wang et al. |
| 7,119,534 | B2 | 10/2006 | Butzmann |
| 7,121,446 | B2 | 10/2006 | Arad et al. |
| 7,121,773 | B2 | 10/2006 | Mikiya et al. |
| 7,122,028 | B2 | 10/2006 | Looper et al. |
| 7,125,403 | B2 | 10/2006 | Julian et al. |
| 7,125,409 | B2 | 10/2006 | Truckai et al. |
| 7,126,303 | B2 | 10/2006 | Farritor et al. |
| 7,126,879 | B2 | 10/2006 | Snyder |
| 7,128,253 | B2 | 10/2006 | Mastri et al. |
| 7,128,254 | B2 | 10/2006 | Shelton, IV et al. |
| 7,128,748 | B2 | 10/2006 | Mooradian et al. |
| 7,131,445 | B2 | 11/2006 | Amoah |
| 7,133,601 | B2 | 11/2006 | Phillips et al. |
| 7,134,364 | B2 | 11/2006 | Kageler et al. |
| 7,134,587 | B2 | 11/2006 | Schwemberger et al. |
| 7,135,027 | B2 | 11/2006 | Delmotte |
| 7,137,980 | B2 | 11/2006 | Buysse et al. |
| 7,137,981 | B2 | 11/2006 | Long |
| 7,139,016 | B2 | 11/2006 | Squilla et al. |
| 7,140,527 | B2 | 11/2006 | Ehrenfels et al. |
| 7,140,528 | B2 | 11/2006 | Shelton, IV |
| 7,141,055 | B2 | 11/2006 | Abrams et al. |
| 7,143,923 | B2 | 12/2006 | Shelton, IV et al. |
| 7,143,924 | B2 | 12/2006 | Scirica et al. |
| 7,143,925 | B2 | 12/2006 | Shelton, IV et al. |
| 7,143,926 | B2 | 12/2006 | Shelton, IV et al. |
| 7,146,191 | B2 | 12/2006 | Kerner et al. |
| 7,147,138 | B2 | 12/2006 | Shelton, IV |
| 7,147,139 | B2 | 12/2006 | Schwemberger et al. |
| 7,147,140 | B2 | 12/2006 | Wukusick et al. |
| 7,147,637 | B2 | 12/2006 | Goble |
| 7,147,648 | B2 | 12/2006 | Lin |
| 7,147,650 | B2 | 12/2006 | Lee |
| 7,150,748 | B2 | 12/2006 | Ebbutt et al. |
| 7,153,300 | B2 | 12/2006 | Goble |
| 7,153,314 | B2 | 12/2006 | Laufer et al. |
| 7,155,316 | B2 | 12/2006 | Sutherland et al. |
| 7,156,863 | B2 | 1/2007 | Sonnenschein et al. |
| 7,159,750 | B2 | 1/2007 | Racenet et al. |
| 7,160,296 | B2 | 1/2007 | Pearson et al. |
| 7,160,299 | B2 | 1/2007 | Baily |
| 7,160,311 | B2 | 1/2007 | Blatter et al. |
| 7,161,036 | B2 | 1/2007 | Oikawa et al. |
| 7,161,580 | B2 | 1/2007 | Bailey et al. |
| 7,162,758 | B2 | 1/2007 | Skinner |
| 7,163,563 | B2 | 1/2007 | Schwartz et al. |
| 7,166,117 | B2 | 1/2007 | Hellenkamp |
| 7,166,133 | B2 | 1/2007 | Evans et al. |
| 7,168,604 | B2 | 1/2007 | Milliman et al. |
| 7,170,910 | B2 | 1/2007 | Chen et al. |
| 7,171,279 | B2 | 1/2007 | Buckingham et al. |
| 7,172,104 | B2 | 2/2007 | Scirica et al. |
| 7,172,593 | B2 | 2/2007 | Trieu et al. |
| 7,172,615 | B2 | 2/2007 | Morriss et al. |
| 7,174,202 | B2 | 2/2007 | Bladen et al. |
| 7,174,636 | B2 | 2/2007 | Lowe |
| 7,177,533 | B2 | 2/2007 | McFarlin et al. |
| 7,179,223 | B2 | 2/2007 | Motoki et al. |
| 7,179,267 | B2 | 2/2007 | Nolan et al. |
| 7,182,239 | B1 | 2/2007 | Myers |
| 7,182,763 | B2 | 2/2007 | Nardella |
| 7,183,737 | B2 | 2/2007 | Kitagawa |
| 7,187,960 | B2 | 3/2007 | Abreu |
| 7,188,758 | B2 | 3/2007 | Viola et al. |
| 7,189,207 | B2 | 3/2007 | Viola |
| 7,190,147 | B2 | 3/2007 | Gileff et al. |
| 7,193,199 | B2 | 3/2007 | Jang |
| 7,195,627 | B2 | 3/2007 | Amoah et al. |
| 7,196,911 | B2 | 3/2007 | Takano et al. |
| D541,418 | S | 4/2007 | Schechter et al. |
| 7,197,965 | B1 | 4/2007 | Anderson |
| 7,199,537 | B2 | 4/2007 | Okamura et al. |
| 7,199,545 | B2 | 4/2007 | Oleynikov et al. |
| 7,202,576 | B1 | 4/2007 | Dechene et al. |
| 7,202,653 | B2 | 4/2007 | Pai |
| 7,204,404 | B2 | 4/2007 | Nguyen et al. |
| 7,204,835 | B2 | 4/2007 | Latterell et al. |
| 7,205,959 | B2 | 4/2007 | Henriksson |
| 7,206,626 | B2 | 4/2007 | Quaid, III |
| 7,207,233 | B2 | 4/2007 | Wadge |
| 7,207,471 | B2 | 4/2007 | Heinrich et al. |
| 7,207,472 | B2 | 4/2007 | Wukusick et al. |
| 7,207,556 | B2 | 4/2007 | Saitoh et al. |
| 7,208,005 | B2 | 4/2007 | Frecker et al. |
| 7,210,609 | B2 | 5/2007 | Leiboff et al. |
| 7,211,081 | B2 | 5/2007 | Goble |
| 7,211,084 | B2 | 5/2007 | Goble et al. |
| 7,211,092 | B2 | 5/2007 | Hughett |
| 7,211,979 | B2 | 5/2007 | Khatib et al. |
| 7,213,736 | B2 | 5/2007 | Wales et al. |
| 7,214,224 | B2 | 5/2007 | Goble |
| 7,215,517 | B2 | 5/2007 | Takamatsu |
| 7,217,285 | B2 | 5/2007 | Vargas et al. |
| 7,220,260 | B2 | 5/2007 | Fleming et al. |
| 7,220,272 | B2 | 5/2007 | Weadock |
| 7,225,959 | B2 | 6/2007 | Patton et al. |
| 7,225,963 | B2 | 6/2007 | Scirica |
| 7,225,964 | B2 | 6/2007 | Mastri et al. |
| 7,226,450 | B2 | 6/2007 | Athanasiou et al. |
| 7,226,467 | B2 | 6/2007 | Lucatero et al. |
| 7,228,505 | B2 | 6/2007 | Shimazu et al. |
| 7,229,408 | B2 | 6/2007 | Douglas et al. |
| 7,234,624 | B2 | 6/2007 | Gresham et al. |
| 7,235,072 | B2 | 6/2007 | Sartor et al. |
| 7,235,089 | B1 | 6/2007 | McGuckin, Jr. |
| 7,235,302 | B2 | 6/2007 | Jing et al. |
| 7,237,708 | B1 | 7/2007 | Guy et al. |
| 7,238,195 | B2 | 7/2007 | Viola |
| 7,238,901 | B2 | 7/2007 | Kim et al. |
| 7,239,657 | B1 | 7/2007 | Gunnarsson |
| 7,241,288 | B2 | 7/2007 | Braun |
| 7,241,289 | B2 | 7/2007 | Braun |
| 7,246,734 | B2 | 7/2007 | Shelton, IV |
| 7,247,161 | B2 | 7/2007 | Johnston et al. |
| 7,249,267 | B2 | 7/2007 | Chapuis |
| 7,252,641 | B2 | 8/2007 | Thompson et al. |
| 7,252,660 | B2 | 8/2007 | Kunz |
| 7,255,012 | B2 | 8/2007 | Hedtke |
| 7,255,696 | B2 | 8/2007 | Goble et al. |
| 7,256,695 | B2 | 8/2007 | Hamel et al. |
| 7,258,262 | B2 | 8/2007 | Mastri et al. |
| 7,258,546 | B2 | 8/2007 | Beier et al. |
| 7,260,431 | B2 | 8/2007 | Libbus et al. |
| 7,265,374 | B2 | 9/2007 | Lee et al. |
| 7,267,677 | B2 | 9/2007 | Johnson et al. |
| 7,267,679 | B2 | 9/2007 | McGuckin, Jr. et al. |

(56) References Cited

U.S. PATENT DOCUMENTS

| | | | |
|---|---|---|---|
| 7,272,002 | B2 | 9/2007 | Drapeau |
| 7,273,483 | B2 | 9/2007 | Wiener et al. |
| 7,273,488 | B2 | 9/2007 | Nakamura et al. |
| D552,623 | S | 10/2007 | Vong et al. |
| 7,275,674 | B2 | 10/2007 | Racenet et al. |
| 7,276,044 | B2 | 10/2007 | Ferry et al. |
| 7,276,068 | B2 | 10/2007 | Johnson et al. |
| 7,278,562 | B2 | 10/2007 | Mastri et al. |
| 7,278,563 | B1 | 10/2007 | Green |
| 7,278,949 | B2 | 10/2007 | Bader |
| 7,278,994 | B2 | 10/2007 | Goble |
| 7,282,048 | B2 | 10/2007 | Goble et al. |
| 7,283,096 | B2 | 10/2007 | Geisheimer et al. |
| 7,286,850 | B2 | 10/2007 | Frielink et al. |
| 7,287,682 | B1 | 10/2007 | Ezzat et al. |
| 7,289,139 | B2 | 10/2007 | Amling et al. |
| 7,293,685 | B2 | 11/2007 | Ehrenfels et al. |
| 7,295,893 | B2 | 11/2007 | Sunaoshi |
| 7,295,907 | B2 | 11/2007 | Lu et al. |
| 7,296,722 | B2 | 11/2007 | Ivanko |
| 7,296,724 | B2 | 11/2007 | Green et al. |
| 7,297,149 | B2 | 11/2007 | Vitali et al. |
| 7,300,373 | B2 | 11/2007 | Jinno et al. |
| 7,300,431 | B2 | 11/2007 | Dubrovsky |
| 7,300,450 | B2 | 11/2007 | Vleugels et al. |
| 7,303,106 | B2 | 12/2007 | Milliman et al. |
| 7,303,107 | B2 | 12/2007 | Milliman et al. |
| 7,303,108 | B2 | 12/2007 | Shelton, IV |
| 7,303,502 | B2 | 12/2007 | Thompson |
| 7,303,556 | B2 | 12/2007 | Metzger |
| 7,306,597 | B2 | 12/2007 | Manzo |
| 7,308,998 | B2 | 12/2007 | Mastri et al. |
| 7,311,238 | B2 | 12/2007 | Liu |
| 7,313,430 | B2 | 12/2007 | Urquhart et al. |
| 7,314,473 | B2 | 1/2008 | Jinno et al. |
| 7,320,704 | B2 | 1/2008 | Lashinski et al. |
| 7,322,859 | B2 | 1/2008 | Evans |
| 7,322,975 | B2 | 1/2008 | Goble et al. |
| 7,322,994 | B2 | 1/2008 | Nicholas et al. |
| 7,324,572 | B2 | 1/2008 | Chang |
| 7,326,203 | B2 | 2/2008 | Papineau et al. |
| 7,326,213 | B2 | 2/2008 | Benderev et al. |
| 7,328,828 | B2 | 2/2008 | Ortiz et al. |
| 7,328,829 | B2 | 2/2008 | Arad et al. |
| 7,330,004 | B2 | 2/2008 | DeJonge et al. |
| 7,331,340 | B2 | 2/2008 | Barney |
| 7,331,343 | B2 | 2/2008 | Schmidt et al. |
| 7,331,403 | B2 | 2/2008 | Berry et al. |
| 7,331,406 | B2 | 2/2008 | Wottreng, Jr. et al. |
| 7,331,969 | B1 | 2/2008 | Inganas et al. |
| 7,334,717 | B2 | 2/2008 | Rethy et al. |
| 7,334,718 | B2 | 2/2008 | McAlister et al. |
| 7,335,199 | B2 | 2/2008 | Goble et al. |
| 7,335,401 | B2 | 2/2008 | Finke et al. |
| 7,336,045 | B2 | 2/2008 | Clermonts |
| 7,336,048 | B2 | 2/2008 | Lohr |
| 7,336,183 | B2 | 2/2008 | Reddy et al. |
| 7,336,184 | B2 | 2/2008 | Smith et al. |
| 7,337,774 | B2 | 3/2008 | Webb |
| 7,338,505 | B2 | 3/2008 | Belson |
| 7,338,513 | B2 | 3/2008 | Lee et al. |
| 7,341,554 | B2 | 3/2008 | Sekine et al. |
| 7,341,555 | B2 | 3/2008 | Ootawara et al. |
| 7,341,591 | B2 | 3/2008 | Grinberg |
| 7,343,920 | B2 | 3/2008 | Toby et al. |
| 7,344,532 | B2 | 3/2008 | Goble et al. |
| 7,344,533 | B2 | 3/2008 | Pearson et al. |
| 7,346,344 | B2 | 3/2008 | Fontaine |
| 7,346,406 | B2 | 3/2008 | Brotto et al. |
| 7,348,763 | B1 | 3/2008 | Reinhart et al. |
| 7,348,875 | B2 | 3/2008 | Hughes et al. |
| RE40,237 | E | 4/2008 | Bilotti et al. |
| 7,351,258 | B2 | 4/2008 | Ricotta et al. |
| 7,354,398 | B2 | 4/2008 | Kanazawa |
| 7,354,447 | B2 | 4/2008 | Shelton, IV et al. |
| 7,354,502 | B2 | 4/2008 | Polat et al. |
| 7,357,287 | B2 | 4/2008 | Shelton, IV et al. |
| 7,357,806 | B2 | 4/2008 | Rivera et al. |
| 7,361,168 | B2 | 4/2008 | Makower et al. |
| 7,361,195 | B2 | 4/2008 | Schwartz et al. |
| 7,362,062 | B2 | 4/2008 | Schneider et al. |
| 7,364,060 | B2 | 4/2008 | Milliman |
| 7,364,061 | B2 | 4/2008 | Swayze et al. |
| 7,367,485 | B2 | 5/2008 | Shelton, IV et al. |
| 7,367,973 | B2 | 5/2008 | Manzo et al. |
| 7,368,124 | B2 | 5/2008 | Chun et al. |
| 7,371,210 | B2 | 5/2008 | Brock et al. |
| 7,371,403 | B2 | 5/2008 | McCarthy et al. |
| 7,375,493 | B2 | 5/2008 | Calhoon et al. |
| 7,377,918 | B2 | 5/2008 | Amoah |
| 7,377,928 | B2 | 5/2008 | Zubik et al. |
| 7,378,817 | B2 | 5/2008 | Calhoon et al. |
| RE40,388 | E | 6/2008 | Gines |
| D570,868 | S | 6/2008 | Hosokawa et al. |
| 7,380,695 | B2 | 6/2008 | Doll et al. |
| 7,380,696 | B2 | 6/2008 | Shelton, IV et al. |
| 7,384,403 | B2 | 6/2008 | Sherman |
| 7,384,417 | B2 | 6/2008 | Cucin |
| 7,386,365 | B2 | 6/2008 | Nixon |
| 7,386,730 | B2 | 6/2008 | Uchikubo |
| 7,388,217 | B2 | 6/2008 | Buschbeck et al. |
| 7,388,484 | B2 | 6/2008 | Hsu |
| 7,391,173 | B2 | 6/2008 | Schena |
| 7,394,190 | B2 | 7/2008 | Huang |
| 7,396,356 | B2 | 7/2008 | Mollenauer |
| 7,397,364 | B2 | 7/2008 | Govari |
| 7,398,707 | B2 | 7/2008 | Morley et al. |
| 7,398,907 | B2 | 7/2008 | Racenet et al. |
| 7,398,908 | B2 | 7/2008 | Holsten et al. |
| 7,400,107 | B2 | 7/2008 | Schneider et al. |
| 7,400,752 | B2 | 7/2008 | Zacharias |
| 7,401,000 | B2 | 7/2008 | Nakamura |
| 7,401,721 | B2 | 7/2008 | Holsten et al. |
| 7,404,449 | B2 | 7/2008 | Bermingham et al. |
| 7,404,508 | B2 | 7/2008 | Smith et al. |
| 7,404,509 | B2 | 7/2008 | Ortiz et al. |
| 7,404,822 | B2 | 7/2008 | Viart et al. |
| D575,793 | S | 8/2008 | Ording |
| 7,407,074 | B2 | 8/2008 | Ortiz et al. |
| 7,407,075 | B2 | 8/2008 | Holsten et al. |
| 7,407,076 | B2 | 8/2008 | Racenet et al. |
| 7,407,077 | B2 | 8/2008 | Ortiz et al. |
| 7,407,078 | B2 | 8/2008 | Shelton, IV et al. |
| 7,408,310 | B2 | 8/2008 | Hong et al. |
| 7,410,085 | B2 | 8/2008 | Wolf et al. |
| 7,410,086 | B2 | 8/2008 | Ortiz et al. |
| 7,410,483 | B2 | 8/2008 | Danitz et al. |
| 7,413,563 | B2 | 8/2008 | Corcoran et al. |
| 7,416,101 | B2 | 8/2008 | Shelton, IV et al. |
| 7,418,078 | B2 | 8/2008 | Blanz et al. |
| RE40,514 | E | 9/2008 | Mastri et al. |
| 7,419,080 | B2 | 9/2008 | Smith et al. |
| 7,419,081 | B2 | 9/2008 | Ehrenfels et al. |
| 7,419,321 | B2 | 9/2008 | Tereschouk |
| 7,419,495 | B2 | 9/2008 | Menn et al. |
| 7,422,136 | B1 | 9/2008 | Marczyk |
| 7,422,138 | B2 | 9/2008 | Bilotti et al. |
| 7,422,139 | B2 | 9/2008 | Shelton, IV et al. |
| 7,424,965 | B2 | 9/2008 | Racenet et al. |
| 7,427,607 | B2 | 9/2008 | Suzuki |
| D578,644 | S | 10/2008 | Shumer et al. |
| 7,430,772 | B2 | 10/2008 | Van Es |
| 7,430,849 | B1 | 10/2008 | Coutts et al. |
| 7,431,188 | B1 | 10/2008 | Marczyk |
| 7,431,189 | B2 | 10/2008 | Shelton, IV et al. |
| 7,431,230 | B2 | 10/2008 | McPherson et al. |
| 7,431,694 | B2 | 10/2008 | Stefanchik et al. |
| 7,431,730 | B2 | 10/2008 | Viola |
| 7,434,715 | B2 | 10/2008 | Shelton, IV et al. |
| 7,434,717 | B2 | 10/2008 | Shelton, IV et al. |
| 7,435,249 | B2 | 10/2008 | Buysse et al. |
| 7,438,209 | B1 | 10/2008 | Hess et al. |
| 7,438,718 | B2 | 10/2008 | Milliman et al. |
| 7,439,354 | B2 | 10/2008 | Lenges et al. |

(56) References Cited

U.S. PATENT DOCUMENTS 7,441,684 B2 10/2008 Shelton, IV et al.
7,441,685 B1 10/2008 Boudreaux
7,442,201 B2 10/2008 Pugsley et al.
7,443,547 B2 10/2008 Moreno et al.
D580,942 S 11/2008 Oshiro et al.
7,446,131 B1 11/2008 Liu et al.
7,448,525 B2 11/2008 Shelton, IV et al.
7,450,010 B1 11/2008 Gravelle et al.
7,450,991 B2 11/2008 Smith et al.
7,451,904 B2 11/2008 Shelton, IV
7,455,208 B2 11/2008 Wales et al.
7,455,676 B2 11/2008 Holsten et al.
7,455,682 B2 11/2008 Viola
7,455,687 B2 11/2008 Saunders et al.
D582,934 S 12/2008 Byeon
7,461,767 B2 12/2008 Viola et al.
7,462,187 B2 12/2008 Johnston et al.
7,464,845 B2 12/2008 Chou
7,464,846 B2 12/2008 Shelton, IV et al.
7,464,847 B2 12/2008 Viola et al.
7,464,848 B2 12/2008 Green et al.
7,464,849 B2 12/2008 Shelton, IV et al.
7,467,740 B2 12/2008 Shelton, IV et al.
7,467,849 B2 12/2008 Silverbrook et al.
7,472,814 B2 1/2009 Mastri et al.
7,472,815 B2 1/2009 Shelton, IV et al.
7,472,816 B2 1/2009 Holsten et al.
7,473,221 B2 1/2009 Ewers et al.
7,473,253 B2 1/2009 Dycus et al.
7,473,263 B2 1/2009 Johnston et al.
7,476,237 B2 1/2009 Taniguchi et al.
7,479,147 B2 1/2009 Honeycutt et al.
7,479,608 B2 1/2009 Smith
7,481,347 B2 1/2009 Roy
7,481,348 B2 1/2009 Marczyk
7,481,349 B2 1/2009 Holsten et al.
7,481,824 B2 1/2009 Boudreaux et al.
7,485,124 B2 2/2009 Kuhns et al.
7,485,133 B2 2/2009 Cannon et al.
7,485,142 B2 2/2009 Milo
7,487,899 B2 2/2009 Shelton, IV et al.
7,489,055 B2 2/2009 Jeong et al.
7,490,749 B2 2/2009 Schall et al.
7,491,232 B2 2/2009 Bolduc et al.
7,492,261 B2 2/2009 Cambre et al.
7,494,039 B2 2/2009 Racenet et al.
7,494,460 B2 2/2009 Haarstad et al.
7,494,499 B2 2/2009 Nagase et al.
7,494,501 B2 2/2009 Ahlberg et al.
7,497,137 B2 3/2009 Tellenbach et al.
7,500,979 B2 3/2009 Hueil et al.
7,501,198 B2 3/2009 Barlev et al.
7,503,474 B2 3/2009 Hillstead et al.
7,506,790 B2 3/2009 Shelton, IV
7,506,791 B2 3/2009 Omaits et al.
7,507,202 B2 3/2009 Schoellhorn
7,510,107 B2 3/2009 Timm et al.
7,510,534 B2 3/2009 Burdorff et al.
7,510,566 B2 3/2009 Jacobs et al.
7,513,407 B1 4/2009 Chang
7,513,408 B2 4/2009 Shelton, IV et al.
7,517,356 B2 4/2009 Heinrich
7,524,320 B2 4/2009 Tierney et al.
7,527,632 B2 5/2009 Houghton et al.
7,530,984 B2 5/2009 Sonnenschein et al.
7,530,985 B2 5/2009 Takemoto et al.
7,533,906 B2 5/2009 Luettgen et al.
7,534,259 B2 5/2009 Lashinski et al.
7,540,867 B2 6/2009 Jinno et al.
7,540,872 B2 6/2009 Schechter et al.
7,542,807 B2 6/2009 Bertolero et al.
7,543,730 B1 6/2009 Marczyk
7,544,197 B2 6/2009 Kelsch et al.
7,546,939 B2 6/2009 Adams et al.
7,546,940 B2 6/2009 Milliman et al.
7,547,287 B2 6/2009 Boecker et al.
7,547,312 B2 6/2009 Bauman et al.
7,549,563 B2 6/2009 Mather et al.
7,549,564 B2 6/2009 Boudreaux
7,549,998 B2 6/2009 Braun
7,552,854 B2 6/2009 Wixey et al.
7,553,173 B2 6/2009 Kowalick
7,553,275 B2 6/2009 Padget et al.
7,554,343 B2 6/2009 Bromfield
7,556,185 B2 7/2009 Viola
7,556,186 B2 7/2009 Milliman
7,556,647 B2 7/2009 Drews et al.
7,559,449 B2 7/2009 Viola
7,559,450 B2 7/2009 Wales et al.
7,559,452 B2 7/2009 Wales et al.
7,559,937 B2 7/2009 de la Torre et al.
7,561,637 B2 7/2009 Jonsson et al.
7,562,910 B2 7/2009 Kertesz et al.
7,563,269 B2 7/2009 Hashiguchi
7,563,862 B2 7/2009 Sieg et al.
7,565,993 B2 7/2009 Milliman et al.
7,566,300 B2 7/2009 Devierre et al.
7,567,045 B2 7/2009 Fristedt
7,568,603 B2 8/2009 Shelton, IV et al.
7,568,604 B2 8/2009 Ehrenfels et al.
7,568,619 B2 8/2009 Todd et al.
7,572,285 B2 8/2009 Frey et al.
7,572,298 B2 8/2009 Roller et al.
7,575,144 B2 8/2009 Ortiz et al.
7,578,825 B2 8/2009 Huebner
D600,712 S 9/2009 LaManna et al.
7,583,063 B2 9/2009 Dooley
7,584,880 B2 9/2009 Racenet et al.
7,586,289 B2 9/2009 Andruk et al.
7,588,174 B2 9/2009 Holsten et al.
7,588,175 B2 9/2009 Timm et al.
7,588,176 B2 9/2009 Timm et al.
7,588,177 B2 9/2009 Racenet
7,591,783 B2 9/2009 Boulais et al.
7,591,818 B2 9/2009 Bertolero et al.
7,593,766 B2 9/2009 Faber et al.
7,595,642 B2 9/2009 Doyle
7,597,229 B2 10/2009 Boudreaux et al.
7,597,230 B2 10/2009 Racenet et al.
7,597,693 B2 10/2009 Garrison
7,597,699 B2 10/2009 Rogers
7,598,972 B2 10/2009 Tomita
7,600,663 B2 10/2009 Green
7,604,118 B2 10/2009 Iio et al.
7,604,150 B2 10/2009 Boudreaux
7,604,151 B2 10/2009 Hess et al.
7,604,668 B2 10/2009 Farnsworth et al.
7,605,826 B2 10/2009 Sauer
7,607,557 B2 10/2009 Shelton, IV et al.
7,608,091 B2 10/2009 Goldfarb et al.
D604,325 S 11/2009 Ebeling et al.
7,611,038 B2 11/2009 Racenet et al.
7,611,474 B2 11/2009 Hibner et al.
7,615,003 B2 11/2009 Stefanchik et al.
7,615,006 B2 11/2009 Abe
7,615,067 B2 11/2009 Lee et al.
7,617,961 B2 11/2009 Viola
7,618,427 B2 11/2009 Ortiz et al.
D605,201 S 12/2009 Lorenz et al.
D606,992 S 12/2009 Liu et al.
D607,010 S 12/2009 Kocmick
7,624,902 B2 12/2009 Marczyk et al.
7,624,903 B2 12/2009 Green et al.
7,625,370 B2 12/2009 Hart et al.
7,625,388 B2 12/2009 Boukhny et al.
7,625,662 B2 12/2009 Vaisnys et al.
7,630,841 B2 12/2009 Comisky et al.
7,631,793 B2 12/2009 Rethy et al.
7,631,794 B2 12/2009 Rethy et al.
7,635,074 B2 12/2009 Olson et al.
7,635,922 B2 12/2009 Becker
7,637,409 B2 12/2009 Marczyk
7,637,410 B2 12/2009 Marczyk
7,638,958 B2 12/2009 Philipp et al.

(56) References Cited

U.S. PATENT DOCUMENTS 7,641,091 B2 1/2010 Olson et al.
7,641,092 B2 1/2010 Kruszynski et al.
7,641,093 B2 1/2010 Doll et al.
7,641,095 B2 1/2010 Viola
7,641,671 B2 1/2010 Crainich
7,644,484 B2 1/2010 Vereschagin
7,644,783 B2 1/2010 Roberts et al.
7,644,848 B2 1/2010 Swayze et al.
7,645,230 B2 1/2010 Mikkaichi et al.
7,648,055 B2 1/2010 Marczyk
7,648,457 B2 1/2010 Stefanchik et al.
7,648,519 B2 1/2010 Lee et al.
7,650,185 B2 1/2010 Maile et al.
7,651,017 B2 1/2010 Ortiz et al.
7,651,498 B2 1/2010 Shifrin et al.
7,654,431 B2 2/2010 Hueil et al.
7,655,003 B2 2/2010 Lorang et al.
7,655,004 B2 2/2010 Long
7,655,288 B2 2/2010 Bauman et al.
7,655,584 B2 2/2010 Biran et al.
7,656,131 B2 2/2010 Embrey et al.
7,658,311 B2 2/2010 Boudreaux
7,658,312 B2 2/2010 Vidal et al.
7,658,705 B2 2/2010 Melvin et al.
7,659,219 B2 2/2010 Biran et al.
7,661,448 B2 2/2010 Kim et al.
7,662,161 B2 2/2010 Briganti et al.
7,665,646 B2 2/2010 Prommersberger
7,665,647 B2 2/2010 Shelton, IV et al.
7,666,195 B2 2/2010 Kelleher et al.
7,669,746 B2 3/2010 Shelton, IV
7,669,747 B2 3/2010 Weisenburgh, II et al.
7,670,334 B2 3/2010 Hueil et al.
7,670,337 B2 3/2010 Young
7,673,780 B2 3/2010 Shelton, IV et al.
7,673,781 B2 3/2010 Swayze et al.
7,673,782 B2 3/2010 Hess et al.
7,673,783 B2 3/2010 Morgan et al.
7,674,253 B2 3/2010 Fisher et al.
7,674,255 B2 3/2010 Braun
7,674,263 B2 3/2010 Ryan
7,674,270 B2 3/2010 Layer
7,678,121 B1 3/2010 Knodel
7,682,307 B2 3/2010 Danitz et al.
7,682,367 B2 3/2010 Shah et al.
7,682,686 B2 3/2010 Curro et al.
7,686,201 B2 3/2010 Csiky
7,686,804 B2 3/2010 Johnson et al.
7,686,826 B2 3/2010 Lee et al.
7,688,028 B2 3/2010 Phillips et al.
7,690,547 B2 4/2010 Racenet et al.
7,691,098 B2 4/2010 Wallace et al.
7,691,103 B2 4/2010 Fernandez et al.
7,691,106 B2 4/2010 Schenberger et al.
7,694,864 B2 4/2010 Okada et al.
7,694,865 B2 4/2010 Scirica
7,695,485 B2 4/2010 Whitman et al.
7,695,493 B2 4/2010 Saadat et al.
7,699,204 B2 4/2010 Viola
7,699,835 B2 4/2010 Lee et al.
7,699,844 B2 4/2010 Utley et al.
7,699,846 B2 4/2010 Ryan
7,699,856 B2 4/2010 Van Wyk et al.
7,699,859 B2 4/2010 Bombard et al.
7,699,860 B2 4/2010 Huitema et al.
7,699,868 B2 4/2010 Frank et al.
7,703,653 B2 4/2010 Shah et al.
7,705,559 B2 4/2010 Powell et al.
7,706,853 B2 4/2010 Hacker et al.
7,708,180 B2 5/2010 Murray et al.
7,708,181 B2 5/2010 Cole et al.
7,708,182 B2 5/2010 Viola
7,708,758 B2 5/2010 Lee et al.
7,708,768 B2 5/2010 Danek et al.
7,709,136 B2 5/2010 Touchton et al.
7,712,182 B2 5/2010 Zeiler et al.
7,713,190 B2 5/2010 Brock et al.
7,713,542 B2 5/2010 Xu et al.
7,714,239 B2 5/2010 Smith
7,714,334 B2 5/2010 Lin
7,717,312 B2 5/2010 Beetel
7,717,313 B2 5/2010 Criscuolo et al.
7,717,846 B2 5/2010 Zirps et al.
7,717,873 B2 5/2010 Swick
7,717,915 B2 5/2010 Miyazawa
7,717,926 B2 5/2010 Whitfield et al.
7,718,180 B2 5/2010 Karp
7,718,556 B2 5/2010 Matsuda et al.
7,721,930 B2 5/2010 McKenna et al.
7,721,931 B2 5/2010 Shelton, IV et al.
7,721,932 B2 5/2010 Cole et al.
7,721,933 B2 5/2010 Ehrenfels et al.
7,721,934 B2 5/2010 Shelton, IV et al.
7,721,936 B2 5/2010 Shalton, IV et al.
7,722,527 B2 5/2010 Bouchier et al.
7,722,607 B2 5/2010 Dumbauld et al.
7,722,610 B2 5/2010 Viola et al.
7,725,214 B2 5/2010 Diolaiti
7,726,171 B2 6/2010 Langlotz et al.
7,726,537 B2 6/2010 Olson et al.
7,726,538 B2 6/2010 Holsten et al.
7,726,539 B2 6/2010 Holsten et al.
7,727,954 B2 6/2010 McKay
7,728,553 B2 6/2010 Carrier et al.
7,729,742 B2 6/2010 Govari
7,731,072 B2 6/2010 Timm et al.
7,731,073 B2 6/2010 Wixey et al.
7,731,724 B2 6/2010 Huitema et al.
7,735,703 B2 6/2010 Morgan et al.
7,735,704 B2 6/2010 Bilotti
7,736,254 B2 6/2010 Schena
7,736,306 B2 6/2010 Brustad et al.
7,736,374 B2 6/2010 Vaughan et al.
7,738,971 B2 6/2010 Swayze et al.
7,740,159 B2 6/2010 Shelton, IV et al.
7,742,036 B2 6/2010 Grant et al.
7,743,960 B2 6/2010 Whitman et al.
7,744,624 B2 6/2010 Bettuchi
7,744,627 B2 6/2010 Orban, III et al.
7,744,628 B2 6/2010 Viola
7,747,146 B2 6/2010 Milano et al.
7,748,587 B2 7/2010 Haramiishi et al.
7,748,632 B2 7/2010 Coleman et al.
7,749,204 B2 7/2010 Dhanaraj et al.
7,749,240 B2 7/2010 Takahashi et al.
7,751,870 B2 7/2010 Whitman
7,753,245 B2 7/2010 Boudreaux et al.
7,753,246 B2 7/2010 Scirica
7,753,904 B2 7/2010 Shelton, IV et al.
7,757,924 B2 7/2010 Gerbi et al.
7,758,594 B2 7/2010 Lamson et al.
7,758,612 B2 7/2010 Shipp
7,758,613 B2 7/2010 Whitman
7,762,462 B2 7/2010 Gelbman
7,762,998 B2 7/2010 Birk et al.
D622,286 S 8/2010 Umezawa
7,766,207 B2 8/2010 Mather et al.
7,766,209 B2 8/2010 Baxter, III et al.
7,766,210 B2 8/2010 Shelton, IV et al.
7,766,821 B2 8/2010 Brunnen et al.
7,766,894 B2 8/2010 Weitzner et al.
7,770,658 B2 8/2010 Ito et al.
7,770,773 B2 8/2010 Whitman et al.
7,770,774 B2 8/2010 Mastri et al.
7,770,775 B2 8/2010 Shelton, IV et al.
7,770,776 B2 8/2010 Chen et al.
7,771,396 B2 8/2010 Stefanchik et al.
7,772,720 B2 8/2010 McGee et al.
7,772,725 B2 8/2010 Siman-Tov
7,775,972 B2 8/2010 Brock et al.
7,776,037 B2 8/2010 Odom
7,776,060 B2 8/2010 Mooradian et al.
7,776,065 B2 8/2010 Griffiths et al.
7,778,004 B2 8/2010 Nerheim et al.

(56) References Cited

U.S. PATENT DOCUMENTS

| | | | |
|---|---|---|---|
| 7,779,614 | B1 | 8/2010 | McGonagle et al. |
| 7,779,737 | B2 | 8/2010 | Newman, Jr. et al. |
| 7,780,054 | B2 | 8/2010 | Wales |
| 7,780,055 | B2 | 8/2010 | Scirica et al. |
| 7,780,309 | B2 | 8/2010 | McMillan et al. |
| 7,780,651 | B2 | 8/2010 | Madhani et al. |
| 7,780,663 | B2 | 8/2010 | Yates et al. |
| 7,780,685 | B2 | 8/2010 | Hunt et al. |
| 7,782,382 | B2 | 8/2010 | Fujimura |
| 7,784,662 | B2 | 8/2010 | Wales et al. |
| 7,784,663 | B2 | 8/2010 | Shelton, IV |
| 7,787,256 | B2 | 8/2010 | Chan et al. |
| 7,789,283 | B2 | 9/2010 | Shah |
| 7,789,875 | B2 | 9/2010 | Brock et al. |
| 7,789,883 | B2 | 9/2010 | Takashino et al. |
| 7,789,889 | B2 | 9/2010 | Zubik et al. |
| 7,793,812 | B2 | 9/2010 | Moore et al. |
| 7,794,475 | B2 | 9/2010 | Hess et al. |
| 7,798,386 | B2 | 9/2010 | Schall et al. |
| 7,799,039 | B2 | 9/2010 | Shelton, IV et al. |
| 7,799,044 | B2 | 9/2010 | Johnston et al. |
| 7,799,965 | B2 | 9/2010 | Patel et al. |
| 7,803,151 | B2 | 9/2010 | Whitman |
| 7,806,871 | B2 | 10/2010 | Li et al. |
| 7,806,891 | B2 | 10/2010 | Nowlin et al. |
| 7,810,690 | B2 | 10/2010 | Bilotti et al. |
| 7,810,691 | B2 | 10/2010 | Boyden et al. |
| 7,810,692 | B2 | 10/2010 | Hall et al. |
| 7,810,693 | B2 | 10/2010 | Broehl et al. |
| 7,811,275 | B2 | 10/2010 | Birk et al. |
| 7,814,816 | B2 | 10/2010 | Alberti et al. |
| 7,815,092 | B2 | 10/2010 | Whitman et al. |
| 7,815,565 | B2 | 10/2010 | Stefanchik et al. |
| 7,815,662 | B2 | 10/2010 | Spivey et al. |
| 7,819,296 | B2 | 10/2010 | Hueil et al. |
| 7,819,297 | B2 | 10/2010 | Doll et al. |
| 7,819,298 | B2 | 10/2010 | Hall et al. |
| 7,819,299 | B2 | 10/2010 | Shelton, IV et al. |
| 7,819,799 | B2 | 10/2010 | Merril et al. |
| 7,819,884 | B2 | 10/2010 | Lee et al. |
| 7,819,885 | B2 | 10/2010 | Cooper |
| 7,819,886 | B2 | 10/2010 | Whitfield et al. |
| 7,819,894 | B2 | 10/2010 | Mitsuishi et al. |
| 7,823,076 | B2 | 10/2010 | Borovsky et al. |
| 7,823,592 | B2 | 11/2010 | Bettuchi et al. |
| 7,823,760 | B2 | 11/2010 | Zemlok et al. |
| 7,824,401 | B2 | 11/2010 | Manzo et al. |
| 7,824,422 | B2 | 11/2010 | Benchetrit |
| 7,824,426 | B2 | 11/2010 | Racenet et al. |
| 7,828,189 | B2 | 11/2010 | Holsten et al. |
| 7,828,794 | B2 | 11/2010 | Sartor |
| 7,828,808 | B2 | 11/2010 | Hinman et al. |
| 7,829,416 | B2 | 11/2010 | Kudou et al. |
| 7,831,292 | B2 | 11/2010 | Quaid et al. |
| 7,832,408 | B2 | 11/2010 | Shelton, IV et al. |
| 7,832,611 | B2 | 11/2010 | Boyden et al. |
| 7,832,612 | B2 | 11/2010 | Baxter, III et al. |
| 7,833,234 | B2 | 11/2010 | Bailly et al. |
| 7,835,823 | B2 | 11/2010 | Sillman et al. |
| 7,836,400 | B2 | 11/2010 | May et al. |
| 7,837,079 | B2 | 11/2010 | Holsten et al. |
| 7,837,080 | B2 | 11/2010 | Schwemberger |
| 7,837,081 | B2 | 11/2010 | Holsten et al. |
| 7,837,425 | B2 | 11/2010 | Saeki et al. |
| 7,837,685 | B2 | 11/2010 | Weinberg et al. |
| 7,837,687 | B2 | 11/2010 | Harp |
| 7,837,694 | B2 | 11/2010 | Tethrake et al. |
| 7,838,789 | B2 | 11/2010 | Stoffers et al. |
| 7,839,109 | B2 | 11/2010 | Carmen, Jr. et al. |
| 7,840,253 | B2 | 11/2010 | Tremblay et al. |
| 7,841,503 | B2 | 11/2010 | Sonnenschein et al. |
| 7,842,025 | B2 | 11/2010 | Coleman et al. |
| 7,842,028 | B2 | 11/2010 | Lee |
| 7,843,158 | B2 | 11/2010 | Prisco |
| 7,845,533 | B2 | 12/2010 | Marczyk et al. |
| 7,845,534 | B2 | 12/2010 | Viola et al. |
| 7,845,535 | B2 | 12/2010 | Scircia |
| 7,845,536 | B2 | 12/2010 | Viola et al. |
| 7,845,537 | B2 | 12/2010 | Shelton, IV et al. |
| 7,845,538 | B2 | 12/2010 | Whitman |
| 7,845,912 | B2 | 12/2010 | Sung et al. |
| 7,846,085 | B2 | 12/2010 | Silverman et al. |
| 7,846,149 | B2 | 12/2010 | Jankowski |
| 7,846,161 | B2 | 12/2010 | Dumbauld et al. |
| 7,848,066 | B2 | 12/2010 | Yanagishima |
| 7,850,623 | B2 | 12/2010 | Griffin et al. |
| 7,850,642 | B2 | 12/2010 | Moll et al. |
| 7,850,982 | B2 | 12/2010 | Stopek et al. |
| 7,853,813 | B2 | 12/2010 | Lee |
| 7,854,735 | B2 | 12/2010 | Houser et al. |
| 7,854,736 | B2 | 12/2010 | Ryan |
| 7,857,183 | B2 | 12/2010 | Shelton, IV |
| 7,857,184 | B2 | 12/2010 | Viola |
| 7,857,185 | B2 | 12/2010 | Swayze et al. |
| 7,857,186 | B2 | 12/2010 | Baxter, III et al. |
| 7,857,813 | B2 | 12/2010 | Schmitz et al. |
| 7,861,906 | B2 | 1/2011 | Doll et al. |
| 7,862,502 | B2 | 1/2011 | Pool et al. |
| 7,862,546 | B2 | 1/2011 | Conlon et al. |
| 7,862,579 | B2 | 1/2011 | Ortiz et al. |
| 7,866,525 | B2 | 1/2011 | Scirica |
| 7,866,527 | B2 | 1/2011 | Hall et al. |
| 7,866,528 | B2 | 1/2011 | Olson et al. |
| 7,870,989 | B2 | 1/2011 | Viola et al. |
| 7,871,418 | B2 | 1/2011 | Thompson et al. |
| 7,871,440 | B2 | 1/2011 | Schwartz et al. |
| 7,875,055 | B2 | 1/2011 | Cichocki, Jr. |
| 7,877,869 | B2 | 2/2011 | Mehdizadeh et al. |
| 7,879,063 | B2 | 2/2011 | Khosravi |
| 7,879,070 | B2 | 2/2011 | Ortiz et al. |
| 7,879,367 | B2 | 2/2011 | Heublein et al. |
| 7,883,461 | B2 | 2/2011 | Albrecht et al. |
| 7,883,465 | B2 | 2/2011 | Donofrio et al. |
| 7,883,540 | B2 | 2/2011 | Niwa et al. |
| 7,886,951 | B2 | 2/2011 | Hessler |
| 7,886,952 | B2 | 2/2011 | Scirica et al. |
| 7,887,530 | B2 | 2/2011 | Zemlok et al. |
| 7,887,535 | B2 | 2/2011 | Lands et al. |
| 7,887,536 | B2 | 2/2011 | Johnson et al. |
| 7,887,563 | B2 | 2/2011 | Cummins |
| 7,887,755 | B2 | 2/2011 | Mingerink et al. |
| 7,891,531 | B1 | 2/2011 | Ward |
| 7,891,532 | B2 | 2/2011 | Mastri et al. |
| 7,892,200 | B2 | 2/2011 | Birk et al. |
| 7,892,245 | B2 | 2/2011 | Liddicoat et al. |
| 7,893,586 | B2 | 2/2011 | West et al. |
| 7,896,214 | B2 | 3/2011 | Farascioni |
| 7,896,215 | B2 | 3/2011 | Adams et al. |
| 7,896,671 | B2 | 3/2011 | Kim et al. |
| 7,896,869 | B2 | 3/2011 | DiSilvestro et al. |
| 7,896,877 | B2 | 3/2011 | Hall et al. |
| 7,896,895 | B2 | 3/2011 | Boudreaux et al. |
| 7,896,897 | B2 | 3/2011 | Gresham et al. |
| 7,896,900 | B2 | 3/2011 | Frank et al. |
| 7,898,198 | B2 | 3/2011 | Murphree |
| 7,900,805 | B2 | 3/2011 | Shelton, IV et al. |
| 7,900,806 | B2 | 3/2011 | Chen et al. |
| 7,901,381 | B2 | 3/2011 | Birk et al. |
| 7,905,380 | B2 | 3/2011 | Shelton, IV et al. |
| 7,905,381 | B2 | 3/2011 | Baxter, III et al. |
| 7,905,881 | B2 | 3/2011 | Masuda et al. |
| 7,905,889 | B2 | 3/2011 | Catanese, III et al. |
| 7,905,890 | B2 | 3/2011 | Whitfield et al. |
| 7,905,902 | B2 | 3/2011 | Huitema et al. |
| 7,909,039 | B2 | 3/2011 | Hur |
| 7,909,191 | B2 | 3/2011 | Baker et al. |
| 7,909,220 | B2 | 3/2011 | Viola |
| 7,909,221 | B2 | 3/2011 | Viola et al. |
| 7,909,224 | B2 | 3/2011 | Prommersberger |
| 7,913,891 | B2 | 3/2011 | Doll et al. |
| 7,913,893 | B2 | 3/2011 | Mastri et al. |
| 7,914,521 | B2 | 3/2011 | Wang et al. |
| 7,914,543 | B2 | 3/2011 | Roth et al. |
| 7,914,551 | B2 | 3/2011 | Ortiz et al. |

(56) References Cited

U.S. PATENT DOCUMENTS

| | | | |
|---|---|---|---|
| 7,918,230 | B2 | 4/2011 | Whitman et al. |
| 7,918,376 | B1 | 4/2011 | Knodel et al. |
| 7,918,377 | B2 | 4/2011 | Measamer et al. |
| 7,918,845 | B2 | 4/2011 | Saadat et al. |
| 7,918,848 | B2 | 4/2011 | Lau et al. |
| 7,918,861 | B2 | 4/2011 | Brock et al. |
| 7,918,867 | B2 | 4/2011 | Dana et al. |
| 7,922,061 | B2 | 4/2011 | Shelton, IV et al. |
| 7,922,063 | B2 | 4/2011 | Zemlok et al. |
| 7,922,743 | B2 | 4/2011 | Heinrich et al. |
| 7,923,144 | B2 | 4/2011 | Kohn et al. |
| 7,926,691 | B2 | 4/2011 | Viola et al. |
| 7,926,692 | B2 | 4/2011 | Racenet et al. |
| 7,927,328 | B2 | 4/2011 | Orszulak et al. |
| 7,928,281 | B2 | 4/2011 | Augustine |
| 7,930,040 | B1 | 4/2011 | Kelsch et al. |
| 7,930,065 | B2 | 4/2011 | Larkin et al. |
| 7,931,660 | B2 | 4/2011 | Aranyi et al. |
| 7,931,695 | B2 | 4/2011 | Ringeisen |
| 7,931,877 | B2 | 4/2011 | Steffens et al. |
| 7,934,630 | B2 | 5/2011 | Shelton, IV et al. |
| 7,934,631 | B2 | 5/2011 | Balbierz et al. |
| 7,934,896 | B2 | 5/2011 | Schnier |
| 7,935,130 | B2 | 5/2011 | Williams |
| 7,935,773 | B2 | 5/2011 | Hadba et al. |
| 7,936,142 | B2 | 5/2011 | Otsuka et al. |
| 7,938,307 | B2 | 5/2011 | Bettuchi |
| 7,939,152 | B2 | 5/2011 | Haskin et al. |
| 7,941,865 | B2 | 5/2011 | Seman, Jr. et al. |
| 7,942,300 | B2 | 5/2011 | Rethy et al. |
| 7,942,303 | B2 | 5/2011 | Shah |
| 7,942,890 | B2 | 5/2011 | D'Agostino et al. |
| 7,944,175 | B2 | 5/2011 | Mori et al. |
| 7,945,792 | B2 | 5/2011 | Cherpantier |
| 7,945,798 | B2 | 5/2011 | Carlson et al. |
| 7,946,453 | B2 | 5/2011 | Voegele et al. |
| 7,947,011 | B2 | 5/2011 | Birk et al. |
| 7,948,381 | B2 | 5/2011 | Lindsay et al. |
| 7,950,560 | B2 | 5/2011 | Zemlok et al. |
| 7,950,561 | B2 | 5/2011 | Aranyi |
| 7,950,562 | B2 | 5/2011 | Beardsley et al. |
| 7,951,071 | B2 | 5/2011 | Whitman et al. |
| 7,951,166 | B2 | 5/2011 | Orban, III et al. |
| 7,952,464 | B2 | 5/2011 | Nikitin et al. |
| 7,954,682 | B2 | 6/2011 | Giordano et al. |
| 7,954,684 | B2 | 6/2011 | Boudreaux |
| 7,954,685 | B2 | 6/2011 | Viola |
| 7,954,686 | B2 | 6/2011 | Baxter, III et al. |
| 7,954,687 | B2 | 6/2011 | Zemlok et al. |
| 7,954,688 | B2 | 6/2011 | Argentine et al. |
| 7,955,253 | B2 | 6/2011 | Ewers et al. |
| 7,955,257 | B2 | 6/2011 | Frasier et al. |
| 7,955,322 | B2 | 6/2011 | Devengenzo et al. |
| 7,955,327 | B2 | 6/2011 | Sartor et al. |
| 7,955,380 | B2 | 6/2011 | Chu et al. |
| 7,959,050 | B2 | 6/2011 | Smith et al. |
| 7,959,051 | B2 | 6/2011 | Smith et al. |
| 7,959,052 | B2 | 6/2011 | Sonnenschein et al. |
| 7,963,432 | B2 | 6/2011 | Knodel et al. |
| 7,963,433 | B2 | 6/2011 | Whitman et al. |
| 7,963,913 | B2 | 6/2011 | Devengenzo et al. |
| 7,963,963 | B2 | 6/2011 | Francischelli et al. |
| 7,963,964 | B2 | 6/2011 | Santilli et al. |
| 7,964,206 | B2 | 6/2011 | Suokas et al. |
| 7,966,236 | B2 | 6/2011 | Noriega et al. |
| 7,966,269 | B2 | 6/2011 | Bauer et al. |
| 7,966,799 | B2 | 6/2011 | Morgan et al. |
| 7,967,178 | B2 | 6/2011 | Scirica et al. |
| 7,967,179 | B2 | 6/2011 | Olson et al. |
| 7,967,180 | B2 | 6/2011 | Scirica |
| 7,967,181 | B2 | 6/2011 | Viola et al. |
| 7,967,791 | B2 | 6/2011 | Franer et al. |
| 7,967,839 | B2 | 6/2011 | Flock et al. |
| 7,972,298 | B2 | 7/2011 | Wallace et al. |
| 7,972,315 | B2 | 7/2011 | Birk et al. |
| 7,976,213 | B2 | 7/2011 | Bertolotti et al. |
| 7,976,508 | B2 | 7/2011 | Hoag |
| 7,976,563 | B2 | 7/2011 | Summerer |
| 7,979,137 | B2 | 7/2011 | Tracey et al. |
| 7,980,443 | B2 | 7/2011 | Scheib et al. |
| 7,981,025 | B2 | 7/2011 | Pool et al. |
| 7,981,102 | B2 | 7/2011 | Patel et al. |
| 7,981,132 | B2 | 7/2011 | Dubrul et al. |
| 7,987,405 | B2 | 7/2011 | Turner et al. |
| 7,988,015 | B2 | 8/2011 | Mason, II et al. |
| 7,988,026 | B2 | 8/2011 | Knodel et al. |
| 7,988,027 | B2 | 8/2011 | Olson et al. |
| 7,988,028 | B2 | 8/2011 | Farascioni et al. |
| 7,988,779 | B2 | 8/2011 | Disalvo et al. |
| 7,992,757 | B2 | 8/2011 | Wheeler et al. |
| 7,993,360 | B2 | 8/2011 | Hacker et al. |
| 7,994,670 | B2 | 8/2011 | Ji |
| 7,997,054 | B2 | 8/2011 | Bertsch et al. |
| 7,997,468 | B2 | 8/2011 | Farascioni |
| 7,997,469 | B2 | 8/2011 | Olson et al. |
| 8,002,696 | B2 | 8/2011 | Suzuki |
| 8,002,784 | B2 | 8/2011 | Jinno et al. |
| 8,002,785 | B2 | 8/2011 | Weiss et al. |
| 8,002,795 | B2 | 8/2011 | Beetel |
| 8,006,365 | B2 | 8/2011 | Levin et al. |
| 8,006,885 | B2 | 8/2011 | Marczyk |
| 8,006,889 | B2 | 8/2011 | Adams et al. |
| 8,007,370 | B2 | 8/2011 | Hirsch et al. |
| 8,007,465 | B2 | 8/2011 | Birk et al. |
| 8,007,479 | B2 | 8/2011 | Birk et al. |
| 8,007,511 | B2 | 8/2011 | Brock et al. |
| 8,007,513 | B2 | 8/2011 | Nalagatla et al. |
| 8,008,598 | B2 | 8/2011 | Whitman et al. |
| 8,010,180 | B2 | 8/2011 | Quaid et al. |
| 8,011,550 | B2 | 9/2011 | Aranyi et al. |
| 8,011,551 | B2 | 9/2011 | Marczyk et al. |
| 8,011,553 | B2 | 9/2011 | Mastri et al. |
| 8,011,555 | B2 | 9/2011 | Tarinelli et al. |
| 8,012,170 | B2 | 9/2011 | Whitman et al. |
| 8,016,176 | B2 | 9/2011 | Kasvikis et al. |
| 8,016,177 | B2 | 9/2011 | Bettuchi et al. |
| 8,016,178 | B2 | 9/2011 | Olson et al. |
| 8,016,849 | B2 | 9/2011 | Wenchell |
| 8,016,855 | B2 | 9/2011 | Whitman et al. |
| 8,016,858 | B2 | 9/2011 | Whitman |
| 8,016,881 | B2 | 9/2011 | Furst |
| 8,020,742 | B2 | 9/2011 | Marczyk |
| 8,020,743 | B2 | 9/2011 | Shelton, IV |
| 8,021,375 | B2 | 9/2011 | Aldrich et al. |
| 8,025,199 | B2 | 9/2011 | Whitman et al. |
| 8,025,896 | B2 | 9/2011 | Malaviya et al. |
| 8,028,835 | B2 | 10/2011 | Yasuda et al. |
| 8,028,882 | B2 | 10/2011 | Viola |
| 8,028,883 | B2 | 10/2011 | Stopek |
| 8,028,884 | B2 | 10/2011 | Sniffin et al. |
| 8,028,885 | B2 | 10/2011 | Smith et al. |
| 8,029,510 | B2 | 10/2011 | Hoegerle |
| 8,031,069 | B2 | 10/2011 | Cohn et al. |
| 8,033,438 | B2 | 10/2011 | Scirica |
| 8,033,439 | B2 | 10/2011 | Racenet et al. |
| 8,033,440 | B2 | 10/2011 | Wenchell et al. |
| 8,033,442 | B2 | 10/2011 | Racenet et al. |
| 8,034,077 | B2 | 10/2011 | Smith et al. |
| 8,034,337 | B2 | 10/2011 | Simard |
| 8,034,363 | B2 | 10/2011 | Li et al. |
| 8,035,487 | B2 | 10/2011 | Malackowski |
| 8,037,591 | B2 | 10/2011 | Spivey et al. |
| 8,038,044 | B2 | 10/2011 | Viola |
| 8,038,045 | B2 | 10/2011 | Bettuchi et al. |
| 8,038,046 | B2 | 10/2011 | Smith et al. |
| 8,038,686 | B2 | 10/2011 | Huitema et al. |
| 8,043,207 | B2 | 10/2011 | Adams |
| 8,043,328 | B2 | 10/2011 | Hahnen et al. |
| 8,044,536 | B2 | 10/2011 | Nguyen et al. |
| 8,044,604 | B2 | 10/2011 | Hagino et al. |
| 8,047,236 | B2 | 11/2011 | Perry |
| 8,048,503 | B2 | 11/2011 | Farnsworth et al. |
| 8,052,636 | B2 | 11/2011 | Moll et al. |
| 8,056,787 | B2 | 11/2011 | Boudreaux et al. |

(56) References Cited

U.S. PATENT DOCUMENTS

| | | | |
|---|---|---|---|
| 8,056,788 | B2 | 11/2011 | Mastri et al. |
| 8,056,789 | B1 | 11/2011 | White et al. |
| 8,057,508 | B2 | 11/2011 | Shelton, IV |
| 8,058,771 | B2 | 11/2011 | Giordano et al. |
| 8,060,250 | B2 | 11/2011 | Reiland et al. |
| 8,061,014 | B2 | 11/2011 | Smith et al. |
| 8,061,576 | B2 | 11/2011 | Cappola |
| 8,062,236 | B2 | 11/2011 | Soltz |
| 8,062,306 | B2 | 11/2011 | Nobis et al. |
| 8,062,330 | B2 | 11/2011 | Prommersberger et al. |
| 8,063,619 | B2 | 11/2011 | Zhu et al. |
| 8,066,158 | B2 | 11/2011 | Vogel et al. |
| 8,066,166 | B2 | 11/2011 | Demmy et al. |
| 8,066,167 | B2 | 11/2011 | Measamer et al. |
| 8,066,168 | B2 | 11/2011 | Vidal et al. |
| 8,066,720 | B2 | 11/2011 | Knodel et al. |
| D650,074 | S | 12/2011 | Hunt et al. |
| D650,789 | S | 12/2011 | Arnold |
| 8,070,033 | B2 | 12/2011 | Milliman et al. |
| 8,070,034 | B1 | 12/2011 | Knodel |
| 8,070,035 | B2 | 12/2011 | Holsten et al. |
| 8,070,743 | B2 | 12/2011 | Kagan et al. |
| 8,074,858 | B2 | 12/2011 | Marczyk |
| 8,074,859 | B2 | 12/2011 | Kostrzewski |
| 8,074,861 | B2 | 12/2011 | Ehrenfels et al. |
| 8,075,476 | B2 | 12/2011 | Vargas |
| 8,075,571 | B2 | 12/2011 | Vitali et al. |
| 8,079,950 | B2 | 12/2011 | Stern et al. |
| 8,079,989 | B2 | 12/2011 | Birk et al. |
| 8,080,004 | B2 | 12/2011 | Downey et al. |
| 8,083,118 | B2 | 12/2011 | Milliman et al. |
| 8,083,119 | B2 | 12/2011 | Prommersberger |
| 8,083,120 | B2 | 12/2011 | Shelton, IV et al. |
| 8,084,001 | B2 | 12/2011 | Burns et al. |
| 8,084,969 | B2 | 12/2011 | David et al. |
| 8,085,013 | B2 | 12/2011 | Wei et al. |
| 8,087,562 | B1 | 1/2012 | Manoux et al. |
| 8,087,563 | B2 | 1/2012 | Milliman et al. |
| 8,089,509 | B2 | 1/2012 | Chatenever et al. |
| 8,091,753 | B2 | 1/2012 | Viola |
| 8,091,756 | B2 | 1/2012 | Viola |
| 8,092,443 | B2 | 1/2012 | Bischoff |
| 8,092,932 | B2 | 1/2012 | Phillips et al. |
| 8,093,572 | B2 | 1/2012 | Kuduvalli |
| 8,096,458 | B2 | 1/2012 | Hessler |
| 8,096,459 | B2 | 1/2012 | Ortiz et al. |
| 8,097,017 | B2 | 1/2012 | Viola |
| 8,100,310 | B2 | 1/2012 | Zemlok |
| 8,100,824 | B2 | 1/2012 | Hegeman et al. |
| 8,100,872 | B2 | 1/2012 | Patel |
| 8,102,138 | B2 | 1/2012 | Sekine et al. |
| 8,102,278 | B2 | 1/2012 | Deck et al. |
| 8,105,320 | B2 | 1/2012 | Manzo |
| 8,105,350 | B2 | 1/2012 | Lee et al. |
| 8,107,925 | B2 | 1/2012 | Natsuno et al. |
| 8,108,033 | B2 | 1/2012 | Drew et al. |
| 8,108,072 | B2 | 1/2012 | Zhao et al. |
| 8,109,426 | B2 | 2/2012 | Milliman et al. |
| 8,110,208 | B1 | 2/2012 | Hen |
| 8,113,405 | B2 | 2/2012 | Milliman |
| 8,113,407 | B2 | 2/2012 | Holsten et al. |
| 8,113,408 | B2 | 2/2012 | Wenchell et al. |
| 8,113,410 | B2 | 2/2012 | Hall et al. |
| 8,114,017 | B2 | 2/2012 | Bacher |
| 8,114,100 | B2 | 2/2012 | Smith et al. |
| 8,114,345 | B2 | 2/2012 | Dlugos, Jr. et al. |
| 8,118,206 | B2 | 2/2012 | Zand et al. |
| 8,118,207 | B2 | 2/2012 | Racenet et al. |
| 8,120,301 | B2 | 2/2012 | Goldberg et al. |
| 8,122,128 | B2 | 2/2012 | Burke, II et al. |
| 8,123,103 | B2 | 2/2012 | Milliman |
| 8,123,523 | B2 | 2/2012 | Carron et al. |
| 8,123,766 | B2 | 2/2012 | Bauman et al. |
| 8,123,767 | B2 | 2/2012 | Bauman et al. |
| 8,125,168 | B2 | 2/2012 | Johnson et al. |
| 8,127,975 | B2 | 3/2012 | Olson et al. |
| 8,127,976 | B2 | 3/2012 | Scirica et al. |
| 8,128,624 | B2 | 3/2012 | Couture et al. |
| 8,128,643 | B2 | 3/2012 | Aranyi et al. |
| 8,128,645 | B2 | 3/2012 | Sonnenschein et al. |
| 8,128,662 | B2 | 3/2012 | Altarac et al. |
| 8,132,703 | B2 | 3/2012 | Milliman et al. |
| 8,132,705 | B2 | 3/2012 | Viola et al. |
| 8,132,706 | B2 | 3/2012 | Marczyk et al. |
| 8,133,500 | B2 | 3/2012 | Ringeisen et al. |
| 8,134,306 | B2 | 3/2012 | Drader et al. |
| 8,136,711 | B2 | 3/2012 | Beardsley et al. |
| 8,136,712 | B2 | 3/2012 | Zingman |
| 8,136,713 | B2 | 3/2012 | Hathaway et al. |
| 8,137,339 | B2 | 3/2012 | Jinno et al. |
| 8,140,417 | B2 | 3/2012 | Shibata |
| 8,141,762 | B2 | 3/2012 | Bedi et al. |
| 8,141,763 | B2 | 3/2012 | Milliman |
| 8,142,200 | B2 | 3/2012 | Crunkilton et al. |
| 8,142,425 | B2 | 3/2012 | Eggers |
| 8,142,461 | B2 | 3/2012 | Houser et al. |
| 8,142,515 | B2 | 3/2012 | Therin et al. |
| 8,143,520 | B2 | 3/2012 | Cutler |
| 8,146,790 | B2 | 4/2012 | Milliman |
| 8,147,421 | B2 | 4/2012 | Farquhar et al. |
| 8,147,456 | B2 | 4/2012 | Fisher et al. |
| 8,147,485 | B2 | 4/2012 | Wham et al. |
| 8,152,041 | B2 | 4/2012 | Kostrzewski |
| 8,152,756 | B2 | 4/2012 | Webster et al. |
| 8,154,239 | B2 | 4/2012 | Katsuki et al. |
| 8,157,145 | B2 | 4/2012 | Shelton, IV et al. |
| 8,157,148 | B2 | 4/2012 | Scirica |
| 8,157,151 | B2 | 4/2012 | Ingmanson et al. |
| 8,157,152 | B2 | 4/2012 | Holsten et al. |
| 8,157,153 | B2 | 4/2012 | Shelton, IV et al. |
| 8,157,793 | B2 | 4/2012 | Omori et al. |
| 8,157,834 | B2 | 4/2012 | Conlon |
| 8,161,977 | B2 | 4/2012 | Shelton, IV et al. |
| 8,162,138 | B2 | 4/2012 | Bettenhausen et al. |
| 8,162,197 | B2 | 4/2012 | Mastri et al. |
| 8,162,668 | B2 | 4/2012 | Toly |
| 8,162,933 | B2 | 4/2012 | Francischelli et al. |
| 8,162,965 | B2 | 4/2012 | Reschke et al. |
| 8,167,185 | B2 | 5/2012 | Shelton, IV et al. |
| 8,167,622 | B2 | 5/2012 | Zhou |
| 8,167,895 | B2 | 5/2012 | D'Agostino et al. |
| 8,167,898 | B1 | 5/2012 | Schaller et al. |
| 8,170,241 | B2 | 5/2012 | Roe et al. |
| 8,172,004 | B2 | 5/2012 | Ho |
| 8,172,120 | B2 | 5/2012 | Boyden et al. |
| 8,172,122 | B2 | 5/2012 | Kasvikis et al. |
| 8,172,124 | B2 | 5/2012 | Shelton, IV et al. |
| 8,177,776 | B2 | 5/2012 | Humayun et al. |
| 8,177,797 | B2 | 5/2012 | Shimoji et al. |
| 8,179,705 | B2 | 5/2012 | Chapuis |
| 8,180,458 | B2 | 5/2012 | Kane et al. |
| 8,181,839 | B2 | 5/2012 | Beetel |
| 8,181,840 | B2 | 5/2012 | Milliman |
| 8,182,422 | B2 | 5/2012 | Bayer et al. |
| 8,182,444 | B2 | 5/2012 | Uber, III et al. |
| 8,183,807 | B2 | 5/2012 | Tsai et al. |
| 8,186,555 | B2 | 5/2012 | Shelton, IV et al. |
| 8,186,556 | B2 | 5/2012 | Viola |
| 8,186,558 | B2 | 5/2012 | Sapienza |
| 8,186,560 | B2 | 5/2012 | Hess et al. |
| 8,190,238 | B2 | 5/2012 | Moll et al. |
| 8,191,752 | B2 | 6/2012 | Scirica |
| 8,192,350 | B2 | 6/2012 | Ortiz et al. |
| 8,192,460 | B2 | 6/2012 | Orban, III et al. |
| 8,192,651 | B2 | 6/2012 | Young et al. |
| 8,193,129 | B2 | 6/2012 | Tagawa et al. |
| 8,196,795 | B2 | 6/2012 | Moore et al. |
| 8,196,796 | B2 | 6/2012 | Shelton, IV et al. |
| 8,197,501 | B2 | 6/2012 | Shadeck et al. |
| 8,197,502 | B2 | 6/2012 | Smith et al. |
| 8,197,837 | B2 | 6/2012 | Jamiolkowski et al. |
| 8,201,720 | B2 | 6/2012 | Hessler |
| 8,201,721 | B2 | 6/2012 | Zemlok et al. |
| 8,202,549 | B2 | 6/2012 | Stucky et al. |

(56) References Cited

U.S. PATENT DOCUMENTS 8,205,779 B2 6/2012 Ma et al.
8,205,780 B2 6/2012 Sorrentino et al.
8,205,781 B2 6/2012 Baxter, III et al.
8,207,863 B2 6/2012 Neubauer et al.
8,210,411 B2 7/2012 Yates et al.
8,210,414 B2 7/2012 Bettuchi et al.
8,210,415 B2 7/2012 Ward
8,210,416 B2 7/2012 Milliman et al.
8,210,721 B2 7/2012 Chen et al.
8,211,125 B2 7/2012 Spivey
8,214,019 B2 7/2012 Govari et al.
8,215,531 B2 7/2012 Shelton, IV et al.
8,215,532 B2 7/2012 Marczyk
8,215,533 B2 7/2012 Viola et al.
8,220,468 B2 7/2012 Cooper et al.
8,220,688 B2 7/2012 Laurent et al.
8,220,690 B2 7/2012 Hess et al.
8,221,402 B2 7/2012 Francischelli et al.
8,221,424 B2 7/2012 Cha
8,221,433 B2 7/2012 Lozier et al.
8,225,799 B2 7/2012 Bettuchi
8,225,979 B2 7/2012 Farascioni et al.
8,226,553 B2 7/2012 Shelton, IV et al.
8,226,635 B2 7/2012 Petrie et al.
8,226,675 B2 7/2012 Houser et al.
8,226,715 B2 7/2012 Hwang et al.
8,227,946 B2 7/2012 Kim
8,228,020 B2 7/2012 Shin et al.
8,228,048 B2 7/2012 Spencer
8,229,549 B2 7/2012 Whitman et al.
8,231,040 B2 7/2012 Zemlok et al.
8,231,042 B2 7/2012 Hessler et al.
8,231,043 B2 7/2012 Tarinelli et al.
8,235,272 B2 8/2012 Nicholas et al.
8,235,274 B2 8/2012 Cappola
8,236,010 B2 8/2012 Ortiz et al.
8,236,011 B2 8/2012 Harris et al.
8,236,020 B2 8/2012 Smith et al.
8,237,388 B2 8/2012 Jinno et al.
8,240,537 B2 8/2012 Marczyk
8,241,271 B2 8/2012 Millman et al.
8,241,284 B2 8/2012 Dycus et al.
8,241,308 B2 8/2012 Kortenbach et al.
8,241,322 B2 8/2012 Whitman et al.
8,245,594 B2 8/2012 Rogers et al.
8,245,898 B2 8/2012 Smith et al.
8,245,899 B2 8/2012 Swensgard et al.
8,245,900 B2 8/2012 Scirica
8,245,901 B2 8/2012 Stopek
8,246,608 B2 8/2012 Omori et al.
8,246,637 B2 8/2012 Viola et al.
8,252,009 B2 8/2012 Weller et al.
8,256,654 B2 9/2012 Bettuchi et al.
8,256,655 B2 9/2012 Sniffin et al.
8,256,656 B2 9/2012 Milliman et al.
8,257,251 B2 9/2012 Shelton, IV et al.
8,257,356 B2 9/2012 Bleich et al.
8,257,386 B2 9/2012 Lee et al.
8,257,391 B2 9/2012 Orban, III et al.
8,257,634 B2 9/2012 Scirica
8,258,745 B2 9/2012 Smith et al.
8,261,958 B1 9/2012 Knodel
8,262,560 B2 9/2012 Whitman
8,262,655 B2 9/2012 Ghabrial et al.
8,266,232 B2 9/2012 Piper et al.
8,267,300 B2 9/2012 Boudreaux
8,267,849 B2 9/2012 Wazer et al.
8,267,924 B2 9/2012 Zemlok et al.
8,267,946 B2 9/2012 Whitfield et al.
8,267,951 B2 9/2012 Whayne et al.
8,268,344 B2 9/2012 Ma et al.
8,269,121 B2 9/2012 Smith
8,272,553 B2 9/2012 Mastri et al.
8,272,554 B2 9/2012 Whitman et al.
8,272,918 B2 9/2012 Lam
8,273,404 B2 9/2012 Dave et al.
8,276,594 B2 10/2012 Shah
8,276,801 B2 10/2012 Zemlok et al.
8,276,802 B2 10/2012 Kostrzewski
8,277,473 B2 10/2012 Sunaoshi et al.
8,281,446 B2 10/2012 Moskovich
8,281,973 B2 10/2012 Wenchell et al.
8,281,974 B2 10/2012 Hessler et al.
8,282,654 B2 10/2012 Ferrari et al.
8,285,367 B2 10/2012 Hyde et al.
8,286,723 B2 10/2012 Puzio et al.
8,286,845 B2 10/2012 Perry et al.
8,286,846 B2 10/2012 Smith et al.
8,286,847 B2 10/2012 Taylor
8,287,487 B2 10/2012 Estes
8,287,522 B2 10/2012 Moses et al.
8,287,561 B2 10/2012 Nunez et al.
8,288,984 B2 10/2012 Yang
8,289,403 B2 10/2012 Dobashi et al.
8,290,883 B2 10/2012 Takeuchi et al.
8,292,147 B2 10/2012 Viola
8,292,148 B2 10/2012 Viola
8,292,150 B2 10/2012 Bryant
8,292,151 B2 10/2012 Viola
8,292,152 B2 10/2012 Milliman et al.
8,292,155 B2 10/2012 Shelton, IV et al.
8,292,157 B2 10/2012 Smith et al.
8,292,158 B2 10/2012 Sapienza
8,292,801 B2 10/2012 Dejima et al.
8,292,888 B2 10/2012 Whitman
8,292,906 B2 10/2012 Taylor et al.
8,294,399 B2 10/2012 Suzuki et al.
8,298,161 B2 10/2012 Vargas
8,298,189 B2 10/2012 Fisher et al.
8,298,233 B2 10/2012 Mueller
8,298,677 B2 10/2012 Wiesner et al.
8,302,323 B2 11/2012 Fortier et al.
8,303,621 B2 11/2012 Miyamoto et al.
8,308,040 B2 11/2012 Huang et al.
8,308,041 B2 11/2012 Kostrzewski
8,308,042 B2 11/2012 Aranyi
8,308,043 B2 11/2012 Bindra et al.
8,308,046 B2 11/2012 Prommersberger
8,308,659 B2 11/2012 Scheibe et al.
8,308,725 B2 11/2012 Bell et al.
8,310,188 B2 11/2012 Nakai
8,313,496 B2 11/2012 Sauer et al.
8,313,499 B2 11/2012 Magnusson et al.
8,313,509 B2 11/2012 Kostrzewski
8,317,070 B2 11/2012 Hueil et al.
8,317,071 B1 11/2012 Knodel
8,317,074 B2 11/2012 Ortiz et al.
8,317,437 B2 11/2012 Merkley et al.
8,317,744 B2 11/2012 Kirschenman
8,317,790 B2 11/2012 Bell et al.
8,319,002 B2 11/2012 Daniels et al.
D672,784 S 12/2012 Clanton et al.
8,322,455 B2 12/2012 Shelton, IV et al.
8,322,589 B2 12/2012 Boudreaux
8,322,590 B2 12/2012 Patel et al.
8,322,901 B2 12/2012 Michelotti
8,323,271 B2 12/2012 Humayun et al.
8,323,789 B2 12/2012 Rozhin et al.
8,324,585 B2 12/2012 McBroom et al.
8,327,514 B2 12/2012 Kim
8,328,061 B2 12/2012 Kasvikis
8,328,062 B2 12/2012 Viola
8,328,063 B2 12/2012 Milliman et al.
8,328,064 B2 12/2012 Racenet et al.
8,328,065 B2 12/2012 Shah
8,328,802 B2 12/2012 Deville et al.
8,328,823 B2 12/2012 Aranyi et al.
8,333,313 B2 12/2012 Boudreaux et al.
8,333,691 B2 12/2012 Schaaf
8,333,764 B2 12/2012 Francischelli et al.
8,333,779 B2 12/2012 Smith et al.
8,334,468 B2 12/2012 Palmer et al.
8,336,753 B2 12/2012 Olson et al.
8,336,754 B2 12/2012 Cappola et al.

(56) References Cited

U.S. PATENT DOCUMENTS 8,342,377 B2 1/2013 Milliman et al.
8,342,378 B2 1/2013 Marczyk et al.
8,342,379 B2 1/2013 Whitman et al.
8,342,380 B2 1/2013 Viola
8,343,150 B2 1/2013 Artale
8,347,978 B2 1/2013 Forster et al.
8,348,118 B2 1/2013 Segura
8,348,123 B2 1/2013 Scirica et al.
8,348,124 B2 1/2013 Scirica
8,348,125 B2 1/2013 Viola et al.
8,348,126 B2 1/2013 Olson et al.
8,348,127 B2 1/2013 Marczyk
8,348,129 B2 1/2013 Bedi et al.
8,348,130 B2 1/2013 Shah et al.
8,348,131 B2 1/2013 Omaits et al.
8,348,837 B2 1/2013 Wenchell
8,348,959 B2 1/2013 Wolford et al.
8,348,972 B2 1/2013 Soltz et al.
8,349,987 B2 1/2013 Kapiamba et al.
8,352,004 B2 1/2013 Mannheimer et al.
8,353,437 B2 1/2013 Boudreaux
8,353,438 B2 1/2013 Baxter, III et al.
8,353,439 B2 1/2013 Baxter, III et al.
8,356,740 B1 1/2013 Knodel
8,357,144 B2 1/2013 Whitman et al.
8,357,158 B2 1/2013 McKenna et al.
8,357,161 B2 1/2013 Mueller
8,359,174 B2 1/2013 Nakashima et al.
8,360,296 B2 1/2013 Zingman
8,360,297 B2 1/2013 Shelton, IV et al.
8,360,298 B2 1/2013 Farascioni et al.
8,360,299 B2 1/2013 Zemlok et al.
8,361,501 B2 1/2013 DiTizio et al.
D676,866 S 2/2013 Chaudhri
8,365,972 B2 2/2013 Aranyi et al.
8,365,973 B1 2/2013 White et al.
8,365,975 B1 2/2013 Manoux et al.
8,365,976 B2 2/2013 Hess et al.
8,366,559 B2 2/2013 Papenfuss et al.
8,366,719 B2 2/2013 Markey et al.
8,366,787 B2 2/2013 Brown et al.
8,368,327 B2 2/2013 Benning et al.
8,369,056 B2 2/2013 Senriuchi et al.
8,371,393 B2 2/2013 Higuchi et al.
8,371,491 B2 2/2013 Huitema et al.
8,371,492 B2 2/2013 Aranyi et al.
8,371,493 B2 2/2013 Aranyi et al.
8,371,494 B2 2/2013 Racenet et al.
8,372,094 B2 2/2013 Bettuchi et al.
8,374,723 B2 2/2013 Zhao et al.
8,376,865 B2 2/2013 Forster et al.
8,377,029 B2 2/2013 Nagao et al.
8,377,044 B2 2/2013 Coe et al.
8,377,059 B2 2/2013 Deville et al.
8,381,828 B2 2/2013 Whitman et al.
8,382,773 B2 2/2013 Whitfield et al.
8,382,790 B2 2/2013 Uenohara et al.
D677,273 S 3/2013 Randall et al.
8,387,848 B2 3/2013 Johnson et al.
8,388,633 B2 3/2013 Rousseau et al.
8,389,588 B2 3/2013 Ringeisen et al.
8,393,513 B2 3/2013 Jankowski
8,393,514 B2 3/2013 Shelton, IV et al.
8,393,516 B2 3/2013 Kostrzewski
8,397,832 B2 3/2013 Blickle et al.
8,397,971 B2 3/2013 Yates et al.
8,397,972 B2 3/2013 Kostrzewski
8,397,973 B1 3/2013 Hausen
8,398,633 B2 3/2013 Mueller
8,398,669 B2 3/2013 Kim
8,398,673 B2 3/2013 Hinchliffe et al.
8,398,674 B2 3/2013 Prestel
8,400,108 B2 3/2013 Powell et al.
8,400,851 B2 3/2013 Byun
8,403,138 B2 3/2013 Weisshaupt et al.
8,403,195 B2 3/2013 Beardsley et al.
8,403,196 B2 3/2013 Beardsley et al.
8,403,198 B2 3/2013 Sorrentino et al.
8,403,832 B2 3/2013 Cunningham et al.
8,403,926 B2 3/2013 Nobis et al.
8,403,945 B2 3/2013 Whitfield et al.
8,403,946 B2 3/2013 Whitfield et al.
8,403,950 B2 3/2013 Palmer et al.
D680,646 S 4/2013 Hunt et al.
8,408,439 B2 4/2013 Huang et al.
8,408,442 B2 4/2013 Racenet et al.
8,409,079 B2 4/2013 Okamoto et al.
8,409,174 B2 4/2013 Omori
8,409,175 B2 4/2013 Lee et al.
8,409,211 B2 4/2013 Baroud
8,409,222 B2 4/2013 Whitfield et al.
8,409,223 B2 4/2013 Sorrentino et al.
8,409,234 B2 4/2013 Stahler et al.
8,411,500 B2 4/2013 Gapihan et al.
8,413,661 B2 4/2013 Rousseau et al.
8,413,870 B2 4/2013 Pastorelli et al.
8,413,871 B2 4/2013 Racenet et al.
8,413,872 B2 4/2013 Patel
8,414,469 B2 4/2013 Diolaiti
8,414,577 B2 4/2013 Boudreaux et al.
8,414,598 B2 4/2013 Brock et al.
8,418,073 B2 4/2013 Mohr et al.
8,418,906 B2 4/2013 Farascioni et al.
8,418,907 B2 4/2013 Johnson et al.
8,418,908 B1 4/2013 Beardsley
8,418,909 B2 4/2013 Kostrzewski
8,419,635 B2 4/2013 Shelton, IV et al.
8,419,717 B2 4/2013 Diolaiti et al.
8,419,747 B2 4/2013 Hinman et al.
8,419,754 B2 4/2013 Laby et al.
8,419,755 B2 4/2013 Deem et al.
8,423,182 B2 4/2013 Robinson et al.
8,424,737 B2 4/2013 Scirica
8,424,739 B2 4/2013 Racenet et al.
8,424,740 B2 4/2013 Shelton, IV et al.
8,424,741 B2 4/2013 McGuckin, Jr. et al.
8,425,600 B2 4/2013 Maxwell
8,427,430 B2 4/2013 Lee et al.
8,430,292 B2 4/2013 Patel et al.
8,430,892 B2 4/2013 Bindra et al.
8,430,898 B2 4/2013 Wiener et al.
8,435,257 B2 5/2013 Smith et al.
8,439,246 B1 5/2013 Knodel
8,439,830 B2 5/2013 McKinley et al.
8,444,036 B2 5/2013 Shelton, IV
8,444,037 B2 5/2013 Nicholas et al.
8,444,549 B2 5/2013 Viola et al.
8,449,536 B2 5/2013 Selig
8,449,560 B2 5/2013 Roth et al.
8,453,904 B2 6/2013 Eskaros et al.
8,453,906 B2 6/2013 Huang et al.
8,453,907 B2 6/2013 Laurent et al.
8,453,908 B2 6/2013 Bedi et al.
8,453,912 B2 6/2013 Mastri et al.
8,453,914 B2 6/2013 Laurent et al.
8,454,495 B2 6/2013 Kawano et al.
8,454,551 B2 6/2013 Allen et al.
8,454,628 B2 6/2013 Smith et al.
8,454,640 B2 6/2013 Johnston et al.
8,457,757 B2 6/2013 Cauller et al.
8,459,520 B2 6/2013 Giordano et al.
8,459,521 B2 6/2013 Zemlok et al.
8,459,524 B2 6/2013 Pribanic et al.
8,459,525 B2 6/2013 Yates et al.
8,464,922 B2 6/2013 Marczyk
8,464,923 B2 6/2013 Shelton, IV
8,464,924 B2 6/2013 Gresham et al.
8,464,925 B2 6/2013 Hull et al.
8,465,475 B2 6/2013 Isbell, Jr.
8,465,502 B2 6/2013 Zergiebel
8,465,515 B2 6/2013 Drew et al.
8,469,254 B2 6/2013 Czernik et al.
8,469,946 B2 6/2013 Sugita
8,469,973 B2 6/2013 Meade et al.

(56) References Cited

U.S. PATENT DOCUMENTS 8,470,355 B2 6/2013 Skalla et al.
D686,240 S 7/2013 Lin
D686,244 S 7/2013 Moriya et al.
8,474,677 B2 7/2013 Woodard, Jr. et al.
8,475,453 B2 7/2013 Marczyk et al.
8,475,454 B1 7/2013 Alshemari
8,475,474 B2 7/2013 Bombard et al.
8,479,968 B2 7/2013 Hodgkinson et al.
8,479,969 B2 7/2013 Shelton, IV
8,480,703 B2 7/2013 Nicholas et al.
8,483,509 B2 7/2013 Matsuzaka
8,485,412 B2 7/2013 Shelton, IV et al.
8,485,413 B2 7/2013 Scheib et al.
8,485,970 B2 7/2013 Widenhouse et al.
8,486,047 B2 7/2013 Stopek
8,487,199 B2 7/2013 Palmer et al.
8,487,487 B2 7/2013 Dietz et al.
8,490,851 B2 7/2013 Blier et al.
8,490,852 B2 7/2013 Viola
8,490,853 B2 7/2013 Criscuolo et al.
8,491,581 B2 7/2013 Deville et al.
8,491,603 B2 7/2013 Yeung et al.
8,496,153 B2 7/2013 Demmy et al.
8,496,154 B2 7/2013 Marczyk et al.
8,496,156 B2 7/2013 Sniffin et al.
8,496,683 B2 7/2013 Prommersberger et al.
8,498,691 B2 7/2013 Moll et al.
8,499,673 B2 8/2013 Keller
8,499,966 B2 8/2013 Palmer et al.
8,499,992 B2 8/2013 Whitman et al.
8,499,993 B2 8/2013 Shelton, IV et al.
8,499,994 B2 8/2013 D'Arcangelo
8,500,721 B2 8/2013 Jinno
8,500,762 B2 8/2013 Sholev et al.
8,502,091 B2 8/2013 Palmer et al.
8,505,799 B2 8/2013 Viola et al.
8,505,801 B2 8/2013 Ehrenfels et al.
8,506,555 B2 8/2013 Ruiz Morales
8,506,557 B2 8/2013 Zemlok et al.
8,506,580 B2 8/2013 Zergiebel et al.
8,506,581 B2 8/2013 Wingardner, III et al.
8,511,308 B2 8/2013 Hecox et al.
8,512,359 B2 8/2013 Whitman et al.
8,512,402 B2 8/2013 Marczyk et al.
8,517,239 B2 8/2013 Scheib et al.
8,517,241 B2 8/2013 Nicholas et al.
8,517,243 B2 8/2013 Giordano et al.
8,517,244 B2 8/2013 Shelton, IV et al.
8,517,938 B2 8/2013 Eisenhardt et al.
8,518,024 B2 8/2013 Williams et al.
8,521,273 B2 8/2013 Kliman
8,523,042 B2 9/2013 Masiakos et al.
8,523,043 B2 9/2013 Ullrich et al.
8,523,787 B2 9/2013 Ludwin et al.
8,523,881 B2 9/2013 Cabiri et al.
8,523,882 B2 9/2013 Huitema et al.
8,523,900 B2 9/2013 Jinno et al.
8,529,588 B2 9/2013 Ahlberg et al.
8,529,599 B2 9/2013 Holsten
8,529,600 B2 9/2013 Woodard, Jr. et al.
8,529,819 B2 9/2013 Ostapoff et al.
8,532,747 B2 9/2013 Nock et al.
8,534,527 B2 9/2013 Brendel et al.
8,534,528 B2 9/2013 Shelton, IV
8,535,304 B2 9/2013 Sklar et al.
8,535,340 B2 9/2013 Allen
8,539,866 B2 9/2013 Nayak et al.
8,540,128 B2 9/2013 Shelton, IV et al.
8,540,129 B2 9/2013 Baxter, III et al.
8,540,130 B2 9/2013 Moore et al.
8,540,131 B2 9/2013 Swayze
8,540,133 B2 9/2013 Bedi et al.
8,540,646 B2 9/2013 Mendez-Coll
8,540,733 B2 9/2013 Whitman et al.
8,540,735 B2 9/2013 Mitelberg et al.
8,550,984 B2 10/2013 Takemoto
8,551,076 B2 10/2013 Duval et al.
8,555,660 B2 10/2013 Takenaka et al.
8,556,151 B2 10/2013 Viola
8,556,918 B2 10/2013 Bauman et al.
8,556,935 B1 10/2013 Knodel et al.
8,560,147 B2 10/2013 Taylor et al.
8,561,617 B2 10/2013 Lindh et al.
8,561,870 B2 10/2013 Baxter, III et al.
8,561,871 B2 10/2013 Rajappa et al.
8,561,873 B2 10/2013 Ingmanson et al.
8,562,592 B2 10/2013 Conlon et al.
8,562,598 B2 10/2013 Falkenstein et al.
8,567,656 B2 10/2013 Shelton, IV et al.
8,568,416 B2 10/2013 Schmitz et al.
8,568,425 B2 10/2013 Ross et al.
D692,916 S 11/2013 Granchi et al.
8,573,459 B2 11/2013 Smith et al.
8,573,461 B2 11/2013 Shelton, IV et al.
8,573,462 B2 11/2013 Smith et al.
8,573,465 B2 11/2013 Shelton, IV
8,574,199 B2 11/2013 von Bulow et al.
8,574,263 B2 11/2013 Mueller
8,575,880 B2 11/2013 Grantz
8,575,895 B2 11/2013 Garrastacho et al.
8,579,176 B2 11/2013 Smith et al.
8,579,178 B2 11/2013 Holsten et al.
8,579,897 B2 11/2013 Vakharia et al.
8,579,937 B2 11/2013 Gresham
8,584,919 B2 11/2013 Hueil et al.
8,584,920 B2 11/2013 Hodgkinson
8,584,921 B2 11/2013 Scirica
8,585,583 B2 11/2013 Sakaguchi et al.
8,585,598 B2 11/2013 Razzaque et al.
8,585,721 B2 11/2013 Kirsch
8,590,760 B2 11/2013 Cummins et al.
8,590,762 B2 11/2013 Hess et al.
8,590,764 B2 11/2013 Hartwick et al.
8,591,400 B2 11/2013 Sugiyama
8,596,515 B2 12/2013 Okoniewski
8,597,745 B2 12/2013 Farnsworth et al.
8,599,450 B2 12/2013 Kubo et al.
8,602,125 B2 12/2013 King
8,602,287 B2 12/2013 Yates et al.
8,602,288 B2 12/2013 Shelton, IV et al.
8,603,077 B2 12/2013 Cooper et al.
8,603,089 B2 12/2013 Viola
8,603,110 B2 12/2013 Maruyama et al.
8,603,135 B2 12/2013 Mueller
8,608,043 B2 12/2013 Scirica
8,608,044 B2 12/2013 Hueil et al.
8,608,045 B2 12/2013 Smith et al.
8,608,046 B2 12/2013 Laurent et al.
8,608,745 B2 12/2013 Guzman et al.
8,613,383 B2 12/2013 Beckman et al.
8,613,384 B2 12/2013 Pastorelli et al.
8,616,427 B2 12/2013 Viola
8,616,431 B2 12/2013 Timm et al.
8,617,155 B2 12/2013 Johnson et al.
8,620,473 B2 12/2013 Diolaiti et al.
8,622,274 B2 1/2014 Yates et al.
8,622,275 B2 1/2014 Baxter, III et al.
8,627,993 B2 1/2014 Smith et al.
8,627,994 B2 1/2014 Zemlok et al.
8,627,995 B2 1/2014 Smith et al.
8,628,467 B2 1/2014 Whitman et al.
8,628,518 B2 1/2014 Blumenkranz et al.
8,628,544 B2 1/2014 Farascioni
8,628,545 B2 1/2014 Cabrera et al.
8,631,987 B2 1/2014 Shelton, IV et al.
8,631,992 B1 1/2014 Hausen et al.
8,631,993 B2 1/2014 Kostrzewski
8,632,462 B2 1/2014 Yoo et al.
8,632,525 B2 1/2014 Kerr et al.
8,632,535 B2 1/2014 Shelton, IV et al.
8,632,539 B2 1/2014 Twomey et al.
8,632,563 B2 1/2014 Nagase et al.
8,636,187 B2 1/2014 Hueil et al.
8,636,190 B2 1/2014 Zemlok et al.

(56) References Cited

U.S. PATENT DOCUMENTS 8,636,191 B2 1/2014 Meagher
8,636,193 B2 1/2014 Whitman et al.
8,636,736 B2 1/2014 Yates et al.
8,636,766 B2 1/2014 Milliman et al.
8,639,936 B2 1/2014 Hu et al.
8,640,788 B2 2/2014 Dachs, II et al.
8,646,674 B2 2/2014 Schulte et al.
8,647,258 B2 2/2014 Aranyi et al.
8,652,120 B2 2/2014 Giordano et al.
8,652,151 B2 2/2014 Lehman et al.
8,652,155 B2 2/2014 Houser et al.
8,656,929 B2 2/2014 Miller et al.
8,657,174 B2 2/2014 Yates et al.
8,657,175 B2 2/2014 Sonnenschein et al.
8,657,176 B2 2/2014 Shelton, IV et al.
8,657,177 B2 2/2014 Scirica et al.
8,657,178 B2 2/2014 Hueil et al.
8,657,482 B2 2/2014 Malackowski et al.
8,657,808 B2 2/2014 McPherson et al.
8,657,814 B2 2/2014 Werneth et al.
8,657,821 B2 2/2014 Palermo
D701,238 S 3/2014 Lai et al.
8,662,370 B2 3/2014 Takei
8,663,106 B2 3/2014 Stivoric et al.
8,663,192 B2 3/2014 Hester et al.
8,663,245 B2 3/2014 Francischelli et al.
8,663,262 B2 3/2014 Smith et al.
8,663,270 B2 3/2014 Donnigan et al.
8,664,792 B2 3/2014 Rebsdorf
8,668,129 B2 3/2014 Olson
8,668,130 B2 3/2014 Hess et al.
8,672,206 B2 3/2014 Aranyi et al.
8,672,207 B2 3/2014 Shelton, IV et al.
8,672,208 B2 3/2014 Hess et al.
8,672,209 B2 3/2014 Crainich
8,672,922 B2 3/2014 Loh et al.
8,672,935 B2 3/2014 Okada et al.
8,672,951 B2 3/2014 Smith et al.
8,673,210 B2 3/2014 Deshays
8,675,820 B2 3/2014 Baic et al.
8,678,263 B2 3/2014 Viola
8,678,994 B2 3/2014 Sonnenschein et al.
8,679,093 B2 3/2014 Farra
8,679,098 B2 3/2014 Hart
8,679,137 B2 3/2014 Bauman et al.
8,679,154 B2 3/2014 Smith et al.
8,679,156 B2 3/2014 Smith et al.
8,679,454 B2 3/2014 Guire et al.
8,684,248 B2 4/2014 Milliman
8,684,249 B2 4/2014 Racenet et al.
8,684,250 B2 4/2014 Bettuchi et al.
8,684,253 B2 4/2014 Giordano et al.
8,684,962 B2 4/2014 Kirschenman et al.
8,685,004 B2 4/2014 Zemlock et al.
8,685,020 B2 4/2014 Weizman et al.
8,690,893 B2 4/2014 Deitch et al.
8,695,866 B2 4/2014 Leimbach et al.
8,696,665 B2 4/2014 Hunt et al.
8,701,958 B2 4/2014 Shelton, IV et al.
8,701,959 B2 4/2014 Shah
8,706,316 B1 4/2014 Hoevenaar
8,708,210 B2 4/2014 Zemlok et al.
8,708,211 B2 4/2014 Zemlok et al.
8,708,212 B2 4/2014 Williams
8,708,213 B2 4/2014 Shelton, IV et al.
8,709,012 B2 4/2014 Muller
8,714,352 B2 5/2014 Farascioni et al.
8,714,429 B2 5/2014 Demmy
8,714,430 B2 5/2014 Natarajan et al.
8,715,256 B2 5/2014 Greener
8,715,302 B2 5/2014 Ibrahim et al.
8,720,766 B2 5/2014 Hess et al.
8,721,630 B2 5/2014 Ortiz et al.
8,721,666 B2 5/2014 Schroeder et al.
8,727,197 B2 5/2014 Hess et al.
8,727,199 B2 5/2014 Wenchell
8,727,200 B2 5/2014 Roy
8,727,961 B2 5/2014 Ziv
8,728,099 B2 5/2014 Cohn et al.
8,728,119 B2 5/2014 Cummins
8,733,470 B2 5/2014 Matthias et al.
8,733,611 B2 5/2014 Milliman
8,733,612 B2 5/2014 Ma
8,733,613 B2 5/2014 Huitema et al.
8,733,614 B2 5/2014 Ross et al.
8,734,336 B2 5/2014 Bonadio et al.
8,734,359 B2 5/2014 Ibanez et al.
8,734,478 B2 5/2014 Widenhouse et al.
8,734,831 B2 5/2014 Kim et al.
8,739,033 B2 5/2014 Rosenberg
8,739,417 B2 6/2014 Tokunaga et al.
8,740,034 B2 6/2014 Morgan et al.
8,740,037 B2 6/2014 Shelton, IV et al.
8,740,038 B2 6/2014 Shelton, IV et al.
8,740,987 B2 6/2014 Geremakis et al.
8,746,529 B2 6/2014 Shelton, IV et al.
8,746,530 B2 6/2014 Giordano et al.
8,746,533 B2 6/2014 Whitman et al.
8,746,535 B2 6/2014 Shelton, IV et al.
8,747,238 B2 6/2014 Shelton, IV et al.
8,747,441 B2 6/2014 Konieczynski et al.
8,752,264 B2 6/2014 Ackley et al.
8,752,699 B2 6/2014 Morgan et al.
8,752,747 B2 6/2014 Shelton, IV et al.
8,752,748 B2 6/2014 Whitman et al.
8,752,749 B2 6/2014 Moore et al.
8,753,664 B2 6/2014 Dao et al.
8,757,287 B2 6/2014 Mak et al.
8,757,465 B2 6/2014 Woodard, Jr. et al.
8,758,235 B2 6/2014 Jaworek
8,758,366 B2 6/2014 McLean et al.
8,758,391 B2 6/2014 Swayze et al.
8,758,438 B2 6/2014 Boyce et al.
8,763,875 B2 7/2014 Morgan et al.
8,763,876 B2 7/2014 Kostrzewski
8,763,877 B2 7/2014 Schall et al.
8,763,879 B2 7/2014 Shelton, IV et al.
8,764,732 B2 7/2014 Hartwell
8,765,942 B2 7/2014 Feraud et al.
8,770,458 B2 7/2014 Scirica
8,770,459 B2 7/2014 Racenet et al.
8,770,460 B2 7/2014 Belzer
8,771,169 B2 7/2014 Whitman et al.
8,771,260 B2 7/2014 Conlon et al.
8,777,004 B2 7/2014 Shelton, IV et al.
8,777,082 B2 7/2014 Scirica
8,777,083 B2 7/2014 Racenet et al.
8,777,898 B2 7/2014 Suon et al.
8,783,541 B2 7/2014 Shelton, IV et al.
8,783,542 B2 7/2014 Riestenberg et al.
8,783,543 B2 7/2014 Shelton, IV et al.
8,784,304 B2 7/2014 Mikkaichi et al.
8,784,404 B2 7/2014 Doyle et al.
8,784,415 B2 7/2014 Malackowski et al.
8,789,737 B2 7/2014 Hodgkinson et al.
8,789,739 B2 7/2014 Swensgard
8,789,740 B2 7/2014 Baxter, III et al.
8,789,741 B2 7/2014 Baxter, III et al.
8,790,658 B2 7/2014 Cigarini et al.
8,790,684 B2 7/2014 Dave et al.
D711,905 S 8/2014 Morrison et al.
8,794,496 B2 8/2014 Scirica
8,794,497 B2 8/2014 Zingman
8,795,159 B2 8/2014 Moriyama
8,795,276 B2 8/2014 Dietz et al.
8,795,308 B2 8/2014 Valin
8,795,324 B2 8/2014 Kawai et al.
8,796,995 B2 8/2014 Cunanan et al.
8,800,681 B2 8/2014 Rousson et al.
8,800,837 B2 8/2014 Zemlok
8,800,838 B2 8/2014 Shelton, IV
8,800,839 B2 8/2014 Beetel
8,800,840 B2 8/2014 Jankowski
8,800,841 B2 8/2014 Ellerhorst et al.

(56) References Cited

U.S. PATENT DOCUMENTS 8,801,710 B2 8/2014 Ullrich et al.
8,801,734 B2 8/2014 Shelton, IV et al.
8,801,735 B2 8/2014 Shelton, IV et al.
8,801,752 B2 8/2014 Fortier et al.
8,801,801 B2 8/2014 Datta et al.
8,806,973 B2 8/2014 Ross et al.
8,807,414 B2 8/2014 Ross et al.
8,808,161 B2 8/2014 Gregg et al.
8,808,164 B2 8/2014 Hoffman et al.
8,808,274 B2 8/2014 Hartwell
8,808,294 B2 8/2014 Fox et al.
8,808,308 B2 8/2014 Boukhny et al.
8,808,311 B2 8/2014 Heinrich et al.
8,808,325 B2 8/2014 Hess et al.
8,810,197 B2 8/2014 Juergens
8,811,017 B2 8/2014 Fujii et al.
8,813,866 B2 8/2014 Suzuki
8,814,024 B2 8/2014 Woodard, Jr. et al.
8,814,025 B2 8/2014 Miller et al.
8,814,836 B2 8/2014 Ignon et al.
8,815,594 B2 8/2014 Harris et al.
8,818,523 B2 8/2014 Olson et al.
8,820,603 B2 9/2014 Shelton, IV et al.
8,820,605 B2 9/2014 Shelton, IV
8,820,606 B2 9/2014 Hodgkinson
8,820,607 B2 9/2014 Marczyk
8,820,608 B2 9/2014 Miyamoto
8,821,514 B2 9/2014 Aranyi
8,822,934 B2 9/2014 Sayeh et al.
8,825,164 B2 9/2014 Tweden et al.
8,827,133 B2 9/2014 Shelton, IV et al.
8,827,134 B2 9/2014 Viola et al.
8,827,903 B2 9/2014 Shelton, IV et al.
8,828,046 B2 9/2014 Stefanchik et al.
8,831,779 B2 9/2014 Ortmaier et al.
8,833,219 B2 9/2014 Pierce
8,833,630 B2 9/2014 Milliman
8,833,632 B2 9/2014 Swensgard
8,834,353 B2 9/2014 Dejima et al.
8,834,465 B2 9/2014 Ramstein et al.
8,834,498 B2 9/2014 Byrum et al.
8,834,518 B2 9/2014 Faller et al.
8,840,003 B2 9/2014 Morgan et al.
8,840,004 B2 9/2014 Holsten et al.
8,840,603 B2 9/2014 Shelton, IV et al.
8,840,609 B2 9/2014 Stuebe
8,840,876 B2 9/2014 Eemeta et al.
8,844,789 B2 9/2014 Shelton, IV et al.
8,844,790 B2 9/2014 Demmy et al.
8,845,622 B2 9/2014 Paik et al.
8,851,215 B2 10/2014 Goto
8,851,354 B2 10/2014 Swensgard et al.
8,851,355 B2 10/2014 Aranyi et al.
8,852,174 B2 10/2014 Burbank
8,852,185 B2 10/2014 Twomey
8,852,199 B2 10/2014 Deslauriers et al.
8,852,218 B2 10/2014 Hughett, Sr. et al.
8,857,693 B2 10/2014 Schuckmann et al.
8,857,694 B2 10/2014 Shelton, IV et al.
8,858,538 B2 10/2014 Belson et al.
8,858,547 B2 10/2014 Brogna
8,858,571 B2 10/2014 Shelton, IV et al.
8,858,590 B2 10/2014 Shelton, IV et al.
8,864,007 B2 10/2014 Widenhouse et al.
8,864,009 B2 10/2014 Shelton, IV et al.
8,864,010 B2 10/2014 Williams
8,864,750 B2 10/2014 Ross et al.
8,869,912 B2 10/2014 Robkamp et al.
8,869,913 B2 10/2014 Matthias et al.
8,870,050 B2 10/2014 Hodgkinson
8,870,867 B2 10/2014 Walberg et al.
8,870,912 B2 10/2014 Brisson et al.
8,871,829 B2 10/2014 Gerold et al.
8,875,971 B2 11/2014 Hall et al.
8,875,972 B2 11/2014 Weisenburgh, II et al.
8,876,698 B2 11/2014 Sakamoto et al.
8,876,857 B2 11/2014 Burbank
8,876,858 B2 11/2014 Braun
8,882,660 B2 11/2014 Phee et al.
8,882,792 B2 11/2014 Dietz et al.
8,884,560 B2 11/2014 Ito
8,887,979 B2 11/2014 Mastri et al.
8,888,688 B2 11/2014 Julian et al.
8,888,695 B2 11/2014 Piskun et al.
8,888,792 B2 11/2014 Harris et al.
8,888,809 B2 11/2014 Davison et al.
8,893,946 B2 11/2014 Boudreaux et al.
8,893,949 B2 11/2014 Shelton, IV et al.
8,894,647 B2 11/2014 Beardsley et al.
8,894,654 B2 11/2014 Anderson
8,899,460 B2 12/2014 Wojcicki
8,899,461 B2 12/2014 Farascioni
8,899,462 B2 12/2014 Kostrzewski et al.
8,899,463 B2 12/2014 Schall et al.
8,899,464 B2 12/2014 Hueil et al.
8,899,465 B2 12/2014 Shelton, IV et al.
8,899,466 B2 12/2014 Baxter, III et al.
8,900,267 B2 12/2014 Woolfson et al.
8,905,287 B2 12/2014 Racenet et al.
8,905,977 B2 12/2014 Shelton et al.
8,910,846 B2 12/2014 Viola
8,910,847 B2 12/2014 Nalagatla et al.
8,911,426 B2 12/2014 Coppeta et al.
8,911,448 B2 12/2014 Stein
8,911,460 B2 12/2014 Neurohr et al.
8,911,471 B2 12/2014 Spivey et al.
8,912,746 B2 12/2014 Reid et al.
8,915,842 B2 12/2014 Weisenburgh, II et al.
8,920,368 B2 12/2014 Sandhu et al.
8,920,433 B2 12/2014 Barrier et al.
8,920,435 B2 12/2014 Smith et al.
8,920,438 B2 12/2014 Aranyi et al.
8,920,443 B2 12/2014 Hiles et al.
8,920,444 B2 12/2014 Hiles et al.
8,922,163 B2 12/2014 Macdonald
8,925,782 B2 1/2015 Shelton, IV
8,925,783 B2 1/2015 Zemlok et al.
8,925,788 B2 1/2015 Hess et al.
8,926,506 B2 1/2015 Widenhouse et al.
8,926,598 B2 1/2015 Mollere et al.
8,931,576 B2 1/2015 Iwata
8,931,679 B2 1/2015 Kostrzewski
8,931,680 B2 1/2015 Milliman
8,931,682 B2 1/2015 Timm et al.
8,931,692 B2 1/2015 Sancak
8,936,614 B2 1/2015 Allen, IV
8,939,343 B2 1/2015 Milliman et al.
8,939,344 B2 1/2015 Olson et al.
8,939,898 B2 1/2015 Omoto
8,944,069 B2 2/2015 Miller et al.
8,945,095 B2 2/2015 Blumenkranz et al.
8,945,098 B2 2/2015 Seibold et al.
8,945,163 B2 2/2015 Voegele et al.
8,955,732 B2 2/2015 Zemlok et al.
8,956,342 B1 2/2015 Russo et al.
8,956,390 B2 2/2015 Shah et al.
8,958,860 B2 2/2015 Banerjee et al.
8,960,519 B2 2/2015 Whitman et al.
8,960,520 B2 2/2015 McCuen
8,960,521 B2 2/2015 Kostrzewski
8,961,191 B2 2/2015 Hanshew
8,961,504 B2 2/2015 Hoarau et al.
8,961,542 B2 2/2015 Whitfield et al.
8,963,714 B2 2/2015 Medhal et al.
D725,674 S 3/2015 Jung et al.
8,967,443 B2 3/2015 McCuen
8,967,444 B2 3/2015 Beetel
8,967,446 B2 3/2015 Beardsley et al.
8,967,448 B2 3/2015 Carter et al.
8,968,276 B2 3/2015 Zemlok et al.
8,968,308 B2 3/2015 Horner et al.
8,968,312 B2 3/2015 Marczyk et al.
8,968,337 B2 3/2015 Whitfield et al.
8,968,340 B2 3/2015 Chowaniec et al.

(56) References Cited

U.S. PATENT DOCUMENTS 8,968,355 B2 3/2015 Malkowski et al.
8,968,358 B2 3/2015 Reschke
8,970,507 B2 3/2015 Holbein et al.
8,973,803 B2 3/2015 Hall et al.
8,973,804 B2 3/2015 Hess et al.
8,973,805 B2 3/2015 Scirica et al.
8,974,440 B2 3/2015 Farritor et al.
8,974,542 B2 3/2015 Fujimoto et al.
8,974,932 B2 3/2015 McGahan et al.
8,978,954 B2 3/2015 Shelton, IV et al.
8,978,955 B2 3/2015 Aronhalt et al.
8,978,956 B2 3/2015 Schall et al.
8,979,843 B2 3/2015 Timm et al.
8,979,890 B2 3/2015 Boudreaux
8,982,195 B2 3/2015 Claus et al.
8,984,711 B2 3/2015 Ota et al.
8,985,240 B2 3/2015 Winnard
8,985,429 B2 3/2015 Balek et al.
8,986,302 B2 3/2015 Aldridge et al.
8,989,903 B2 3/2015 Weir et al.
8,991,676 B2 3/2015 Hess et al.
8,991,677 B2 3/2015 Moore et al.
8,991,678 B2 3/2015 Wellman et al.
8,992,042 B2 3/2015 Eichenholz
8,992,422 B2 3/2015 Spivey et al.
8,992,565 B2 3/2015 Brisson et al.
8,996,165 B2 3/2015 Wang et al.
8,998,058 B2 4/2015 Moore et al.
8,998,059 B2 4/2015 Smith et al.
8,998,060 B2 4/2015 Bruewer et al.
8,998,061 B2 4/2015 Williams et al.
8,998,939 B2 4/2015 Price et al.
9,000,720 B2 4/2015 Stulen et al.
9,002,518 B2 4/2015 Manzo et al.
9,004,339 B1 4/2015 Park
9,004,799 B1 4/2015 Tibbits
9,005,230 B2 4/2015 Yates et al.
9,005,238 B2 4/2015 DeSantis et al.
9,005,243 B2 4/2015 Stopek et al.
9,010,606 B2 4/2015 Aranyi et al.
9,010,608 B2 4/2015 Casasanta, Jr. et al.
9,010,611 B2 4/2015 Ross et al.
9,011,437 B2 4/2015 Woodruff et al.
9,011,439 B2 4/2015 Shalaby et al.
9,011,471 B2 4/2015 Timm et al.
9,014,856 B2 4/2015 Manzo et al.
9,016,539 B2 4/2015 Kostrzewski et al.
9,016,540 B2 4/2015 Whitman et al.
9,016,541 B2 4/2015 Viola et al.
9,016,542 B2 4/2015 Shelton, IV et al.
9,016,545 B2 4/2015 Aranyi et al.
9,017,331 B2 4/2015 Fox
9,017,355 B2 4/2015 Smith et al.
9,017,369 B2 4/2015 Renger et al.
9,017,371 B2 4/2015 Whitman et al.
9,017,849 B2 4/2015 Stulen et al.
9,017,851 B2 4/2015 Felder et al.
D729,274 S 5/2015 Clement et al.
9,021,684 B2 5/2015 Lenker et al.
9,023,014 B2 5/2015 Chowaniec et al.
9,023,069 B2 5/2015 Kasvikis et al.
9,023,071 B2 5/2015 Miller et al.
9,026,347 B2 5/2015 Gadh et al.
9,027,817 B2 5/2015 Milliman et al.
9,028,468 B2 5/2015 Scarfogliero et al.
9,028,494 B2 5/2015 Shelton, IV et al.
9,028,495 B2 5/2015 Mueller et al.
9,028,510 B2 5/2015 Miyamoto et al.
9,028,511 B2 5/2015 Weller et al.
9,028,519 B2 5/2015 Yates et al.
9,028,529 B2 5/2015 Fox et al.
9,030,166 B2 5/2015 Kano
9,030,169 B2 5/2015 Christensen et al.
9,033,203 B2 5/2015 Woodard, Jr. et al.
9,033,204 B2 5/2015 Shelton, IV et al.
9,034,505 B2 5/2015 Detry et al.
9,038,881 B1 5/2015 Schaller et al.
9,039,690 B2 5/2015 Kersten et al.
9,039,694 B2 5/2015 Ross et al.
9,039,720 B2 5/2015 Madan
9,039,736 B2 5/2015 Scirica et al.
9,040,062 B2 5/2015 Maeda et al.
9,043,027 B2 5/2015 Durant et al.
9,044,227 B2 6/2015 Shelton, IV et al.
9,044,228 B2 6/2015 Woodard, Jr. et al.
9,044,229 B2 6/2015 Scheib et al.
9,044,230 B2 6/2015 Morgan et al.
9,044,238 B2 6/2015 Orszulak
9,044,241 B2 6/2015 Barner et al.
9,044,261 B2 6/2015 Houser
9,044,281 B2 6/2015 Pool et al.
9,050,083 B2 6/2015 Yates et al.
9,050,084 B2 6/2015 Schmid et al.
9,050,089 B2 6/2015 Orszulak
9,050,100 B2 6/2015 Yates et al.
9,050,120 B2 6/2015 Swarup et al.
9,050,123 B2 6/2015 Krause et al.
9,050,176 B2 6/2015 Datta et al.
9,050,192 B2 6/2015 Mansmann
9,055,941 B2 6/2015 Schmid et al.
9,055,942 B2 6/2015 Balbierz et al.
9,055,943 B2 6/2015 Zemlok et al.
9,055,944 B2 6/2015 Hodgkinson et al.
9,055,961 B2 6/2015 Manzo et al.
9,060,770 B2 6/2015 Shelton, IV et al.
9,060,776 B2 6/2015 Yates et al.
9,060,794 B2 6/2015 Kang et al.
9,060,894 B2 6/2015 Wubbeling
9,061,392 B2 6/2015 Forgues et al.
9,070,068 B2 6/2015 Coveley et al.
9,072,515 B2 7/2015 Hall et al.
9,072,523 B2 7/2015 Houser et al.
9,072,535 B2 7/2015 Shelton, IV et al.
9,072,536 B2 7/2015 Shelton, IV et al.
9,078,653 B2 7/2015 Leimbach et al.
9,078,654 B2 7/2015 Whitman et al.
9,084,586 B2 7/2015 Hafner et al.
9,084,601 B2 7/2015 Moore et al.
9,084,602 B2 7/2015 Gleiman
9,086,875 B2 7/2015 Harrat et al.
9,089,326 B2 7/2015 Krumanaker et al.
9,089,330 B2 7/2015 Widenhouse et al.
9,089,338 B2 7/2015 Smith et al.
9,089,352 B2 7/2015 Jeong
9,089,360 B2 7/2015 Messerly et al.
9,091,588 B2 7/2015 Lefler
D736,792 S 8/2015 Brinda et al.
9,095,339 B2 8/2015 Moore et al.
9,095,346 B2 8/2015 Houser et al.
9,095,362 B2 8/2015 Dachs, II et al.
9,095,367 B2 8/2015 Olson et al.
9,095,642 B2 8/2015 Harder et al.
9,096,033 B2 8/2015 Holop et al.
9,098,153 B2 8/2015 Shen et al.
9,099,863 B2 8/2015 Smith et al.
9,099,877 B2 8/2015 Banos et al.
9,099,922 B2 8/2015 Toosky et al.
9,101,358 B2 8/2015 Kerr et al.
9,101,359 B2 8/2015 Smith et al.
9,101,385 B2 8/2015 Shelton, IV et al.
9,101,475 B2 8/2015 Wei et al.
9,101,621 B2 8/2015 Zeldis
9,107,663 B2 8/2015 Swensgard
9,107,667 B2 8/2015 Hodgkinson
9,107,690 B2 8/2015 Bales, Jr. et al.
9,110,587 B2 8/2015 Kim et al.
9,113,862 B2 8/2015 Morgan et al.
9,113,864 B2 8/2015 Morgan et al.
9,113,865 B2 8/2015 Shelton, IV et al.
9,113,868 B2 8/2015 Felder et al.
9,113,873 B2 8/2015 Marczyk et al.
9,113,874 B2 8/2015 Shelton, IV et al.
9,113,875 B2 8/2015 Viola et al.
9,113,876 B2 8/2015 Zemlok et al.

(56) References Cited

U.S. PATENT DOCUMENTS

| | | | |
|---|---|---|---|
| 9,113,879 | B2 | 8/2015 | Felder et al. |
| 9,113,880 | B2 | 8/2015 | Zemlok et al. |
| 9,113,881 | B2 | 8/2015 | Scirica |
| 9,113,883 | B2 | 8/2015 | Aronhalt et al. |
| 9,113,884 | B2 | 8/2015 | Shelton, IV et al. |
| 9,113,887 | B2 | 8/2015 | Behnke, II et al. |
| 9,119,615 | B2 | 9/2015 | Felder et al. |
| 9,119,657 | B2 | 9/2015 | Shelton, IV et al. |
| 9,119,898 | B2 | 9/2015 | Bayon et al. |
| 9,119,957 | B2 | 9/2015 | Gantz et al. |
| 9,123,286 | B2 | 9/2015 | Park |
| 9,124,097 | B2 | 9/2015 | Cruz |
| 9,125,651 | B2 | 9/2015 | Mandakolathur Vasudevan et al. |
| 9,125,654 | B2 | 9/2015 | Aronhalt et al. |
| 9,125,662 | B2 | 9/2015 | Shelton, IV |
| 9,126,317 | B2 | 9/2015 | Lawton et al. |
| 9,131,835 | B2 | 9/2015 | Widenhouse et al. |
| 9,131,940 | B2 | 9/2015 | Huitema et al. |
| 9,131,950 | B2 | 9/2015 | Matthew |
| 9,131,957 | B2 | 9/2015 | Skarbnik et al. |
| 9,138,225 | B2 | 9/2015 | Huang et al. |
| 9,138,226 | B2 | 9/2015 | Racenet et al. |
| 9,144,455 | B2 | 9/2015 | Kennedy et al. |
| D740,414 | S | 10/2015 | Katsura |
| D741,882 | S | 10/2015 | Shmilov et al. |
| 9,149,274 | B2 | 10/2015 | Spivey et al. |
| 9,149,324 | B2 | 10/2015 | Huang et al. |
| 9,149,325 | B2 | 10/2015 | Worrell et al. |
| 9,153,994 | B2 | 10/2015 | Wood et al. |
| 9,161,753 | B2 | 10/2015 | Prior |
| 9,161,769 | B2 | 10/2015 | Stoddard et al. |
| 9,161,803 | B2 | 10/2015 | Yates et al. |
| 9,161,807 | B2 | 10/2015 | Garrison |
| 9,161,855 | B2 | 10/2015 | Rousseau et al. |
| 9,164,271 | B2 | 10/2015 | Ebata et al. |
| 9,167,960 | B2 | 10/2015 | Yamaguchi et al. |
| 9,168,038 | B2 | 10/2015 | Shelton, IV et al. |
| 9,168,039 | B1 | 10/2015 | Knodel |
| 9,168,042 | B2 | 10/2015 | Milliman |
| 9,168,054 | B2 | 10/2015 | Turner et al. |
| 9,168,144 | B2 | 10/2015 | Rivin et al. |
| 9,171,244 | B2 | 10/2015 | Endou et al. |
| 9,179,832 | B2 | 11/2015 | Diolaiti |
| 9,179,911 | B2 | 11/2015 | Morgan et al. |
| 9,179,912 | B2 | 11/2015 | Yates et al. |
| 9,180,223 | B2 | 11/2015 | Yu et al. |
| 9,182,244 | B2 | 11/2015 | Luke et al. |
| 9,186,046 | B2 | 11/2015 | Ramamurthy et al. |
| 9,186,137 | B2 | 11/2015 | Farascioni et al. |
| 9,186,140 | B2 | 11/2015 | Hiles et al. |
| 9,186,142 | B2 | 11/2015 | Fanelli et al. |
| 9,186,143 | B2 | 11/2015 | Timm et al. |
| 9,186,148 | B2 | 11/2015 | Felder et al. |
| 9,186,221 | B2 | 11/2015 | Burbank |
| 9,192,376 | B2 | 11/2015 | Almodovar |
| 9,192,380 | B2 | 11/2015 | (Tarinelli) Racenet et al. |
| 9,192,384 | B2 | 11/2015 | Bettuchi |
| 9,192,430 | B2 | 11/2015 | Rachlin et al. |
| 9,192,434 | B2 | 11/2015 | Twomey et al. |
| 9,193,045 | B2 | 11/2015 | Saur et al. |
| 9,197,079 | B2 | 11/2015 | Yip et al. |
| D744,528 | S | 12/2015 | Agrawal |
| D746,459 | S | 12/2015 | Kaercher et al. |
| 9,198,642 | B2 | 12/2015 | Storz |
| 9,198,644 | B2 | 12/2015 | Balek et al. |
| 9,198,661 | B2 | 12/2015 | Swensgard |
| 9,198,662 | B2 | 12/2015 | Barton et al. |
| 9,198,683 | B2 | 12/2015 | Friedman et al. |
| 9,204,830 | B2 | 12/2015 | Zand et al. |
| 9,204,877 | B2 | 12/2015 | Whitman et al. |
| 9,204,878 | B2 | 12/2015 | Hall et al. |
| 9,204,879 | B2 | 12/2015 | Shelton, IV |
| 9,204,880 | B2 | 12/2015 | Baxter, III et al. |
| 9,204,881 | B2 | 12/2015 | Penna |
| 9,204,923 | B2 | 12/2015 | Manzo et al. |
| 9,204,924 | B2 | 12/2015 | Marczyk et al. |
| 9,211,120 | B2 | 12/2015 | Scheib et al. |
| 9,211,121 | B2 | 12/2015 | Hall et al. |
| 9,211,122 | B2 | 12/2015 | Hagerty et al. |
| 9,216,013 | B2 | 12/2015 | Scirica et al. |
| 9,216,019 | B2 | 12/2015 | Schmid et al. |
| 9,216,020 | B2 | 12/2015 | Zhang et al. |
| 9,216,030 | B2 | 12/2015 | Fan et al. |
| 9,216,062 | B2 | 12/2015 | Duque et al. |
| 9,220,500 | B2 | 12/2015 | Swayze et al. |
| 9,220,501 | B2 | 12/2015 | Baxter, III et al. |
| 9,220,502 | B2 | 12/2015 | Zemlok et al. |
| 9,220,504 | B2 | 12/2015 | Viola et al. |
| 9,220,508 | B2 | 12/2015 | Dannaher |
| 9,220,559 | B2 | 12/2015 | Worrell et al. |
| 9,220,570 | B2 | 12/2015 | Kim et al. |
| D746,854 | S | 1/2016 | Shardlow et al. |
| 9,226,686 | B2 | 1/2016 | Blair |
| 9,226,750 | B2 | 1/2016 | Weir et al. |
| 9,226,751 | B2 | 1/2016 | Shelton, IV et al. |
| 9,226,754 | B2 | 1/2016 | D'Agostino et al. |
| 9,226,760 | B2 | 1/2016 | Shelton, IV |
| 9,226,761 | B2 | 1/2016 | Burbank |
| 9,226,767 | B2 | 1/2016 | Stulen et al. |
| 9,226,799 | B2 | 1/2016 | Lightcap et al. |
| 9,232,941 | B2 | 1/2016 | Mandakolathur Vasudevan et al. |
| 9,232,945 | B2 | 1/2016 | Zingman |
| 9,232,979 | B2 | 1/2016 | Parihar et al. |
| 9,233,610 | B2 | 1/2016 | Kim et al. |
| 9,237,891 | B2 | 1/2016 | Shelton, IV |
| 9,237,892 | B2 | 1/2016 | Hodgkinson |
| 9,237,895 | B2 | 1/2016 | McCarthy et al. |
| 9,237,900 | B2 | 1/2016 | Boudreaux et al. |
| 9,237,921 | B2 | 1/2016 | Messerly et al. |
| 9,239,064 | B2 | 1/2016 | Helbig et al. |
| 9,240,740 | B2 | 1/2016 | Zeng et al. |
| 9,241,711 | B2 | 1/2016 | Ivanko |
| 9,241,712 | B2 | 1/2016 | Zemlok et al. |
| 9,241,714 | B2 | 1/2016 | Timm et al. |
| 9,241,716 | B2 | 1/2016 | Whitman |
| 9,241,731 | B2 | 1/2016 | Boudreaux et al. |
| 9,241,758 | B2 | 1/2016 | Franer et al. |
| 9,244,524 | B2 | 1/2016 | Inoue et al. |
| D748,668 | S | 2/2016 | Kim et al. |
| D749,128 | S | 2/2016 | Perez et al. |
| D749,623 | S | 2/2016 | Gray et al. |
| D750,122 | S | 2/2016 | Shardlow et al. |
| D750,129 | S | 2/2016 | Kwon |
| 9,254,131 | B2 | 2/2016 | Soltz et al. |
| 9,254,170 | B2 | 2/2016 | Parihar et al. |
| 9,259,265 | B2 | 2/2016 | Harris et al. |
| 9,259,274 | B2 | 2/2016 | Prisco |
| 9,259,275 | B2 | 2/2016 | Burbank |
| 9,261,172 | B2 | 2/2016 | Solomon et al. |
| 9,265,500 | B2 | 2/2016 | Sorrentino et al. |
| 9,265,510 | B2 | 2/2016 | Dietzel et al. |
| 9,265,516 | B2 | 2/2016 | Casey et al. |
| 9,265,585 | B2 | 2/2016 | Wingardner et al. |
| 9,271,718 | B2 | 3/2016 | Milad et al. |
| 9,271,727 | B2 | 3/2016 | McGuckin, Jr. et al. |
| 9,271,753 | B2 | 3/2016 | Butler et al. |
| 9,271,799 | B2 | 3/2016 | Shelton, IV et al. |
| 9,272,406 | B2 | 3/2016 | Aronhalt et al. |
| 9,274,095 | B2 | 3/2016 | Humayun et al. |
| 9,277,919 | B2 | 3/2016 | Timmer et al. |
| 9,277,922 | B2 | 3/2016 | Carter et al. |
| 9,277,969 | B2 | 3/2016 | Brannan et al. |
| 9,282,962 | B2 | 3/2016 | Schmid et al. |
| 9,282,963 | B2 | 3/2016 | Bryant |
| 9,282,966 | B2 | 3/2016 | Shelton, IV et al. |
| 9,282,974 | B2 | 3/2016 | Shelton, IV |
| 9,283,028 | B2 | 3/2016 | Johnson |
| 9,283,045 | B2 | 3/2016 | Rhee et al. |
| 9,283,054 | B2 | 3/2016 | Morgan et al. |
| 9,283,334 | B2 | 3/2016 | Mantell et al. |
| 9,289,206 | B2 | 3/2016 | Hess et al. |
| 9,289,207 | B2 | 3/2016 | Shelton, IV |
| 9,289,210 | B2 | 3/2016 | Baxter, III et al. |
| 9,289,211 | B2 | 3/2016 | Williams et al. |

(56) References Cited

U.S. PATENT DOCUMENTS 9,289,212 B2 3/2016 Shelton, IV et al.
9,289,225 B2 3/2016 Shelton, IV et al.
9,289,256 B2 3/2016 Shelton, IV et al.
9,293,757 B2 3/2016 Toussaint et al.
9,295,464 B2 3/2016 Shelton, IV et al.
9,295,465 B2 3/2016 Farascioni
9,295,466 B2 3/2016 Hodgkinson et al.
9,295,467 B2 3/2016 Scirica
9,295,468 B2 3/2016 Heinrich et al.
9,295,514 B2 3/2016 Shelton, IV et al.
9,295,522 B2 3/2016 Kostrzewski
9,295,565 B2 3/2016 McLean
9,295,784 B2 3/2016 Eggert et al.
D753,167 S 4/2016 Yu et al.
9,301,691 B2 4/2016 Hufnagel et al.
9,301,752 B2 4/2016 Mandakolathur Vasudevan et al.
9,301,753 B2 4/2016 Aldridge et al.
9,301,755 B2 4/2016 Shelton, IV et al.
9,301,759 B2 4/2016 Spivey et al.
9,301,811 B2 4/2016 Goldberg et al.
9,307,965 B2 4/2016 Ming et al.
9,307,986 B2 4/2016 Hall et al.
9,307,987 B2 4/2016 Swensgard et al.
9,307,988 B2 4/2016 Shelton, IV
9,307,989 B2 4/2016 Shelton, IV et al.
9,307,994 B2 4/2016 Gresham et al.
9,308,009 B2 4/2016 Madan et al.
9,308,011 B2 4/2016 Chao et al.
9,308,646 B2 4/2016 Lim et al.
9,313,915 B2 4/2016 Niu et al.
9,314,246 B2 4/2016 Shelton, IV et al.
9,314,247 B2 4/2016 Shelton, IV et al.
9,314,261 B2 4/2016 Bales, Jr. et al.
9,314,291 B2 4/2016 Schall et al.
9,314,339 B2 4/2016 Mansmann
9,314,908 B2 4/2016 Tanimoto et al.
9,320,518 B2 4/2016 Henderson et al.
9,320,520 B2 4/2016 Shelton, IV et al.
9,320,521 B2 4/2016 Shelton, IV et al.
9,320,523 B2 4/2016 Shelton, IV et al.
9,325,516 B2 4/2016 Pera et al.
D755,196 S 5/2016 Meyers et al.
D756,373 S 5/2016 Raskin et al.
D756,377 S 5/2016 Connolly et al.
D757,028 S 5/2016 Goldenberg et al.
9,326,767 B2 5/2016 Koch et al.
9,326,768 B2 5/2016 Shelton, IV
9,326,769 B2 5/2016 Shelton, IV et al.
9,326,770 B2 5/2016 Shelton, IV et al.
9,326,771 B2 5/2016 Baxter, III et al.
9,326,788 B2 5/2016 Batross et al.
9,326,812 B2 5/2016 Waaler et al.
9,326,824 B2 5/2016 Inoue et al.
9,327,061 B2 5/2016 Govil et al.
9,331,721 B2 5/2016 Martinez Nuevo et al.
9,332,890 B2 5/2016 Ozawa
9,332,974 B2 5/2016 Henderson et al.
9,332,984 B2 5/2016 Weaner et al.
9,332,987 B2 5/2016 Leimbach et al.
9,333,040 B2 5/2016 Shellenberger et al.
9,333,082 B2 5/2016 Wei et al.
9,337,668 B2 5/2016 Yip
9,339,226 B2 5/2016 van der Walt et al.
9,339,342 B2 5/2016 Prisco et al.
9,345,477 B2 5/2016 Anim et al.
9,345,479 B2 5/2016 (Tarinelli) Racenet et al.
9,345,480 B2 5/2016 Hessler et al.
9,345,481 B2 5/2016 Hall et al.
9,345,503 B2 5/2016 Ishida et al.
9,351,726 B2 5/2016 Leimbach et al.
9,351,727 B2 5/2016 Leimbach et al.
9,351,728 B2 5/2016 Sniffin et al.
9,351,730 B2 5/2016 Schmid et al.
9,351,731 B2 5/2016 Carter et al.
9,351,732 B2 5/2016 Hodgkinson
9,352,071 B2 5/2016 Landgrebe et al.
D758,433 S 6/2016 Lee et al.
D759,063 S 6/2016 Chen
9,358,003 B2 6/2016 Hall et al.
9,358,004 B2 6/2016 Sniffin et al.
9,358,005 B2 6/2016 Shelton, IV et al.
9,358,015 B2 6/2016 Sorrentino et al.
9,358,031 B2 6/2016 Manzo
9,358,065 B2 6/2016 Ladtkow et al.
9,364,217 B2 6/2016 Kostrzewski et al.
9,364,219 B2 6/2016 Olson et al.
9,364,220 B2 6/2016 Williams
9,364,223 B2 6/2016 Scirica
9,364,226 B2 6/2016 Zemlok et al.
9,364,228 B2 6/2016 Straehnz et al.
9,364,229 B2 6/2016 D'Agostino et al.
9,364,230 B2 6/2016 Shelton, IV et al.
9,364,231 B2 6/2016 Wenchell
9,364,233 B2 6/2016 Alexander, III et al.
9,364,279 B2 6/2016 Houser et al.
9,368,991 B2 6/2016 Qahouq
9,370,341 B2 6/2016 Ceniccola et al.
9,370,358 B2 6/2016 Shelton, IV et al.
9,370,361 B2 6/2016 Viola et al.
9,370,362 B2 6/2016 Petty et al.
9,370,364 B2 6/2016 Smith et al.
9,370,400 B2 6/2016 Parihar
9,375,206 B2 6/2016 Vidal et al.
9,375,218 B2 6/2016 Wheeler et al.
9,375,230 B2 6/2016 Ross et al.
9,375,232 B2 6/2016 Hunt et al.
9,375,255 B2 6/2016 Houser et al.
D761,309 S 7/2016 Lee et al.
9,381,058 B2 7/2016 Houser et al.
9,383,881 B2 7/2016 Day et al.
9,385,640 B2 7/2016 Sun et al.
9,386,983 B2 7/2016 Swensgard et al.
9,386,984 B2 7/2016 Aronhalt et al.
9,386,985 B2 7/2016 Koch, Jr. et al.
9,386,988 B2 7/2016 Baxter, III et al.
9,387,003 B2 7/2016 Kaercher et al.
9,392,885 B2 7/2016 Vogler et al.
9,393,015 B2 7/2016 Laurent et al.
9,393,017 B2 7/2016 Flanagan et al.
9,393,018 B2 7/2016 Wang et al.
9,393,354 B2 7/2016 Freedman et al.
9,396,369 B1 7/2016 Whitehurst et al.
9,396,669 B2 7/2016 Karkanias et al.
9,398,905 B2 7/2016 Martin
9,398,911 B2 7/2016 Auld
D763,277 S 8/2016 Ahmed et al.
D764,498 S 8/2016 Capela et al.
9,402,604 B2 8/2016 Williams et al.
9,402,625 B2 8/2016 Coleman et al.
9,402,626 B2 8/2016 Ortiz et al.
9,402,627 B2 8/2016 Stevenson et al.
9,402,629 B2 8/2016 Ehrenfels et al.
9,402,679 B2 8/2016 Ginnebaugh et al.
9,402,682 B2 8/2016 Worrell et al.
9,402,688 B2 8/2016 Min et al.
9,408,604 B2 8/2016 Shelton, IV et al.
9,408,605 B1 8/2016 Knodel et al.
9,408,606 B2 8/2016 Shelton, IV
9,408,622 B2 8/2016 Stulen et al.
9,411,370 B2 8/2016 Benni et al.
9,413,128 B2 8/2016 Tien et al.
9,414,838 B2 8/2016 Shelton, IV et al.
9,414,849 B2 8/2016 Nagashimada
9,414,880 B2 8/2016 Monson et al.
9,420,967 B2 8/2016 Zand et al.
9,421,003 B2 8/2016 Williams et al.
9,421,014 B2 8/2016 Ingmanson et al.
9,421,030 B2 8/2016 Cole et al.
9,421,060 B2 8/2016 Monson et al.
9,421,062 B2 8/2016 Houser et al.
9,421,682 B2 8/2016 McClaskey et al.
9,427,223 B2 8/2016 Park et al.
9,427,231 B2 8/2016 Racenet et al.
9,429,204 B2 8/2016 Stefan et al.

(56) References Cited

U.S. PATENT DOCUMENTS

| | | | |
|---|---|---|---|
| D767,624 | S | 9/2016 | Lee et al. |
| 9,433,411 | B2 | 9/2016 | Racenet et al. |
| 9,433,414 | B2 | 9/2016 | Chen et al. |
| 9,433,419 | B2 | 9/2016 | Gonzalez et al. |
| 9,433,420 | B2 | 9/2016 | Hodgkinson |
| 9,439,649 | B2 | 9/2016 | Shelton, IV et al. |
| 9,439,650 | B2 | 9/2016 | McGuckin, Jr. et al. |
| 9,439,651 | B2 | 9/2016 | Smith et al. |
| 9,439,668 | B2 | 9/2016 | Timm et al. |
| 9,445,808 | B2 | 9/2016 | Woodard, Jr. et al. |
| 9,445,813 | B2 | 9/2016 | Shelton, IV et al. |
| 9,445,816 | B2 | 9/2016 | Swayze et al. |
| 9,445,817 | B2 | 9/2016 | Bettuchi |
| 9,446,226 | B2 | 9/2016 | Zilberman |
| 9,451,938 | B2 | 9/2016 | Overes et al. |
| 9,451,958 | B2 | 9/2016 | Shelton, IV et al. |
| 9,452,020 | B2 | 9/2016 | Griffiths et al. |
| D768,152 | S | 10/2016 | Gutierrez et al. |
| D768,156 | S | 10/2016 | Frincke |
| D768,167 | S | 10/2016 | Jones et al. |
| D769,315 | S | 10/2016 | Scotti |
| D769,930 | S | 10/2016 | Agrawal |
| 9,461,340 | B2 | 10/2016 | Li et al. |
| 9,463,012 | B2 | 10/2016 | Bonutti et al. |
| 9,463,040 | B2 | 10/2016 | Jeong et al. |
| 9,463,260 | B2 | 10/2016 | Stopek |
| 9,468,438 | B2 | 10/2016 | Baber et al. |
| 9,468,447 | B2 | 10/2016 | Aman et al. |
| 9,470,297 | B2 | 10/2016 | Aranyi et al. |
| 9,471,969 | B2 | 10/2016 | Zeng et al. |
| 9,474,506 | B2 | 10/2016 | Magnin et al. |
| 9,474,513 | B2 | 10/2016 | Ishida et al. |
| 9,474,523 | B2 | 10/2016 | Meade et al. |
| 9,474,540 | B2 | 10/2016 | Stokes et al. |
| 9,475,180 | B2 | 10/2016 | Eshleman et al. |
| D770,476 | S | 11/2016 | Jitkoff et al. |
| D770,515 | S | 11/2016 | Cho et al. |
| D771,116 | S | 11/2016 | Dellinger et al. |
| D772,905 | S | 11/2016 | Ingenlath |
| 9,480,476 | B2 | 11/2016 | Aldridge et al. |
| 9,480,492 | B2 | 11/2016 | Aranyi et al. |
| 9,483,095 | B2 | 11/2016 | Tran et al. |
| 9,486,186 | B2 | 11/2016 | Fiebig et al. |
| 9,486,213 | B2 | 11/2016 | Altman et al. |
| 9,486,214 | B2 | 11/2016 | Shelton, IV |
| 9,486,215 | B2 | 11/2016 | Olson et al. |
| 9,486,302 | B2 | 11/2016 | Boey et al. |
| 9,488,197 | B2 | 11/2016 | Wi |
| 9,492,146 | B2 | 11/2016 | Kostrzewski et al. |
| 9,492,167 | B2 | 11/2016 | Shelton, IV et al. |
| 9,492,170 | B2 | 11/2016 | Bear et al. |
| 9,492,172 | B2 | 11/2016 | Weisshaupt et al. |
| 9,492,189 | B2 | 11/2016 | Williams et al. |
| 9,492,192 | B2 | 11/2016 | To et al. |
| 9,492,237 | B2 | 11/2016 | Kang et al. |
| 9,498,213 | B2 | 11/2016 | Marczyk et al. |
| 9,498,219 | B2 | 11/2016 | Moore et al. |
| 9,498,231 | B2 | 11/2016 | Haider et al. |
| 9,504,455 | B2 | 11/2016 | Whitman et al. |
| 9,504,483 | B2 | 11/2016 | Houser et al. |
| 9,504,520 | B2 | 11/2016 | Worrell et al. |
| 9,504,521 | B2 | 11/2016 | Deutmeyer et al. |
| 9,504,528 | B2 | 11/2016 | Ivinson et al. |
| 9,507,399 | B2 | 11/2016 | Chien |
| D774,547 | S | 12/2016 | Capela et al. |
| D775,336 | S | 12/2016 | Shelton, IV et al. |
| 9,510,827 | B2 | 12/2016 | Kostrzewski |
| 9,510,828 | B2 | 12/2016 | Yates et al. |
| 9,510,830 | B2 | 12/2016 | Shelton, IV et al. |
| 9,510,846 | B2 | 12/2016 | Sholev et al. |
| 9,510,895 | B2 | 12/2016 | Houser et al. |
| 9,510,925 | B2 | 12/2016 | Hotter et al. |
| 9,517,063 | B2 | 12/2016 | Swayze et al. |
| 9,517,065 | B2 | 12/2016 | Simms et al. |
| 9,517,068 | B2 | 12/2016 | Shelton, IV et al. |
| 9,517,326 | B2 | 12/2016 | Hinman et al. |
| 9,521,996 | B2 | 12/2016 | Armstrong |
| 9,522,003 | B2 | 12/2016 | Weir et al. |
| 9,522,014 | B2 | 12/2016 | Nishizawa et al. |
| 9,522,029 | B2 | 12/2016 | Yates et al. |
| 9,526,481 | B2 | 12/2016 | Storz et al. |
| 9,526,499 | B2 | 12/2016 | Kostrzewski et al. |
| 9,526,563 | B2 | 12/2016 | Twomey |
| 9,526,564 | B2 | 12/2016 | Rusin |
| 9,526,921 | B2 | 12/2016 | Kimball et al. |
| D776,683 | S | 1/2017 | Gobinski et al. |
| D777,773 | S | 1/2017 | Shi |
| 9,532,783 | B2 | 1/2017 | Swayze et al. |
| 9,539,060 | B2 | 1/2017 | Lightcap et al. |
| 9,539,726 | B2 | 1/2017 | Simaan et al. |
| 9,545,253 | B2 | 1/2017 | Worrell et al. |
| 9,545,258 | B2 | 1/2017 | Smith et al. |
| 9,549,732 | B2 | 1/2017 | Yates et al. |
| 9,549,733 | B2 | 1/2017 | Knodel |
| 9,549,735 | B2 | 1/2017 | Shelton, IV et al. |
| 9,549,750 | B2 | 1/2017 | Shelton, IV et al. |
| 9,554,794 | B2 | 1/2017 | Baber et al. |
| 9,554,796 | B2 | 1/2017 | Kostrzewski |
| 9,554,803 | B2 | 1/2017 | Smith et al. |
| 9,554,812 | B2 | 1/2017 | Inkpen et al. |
| 9,554,854 | B2 | 1/2017 | Yates et al. |
| 9,559,624 | B2 | 1/2017 | Philipp |
| 9,561,013 | B2 | 2/2017 | Tsuchiya |
| 9,561,029 | B2 | 2/2017 | Scheib et al. |
| 9,561,030 | B2 | 2/2017 | Zhang et al. |
| 9,561,031 | B2 | 2/2017 | Heinrich et al. |
| 9,561,032 | B2 | 2/2017 | Shelton, IV et al. |
| 9,561,038 | B2 | 2/2017 | Shelton, IV et al. |
| 9,561,045 | B2 | 2/2017 | Hinman et al. |
| 9,561,072 | B2 | 2/2017 | Ko |
| 9,566,061 | B2 | 2/2017 | Aronhalt et al. |
| 9,566,062 | B2 | 2/2017 | Boudreaux |
| 9,566,064 | B2 | 2/2017 | Williams et al. |
| 9,566,065 | B2 | 2/2017 | Knodel |
| 9,566,067 | B2 | 2/2017 | Milliman et al. |
| 9,572,574 | B2 | 2/2017 | Shelton, IV et al. |
| 9,572,576 | B2 | 2/2017 | Hodgkinson et al. |
| 9,572,577 | B2 | 2/2017 | Lloyd et al. |
| 9,572,592 | B2 | 2/2017 | Price et al. |
| 9,574,644 | B2 | 2/2017 | Parihar |
| 9,579,088 | B2 | 2/2017 | Farritor et al. |
| 9,579,143 | B2 | 2/2017 | Ullrich et al. |
| 9,579,158 | B2 | 2/2017 | Brianza et al. |
| D780,803 | S | 3/2017 | Gill et al. |
| D781,879 | S | 3/2017 | Butcher et al. |
| D782,530 | S | 3/2017 | Paek et al. |
| 9,585,550 | B2 | 3/2017 | Abel et al. |
| 9,585,657 | B2 | 3/2017 | Shelton, IV et al. |
| 9,585,658 | B2 | 3/2017 | Shelton, IV |
| 9,585,659 | B2 | 3/2017 | Viola et al. |
| 9,585,660 | B2 | 3/2017 | Laurent et al. |
| 9,585,662 | B2 | 3/2017 | Shelton, IV et al. |
| 9,585,663 | B2 | 3/2017 | Shelton, IV et al. |
| 9,585,672 | B2 | 3/2017 | Bastia |
| 9,590,433 | B2 | 3/2017 | Li |
| 9,592,050 | B2 | 3/2017 | Schmid et al. |
| 9,592,052 | B2 | 3/2017 | Shelton, IV |
| 9,592,053 | B2 | 3/2017 | Shelton, IV et al. |
| 9,592,054 | B2 | 3/2017 | Schmid et al. |
| 9,597,073 | B2 | 3/2017 | Sorrentino et al. |
| 9,597,075 | B2 | 3/2017 | Shelton, IV et al. |
| 9,597,078 | B2 | 3/2017 | Scirica et al. |
| 9,597,080 | B2 | 3/2017 | Milliman et al. |
| 9,597,104 | B2 | 3/2017 | Nicholas et al. |
| 9,597,143 | B2 | 3/2017 | Madan et al. |
| 9,603,595 | B2 | 3/2017 | Shelton, IV et al. |
| 9,603,598 | B2 | 3/2017 | Shelton, IV et al. |
| 9,603,599 | B2 | 3/2017 | Miller et al. |
| 9,603,991 | B2 | 3/2017 | Shelton, IV et al. |
| D783,658 | S | 4/2017 | Hurst et al. |
| 9,610,068 | B2 | 4/2017 | Kappel et al. |
| 9,610,079 | B2 | 4/2017 | Kamei et al. |
| 9,610,080 | B2 | 4/2017 | Whitfield et al. |
| 9,610,412 | B2 | 4/2017 | Zemlok et al. |

(56) References Cited

U.S. PATENT DOCUMENTS

| | | | |
|---|---|---|---|
| 9,614,258 | B2 | 4/2017 | Takahashi et al. |
| 9,615,826 | B2 | 4/2017 | Shelton, IV et al. |
| 9,622,745 | B2 | 4/2017 | Ingmanson et al. |
| 9,622,746 | B2 | 4/2017 | Simms et al. |
| 9,629,623 | B2 | 4/2017 | Lytle, IV et al. |
| 9,629,626 | B2 | 4/2017 | Soltz et al. |
| 9,629,627 | B2 | 4/2017 | Kostrzewski et al. |
| 9,629,628 | B2 | 4/2017 | Aranyi |
| 9,629,629 | B2 | 4/2017 | Leimbach et al. |
| 9,629,631 | B2 | 4/2017 | Nicholas et al. |
| 9,629,632 | B2 | 4/2017 | Linder et al. |
| 9,629,652 | B2 | 4/2017 | Mumaw et al. |
| 9,629,814 | B2 | 4/2017 | Widenhouse et al. |
| D785,794 | S | 5/2017 | Magno, Jr. |
| D786,280 | S | 5/2017 | Ma |
| D786,896 | S | 5/2017 | Kim et al. |
| D787,547 | S | 5/2017 | Basargin et al. |
| D788,123 | S | 5/2017 | Shan et al. |
| D788,140 | S | 5/2017 | Hemsley et al. |
| 9,636,091 | B2 | 5/2017 | Beardsley et al. |
| 9,636,111 | B2 | 5/2017 | Wenchell |
| 9,636,112 | B2 | 5/2017 | Penna et al. |
| 9,636,113 | B2 | 5/2017 | Wenchell |
| 9,636,850 | B2 | 5/2017 | Stopek (nee Prommersberger) et al. |
| 9,641,122 | B2 | 5/2017 | Romanowich et al. |
| 9,642,620 | B2 | 5/2017 | Baxter, III et al. |
| 9,642,642 | B2 | 5/2017 | Lim |
| 9,649,096 | B2 | 5/2017 | Sholev |
| 9,649,110 | B2 | 5/2017 | Parihar et al. |
| 9,649,111 | B2 | 5/2017 | Shelton, IV et al. |
| 9,649,190 | B2 | 5/2017 | Mathies |
| 9,651,032 | B2 | 5/2017 | Weaver et al. |
| 9,655,613 | B2 | 5/2017 | Schaller |
| 9,655,614 | B2 | 5/2017 | Swensgard et al. |
| 9,655,615 | B2 | 5/2017 | Knodel et al. |
| 9,655,616 | B2 | 5/2017 | Aranyi |
| 9,655,624 | B2 | 5/2017 | Shelton, IV et al. |
| 9,661,991 | B2 | 5/2017 | Glossop |
| 9,662,108 | B2 | 5/2017 | Williams |
| 9,662,110 | B2 | 5/2017 | Huang et al. |
| 9,662,111 | B2 | 5/2017 | Holsten et al. |
| 9,662,116 | B2 | 5/2017 | Smith et al. |
| 9,662,131 | B2 | 5/2017 | Omori et al. |
| D788,792 | S | 6/2017 | Alessandri et al. |
| D789,384 | S | 6/2017 | Lin et al. |
| D790,570 | S | 6/2017 | Butcher et al. |
| 9,668,728 | B2 | 6/2017 | Williams et al. |
| 9,668,729 | B2 | 6/2017 | Williams et al. |
| 9,668,732 | B2 | 6/2017 | Patel et al. |
| 9,668,733 | B2 | 6/2017 | Williams |
| 9,668,734 | B2 | 6/2017 | Kostrzewski et al. |
| 9,668,735 | B2 | 6/2017 | Beetel |
| 9,675,344 | B2 | 6/2017 | Combrowski et al. |
| 9,675,348 | B2 | 6/2017 | Smith et al. |
| 9,675,351 | B2 | 6/2017 | Hodgkinson et al. |
| 9,675,354 | B2 | 6/2017 | Weir et al. |
| 9,675,355 | B2 | 6/2017 | Shelton, IV et al. |
| 9,675,368 | B2 | 6/2017 | Guo et al. |
| 9,675,372 | B2 | 6/2017 | Laurent et al. |
| 9,675,375 | B2 | 6/2017 | Houser et al. |
| 9,675,405 | B2 | 6/2017 | Trees et al. |
| 9,675,819 | B2 | 6/2017 | Dunbar et al. |
| 9,681,870 | B2 | 6/2017 | Baxter, III et al. |
| 9,681,873 | B2 | 6/2017 | Smith et al. |
| 9,681,884 | B2 | 6/2017 | Clem et al. |
| 9,687,230 | B2 | 6/2017 | Leimbach et al. |
| 9,687,231 | B2 | 6/2017 | Baxter, III et al. |
| 9,687,232 | B2 | 6/2017 | Shelton, IV et al. |
| 9,687,233 | B2 | 6/2017 | Fernandez et al. |
| 9,687,236 | B2 | 6/2017 | Leimbach et al. |
| 9,687,237 | B2 | 6/2017 | Schmid et al. |
| 9,687,253 | B2 | 6/2017 | Detry et al. |
| 9,689,466 | B2 | 6/2017 | Kanai et al. |
| 9,690,362 | B2 | 6/2017 | Leimbach et al. |
| 9,693,772 | B2 | 7/2017 | Ingmanson et al. |
| 9,693,774 | B2 | 7/2017 | Gettinger et al. |
| 9,693,775 | B2 | 7/2017 | Agarwal et al. |
| 9,693,777 | B2 | 7/2017 | Schellin et al. |
| 9,700,309 | B2 | 7/2017 | Jaworek et al. |
| 9,700,310 | B2 | 7/2017 | Morgan et al. |
| 9,700,312 | B2 | 7/2017 | Kostrzewski et al. |
| 9,700,314 | B2 | 7/2017 | Marczyk |
| 9,700,315 | B2 | 7/2017 | Chen et al. |
| 9,700,317 | B2 | 7/2017 | Aronhalt et al. |
| 9,700,318 | B2 | 7/2017 | Scirica et al. |
| 9,700,319 | B2 | 7/2017 | Motooka et al. |
| 9,700,320 | B2 | 7/2017 | Dinardo et al. |
| 9,700,321 | B2 | 7/2017 | Shelton, IV et al. |
| 9,700,334 | B2 | 7/2017 | Hinman et al. |
| 9,700,381 | B2 | 7/2017 | Amat Girbau |
| 9,702,823 | B2 | 7/2017 | Maher et al. |
| 9,706,674 | B2 | 7/2017 | Collins et al. |
| 9,706,981 | B2 | 7/2017 | Nicholas et al. |
| 9,706,991 | B2 | 7/2017 | Hess et al. |
| 9,706,993 | B2 | 7/2017 | Hessler et al. |
| 9,707,003 | B2 | 7/2017 | Hoell, Jr. et al. |
| 9,707,005 | B2 | 7/2017 | Strobl et al. |
| 9,707,026 | B2 | 7/2017 | Malackowski et al. |
| 9,707,033 | B2 | 7/2017 | Parihar et al. |
| 9,707,043 | B2 | 7/2017 | Bozung |
| 9,707,684 | B2 | 7/2017 | Ruiz Morales et al. |
| 9,713,466 | B2 | 7/2017 | Kostrzewski |
| 9,713,468 | B2 | 7/2017 | Harris et al. |
| 9,713,470 | B2 | 7/2017 | Scirica et al. |
| 9,713,474 | B2 | 7/2017 | Lorenz |
| D795,919 | S | 8/2017 | Bischoff et al. |
| 9,717,497 | B2 | 8/2017 | Zerkle et al. |
| 9,717,498 | B2 | 8/2017 | Aranyi et al. |
| 9,718,190 | B2 | 8/2017 | Larkin et al. |
| 9,722,236 | B2 | 8/2017 | Sathrum |
| 9,724,091 | B2 | 8/2017 | Shelton, IV et al. |
| 9,724,092 | B2 | 8/2017 | Baxter, III et al. |
| 9,724,094 | B2 | 8/2017 | Baber et al. |
| 9,724,095 | B2 | 8/2017 | Gupta et al. |
| 9,724,096 | B2 | 8/2017 | Thompson et al. |
| 9,724,098 | B2 | 8/2017 | Baxter, III et al. |
| 9,724,118 | B2 | 8/2017 | Schulte et al. |
| 9,724,163 | B2 | 8/2017 | Orban |
| 9,730,692 | B2 | 8/2017 | Shelton, IV et al. |
| 9,730,695 | B2 | 8/2017 | Leimbach et al. |
| 9,730,697 | B2 | 8/2017 | Morgan et al. |
| 9,730,717 | B2 | 8/2017 | Katsuki et al. |
| 9,730,757 | B2 | 8/2017 | Brudniok |
| 9,731,410 | B2 | 8/2017 | Hirabayashi et al. |
| 9,733,663 | B2 | 8/2017 | Leimbach et al. |
| 9,737,297 | B2 | 8/2017 | Racenet et al. |
| 9,737,298 | B2 | 8/2017 | Isbell, Jr. |
| 9,737,299 | B2 | 8/2017 | Yan |
| 9,737,301 | B2 | 8/2017 | Baber et al. |
| 9,737,302 | B2 | 8/2017 | Shelton, IV et al. |
| 9,737,303 | B2 | 8/2017 | Shelton, IV et al. |
| 9,737,365 | B2 | 8/2017 | Hegeman et al. |
| 9,743,927 | B2 | 8/2017 | Whitman |
| 9,743,928 | B2 | 8/2017 | Shelton, IV et al. |
| 9,743,929 | B2 | 8/2017 | Leimbach et al. |
| D798,319 | S | 9/2017 | Bergstrand et al. |
| 9,750,498 | B2 | 9/2017 | Timm et al. |
| 9,750,499 | B2 | 9/2017 | Leimbach et al. |
| 9,750,501 | B2 | 9/2017 | Shelton, IV et al. |
| 9,750,502 | B2 | 9/2017 | Scirica et al. |
| 9,750,503 | B2 | 9/2017 | Milliman |
| 9,750,639 | B2 | 9/2017 | Barnes et al. |
| 9,757,123 | B2 | 9/2017 | Giordano et al. |
| 9,757,124 | B2 | 9/2017 | Schellin et al. |
| 9,757,126 | B2 | 9/2017 | Cappola |
| 9,757,128 | B2 | 9/2017 | Baber et al. |
| 9,757,129 | B2 | 9/2017 | Williams |
| 9,757,130 | B2 | 9/2017 | Shelton, IV |
| 9,763,662 | B2 | 9/2017 | Shelton, IV et al. |
| 9,763,668 | B2 | 9/2017 | Whitfield et al. |
| 9,770,245 | B2 | 9/2017 | Swayze et al. |
| 9,770,274 | B2 | 9/2017 | Pool et al. |
| D798,886 | S | 10/2017 | Prophete et al. |

(56) References Cited

U.S. PATENT DOCUMENTS

| | | | |
|---|---|---|---|
| D800,742 | S | 10/2017 | Rhodes |
| D800,744 | S | 10/2017 | Jitkoff et al. |
| D800,766 | S | 10/2017 | Park et al. |
| D800,904 | S | 10/2017 | Leimbach et al. |
| 9,775,608 | B2 | 10/2017 | Aronhalt et al. |
| 9,775,609 | B2 | 10/2017 | Shelton, IV et al. |
| 9,775,610 | B2 | 10/2017 | Nicholas et al. |
| 9,775,611 | B2 | 10/2017 | Kostrzewski |
| 9,775,613 | B2 | 10/2017 | Shelton, IV et al. |
| 9,775,614 | B2 | 10/2017 | Shelton, IV et al. |
| 9,775,618 | B2 | 10/2017 | Bettuchi et al. |
| 9,775,635 | B2 | 10/2017 | Take |
| 9,775,678 | B2 | 10/2017 | Lohmeier |
| 9,782,169 | B2 | 10/2017 | Kimsey et al. |
| 9,782,170 | B2 | 10/2017 | Zemlok et al. |
| 9,782,180 | B2 | 10/2017 | Smith et al. |
| 9,782,187 | B2 | 10/2017 | Zergiebel et al. |
| 9,782,193 | B2 | 10/2017 | Thistle |
| 9,782,214 | B2 | 10/2017 | Houser et al. |
| 9,788,834 | B2 | 10/2017 | Schmid et al. |
| 9,788,835 | B2 | 10/2017 | Morgan et al. |
| 9,788,836 | B2 | 10/2017 | Overmyer et al. |
| 9,788,847 | B2 | 10/2017 | Jinno |
| 9,788,851 | B2 | 10/2017 | Dannaher et al. |
| 9,788,902 | B2 | 10/2017 | Inoue et al. |
| 9,795,379 | B2 | 10/2017 | Leimbach et al. |
| 9,795,380 | B2 | 10/2017 | Shelton, IV et al. |
| 9,795,381 | B2 | 10/2017 | Shelton, IV |
| 9,795,382 | B2 | 10/2017 | Shelton, IV |
| 9,795,383 | B2 | 10/2017 | Aldridge et al. |
| 9,795,384 | B2 | 10/2017 | Weaner et al. |
| 9,797,486 | B2 | 10/2017 | Zergiebel et al. |
| 9,801,626 | B2 | 10/2017 | Parihar et al. |
| 9,801,627 | B2 | 10/2017 | Harris et al. |
| 9,801,628 | B2 | 10/2017 | Harris et al. |
| 9,801,634 | B2 | 10/2017 | Shelton, IV et al. |
| 9,801,679 | B2 | 10/2017 | Trees et al. |
| 9,802,033 | B2 | 10/2017 | Hibner et al. |
| 9,804,618 | B2 | 10/2017 | Leimbach et al. |
| D803,234 | S | 11/2017 | Day et al. |
| D803,235 | S | 11/2017 | Markson et al. |
| D803,850 | S | 11/2017 | Chang et al. |
| 9,808,244 | B2 | 11/2017 | Leimbach et al. |
| 9,808,246 | B2 | 11/2017 | Shelton, IV et al. |
| 9,808,247 | B2 | 11/2017 | Shelton, IV et al. |
| 9,808,248 | B2 | 11/2017 | Hoffman |
| 9,808,249 | B2 | 11/2017 | Shelton, IV |
| 9,814,460 | B2 | 11/2017 | Kimsey et al. |
| 9,814,462 | B2 | 11/2017 | Woodard, Jr. et al. |
| 9,814,463 | B2 | 11/2017 | Williams et al. |
| 9,814,530 | B2 | 11/2017 | Weir et al. |
| 9,814,561 | B2 | 11/2017 | Forsell |
| 9,815,118 | B1 | 11/2017 | Schmitt et al. |
| 9,820,445 | B2 | 11/2017 | Simpson et al. |
| 9,820,737 | B2 | 11/2017 | Beardsley et al. |
| 9,820,738 | B2 | 11/2017 | Lytle, IV et al. |
| 9,820,741 | B2 | 11/2017 | Kostrzewski |
| 9,820,768 | B2 | 11/2017 | Gee et al. |
| 9,825,455 | B2 | 11/2017 | Sandhu et al. |
| 9,826,976 | B2 | 11/2017 | Parihar et al. |
| 9,826,977 | B2 | 11/2017 | Leimbach et al. |
| 9,826,978 | B2 | 11/2017 | Shelton, IV et al. |
| 9,829,698 | B2 | 11/2017 | Haraguchi et al. |
| D806,108 | S | 12/2017 | Day |
| 9,833,235 | B2 | 12/2017 | Penna et al. |
| 9,833,236 | B2 | 12/2017 | Shelton, IV et al. |
| 9,833,238 | B2 | 12/2017 | Baxter, III et al. |
| 9,833,239 | B2 | 12/2017 | Yates et al. |
| 9,833,241 | B2 | 12/2017 | Huitema et al. |
| 9,833,242 | B2 | 12/2017 | Baxter, III et al. |
| 9,839,420 | B2 | 12/2017 | Shelton, IV et al. |
| 9,839,421 | B2 | 12/2017 | Zerkle et al. |
| 9,839,422 | B2 | 12/2017 | Schellin et al. |
| 9,839,423 | B2 | 12/2017 | Vendely et al. |
| 9,839,427 | B2 | 12/2017 | Swayze et al. |
| 9,839,428 | B2 | 12/2017 | Baxter, III et al. |
| 9,839,429 | B2 | 12/2017 | Weisenburgh, II et al. |
| 9,839,480 | B2 | 12/2017 | Pribanic et al. |
| 9,839,481 | B2 | 12/2017 | Blumenkranz et al. |
| 9,844,368 | B2 | 12/2017 | Boudreaux et al. |
| 9,844,369 | B2 | 12/2017 | Huitema et al. |
| 9,844,372 | B2 | 12/2017 | Shelton, IV et al. |
| 9,844,373 | B2 | 12/2017 | Swayze et al. |
| 9,844,374 | B2 | 12/2017 | Lytle, IV et al. |
| 9,844,375 | B2 | 12/2017 | Overmyer et al. |
| 9,844,376 | B2 | 12/2017 | Baxter, III et al. |
| 9,844,379 | B2 | 12/2017 | Shelton, IV et al. |
| 9,848,871 | B2 | 12/2017 | Harris et al. |
| 9,848,873 | B2 | 12/2017 | Shelton, IV |
| 9,848,875 | B2 | 12/2017 | Aronhalt et al. |
| 9,848,877 | B2 | 12/2017 | Shelton, IV et al. |
| 9,850,994 | B2 | 12/2017 | Schena |
| D808,989 | S | 1/2018 | Ayvazian et al. |
| 9,855,039 | B2 | 1/2018 | Racenet et al. |
| 9,855,040 | B2 | 1/2018 | Kostrzewski |
| 9,855,662 | B2 | 1/2018 | Ruiz Morales et al. |
| 9,861,261 | B2 | 1/2018 | Shahinian |
| 9,861,359 | B2 | 1/2018 | Shelton, IV et al. |
| 9,861,361 | B2 | 1/2018 | Aronhalt et al. |
| 9,861,362 | B2 | 1/2018 | Whitman et al. |
| 9,861,366 | B2 | 1/2018 | Aranyi |
| 9,861,382 | B2 | 1/2018 | Smith et al. |
| 9,861,446 | B2 | 1/2018 | Lang |
| 9,867,612 | B2 | 1/2018 | Parihar et al. |
| 9,867,613 | B2 | 1/2018 | Marczyk et al. |
| 9,867,615 | B2 | 1/2018 | Fanelli et al. |
| 9,867,617 | B2 | 1/2018 | Ma |
| 9,867,618 | B2 | 1/2018 | Hall et al. |
| 9,867,620 | B2 | 1/2018 | Fischvogt et al. |
| 9,868,198 | B2 | 1/2018 | Nicholas et al. |
| 9,872,682 | B2 | 1/2018 | Hess et al. |
| 9,872,683 | B2 | 1/2018 | Hopkins et al. |
| 9,872,684 | B2 | 1/2018 | Hall et al. |
| 9,872,722 | B2 | 1/2018 | Lech |
| 9,877,721 | B2 | 1/2018 | Schellin et al. |
| 9,877,722 | B2 | 1/2018 | Schellin et al. |
| 9,877,723 | B2 | 1/2018 | Hall et al. |
| 9,877,776 | B2 | 1/2018 | Boudreaux |
| D810,099 | S | 2/2018 | Riedel |
| 9,883,843 | B2 | 2/2018 | Garlow |
| 9,883,860 | B2 | 2/2018 | Leimbach |
| 9,883,861 | B2 | 2/2018 | Shelton, IV et al. |
| 9,884,456 | B2 | 2/2018 | Schellin et al. |
| 9,888,914 | B2 | 2/2018 | Martin et al. |
| 9,888,919 | B2 | 2/2018 | Leimbach et al. |
| 9,888,921 | B2 | 2/2018 | Williams et al. |
| 9,888,924 | B2 | 2/2018 | Ebersole et al. |
| 9,889,230 | B2 | 2/2018 | Bennett et al. |
| 9,895,147 | B2 | 2/2018 | Shelton, IV |
| 9,895,148 | B2 | 2/2018 | Shelton, IV et al. |
| 9,895,813 | B2 | 2/2018 | Blumenkranz et al. |
| 9,901,339 | B2 | 2/2018 | Farascioni |
| 9,901,341 | B2 | 2/2018 | Kostrzewski |
| 9,901,342 | B2 | 2/2018 | Shelton, IV et al. |
| 9,901,344 | B2 | 2/2018 | Moore et al. |
| 9,901,345 | B2 | 2/2018 | Moore et al. |
| 9,901,346 | B2 | 2/2018 | Moore et al. |
| 9,901,358 | B2 | 2/2018 | Faller et al. |
| 9,901,406 | B2 | 2/2018 | State et al. |
| 9,901,412 | B2 | 2/2018 | Lathrop et al. |
| D813,899 | S | 3/2018 | Erant et al. |
| 9,907,456 | B2 | 3/2018 | Miyoshi |
| 9,907,552 | B2 | 3/2018 | Measamer et al. |
| 9,907,553 | B2 | 3/2018 | Cole et al. |
| 9,907,600 | B2 | 3/2018 | Stulen et al. |
| 9,907,620 | B2 | 3/2018 | Shelton, IV et al. |
| 9,913,641 | B2 | 3/2018 | Takemoto et al. |
| 9,913,642 | B2 | 3/2018 | Leimbach et al. |
| 9,913,644 | B2 | 3/2018 | McCuen |
| 9,913,646 | B2 | 3/2018 | Shelton, IV |
| 9,913,647 | B2 | 3/2018 | Weisenburgh, II et al. |
| 9,913,648 | B2 | 3/2018 | Shelton, IV et al. |
| 9,913,694 | B2 | 3/2018 | Brisson |
| 9,913,733 | B2 | 3/2018 | Piron et al. |

(56) References Cited

U.S. PATENT DOCUMENTS 9,918,704 B2 3/2018 Shelton, IV et al.
9,918,714 B2 3/2018 Gibbons, Jr.
9,918,715 B2 3/2018 Menn
9,918,716 B2 3/2018 Baxter, III et al.
9,918,717 B2 3/2018 Czernik
9,918,730 B2 3/2018 Trees et al.
9,924,941 B2 3/2018 Burbank
9,924,942 B2 3/2018 Swayze et al.
9,924,943 B2 3/2018 Mohan Pinjala et al.
9,924,944 B2 3/2018 Shelton, IV et al.
9,924,945 B2 3/2018 Zheng et al.
9,924,946 B2 3/2018 Vendely et al.
9,924,947 B2 3/2018 Shelton, IV et al.
9,924,961 B2 3/2018 Shelton, IV et al.
9,931,106 B2 4/2018 Au et al.
9,931,116 B2 4/2018 Racenet et al.
9,931,117 B2 4/2018 Hathaway et al.
9,931,118 B2 4/2018 Shelton, IV et al.
9,931,120 B2 4/2018 Chen et al.
9,936,949 B2 4/2018 Measamer et al.
9,936,950 B2 4/2018 Shelton, IV et al.
9,936,951 B2 4/2018 Hufnagel et al.
9,936,952 B2 4/2018 Demmy
9,936,954 B2 4/2018 Shelton, IV et al.
9,937,626 B2 4/2018 Rockrohr
9,943,309 B2 4/2018 Shelton, IV et al.
9,943,310 B2 4/2018 Harris et al.
9,943,312 B2 4/2018 Posada et al.
9,949,754 B2 4/2018 Newhauser et al.
9,953,193 B2 4/2018 Butler et al.
D819,072 S 5/2018 Clediere
9,955,954 B2 5/2018 Destoumieux et al.
9,955,965 B2 5/2018 Chen et al.
9,955,966 B2 5/2018 Zergiebel
9,956,677 B2 5/2018 Baskar et al.
9,962,129 B2 5/2018 Jerebko et al.
9,962,157 B2 5/2018 Sapre
9,962,158 B2 5/2018 Hall et al.
9,962,159 B2 5/2018 Heinrich et al.
9,962,161 B2 5/2018 Scheib et al.
9,968,354 B2 5/2018 Shelton, IV et al.
9,968,355 B2 5/2018 Shelton, IV et al.
9,968,356 B2 5/2018 Shelton, IV et al.
9,968,397 B2 5/2018 Taylor et al.
9,974,529 B2 5/2018 Shelton, IV et al.
9,974,538 B2 5/2018 Baxter, III et al.
9,974,539 B2 5/2018 Yates et al.
9,974,541 B2 5/2018 Calderoni
9,974,542 B2 5/2018 Hodgkinson
9,980,713 B2 5/2018 Aronhalt et al.
9,980,724 B2 5/2018 Farascioni et al.
9,980,729 B2 5/2018 Moore et al.
9,980,769 B2 5/2018 Trees et al.
D819,680 S 6/2018 Nguyen
D819,682 S 6/2018 Howard et al.
D819,684 S 6/2018 Dart
D820,307 S 6/2018 Jian et al.
D820,867 S 6/2018 Dickens et al.
9,987,000 B2 6/2018 Shelton, IV et al.
9,987,003 B2 6/2018 Timm et al.
9,987,006 B2 6/2018 Morgan et al.
9,987,008 B2 6/2018 Scirica et al.
9,987,095 B2 6/2018 Chowaniec et al.
9,987,097 B2 6/2018 van der Weide et al.
9,987,099 B2 6/2018 Chen et al.
9,993,248 B2 6/2018 Shelton, IV et al.
9,993,258 B2 6/2018 Shelton, IV et al.
9,993,284 B2 6/2018 Boudreaux
9,999,408 B2 6/2018 Boudreaux et al.
9,999,423 B2 6/2018 Schuckmann et al.
9,999,426 B2 6/2018 Moore et al.
9,999,431 B2 6/2018 Shelton, IV et al.
9,999,472 B2 6/2018 Weir et al.
10,004,497 B2 6/2018 Overmyer et al.
10,004,498 B2 6/2018 Morgan et al.
10,004,500 B2 6/2018 Shelton, IV et al.
10,004,501 B2 6/2018 Shelton, IV et al.
10,004,505 B2 6/2018 Moore et al.
10,004,506 B2 6/2018 Shelton, IV et al.
10,004,552 B1 6/2018 Kleyman et al.
D822,206 S 7/2018 Shelton, IV et al.
10,010,322 B2 7/2018 Shelton, IV et al.
10,010,324 B2 7/2018 Huitema et al.
10,010,395 B2 7/2018 Puckett et al.
10,013,049 B2 7/2018 Leimbach et al.
10,016,199 B2 7/2018 Baber et al.
10,016,656 B2 7/2018 Devor et al.
10,022,120 B2 7/2018 Martin et al.
10,022,123 B2 7/2018 Williams et al.
10,022,125 B2 7/2018 (Prommersberger) Stopek et al.
10,024,407 B2 7/2018 Aranyi et al.
10,028,742 B2 7/2018 Shelton, IV et al.
10,028,743 B2 7/2018 Shelton, IV et al.
10,028,744 B2 7/2018 Shelton, IV et al.
10,028,761 B2 7/2018 Leimbach et al.
10,029,108 B2 7/2018 Powers et al.
10,029,125 B2 7/2018 Shapiro et al.
10,034,344 B2 7/2018 Yoshida
10,034,668 B2 7/2018 Ebner
D826,405 S 8/2018 Shelton, IV et al.
10,039,440 B2 8/2018 Fenech et al.
10,039,529 B2 8/2018 Kerr et al.
10,039,532 B2 8/2018 Srinivas et al.
10,039,545 B2 8/2018 Sadowski et al.
10,041,822 B2 8/2018 Zemlok
10,045,769 B2 8/2018 Aronhalt et al.
10,045,776 B2 8/2018 Shelton, IV et al.
10,045,778 B2 8/2018 Yates et al.
10,045,779 B2 8/2018 Savage et al.
10,045,781 B2 8/2018 Cropper et al.
10,045,782 B2 8/2018 Murthy Aravalli
10,045,869 B2 8/2018 Forsell
10,046,904 B2 8/2018 Evans et al.
10,052,044 B2 8/2018 Shelton, IV et al.
10,052,099 B2 8/2018 Morgan et al.
10,052,100 B2 8/2018 Morgan et al.
10,052,102 B2 8/2018 Baxter, III et al.
10,052,104 B2 8/2018 Shelton, IV et al.
10,052,164 B2 8/2018 Overmyer
10,058,317 B2 8/2018 Fan et al.
10,058,327 B2 8/2018 Weisenburgh, II et al.
10,058,373 B2 8/2018 Takashino et al.
10,058,395 B2 8/2018 Devengenzo et al.
10,058,963 B2 8/2018 Shelton, IV et al.
10,064,620 B2 9/2018 Gettinger et al.
10,064,621 B2 9/2018 Kerr et al.
10,064,622 B2 9/2018 Murthy Aravalli
10,064,624 B2 9/2018 Shelton, IV et al.
10,064,639 B2 9/2018 Ishida et al.
10,064,649 B2 9/2018 Golebieski et al.
10,064,688 B2 9/2018 Shelton, IV et al.
10,070,861 B2 9/2018 Spivey et al.
10,070,863 B2 9/2018 Swayze et al.
10,071,452 B2 9/2018 Shelton, IV et al.
10,076,325 B2 9/2018 Huang et al.
10,076,326 B2 9/2018 Yates et al.
10,076,340 B2 9/2018 Belagali et al.
10,080,552 B2 9/2018 Nicholas et al.
D830,550 S 10/2018 Miller et al.
D831,209 S 10/2018 Huitema et al.
D831,676 S 10/2018 Park et al.
D832,301 S 10/2018 Smith
10,085,624 B2 10/2018 Isoda et al.
10,085,643 B2 10/2018 Bandic et al.
10,085,728 B2 10/2018 Jogasaki et al.
10,085,746 B2 10/2018 Fischvogt
10,085,748 B2 10/2018 Morgan et al.
10,085,749 B2 10/2018 Cappola et al.
10,085,750 B2 10/2018 Zergiebel et al.
10,085,751 B2 10/2018 Overmyer et al.
10,085,754 B2 10/2018 Sniffin et al.
10,085,806 B2 10/2018 Hagn et al.
10,092,290 B2 10/2018 Yigit et al.
10,092,292 B2 10/2018 Boudreaux et al.

(56) References Cited

U.S. PATENT DOCUMENTS 10,098,635 B2 10/2018 Burbank
10,098,636 B2 10/2018 Shelton, IV et al.
10,098,640 B2 10/2018 Bertolero et al.
10,098,642 B2 10/2018 Baxter, III et al.
10,099,303 B2 10/2018 Yoshida et al.
10,101,861 B2 10/2018 Kiyoto
10,105,126 B2 10/2018 Sauer
10,105,128 B2 10/2018 Cooper et al.
10,105,136 B2 10/2018 Yates et al.
10,105,139 B2 10/2018 Yates et al.
10,105,140 B2 10/2018 Malinouskas et al.
10,105,142 B2 10/2018 Baxter, III et al.
10,105,149 B2 10/2018 Haider et al.
10,106,932 B2 10/2018 Anderson et al.
10,111,657 B2 10/2018 McCuen
10,111,658 B2 10/2018 Chowaniec et al.
10,111,660 B2 10/2018 Hemmann
10,111,665 B2 10/2018 Aranyi et al.
10,111,679 B2 10/2018 Baber et al.
10,111,698 B2 10/2018 Scheib et al.
10,111,702 B2 10/2018 Kostrzewski
D833,608 S 11/2018 Miller et al.
10,117,649 B2 11/2018 Baxter et al.
10,117,650 B2 11/2018 Nicholas et al.
10,117,652 B2 11/2018 Schmid et al.
10,117,653 B2 11/2018 Leimbach et al.
10,117,654 B2 11/2018 Ingmanson et al.
10,123,798 B2 11/2018 Baxter, III et al.
10,123,845 B2 11/2018 Yeung
10,124,493 B2 11/2018 Rothfuss et al.
10,130,352 B2 11/2018 Widenhouse et al.
10,130,359 B2 11/2018 Hess et al.
10,130,360 B2 11/2018 Olson et al.
10,130,361 B2 11/2018 Yates et al.
10,130,363 B2 11/2018 Huitema et al.
10,130,366 B2 11/2018 Shelton, IV et al.
10,130,367 B2 11/2018 Cappola et al.
10,130,382 B2 11/2018 Gladstone
10,130,738 B2 11/2018 Shelton, IV et al.
10,130,830 B2 11/2018 Miret Carceller et al.
10,133,248 B2 11/2018 Fitzsimmons et al.
10,135,242 B2 11/2018 Baber et al.
10,136,879 B2 11/2018 Ross et al.
10,136,887 B2 11/2018 Shelton, IV et al.
10,136,889 B2 11/2018 Shelton, IV et al.
10,136,890 B2 11/2018 Shelton, IV et al.
10,136,891 B2 11/2018 Shelton, IV et al.
D835,659 S 12/2018 Anzures et al.
D836,124 S 12/2018 Fan
10,143,474 B2 12/2018 Bucciaglia et al.
10,149,679 B2 12/2018 Shelton, IV et al.
10,149,680 B2 12/2018 Parihar et al.
10,149,682 B2 12/2018 Shelton, IV et al.
10,149,683 B2 12/2018 Smith et al.
10,149,712 B2 12/2018 Manwaring et al.
10,152,789 B2 12/2018 Carnes et al.
10,154,841 B2 12/2018 Weaner et al.
10,159,481 B2 12/2018 Whitman et al.
10,159,482 B2 12/2018 Swayze et al.
10,159,483 B2 12/2018 Beckman et al.
10,159,506 B2 12/2018 Boudreaux et al.
10,161,816 B2 12/2018 Jackson et al.
10,163,065 B1 12/2018 Koski et al.
10,163,589 B2 12/2018 Zergiebel et al.
10,164,466 B2 12/2018 Calderoni
D837,244 S 1/2019 Kuo et al.
D837,245 S 1/2019 Kuo et al.
10,166,023 B2 1/2019 Vendely et al.
10,166,025 B2 1/2019 Leimbach et al.
10,166,026 B2 1/2019 Shelton, IV et al.
10,172,611 B2 1/2019 Shelton, IV et al.
10,172,615 B2 1/2019 Marczyk et al.
10,172,616 B2 1/2019 Murray et al.
10,172,617 B2 1/2019 Shelton, IV et al.
10,172,618 B2 1/2019 Shelton, IV et al.
10,172,619 B2 1/2019 Harris et al.
10,172,620 B2 1/2019 Harris et al.
10,172,636 B2 1/2019 Stulen et al.
10,172,669 B2 1/2019 Felder et al.
10,175,127 B2 1/2019 Collins et al.
10,178,992 B2 1/2019 Wise et al.
10,180,463 B2 1/2019 Beckman et al.
10,182,813 B2 1/2019 Leimbach et al.
10,182,815 B2 1/2019 Williams et al.
10,182,816 B2 1/2019 Shelton, IV et al.
10,182,818 B2 1/2019 Hensel et al.
10,182,819 B2 1/2019 Shelton, IV
10,182,868 B2 1/2019 Meier et al.
10,188,385 B2 1/2019 Kerr et al.
10,188,389 B2 1/2019 Vendely et al.
10,188,393 B2 1/2019 Smith et al.
10,188,394 B2 1/2019 Shelton, IV et al.
10,190,888 B2 1/2019 Hryb et al.
D839,900 S 2/2019 Gan
D841,667 S 2/2019 Coren
10,194,801 B2 2/2019 Elhawary et al.
10,194,904 B2 2/2019 Viola et al.
10,194,907 B2 2/2019 Marczyk et al.
10,194,908 B2 2/2019 Duque et al.
10,194,910 B2 2/2019 Shelton, IV et al.
10,194,911 B2 2/2019 Miller et al.
10,194,912 B2 2/2019 Scheib et al.
10,194,913 B2 2/2019 Nalagatla et al.
10,194,976 B2 2/2019 Boudreaux
10,194,992 B2 2/2019 Robinson
10,201,348 B2 2/2019 Scheib et al.
10,201,349 B2 2/2019 Leimbach et al.
10,201,363 B2 2/2019 Shelton, IV
10,201,364 B2 2/2019 Leimbach et al.
10,201,365 B2 2/2019 Boudreaux et al.
10,201,381 B2 2/2019 Zergiebel et al.
10,206,605 B2 2/2019 Shelton, IV et al.
10,206,676 B2 2/2019 Shelton, IV
10,206,677 B2 2/2019 Harris et al.
10,206,678 B2 2/2019 Shelton, IV et al.
10,206,748 B2 2/2019 Burbank
10,210,244 B1 2/2019 Branavan et al.
10,211,586 B2 2/2019 Adams et al.
10,213,198 B2 2/2019 Aronhalt et al.
10,213,201 B2 2/2019 Shelton, IV et al.
10,213,202 B2 2/2019 Flanagan et al.
10,213,203 B2 2/2019 Swayze et al.
10,213,204 B2 2/2019 Aranyi et al.
10,213,262 B2 2/2019 Shelton, IV et al.
D842,328 S 3/2019 Jian et al.
10,219,811 B2 3/2019 Haider et al.
10,219,832 B2 3/2019 Bagwell et al.
10,220,522 B2 3/2019 Rockrohr
10,226,239 B2 3/2019 Nicholas et al.
10,226,249 B2 3/2019 Jaworek et al.
10,226,250 B2 3/2019 Beckman et al.
10,226,251 B2 3/2019 Scheib et al.
10,226,274 B2 3/2019 Worrell et al.
10,231,634 B2 3/2019 Zand et al.
10,231,653 B2 3/2019 Bohm et al.
10,231,734 B2 3/2019 Thompson et al.
10,231,794 B2 3/2019 Shelton, IV et al.
10,238,385 B2 3/2019 Yates et al.
10,238,386 B2 3/2019 Overmyer et al.
10,238,387 B2 3/2019 Yates et al.
10,238,389 B2 3/2019 Yates et al.
10,238,390 B2 3/2019 Harris et al.
10,238,391 B2 3/2019 Leimbach et al.
D844,666 S 4/2019 Espeleta et al.
D844,667 S 4/2019 Espeleta et al.
D845,342 S 4/2019 Espeleta et al.
D847,199 S 4/2019 Whitmore
10,244,991 B2 4/2019 Shademan et al.
10,245,027 B2 4/2019 Shelton, IV et al.
10,245,028 B2 4/2019 Shelton, IV et al.
10,245,029 B2 4/2019 Hunter et al.
10,245,030 B2 4/2019 Hunter et al.
10,245,032 B2 4/2019 Shelton, IV
10,245,033 B2 4/2019 Overmyer et al.

(56) References Cited

U.S. PATENT DOCUMENTS 10,245,034 B2 4/2019 Shelton, IV et al.
10,245,035 B2 4/2019 Swayze et al.
10,245,038 B2 4/2019 Hopkins et al.
10,245,058 B2 4/2019 Omori et al.
10,251,648 B2 4/2019 Harris et al.
10,251,649 B2 4/2019 Schellin et al.
10,251,725 B2 4/2019 Valentine et al.
10,258,322 B2 4/2019 Fanton et al.
10,258,330 B2 4/2019 Shelton, IV et al.
10,258,331 B2 4/2019 Shelton, IV et al.
10,258,332 B2 4/2019 Schmid et al.
10,258,333 B2 4/2019 Shelton, IV et al.
10,258,336 B2 4/2019 Baxter, III et al.
10,258,363 B2 4/2019 Worrell et al.
10,258,418 B2 4/2019 Shelton, IV et al.
10,264,797 B2 4/2019 Zhang et al.
10,265,065 B2 4/2019 Shelton, IV et al.
10,265,067 B2 4/2019 Yates et al.
10,265,068 B2 4/2019 Harris et al.
10,265,072 B2 4/2019 Shelton, IV et al.
10,265,073 B2 4/2019 Scheib et al.
10,265,074 B2 4/2019 Shelton, IV et al.
10,265,090 B2 4/2019 Ingmanson et al.
10,271,840 B2 4/2019 Sapre
10,271,844 B2 4/2019 Valentine et al.
10,271,845 B2 4/2019 Shelton, IV
10,271,846 B2 4/2019 Shelton, IV et al.
10,271,847 B2 4/2019 Racenet et al.
10,271,849 B2 4/2019 Vendely et al.
10,271,851 B2 4/2019 Shelton, IV et al.
D847,989 S 5/2019 Shelton, IV et al.
D848,473 S 5/2019 Zhu et al.
D849,046 S 5/2019 Kuo et al.
10,278,696 B2 5/2019 Gurumurthy et al.
10,278,697 B2 5/2019 Shelton, IV et al.
10,278,702 B2 5/2019 Shelton, IV et al.
10,278,703 B2 5/2019 Nativ et al.
10,278,707 B2 5/2019 Thompson et al.
10,278,722 B2 5/2019 Shelton, IV et al.
10,278,780 B2 5/2019 Shelton, IV
10,285,694 B2 5/2019 Viola et al.
10,285,695 B2 5/2019 Jaworek et al.
10,285,699 B2 5/2019 Vendely et al.
10,285,700 B2 5/2019 Scheib
10,285,705 B2 5/2019 Shelton, IV et al.
10,285,724 B2 5/2019 Faller et al.
10,285,750 B2 5/2019 Coulson et al.
10,292,701 B2 5/2019 Scheib et al.
10,292,704 B2 5/2019 Harris et al.
10,292,707 B2 5/2019 Shelton, IV et al.
10,293,100 B2 5/2019 Shelton, IV et al.
10,293,553 B2 5/2019 Racenet et al.
10,299,787 B2 5/2019 Shelton, IV
10,299,788 B2 5/2019 Heinrich et al.
10,299,789 B2 5/2019 Marczyk et al.
10,299,790 B2 5/2019 Beardsley
10,299,792 B2 5/2019 Huitema et al.
10,299,817 B2 5/2019 Shelton, IV et al.
10,299,818 B2 5/2019 Riva
10,299,878 B2 5/2019 Shelton, IV et al.
10,303,851 B2 5/2019 Nguyen et al.
D850,617 S 6/2019 Shelton, IV et al.
D851,676 S 6/2019 Foss et al.
D851,762 S 6/2019 Shelton, IV et al.
10,307,159 B2 6/2019 Harris et al.
10,307,160 B2 6/2019 Vendely et al.
10,307,161 B2 6/2019 Jankowski
10,307,163 B2 6/2019 Moore et al.
10,307,170 B2 6/2019 Parfett et al.
10,307,202 B2 6/2019 Smith et al.
10,314,559 B2 6/2019 Razzaque et al.
10,314,577 B2 6/2019 Laurent et al.
10,314,578 B2 6/2019 Leimbach et al.
10,314,579 B2 6/2019 Chowaniec et al.
10,314,580 B2 6/2019 Scheib et al.
10,314,582 B2 6/2019 Shelton, IV et al.
10,314,584 B2 6/2019 Scirica et al.
10,314,587 B2 6/2019 Harris et al.
10,314,588 B2 6/2019 Turner et al.
10,314,589 B2 6/2019 Shelton, IV et al.
10,314,590 B2 6/2019 Shelton, IV et al.
10,315,566 B2 6/2019 Choi et al.
10,321,907 B2 6/2019 Shelton, IV et al.
10,321,909 B2 6/2019 Shelton, IV et al.
10,321,927 B2 6/2019 Hinman
10,327,743 B2 6/2019 St. Goar et al.
10,327,764 B2 6/2019 Harris et al.
10,327,765 B2 6/2019 Timm et al.
10,327,767 B2 6/2019 Shelton, IV et al.
10,327,769 B2 6/2019 Overmyer et al.
10,327,776 B2 6/2019 Harris et al.
10,327,777 B2 6/2019 Harris et al.
D854,032 S 7/2019 Jones et al.
D854,151 S 7/2019 Shelton, IV et al.
10,335,144 B2 7/2019 Shelton, IV et al.
10,335,145 B2 7/2019 Harris et al.
10,335,147 B2 7/2019 Rector et al.
10,335,148 B2 7/2019 Shelton, IV et al.
10,335,149 B2 7/2019 Baxter, III et al.
10,335,150 B2 7/2019 Shelton, IV
10,335,151 B2 7/2019 Shelton, IV et al.
10,337,148 B2 7/2019 Rouse et al.
10,342,533 B2 7/2019 Shelton, IV et al.
10,342,535 B2 7/2019 Scheib et al.
10,342,541 B2 7/2019 Shelton, IV et al.
10,342,543 B2 7/2019 Shelton, IV et al.
10,342,623 B2 7/2019 Huelman et al.
10,349,937 B2 7/2019 Williams
10,349,939 B2 7/2019 Shelton, IV et al.
10,349,941 B2 7/2019 Marczyk et al.
10,349,963 B2 7/2019 Fiksen et al.
10,350,016 B2 7/2019 Burbank et al.
10,357,246 B2 7/2019 Shelton, IV et al.
10,357,247 B2 7/2019 Shelton, IV et al.
10,357,248 B2 7/2019 Dalessandro et al.
10,357,252 B2 7/2019 Harris et al.
10,363,031 B2 7/2019 Alexander, III et al.
10,363,033 B2 7/2019 Timm et al.
10,363,036 B2 7/2019 Yates et al.
10,363,037 B2 7/2019 Aronhalt et al.
D855,634 S 8/2019 Kim
D856,359 S 8/2019 Huang et al.
10,368,838 B2 8/2019 Williams et al.
10,368,861 B2 8/2019 Baxter, III et al.
10,368,863 B2 8/2019 Timm et al.
10,368,864 B2 8/2019 Harris et al.
10,368,865 B2 8/2019 Harris et al.
10,368,866 B2 8/2019 Wang et al.
10,368,867 B2 8/2019 Harris et al.
10,368,892 B2 8/2019 Stulen et al.
10,376,263 B2 8/2019 Morgan et al.
10,383,626 B2 8/2019 Soltz
10,383,628 B2 8/2019 Kang et al.
10,383,629 B2 8/2019 Ross et al.
10,383,630 B2 8/2019 Shelton, IV et al.
10,383,633 B2 8/2019 Shelton, IV et al.
10,383,634 B2 8/2019 Shelton, IV et al.
10,390,823 B2 8/2019 Shelton, IV et al.
10,390,825 B2 8/2019 Shelton, IV et al.
10,390,828 B2 8/2019 Vendely et al.
10,390,829 B2 8/2019 Eckert et al.
10,390,830 B2 8/2019 Schulz
10,390,841 B2 8/2019 Shelton, IV et al.
10,390,897 B2 8/2019 Kostrzewski
D859,466 S 9/2019 Okada et al.
D860,219 S 9/2019 Rasmussen et al.
D861,035 S 9/2019 Park et al.
10,398,433 B2 9/2019 Boudreaux et al.
10,398,434 B2 9/2019 Shelton, IV et al.
10,398,436 B2 9/2019 Shelton, IV et al.
10,398,460 B2 9/2019 Overmyer
10,404,136 B2 9/2019 Oktavec et al.
10,405,854 B2 9/2019 Schmid et al.
10,405,857 B2 9/2019 Shelton, IV et al.

(56) References Cited

U.S. PATENT DOCUMENTS

| | | | |
|---|---|---|---|
| 10,405,859 | B2 | 9/2019 | Harris et al. |
| 10,405,863 | B2 | 9/2019 | Wise et al. |
| 10,405,914 | B2 | 9/2019 | Manwaring et al. |
| 10,405,932 | B2 | 9/2019 | Overmyer |
| 10,405,937 | B2 | 9/2019 | Black et al. |
| 10,413,155 | B2 | 9/2019 | Inoue |
| 10,413,291 | B2 | 9/2019 | Worthington et al. |
| 10,413,293 | B2 | 9/2019 | Shelton, IV et al. |
| 10,413,294 | B2 | 9/2019 | Shelton, IV et al. |
| 10,413,297 | B2 | 9/2019 | Harris et al. |
| 10,413,370 | B2 | 9/2019 | Yates et al. |
| 10,413,373 | B2 | 9/2019 | Yates et al. |
| 10,420,548 | B2 | 9/2019 | Whitman et al. |
| 10,420,549 | B2 | 9/2019 | Yates et al. |
| 10,420,550 | B2 | 9/2019 | Shelton, IV |
| 10,420,551 | B2 | 9/2019 | Calderoni |
| 10,420,552 | B2 | 9/2019 | Shelton, IV et al. |
| 10,420,553 | B2 | 9/2019 | Shelton, IV et al. |
| 10,420,554 | B2 | 9/2019 | Collings et al. |
| 10,420,555 | B2 | 9/2019 | Shelton, IV et al. |
| 10,420,558 | B2 | 9/2019 | Nalagatla et al. |
| 10,420,559 | B2 | 9/2019 | Marczyk et al. |
| 10,420,560 | B2 | 9/2019 | Shelton, IV et al. |
| 10,420,561 | B2 | 9/2019 | Shelton, IV et al. |
| 10,420,577 | B2 | 9/2019 | Chowaniec et al. |
| D861,707 | S | 10/2019 | Yang |
| D862,518 | S | 10/2019 | Niven et al. |
| D863,343 | S | 10/2019 | Mazlish et al. |
| D864,388 | S | 10/2019 | Barber |
| D865,174 | S | 10/2019 | Auld et al. |
| D865,175 | S | 10/2019 | Widenhouse et al. |
| 10,426,463 | B2 | 10/2019 | Shelton, IV et al. |
| 10,426,466 | B2 | 10/2019 | Contini et al. |
| 10,426,467 | B2 | 10/2019 | Miller et al. |
| 10,426,468 | B2 | 10/2019 | Contini et al. |
| 10,426,469 | B2 | 10/2019 | Shelton, IV et al. |
| 10,426,471 | B2 | 10/2019 | Shelton, IV et al. |
| 10,426,476 | B2 | 10/2019 | Harris et al. |
| 10,426,477 | B2 | 10/2019 | Harris et al. |
| 10,426,478 | B2 | 10/2019 | Shelton, IV et al. |
| 10,426,481 | B2 | 10/2019 | Aronhalt et al. |
| 10,426,555 | B2 | 10/2019 | Crowley et al. |
| 10,433,837 | B2 | 10/2019 | Worthington et al. |
| 10,433,839 | B2 | 10/2019 | Scheib et al. |
| 10,433,840 | B2 | 10/2019 | Shelton, IV et al. |
| 10,433,842 | B2 | 10/2019 | Amariglio et al. |
| 10,433,844 | B2 | 10/2019 | Shelton, IV et al. |
| 10,433,845 | B2 | 10/2019 | Baxter, III et al. |
| 10,433,846 | B2 | 10/2019 | Vendely et al. |
| 10,433,849 | B2 | 10/2019 | Shelton, IV et al. |
| 10,433,918 | B2 | 10/2019 | Shelton, IV et al. |
| 10,441,279 | B2 | 10/2019 | Shelton, IV et al. |
| 10,441,280 | B2 | 10/2019 | Timm et al. |
| 10,441,281 | B2 | 10/2019 | Shelton, IV et al. |
| 10,441,285 | B2 | 10/2019 | Shelton, IV et al. |
| 10,441,286 | B2 | 10/2019 | Shelton, IV et al. |
| 10,441,345 | B2 | 10/2019 | Aldridge et al. |
| 10,441,369 | B2 | 10/2019 | Shelton, IV et al. |
| 10,448,948 | B2 | 10/2019 | Shelton, IV et al. |
| 10,448,950 | B2 | 10/2019 | Shelton, IV et al. |
| 10,448,952 | B2 | 10/2019 | Shelton, IV et al. |
| 10,456,122 | B2 | 10/2019 | Koltz et al. |
| 10,456,132 | B2 | 10/2019 | Gettinger et al. |
| 10,456,133 | B2 | 10/2019 | Yates et al. |
| 10,456,137 | B2 | 10/2019 | Vendely et al. |
| 10,456,140 | B2 | 10/2019 | Shelton, IV et al. |
| D865,796 | S | 11/2019 | Xu et al. |
| 10,463,367 | B2 | 11/2019 | Kostrzewski et al. |
| 10,463,369 | B2 | 11/2019 | Shelton, IV et al. |
| 10,463,370 | B2 | 11/2019 | Yates et al. |
| 10,463,371 | B2 | 11/2019 | Kostrzewski |
| 10,463,372 | B2 | 11/2019 | Shelton, IV et al. |
| 10,463,373 | B2 | 11/2019 | Mozdzierz et al. |
| 10,463,382 | B2 | 11/2019 | Ingmanson et al. |
| 10,463,383 | B2 | 11/2019 | Shelton, IV et al. |
| 10,463,384 | B2 | 11/2019 | Shelton, IV et al. |
| 10,470,762 | B2 | 11/2019 | Leimbach et al. |
| 10,470,763 | B2 | 11/2019 | Yates et al. |
| 10,470,764 | B2 | 11/2019 | Baxter, III et al. |
| 10,470,767 | B2 | 11/2019 | Gleiman et al. |
| 10,470,768 | B2 | 11/2019 | Harris et al. |
| 10,470,769 | B2 | 11/2019 | Shelton, IV et al. |
| 10,471,282 | B2 | 11/2019 | Kirk et al. |
| 10,471,576 | B2 | 11/2019 | Totsu |
| 10,471,607 | B2 | 11/2019 | Butt et al. |
| 10,478,181 | B2 | 11/2019 | Shelton, IV et al. |
| 10,478,182 | B2 | 11/2019 | Taylor |
| 10,478,185 | B2 | 11/2019 | Nicholas |
| 10,478,187 | B2 | 11/2019 | Shelton, IV et al. |
| 10,478,188 | B2 | 11/2019 | Harris et al. |
| 10,478,189 | B2 | 11/2019 | Bear et al. |
| 10,478,190 | B2 | 11/2019 | Miller et al. |
| 10,478,207 | B2 | 11/2019 | Lathrop |
| 10,482,292 | B2 | 11/2019 | Clouser et al. |
| 10,485,536 | B2 | 11/2019 | Ming et al. |
| 10,485,537 | B2 | 11/2019 | Yates et al. |
| 10,485,539 | B2 | 11/2019 | Shelton, IV et al. |
| 10,485,541 | B2 | 11/2019 | Shelton, IV et al. |
| 10,485,542 | B2 | 11/2019 | Shelton, IV et al. |
| 10,485,543 | B2 | 11/2019 | Shelton, IV et al. |
| 10,485,546 | B2 | 11/2019 | Shelton, IV et al. |
| 10,485,547 | B2 | 11/2019 | Shelton, IV et al. |
| D869,655 | S | 12/2019 | Shelton, IV et al. |
| D870,742 | S | 12/2019 | Cornell |
| 10,492,783 | B2 | 12/2019 | Shelton, IV et al. |
| 10,492,785 | B2 | 12/2019 | Overmyer et al. |
| 10,492,787 | B2 | 12/2019 | Smith et al. |
| 10,492,814 | B2 | 12/2019 | Snow et al. |
| 10,492,847 | B2 | 12/2019 | Godara et al. |
| 10,492,851 | B2 | 12/2019 | Hughett, Sr. et al. |
| 10,498,269 | B2 | 12/2019 | Zemlok et al. |
| 10,499,890 | B2 | 12/2019 | Shelton, IV et al. |
| 10,499,914 | B2 | 12/2019 | Huang et al. |
| 10,499,917 | B2 | 12/2019 | Scheib et al. |
| 10,499,918 | B2 | 12/2019 | Schellin et al. |
| 10,500,000 | B2 | 12/2019 | Swayze et al. |
| 10,500,309 | B2 | 12/2019 | Shah et al. |
| 10,507,034 | B2 | 12/2019 | Timm |
| 10,508,720 | B2 | 12/2019 | Nicholas |
| 10,512,461 | B2 | 12/2019 | Gupta et al. |
| 10,512,462 | B2 | 12/2019 | Felder et al. |
| 10,512,464 | B2 | 12/2019 | Park et al. |
| 10,517,590 | B2 | 12/2019 | Giordano et al. |
| 10,517,592 | B2 | 12/2019 | Shelton, IV et al. |
| 10,517,594 | B2 | 12/2019 | Shelton, IV et al. |
| 10,517,595 | B2 | 12/2019 | Hunter et al. |
| 10,517,596 | B2 | 12/2019 | Hunter et al. |
| 10,517,599 | B2 | 12/2019 | Baxter, III et al. |
| 10,517,682 | B2 | 12/2019 | Giordano et al. |
| 10,524,784 | B2 | 1/2020 | Kostrzewski |
| 10,524,787 | B2 | 1/2020 | Shelton, IV et al. |
| 10,524,788 | B2 | 1/2020 | Vendely et al. |
| 10,524,789 | B2 | 1/2020 | Swayze et al. |
| 10,524,790 | B2 | 1/2020 | Shelton, IV et al. |
| 10,524,795 | B2 | 1/2020 | Nalagatla et al. |
| 10,524,870 | B2 | 1/2020 | Saraliev et al. |
| 10,531,874 | B2 | 1/2020 | Morgan et al. |
| 10,531,887 | B2 | 1/2020 | Shelton, IV et al. |
| 10,537,324 | B2 | 1/2020 | Shelton, IV et al. |
| 10,537,325 | B2 | 1/2020 | Bakos et al. |
| 10,537,351 | B2 | 1/2020 | Shelton, IV et al. |
| 10,542,908 | B2 | 1/2020 | Mei et al. |
| 10,542,974 | B2 | 1/2020 | Yates et al. |
| 10,542,976 | B2 | 1/2020 | Calderoni et al. |
| 10,542,978 | B2 | 1/2020 | Chowaniec et al. |
| 10,542,979 | B2 | 1/2020 | Shelton, IV et al. |
| 10,542,982 | B2 | 1/2020 | Beckman et al. |
| 10,542,985 | B2 | 1/2020 | Zhan et al. |
| 10,542,988 | B2 | 1/2020 | Schellin et al. |
| 10,542,991 | B2 | 1/2020 | Shelton, IV et al. |
| 10,548,504 | B2 | 2/2020 | Shelton, IV et al. |
| 10,548,593 | B2 | 2/2020 | Shelton, IV et al. |
| 10,548,600 | B2 | 2/2020 | Shelton, IV et al. |
| 10,548,673 | B2 | 2/2020 | Harris et al. |

(56) References Cited

U.S. PATENT DOCUMENTS

| | | | |
|---|---|---|---|
| 10,561,418 | B2 | 2/2020 | Richard et al. |
| 10,561,419 | B2 | 2/2020 | Beardsley |
| 10,561,420 | B2 | 2/2020 | Harris et al. |
| 10,561,422 | B2 | 2/2020 | Schellin et al. |
| 10,561,432 | B2 | 2/2020 | Estrella et al. |
| 10,561,474 | B2 | 2/2020 | Adams et al. |
| 10,562,160 | B2 | 2/2020 | Iwata et al. |
| 10,568,493 | B2 | 2/2020 | Blase et al. |
| 10,568,621 | B2 | 2/2020 | Shelton, IV et al. |
| 10,568,624 | B2 | 2/2020 | Shelton, IV et al. |
| 10,568,625 | B2 | 2/2020 | Harris et al. |
| 10,568,626 | B2 | 2/2020 | Shelton, IV et al. |
| 10,568,629 | B2 | 2/2020 | Shelton, IV et al. |
| 10,568,632 | B2 | 2/2020 | Miller et al. |
| 10,568,652 | B2 | 2/2020 | Hess et al. |
| 10,569,071 | B2 | 2/2020 | Harris et al. |
| D879,808 | S | 3/2020 | Harris et al. |
| D879,809 | S | 3/2020 | Harris et al. |
| 10,575,868 | B2 | 3/2020 | Hall et al. |
| 10,580,320 | B2 | 3/2020 | Kamiguchi et al. |
| 10,582,928 | B2 | 3/2020 | Hunter et al. |
| 10,588,231 | B2 | 3/2020 | Sgroi, Jr. et al. |
| 10,588,623 | B2 | 3/2020 | Schmid et al. |
| 10,588,625 | B2 | 3/2020 | Weaner et al. |
| 10,588,626 | B2 | 3/2020 | Overmyer et al. |
| 10,588,629 | B2 | 3/2020 | Malinouskas et al. |
| 10,588,630 | B2 | 3/2020 | Shelton, IV et al. |
| 10,588,631 | B2 | 3/2020 | Shelton, IV et al. |
| 10,588,632 | B2 | 3/2020 | Shelton, IV et al. |
| 10,588,633 | B2 | 3/2020 | Shelton, IV et al. |
| 10,595,835 | B2 | 3/2020 | Kerr et al. |
| 10,595,862 | B2 | 3/2020 | Shelton, IV et al. |
| 10,595,882 | B2 | 3/2020 | Parfett et al. |
| 10,595,887 | B2 | 3/2020 | Shelton, IV et al. |
| 10,595,929 | B2 | 3/2020 | Boudreaux et al. |
| 10,603,036 | B2 | 3/2020 | Hunter et al. |
| 10,603,039 | B2 | 3/2020 | Vendely et al. |
| 10,603,041 | B2 | 3/2020 | Miller et al. |
| 10,603,117 | B2 | 3/2020 | Schings et al. |
| 10,603,128 | B2 | 3/2020 | Zergiebel et al. |
| D882,783 | S | 4/2020 | Shelton, IV et al. |
| 10,610,224 | B2 | 4/2020 | Shelton, IV et al. |
| 10,610,225 | B2 | 4/2020 | Reed et al. |
| 10,610,236 | B2 | 4/2020 | Baril |
| 10,610,313 | B2 | 4/2020 | Bailey et al. |
| 10,610,346 | B2 | 4/2020 | Schwartz |
| 10,617,411 | B2 | 4/2020 | Williams |
| 10,617,412 | B2 | 4/2020 | Shelton, IV et al. |
| 10,617,413 | B2 | 4/2020 | Shelton, IV et al. |
| 10,617,414 | B2 | 4/2020 | Shelton, IV et al. |
| 10,617,416 | B2 | 4/2020 | Leimbach et al. |
| 10,617,417 | B2 | 4/2020 | Baxter, III et al. |
| 10,617,418 | B2 | 4/2020 | Barton et al. |
| 10,617,420 | B2 | 4/2020 | Shelton, IV et al. |
| 10,617,438 | B2 | 4/2020 | O'Keefe et al. |
| 10,624,616 | B2 | 4/2020 | Mukherjee et al. |
| 10,624,630 | B2 | 4/2020 | Deville et al. |
| 10,624,633 | B2 | 4/2020 | Shelton, IV et al. |
| 10,624,634 | B2 | 4/2020 | Shelton, IV et al. |
| 10,624,635 | B2 | 4/2020 | Harris et al. |
| 10,624,709 | B2 | 4/2020 | Remm |
| 10,624,861 | B2 | 4/2020 | Widenhouse et al. |
| 10,625,062 | B2 | 4/2020 | Matlock et al. |
| 10,631,857 | B2 | 4/2020 | Kostrzewski |
| 10,631,858 | B2 | 4/2020 | Burbank |
| 10,631,859 | B2 | 4/2020 | Shelton, IV et al. |
| 10,631,860 | B2 | 4/2020 | Bakos et al. |
| 10,636,104 | B2 | 4/2020 | Mazar et al. |
| 10,639,018 | B2 | 5/2020 | Shelton, IV et al. |
| 10,639,034 | B2 | 5/2020 | Harris et al. |
| 10,639,035 | B2 | 5/2020 | Shelton, IV et al. |
| 10,639,036 | B2 | 5/2020 | Yates et al. |
| 10,639,037 | B2 | 5/2020 | Shelton, IV et al. |
| 10,639,089 | B2 | 5/2020 | Manwaring et al. |
| 10,639,115 | B2 | 5/2020 | Shelton, IV et al. |
| 10,642,633 | B1 | 5/2020 | Chopra et al. |
| 10,645,905 | B2 | 5/2020 | Gandola et al. |
| 10,646,220 | B2 | 5/2020 | Shelton, IV et al. |
| 10,646,292 | B2 | 5/2020 | Solomon et al. |
| 10,653,413 | B2 | 5/2020 | Worthington et al. |
| 10,653,417 | B2 | 5/2020 | Shelton, IV et al. |
| 10,653,435 | B2 | 5/2020 | Shelton, IV et al. |
| 10,660,640 | B2 | 5/2020 | Yates et al. |
| 10,667,408 | B2 | 5/2020 | Sgroi, Jr. et al. |
| D888,953 | S | 6/2020 | Baxter, III et al. |
| 10,667,808 | B2 | 6/2020 | Baxter, III et al. |
| 10,667,809 | B2 | 6/2020 | Bakos et al. |
| 10,667,810 | B2 | 6/2020 | Shelton, IV et al. |
| 10,667,811 | B2 | 6/2020 | Harris et al. |
| 10,667,818 | B2 | 6/2020 | McLain et al. |
| 10,674,895 | B2 | 6/2020 | Yeung et al. |
| 10,675,021 | B2 | 6/2020 | Harris et al. |
| 10,675,024 | B2 | 6/2020 | Shelton, IV et al. |
| 10,675,025 | B2 | 6/2020 | Swayze et al. |
| 10,675,026 | B2 | 6/2020 | Harris et al. |
| 10,675,028 | B2 | 6/2020 | Shelton, IV et al. |
| 10,675,035 | B2 | 6/2020 | Zingman |
| 10,675,102 | B2 | 6/2020 | Forgione et al. |
| 10,677,035 | B2 | 6/2020 | Balan et al. |
| 10,682,134 | B2 | 6/2020 | Shelton, IV et al. |
| 10,682,136 | B2 | 6/2020 | Harris et al. |
| 10,682,137 | B2 | 6/2020 | Stokes et al. |
| 10,682,138 | B2 | 6/2020 | Shelton, IV et al. |
| 10,682,141 | B2 | 6/2020 | Moore et al. |
| 10,682,142 | B2 | 6/2020 | Shelton, IV et al. |
| 10,687,806 | B2 | 6/2020 | Shelton, IV et al. |
| 10,687,809 | B2 | 6/2020 | Shelton, IV et al. |
| 10,687,810 | B2 | 6/2020 | Shelton, IV et al. |
| 10,687,812 | B2 | 6/2020 | Shelton, IV et al. |
| 10,687,813 | B2 | 6/2020 | Shelton, IV et al. |
| 10,687,817 | B2 | 6/2020 | Shelton, IV et al. |
| 10,687,819 | B2 | 6/2020 | Stokes et al. |
| 10,687,904 | B2 | 6/2020 | Harris et al. |
| 10,695,053 | B2 | 6/2020 | Hess et al. |
| 10,695,055 | B2 | 6/2020 | Shelton, IV et al. |
| 10,695,057 | B2 | 6/2020 | Shelton, IV et al. |
| 10,695,058 | B2 | 6/2020 | Lytle, IV et al. |
| 10,695,062 | B2 | 6/2020 | Leimbach et al. |
| 10,695,063 | B2 | 6/2020 | Morgan et al. |
| 10,695,074 | B2 | 6/2020 | Carusillo |
| 10,695,081 | B2 | 6/2020 | Shelton, IV et al. |
| 10,695,123 | B2 | 6/2020 | Allen, IV |
| 10,695,187 | B2 | 6/2020 | Moskowitz et al. |
| D890,784 | S | 7/2020 | Shelton, IV et al. |
| 10,702,266 | B2 | 7/2020 | Parihar et al. |
| 10,702,267 | B2 | 7/2020 | Hess et al. |
| 10,702,270 | B2 | 7/2020 | Shelton, IV et al. |
| 10,702,271 | B2 | 7/2020 | Aranyi et al. |
| 10,705,660 | B2 | 7/2020 | Xiao |
| 10,709,446 | B2 | 7/2020 | Harris et al. |
| 10,709,468 | B2 | 7/2020 | Shelton, IV et al. |
| 10,709,469 | B2 | 7/2020 | Shelton, IV et al. |
| 10,709,496 | B2 | 7/2020 | Moua et al. |
| 10,716,563 | B2 | 7/2020 | Shelton, IV et al. |
| 10,716,565 | B2 | 7/2020 | Shelton, IV et al. |
| 10,716,568 | B2 | 7/2020 | Hall et al. |
| 10,716,614 | B2 | 7/2020 | Yates et al. |
| 10,717,179 | B2 | 7/2020 | Koenig et al. |
| 10,722,232 | B2 | 7/2020 | Yates et al. |
| 10,722,233 | B2 | 7/2020 | Wellman |
| 10,722,292 | B2 | 7/2020 | Arya et al. |
| 10,722,293 | B2 | 7/2020 | Arya et al. |
| 10,722,317 | B2 | 7/2020 | Ward et al. |
| D893,717 | S | 8/2020 | Messerly et al. |
| 10,729,432 | B2 | 8/2020 | Shelton, IV et al. |
| 10,729,434 | B2 | 8/2020 | Harris et al. |
| 10,729,435 | B2 | 8/2020 | Richard |
| 10,729,436 | B2 | 8/2020 | Shelton, IV et al. |
| 10,729,443 | B2 | 8/2020 | Cabrera et al. |
| 10,729,458 | B2 | 8/2020 | Stoddard et al. |
| 10,729,501 | B2 | 8/2020 | Leimbach et al. |
| 10,729,509 | B2 | 8/2020 | Shelton, IV et al. |
| 10,736,616 | B2 | 8/2020 | Scheib et al. |
| 10,736,628 | B2 | 8/2020 | Yates et al. |

(56) References Cited

U.S. PATENT DOCUMENTS 10,736,629 B2 8/2020 Shelton, IV et al.
10,736,630 B2 8/2020 Huang et al.
10,736,633 B2 8/2020 Vendely et al.
10,736,634 B2 8/2020 Shelton, IV et al.
10,736,636 B2 8/2020 Baxter, III et al.
10,736,644 B2 8/2020 Windolf et al.
10,736,702 B2 8/2020 Harris et al.
10,737,398 B2 8/2020 Remirez et al.
10,743,849 B2 8/2020 Shelton, IV et al.
10,743,850 B2 8/2020 Hibner et al.
10,743,851 B2 8/2020 Swayze et al.
10,743,868 B2 8/2020 Shelton, IV et al.
10,743,870 B2 8/2020 Hall et al.
10,743,872 B2 8/2020 Leimbach et al.
10,743,873 B2 8/2020 Overmyer et al.
10,743,874 B2 8/2020 Shelton, IV et al.
10,743,875 B2 8/2020 Shelton, IV et al.
10,743,877 B2 8/2020 Shelton, IV et al.
10,743,930 B2 8/2020 Nagtegaal
10,751,048 B2 8/2020 Whitman et al.
10,751,053 B2 8/2020 Harris et al.
10,751,076 B2 8/2020 Laurent et al.
10,751,138 B2 8/2020 Giordano et al.
10,758,229 B2 9/2020 Shelton, IV et al.
10,758,230 B2 9/2020 Shelton, IV et al.
10,758,232 B2 9/2020 Shelton, IV et al.
10,758,233 B2 9/2020 Scheib et al.
10,758,259 B2 9/2020 Demmy et al.
10,765,425 B2 9/2020 Yates et al.
10,765,427 B2 9/2020 Shelton, IV et al.
10,765,429 B2 9/2020 Leimbach et al.
10,765,430 B2 9/2020 Wixey
10,765,432 B2 9/2020 Moore et al.
10,765,442 B2 9/2020 Strobl
10,772,625 B2 9/2020 Shelton, IV et al.
10,772,628 B2 9/2020 Chen et al.
10,772,629 B2 9/2020 Shelton, IV et al.
10,772,630 B2 9/2020 Wixey
10,772,631 B2 9/2020 Zergiebel et al.
10,772,632 B2 9/2020 Kostrzewski
10,772,651 B2 9/2020 Shelton, IV et al.
10,779,818 B2 9/2020 Zemlok et al.
10,779,820 B2 9/2020 Harris et al.
10,779,821 B2 9/2020 Harris et al.
10,779,822 B2 9/2020 Yates et al.
10,779,823 B2 9/2020 Shelton, IV et al.
10,779,824 B2 9/2020 Shelton, IV et al.
10,779,825 B2 9/2020 Shelton, IV et al.
10,779,826 B2 9/2020 Shelton, IV et al.
10,779,903 B2 9/2020 Wise et al.
10,780,539 B2 9/2020 Shelton, IV et al.
10,786,248 B2 9/2020 Rousseau et al.
10,786,253 B2 9/2020 Shelton, IV et al.
10,786,255 B2 9/2020 Hodgkinson et al.
10,792,038 B2 10/2020 Becerra et al.
10,796,471 B2 10/2020 Leimbach et al.
10,799,240 B2 10/2020 Shelton, IV et al.
10,799,306 B2 10/2020 Robinson et al.
10,806,448 B2 10/2020 Shelton, IV et al.
10,806,449 B2 10/2020 Shelton, IV et al.
10,806,450 B2 10/2020 Yates et al.
10,806,451 B2 10/2020 Harris et al.
10,806,453 B2 10/2020 Chen et al.
10,806,479 B2 10/2020 Shelton, IV et al.
10,813,638 B2 10/2020 Shelton, IV et al.
10,813,639 B2 10/2020 Shelton, IV et al.
10,813,640 B2 10/2020 Adams et al.
10,813,641 B2 10/2020 Setser et al.
10,813,683 B2 10/2020 Baxter, III et al.
10,813,705 B2 10/2020 Hares et al.
10,813,710 B2 10/2020 Grubbs
10,820,939 B2 11/2020 Sartor
10,828,028 B2 11/2020 Harris et al.
10,828,030 B2 11/2020 Weir et al.
10,828,032 B2 11/2020 Leimbach et al.
10,828,033 B2 11/2020 Shelton, IV et al.
10,828,089 B2 11/2020 Clark et al.
10,835,245 B2 11/2020 Swayze et al.
10,835,246 B2 11/2020 Shelton, IV et al.
10,835,247 B2 11/2020 Shelton, IV et al.
10,835,249 B2 11/2020 Schellin et al.
10,835,251 B2 11/2020 Shelton, IV et al.
10,835,330 B2 11/2020 Shelton, IV et al.
10,842,357 B2 11/2020 Moskowitz et al.
10,842,473 B2 11/2020 Scheib et al.
10,842,488 B2 11/2020 Swayze et al.
10,842,489 B2 11/2020 Shelton, IV
10,842,490 B2 11/2020 DiNardo et al.
10,842,491 B2 11/2020 Shelton, IV et al.
10,842,492 B2 11/2020 Shelton, IV et al.
D904,612 S 12/2020 Wynn et al.
D904,613 S 12/2020 Wynn et al.
D906,355 S 12/2020 Messerly et al.
10,849,621 B2 12/2020 Whitfield et al.
10,849,623 B2 12/2020 Dunki-Jacobs et al.
10,849,697 B2 12/2020 Yates et al.
10,856,866 B2 12/2020 Shelton, IV et al.
10,856,867 B2 12/2020 Shelton, IV et al.
10,856,868 B2 12/2020 Shelton, IV et al.
10,856,869 B2 12/2020 Shelton, IV et al.
10,856,870 B2 12/2020 Harris et al.
10,863,981 B2 12/2020 Overmyer et al.
10,863,984 B2 12/2020 Shelton, IV et al.
10,863,986 B2 12/2020 Yates et al.
10,869,663 B2 12/2020 Shelton, IV et al.
10,869,664 B2 12/2020 Shelton, IV
10,869,665 B2 12/2020 Shelton, IV et al.
10,869,666 B2 12/2020 Shelton, IV et al.
10,869,669 B2 12/2020 Shelton, IV et al.
10,874,290 B2 12/2020 Walen et al.
10,874,391 B2 12/2020 Shelton, IV et al.
10,874,392 B2 12/2020 Scirica et al.
10,874,393 B2 12/2020 Satti, III et al.
10,874,396 B2 12/2020 Moore et al.
10,874,399 B2 12/2020 Zhang
10,879,275 B2 12/2020 Li et al.
D907,647 S 1/2021 Siebel et al.
D907,648 S 1/2021 Siebel et al.
D908,216 S 1/2021 Messerly et al.
10,881,395 B2 1/2021 Merchant et al.
10,881,396 B2 1/2021 Shelton, IV et al.
10,881,399 B2 1/2021 Shelton, IV et al.
10,881,401 B2 1/2021 Baber et al.
10,881,446 B2 1/2021 Strobl
10,888,318 B2 1/2021 Parihar et al.
10,888,321 B2 1/2021 Shelton, IV et al.
10,888,322 B2 1/2021 Morgan et al.
10,888,323 B2 1/2021 Chen et al.
10,888,325 B2 1/2021 Harris et al.
10,888,328 B2 1/2021 Shelton, IV et al.
10,888,329 B2 1/2021 Moore et al.
10,888,330 B2 1/2021 Moore et al.
10,888,369 B2 1/2021 Messerly et al.
10,892,899 B2 1/2021 Shelton, IV et al.
10,893,853 B2 1/2021 Shelton, IV et al.
10,893,863 B2 1/2021 Shelton, IV et al.
10,893,864 B2 1/2021 Harris et al.
10,893,867 B2 1/2021 Leimbach et al.
10,898,183 B2 1/2021 Shelton, IV et al.
10,898,184 B2 1/2021 Yates et al.
10,898,185 B2 1/2021 Overmyer et al.
10,898,186 B2 1/2021 Bakos et al.
10,898,190 B2 1/2021 Yates et al.
10,898,193 B2 1/2021 Shelton, IV et al.
10,898,194 B2 1/2021 Moore et al.
10,898,195 B2 1/2021 Moore et al.
10,903,685 B2 1/2021 Yates et al.
D910,847 S 2/2021 Shelton, IV et al.
10,905,415 B2 2/2021 DiNardo et al.
10,905,418 B2 2/2021 Shelton, IV et al.
10,905,420 B2 2/2021 Jasemian et al.
10,905,422 B2 2/2021 Bakos et al.
10,905,423 B2 2/2021 Baber et al.
10,905,426 B2 2/2021 Moore et al.

(56) References Cited

U.S. PATENT DOCUMENTS

| | | | |
|---|---|---|---|
| 10,905,427 | B2 | 2/2021 | Moore et al. |
| 10,911,515 | B2 | 2/2021 | Biasi et al. |
| 10,912,559 | B2 | 2/2021 | Harris et al. |
| 10,912,562 | B2 | 2/2021 | Dunki-Jacobs et al. |
| 10,912,575 | B2 | 2/2021 | Shelton, IV et al. |
| 10,918,364 | B2 | 2/2021 | Applegate et al. |
| 10,918,380 | B2 | 2/2021 | Morgan et al. |
| 10,918,385 | B2 | 2/2021 | Overmyer et al. |
| 10,918,386 | B2 | 2/2021 | Shelton, IV et al. |
| 10,919,156 | B2 | 2/2021 | Roberts et al. |
| 10,925,600 | B2 | 2/2021 | McCuen |
| 10,925,605 | B2 | 2/2021 | Moore et al. |
| D914,878 | S | 3/2021 | Shelton, IV et al. |
| 10,932,772 | B2 | 3/2021 | Shelton, IV et al. |
| 10,932,774 | B2 | 3/2021 | Shelton, IV |
| 10,932,775 | B2 | 3/2021 | Shelton, IV et al. |
| 10,932,778 | B2 | 3/2021 | Smith et al. |
| 10,932,779 | B2 | 3/2021 | Vendely et al. |
| 10,932,784 | B2 | 3/2021 | Mozdzierz et al. |
| 10,932,804 | B2 | 3/2021 | Scheib et al. |
| 10,932,806 | B2 | 3/2021 | Shelton, IV et al. |
| 10,932,872 | B2 | 3/2021 | Shelton, IV et al. |
| 10,944,728 | B2 | 3/2021 | Wiener et al. |
| 10,945,727 | B2 | 3/2021 | Shelton, IV et al. |
| 10,945,728 | B2 | 3/2021 | Morgan et al. |
| 10,945,729 | B2 | 3/2021 | Shelton, IV et al. |
| 10,945,731 | B2 | 3/2021 | Baxter, III et al. |
| 10,952,708 | B2 | 3/2021 | Scheib et al. |
| 10,952,726 | B2 | 3/2021 | Chowaniec |
| 10,952,727 | B2 | 3/2021 | Giordano et al. |
| 10,952,728 | B2 | 3/2021 | Shelton, IV et al. |
| 10,952,759 | B2 | 3/2021 | Messerly et al. |
| 10,952,767 | B2 | 3/2021 | Kostrzewski et al. |
| 10,959,722 | B2 | 3/2021 | Morgan et al. |
| 10,959,725 | B2 | 3/2021 | Kerr et al. |
| 10,959,726 | B2 | 3/2021 | Williams et al. |
| 10,959,727 | B2 | 3/2021 | Hunter et al. |
| 10,959,731 | B2 | 3/2021 | Casasanta, Jr. et al. |
| 10,959,744 | B2 | 3/2021 | Shelton, IV et al. |
| 10,959,797 | B2 | 3/2021 | Licht et al. |
| D917,500 | S | 4/2021 | Siebel et al. |
| 10,966,627 | B2 | 4/2021 | Shelton, IV et al. |
| 10,966,717 | B2 | 4/2021 | Shah et al. |
| 10,966,718 | B2 | 4/2021 | Shelton, IV et al. |
| 10,966,791 | B2 | 4/2021 | Harris et al. |
| 10,973,515 | B2 | 4/2021 | Harris et al. |
| 10,973,516 | B2 | 4/2021 | Shelton, IV et al. |
| 10,973,517 | B2 | 4/2021 | Wixey |
| 10,973,519 | B2 | 4/2021 | Weir et al. |
| 10,973,520 | B2 | 4/2021 | Shelton, IV et al. |
| 10,980,534 | B2 | 4/2021 | Yates et al. |
| 10,980,535 | B2 | 4/2021 | Yates et al. |
| 10,980,536 | B2 | 4/2021 | Weaner et al. |
| 10,980,537 | B2 | 4/2021 | Shelton, IV et al. |
| 10,980,538 | B2 | 4/2021 | Nalagatla et al. |
| 10,980,539 | B2 | 4/2021 | Harris et al. |
| 10,980,560 | B2 | 4/2021 | Shelton, IV et al. |
| 10,983,646 | B2 | 4/2021 | Yoon et al. |
| 10,987,102 | B2 | 4/2021 | Gonzalez et al. |
| 10,987,178 | B2 | 4/2021 | Shelton, IV et al. |
| 10,993,713 | B2 | 5/2021 | Shelton, IV et al. |
| 10,993,715 | B2 | 5/2021 | Shelton, IV et al. |
| 10,993,716 | B2 | 5/2021 | Shelton, IV et al. |
| 10,993,717 | B2 | 5/2021 | Shelton, IV et al. |
| 11,000,274 | B2 | 5/2021 | Shelton, IV et al. |
| 11,000,275 | B2 | 5/2021 | Shelton, IV et al. |
| 11,000,277 | B2 | 5/2021 | Giordano et al. |
| 11,000,278 | B2 | 5/2021 | Shelton, IV et al. |
| 11,000,279 | B2 | 5/2021 | Shelton, IV et al. |
| 11,006,951 | B2 | 5/2021 | Giordano et al. |
| 11,006,955 | B2 | 5/2021 | Shelton, IV et al. |
| 11,007,004 | B2 | 5/2021 | Shelton, IV et al. |
| 11,007,022 | B2 | 5/2021 | Shelton, IV et al. |
| 11,013,511 | B2 | 5/2021 | Huang et al. |
| 11,013,552 | B2 | 5/2021 | Widenhouse et al. |
| 11,013,563 | B2 | 5/2021 | Shelton, IV et al. |
| 11,020,016 | B2 | 6/2021 | Wallace et al. |
| 11,020,112 | B2 | 6/2021 | Shelton, IV et al. |
| 11,020,113 | B2 | 6/2021 | Shelton, IV et al. |
| 11,020,114 | B2 | 6/2021 | Shelton, IV et al. |
| 11,020,115 | B2 | 6/2021 | Scheib et al. |
| 11,026,678 | B2 | 6/2021 | Overmyer et al. |
| 11,026,680 | B2 | 6/2021 | Shelton, IV et al. |
| 11,026,684 | B2 | 6/2021 | Shelton, IV et al. |
| 11,026,687 | B2 | 6/2021 | Shelton, IV et al. |
| 11,026,712 | B2 | 6/2021 | Shelton, IV et al. |
| 11,026,713 | B2 | 6/2021 | Stokes et al. |
| 11,026,751 | B2 | 6/2021 | Shelton, IV et al. |
| 11,033,267 | B2 | 6/2021 | Shelton, IV et al. |
| 11,039,834 | B2 | 6/2021 | Harris et al. |
| 11,039,836 | B2 | 6/2021 | Shelton, IV et al. |
| 11,039,837 | B2 | 6/2021 | Shelton, IV et al. |
| 11,039,849 | B2 | 6/2021 | Bucciaglia et al. |
| 11,045,189 | B2 | 6/2021 | Yates et al. |
| 11,045,191 | B2 | 6/2021 | Shelton, IV et al. |
| 11,045,192 | B2 | 6/2021 | Harris et al. |
| 11,045,196 | B2 | 6/2021 | Olson et al. |
| 11,045,197 | B2 | 6/2021 | Shelton, IV et al. |
| 11,045,199 | B2 | 6/2021 | Mozdzierz et al. |
| 11,045,270 | B2 | 6/2021 | Shelton, IV et al. |
| 11,051,807 | B2 | 7/2021 | Shelton, IV et al. |
| 11,051,810 | B2 | 7/2021 | Harris et al. |
| 11,051,811 | B2 | 7/2021 | Shelton, IV et al. |
| 11,051,813 | B2 | 7/2021 | Shelton, IV et al. |
| 11,051,836 | B2 | 7/2021 | Shelton, IV et al. |
| 11,051,840 | B2 | 7/2021 | Shelton, IV et al. |
| 11,051,873 | B2 | 7/2021 | Wiener et al. |
| 11,058,418 | B2 | 7/2021 | Shelton, IV et al. |
| 11,058,420 | B2 | 7/2021 | Shelton, IV et al. |
| 11,058,422 | B2 | 7/2021 | Harris et al. |
| 11,058,423 | B2 | 7/2021 | Shelton, IV et al. |
| 11,058,424 | B2 | 7/2021 | Shelton, IV et al. |
| 11,058,425 | B2 | 7/2021 | Widenhouse et al. |
| 11,058,426 | B2 | 7/2021 | Nalagatla et al. |
| 11,058,498 | B2 | 7/2021 | Shelton, IV et al. |
| 11,064,997 | B2 | 7/2021 | Shelton, IV et al. |
| 11,064,998 | B2 | 7/2021 | Shelton, IV |
| 11,065,048 | B2 | 7/2021 | Messerly et al. |
| 11,069,012 | B2 | 7/2021 | Shelton, IV et al. |
| 11,071,542 | B2 | 7/2021 | Chen et al. |
| 11,071,543 | B2 | 7/2021 | Shelton, IV et al. |
| 11,071,545 | B2 | 7/2021 | Baber et al. |
| 11,071,554 | B2 | 7/2021 | Parfett et al. |
| 11,071,560 | B2 | 7/2021 | Deck et al. |
| 11,076,853 | B2 | 8/2021 | Parfett et al. |
| 11,076,854 | B2 | 8/2021 | Baber et al. |
| 11,076,921 | B2 | 8/2021 | Shelton, IV et al. |
| 11,076,929 | B2 | 8/2021 | Shelton, IV et al. |
| 11,083,452 | B2 | 8/2021 | Schmid et al. |
| 11,083,453 | B2 | 8/2021 | Shelton, IV et al. |
| 11,083,454 | B2 | 8/2021 | Harris et al. |
| 11,083,455 | B2 | 8/2021 | Shelton, IV et al. |
| 11,083,456 | B2 | 8/2021 | Shelton, IV et al. |
| 11,083,457 | B2 | 8/2021 | Shelton, IV et al. |
| 11,083,458 | B2 | 8/2021 | Harris et al. |
| 11,090,045 | B2 | 8/2021 | Shelton, IV |
| 11,090,046 | B2 | 8/2021 | Shelton, IV et al. |
| 11,090,047 | B2 | 8/2021 | Shelton, IV et al. |
| 11,090,048 | B2 | 8/2021 | Fanelli et al. |
| 11,090,049 | B2 | 8/2021 | Bakos et al. |
| 11,090,075 | B2 | 8/2021 | Hunter et al. |
| 11,096,688 | B2 | 8/2021 | Shelton, IV et al. |
| 11,096,689 | B2 | 8/2021 | Overmyer et al. |
| 11,100,631 | B2 | 8/2021 | Yates et al. |
| 11,103,241 | B2 | 8/2021 | Yates et al. |
| 11,103,248 | B2 | 8/2021 | Shelton, IV et al. |
| 11,103,268 | B2 | 8/2021 | Shelton, IV et al. |
| 11,103,269 | B2 | 8/2021 | Shelton, IV et al. |
| 11,109,858 | B2 | 9/2021 | Shelton, IV et al. |
| 11,109,859 | B2 | 9/2021 | Overmyer et al. |
| 11,109,860 | B2 | 9/2021 | Shelton, IV et al. |
| 11,109,866 | B2 | 9/2021 | Shelton, IV et al. |
| 11,109,878 | B2 | 9/2021 | Shelton, IV et al. |
| 11,109,925 | B2 | 9/2021 | Cooper et al. |

(56) References Cited

U.S. PATENT DOCUMENTS

| | | | |
|---|---|---|---|
| 11,116,485 | B2 | 9/2021 | Scheib et al. |
| 11,116,502 | B2 | 9/2021 | Shelton, IV et al. |
| 11,123,069 | B2 | 9/2021 | Baxter, III et al. |
| 11,123,070 | B2 | 9/2021 | Shelton, IV et al. |
| 11,129,611 | B2 | 9/2021 | Shelton, IV et al. |
| 11,129,613 | B2 | 9/2021 | Harris et al. |
| 11,129,615 | B2 | 9/2021 | Scheib et al. |
| 11,129,616 | B2 | 9/2021 | Shelton, IV et al. |
| 11,129,634 | B2 | 9/2021 | Scheib et al. |
| 11,129,636 | B2 | 9/2021 | Shelton, IV et al. |
| 11,129,666 | B2 | 9/2021 | Messerly et al. |
| 11,129,680 | B2 | 9/2021 | Shelton, IV et al. |
| 11,132,462 | B2 | 9/2021 | Shelton, IV et al. |
| 11,133,106 | B2 | 9/2021 | Shelton, IV et al. |
| 11,134,938 | B2 | 10/2021 | Timm et al. |
| 11,134,940 | B2 | 10/2021 | Shelton, IV et al. |
| 11,134,942 | B2 | 10/2021 | Harris et al. |
| 11,134,943 | B2 | 10/2021 | Giordano et al. |
| 11,134,944 | B2 | 10/2021 | Wise et al. |
| 11,134,947 | B2 | 10/2021 | Shelton, IV et al. |
| 11,135,352 | B2 | 10/2021 | Shelton, IV et al. |
| 11,141,153 | B2 | 10/2021 | Shelton, IV et al. |
| 11,141,154 | B2 | 10/2021 | Shelton, IV et al. |
| 11,141,155 | B2 | 10/2021 | Shelton, IV |
| 11,141,156 | B2 | 10/2021 | Shelton, IV |
| 11,141,159 | B2 | 10/2021 | Scheib et al. |
| 11,141,160 | B2 | 10/2021 | Shelton, IV et al. |
| 11,147,547 | B2 | 10/2021 | Shelton, IV et al. |
| 11,147,549 | B2 | 10/2021 | Timm et al. |
| 11,147,551 | B2 | 10/2021 | Shelton, IV |
| 11,147,553 | B2 | 10/2021 | Shelton, IV |
| 11,147,554 | B2 | 10/2021 | Aronhalt et al. |
| 11,154,296 | B2 | 10/2021 | Aronhalt et al. |
| 11,154,297 | B2 | 10/2021 | Swayze et al. |
| 11,154,298 | B2 | 10/2021 | Timm et al. |
| 11,154,299 | B2 | 10/2021 | Shelton, IV et al. |
| 11,154,300 | B2 | 10/2021 | Nalagatla et al. |
| 11,154,301 | B2 | 10/2021 | Beckman et al. |
| 11,160,551 | B2 | 11/2021 | Shelton, IV et al. |
| 11,160,553 | B2 | 11/2021 | Simms et al. |
| 11,160,601 | B2 | 11/2021 | Worrell et al. |
| 11,166,716 | B2 | 11/2021 | Shelton, IV et al. |
| 11,166,717 | B2 | 11/2021 | Shelton, IV et al. |
| 11,166,720 | B2 | 11/2021 | Giordano et al. |
| 11,166,772 | B2 | 11/2021 | Shelton, IV et al. |
| 11,166,773 | B2 | 11/2021 | Ragosta et al. |
| 11,172,580 | B2 | 11/2021 | Gaertner, II |
| 11,172,927 | B2 | 11/2021 | Shelton, IV |
| 11,172,929 | B2 | 11/2021 | Shelton, IV |
| 11,179,150 | B2 | 11/2021 | Yates et al. |
| 11,179,151 | B2 | 11/2021 | Shelton, IV et al. |
| 11,179,152 | B2 | 11/2021 | Morgan et al. |
| 11,179,153 | B2 | 11/2021 | Shelton, IV |
| 11,179,155 | B2 | 11/2021 | Shelton, IV et al. |
| 11,179,208 | B2 | 11/2021 | Yates et al. |
| 11,185,325 | B2 | 11/2021 | Shelton, IV et al. |
| 11,185,330 | B2 | 11/2021 | Huitema et al. |
| 11,191,539 | B2 | 12/2021 | Overmyer et al. |
| 11,191,540 | B2 | 12/2021 | Aronhalt et al. |
| 11,191,543 | B2 | 12/2021 | Overmyer et al. |
| 11,191,545 | B2 | 12/2021 | Vendely et al. |
| 11,197,668 | B2 | 12/2021 | Shelton, IV et al. |
| 11,197,670 | B2 | 12/2021 | Shelton, IV et al. |
| 11,197,671 | B2 | 12/2021 | Shelton, IV et al. |
| 11,197,672 | B2 | 12/2021 | Dunki-Jacobs et al. |
| 11,202,570 | B2 | 12/2021 | Shelton, IV et al. |
| 11,202,631 | B2 | 12/2021 | Shelton, IV et al. |
| 11,202,633 | B2 | 12/2021 | Harris et al. |
| 11,207,064 | B2 | 12/2021 | Shelton, IV et al. |
| 11,207,065 | B2 | 12/2021 | Harris et al. |
| 11,207,067 | B2 | 12/2021 | Shelton, IV et al. |
| 11,207,090 | B2 | 12/2021 | Shelton, IV et al. |
| 11,207,146 | B2 | 12/2021 | Shelton, IV et al. |
| 11,213,293 | B2 | 1/2022 | Worthington et al. |
| 11,213,294 | B2 | 1/2022 | Shelton, IV et al. |
| 11,213,302 | B2 | 1/2022 | Parfett et al. |
| 11,213,359 | B2 | 1/2022 | Shelton, IV et al. |
| 11,219,453 | B2 | 1/2022 | Shelton, IV et al. |
| 11,219,455 | B2 | 1/2022 | Shelton, IV et al. |
| 11,224,423 | B2 | 1/2022 | Shelton, IV et al. |
| 11,224,426 | B2 | 1/2022 | Shelton, IV et al. |
| 11,224,427 | B2 | 1/2022 | Shelton, IV et al. |
| 11,224,428 | B2 | 1/2022 | Scott et al. |
| 11,224,454 | B2 | 1/2022 | Shelton, IV et al. |
| 11,224,497 | B2 | 1/2022 | Shelton, IV et al. |
| 11,229,436 | B2 | 1/2022 | Shelton, IV et al. |
| 11,229,437 | B2 | 1/2022 | Shelton, IV et al. |
| 11,234,698 | B2 | 2/2022 | Shelton, IV et al. |
| 11,234,700 | B2 | 2/2022 | Ragosta et al. |
| 11,241,229 | B2 | 2/2022 | Shelton, IV et al. |
| 11,241,230 | B2 | 2/2022 | Shelton, IV et al. |
| 11,241,235 | B2 | 2/2022 | Shelton, IV et al. |
| 11,246,590 | B2 | 2/2022 | Swayze et al. |
| 11,246,592 | B2 | 2/2022 | Shelton, IV et al. |
| 11,246,616 | B2 | 2/2022 | Shelton, IV et al. |
| 11,246,618 | B2 | 2/2022 | Hall et al. |
| 11,246,678 | B2 | 2/2022 | Shelton, IV et al. |
| 11,253,254 | B2 | 2/2022 | Kimball et al. |
| 11,253,256 | B2 | 2/2022 | Harris et al. |
| 11,259,799 | B2 | 3/2022 | Overmyer et al. |
| 11,259,803 | B2 | 3/2022 | Shelton, IV et al. |
| 11,259,805 | B2 | 3/2022 | Shelton, IV et al. |
| 11,259,806 | B2 | 3/2022 | Shelton, IV et al. |
| 11,259,807 | B2 | 3/2022 | Shelton, IV et al. |
| 11,266,405 | B2 | 3/2022 | Shelton, IV et al. |
| 11,266,406 | B2 | 3/2022 | Leimbach et al. |
| 11,266,409 | B2 | 3/2022 | Huitema et al. |
| 11,266,410 | B2 | 3/2022 | Shelton, IV et al. |
| 11,266,468 | B2 | 3/2022 | Shelton, IV et al. |
| 11,272,927 | B2 | 3/2022 | Swayze et al. |
| 11,272,928 | B2 | 3/2022 | Shelton, IV |
| 11,272,931 | B2 | 3/2022 | Boudreaux et al. |
| 11,272,938 | B2 | 3/2022 | Shelton, IV et al. |
| 11,278,279 | B2 | 3/2022 | Morgan et al. |
| 11,278,280 | B2 | 3/2022 | Shelton, IV et al. |
| 11,278,284 | B2 | 3/2022 | Shelton, IV et al. |
| 11,284,890 | B2 | 3/2022 | Nalagatla et al. |
| 11,284,891 | B2 | 3/2022 | Shelton, IV et al. |
| 11,284,898 | B2 | 3/2022 | Baxter, III et al. |
| 11,284,953 | B2 | 3/2022 | Shelton, IV et al. |
| 11,291,440 | B2 | 4/2022 | Harris et al. |
| 11,291,441 | B2 | 4/2022 | Giordano et al. |
| 11,291,444 | B2 | 4/2022 | Boudreaux et al. |
| 11,291,445 | B2 | 4/2022 | Shelton, IV et al. |
| 11,291,447 | B2 | 4/2022 | Shelton, IV et al. |
| 11,291,449 | B2 | 4/2022 | Swensgard et al. |
| 11,291,451 | B2 | 4/2022 | Shelton, IV |
| 11,291,465 | B2 | 4/2022 | Parihar et al. |
| 11,291,510 | B2 | 4/2022 | Shelton, IV et al. |
| 11,298,125 | B2 | 4/2022 | Ming et al. |
| 11,298,127 | B2 | 4/2022 | Shelton, IV |
| 11,298,128 | B2 | 4/2022 | Messerly et al. |
| 11,298,129 | B2 | 4/2022 | Bakos et al. |
| 11,298,130 | B2 | 4/2022 | Bakos et al. |
| 11,298,132 | B2 | 4/2022 | Shelton, IV et al. |
| 11,298,134 | B2 | 4/2022 | Huitema et al. |
| 11,304,695 | B2 | 4/2022 | Shelton, IV et al. |
| 11,304,696 | B2 | 4/2022 | Shelton, IV et al. |
| 11,304,699 | B2 | 4/2022 | Shelton, IV et al. |
| 11,304,704 | B2 | 4/2022 | Thomas et al. |
| 11,311,290 | B2 | 4/2022 | Shelton, IV et al. |
| 11,311,292 | B2 | 4/2022 | Shelton, IV et al. |
| 11,311,294 | B2 | 4/2022 | Swayze et al. |
| 11,311,295 | B2 | 4/2022 | Wingardner et al. |
| 11,311,342 | B2 | 4/2022 | Parihar et al. |
| D950,728 | S | 5/2022 | Bakos et al. |
| D952,144 | S | 5/2022 | Boudreaux |
| 11,317,910 | B2 | 5/2022 | Miller et al. |
| 11,317,912 | B2 | 5/2022 | Jenkins et al. |
| 11,317,913 | B2 | 5/2022 | Shelton, IV et al. |
| 11,317,915 | B2 | 5/2022 | Boudreaux et al. |
| 11,317,917 | B2 | 5/2022 | Shelton, IV et al. |
| 11,317,919 | B2 | 5/2022 | Shelton, IV et al. |
| 11,317,978 | B2 | 5/2022 | Cameron et al. |

(56) References Cited

U.S. PATENT DOCUMENTS 11,324,501 B2 5/2022 Shelton, IV et al.
11,324,503 B2 5/2022 Shelton, IV et al.
11,324,506 B2 5/2022 Beckman et al.
11,324,557 B2 5/2022 Shelton, IV et al.
11,331,100 B2 5/2022 Boudreaux et al.
11,331,101 B2 5/2022 Harris et al.
11,337,691 B2 5/2022 Widenhouse et al.
11,337,693 B2 5/2022 Hess et al.
11,337,698 B2 5/2022 Baxter, III et al.
11,344,299 B2 5/2022 Yates et al.
11,344,303 B2 5/2022 Shelton, IV et al.
11,350,843 B2 6/2022 Shelton, IV et al.
11,350,916 B2 6/2022 Shelton, IV et al.
11,350,928 B2 6/2022 Shelton, IV et al.
11,350,929 B2 6/2022 Giordano et al.
11,350,932 B2 6/2022 Shelton, IV et al.
11,350,934 B2 6/2022 Bakos et al.
11,350,935 B2 6/2022 Shelton, IV et al.
11,350,938 B2 6/2022 Shelton, IV et al.
11,357,503 B2 6/2022 Bakos et al.
11,361,176 B2 6/2022 Shelton, IV et al.
11,364,027 B2 6/2022 Harris et al.
11,364,046 B2 6/2022 Shelton, IV et al.
11,369,368 B2 6/2022 Shelton, IV et al.
11,369,376 B2 6/2022 Simms et al.
11,369,377 B2 6/2022 Boudreaux et al.
11,373,755 B2 6/2022 Shelton, IV et al.
11,376,001 B2 7/2022 Shelton, IV et al.
11,376,098 B2 7/2022 Shelton, IV et al.
11,382,625 B2 7/2022 Huitema et al.
11,382,626 B2 7/2022 Shelton, IV et al.
11,382,627 B2 7/2022 Huitema et al.
11,382,628 B2 7/2022 Baxter, III et al.
11,382,638 B2 7/2022 Harris et al.
11,382,697 B2 7/2022 Shelton, IV et al.
11,389,160 B2 7/2022 Shelton, IV et al.
11,389,161 B2 7/2022 Shelton, IV et al.
11,389,162 B2 7/2022 Baber et al.
11,389,164 B2 7/2022 Yates et al.
11,395,651 B2 7/2022 Shelton, IV et al.
11,395,652 B2 7/2022 Parihar et al.
11,399,828 B2 8/2022 Swayze et al.
11,399,829 B2 8/2022 Leimbach et al.
11,399,831 B2 8/2022 Overmyer et al.
11,399,837 B2 8/2022 Shelton, IV et al.
11,406,377 B2 8/2022 Schmid et al.
11,406,378 B2 8/2022 Baxter, III et al.
11,406,380 B2 8/2022 Yates et al.
11,406,381 B2 8/2022 Parihar et al.
11,406,382 B2 8/2022 Shelton, IV et al.
11,406,386 B2 8/2022 Baber et al.
11,406,390 B2 8/2022 Shelton, IV et al.
11,410,259 B2 8/2022 Harris et al.
11,413,042 B2 8/2022 Shelton, IV et al.
11,413,102 B2 8/2022 Shelton, IV et al.
11,419,606 B2 8/2022 Overmyer et al.
11,419,630 B2 8/2022 Yates et al.
11,424,027 B2 8/2022 Shelton, IV
11,426,160 B2 8/2022 Shelton, IV et al.
11,426,167 B2 8/2022 Shelton, IV et al.
11,426,251 B2 8/2022 Kimball et al.
11,432,816 B2 9/2022 Leimbach et al.
11,432,885 B2 9/2022 Shelton, IV et al.
11,439,470 B2 9/2022 Spivey et al.
11,446,029 B2 9/2022 Shelton, IV et al.
11,446,034 B2 9/2022 Shelton, IV et al.
11,452,528 B2 9/2022 Leimbach et al.
D966,512 S 10/2022 Shelton, IV et al.
D967,421 S 10/2022 Shelton, IV et al.
11,457,918 B2 10/2022 Shelton, IV et al.
11,464,511 B2 10/2022 Timm et al.
11,464,512 B2 10/2022 Shelton, IV et al.
11,464,513 B2 10/2022 Shelton, IV et al.
11,464,514 B2 10/2022 Yates et al.
11,464,601 B2 10/2022 Shelton, IV et al.
11,471,155 B2 10/2022 Shelton, IV et al.
11,471,156 B2 10/2022 Shelton, IV et al.
11,471,157 B2 10/2022 Baxter, III et al.
11,478,241 B2 10/2022 Shelton, IV et al.
11,478,242 B2 10/2022 Shelton, IV et al.
11,478,244 B2 10/2022 DiNardo et al.
D971,232 S 11/2022 Siebel et al.
11,484,307 B2 11/2022 Hall et al.
11,484,309 B2 11/2022 Harris et al.
11,484,310 B2 11/2022 Shelton, IV et al.
11,484,311 B2 11/2022 Shelton, IV et al.
11,484,312 B2 11/2022 Shelton, IV et al.
11,490,889 B2 11/2022 Overmyer et al.
11,497,488 B2 11/2022 Leimbach et al.
11,497,489 B2 11/2022 Baxter, III et al.
11,497,492 B2 11/2022 Shelton, IV
11,497,499 B2 11/2022 Shelton, IV et al.
11,504,116 B2 11/2022 Schmid et al.
11,504,119 B2 11/2022 Shelton, IV et al.
11,504,122 B2 11/2022 Shelton, IV et al.
11,504,192 B2 11/2022 Shelton, IV et al.
11,510,671 B2 11/2022 Shelton, IV et al.
11,510,741 B2 11/2022 Shelton, IV et al.
11,517,304 B2 12/2022 Yates et al.
11,517,306 B2 12/2022 Miller et al.
11,517,309 B2 12/2022 Bakos et al.
11,517,311 B2 12/2022 Lytle, IV et al.
11,517,315 B2 12/2022 Huitema et al.
11,517,325 B2 12/2022 Shelton, IV et al.
11,517,390 B2 12/2022 Baxter, III
2001/0000531 A1 4/2001 Casscells et al.
2001/0025183 A1 9/2001 Shahidi
2001/0025184 A1 9/2001 Messerly
2001/0034530 A1 10/2001 Malackowski et al.
2002/0014510 A1 2/2002 Richter et al.
2002/0022810 A1 2/2002 Urich
2002/0022836 A1 2/2002 Goble et al.
2002/0022861 A1 2/2002 Jacobs et al.
2002/0023126 A1 2/2002 Flavin
2002/0029032 A1 3/2002 Arkin
2002/0029036 A1 3/2002 Goble et al.
2002/0042620 A1 4/2002 Julian et al.
2002/0054158 A1 5/2002 Asami
2002/0082612 A1 6/2002 Moll et al.
2002/0087048 A1 7/2002 Brock et al.
2002/0087148 A1 7/2002 Brock et al.
2002/0091374 A1 7/2002 Cooper
2002/0095175 A1 7/2002 Brock et al.
2002/0103494 A1 8/2002 Pacey
2002/0111621 A1 8/2002 Wallace et al.
2002/0111624 A1 8/2002 Witt et al.
2002/0116063 A1 8/2002 Giannetti et al.
2002/0117534 A1 8/2002 Green et al.
2002/0127265 A1 9/2002 Bowman et al.
2002/0128633 A1 9/2002 Brock et al.
2002/0134811 A1 9/2002 Napier et al.
2002/0135474 A1 9/2002 Sylliassen
2002/0138086 A1 9/2002 Sixto et al.
2002/0143340 A1 10/2002 Kaneko
2002/0151770 A1 10/2002 Noll et al.
2002/0158593 A1 10/2002 Henderson et al.
2002/0161277 A1 10/2002 Boone et al.
2002/0177848 A1 11/2002 Truckai et al.
2002/0185514 A1 12/2002 Adams et al.
2002/0188170 A1 12/2002 Santamore et al.
2002/0188287 A1 12/2002 Zvuloni et al.
2003/0009193 A1 1/2003 Corsaro
2003/0011245 A1 1/2003 Fiebig
2003/0012805 A1 1/2003 Chen et al.
2003/0018323 A1 1/2003 Wallace et al.
2003/0028236 A1 2/2003 Gillick et al.
2003/0040670 A1 2/2003 Govari
2003/0045835 A1 3/2003 Anderson et al.
2003/0047230 A1 3/2003 Kim
2003/0047582 A1 3/2003 Sonnenschein et al.
2003/0050654 A1 3/2003 Whitman et al.
2003/0066858 A1 4/2003 Holgersson
2003/0078647 A1 4/2003 Vallana et al.
2003/0083648 A1 5/2003 Wang et al.

(56) References Cited

U.S. PATENT DOCUMENTS

| | | | |
|---|---|---|---|
| 2003/0084983 | A1 | 5/2003 | Rangachari et al. |
| 2003/0093103 | A1 | 5/2003 | Malackowski et al. |
| 2003/0094356 | A1 | 5/2003 | Waldron |
| 2003/0096158 | A1 | 5/2003 | Takano et al. |
| 2003/0105475 | A1 | 6/2003 | Sancoff et al. |
| 2003/0114851 | A1 | 6/2003 | Truckai et al. |
| 2003/0121586 | A1 | 7/2003 | Mitra et al. |
| 2003/0135204 | A1 | 7/2003 | Lee et al. |
| 2003/0139741 | A1 | 7/2003 | Goble et al. |
| 2003/0144660 | A1 | 7/2003 | Mollenauer |
| 2003/0149406 | A1 | 8/2003 | Martineau et al. |
| 2003/0153908 | A1 | 8/2003 | Goble et al. |
| 2003/0153968 | A1 | 8/2003 | Geis et al. |
| 2003/0163029 | A1 | 8/2003 | Sonnenschein et al. |
| 2003/0163085 | A1 | 8/2003 | Tanner et al. |
| 2003/0164172 | A1 | 9/2003 | Chumas et al. |
| 2003/0181800 | A1 | 9/2003 | Bonutti |
| 2003/0181900 | A1 | 9/2003 | Long |
| 2003/0190584 | A1 | 10/2003 | Heasley |
| 2003/0195387 | A1 | 10/2003 | Kortenbach et al. |
| 2003/0205029 | A1 | 11/2003 | Chapolini et al. |
| 2003/0212005 | A1 | 11/2003 | Petito et al. |
| 2003/0216732 | A1 | 11/2003 | Truckai et al. |
| 2003/0236505 | A1 | 12/2003 | Bonadio et al. |
| 2004/0006335 | A1 | 1/2004 | Garrison |
| 2004/0006340 | A1 | 1/2004 | Latterell et al. |
| 2004/0007608 | A1 | 1/2004 | Ehrenfels et al. |
| 2004/0024457 | A1 | 2/2004 | Boyce et al. |
| 2004/0028502 | A1 | 2/2004 | Cummins |
| 2004/0030333 | A1 | 2/2004 | Goble |
| 2004/0034287 | A1 | 2/2004 | Hickle |
| 2004/0034357 | A1 | 2/2004 | Beane et al. |
| 2004/0044295 | A1 | 3/2004 | Reinert et al. |
| 2004/0044364 | A1 | 3/2004 | DeVries et al. |
| 2004/0049121 | A1 | 3/2004 | Yaron |
| 2004/0049172 | A1 | 3/2004 | Root et al. |
| 2004/0059362 | A1 | 3/2004 | Knodel et al. |
| 2004/0068161 | A1 | 4/2004 | Couvillon |
| 2004/0068224 | A1 | 4/2004 | Couvillon et al. |
| 2004/0068307 | A1 | 4/2004 | Goble |
| 2004/0070369 | A1 | 4/2004 | Sakakibara |
| 2004/0073222 | A1 | 4/2004 | Koseki |
| 2004/0078037 | A1 | 4/2004 | Batchelor et al. |
| 2004/0082952 | A1 | 4/2004 | Dycus et al. |
| 2004/0085180 | A1 | 5/2004 | Juang |
| 2004/0092992 | A1 | 5/2004 | Adams et al. |
| 2004/0093020 | A1 | 5/2004 | Sinton |
| 2004/0093024 | A1 | 5/2004 | Lousararian et al. |
| 2004/0098040 | A1 | 5/2004 | Taniguchi et al. |
| 2004/0101822 | A1 | 5/2004 | Wiesner et al. |
| 2004/0102783 | A1 | 5/2004 | Sutterlin et al. |
| 2004/0108357 | A1 | 6/2004 | Milliman et al. |
| 2004/0110439 | A1 | 6/2004 | Chaikof et al. |
| 2004/0115022 | A1 | 6/2004 | Albertson et al. |
| 2004/0116952 | A1 | 6/2004 | Sakurai et al. |
| 2004/0119185 | A1 | 6/2004 | Chen |
| 2004/0122419 | A1 | 6/2004 | Neuberger |
| 2004/0122423 | A1 | 6/2004 | Dycus et al. |
| 2004/0133095 | A1 | 7/2004 | Dunki-Jacobs et al. |
| 2004/0133189 | A1 | 7/2004 | Sakurai |
| 2004/0143297 | A1 | 7/2004 | Ramsey |
| 2004/0147909 | A1 | 7/2004 | Johnston et al. |
| 2004/0153100 | A1 | 8/2004 | Ahlberg et al. |
| 2004/0158261 | A1 | 8/2004 | Vu |
| 2004/0164123 | A1 | 8/2004 | Racenet et al. |
| 2004/0166169 | A1 | 8/2004 | Malaviya et al. |
| 2004/0167572 | A1 | 8/2004 | Roth et al. |
| 2004/0181219 | A1 | 9/2004 | Goble et al. |
| 2004/0193189 | A1 | 9/2004 | Kortenbach et al. |
| 2004/0197367 | A1 | 10/2004 | Rezania et al. |
| 2004/0199181 | A1 | 10/2004 | Knodel et al. |
| 2004/0204735 | A1 | 10/2004 | Shiroff et al. |
| 2004/0218451 | A1 | 11/2004 | Said et al. |
| 2004/0222268 | A1 | 11/2004 | Bilotti et al. |
| 2004/0225186 | A1 | 11/2004 | Horne et al. |
| 2004/0232201 | A1 | 11/2004 | Wenchell et al. |
| 2004/0236352 | A1 | 11/2004 | Wang et al. |
| 2004/0239582 | A1 | 12/2004 | Seymour |
| 2004/0243147 | A1 | 12/2004 | Lipow |
| 2004/0243151 | A1 | 12/2004 | Demmy et al. |
| 2004/0243163 | A1 | 12/2004 | Casiano et al. |
| 2004/0247415 | A1 | 12/2004 | Mangone |
| 2004/0249366 | A1 | 12/2004 | Kunz |
| 2004/0254455 | A1 | 12/2004 | Iddan |
| 2004/0254566 | A1 | 12/2004 | Plicchi et al. |
| 2004/0254590 | A1 | 12/2004 | Hoffman et al. |
| 2004/0254680 | A1 | 12/2004 | Sunaoshi |
| 2004/0260315 | A1 | 12/2004 | Dell et al. |
| 2004/0267310 | A1 | 12/2004 | Racenet et al. |
| 2005/0010158 | A1 | 1/2005 | Brugger et al. |
| 2005/0010213 | A1 | 1/2005 | Stad et al. |
| 2005/0021078 | A1 | 1/2005 | Vleugels et al. |
| 2005/0023325 | A1 | 2/2005 | Gresham et al. |
| 2005/0032511 | A1 | 2/2005 | Malone et al. |
| 2005/0033352 | A1 | 2/2005 | Zepf et al. |
| 2005/0044489 | A1 | 2/2005 | Yamagami et al. |
| 2005/0051163 | A1 | 3/2005 | Deem et al. |
| 2005/0054946 | A1 | 3/2005 | Krzyzanowski |
| 2005/0057225 | A1 | 3/2005 | Marquet |
| 2005/0058890 | A1 | 3/2005 | Brazell et al. |
| 2005/0059997 | A1 | 3/2005 | Bauman et al. |
| 2005/0067548 | A1 | 3/2005 | Inoue |
| 2005/0070929 | A1 | 3/2005 | Dalessandro et al. |
| 2005/0075561 | A1 | 4/2005 | Golden |
| 2005/0079088 | A1 | 4/2005 | Wirth et al. |
| 2005/0080342 | A1 | 4/2005 | Gilreath et al. |
| 2005/0085693 | A1 | 4/2005 | Belson et al. |
| 2005/0090709 | A1 | 4/2005 | Okada et al. |
| 2005/0090817 | A1 | 4/2005 | Phan |
| 2005/0096683 | A1 | 5/2005 | Ellins et al. |
| 2005/0116673 | A1 | 6/2005 | Carl et al. |
| 2005/0120836 | A1 | 6/2005 | Anderson |
| 2005/0124855 | A1 | 6/2005 | Jaffe et al. |
| 2005/0125897 | A1 | 6/2005 | Wyslucha et al. |
| 2005/0129735 | A1 | 6/2005 | Cook et al. |
| 2005/0130682 | A1 | 6/2005 | Takara et al. |
| 2005/0131173 | A1 | 6/2005 | McDaniel et al. |
| 2005/0131211 | A1 | 6/2005 | Bayley et al. |
| 2005/0131390 | A1 | 6/2005 | Heinrich et al. |
| 2005/0131436 | A1 | 6/2005 | Johnston et al. |
| 2005/0131457 | A1 | 6/2005 | Douglas et al. |
| 2005/0137454 | A1 | 6/2005 | Saadat et al. |
| 2005/0137455 | A1 | 6/2005 | Ewers et al. |
| 2005/0139636 | A1 | 6/2005 | Schwemberger et al. |
| 2005/0143759 | A1 | 6/2005 | Kelly |
| 2005/0143769 | A1 | 6/2005 | White et al. |
| 2005/0145671 | A1 | 7/2005 | Viola |
| 2005/0145672 | A1 | 7/2005 | Schwemberger et al. |
| 2005/0150928 | A1 | 7/2005 | Kameyama et al. |
| 2005/0154258 | A1 | 7/2005 | Tartaglia et al. |
| 2005/0154406 | A1 | 7/2005 | Bombard et al. |
| 2005/0159778 | A1 | 7/2005 | Heinrich et al. |
| 2005/0165419 | A1 | 7/2005 | Sauer et al. |
| 2005/0169974 | A1 | 8/2005 | Tenerz et al. |
| 2005/0171522 | A1 | 8/2005 | Christopherson |
| 2005/0177176 | A1 | 8/2005 | Gerbi et al. |
| 2005/0177181 | A1 | 8/2005 | Kagan et al. |
| 2005/0177249 | A1 | 8/2005 | Kladakis et al. |
| 2005/0182298 | A1 | 8/2005 | Ikeda et al. |
| 2005/0182443 | A1 | 8/2005 | Jonn et al. |
| 2005/0184121 | A1 | 8/2005 | Heinrich |
| 2005/0186240 | A1 | 8/2005 | Ringeisen et al. |
| 2005/0187545 | A1 | 8/2005 | Hooven et al. |
| 2005/0191936 | A1 | 9/2005 | Marine et al. |
| 2005/0203550 | A1 | 9/2005 | Laufer et al. |
| 2005/0209614 | A1 | 9/2005 | Fenter et al. |
| 2005/0216055 | A1 | 9/2005 | Scirica et al. |
| 2005/0222587 | A1 | 10/2005 | Jinno et al. |
| 2005/0222611 | A1 | 10/2005 | Weitkamp |
| 2005/0222616 | A1 | 10/2005 | Rethy et al. |
| 2005/0222665 | A1 | 10/2005 | Aranyi |
| 2005/0228224 | A1 | 10/2005 | Okada et al. |
| 2005/0228446 | A1 | 10/2005 | Mooradian et al. |
| 2005/0230453 | A1 | 10/2005 | Viola |

(56) References Cited

U.S. PATENT DOCUMENTS

2005/0240178 A1 10/2005 Morley et al.
2005/0242950 A1 11/2005 Lindsay et al.
2005/0245965 A1 11/2005 Orban, III et al.
2005/0246881 A1 11/2005 Kelly et al.
2005/0251063 A1 11/2005 Basude
2005/0256452 A1 11/2005 DeMarchi et al.
2005/0256546 A1 11/2005 Vaisnys et al.
2005/0258963 A1 11/2005 Rodriguez et al.
2005/0261676 A1 11/2005 Hall et al.
2005/0263563 A1 12/2005 Racenet et al.
2005/0267455 A1 12/2005 Eggers et al.
2005/0274034 A1 12/2005 Hayashida et al.
2005/0283188 A1 12/2005 Loshakove et al.
2005/0283226 A1 12/2005 Haverkost
2006/0008787 A1 1/2006 Hayman et al.
2006/0011698 A1 1/2006 Okada et al.
2006/0015009 A1 1/2006 Jaffe et al.
2006/0020167 A1 1/2006 Sitzmann
2006/0020258 A1 1/2006 Strauss et al.
2006/0020272 A1 1/2006 Gildenberg
2006/0020336 A1 1/2006 Liddicoat
2006/0025812 A1 2/2006 Shelton
2006/0041188 A1 2/2006 Dirusso et al.
2006/0047275 A1 3/2006 Goble
2006/0049229 A1 3/2006 Milliman et al.
2006/0052824 A1 3/2006 Ransick et al.
2006/0052825 A1 3/2006 Ransick et al.
2006/0064086 A1 3/2006 Odom
2006/0079735 A1 4/2006 Martone et al.
2006/0079874 A1 4/2006 Faller et al.
2006/0079879 A1 4/2006 Faller et al.
2006/0086032 A1 4/2006 Valencic et al.
2006/0087746 A1 4/2006 Lipow
2006/0089535 A1 4/2006 Raz et al.
2006/0097699 A1 5/2006 Kamenoff
2006/0100643 A1 5/2006 Laufer et al.
2006/0100649 A1 5/2006 Hart
2006/0106369 A1 5/2006 Desai et al.
2006/0111711 A1 5/2006 Goble
2006/0111723 A1 5/2006 Chapolini et al.
2006/0116634 A1 6/2006 Shachar
2006/0142772 A1 6/2006 Ralph et al.
2006/0144898 A1 7/2006 Bilotti et al.
2006/0154546 A1 7/2006 Murphy et al.
2006/0161050 A1 7/2006 Butler et al.
2006/0161185 A1 7/2006 Saadat et al.
2006/0167471 A1 7/2006 Phillips
2006/0173290 A1 8/2006 Lavallee et al.
2006/0173470 A1 8/2006 Oray et al.
2006/0176031 A1 8/2006 Forman et al.
2006/0176242 A1 8/2006 Jaramaz et al.
2006/0178556 A1 8/2006 Hasser et al.
2006/0180633 A1 8/2006 Emmons
2006/0180634 A1 8/2006 Shelton et al.
2006/0185682 A1 8/2006 Marczyk
2006/0199999 A1 9/2006 Ikeda et al.
2006/0201989 A1 9/2006 Ojeda
2006/0206100 A1 9/2006 Eskridge et al.
2006/0217729 A1 9/2006 Eskridge et al.
2006/0226957 A1 10/2006 Miller et al.
2006/0235368 A1 10/2006 Oz
2006/0241666 A1 10/2006 Briggs et al.
2006/0244460 A1 11/2006 Weaver
2006/0247584 A1 11/2006 Sheetz et al.
2006/0252981 A1 11/2006 Matsuda et al.
2006/0252990 A1 11/2006 Kubach
2006/0252993 A1 11/2006 Freed et al.
2006/0258904 A1 11/2006 Stefanchik et al.
2006/0259073 A1 11/2006 Miyamoto et al.
2006/0261763 A1 11/2006 Iott et al.
2006/0263444 A1 11/2006 Ming et al.
2006/0264831 A1 11/2006 Skwarek et al.
2006/0264929 A1 11/2006 Goble et al.
2006/0271042 A1 11/2006 Latterell et al.
2006/0271102 A1 11/2006 Bosshard et al.
2006/0282064 A1 12/2006 Shimizu et al.
2006/0284730 A1 12/2006 Schmid et al.
2006/0287576 A1 12/2006 Tsuji et al.
2006/0289602 A1 12/2006 Wales et al.
2006/0291981 A1 12/2006 Viola et al.
2007/0005045 A1 1/2007 Mintz et al.
2007/0009570 A1 1/2007 Kim et al.
2007/0010702 A1 1/2007 Wang et al.
2007/0010838 A1 1/2007 Shelton et al.
2007/0016235 A1 1/2007 Tanaka et al.
2007/0018958 A1 1/2007 Tavakoli et al.
2007/0026039 A1 2/2007 Drumheller et al.
2007/0026040 A1 2/2007 Crawley et al.
2007/0027468 A1 2/2007 Wales et al.
2007/0027551 A1 2/2007 Farnsworth et al.
2007/0043338 A1 2/2007 Moll et al.
2007/0043387 A1 2/2007 Vargas et al.
2007/0049951 A1 3/2007 Menn
2007/0049966 A1 3/2007 Bonadio et al.
2007/0051375 A1 3/2007 Milliman
2007/0055228 A1 3/2007 Berg et al.
2007/0055305 A1 3/2007 Schnyder et al.
2007/0073341 A1 3/2007 Smith et al.
2007/0073389 A1 3/2007 Bolduc et al.
2007/0078328 A1 4/2007 Ozaki et al.
2007/0078484 A1 4/2007 Talarico et al.
2007/0084897 A1 4/2007 Shelton et al.
2007/0088376 A1 4/2007 Zacharias
2007/0090788 A1 4/2007 Hansford et al.
2007/0093869 A1 4/2007 Bloom et al.
2007/0102472 A1 5/2007 Shelton
2007/0103437 A1 5/2007 Rosenberg
2007/0106113 A1 5/2007 Ravo
2007/0106317 A1 5/2007 Shelton et al.
2007/0118115 A1 5/2007 Artale et al.
2007/0134251 A1 6/2007 Ashkenazi et al.
2007/0135686 A1 6/2007 Pruitt et al.
2007/0135803 A1 6/2007 Belson
2007/0152612 A1 7/2007 Chen et al.
2007/0152829 A1 7/2007 Lindsay et al.
2007/0155010 A1 7/2007 Farnsworth et al.
2007/0170225 A1 7/2007 Shelton et al.
2007/0173687 A1 7/2007 Shima et al.
2007/0173813 A1 7/2007 Odom
2007/0173872 A1 7/2007 Neuenfeldt
2007/0175950 A1 * 8/2007 Shelton, IV ..... A61B 17/07207 227/176.1
2007/0175951 A1 8/2007 Shelton et al.
2007/0175955 A1 8/2007 Shelton et al.
2007/0179477 A1 8/2007 Danger
2007/0185545 A1 8/2007 Duke
2007/0187857 A1 8/2007 Riley et al.
2007/0190110 A1 8/2007 Pameijer et al.
2007/0191868 A1 8/2007 Theroux et al.
2007/0191915 A1 8/2007 Strother et al.
2007/0194079 A1 8/2007 Hueil et al.
2007/0194082 A1 8/2007 Morgan et al.
2007/0197954 A1 8/2007 Keenan
2007/0198039 A1 8/2007 Jones et al.
2007/0203510 A1 8/2007 Bettuchi
2007/0207010 A1 9/2007 Caspi
2007/0208359 A1 9/2007 Hoffman
2007/0208375 A1 9/2007 Nishizawa et al.
2007/0213750 A1 9/2007 Weadock
2007/0221701 A1 9/2007 Ortiz et al.
2007/0225562 A1 9/2007 Spivey et al.
2007/0233163 A1 10/2007 Bombard et al.
2007/0243227 A1 10/2007 Gertner
2007/0244471 A1 10/2007 Malackowski
2007/0244496 A1 10/2007 Hellenkamp
2007/0246505 A1 10/2007 Pace-Floridia et al.
2007/0260132 A1 11/2007 Sterling
2007/0262592 A1 11/2007 Hwang et al.
2007/0270660 A1 11/2007 Caylor et al.
2007/0275035 A1 11/2007 Herman et al.
2007/0276409 A1 11/2007 Ortiz et al.
2007/0279011 A1 12/2007 Jones et al.
2007/0286892 A1 12/2007 Herzberg et al.
2007/0290027 A1 12/2007 Maatta et al.

(56) References Cited

U.S. PATENT DOCUMENTS

2007/0296286 A1 12/2007 Avenell
2008/0000941 A1 1/2008 Sonnenschein et al.
2008/0003196 A1 1/2008 Jonn et al.
2008/0007237 A1 1/2008 Nagashima et al.
2008/0015598 A1 1/2008 Prommersberger
2008/0021486 A1 1/2008 Oyola et al.
2008/0029570 A1 2/2008 Shelton et al.
2008/0029573 A1 2/2008 Shelton et al.
2008/0029574 A1 2/2008 Shelton et al.
2008/0029575 A1 2/2008 Shelton et al.
2008/0030170 A1 2/2008 Dacquay et al.
2008/0039746 A1 2/2008 Hissong et al.
2008/0042861 A1 2/2008 Dacquay et al.
2008/0046000 A1 2/2008 Lee et al.
2008/0051833 A1 2/2008 Gramuglia et al.
2008/0064920 A1 3/2008 Bakos et al.
2008/0064921 A1 3/2008 Larkin et al.
2008/0065153 A1 3/2008 Allard et al.
2008/0069736 A1 3/2008 Mingerink et al.
2008/0071328 A1 3/2008 Haubrich et al.
2008/0077158 A1 3/2008 Haider et al.
2008/0078801 A1* 4/2008 Shelton .............. A61B 17/0644 227/175.1
2008/0078802 A1 4/2008 Hess et al.
2008/0081948 A1 4/2008 Weisenburgh et al.
2008/0082114 A1 4/2008 McKenna et al.
2008/0082125 A1 4/2008 Murray et al.
2008/0082126 A1 4/2008 Murray et al.
2008/0083807 A1 4/2008 Beardsley et al.
2008/0083811 A1 4/2008 Marczyk
2008/0085296 A1 4/2008 Powell et al.
2008/0086078 A1 4/2008 Powell et al.
2008/0091072 A1 4/2008 Omori et al.
2008/0108443 A1 5/2008 Jinno et al.
2008/0114250 A1 5/2008 Urbano et al.
2008/0125634 A1 5/2008 Ryan et al.
2008/0125749 A1 5/2008 Olson
2008/0126984 A1 5/2008 Fleishman et al.
2008/0128469 A1 6/2008 Dalessandro et al.
2008/0129253 A1 6/2008 Shiue et al.
2008/0135600 A1 6/2008 Hiranuma et al.
2008/0140115 A1 6/2008 Stopek
2008/0140159 A1 6/2008 Bornhoft et al.
2008/0149682 A1 6/2008 Uhm
2008/0154299 A1 6/2008 Livneh
2008/0154335 A1 6/2008 Thrope et al.
2008/0169328 A1 7/2008 Shelton
2008/0169332 A1 7/2008 Shelton et al.
2008/0169333 A1 7/2008 Shelton et al.
2008/0172087 A1 7/2008 Fuchs et al.
2008/0177392 A1 7/2008 Williams et al.
2008/0190989 A1 8/2008 Crews et al.
2008/0196253 A1 8/2008 Ezra et al.
2008/0196419 A1 8/2008 Dube
2008/0197167 A1 8/2008 Viola et al.
2008/0200755 A1 8/2008 Bakos
2008/0200762 A1 8/2008 Stokes et al.
2008/0200835 A1 8/2008 Monson et al.
2008/0200911 A1 8/2008 Long
2008/0200933 A1 8/2008 Bakos et al.
2008/0200934 A1 8/2008 Fox
2008/0206186 A1 8/2008 Butler et al.
2008/0208058 A1 8/2008 Sabata et al.
2008/0216704 A1 9/2008 Eisenbeis et al.
2008/0234709 A1 9/2008 Houser
2008/0234866 A1 9/2008 Kishi et al.
2008/0242939 A1 10/2008 Johnston
2008/0243088 A1 10/2008 Evans
2008/0249536 A1 10/2008 Stahler et al.
2008/0249608 A1 10/2008 Dave
2008/0255413 A1 10/2008 Zemlok et al.
2008/0255420 A1 10/2008 Lee et al.
2008/0255421 A1 10/2008 Hegeman et al.
2008/0255663 A1 10/2008 Akpek et al.
2008/0262654 A1 10/2008 Omori et al.
2008/0269596 A1 10/2008 Revie et al.
2008/0281171 A1 11/2008 Fennell et al.
2008/0281332 A1 11/2008 Taylor
2008/0287944 A1 11/2008 Pearson et al.
2008/0293910 A1 11/2008 Kapiamba et al.
2008/0294179 A1 11/2008 Balbierz et al.
2008/0296346 A1 12/2008 Shelton, IV et al.
2008/0297287 A1 12/2008 Shachar et al.
2008/0298784 A1 12/2008 Kastner
2008/0308504 A1 12/2008 Hallan et al.
2008/0308602 A1 12/2008 Timm et al.
2008/0308603 A1 12/2008 Shelton et al.
2008/0308607 A1 12/2008 Timm et al.
2008/0308807 A1 12/2008 Yamazaki et al.
2008/0312686 A1 12/2008 Ellingwood
2008/0312687 A1 12/2008 Blier
2008/0315829 A1 12/2008 Jones et al.
2009/0001121 A1 1/2009 Hess et al.
2009/0001130 A1 1/2009 Hess et al.
2009/0004455 A1 1/2009 Gravagna et al.
2009/0005809 A1 1/2009 Hess et al.
2009/0007014 A1 1/2009 Coomer et al.
2009/0012534 A1 1/2009 Madhani et al.
2009/0015195 A1 1/2009 Loth-Krausser
2009/0020958 A1 1/2009 Soul
2009/0048583 A1 2/2009 Williams et al.
2009/0048589 A1 2/2009 Takashino et al.
2009/0076506 A1 3/2009 Baker
2009/0078736 A1 3/2009 Van Lue
2009/0081313 A1 3/2009 Aghion et al.
2009/0088659 A1 4/2009 Graham et al.
2009/0090763 A1 4/2009 Zemlok et al.
2009/0099579 A1 4/2009 Nentwick et al.
2009/0099876 A1 4/2009 Whitman
2009/0110533 A1 4/2009 Jinno
2009/0112234 A1 4/2009 Crainich et al.
2009/0114701 A1 5/2009 Zemlok et al.
2009/0118762 A1 5/2009 Crainch et al.
2009/0119011 A1 5/2009 Kondo et al.
2009/0120994 A1 5/2009 Murray et al.
2009/0131819 A1 5/2009 Ritchie et al.
2009/0132400 A1 5/2009 Conway
2009/0135280 A1 5/2009 Johnston et al.
2009/0138003 A1 5/2009 Deville et al.
2009/0143797 A1 6/2009 Smith et al.
2009/0143855 A1 6/2009 Weber et al.
2009/0149871 A9 6/2009 Kagan et al.
2009/0167548 A1 7/2009 Sugahara
2009/0171147 A1 7/2009 Lee et al.
2009/0177218 A1 7/2009 Young et al.
2009/0177226 A1 7/2009 Reinprecht et al.
2009/0181290 A1 7/2009 Baldwin et al.
2009/0188964 A1 7/2009 Orlov
2009/0192534 A1 7/2009 Ortiz et al.
2009/0198272 A1 8/2009 Kerver et al.
2009/0204108 A1 8/2009 Steffen
2009/0204109 A1 8/2009 Grove et al.
2009/0204126 A1 8/2009 Le
2009/0204925 A1 8/2009 Bhat et al.
2009/0206125 A1 8/2009 Huitema et al.
2009/0206126 A1 8/2009 Huitema et al.
2009/0206131 A1 8/2009 Weisenburgh, II et al.
2009/0206133 A1 8/2009 Morgan et al.
2009/0206137 A1 8/2009 Hall et al.
2009/0206139 A1 8/2009 Hall et al.
2009/0206141 A1 8/2009 Huitema et al.
2009/0206142 A1 8/2009 Huitema et al.
2009/0206143 A1 8/2009 Huitema et al.
2009/0221993 A1 9/2009 Sohi et al.
2009/0227834 A1 9/2009 Nakamoto et al.
2009/0234273 A1 9/2009 Intoccia et al.
2009/0242610 A1 10/2009 Shelton, IV et al.
2009/0246873 A1 10/2009 Yamamoto et al.
2009/0247368 A1 10/2009 Chiang
2009/0247901 A1 10/2009 Zimmer
2009/0248100 A1 10/2009 Vaisnys et al.
2009/0253959 A1 10/2009 Yoshie et al.
2009/0255974 A1 10/2009 Viola
2009/0261141 A1 10/2009 Stratton et al.

(56) References Cited

U.S. PATENT DOCUMENTS

2009/0262078 A1 10/2009 Pizzi
2009/0270895 A1 10/2009 Churchill et al.
2009/0273353 A1 11/2009 Kroh et al.
2009/0277288 A1 11/2009 Doepker et al.
2009/0278406 A1 11/2009 Hoffman
2009/0290016 A1 11/2009 Suda
2009/0292283 A1 11/2009 Odom
2009/0306639 A1 12/2009 Nevo et al.
2009/0308907 A1 12/2009 Nalagatla et al.
2009/0318557 A1 12/2009 Stockel
2009/0325859 A1 12/2009 Ameer et al.
2010/0002013 A1 1/2010 Kagaya
2010/0005035 A1 1/2010 Carpenter et al.
2010/0012703 A1 1/2010 Calabrese et al.
2010/0015104 A1 1/2010 Fraser et al.
2010/0016853 A1 1/2010 Burbank
2010/0016888 A1 1/2010 Calabrese et al.
2010/0017715 A1 1/2010 Balassanian
2010/0023024 A1 1/2010 Zeiner et al.
2010/0030233 A1 2/2010 Whitman et al.
2010/0030239 A1 2/2010 Viola et al.
2010/0032179 A1 2/2010 Hanspers et al.
2010/0036370 A1 2/2010 Mirel et al.
2010/0036441 A1 2/2010 Procter
2010/0051668 A1 3/2010 Milliman et al.
2010/0057118 A1 3/2010 Dietz et al.
2010/0065604 A1 3/2010 Weng
2010/0069833 A1 3/2010 Wenderow et al.
2010/0069942 A1 3/2010 Shelton, IV
2010/0076483 A1 3/2010 Imuta
2010/0076489 A1 3/2010 Stopek et al.
2010/0081883 A1 4/2010 Murray et al.
2010/0094340 A1 4/2010 Stopek et al.
2010/0094400 A1 4/2010 Bolduc et al.
2010/0100123 A1 4/2010 Bennett
2010/0100124 A1 4/2010 Calabrese et al.
2010/0116519 A1 5/2010 Gareis
2010/0122339 A1 5/2010 Boccacci
2010/0125786 A1 5/2010 Ozawa et al.
2010/0133317 A1 6/2010 Shelton, IV et al.
2010/0137990 A1 6/2010 Apatsidis et al.
2010/0138659 A1 6/2010 Carmichael et al.
2010/0145146 A1 6/2010 Melder
2010/0147921 A1 6/2010 Olson
2010/0147922 A1 6/2010 Olson
2010/0159435 A1 6/2010 Mueller et al.
2010/0168741 A1 7/2010 Sanai et al.
2010/0179022 A1 7/2010 Shirokoshi
2010/0180711 A1 7/2010 Kilibarda et al.
2010/0191262 A1 7/2010 Harris et al.
2010/0191292 A1 7/2010 DeMeo et al.
2010/0193566 A1 8/2010 Scheib et al.
2010/0198159 A1 8/2010 Voss et al.
2010/0204717 A1 8/2010 Knodel
2010/0204721 A1 8/2010 Young et al.
2010/0217281 A1 8/2010 Matsuoka et al.
2010/0222901 A1 9/2010 Swayze et al.
2010/0228250 A1 9/2010 Brogna
2010/0234687 A1 9/2010 Azarbarzin et al.
2010/0241137 A1 9/2010 Doyle et al.
2010/0245102 A1 9/2010 Yokoi
2010/0249497 A1 9/2010 Peine et al.
2010/0249947 A1 9/2010 Lesh et al.
2010/0256675 A1 10/2010 Romans
2010/0258327 A1 10/2010 Esenwein et al.
2010/0267662 A1 10/2010 Fielder et al.
2010/0274160 A1 10/2010 Yachi et al.
2010/0291184 A1 11/2010 Clark et al.
2010/0292540 A1 11/2010 Hess et al.
2010/0298636 A1 11/2010 Castro et al.
2010/0301097 A1 12/2010 Scirica et al.
2010/0310623 A1 12/2010 Laurencin et al.
2010/0312261 A1 12/2010 Suzuki et al.
2010/0318085 A1 12/2010 Austin et al.
2010/0325568 A1 12/2010 Pedersen et al.
2010/0327041 A1 12/2010 Milliman et al.
2010/0331856 A1 12/2010 Carlson et al.
2011/0006101 A1 1/2011 Hall et al.
2011/0009694 A1 1/2011 Schultz et al.
2011/0011916 A1 1/2011 Levine
2011/0016960 A1 1/2011 Debrailly
2011/0021871 A1 1/2011 Berkelaar
2011/0022032 A1 1/2011 Zemlok et al.
2011/0024477 A1 2/2011 Hall
2011/0024478 A1 2/2011 Shelton, IV
2011/0025311 A1 2/2011 Chauvin et al.
2011/0028991 A1 2/2011 Ikeda et al.
2011/0029270 A1 2/2011 Mueglitz
2011/0036891 A1 2/2011 Zemlok et al.
2011/0046667 A1 2/2011 Culligan et al.
2011/0052660 A1 3/2011 Yang et al.
2011/0056717 A1 3/2011 Herisse
2011/0060363 A1 3/2011 Hess et al.
2011/0066156 A1 3/2011 McGahan et al.
2011/0082538 A1 4/2011 Dahlgren et al.
2011/0087276 A1 4/2011 Bedi et al.
2011/0088921 A1 4/2011 Forgues et al.
2011/0091515 A1 4/2011 Zilberman et al.
2011/0095064 A1 4/2011 Taylor et al.
2011/0095067 A1 4/2011 Ohdaira
2011/0101069 A1 5/2011 Bombard et al.
2011/0101794 A1 5/2011 Schroeder et al.
2011/0112517 A1 5/2011 Peine et al.
2011/0112530 A1 5/2011 Keller
2011/0114697 A1 5/2011 Baxter, III et al.
2011/0118708 A1 5/2011 Burbank et al.
2011/0118754 A1 5/2011 Dachs, II et al.
2011/0125149 A1 5/2011 El-Galley et al.
2011/0125176 A1 5/2011 Yates et al.
2011/0127945 A1 6/2011 Yoneda
2011/0129706 A1 6/2011 Takahashi et al.
2011/0144764 A1 6/2011 Bagga et al.
2011/0147433 A1 6/2011 Shelton, IV et al.
2011/0160725 A1 6/2011 Kabaya et al.
2011/0163146 A1 7/2011 Ortiz et al.
2011/0172495 A1 7/2011 Armstrong
2011/0174861 A1 7/2011 Shelton, IV et al.
2011/0192882 A1 8/2011 Hess et al.
2011/0199225 A1 8/2011 Touchberry et al.
2011/0218400 A1 9/2011 Ma et al.
2011/0218550 A1 9/2011 Ma
2011/0220381 A1 9/2011 Friese et al.
2011/0224543 A1 9/2011 Johnson et al.
2011/0225105 A1 9/2011 Scholer et al.
2011/0230713 A1 9/2011 Kleemann et al.
2011/0235168 A1 9/2011 Sander
2011/0238044 A1 9/2011 Main et al.
2011/0241597 A1 10/2011 Zhu et al.
2011/0251606 A1 10/2011 Kerr
2011/0256266 A1 10/2011 Orme et al.
2011/0271186 A1 11/2011 Owens
2011/0275901 A1 11/2011 Shelton, IV
2011/0276083 A1 11/2011 Shelton, IV et al.
2011/0278035 A1 11/2011 Chen
2011/0278343 A1 11/2011 Knodel et al.
2011/0279268 A1 11/2011 Konishi et al.
2011/0285507 A1 11/2011 Nelson
2011/0290856 A1 12/2011 Shelton, IV et al.
2011/0290858 A1 12/2011 Whitman et al.
2011/0292258 A1 12/2011 Adler et al.
2011/0293690 A1 12/2011 Griffin et al.
2011/0295295 A1 12/2011 Shelton, IV et al.
2011/0295299 A1 12/2011 Braithwaite et al.
2011/0313894 A1 12/2011 Dye et al.
2011/0315413 A1 12/2011 Fisher et al.
2012/0004636 A1 1/2012 Lo
2012/0007442 A1 1/2012 Rhodes et al.
2012/0008880 A1 1/2012 Toth
2012/0016239 A1 1/2012 Barthe et al.
2012/0016413 A1 1/2012 Timm et al.
2012/0016467 A1 1/2012 Chen et al.
2012/0029272 A1 2/2012 Shelton, IV et al.
2012/0033360 A1 2/2012 Hsu
2012/0059286 A1 3/2012 Hastings et al.

(56) References Cited

U.S. PATENT DOCUMENTS

2012/0064483 A1 3/2012 Lint et al.
2012/0074200 A1 3/2012 Schmid et al.
2012/0078243 A1 3/2012 Worrell et al.
2012/0078244 A1 3/2012 Worrell et al.
2012/0080336 A1 4/2012 Shelton, IV et al.
2012/0080344 A1 4/2012 Shelton, IV
2012/0080478 A1 4/2012 Morgan et al.
2012/0080498 A1 4/2012 Shelton, IV et al.
2012/0086276 A1 4/2012 Sawyers
2012/0095458 A1 4/2012 Cybulski et al.
2012/0109186 A1 5/2012 Parrott et al.
2012/0116261 A1 5/2012 Mumaw et al.
2012/0116262 A1 5/2012 Houser et al.
2012/0116265 A1 5/2012 Houser et al.
2012/0116266 A1 5/2012 Houser et al.
2012/0116381 A1 5/2012 Houser et al.
2012/0118595 A1 5/2012 Pellenc
2012/0123463 A1 5/2012 Jacobs
2012/0125792 A1 5/2012 Cassivi
2012/0130217 A1 5/2012 Kauphusman et al.
2012/0132286 A1 5/2012 Lim et al.
2012/0143175 A1 6/2012 Hermann et al.
2012/0171539 A1 7/2012 Rejman et al.
2012/0175398 A1 7/2012 Sandborn et al.
2012/0190964 A1 7/2012 Hyde et al.
2012/0197239 A1 8/2012 Smith et al.
2012/0197272 A1 8/2012 Oray et al.
2012/0203213 A1 8/2012 Kimball et al.
2012/0211542 A1 8/2012 Racenet
2012/0220990 A1 8/2012 Mckenzie et al.
2012/0234895 A1 9/2012 O'Connor et al.
2012/0234897 A1 9/2012 Shelton, IV et al.
2012/0239068 A1 9/2012 Morris et al.
2012/0241494 A1 9/2012 Marczyk
2012/0248169 A1 10/2012 Widenhouse et al.
2012/0251861 A1 10/2012 Liang et al.
2012/0253328 A1 10/2012 Cunningham et al.
2012/0271327 A1 10/2012 West et al.
2012/0283707 A1 11/2012 Giordano et al.
2012/0289811 A1 11/2012 Viola et al.
2012/0289979 A1 11/2012 Eskaros et al.
2012/0292367 A1 11/2012 Morgan et al.
2012/0296316 A1 11/2012 Imuta
2012/0296342 A1 11/2012 Haglund Wendelschafer
2012/0298722 A1 11/2012 Hess et al.
2012/0301498 A1 11/2012 Altreuter et al.
2012/0310254 A1 12/2012 Manzo et al.
2012/0316424 A1 12/2012 Stopek
2012/0330329 A1 12/2012 Harris et al.
2013/0006227 A1 1/2013 Takashino
2013/0008937 A1 1/2013 Viola
2013/0012983 A1 1/2013 Kleyman
2013/0018400 A1 1/2013 Milton et al.
2013/0020375 A1 1/2013 Shelton, IV et al.
2013/0020376 A1 1/2013 Shelton, IV et al.
2013/0023861 A1 1/2013 Shelton, IV et al.
2013/0023910 A1 1/2013 Solomon et al.
2013/0026208 A1 1/2013 Shelton, IV et al.
2013/0026210 A1 1/2013 Shelton, IV et al.
2013/0030462 A1 1/2013 Keating et al.
2013/0041292 A1 2/2013 Cunningham
2013/0057162 A1 3/2013 Pollischansky
2013/0068816 A1 3/2013 Mandakolathur Vasudevan et al.
2013/0069088 A1 3/2013 Speck et al.
2013/0075447 A1 3/2013 Weisenburgh, II et al.
2013/0087597 A1 4/2013 Shelton, IV et al.
2013/0090534 A1 4/2013 Burns et al.
2013/0096568 A1 4/2013 Justis
2013/0098970 A1 4/2013 Racenet et al.
2013/0106352 A1 5/2013 Nagamine
2013/0112729 A1 5/2013 Beardsley et al.
2013/0116669 A1 5/2013 Shelton, IV et al.
2013/0123816 A1 5/2013 Hodgkinson et al.
2013/0126202 A1 5/2013 Oomori et al.
2013/0131476 A1 5/2013 Siu et al.
2013/0131651 A1 5/2013 Strobl et al.
2013/0136969 A1 5/2013 Yasui et al.
2013/0153639 A1 6/2013 Hodgkinson et al.
2013/0153641 A1 6/2013 Shelton, IV et al.
2013/0158390 A1 6/2013 Tan et al.
2013/0162198 A1 6/2013 Yokota et al.
2013/0169217 A1 7/2013 Watanabe et al.
2013/0172713 A1 7/2013 Kirschenman
2013/0172878 A1 7/2013 Smith
2013/0175317 A1 7/2013 Yates et al.
2013/0183769 A1 7/2013 Tajima
2013/0211244 A1 8/2013 Nathaniel
2013/0214025 A1 8/2013 Zemlok et al.
2013/0215449 A1 8/2013 Yamasaki
2013/0231681 A1 9/2013 Robinson et al.
2013/0233906 A1 9/2013 Hess et al.
2013/0238021 A1 9/2013 Gross et al.
2013/0248578 A1 9/2013 Arteaga Gonzalez
2013/0253480 A1 9/2013 Kimball et al.
2013/0256373 A1 10/2013 Schmid et al.
2013/0256380 A1 10/2013 Schmid et al.
2013/0267950 A1 10/2013 Rosa et al.
2013/0267978 A1 10/2013 Trissel
2013/0270322 A1 10/2013 Scheib et al.
2013/0277410 A1 10/2013 Fernandez et al.
2013/0284792 A1 10/2013 Ma
2013/0289565 A1 10/2013 Hassler, Jr.
2013/0293353 A1 11/2013 McPherson et al.
2013/0303845 A1 11/2013 Skula et al.
2013/0306704 A1 11/2013 Balbierz et al.
2013/0327552 A1 12/2013 Lovelass et al.
2013/0333910 A1 12/2013 Tanimoto et al.
2013/0334280 A1 12/2013 Krehel et al.
2013/0334283 A1 12/2013 Swayze et al.
2013/0334285 A1 12/2013 Swayze et al.
2013/0341374 A1 12/2013 Shelton, IV et al.
2014/0001231 A1 1/2014 Shelton, IV et al.
2014/0001234 A1 1/2014 Shelton, IV et al.
2014/0005640 A1 1/2014 Shelton, IV et al.
2014/0005678 A1 1/2014 Shelton, IV et al.
2014/0005702 A1 1/2014 Timm et al.
2014/0005718 A1 1/2014 Shelton, IV et al.
2014/0008289 A1 1/2014 Williams et al.
2014/0014704 A1 1/2014 Onukuri et al.
2014/0014705 A1 1/2014 Baxter, III
2014/0014707 A1 1/2014 Onukuri et al.
2014/0018832 A1 1/2014 Shelton, IV
2014/0022283 A1 1/2014 Chan et al.
2014/0039549 A1 2/2014 Belsky et al.
2014/0041191 A1 2/2014 Knodel
2014/0048580 A1 2/2014 Merchant et al.
2014/0069240 A1 3/2014 Dauvin et al.
2014/0078715 A1 3/2014 Pickard et al.
2014/0081176 A1 3/2014 Hassan
2014/0094681 A1 4/2014 Valentine et al.
2014/0100558 A1 4/2014 Schmitz et al.
2014/0107697 A1 4/2014 Patani et al.
2014/0115229 A1 4/2014 Kothamasu et al.
2014/0131418 A1 5/2014 Kostrzewski
2014/0131419 A1 5/2014 Bettuchi
2014/0135832 A1 5/2014 Park et al.
2014/0151433 A1 6/2014 Shelton, IV et al.
2014/0155916 A1 6/2014 Hodgkinson et al.
2014/0158747 A1 6/2014 Measamer et al.
2014/0166723 A1 6/2014 Beardsley et al.
2014/0166724 A1 6/2014 Schellin et al.
2014/0166725 A1 6/2014 Schellin et al.
2014/0166726 A1 6/2014 Schellin et al.
2014/0175147 A1 6/2014 Manoux et al.
2014/0175150 A1 6/2014 Shelton, IV et al.
2014/0175152 A1 6/2014 Hess et al.
2014/0181710 A1 6/2014 Baalu et al.
2014/0183244 A1 7/2014 Duque et al.
2014/0188091 A1 7/2014 Vidal et al.
2014/0188101 A1 7/2014 Bales, Jr. et al.
2014/0188159 A1 7/2014 Steege
2014/0207124 A1 7/2014 Aldridge et al.
2014/0209658 A1 7/2014 Skalla et al.
2014/0224857 A1 8/2014 Schmid

(56) References Cited

U.S. PATENT DOCUMENTS

2014/0228632 A1 8/2014 Sholev et al.
2014/0228867 A1 8/2014 Thomas et al.
2014/0239047 A1 8/2014 Hodgkinson et al.
2014/0243865 A1 8/2014 Swayze et al.
2014/0246475 A1 9/2014 Hall et al.
2014/0248167 A1 9/2014 Sugimoto et al.
2014/0249557 A1 9/2014 Koch et al.
2014/0249573 A1 9/2014 Arav
2014/0262408 A1 9/2014 Woodard
2014/0263541 A1 9/2014 Leimbach et al.
2014/0263552 A1 9/2014 Hall et al.
2014/0263558 A1 9/2014 Hausen et al.
2014/0276730 A1 9/2014 Boudreaux et al.
2014/0284371 A1 9/2014 Morgan et al.
2014/0287703 A1 9/2014 Herbsommer et al.
2014/0288460 A1 9/2014 Ouyang et al.
2014/0291379 A1 10/2014 Schellin et al.
2014/0291383 A1 10/2014 Spivey et al.
2014/0299648 A1 10/2014 Shelton, IV et al.
2014/0303645 A1 10/2014 Morgan et al.
2014/0303660 A1 10/2014 Boyden et al.
2014/0330161 A1 11/2014 Swayze et al.
2014/0330298 A1 11/2014 Arshonsky et al.
2014/0330579 A1 11/2014 Cashman et al.
2014/0358163 A1 12/2014 Farin et al.
2014/0367445 A1 12/2014 Ingmanson et al.
2014/0374130 A1 12/2014 Nakamura et al.
2014/0378950 A1 12/2014 Chiu
2015/0001272 A1 1/2015 Sniffin et al.
2015/0002089 A1 1/2015 Rejman et al.
2015/0025549 A1 1/2015 Kilroy et al.
2015/0025571 A1 1/2015 Suzuki et al.
2015/0034697 A1 2/2015 Mastri et al.
2015/0039010 A1 2/2015 Beardsley et al.
2015/0053737 A1 2/2015 Leimbach et al.
2015/0053743 A1 2/2015 Yates et al.
2015/0053746 A1 2/2015 Shelton, IV et al.
2015/0053748 A1 2/2015 Yates et al.
2015/0060516 A1 3/2015 Collings et al.
2015/0060519 A1 3/2015 Shelton, IV et al.
2015/0060520 A1 3/2015 Shelton, IV et al.
2015/0060521 A1 3/2015 Weisenburgh, II et al.
2015/0066000 A1 3/2015 An et al.
2015/0067582 A1 3/2015 Donnelly et al.
2015/0076208 A1 3/2015 Shelton, IV
2015/0076209 A1 3/2015 Shelton, IV et al.
2015/0076210 A1 3/2015 Shelton, IV et al.
2015/0076211 A1 3/2015 Irka et al.
2015/0082624 A1 3/2015 Craig et al.
2015/0083781 A1 3/2015 Giordano et al.
2015/0087952 A1 3/2015 Albert et al.
2015/0088127 A1 3/2015 Craig et al.
2015/0088547 A1 3/2015 Balram et al.
2015/0090760 A1 4/2015 Giordano et al.
2015/0090762 A1 4/2015 Giordano et al.
2015/0127021 A1 5/2015 Harris et al.
2015/0134077 A1 5/2015 Shelton, IV et al.
2015/0150620 A1 6/2015 Miyamoto et al.
2015/0173749 A1 6/2015 Shelton, IV et al.
2015/0173756 A1 6/2015 Baxter, III et al.
2015/0173789 A1 6/2015 Baxter, III et al.
2015/0196295 A1 7/2015 Shelton, IV et al.
2015/0196299 A1 7/2015 Swayze et al.
2015/0201918 A1 7/2015 Kumar et al.
2015/0201932 A1 7/2015 Swayze et al.
2015/0201936 A1 7/2015 Swayze et al.
2015/0201937 A1 7/2015 Swayze et al.
2015/0201938 A1 7/2015 Swayze et al.
2015/0201939 A1 7/2015 Swayze et al.
2015/0201940 A1 7/2015 Swayze et al.
2015/0201941 A1 7/2015 Swayze et al.
2015/0209045 A1 7/2015 Hodgkinson et al.
2015/0216605 A1 8/2015 Baldwin
2015/0222212 A1 8/2015 Iwata
2015/0223868 A1 8/2015 Brandt et al.
2015/0230697 A1 8/2015 Phee et al.
2015/0230794 A1 8/2015 Wellman et al.
2015/0230861 A1 8/2015 Woloszko et al.
2015/0231409 A1 8/2015 Racenet et al.
2015/0238118 A1 8/2015 Legassey et al.
2015/0272557 A1 10/2015 Overmyer et al.
2015/0272571 A1 10/2015 Leimbach et al.
2015/0272580 A1 10/2015 Leimbach et al.
2015/0272582 A1 10/2015 Leimbach et al.
2015/0297200 A1 10/2015 Fitzsimmons et al.
2015/0297222 A1 10/2015 Huitema et al.
2015/0297223 A1 10/2015 Huitema et al.
2015/0297225 A1 10/2015 Huitema et al.
2015/0297824 A1 10/2015 Cabiri et al.
2015/0303417 A1 10/2015 Koeder et al.
2015/0313594 A1 11/2015 Shelton, IV et al.
2015/0324317 A1 11/2015 Collins et al.
2015/0352699 A1 12/2015 Sakai et al.
2015/0366585 A1 12/2015 Lemay et al.
2015/0367497 A1 12/2015 Ito et al.
2015/0372265 A1 12/2015 Morisaku et al.
2015/0374372 A1 12/2015 Zergiebel et al.
2015/0374378 A1 12/2015 Giordano et al.
2016/0000437 A1 1/2016 Giordano et al.
2016/0000452 A1 1/2016 Yates et al.
2016/0000453 A1 1/2016 Yates et al.
2016/0029998 A1 2/2016 Brister et al.
2016/0030042 A1 2/2016 Heinrich et al.
2016/0030043 A1 2/2016 Fanelli et al.
2016/0030076 A1 2/2016 Faller et al.
2016/0051316 A1 2/2016 Boudreaux
2016/0066913 A1 3/2016 Swayze et al.
2016/0069449 A1 3/2016 Kanai et al.
2016/0074035 A1 3/2016 Whitman et al.
2016/0074040 A1 3/2016 Widenhouse et al.
2016/0082161 A1 3/2016 Zilberman et al.
2016/0118201 A1 4/2016 Nicholas et al.
2016/0132026 A1 5/2016 Wingardner et al.
2016/0135835 A1 5/2016 Onuma
2016/0135895 A1 5/2016 Faasse et al.
2016/0139666 A1 5/2016 Rubin et al.
2016/0174969 A1 6/2016 Kerr et al.
2016/0174983 A1 6/2016 Shelton, IV et al.
2016/0183939 A1 6/2016 Shelton, IV et al.
2016/0183943 A1 6/2016 Shelton, IV
2016/0183944 A1 6/2016 Swensgard et al.
2016/0192927 A1 7/2016 Kostrzewski
2016/0192960 A1 7/2016 Bueno et al.
2016/0199063 A1 7/2016 Mandakolathur Vasudevan et al.
2016/0199956 A1 7/2016 Shelton, IV et al.
2016/0220150 A1 8/2016 Sharonov
2016/0235494 A1 8/2016 Shelton, IV et al.
2016/0242783 A1 8/2016 Shelton, IV et al.
2016/0242855 A1 8/2016 Fichtinger et al.
2016/0249910 A1 9/2016 Shelton, IV et al.
2016/0249922 A1 9/2016 Morgan et al.
2016/0249929 A1 9/2016 Cappola et al.
2016/0256159 A1 9/2016 Pinjala et al.
2016/0256184 A1 9/2016 Shelton, IV et al.
2016/0256221 A1 9/2016 Smith
2016/0256229 A1 9/2016 Morgan et al.
2016/0262745 A1 9/2016 Morgan et al.
2016/0262921 A1 9/2016 Balbierz et al.
2016/0270781 A1 9/2016 Scirica
2016/0287265 A1 10/2016 Macdonald et al.
2016/0287279 A1 10/2016 Bovay et al.
2016/0302820 A1 10/2016 Hibner et al.
2016/0310143 A1 10/2016 Bettuchi
2016/0314716 A1 10/2016 Grubbs
2016/0314717 A1 10/2016 Grubbs
2016/0345972 A1 12/2016 Beardsley et al.
2016/0367122 A1 12/2016 Ichimura et al.
2016/0374669 A1 12/2016 Overmyer et al.
2016/0374716 A1 12/2016 Kessler
2017/0007234 A1 1/2017 Chin et al.
2017/0007244 A1 1/2017 Shelton, IV et al.
2017/0007245 A1 1/2017 Shelton, IV et al.
2017/0007347 A1 1/2017 Jaworek et al.
2017/0020616 A1 1/2017 Vale et al.

(56) References Cited

U.S. PATENT DOCUMENTS

| | | | |
|---|---|---|---|
| 2017/0055819 | A1 | 3/2017 | Hansen et al. |
| 2017/0066054 | A1 | 3/2017 | Birky |
| 2017/0079642 | A1 | 3/2017 | Overmyer et al. |
| 2017/0086829 | A1 | 3/2017 | Vendely et al. |
| 2017/0086830 | A1 | 3/2017 | Yates et al. |
| 2017/0086842 | A1 | 3/2017 | Shelton, IV et al. |
| 2017/0086930 | A1 | 3/2017 | Thompson et al. |
| 2017/0086932 | A1 | 3/2017 | Auld et al. |
| 2017/0095922 | A1 | 4/2017 | Licht et al. |
| 2017/0105727 | A1 | 4/2017 | Scheib et al. |
| 2017/0105733 | A1 | 4/2017 | Scheib et al. |
| 2017/0105786 | A1 | 4/2017 | Scheib et al. |
| 2017/0106302 | A1 | 4/2017 | Cummings et al. |
| 2017/0135711 | A1 | 5/2017 | Overmyer et al. |
| 2017/0135717 | A1 | 5/2017 | Boudreaux et al. |
| 2017/0135747 | A1 | 5/2017 | Broderick et al. |
| 2017/0168187 | A1 | 6/2017 | Calderoni et al. |
| 2017/0172382 | A1 | 6/2017 | Nir et al. |
| 2017/0172549 | A1 | 6/2017 | Smaby et al. |
| 2017/0172662 | A1 | 6/2017 | Panescu et al. |
| 2017/0182195 | A1 | 6/2017 | Wagner |
| 2017/0182211 | A1 | 6/2017 | Raxworthy et al. |
| 2017/0196558 | A1 | 7/2017 | Morgan et al. |
| 2017/0196649 | A1 | 7/2017 | Yates et al. |
| 2017/0202607 | A1 | 7/2017 | Shelton, IV et al. |
| 2017/0202770 | A1 | 7/2017 | Friedrich et al. |
| 2017/0224332 | A1 | 8/2017 | Hunter et al. |
| 2017/0231628 | A1 | 8/2017 | Shelton, IV et al. |
| 2017/0231629 | A1 | 8/2017 | Stopek et al. |
| 2017/0238962 | A1 | 8/2017 | Hansen et al. |
| 2017/0242455 | A1 | 8/2017 | Dickens |
| 2017/0245949 | A1 | 8/2017 | Randle |
| 2017/0249431 | A1 | 8/2017 | Shelton, IV et al. |
| 2017/0252060 | A1 | 9/2017 | Ellingson et al. |
| 2017/0255799 | A1 | 9/2017 | Zhao et al. |
| 2017/0262110 | A1 | 9/2017 | Polishchuk et al. |
| 2017/0265774 | A1 | 9/2017 | Johnson et al. |
| 2017/0281186 | A1 | 10/2017 | Shelton, IV et al. |
| 2017/0296173 | A1 | 10/2017 | Shelton, IV et al. |
| 2017/0296185 | A1 | 10/2017 | Swensgard et al. |
| 2017/0296213 | A1 | 10/2017 | Swensgard et al. |
| 2017/0303984 | A1 | 10/2017 | Malackowski |
| 2017/0312042 | A1 | 11/2017 | Giordano et al. |
| 2017/0319047 | A1 | 11/2017 | Poulsen et al. |
| 2017/0319201 | A1 | 11/2017 | Morgan et al. |
| 2017/0333034 | A1 | 11/2017 | Morgan et al. |
| 2017/0333035 | A1 | 11/2017 | Morgan et al. |
| 2017/0348010 | A1 | 12/2017 | Chiang |
| 2017/0348043 | A1 | 12/2017 | Wang et al. |
| 2017/0354413 | A1 | 12/2017 | Chen et al. |
| 2017/0358052 | A1 | 12/2017 | Yuan |
| 2017/0360441 | A1 | 12/2017 | Sgroi |
| 2018/0049738 | A1 | 2/2018 | Meloul et al. |
| 2018/0049794 | A1 | 2/2018 | Swayze et al. |
| 2018/0051780 | A1 | 2/2018 | Shelton, IV et al. |
| 2018/0055501 | A1 | 3/2018 | Zemlok et al. |
| 2018/0085117 | A1 | 3/2018 | Shelton, IV et al. |
| 2018/0085120 | A1 | 3/2018 | Viola |
| 2018/0092710 | A1 | 4/2018 | Bosisio et al. |
| 2018/0114591 | A1 | 4/2018 | Pribanic et al. |
| 2018/0116658 | A1 | 5/2018 | Aronhalt, IV et al. |
| 2018/0125481 | A1 | 5/2018 | Yates et al. |
| 2018/0125487 | A1 | 5/2018 | Beardsley |
| 2018/0125488 | A1 | 5/2018 | Morgan et al. |
| 2018/0125594 | A1 | 5/2018 | Beardsley |
| 2018/0132849 | A1 | 5/2018 | Miller et al. |
| 2018/0132850 | A1 | 5/2018 | Leimbach et al. |
| 2018/0132926 | A1 | 5/2018 | Asher et al. |
| 2018/0132952 | A1 | 5/2018 | Spivey et al. |
| 2018/0133521 | A1 | 5/2018 | Frushour et al. |
| 2018/0140299 | A1 | 5/2018 | Weaner et al. |
| 2018/0146960 | A1 | 5/2018 | Shelton, IV et al. |
| 2018/0153542 | A1 | 6/2018 | Shelton, IV et al. |
| 2018/0153634 | A1 | 6/2018 | Zemlok et al. |
| 2018/0161034 | A1 | 6/2018 | Scheib et al. |
| 2018/0168572 | A1 | 6/2018 | Burbank |
| 2018/0168574 | A1 | 6/2018 | Robinson et al. |
| 2018/0168575 | A1 | 6/2018 | Simms et al. |
| 2018/0168577 | A1 | 6/2018 | Aronhalt et al. |
| 2018/0168579 | A1 | 6/2018 | Aronhalt et al. |
| 2018/0168598 | A1 | 6/2018 | Shelton, IV et al. |
| 2018/0168608 | A1 | 6/2018 | Shelton, IV et al. |
| 2018/0168609 | A1 | 6/2018 | Fanelli et al. |
| 2018/0168610 | A1 | 6/2018 | Shelton, IV et al. |
| 2018/0168615 | A1 | 6/2018 | Shelton, IV et al. |
| 2018/0168618 | A1 | 6/2018 | Scott et al. |
| 2018/0168619 | A1 | 6/2018 | Scott et al. |
| 2018/0168623 | A1 | 6/2018 | Simms et al. |
| 2018/0168625 | A1 | 6/2018 | Posada et al. |
| 2018/0168633 | A1 | 6/2018 | Shelton, IV et al. |
| 2018/0168647 | A1 | 6/2018 | Shelton, IV et al. |
| 2018/0168648 | A1 | 6/2018 | Shelton, IV et al. |
| 2018/0168650 | A1 | 6/2018 | Shelton, IV et al. |
| 2018/0168754 | A1 | 6/2018 | Overmyer |
| 2018/0228490 | A1 | 8/2018 | Richard et al. |
| 2018/0231475 | A1 | 8/2018 | Brown et al. |
| 2018/0235609 | A1 | 8/2018 | Harris et al. |
| 2018/0235626 | A1 | 8/2018 | Shelton, IV et al. |
| 2018/0236181 | A1 | 8/2018 | Marlin et al. |
| 2018/0242970 | A1 | 8/2018 | Mozdzierz |
| 2018/0250002 | A1 | 9/2018 | Eschbach |
| 2018/0271520 | A1 | 9/2018 | Shelton, IV et al. |
| 2018/0271604 | A1 | 9/2018 | Grout et al. |
| 2018/0273597 | A1 | 9/2018 | Stimson |
| 2018/0280073 | A1 | 10/2018 | Sanai et al. |
| 2018/0289371 | A1 | 10/2018 | Wang et al. |
| 2018/0296216 | A1 | 10/2018 | Shelton, IV et al. |
| 2018/0296290 | A1 | 10/2018 | Namiki et al. |
| 2018/0317905 | A1 | 11/2018 | Olson et al. |
| 2018/0333169 | A1 | 11/2018 | Leimbach et al. |
| 2018/0360446 | A1 | 12/2018 | Shelton, IV et al. |
| 2018/0360456 | A1 | 12/2018 | Shelton, IV et al. |
| 2018/0368066 | A1 | 12/2018 | Howell et al. |
| 2018/0368844 | A1 | 12/2018 | Bakos et al. |
| 2018/0372806 | A1 | 12/2018 | Laughery et al. |
| 2019/0000459 | A1 | 1/2019 | Shelton, IV et al. |
| 2019/0000461 | A1 | 1/2019 | Shelton, IV et al. |
| 2019/0000470 | A1 | 1/2019 | Yates et al. |
| 2019/0000475 | A1 | 1/2019 | Shelton, IV et al. |
| 2019/0000477 | A1 | 1/2019 | Shelton, IV et al. |
| 2019/0000481 | A1 | 1/2019 | Harris et al. |
| 2019/0000535 | A1 | 1/2019 | Messerly et al. |
| 2019/0000536 | A1 | 1/2019 | Yates et al. |
| 2019/0008515 | A1 | 1/2019 | Beardsley et al. |
| 2019/0015102 | A1 | 1/2019 | Baber et al. |
| 2019/0015165 | A1 | 1/2019 | Giordano et al. |
| 2019/0017311 | A1 | 1/2019 | McGettrick et al. |
| 2019/0021733 | A1 | 1/2019 | Burbank |
| 2019/0029682 | A1 | 1/2019 | Huitema et al. |
| 2019/0029701 | A1 | 1/2019 | Shelton, IV et al. |
| 2019/0038281 | A1 | 2/2019 | Shelton, IV et al. |
| 2019/0038283 | A1 | 2/2019 | Shelton, IV et al. |
| 2019/0038285 | A1 | 2/2019 | Mozdzierz |
| 2019/0059986 | A1 | 2/2019 | Shelton, IV et al. |
| 2019/0076143 | A1 | 3/2019 | Smith |
| 2019/0090871 | A1 | 3/2019 | Shelton, IV et al. |
| 2019/0091183 | A1 | 3/2019 | Tomat et al. |
| 2019/0104919 | A1 | 4/2019 | Shelton, IV et al. |
| 2019/0105035 | A1 | 4/2019 | Shelton, IV et al. |
| 2019/0105036 | A1 | 4/2019 | Morgan et al. |
| 2019/0105037 | A1 | 4/2019 | Morgan et al. |
| 2019/0105039 | A1 | 4/2019 | Morgan et al. |
| 2019/0105043 | A1 | 4/2019 | Jaworek et al. |
| 2019/0105044 | A1 | 4/2019 | Shelton, IV et al. |
| 2019/0110779 | A1 | 4/2019 | Gardner et al. |
| 2019/0110791 | A1 | 4/2019 | Shelton, IV et al. |
| 2019/0117224 | A1 | 4/2019 | Setser et al. |
| 2019/0125320 | A1 | 5/2019 | Shelton, IV et al. |
| 2019/0125335 | A1 | 5/2019 | Shelton, IV et al. |
| 2019/0125336 | A1 | 5/2019 | Deck et al. |
| 2019/0125338 | A1 | 5/2019 | Shelton, IV et al. |
| 2019/0125342 | A1 | 5/2019 | Beardsley et al. |
| 2019/0125344 | A1 | 5/2019 | DiNardo et al. |
| 2019/0125361 | A1 | 5/2019 | Shelton, IV et al. |

(56) References Cited

U.S. PATENT DOCUMENTS

| | | | |
|---|---|---|---|
| 2019/0125377 | A1 | 5/2019 | Shelton, IV |
| 2019/0125378 | A1 | 5/2019 | Shelton, IV et al. |
| 2019/0125388 | A1 | 5/2019 | Shelton, IV et al. |
| 2019/0125430 | A1 | 5/2019 | Shelton, IV et al. |
| 2019/0125431 | A1 | 5/2019 | Shelton, IV et al. |
| 2019/0125432 | A1 | 5/2019 | Shelton, IV et al. |
| 2019/0125454 | A1 | 5/2019 | Stokes et al. |
| 2019/0125455 | A1 | 5/2019 | Shelton, IV et al. |
| 2019/0125476 | A1 | 5/2019 | Shelton, IV et al. |
| 2019/0133422 | A1 | 5/2019 | Nakamura |
| 2019/0138770 | A1 | 5/2019 | Compaijen et al. |
| 2019/0142421 | A1 | 5/2019 | Shelton, IV |
| 2019/0150925 | A1 | 5/2019 | Marczyk et al. |
| 2019/0151029 | A1 | 5/2019 | Robinson |
| 2019/0175847 | A1 | 6/2019 | Pocreva, III et al. |
| 2019/0183502 | A1 | 6/2019 | Shelton, IV et al. |
| 2019/0192141 | A1 | 6/2019 | Shelton, IV et al. |
| 2019/0192146 | A1 | 6/2019 | Widenhouse et al. |
| 2019/0192147 | A1 | 6/2019 | Shelton, IV et al. |
| 2019/0192148 | A1 | 6/2019 | Shelton, IV et al. |
| 2019/0192151 | A1 | 6/2019 | Shelton, IV et al. |
| 2019/0192153 | A1 | 6/2019 | Shelton, IV et al. |
| 2019/0192155 | A1 | 6/2019 | Shelton, IV et al. |
| 2019/0192157 | A1 | 6/2019 | Scott et al. |
| 2019/0200844 | A1 | 7/2019 | Shelton, IV et al. |
| 2019/0200905 | A1 | 7/2019 | Shelton, IV et al. |
| 2019/0200906 | A1 | 7/2019 | Shelton, IV et al. |
| 2019/0200977 | A1 | 7/2019 | Shelton, IV et al. |
| 2019/0200981 | A1 | 7/2019 | Harris et al. |
| 2019/0200986 | A1 | 7/2019 | Shelton, IV et al. |
| 2019/0200987 | A1 | 7/2019 | Shelton, IV et al. |
| 2019/0200989 | A1 | 7/2019 | Burbank et al. |
| 2019/0200998 | A1 | 7/2019 | Shelton, IV et al. |
| 2019/0201020 | A1 | 7/2019 | Shelton, IV et al. |
| 2019/0201024 | A1 | 7/2019 | Shelton, IV et al. |
| 2019/0201025 | A1 | 7/2019 | Shelton, IV et al. |
| 2019/0201026 | A1 | 7/2019 | Shelton, IV et al. |
| 2019/0201027 | A1 | 7/2019 | Shelton, IV et al. |
| 2019/0201029 | A1 | 7/2019 | Shelton, IV et al. |
| 2019/0201030 | A1 | 7/2019 | Shelton, IV et al. |
| 2019/0201034 | A1 | 7/2019 | Shelton, IV et al. |
| 2019/0201045 | A1 | 7/2019 | Yates et al. |
| 2019/0201046 | A1 | 7/2019 | Shelton, IV et al. |
| 2019/0201047 | A1 | 7/2019 | Yates et al. |
| 2019/0201079 | A1 | 7/2019 | Shelton, IV et al. |
| 2019/0201104 | A1 | 7/2019 | Shelton, IV et al. |
| 2019/0201112 | A1 | 7/2019 | Wiener et al. |
| 2019/0201113 | A1 | 7/2019 | Shelton, IV et al. |
| 2019/0201115 | A1 | 7/2019 | Shelton, IV et al. |
| 2019/0201118 | A1 | 7/2019 | Shelton, IV et al. |
| 2019/0201136 | A1 | 7/2019 | Shelton, IV et al. |
| 2019/0201137 | A1 | 7/2019 | Shelton, IV et al. |
| 2019/0201139 | A1 | 7/2019 | Shelton, IV et al. |
| 2019/0201140 | A1 | 7/2019 | Yates et al. |
| 2019/0201142 | A1 | 7/2019 | Shelton, IV et al. |
| 2019/0201594 | A1 | 7/2019 | Shelton, IV et al. |
| 2019/0205001 | A1 | 7/2019 | Messerly et al. |
| 2019/0205567 | A1 | 7/2019 | Shelton, IV et al. |
| 2019/0206551 | A1 | 7/2019 | Yates et al. |
| 2019/0206555 | A1 | 7/2019 | Morgan et al. |
| 2019/0206561 | A1 | 7/2019 | Shelton, IV et al. |
| 2019/0206562 | A1 | 7/2019 | Shelton, IV et al. |
| 2019/0206564 | A1 | 7/2019 | Shelton, IV et al. |
| 2019/0206569 | A1 | 7/2019 | Shelton, IV et al. |
| 2019/0209172 | A1 | 7/2019 | Shelton, IV et al. |
| 2019/0209247 | A1 | 7/2019 | Giordano et al. |
| 2019/0209248 | A1 | 7/2019 | Giordano et al. |
| 2019/0209249 | A1 | 7/2019 | Giordano et al. |
| 2019/0209250 | A1 | 7/2019 | Giordano et al. |
| 2019/0216558 | A1 | 7/2019 | Giordano et al. |
| 2019/0261982 | A1 | 8/2019 | Holsten |
| 2019/0261983 | A1 | 8/2019 | Granger et al. |
| 2019/0261984 | A1 | 8/2019 | Nelson et al. |
| 2019/0261987 | A1 | 8/2019 | Viola et al. |
| 2019/0269400 | A1 | 9/2019 | Mandakolathur Vasudevan et al. |
| 2019/0269402 | A1 | 9/2019 | Murray et al. |
| 2019/0269428 | A1 | 9/2019 | Allen et al. |
| 2019/0274685 | A1 | 9/2019 | Olson et al. |
| 2019/0282233 | A1 | 9/2019 | Burbank et al. |
| 2019/0290264 | A1 | 9/2019 | Morgan et al. |
| 2019/0290266 | A1 | 9/2019 | Scheib et al. |
| 2019/0290267 | A1 | 9/2019 | Baxter, III et al. |
| 2019/0290297 | A1 | 9/2019 | Haider et al. |
| 2019/0298350 | A1 | 10/2019 | Shelton, IV et al. |
| 2019/0298353 | A1 | 10/2019 | Shelton, IV et al. |
| 2019/0298360 | A1 | 10/2019 | Shelton, IV et al. |
| 2019/0298361 | A1 | 10/2019 | Shelton, IV et al. |
| 2019/0298362 | A1 | 10/2019 | Shelton, IV et al. |
| 2019/0307452 | A1 | 10/2019 | Shelton, IV et al. |
| 2019/0307453 | A1 | 10/2019 | Shelton, IV et al. |
| 2019/0307454 | A1 | 10/2019 | Shelton, IV et al. |
| 2019/0307456 | A1 | 10/2019 | Shelton, IV et al. |
| 2019/0314015 | A1 | 10/2019 | Shelton, IV et al. |
| 2019/0321040 | A1 | 10/2019 | Shelton, IV |
| 2019/0321062 | A1 | 10/2019 | Williams |
| 2019/0328387 | A1 | 10/2019 | Overmyer et al. |
| 2019/0328390 | A1 | 10/2019 | Harris et al. |
| 2019/0343515 | A1 | 11/2019 | Morgan et al. |
| 2019/0357909 | A1 | 11/2019 | Huitema et al. |
| 2019/0388091 | A1 | 12/2019 | Eschbach et al. |
| 2020/0000531 | A1 | 1/2020 | Giordano et al. |
| 2020/0008802 | A1 | 1/2020 | Aronhalt et al. |
| 2020/0008809 | A1 | 1/2020 | Shelton, IV et al. |
| 2020/0008827 | A1 | 1/2020 | Dearden et al. |
| 2020/0015819 | A1 | 1/2020 | Shelton, IV et al. |
| 2020/0015915 | A1 | 1/2020 | Swayze et al. |
| 2020/0037939 | A1 | 2/2020 | Castagna et al. |
| 2020/0038016 | A1 | 2/2020 | Shelton, IV et al. |
| 2020/0038018 | A1 | 2/2020 | Shelton, IV et al. |
| 2020/0038020 | A1 | 2/2020 | Yates et al. |
| 2020/0054320 | A1 | 2/2020 | Harris et al. |
| 2020/0054321 | A1 | 2/2020 | Harris et al. |
| 2020/0054329 | A1 | 2/2020 | Shelton, IV et al. |
| 2020/0054332 | A1 | 2/2020 | Shelton, IV et al. |
| 2020/0054333 | A1 | 2/2020 | Shelton, IV et al. |
| 2020/0054334 | A1 | 2/2020 | Shelton, IV et al. |
| 2020/0054355 | A1 | 2/2020 | Laurent et al. |
| 2020/0060523 | A1 | 2/2020 | Matsuda et al. |
| 2020/0060680 | A1 | 2/2020 | Shelton, IV et al. |
| 2020/0060713 | A1 | 2/2020 | Leimbach et al. |
| 2020/0085431 | A1 | 3/2020 | Swayze et al. |
| 2020/0085435 | A1 | 3/2020 | Shelton, IV et al. |
| 2020/0085518 | A1 | 3/2020 | Giordano et al. |
| 2020/0093484 | A1 | 3/2020 | Shelton, IV et al. |
| 2020/0093506 | A1 | 3/2020 | Leimbach et al. |
| 2020/0093550 | A1 | 3/2020 | Spivey et al. |
| 2020/0100783 | A1 | 4/2020 | Yates et al. |
| 2020/0107829 | A1 | 4/2020 | Shelton, IV et al. |
| 2020/0114505 | A1 | 4/2020 | Kikuchi |
| 2020/0138436 | A1 | 5/2020 | Yates et al. |
| 2020/0138534 | A1 | 5/2020 | Garcia Kilroy et al. |
| 2020/0146741 | A1 | 5/2020 | Long et al. |
| 2020/0187943 | A1 | 6/2020 | Shelton, IV et al. |
| 2020/0197027 | A1 | 6/2020 | Hershberger et al. |
| 2020/0205810 | A1 | 7/2020 | Posey et al. |
| 2020/0205811 | A1 | 7/2020 | Posey et al. |
| 2020/0214706 | A1 | 7/2020 | Vendely et al. |
| 2020/0214731 | A1 | 7/2020 | Shelton, IV et al. |
| 2020/0229814 | A1 | 7/2020 | Amariglio et al. |
| 2020/0237371 | A1 | 7/2020 | Huitema et al. |
| 2020/0253605 | A1 | 8/2020 | Swayze et al. |
| 2020/0261086 | A1 | 8/2020 | Zeiner et al. |
| 2020/0261106 | A1 | 8/2020 | Hess et al. |
| 2020/0268377 | A1 | 8/2020 | Schmid et al. |
| 2020/0275927 | A1 | 9/2020 | Shelton, IV et al. |
| 2020/0275930 | A1 | 9/2020 | Harris et al. |
| 2020/0280219 | A1 | 9/2020 | Laughery et al. |
| 2020/0281585 | A1 | 9/2020 | Timm et al. |
| 2020/0281590 | A1 | 9/2020 | Shelton, IV et al. |
| 2020/0289112 | A1 | 9/2020 | Whitfield et al. |
| 2020/0297341 | A1 | 9/2020 | Yates et al. |
| 2020/0297346 | A1 | 9/2020 | Shelton, IV et al. |
| 2020/0305862 | A1 | 10/2020 | Yates et al. |
| 2020/0305863 | A1 | 10/2020 | Yates et al. |

(56) References Cited

U.S. PATENT DOCUMENTS

2020/0305864 A1 10/2020 Yates et al.
2020/0305870 A1 10/2020 Shelton, IV
2020/0305872 A1 10/2020 Weidner et al.
2020/0305874 A1 10/2020 Huitema et al.
2020/0315612 A1 10/2020 Shelton, IV et al.
2020/0315983 A1 10/2020 Widenhouse et al.
2020/0323526 A1 10/2020 Huang et al.
2020/0330092 A1 10/2020 Shelton, IV et al.
2020/0330093 A1 10/2020 Shelton, IV et al.
2020/0330096 A1 10/2020 Shelton, IV et al.
2020/0330181 A1 10/2020 Junger et al.
2020/0337693 A1 10/2020 Shelton, IV et al.
2020/0337791 A1 10/2020 Shelton, IV et al.
2020/0345346 A1 11/2020 Shelton, IV et al.
2020/0345349 A1 11/2020 Kimball et al.
2020/0345352 A1 11/2020 Shelton, IV et al.
2020/0345353 A1 11/2020 Leimbach et al.
2020/0345356 A1 11/2020 Leimbach et al.
2020/0345357 A1 11/2020 Leimbach et al.
2020/0345358 A1 11/2020 Jenkins
2020/0345359 A1 11/2020 Baxter, III et al.
2020/0345363 A1 11/2020 Shelton, IV et al.
2020/0345435 A1 11/2020 Traina
2020/0352562 A1 11/2020 Timm et al.
2020/0367886 A1 11/2020 Shelton, IV et al.
2020/0375585 A1 12/2020 Swayze et al.
2020/0375593 A1 12/2020 Hunter et al.
2020/0375597 A1 12/2020 Shelton, IV et al.
2020/0390444 A1 12/2020 Harris et al.
2020/0397430 A1 12/2020 Patel et al.
2020/0405290 A1 12/2020 Shelton, IV et al.
2020/0405292 A1 12/2020 Shelton, IV et al.
2020/0405293 A1 12/2020 Shelton, IV et al.
2020/0405296 A1 12/2020 Shelton, IV et al.
2020/0405302 A1 12/2020 Shelton, IV et al.
2020/0405304 A1 12/2020 Mozdzierz et al.
2020/0405306 A1 12/2020 Shelton, IV et al.
2020/0405307 A1 12/2020 Shelton, IV et al.
2020/0405308 A1 12/2020 Shelton, IV
2020/0405316 A1 12/2020 Shelton, IV et al.
2020/0405341 A1 12/2020 Hess et al.
2020/0405409 A1 12/2020 Shelton, IV et al.
2020/0405410 A1 12/2020 Shelton, IV
2020/0405439 A1 12/2020 Shelton, IV et al.
2020/0410177 A1 12/2020 Shelton, IV
2021/0000466 A1 1/2021 Leimbach et al.
2021/0000467 A1 1/2021 Shelton, IV et al.
2021/0000470 A1 1/2021 Leimbach et al.
2021/0015480 A1 1/2021 Shelton, IV et al.
2021/0030416 A1 2/2021 Shelton, IV et al.
2021/0045742 A1 2/2021 Shelton, IV et al.
2021/0052271 A1 2/2021 Harris et al.
2021/0059661 A1 3/2021 Schmid et al.
2021/0059662 A1 3/2021 Shelton, IV
2021/0059664 A1 3/2021 Hensel et al.
2021/0059670 A1 3/2021 Overmyer et al.
2021/0059672 A1 3/2021 Giordano et al.
2021/0059673 A1 3/2021 Shelton, IV et al.
2021/0068817 A1 3/2021 Shelton, IV et al.
2021/0068820 A1 3/2021 Parihar et al.
2021/0068829 A1 3/2021 Miller et al.
2021/0068832 A1 3/2021 Yates et al.
2021/0068835 A1 3/2021 Shelton, IV et al.
2021/0077099 A1 3/2021 Shelton, IV et al.
2021/0077100 A1 3/2021 Shelton, IV et al.
2021/0077109 A1 3/2021 Harris et al.
2021/0085313 A1 3/2021 Morgan et al.
2021/0085314 A1 3/2021 Schmid et al.
2021/0085315 A1 3/2021 Aronhalt et al.
2021/0085316 A1 3/2021 Harris et al.
2021/0085318 A1 3/2021 Swayze et al.
2021/0085320 A1 3/2021 Leimbach et al.
2021/0085321 A1 3/2021 Shelton, IV et al.
2021/0085325 A1 3/2021 Shelton, IV et al.
2021/0085326 A1 3/2021 Vendely et al.
2021/0093321 A1 4/2021 Auld et al.
2021/0093323 A1 4/2021 Scirica et al.
2021/0100541 A1 4/2021 Shelton, IV et al.
2021/0100550 A1 4/2021 Shelton, IV et al.
2021/0100982 A1 4/2021 Laby et al.
2021/0106333 A1 4/2021 Shelton, IV et al.
2021/0107031 A1 4/2021 Bales, Jr. et al.
2021/0121175 A1 4/2021 Yates et al.
2021/0128146 A1 5/2021 Shelton, IV et al.
2021/0128153 A1 5/2021 Sgroi
2021/0137522 A1 5/2021 Shelton, IV et al.
2021/0153866 A1 5/2021 Knapp et al.
2021/0186492 A1 6/2021 Shelton, IV et al.
2021/0186493 A1 6/2021 Shelton, IV et al.
2021/0186494 A1 6/2021 Shelton, IV et al.
2021/0186495 A1 6/2021 Shelton, IV et al.
2021/0186497 A1 6/2021 Shelton, IV et al.
2021/0186498 A1 6/2021 Boudreaux et al.
2021/0186499 A1 6/2021 Shelton, IV et al.
2021/0186501 A1 6/2021 Shelton, IV et al.
2021/0186502 A1 6/2021 Shelton, IV et al.
2021/0186504 A1 6/2021 Shelton, IV et al.
2021/0204941 A1 7/2021 Dewaele et al.
2021/0212691 A1 7/2021 Smith et al.
2021/0212776 A1 7/2021 Schmitt et al.
2021/0228209 A1 7/2021 Shelton, IV et al.
2021/0236117 A1 8/2021 Morgan et al.
2021/0236124 A1 8/2021 Shelton, IV et al.
2021/0244406 A1 8/2021 Kerr et al.
2021/0244407 A1 8/2021 Shelton, IV et al.
2021/0244410 A1 8/2021 Swayze et al.
2021/0244411 A1 8/2021 Smith et al.
2021/0244412 A1 8/2021 Vendely et al.
2021/0259681 A1 8/2021 Shelton, IV et al.
2021/0259687 A1 8/2021 Gonzalez et al.
2021/0259986 A1 8/2021 Widenhouse et al.
2021/0259987 A1 8/2021 Widenhouse et al.
2021/0267589 A1 9/2021 Swayze et al.
2021/0267594 A1 9/2021 Morgan et al.
2021/0267595 A1 9/2021 Posada et al.
2021/0267596 A1 9/2021 Fanelli et al.
2021/0275053 A1 9/2021 Shelton, IV et al.
2021/0275172 A1 9/2021 Harris et al.
2021/0275173 A1 9/2021 Shelton, IV et al.
2021/0275176 A1 9/2021 Beckman et al.
2021/0282767 A1 9/2021 Shelton, IV et al.
2021/0282769 A1 9/2021 Baxter, III et al.
2021/0282774 A1 9/2021 Shelton, IV et al.
2021/0282776 A1 9/2021 Overmyer et al.
2021/0290226 A1 9/2021 Mandakolathur Vasudevan et al.
2021/0290231 A1 9/2021 Baxter, III et al.
2021/0290232 A1 9/2021 Harris et al.
2021/0290233 A1 9/2021 Shelton, IV et al.
2021/0290236 A1 9/2021 Moore et al.
2021/0290322 A1 9/2021 Traina
2021/0298745 A1 9/2021 Leimbach et al.
2021/0298746 A1 9/2021 Leimbach et al.
2021/0307748 A1 10/2021 Harris et al.
2021/0307754 A1 10/2021 Shelton, IV et al.
2021/0315566 A1 10/2021 Yates et al.
2021/0315570 A1 10/2021 Shelton, IV
2021/0315571 A1 10/2021 Swayze et al.
2021/0315573 A1 10/2021 Shelton, IV et al.
2021/0315574 A1 10/2021 Shelton, IV et al.
2021/0315576 A1 10/2021 Shelton, IV et al.
2021/0315577 A1 10/2021 Shelton, IV et al.
2021/0322009 A1 10/2021 Huang et al.
2021/0330321 A1 10/2021 Leimbach et al.
2021/0338233 A1 11/2021 Shelton, IV et al.
2021/0338234 A1 11/2021 Shelton, IV et al.
2021/0338260 A1 11/2021 Le Rolland et al.
2021/0353284 A1 11/2021 Yang et al.
2021/0369271 A1 12/2021 Schings et al.
2021/0369273 A1 12/2021 Yates et al.
2021/0393260 A1 12/2021 Shelton, IV et al.
2021/0393261 A1 12/2021 Harris et al.
2021/0393262 A1 12/2021 Shelton, IV et al.
2021/0393268 A1 12/2021 Shelton, IV et al.
2021/0393366 A1 12/2021 Shelton, IV et al.

(56) References Cited

U.S. PATENT DOCUMENTS

2022/0000478 A1 1/2022 Shelton, IV et al.
2022/0031313 A1 2/2022 Bakos et al.
2022/0031314 A1 2/2022 Bakos et al.
2022/0031315 A1 2/2022 Bakos et al.
2022/0031319 A1 2/2022 Witte et al.
2022/0031320 A1 2/2022 Hall et al.
2022/0031322 A1 2/2022 Parks
2022/0031323 A1 2/2022 Witte
2022/0031324 A1 2/2022 Hall et al.
2022/0031345 A1 2/2022 Witte
2022/0031346 A1 2/2022 Parks
2022/0031350 A1 2/2022 Witte
2022/0031351 A1 2/2022 Moubarak et al.
2022/0054125 A1 2/2022 Ji et al.
2022/0054130 A1 2/2022 Overmyer et al.
2022/0061836 A1 3/2022 Parihar et al.
2022/0061843 A1 3/2022 Vendely et al.
2022/0061845 A1 3/2022 Shelton, IV et al.
2022/0061862 A1 3/2022 Shelton, IV et al.
2022/0071630 A1 3/2022 Swayze et al.
2022/0071631 A1 3/2022 Harris et al.
2022/0071632 A1 3/2022 Patel et al.
2022/0071635 A1 3/2022 Shelton, IV et al.
2022/0079580 A1 3/2022 Vendely et al.
2022/0079588 A1 3/2022 Harris et al.
2022/0079589 A1 3/2022 Harris et al.
2022/0079590 A1 3/2022 Harris et al.
2022/0079595 A1 3/2022 Huitema et al.
2022/0079596 A1 3/2022 Huitema et al.
2022/0087676 A1 3/2022 Shelton, IV et al.
2022/0104816 A1 4/2022 Fernandes et al.
2022/0117602 A1 4/2022 Wise et al.
2022/0133299 A1 5/2022 Baxter, III
2022/0133300 A1 5/2022 Leimbach et al.
2022/0133301 A1 5/2022 Leimbach
2022/0133302 A1 5/2022 Zerkle et al.
2022/0133303 A1 5/2022 Huang
2022/0133304 A1 5/2022 Leimbach et al.
2022/0133310 A1 5/2022 Ross
2022/0133311 A1 5/2022 Huang
2022/0133312 A1 5/2022 Huang
2022/0133428 A1 5/2022 Leimbach et al.
2022/0142643 A1 5/2022 Shelton, IV et al.
2022/0151611 A1 5/2022 Shelton, IV et al.
2022/0151613 A1 5/2022 Vendely et al.
2022/0151614 A1 5/2022 Vendely et al.
2022/0151615 A1 5/2022 Shelton, IV et al.
2022/0151616 A1 5/2022 Shelton, IV et al.
2022/0160358 A1 5/2022 Wixey
2022/0167968 A1 6/2022 Worthington et al.
2022/0167970 A1 6/2022 Aronhalt et al.
2022/0167971 A1 6/2022 Shelton, IV et al.
2022/0167972 A1 6/2022 Shelton, IV et al.
2022/0167973 A1 6/2022 Shelton, IV et al.
2022/0167974 A1 6/2022 Shelton, IV et al.
2022/0167975 A1 6/2022 Shelton, IV et al.
2022/0167977 A1 6/2022 Shelton, IV et al.
2022/0167979 A1 6/2022 Yates et al.
2022/0167980 A1 6/2022 Shelton, IV et al.
2022/0167981 A1 6/2022 Shelton, IV et al.
2022/0167982 A1 6/2022 Shelton, IV et al.
2022/0167983 A1 6/2022 Shelton, IV et al.
2022/0167984 A1 6/2022 Shelton, IV et al.
2022/0167995 A1 6/2022 Parfett et al.
2022/0168038 A1 6/2022 Shelton, IV et al.
2022/0175370 A1 6/2022 Shelton, IV et al.
2022/0175371 A1 6/2022 Hess et al.
2022/0175372 A1 6/2022 Shelton, IV et al.
2022/0175375 A1 6/2022 Harris et al.
2022/0175378 A1 6/2022 Leimbach et al.
2022/0175381 A1 6/2022 Scheib et al.
2022/0183685 A1 6/2022 Shelton, IV et al.
2022/0211367 A1 7/2022 Schmid et al.
2022/0218332 A1 7/2022 Shelton, IV et al.
2022/0218333 A1 7/2022 Parihar et al.
2022/0218334 A1 7/2022 Parihar et al.
2022/0218336 A1 7/2022 Timm et al.
2022/0218337 A1 7/2022 Timm et al.
2022/0218338 A1 7/2022 Shelton, IV et al.
2022/0218340 A1 7/2022 Harris et al.
2022/0218344 A1 7/2022 Leimbach et al.
2022/0218345 A1 7/2022 Shelton, IV et al.
2022/0218346 A1 7/2022 Shelton, IV et al.
2022/0218347 A1 7/2022 Shelton, IV et al.
2022/0218348 A1 7/2022 Swensgard et al.
2022/0218349 A1 7/2022 Shelton, IV et al.
2022/0218350 A1 7/2022 Shelton, IV et al.
2022/0218351 A1 7/2022 Shelton, IV et al.
2022/0218376 A1 7/2022 Shelton, IV et al.
2022/0218378 A1 7/2022 Shelton, IV et al.
2022/0218381 A1 7/2022 Leimbach et al.
2022/0218382 A1 7/2022 Leimbach et al.
2022/0225980 A1 7/2022 Shelton, IV et al.
2022/0225981 A1 7/2022 Shelton, IV et al.
2022/0225982 A1 7/2022 Yates et al.
2022/0225986 A1 7/2022 Shelton, IV et al.
2022/0225992 A1 7/2022 Smith et al.
2022/0225993 A1 7/2022 Huitema et al.
2022/0225994 A1 7/2022 Setser et al.
2022/0226012 A1 7/2022 Shelton, IV et al.
2022/0226013 A1 7/2022 Hall et al.
2022/0233184 A1 7/2022 Parihar et al.
2022/0233185 A1 7/2022 Parihar et al.
2022/0233186 A1 7/2022 Timm et al.
2022/0233187 A1 7/2022 Timm et al.
2022/0233188 A1 7/2022 Timm et al.
2022/0233194 A1 7/2022 Baxter, III et al.
2022/0233195 A1 7/2022 Shelton, IV et al.
2022/0233257 A1 7/2022 Shelton, IV et al.
2022/0240927 A1 8/2022 Timm et al.
2022/0240928 A1 8/2022 Timm et al.
2022/0240929 A1 8/2022 Timm et al.
2022/0240930 A1 8/2022 Yates et al.
2022/0240936 A1 8/2022 Huitema et al.
2022/0240937 A1 8/2022 Shelton, IV et al.
2022/0249095 A1 8/2022 Shelton, IV et al.
2022/0265272 A1 8/2022 Li et al.
2022/0273291 A1 9/2022 Shelton, IV et al.
2022/0273292 A1 9/2022 Shelton, IV et al.
2022/0273293 A1 9/2022 Shelton, IV et al.
2022/0273294 A1 9/2022 Creamer et al.
2022/0273299 A1 9/2022 Shelton, IV et al.
2022/0273300 A1 9/2022 Shelton, IV et al.
2022/0273301 A1 9/2022 Creamer et al.
2022/0273302 A1 9/2022 Shelton, IV et al.
2022/0273303 A1 9/2022 Creamer et al.
2022/0273304 A1 9/2022 Shelton, IV et al.
2022/0273305 A1 9/2022 Shelton, IV et al.
2022/0273306 A1 9/2022 Shelton, IV et al.
2022/0273307 A1 9/2022 Shelton, IV et al.
2022/0273308 A1 9/2022 Shelton, IV et al.
2022/0278438 A1 9/2022 Shelton, IV et al.
2022/0287711 A1 9/2022 Ming et al.
2022/0304679 A1 9/2022 Bakos et al.
2022/0304680 A1 9/2022 Shelton, IV et al.
2022/0304681 A1 9/2022 Shelton, IV et al.
2022/0304682 A1 9/2022 Shelton, IV et al.
2022/0304683 A1 9/2022 Shelton, IV et al.
2022/0304684 A1 9/2022 Bakos et al.
2022/0304685 A1 9/2022 Bakos et al.
2022/0304686 A1 9/2022 Shelton, IV et al.
2022/0304687 A1 9/2022 Shelton, IV et al.
2022/0304688 A1 9/2022 Shelton, IV et al.
2022/0304689 A1 9/2022 Shelton, IV
2022/0304690 A1 9/2022 Baxter, III et al.
2022/0304714 A1 9/2022 Shelton, IV et al.
2022/0304715 A1 9/2022 Shelton, IV

FOREIGN PATENT DOCUMENTS

AU 2012268848 A1 1/2013
AU 2011218702 B2 6/2013
AU 2012200178 B2 7/2013
BR 112013007744 A2 6/2016

(56) References Cited

FOREIGN PATENT DOCUMENTS

| | | | |
|---|---|---|---|
| BR | 112013027777 | A2 | 1/2017 |
| CA | 1015829 | A | 8/1977 |
| CA | 1125615 | A | 6/1982 |
| CA | 2520413 | A1 | 3/2007 |
| CA | 2725181 | A1 | 11/2007 |
| CA | 2851239 | A1 | 11/2007 |
| CA | 2664874 | A1 | 11/2009 |
| CA | 2813230 | A1 | 4/2012 |
| CA | 2940510 | A1 | 8/2015 |
| CA | 2698728 | C | 8/2016 |
| CN | 1163558 | A | 10/1997 |
| CN | 2488482 | Y | 5/2002 |
| CN | 1634601 | A | 7/2005 |
| CN | 2716900 | Y | 8/2005 |
| CN | 2738962 | Y | 11/2005 |
| CN | 1777406 | A | 5/2006 |
| CN | 2785249 | Y | 5/2006 |
| CN | 2796654 | Y | 7/2006 |
| CN | 2868212 | Y | 2/2007 |
| CN | 200942099 | Y | 9/2007 |
| CN | 200984209 | Y | 12/2007 |
| CN | 200991269 | Y | 12/2007 |
| CN | 201001747 | Y | 1/2008 |
| CN | 101143105 | A | 3/2008 |
| CN | 201029899 | Y | 3/2008 |
| CN | 101188900 | A | 5/2008 |
| CN | 101203085 | A | 6/2008 |
| CN | 101273908 | A | 10/2008 |
| CN | 101378791 | A | 3/2009 |
| CN | 101507635 | A | 8/2009 |
| CN | 101522120 | A | 9/2009 |
| CN | 101669833 | A | 3/2010 |
| CN | 101716090 | A | 6/2010 |
| CN | 101721236 | A | 6/2010 |
| CN | 101756727 | A | 6/2010 |
| CN | 101828940 | A | 9/2010 |
| CN | 101856250 | A | 10/2010 |
| CN | 101873834 | A | 10/2010 |
| CN | 201719298 | U | 1/2011 |
| CN | 102038532 | A | 5/2011 |
| CN | 201879759 | U | 6/2011 |
| CN | 201949071 | U | 8/2011 |
| CN | 102217961 | A | 10/2011 |
| CN | 102217963 | A | 10/2011 |
| CN | 102243850 | A | 11/2011 |
| CN | 102247182 | A | 11/2011 |
| CN | 102247183 | A | 11/2011 |
| CN | 101779977 | B | 12/2011 |
| CN | 102309352 | A | 1/2012 |
| CN | 101912284 | B | 7/2012 |
| CN | 102125450 | B | 7/2012 |
| CN | 202313537 | U | 7/2012 |
| CN | 202397539 | U | 8/2012 |
| CN | 202426586 | U | 9/2012 |
| CN | 102743201 | A | 10/2012 |
| CN | 202489990 | U | 10/2012 |
| CN | 102228387 | B | 11/2012 |
| CN | 102835977 | A | 12/2012 |
| CN | 202568350 | U | 12/2012 |
| CN | 103037781 | A | 4/2013 |
| CN | 103083053 | A | 5/2013 |
| CN | 103391037 | A | 11/2013 |
| CN | 203328751 | U | 12/2013 |
| CN | 103505264 | A | 1/2014 |
| CN | 103584893 | A | 2/2014 |
| CN | 103635150 | A | 3/2014 |
| CN | 103690212 | A | 4/2014 |
| CN | 203564285 | U | 4/2014 |
| CN | 203564287 | U | 4/2014 |
| CN | 203597997 | U | 5/2014 |
| CN | 103829981 | A | 6/2014 |
| CN | 103829983 | A | 6/2014 |
| CN | 103860221 | A | 6/2014 |
| CN | 103908313 | A | 7/2014 |
| CN | 203693685 | U | 7/2014 |
| CN | 203736251 | U | 7/2014 |
| CN | 103981635 | A | 8/2014 |
| CN | 104027145 | A | 9/2014 |
| CN | 203815517 | U | 9/2014 |
| CN | 102783741 | B | 10/2014 |
| CN | 102973300 | B | 10/2014 |
| CN | 204092074 | U | 1/2015 |
| CN | 104337556 | A | 2/2015 |
| CN | 204158440 | U | 2/2015 |
| CN | 204158441 | U | 2/2015 |
| CN | 102469995 | B | 3/2015 |
| CN | 104422849 | A | 3/2015 |
| CN | 104586463 | A | 5/2015 |
| CN | 204520822 | U | 8/2015 |
| CN | 204636451 | U | 9/2015 |
| CN | 103860225 | B | 3/2016 |
| CN | 103750872 | B | 5/2016 |
| CN | 105919642 | A | 9/2016 |
| CN | 103648410 | B | 10/2016 |
| CN | 105997173 | A | 10/2016 |
| CN | 106344091 | A | 1/2017 |
| CN | 104921730 | B | 9/2017 |
| CN | 104349800 | B | 11/2017 |
| CN | 107635483 | A | 1/2018 |
| CN | 208625784 | U | 3/2019 |
| DE | 273689 | C | 5/1914 |
| DE | 1775926 | A | 1/1972 |
| DE | 3036217 | A1 | 4/1982 |
| DE | 3210466 | A1 | 9/1983 |
| DE | 3709067 | A1 | 9/1988 |
| DE | 19534043 | A1 | 3/1997 |
| DE | 19851291 | A1 | 1/2000 |
| DE | 19924311 | A1 | 11/2000 |
| DE | 20016423 | U1 | 2/2001 |
| DE | 20112837 | U1 | 10/2001 |
| DE | 20121753 | U1 | 4/2003 |
| DE | 202004012389 | U1 | 9/2004 |
| DE | 10314072 | A1 | 10/2004 |
| DE | 102004014011 | A1 | 10/2005 |
| DE | 102004041871 | A1 | 3/2006 |
| DE | 102004063606 | A1 | 7/2006 |
| DE | 202007003114 | U1 | 6/2007 |
| DE | 102010013150 | A1 | 9/2011 |
| DE | 102012213322 | A1 | 1/2014 |
| DE | 102013101158 | A1 | 8/2014 |
| EM | 002220467-0008 | | 4/2013 |
| EP | 0000756 | A1 | 2/1979 |
| EP | 0122046 | A1 | 10/1984 |
| EP | 0129442 | B1 | 11/1987 |
| EP | 0251444 | A1 | 1/1988 |
| EP | 0255631 | A1 | 2/1988 |
| EP | 0169044 | B1 | 6/1991 |
| EP | 0541950 | A1 | 5/1993 |
| EP | 0548998 | A1 | 6/1993 |
| EP | 0594148 | A1 | 4/1994 |
| EP | 0646357 | A1 | 4/1995 |
| EP | 0505036 | B1 | 5/1995 |
| EP | 0669104 | A1 | 8/1995 |
| EP | 0516544 | B1 | 3/1996 |
| EP | 0705571 | A1 | 4/1996 |
| EP | 0528478 | B1 | 5/1996 |
| EP | 0770355 | A1 | 5/1997 |
| EP | 0625335 | B1 | 11/1997 |
| EP | 0879742 | A1 | 11/1998 |
| EP | 0650701 | B1 | 3/1999 |
| EP | 0923907 | A1 | 6/1999 |
| EP | 0484677 | B2 | 7/2000 |
| EP | 1034747 | A1 | 9/2000 |
| EP | 1034748 | A1 | 9/2000 |
| EP | 0726632 | B1 | 10/2000 |
| EP | 1053719 | A1 | 11/2000 |
| EP | 1055399 | A1 | 11/2000 |
| EP | 1055400 | A1 | 11/2000 |
| EP | 1064882 | A1 | 1/2001 |
| EP | 1080694 | A1 | 3/2001 |
| EP | 1090592 | A1 | 4/2001 |
| EP | 1095627 | A1 | 5/2001 |
| EP | 0806914 | B1 | 9/2001 |
| EP | 1234587 | A1 | 8/2002 |

(56) References Cited

FOREIGN PATENT DOCUMENTS

| | | | |
|---|---|---|---|
| EP | 1284120 | A1 | 2/2003 |
| EP | 0717967 | B1 | 5/2003 |
| EP | 0869742 | B1 | 5/2003 |
| EP | 1374788 | A1 | 1/2004 |
| EP | 1407719 | A2 | 4/2004 |
| EP | 0996378 | B1 | 6/2004 |
| EP | 1558161 | A1 | 8/2005 |
| EP | 1157666 | B1 | 9/2005 |
| EP | 0880338 | B1 | 10/2005 |
| EP | 1158917 | B1 | 11/2005 |
| EP | 1344498 | B1 | 11/2005 |
| EP | 1330989 | B1 | 12/2005 |
| EP | 1632191 | A2 | 3/2006 |
| EP | 1082944 | B1 | 5/2006 |
| EP | 1253866 | B1 | 7/2006 |
| EP | 1723914 | A1 | 11/2006 |
| EP | 1285633 | B1 | 12/2006 |
| EP | 1011494 | B1 | 1/2007 |
| EP | 1767163 | A1 | 3/2007 |
| EP | 1837041 | A1 | 9/2007 |
| EP | 0922435 | B1 | 10/2007 |
| EP | 1599146 | B1 | 10/2007 |
| EP | 1330201 | B1 | 6/2008 |
| EP | 2039302 | A2 | 3/2009 |
| EP | 1719461 | B1 | 6/2009 |
| EP | 2116196 | A2 | 11/2009 |
| EP | 2153793 | A2 | 2/2010 |
| EP | 1769754 | B1 | 6/2010 |
| EP | 1627605 | B1 | 12/2010 |
| EP | 2316345 | A1 | 5/2011 |
| EP | 1962711 | B1 | 2/2012 |
| EP | 2486862 | A2 | 8/2012 |
| EP | 2486868 | A2 | 8/2012 |
| EP | 2517638 | A1 | 10/2012 |
| EP | 2606812 | A1 | 6/2013 |
| EP | 2649948 | A1 | 10/2013 |
| EP | 2649949 | A1 | 10/2013 |
| EP | 2668910 | A2 | 12/2013 |
| EP | 2687164 | A2 | 1/2014 |
| EP | 2713902 | A1 | 4/2014 |
| EP | 2743042 | A2 | 6/2014 |
| EP | 2764827 | A2 | 8/2014 |
| EP | 2777524 | A2 | 9/2014 |
| EP | 2789299 | A1 | 10/2014 |
| EP | 2842500 | A1 | 3/2015 |
| EP | 2853220 | A1 | 4/2015 |
| EP | 2878274 | A1 | 6/2015 |
| EP | 2298220 | B1 | 6/2016 |
| EP | 2510891 | B1 | 6/2016 |
| EP | 3031404 | A1 | 6/2016 |
| EP | 3047806 | A1 | 7/2016 |
| EP | 3078334 | A1 | 10/2016 |
| EP | 2364651 | B1 | 11/2016 |
| EP | 2747235 | B1 | 11/2016 |
| EP | 3095399 | A2 | 11/2016 |
| EP | 3120781 | A2 | 1/2017 |
| EP | 3135225 | A2 | 3/2017 |
| EP | 2789299 | B1 | 5/2017 |
| EP | 3225190 | A2 | 10/2017 |
| EP | 3326548 | A1 | 5/2018 |
| EP | 3363378 | A1 | 8/2018 |
| EP | 3409216 | A1 | 12/2018 |
| EP | 3476334 | A1 | 5/2019 |
| EP | 3275378 | B1 | 7/2019 |
| EP | 3505095 | A1 | 7/2019 |
| EP | 3791810 | A1 | 3/2021 |
| ES | 1070456 | U | 9/2009 |
| FR | 459743 | A | 11/1913 |
| FR | 999646 | A | 2/1952 |
| FR | 1112936 | A | 3/1956 |
| FR | 2598905 | A1 | 11/1987 |
| FR | 2689749 | B1 | 7/1994 |
| FR | 2765794 | A1 | 1/1999 |
| FR | 2815842 | A1 | 5/2002 |
| GB | 939929 | A | 10/1963 |
| GB | 1210522 | A | 10/1970 |
| GB | 1217159 | A | 12/1970 |
| GB | 1339394 | A | 12/1973 |
| GB | 2024012 | A | 1/1980 |
| GB | 2109241 | A | 6/1983 |
| GB | 2090534 | B | 6/1984 |
| GB | 2272159 | A | 5/1994 |
| GB | 2336214 | A | 10/1999 |
| GB | 2509523 | A | 7/2014 |
| GR | 930100110 | A | 11/1993 |
| JP | S4711908 | Y1 | 5/1972 |
| JP | S5033988 | U | 4/1975 |
| JP | S5367286 | A | 6/1978 |
| JP | S56112235 | A | 9/1981 |
| JP | S60113007 | A | 6/1985 |
| JP | S62170011 | U | 10/1987 |
| JP | S6333137 | A | 2/1988 |
| JP | S63270040 | A | 11/1988 |
| JP | S63318824 | A | 12/1988 |
| JP | H0129503 | B2 | 6/1989 |
| JP | H02106189 | A | 4/1990 |
| JP | H0378514 | U | 8/1991 |
| JP | H0385009 | U | 8/1991 |
| JP | H0489041 | A | 3/1992 |
| JP | H04215747 | A | 8/1992 |
| JP | H04131860 | U | 12/1992 |
| JP | H0584252 | A | 4/1993 |
| JP | H05123325 | A | 5/1993 |
| JP | H05226945 | A | 9/1993 |
| JP | H0630945 | A | 2/1994 |
| JP | H0636757 | A | 2/1994 |
| JP | H06237937 | A | 8/1994 |
| JP | H06304176 | A | 11/1994 |
| JP | H06327684 | A | 11/1994 |
| JP | H079622 | U | 2/1995 |
| JP | H07124166 | A | 5/1995 |
| JP | H07163573 | A | 6/1995 |
| JP | H07255735 | A | 10/1995 |
| JP | H07285089 | A | 10/1995 |
| JP | H0833642 | A | 2/1996 |
| JP | H08164141 | A | 6/1996 |
| JP | H08182684 | A | 7/1996 |
| JP | H08507708 | A | 8/1996 |
| JP | H08229050 | A | 9/1996 |
| JP | H08289895 | A | 11/1996 |
| JP | H0950795 | A | 2/1997 |
| JP | H09-323068 | A | 12/1997 |
| JP | H10118090 | A | 5/1998 |
| JP | H10-200699 | A | 7/1998 |
| JP | H10296660 | A | 11/1998 |
| JP | 2000014632 | A | 1/2000 |
| JP | 2000033071 | A | 2/2000 |
| JP | 2000112002 | A | 4/2000 |
| JP | 2000166932 | A | 6/2000 |
| JP | 2000171730 | A | 6/2000 |
| JP | 2000210299 | A | 8/2000 |
| JP | 2000271141 | A | 10/2000 |
| JP | 2000287987 | A | 10/2000 |
| JP | 2000325303 | A | 11/2000 |
| JP | 2001-69758 | A | 3/2001 |
| JP | 2001087272 | A | 4/2001 |
| JP | 2001208655 | A | 8/2001 |
| JP | 2001514541 | A | 9/2001 |
| JP | 2001276091 | A | 10/2001 |
| JP | 2002051974 | A | 2/2002 |
| JP | 2002054903 | A | 2/2002 |
| JP | 2002085415 | A | 3/2002 |
| JP | 2002143078 | A | 5/2002 |
| JP | 2002153481 | A | 5/2002 |
| JP | 2002528161 | A | 9/2002 |
| JP | 2002314298 | A | 10/2002 |
| JP | 2003135473 | A | 5/2003 |
| JP | 2003521301 | A | 7/2003 |
| JP | 3442423 | B2 | 9/2003 |
| JP | 2003300416 | A | 10/2003 |
| JP | 2004147701 | A | 5/2004 |
| JP | 2004162035 | A | 6/2004 |
| JP | 2004229976 | A | 8/2004 |
| JP | 2005013573 | A | 1/2005 |

(56) References Cited

FOREIGN PATENT DOCUMENTS

| | | | |
|---|---|---|---|
| JP | 2005080702 | A | 3/2005 |
| JP | 2005131163 | A | 5/2005 |
| JP | 2005131164 | A | 5/2005 |
| JP | 2005131173 | A | 5/2005 |
| JP | 2005131211 | A | 5/2005 |
| JP | 2005131212 | A | 5/2005 |
| JP | 2005137423 | A | 6/2005 |
| JP | 2005187954 | A | 7/2005 |
| JP | 2005211455 | A | 8/2005 |
| JP | 2005328882 | A | 12/2005 |
| JP | 2005335432 | A | 12/2005 |
| JP | 2005342267 | A | 12/2005 |
| JP | 3791856 | B2 | 6/2006 |
| JP | 2006187649 | A | 7/2006 |
| JP | 2006218228 | A | 8/2006 |
| JP | 2006281405 | A | 10/2006 |
| JP | 2006291180 | A | 10/2006 |
| JP | 2006346445 | A | 12/2006 |
| JP | 2007-97252 | A | 4/2007 |
| JP | 2007289715 | A | 11/2007 |
| JP | 2007304057 | A | 11/2007 |
| JP | 2007306710 | A | 11/2007 |
| JP | D1322057 | | 2/2008 |
| JP | 2008154804 | A | 7/2008 |
| JP | 2008220032 | A | 9/2008 |
| JP | 2009507526 | A | 2/2009 |
| JP | 2009189838 | A | 8/2009 |
| JP | 2009189846 | A | 8/2009 |
| JP | 2009207260 | A | 9/2009 |
| JP | 2009226028 | A | 10/2009 |
| JP | 2009538684 | A | 11/2009 |
| JP | 2009539420 | A | 11/2009 |
| JP | D1383743 | | 2/2010 |
| JP | 2010065594 | A | 3/2010 |
| JP | 2010069307 | A | 4/2010 |
| JP | 2010069310 | A | 4/2010 |
| JP | 2010098844 | A | 4/2010 |
| JP | 2010214128 | A | 9/2010 |
| JP | 2011072574 | A | 4/2011 |
| JP | 4722849 | B2 | 7/2011 |
| JP | 4728996 | B2 | 7/2011 |
| JP | 2011524199 | A | 9/2011 |
| JP | 2011200665 | A | 10/2011 |
| JP | D1432094 | | 12/2011 |
| JP | 2012115542 | A | 6/2012 |
| JP | 2012143283 | A | 8/2012 |
| JP | 5154710 | B1 | 2/2013 |
| JP | 2013099551 | A | 5/2013 |
| JP | 2013126430 | A | 6/2013 |
| JP | D1481426 | | 9/2013 |
| JP | 2013541982 | A | 11/2013 |
| JP | 2013541983 | A | 11/2013 |
| JP | 2013541997 | A | 11/2013 |
| JP | 2014018667 | A | 2/2014 |
| JP | D1492363 | | 2/2014 |
| JP | 2014121599 | A | 7/2014 |
| JP | 2014171879 | A | 9/2014 |
| JP | 1517663 | S | 2/2015 |
| JP | 2015512725 | A | 4/2015 |
| JP | 2015513956 | A | 5/2015 |
| JP | 2015513958 | A | 5/2015 |
| JP | 2015514471 | A | 5/2015 |
| JP | 2015516838 | A | 6/2015 |
| JP | 2015521524 | A | 7/2015 |
| JP | 2015521525 | A | 7/2015 |
| JP | 2016007800 | A | 1/2016 |
| JP | 2016508792 | A | 3/2016 |
| JP | 2016512057 | A | 4/2016 |
| JP | 2016530949 | A | 10/2016 |
| JP | 2017513563 | A | 6/2017 |
| JP | 1601498 | S | 4/2018 |
| JP | 2019513530 | A | 5/2019 |
| JP | D1677030 | S | 1/2021 |
| JP | D1696539 | S | 10/2021 |
| KR | 20100110134 | A | 10/2010 |
| KR | 20110003229 | A | 1/2011 |
| KR | 300631507 | | 3/2012 |
| KR | 300747646 | | 6/2014 |
| KR | 20180053811 | A | 5/2018 |
| RU | 1814161 | C | 5/1993 |
| RU | 2008830 | C1 | 3/1994 |
| RU | 2052979 | C1 | 1/1996 |
| RU | 2066128 | C1 | 9/1996 |
| RU | 2069981 | C1 | 12/1996 |
| RU | 2098025 | C1 | 12/1997 |
| RU | 2104671 | C1 | 2/1998 |
| RU | 2110965 | C1 | 5/1998 |
| RU | 2141279 | C1 | 11/1999 |
| RU | 2144791 | C1 | 1/2000 |
| RU | 2161450 | C1 | 1/2001 |
| RU | 2181566 | C2 | 4/2002 |
| RU | 2187249 | C2 | 8/2002 |
| RU | 32984 | U1 | 10/2003 |
| RU | 2225170 | C2 | 3/2004 |
| RU | 42750 | U1 | 12/2004 |
| RU | 61114 | U1 | 2/2007 |
| RU | 61122 | U1 | 2/2007 |
| RU | 2430692 | C2 | 10/2011 |
| SU | 189517 | A | 1/1967 |
| SU | 297156 | A | 5/1971 |
| SU | 328636 | A | 9/1972 |
| SU | 511939 | A1 | 4/1976 |
| SU | 674747 | A1 | 7/1979 |
| SU | 728848 | A1 | 4/1980 |
| SU | 1009439 | A | 4/1983 |
| SU | 1042742 | A1 | 9/1983 |
| SU | 1271497 | A1 | 11/1986 |
| SU | 1333319 | A2 | 8/1987 |
| SU | 1377052 | A1 | 2/1988 |
| SU | 1377053 | A1 | 2/1988 |
| SU | 1443874 | A1 | 12/1988 |
| SU | 1509051 | A1 | 9/1989 |
| SU | 1561964 | A1 | 5/1990 |
| SU | 1708312 | A1 | 1/1992 |
| SU | 1722476 | A1 | 3/1992 |
| SU | 1752361 | A1 | 8/1992 |
| SU | 1814161 | A1 | 5/1993 |
| WO | WO-9308754 | A1 | 5/1993 |
| WO | WO-9315648 | A1 | 8/1993 |
| WO | WO-9420030 | A1 | 9/1994 |
| WO | WO-9517855 | A1 | 7/1995 |
| WO | WO-9520360 | A1 | 8/1995 |
| WO | WO-9623448 | A1 | 8/1996 |
| WO | WO-9635464 | A1 | 11/1996 |
| WO | WO-9639086 | A1 | 12/1996 |
| WO | WO-9639088 | A1 | 12/1996 |
| WO | WO-9724073 | A1 | 7/1997 |
| WO | WO-9734533 | A1 | 9/1997 |
| WO | WO-9827870 | A1 | 7/1998 |
| WO | WO-9903407 | A1 | 1/1999 |
| WO | WO-9903409 | A1 | 1/1999 |
| WO | WO-9948430 | A1 | 9/1999 |
| WO | WO-0024322 | A1 | 5/2000 |
| WO | WO-0024330 | A1 | 5/2000 |
| WO | WO-0036690 | A2 | 6/2000 |
| WO | WO-0053112 | A2 | 9/2000 |
| WO | WO-0024448 | A2 | 10/2000 |
| WO | WO-0057796 | A1 | 10/2000 |
| WO | WO-0105702 | A1 | 1/2001 |
| WO | WO-0154594 | A1 | 8/2001 |
| WO | WO-0158371 | A1 | 8/2001 |
| WO | WO-0162164 | A2 | 8/2001 |
| WO | WO-0162169 | A2 | 8/2001 |
| WO | WO-0191646 | A1 | 12/2001 |
| WO | WO-0219932 | A1 | 3/2002 |
| WO | WO-0226143 | A1 | 4/2002 |
| WO | WO-0236028 | A1 | 5/2002 |
| WO | WO-02065933 | A2 | 8/2002 |
| WO | WO-03055402 | A1 | 7/2003 |
| WO | WO-03094747 | A1 | 11/2003 |
| WO | WO-03079909 | A3 | 3/2004 |
| WO | WO-2004019803 | A1 | 3/2004 |
| WO | WO-2004032783 | A1 | 4/2004 |
| WO | WO-2004047626 | A1 | 6/2004 |

(56) References Cited

FOREIGN PATENT DOCUMENTS

| | | | |
|---|---|---|---|
| WO | WO-2004047653 | A2 | 6/2004 |
| WO | WO-2004056277 | A1 | 7/2004 |
| WO | WO-2004078050 | A2 | 9/2004 |
| WO | WO-2004078051 | A2 | 9/2004 |
| WO | WO-2004096015 | A2 | 11/2004 |
| WO | WO-2006044581 | A2 | 4/2006 |
| WO | WO-2006051252 | A1 | 5/2006 |
| WO | WO-2006059067 | A1 | 6/2006 |
| WO | WO-2006073581 | A2 | 7/2006 |
| WO | WO-2006085389 | A1 | 8/2006 |
| WO | WO-2007015971 | A2 | 2/2007 |
| WO | WO-2007074430 | A1 | 7/2007 |
| WO | WO-2007129121 | A1 | 11/2007 |
| WO | WO-2007137304 | A2 | 11/2007 |
| WO | WO-2007142625 | A2 | 12/2007 |
| WO | WO-2008021969 | A2 | 2/2008 |
| WO | WO-2008061566 | A1 | 5/2008 |
| WO | WO-2008089404 | A2 | 7/2008 |
| WO | WO-2009005969 | A2 | 1/2009 |
| WO | WO-2009067649 | A2 | 5/2009 |
| WO | WO-2009091497 | A2 | 7/2009 |
| WO | WO-2010126129 | A1 | 11/2010 |
| WO | WO-2010134913 | A1 | 11/2010 |
| WO | WO-2011008672 | A2 | 1/2011 |
| WO | WO-2011044343 | A2 | 4/2011 |
| WO | WO-2012006306 | A2 | 1/2012 |
| WO | WO-2012013577 | A1 | 2/2012 |
| WO | WO-2012044606 | A2 | 4/2012 |
| WO | WO-2012061725 | A1 | 5/2012 |
| WO | WO-2012072133 | A1 | 6/2012 |
| WO | WO-2012166503 | A1 | 12/2012 |
| WO | WO-2013087092 | A1 | 6/2013 |
| WO | WO-2013151888 | A1 | 10/2013 |
| WO | WO-2014004209 | A2 | 1/2014 |
| WO | WO-2014113438 | A1 | 7/2014 |
| WO | WO-2014175894 | A1 | 10/2014 |
| WO | WO-2015032797 | A1 | 3/2015 |
| WO | WO-2015076780 | A1 | 5/2015 |
| WO | WO-2015137040 | A1 | 9/2015 |
| WO | WO-2015138760 | A1 | 9/2015 |
| WO | WO-2015187107 | A1 | 12/2015 |
| WO | WO-2016100682 | A1 | 6/2016 |
| WO | WO-2016107448 | A1 | 7/2016 |
| WO | WO-2018011664 | A1 | 1/2018 |
| WO | WO-2019036490 | A1 | 2/2019 |
| WO | WO-2021189234 | A1 | 9/2021 |

OTHER PUBLICATIONS

ASTM procedure D2240-05, "Standard Test Method for Rubber Property-Durometer Hardness," (Published Apr. 2010).

Van Meer et al., "A Disposable Plastic Compact Wrist for Smart Minimally Invasive Surgical Tools," LAAS/CNRS (Aug. 2005).

Breedveld et al., "A New, Easily Miniaturized Sterrable Endoscope," IEEE Engineering in Medicine and Biology Magazine (Nov./Dec. 2005).

Disclosed Anonymously, "Motor-Driven Surgical Stapler Improvements," Research Disclosure Database No. 526041, Published: Feb. 2008.

B.R. Coolman, DVM, MS et al., "Comparison of Skin Staples With Sutures for Anastomosis of the Small Intestine in Dogs," Abstract; http://www.blackwell-synergy.com/doi/abs/10.1053/jvet.2000.7539?cookieSet=1&journalCode=vsu which redirects to http://www3.interscience.wiley.com/journal/119040681/abstract?CRETRY=1&SRETRY=0; [online] accessed: Sep. 22, 2008 (2 pages).

D. Tuite, Ed., "Get the Lowdown on Ultracapacitors," Nov. 15, 2007; [online] URL: http://electronicdesign.com/Articles/Print.cfm?ArticleID=17465, accessed Jan. 15, 2008 (5 pages).

Datasheet for Panasonic TK Relays Ultra Low Profile 2 a Polarized Relay, Copyright Matsushita Electric Works, Ltd. (Known of at least as early as Aug. 17, 2010), 5 pages.

Schellhammer et al., "Poly-Lactic-Acid for Coating of Endovascular Stents: Preliminary Results in Canine Experimental Av-Fistulae," Mat.-wiss. u. Werkstofftech., 32, pp. 193-199 (2001).

Miyata et al., "Biomolecule-Sensitive Hydrogels," Advanced Drug Delivery Reviews, 54 (2002) pp. 79-98.

Jeong et al., "Thermosensitive Sol-Gel Reversible Hydrogels," Advanced Drug Delivery Reviews, 54 (2002) pp. 37-51.

Covidien Brochure, "Endo GIA™ Ultra Universal Stapler," (2010), 2 pages.

Qiu et al., "Environment-Sensitive Hydrogels for Drug Delivery," Advanced Drug Delivery Reviews, 53 (2001) pp. 321-339.

Hoffman, "Hydrogels for Biomedical Applications," Advanced Drug Delivery Reviews, 43 (2002) pp. 3-12.

Hoffman, "Hydrogels for Biomedical Applications," Advanced Drug Delivery Reviews, 54 (2002) pp. 3-12.

Peppas, "Physiologically Responsive Hydrogels," Journal of Bioactive and Compatible Polymers, vol. 6 (Jul. 1991) pp. 241-246.

Peppas, Editor "Hydrogels in Medicine and Pharmacy," vol. I, Fundamentals, CRC Press, 1986.

Young, "Microcellular foams via phase separation," Journal of Vacuum Science & Technology A 4(3), (May/Jun. 1986).

Ebara, "Carbohydrate-Derived Hydrogels and Microgels," Engineered Carbohydrate-Based Materials for Biomedical Applications: Polymers, Surfaes, Dendrimers, Nanoparticles, and Hydrogels, Edited by Ravin Narain, 2011, pp. 337-345.

http://ninpgan.net/publications/51-100/89.pdf; 2004, Ning Pan, On Uniqueness of Fibrous Materials, Design & Nature II. Eds: Colins, M. and Brebbia, C. WIT Press, Boston, 493-504.

Solorio et al., "Gelatin Microspheres Crosslinked with Genipin for Local Delivery of Growth Factors," J. Tissue Eng. Regen. Med. (2010), 4(7): pp. 514-523.

Covidien iDrive™ Ultra in Service Reference Card, "iDrive™ Ultra Powered Stapling Device," (4 pages).

Covidien iDrive™ Ultra Powered Stapling System ibrochure, "The Power of iDrive™ Ultra Powered Stapling System and Tri-Staple™ Technology," (23 pages).

Covidien "iDrive™ Ultra Powered Stapling System, A Guide for Surgeons," (6 pages).

Covidien "iDrive™ Ultra Powered Stapling System, Cleaning and Sterilization Guide," (2 pages).

Covidien Brochure "iDrive™ Ultra Powered Stapling System," (6 pages).

Covidien Brochure, "Endo GIA™ Reloads with Tri-Staple™ Technology," (2010), 1 page.

Covidien Brochure, "Endo GIA™ Reloads with Tri-Staple™ Technology and Endo GIA™ Ultra Universal Staplers," (2010), 2 pages.

Covidien Brochure, "Endo GIA™ Curved Tip Reload with Tri-Staple™ Technology," (2012), 2 pages.

Covidien Brochure, "Endo GIA™ Reloads with Tri-Staple™ Technology," (2010), 2 pages.

Pitt et al., "Attachment of Hyaluronan to Metallic Surfaces," J. Biomed. Mater. Res. 68A: pp. 95-106, 2004.

Indian Standard: Automotive Vehicles—Brakes and Braking Systems (IS 11852-1:2001), Mar. 1, 2001.

Patrick J. Sweeney: "RFID for Dummies", Mar. 11, 2010, pp. 365-365, XP055150775, ISBN: 978-1-11-805447-5, Retrieved from the Internet: URL: books.google.de/books?isbn=1118054474 [retrieved on Nov. 4, 2014]—book not attached.

Allegro MicroSystems, LLC, Automotive Full Bridge MOSFET Driver, A3941-DS, Rev. 5, 21 pages, http://www.allegromicro.com/~/media/Files/Datasheets/A3941-Datasheet.ashx?la=en.

Data Sheet of LM4F230H5QR, 2007.

Seils et al., Covidien Summary: Clinical Study "UCONN Biodynamics: Final Report on Results," (2 pages).

Byrne et al., "Molecular Imprinting Within Hydrogels," Advanced Drug Delivery Reviews, 54 (2002) pp. 149-161.

Fast, Versatile Blackfin Processors Handle Advanced RFID Reader Applications; Analog Dialogue: vol. 40—Sep. 2006; http://www.analog.com/library/analogDialogue/archives/40-09/rfid.pdf; Wayback Machine to Feb. 15, 2012.

Chen et al., "Elastomeric Biomaterials for Tissue Engineering," Progress in Polymer Science 38 (2013), pp. 584-671.

(56) References Cited

OTHER PUBLICATIONS

Matsuda, "Thermodynamics of Formation of Porous Polymeric Membrane from Solutions," Polymer Journal, vol. 23, No. 5, pp. 435-444 (1991).
Covidien Brochure, "Endo GIA™ Black Reload with Tri-Staple™ Technology," (2012), 2 pages.
Biomedical Coatings, Fort Wayne Metals, Research Products Corporation, obtained online at www.fwmetals.com on Jun. 21, 2010 (1 page).
The Sodem Aseptic Battery Transfer Kit, Sodem Systems, 2000, 3 pages.
C.C. Thompson et al., "Peroral Endoscopic Reduction of Dilated Gastrojejunal Anastomosis After Roux-en-Y Gastric Bypass: A Possible New Option for Patients with Weight Regain," Surg Endosc (2006) vol. 20., pp. 1744-1748.
Serial Communication Protocol; Michael Lemmon Feb. 1, 2009; http://www3.nd.edu/~lemmon/courses/ee224/web-manual/web-manual/lab12/node2.html; Wayback Machine to Apr. 29, 2012.
Lyon et al. "The Relationship Between Current Load and Temperature for Quasi-Steady State and Transient Conditions," SPIE—International Society for Optical Engineering. Proceedings, vol. 4020, (pp. 62-70), Mar. 30, 2000.
Anonymous: "Sense & Control Application Note Current Sensing Using Linear Hall Sensors," Feb. 3, 2009, pp. 1-18. Retrieved from the Internet: URL: http://www.infineon.com/dgdl/Current_Sensing_Rev.1.1.pdf?fileld=db3a304332d040720132d939503e5f17 [retrieved on Oct. 18, 2016].
Mouser Electronics, "LM317M 3-Terminal Adjustable Regulator with Overcurrent/Overtemperature Self Protection", Mar. 31, 2014 (Mar. 31, 2014), XP0555246104, Retrieved from the Internet: URL: http://www.mouser.com/ds/2/405/lm317m-440423.pdf, pp. 1-8.
Mouser Electronics, "LM317 3-Terminal Adjustable Regulator with Overcurrent/Overtemperature Self Protection", Sep. 30, 2016 (Sep. 30, 2016), XP0555246104, Retrieved from the Internet: URL: http://www.mouser.com/ds/2/405/lm317m-440423.pdf, pp. 1-9.
Cuper et al., "The Use of Near-Infrared Light for Safe and Effective Visualization of Subsurface Blood Vessels to Facilitate Blood Withdrawal in Children," Medical Engineering & Physics, vol. 35, No. 4, pp. 433-440 (2013).
Yan et al., Comparison of the effects of Mg-6Zn and Ti-3Al-2.5V alloys on TGF-β/TNF-α/VEGF/b-FGF in the healing of the intestinal track in vivo, Biomed. Mater. 9 (2014), 11 pages.
Pellicer et al. "On the biodegradability, mechanical behavior, and cytocompatibility of amorphous Mg72Zn23Ca5 and crystalline Mg70Zn23Ca5Pd2 alloys as temporary implant materials," J Biomed Mater Res Part A ,2013:101A:502-517.
Anonymous, Analog Devices Wiki, Chapter 11: The Current Mirror, Aug. 20, 2017, 22 pages. https://wiki.analog.com/university/courses/electronics/text/chapter-11?rev=1503222341.
Yan et al., "Comparison of the effects of Mg-6Zn and titanium on intestinal tract in vivo," J Mater Sci: Mater Med (2013), 11 pages.
Brar et al., "Investigation of the mechanical and degradation properties of Mg—Sr and Mg—Zn—Sr alloys for use as potential biodegradable implant materials," J. Mech. Behavior of Biomed. Mater. 7 (2012) pp. 87-95.
Texas Instruments: "Current Recirculation and Decay Modes," Application Report SLVA321—Mar. 2009; Retrieved from the Internet: URL:http://www.ti.com/lit/an/slva321/slva321 [retrieved on Apr. 25, 2017], 7 pages.
Qiu Li Loh et al.: "Three-Dimensional Scaffolds for Tissue Engineering Applications: Role of Porosity and Pore Size", Tissue Engineering Part B-Reviews, vol. 19, No. 6, Dec. 1, 2013, pp. 485-502.
Gao et al., "Mechanical Signature Enhancement of Response Vibrations in the Time Lag Domain," Fifth International Congress on Sound and Vibration, Dec. 15-18, 1997, pp. 1-8.
Trendafilova et al., "Vibration-based Methods for Structural and Machinery Fault Diagnosis Based on Nonlinear Dynamics Tools," In: Fault Diagnosis in Robotic and Industrial Systems, IConcept Press LTD, 2012, pp. 1-29.
Youtube.com; video by Fibran (retrieved from URL https://www.youtube.com/watch?v=vN2Qjt51gFQ); (Year: 2018).
Foot and Ankle: Core Knowledge in Orthopaedics; by DiGiovanni MD, Elsevier; (p. 27, left column, heading "Materials for Soft Orthoses", 7th bullet point); (Year: 2007).
Lee, Youbok, "Antenna Circuit Design for RFID Applications," 2003, pp. 1-50, DS00710C, Microchip Technology Inc., Available: http://ww1.microchip.com/downloads/en/AppNotes/00710c.pdf.
Kawamura, Atsuo, et al. "Wireless Transmission of Power and Information Through One High-Frequency Resonant AC Link Inverter for Robot Manipulator Applications," Journal, May/Jun. 1996, pp. 503-508, vol. 32, No. 3, IEEE Transactions on Industry Applications.
Honda HS1332AT and ATD Model Info, powerequipment.honda.com [online], published on or before Mar. 22, 2016, [retrieved on May 31, 2019], retrieved from the Internet [URL: https://powerequipment.honda.com/snowblowers/models/hss1332at-hss1332atd] {Year: 2016).
Slow Safety Sign, shutterstock.com [online], published on or before May 9, 2017, [retrieved on May 31, 2019], retrieved from the https://www.shutterstock.com/image-victor/slow-safety-sign-twodimensional-turtle-symbolizing- . . . see PDF in file for full URL] (Year: 2017).
Warning Sign Beveled Buttons, by Peter, flarestock.com [online], published on or before Jan. 1, 2017, [retrieved on Jun. 4, 2019], retrieved from the Internet [URL: https://www.flarestock.com/stock-images/warning-sign-beveled-buttons/70257] (Year: 2017).
Arrow Sign Icon Next Button, by Blan-k, shutterstock.com [online], published on or before Aug. 6, 2014, [retrieved on Jun. 4, 2019], retrieved from the Internet [URL:https://www.shutterstock.com/de/image-vector/arrow-sign-icon-next-button-navigation-207700303?irgwc=1&utm . . . see PDF in file for full URL] (Year: 2014).
Elite Icons, by smart/icons, iconfinder.com [online], published on Aug. 18, 2016, [retrieved on Jun. 4, 2019], retrieved from the Internet [URL: https://www.iconfinder.com/iconsets/elite] (Year: 2016).
Tutorial overview of inductively coupled RFID Systems, UPM, May 2003, pp. 1-7, UPM Rafsec, <http://cdn.mobiusconsulting.com/papers/rfidsystems.pdf>.
Schroeter, John, "Demystifying UHF Gen 2 RFID, HF RFID," Online Article, Jun. 2, 2008, pp. 1-3, <https://www.edn.com/design/industrial-control/4019123/Demystifying-UHF-Gen-2-RFID-HF-RFID>.
Adeeb, et al., "An Inductive Link-Based Wireless Power Transfer System for Biomedical Applications," Research Article, Nov. 14, 2011, pp. 1-12, vol. 2012, Article ID 879294, Hindawi Publishing Corporation.
Pushing Pixels (GIF), published on dribble.com, 2013.
Sodium stearate C18H35NaO2, Chemspider Search and Share Chemistry, Royal Society of Chemistry, pp. 1-3, 2015, http://www.chemspider.com/Chemical-Structure.12639.html, accessed May 23, 2016.
NF Monographs: Sodium Stearate, U.S. Pharmacopeia, http://www.pharmacopeia.cn/v29240/usp29nf24s0_m77360.html, accessed May 23, 2016.
Fischer, Martin H, "Colloid-Chemical Studies on Soaps", The Chemical Engineer, pp. 184-193, Aug. 1919.
V.K. Ahluwalia and Madhuri Goyal, A Textbook of Organic Chemistry, Section 19.11.3, p. 356, 2000.
A.V. Kasture and S.G. Wadodkar, Pharmaceutical Chemistry-II: Second Year Diploma in Pharmacy, Nirali Prakashan, p. 339, 2007.
Forum discussion regarding "Speed is Faster", published on Oct. 1, 2014 and retrieved on Nov. 8, 2019 from URL https://english.stackexchange.com/questions/199018/how-is-that-correct-speed-is-faster-or-prices-are-cheaper (Year: 2014).
"Understanding the Requirements of ISO/IEC 14443 for Type B Proximity Contactless Identification Cards," retrieved from https://www.digchip.com/application-notes/22/15746.php on Mar. 2, 2020, pp. 1-28 (Nov. 2005).
Jauchem, J.R., "Effects of low-level radio-frequency (3 kHz to 300 GHZ) enery on human cardiovascular, reproductive, immune, and other systems: A review of the recent literatured," Int. J. Hyg. Environ. Health 211 (2008) 1-29.

(56) References Cited

OTHER PUBLICATIONS

Sandvik, "Welding Handbook," https://www.meting.rs/wp-content/uploads/2018/05/welding-handbook.pdf, retrieved on Jun. 22, 2020. pp. 5-6.
Ludois, Daniel C., "Capacitive Power Transfer for Rotor Field Current in Synchronous Machines," IEEE Transactions on Power Electronics, Institute of Electrical and Electronics Engineers, USA, vol. 27, No. 11, Nov. 1, 2012, pp. 4638-4645.
Rotary Systems: Sealed Slip Ring Categories, Rotary Systems, May 22, 2017, retrieved from the internet: http://web.archive.org/we/20170522174710/http:/rotarysystems.com: 80/slip-rings/sealed/, retrieved on Aug. 12, 2020, pp. 1-2.
IEEE Std 802.3-2012 (Revision of IEEE Std 802.3-2008, published Dec. 28, 2012.
"ATM-MPLS Network Interworking Version 2.0, af-aic-0178.001" ATM Standard, The ATM Forum Technical Committee, published Aug. 2003.
Yang et al.; "4D printing reconfigurable, deployable and mechanically tunable metamaterials," Material Horizions, vol. 6, pp. 1244-1250 (2019).
"Council Directive 93/42/EEC of Jun. 14, 1993 Concerning Medical Devices," Official Journal of the European Communities, L&C. Ligislation and Competition, S, No. L 169, Jun. 14, 1993, pp. 1-43.
Arjo Loeve et al., Scopes Too Flexible . . . and Too Stiff, 2010, IEEE Pulse, Nov./Dec. 2010 (Year: 2010), 16 pages.
Molina, "Low Level Reader Protocol (LLRP)," Oct. 13, 2010, pp. 1-198.

* cited by examiner

ARTICULATABLE SURGICAL INSTRUMENTS WITH MOVABLE JAWS LOCATED IN CLOSE PROXIMITY TO AN ARTICULATION AXIS

CROSS-REFERENCE TO RELATED APPLICATIONS

This application is a continuation application claiming priority under 35 U.S.C. § 120 to U.S. patent application Ser. No. 15/635,612, entitled JAW RETAINER ARRANGEMENT FOR RETAINING A PIVOTABLE SURGICAL INSTRUMENT JAW IN PIVOTABLE RETAINING ENGAGEMENT WITH A SECOND SURGICAL INSTRUMENT JAW, filed Jun. 28, 2017 which issued on Oct. 25, 2022 as U.S. Pat. No. 11,478,242, the entire disclosure of which is hereby incorporated by reference herein.

BACKGROUND

The present invention relates to surgical instruments and, in various arrangements, to surgical stapling and cutting instruments and staple cartridges for use therewith that are designed to staple and cut tissue.

BRIEF DESCRIPTION OF THE DRAWINGS

Various features of the embodiments described herein, together with advantages thereof, may be understood in accordance with the following description taken in conjunction with the accompanying drawings as follows.

Corresponding reference characters indicate corresponding parts throughout the several views. The exemplifications set out herein illustrate various embodiments of the invention, in one form, and such exemplifications are not to be construed as limiting the scope of the invention in any manner.

DETAILED DESCRIPTION

Figure 1:
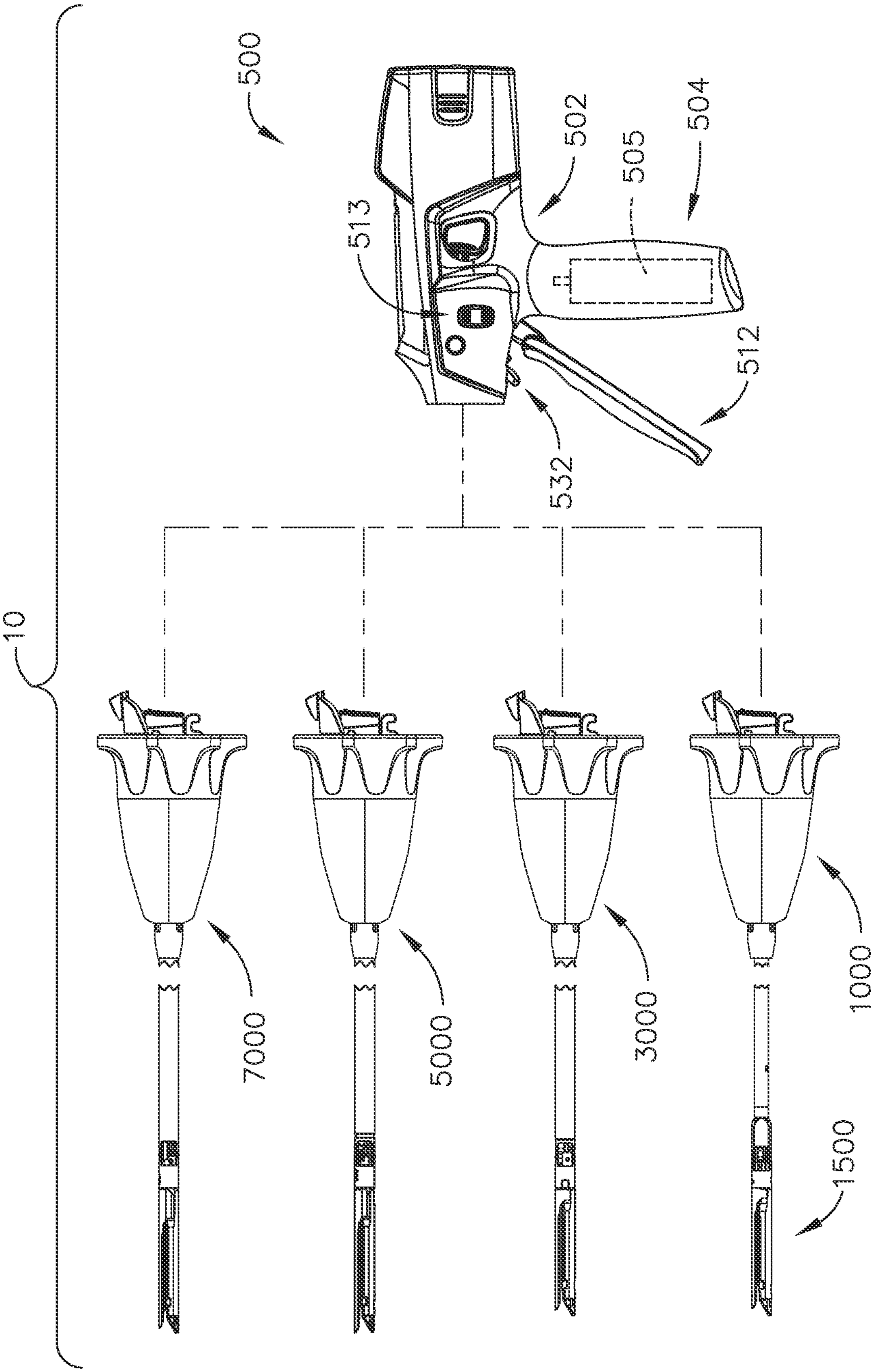
FIG. 1 is a side elevational view of a surgical system comprising a handle assembly and multiple interchangeable surgical tool assemblies that may be used therewith.

Applicant of the present application owns the following U.S. Patent Applications that were filed on Jun. 28, 2017 and which are each herein incorporated by reference in their respective entireties:

- U.S. patent application Ser. No. 15/635,693, entitled SURGICAL INSTRUMENT COMPRISING AN OFFSET ARTICULATION JOINT, now U.S. Patent Application Publication No. 2019/0000466;
- U.S. patent application Ser. No. 15/635,729, entitled SURGICAL INSTRUMENT COMPRISING AN ARTICULATION SYSTEM RATIO, now U.S. Pat. No. 11,000,279;
- U.S. patent application Ser. No. 15/635,785, entitled SURGICAL INSTRUMENT COMPRISING AN ARTICULATION SYSTEM RATIO, now U.S. Patent Application Publication No. 2019/0000469;
- U.S. patent application Ser. No. 15/635,808, entitled SURGICAL INSTRUMENT COMPRISING FIRING MEMBER SUPPORTS, now U.S. Patent Application Publication No. 2019/0000471;
- U.S. patent application Ser. No. 15/635,837, entitled SURGICAL INSTRUMENT COMPRISING AN ARTICULATION SYSTEM LOCKABLE TO A FRAME, now U.S. Patent Application Publication No. 2019/0000472;
- U.S. patent application Ser. No. 15/635,941, entitled SURGICAL INSTRUMENT COMPRISING AN ARTICULATION SYSTEM LOCKABLE BY A CLOSURE SYSTEM, now U.S. Pat. No. 10,779,824;
- U.S. patent application Ser. No. 15/636,029, entitled SURGICAL INSTRUMENT COMPRISING A SHAFT INCLUDING A HOUSING ARRANGEMENT, now U.S. Patent Application Publication No. 2019/0000477;
- U.S. patent application Ser. No. 15/635,958, entitled SURGICAL INSTRUMENT COMPRISING SELECTIVELY ACTUATABLE ROTATABLE COUPLERS, now U.S. Patent Application Publication No. 2019/0000474;
- U.S. patent application Ser. No. 15/635,981, entitled SURGICAL STAPLING INSTRUMENTS COMPRISING SHORTENED STAPLE CARTRIDGE NOSES, now U.S. Patent Application Publication No. 2019/0000475;
- U.S. patent application Ser. No. 15/636,009, entitled SURGICAL INSTRUMENT COMPRISING A SHAFT INCLUDING A CLOSURE TUBE PROFILE, now U.S. Patent Application Publication No. 2019/0000476;
- U.S. patent application Ser. No. 15/635,663, entitled METHOD FOR ARTICULATING A SURGICAL INSTRUMENT, now U.S. Pat. No. 10,765,427;
- U.S. patent application Ser. No. 15/635,530, entitled SURGICAL INSTRUMENTS WITH ARTICULATABLE END EFFECTOR WITH AXIALLY SHORTENED ARTICULATION JOINT CONFIGURATIONS, now U.S. Pat. No. 11,020,114;
- U.S. patent application Ser. No. 15/635,549, entitled SURGICAL INSTRUMENTS WITH OPEN AND CLOSABLE JAWS AND AXIALLY MOVABLE FIRING MEMBER THAT IS INITIALLY PARKED IN CLOSE PROXIMITY TO THE JAWS PRIOR TO FIRING, now U.S. Pat. No. 10,588,633;
- U.S. patent application Ser. No. 15/635,559, entitled SURGICAL INSTRUMENTS WITH JAWS CONSTRAINED TO PIVOT ABOUT AN AXIS UPON CONTACT WITH A CLOSURE MEMBER THAT IS PARKED IN CLOSE PROXIMITY TO THE PIVOT AXIS, now U.S. Patent Application Publication No. 2019/0000459;
- U.S. patent application Ser. No. 15/635,578, entitled SURGICAL END EFFECTORS WITH IMPROVED JAW APERTURE ARRANGEMENTS, now U.S. Pat. No. 10,786,253;
- U.S. patent application Ser. No. 15/635,594, entitled SURGICAL CUTTING AND FASTENING DEVICES WITH PIVOTABLE ANVIL WITH A TISSUE LOCATING ARRANGEMENT IN CLOSE PROXIMITY TO AN ANVIL PIVOT, now U.S. Patent Application Publication No. 2019/0000461;

U.S. patent application Ser. No. 15/635,621, entitled SURGICAL INSTRUMENT WITH POSITIVE JAW OPENING FEATURES, now U.S. Pat. No. 10,758,232;

U.S. patent application Ser. No. 15/635,631, entitled SURGICAL INSTRUMENT WITH AXIALLY MOVABLE CLOSURE MEMBER, now U.S. Pat. No. 10,639,037;

U.S. patent application Ser. No. 15/635,521, entitled SURGICAL INSTRUMENT LOCKOUT ARRANGEMENT, now U.S. Pat. No. 10,695,057;

U.S. Design patent application Ser. No. 29/609,087, entitled STAPLE FORMING ANVIL, now U.S. Design Pat. No. D851,762;

U.S. Design patent application Ser. No. 29/609,083, entitled SURGICAL INSTRUMENT SHAFT, now U.S. Design Pat. No. D854,151; and U.S. Design patent application Ser. No. 29/609,093, entitled SURGICAL FASTENER CARTRIDGE, now U.S. Design Pat. No. D869,655.

Applicant of the present application owns the following U.S. Patent Applications that were filed on Jun. 27, 2017 and which are each herein incorporated by reference in their respective entireties:

U.S. patent application Ser. No. 15/634,024, entitled SURGICAL ANVIL MANUFACTURING METHODS, now U.S. Patent Application Publication No. 2018/0368839;

U.S. patent application Ser. No. 15/634,035, entitled SURGICAL ANVIL ARRANGEMENTS, now U.S. Pat. No. 10,772,629;

U.S. patent application Ser. No. 15/634,046, entitled SURGICAL ANVIL ARRANGEMENTS, now U.S. Pat. No. 10,993,716;

U.S. patent application Ser. No. 15/634,054, entitled SURGICAL ANVIL ARRANGEMENTS, now U.S. Pat. No. 10,856,869;

U.S. patent application Ser. No. 15/634,068, entitled SURGICAL FIRING MEMBER ARRANGEMENTS, now U.S. Patent Application Publication No. 2018/0368843;

U.S. patent application Ser. No. 15/634,076, entitled STAPLE FORMING POCKET ARRANGEMENTS, now U.S. Patent Application Publication No. 2018/0368844;

U.S. patent application Ser. No. 15/634,090, entitled STAPLE FORMING POCKET ARRANGEMENTS, now U.S. Patent Application Publication No. 2018/0368845;

U.S. patent application Ser. No. 15/634,099, entitled SURGICAL END EFFECTORS AND ANVILS, now U.S. Patent Application Publication No. 2018/0368846; and U.S. patent application Ser. No. 15/634,117, entitled ARTICULATION SYSTEMS FOR SURGICAL INSTRUMENTS, now U.S. Pat. No. 10,631,859.

Applicant of the present application owns the following U.S. Patent Applications that were filed on Dec. 21, 2016 and which are each herein incorporated by reference in their respective entireties:

U.S. patent application Ser. No. 15/386,185, entitled SURGICAL STAPLING INSTRUMENTS AND REPLACEABLE TOOL ASSEMBLIES THEREOF, now U.S. Pat. No. 10,639,035;

U.S. patent application Ser. No. 15/386,230, entitled ARTICULATABLE SURGICAL STAPLING INSTRUMENTS, now U.S. Patent Application Publication No. 2018/0168649;

U.S. patent application Ser. No. 15/386,221, entitled LOCKOUT ARRANGEMENTS FOR SURGICAL END EFFECTORS, now U.S. Pat. No. 10,835,247;

U.S. patent application Ser. No. 15/386,209, entitled SURGICAL END EFFECTORS AND FIRING MEMBERS THEREOF, now U.S. Pat. No. 10,588,632;

U.S. patent application Ser. No. 15/386,198, entitled LOCKOUT ARRANGEMENTS FOR SURGICAL END EFFECTORS AND REPLACEABLE TOOL ASSEMBLIES, now U.S. Pat. No. 10,610,224;

U.S. patent application Ser. No. 15/386,240, entitled SURGICAL END EFFECTORS AND ADAPTABLE FIRING MEMBERS THEREFOR, now U.S. Pat. No. 10,973,516;

U.S. patent application Ser. No. 15/385,939, entitled STAPLE CARTRIDGES AND ARRANGEMENTS OF STAPLES AND STAPLE CAVITIES THEREIN, now U.S. Pat. No. 10,835,246;

U.S. patent application Ser. No. 15/385,941, entitled SURGICAL TOOL ASSEMBLIES WITH CLUTCHING ARRANGEMENTS FOR SHIFTING BETWEEN CLOSURE SYSTEMS WITH CLOSURE STROKE REDUCTION FEATURES AND ARTICULATION AND FIRING SYSTEMS, now U.S. Pat. No. 10,736,629;

U.S. patent application Ser. No. 15/385,943, entitled SURGICAL STAPLING INSTRUMENTS AND STAPLE-FORMING ANVILS, now U.S. Pat. No. 10,667,811;

U.S. patent application Ser. No. 15/385,950, entitled SURGICAL TOOL ASSEMBLIES WITH CLOSURE STROKE REDUCTION FEATURES, now U.S. Pat. No. 10,588,630;

U.S. patent application Ser. No. 15/385,945, entitled STAPLE CARTRIDGES AND ARRANGEMENTS OF STAPLES AND STAPLE CAVITIES THEREIN, now U.S. Pat. No. 10,893,864;

U.S. patent application Ser. No. 15/385,946, entitled SURGICAL STAPLING INSTRUMENTS AND STAPLE-FORMING ANVILS, now U.S. Patent Application Publication No. 2018/0168633;

U.S. patent application Ser. No. 15/385,951, entitled SURGICAL INSTRUMENTS WITH JAW OPENING FEATURES FOR INCREASING A JAW OPENING DISTANCE, now U.S. Pat. No. 10,568,626;

U.S. patent application Ser. No. 15/385,953, entitled METHODS OF STAPLING TISSUE, now U.S. Pat. No. 10,675,026;

U.S. patent application Ser. No. 15/385,954, entitled FIRING MEMBERS WITH NON-PARALLEL JAW ENGAGEMENT FEATURES FOR SURGICAL END EFFECTORS, now U.S. Pat. No. 10,624,635;

U.S. patent application Ser. No. 15/385,955, entitled SURGICAL END EFFECTORS WITH EXPANDABLE TISSUE STOP ARRANGEMENTS, now U.S. Pat. No. 10,813,638;

U.S. patent application Ser. No. 15/385,948, entitled SURGICAL STAPLING INSTRUMENTS AND STAPLE-FORMING ANVILS, now U.S. Patent Application Publication No. 2018/0168584;

U.S. patent application Ser. No. 15/385,956, entitled SURGICAL INSTRUMENTS WITH POSITIVE JAW OPENING FEATURES, now U.S. Pat. No. 10,588,631;

U.S. patent application Ser. No. 15/385,958, entitled SURGICAL INSTRUMENTS WITH LOCKOUT ARRANGEMENTS FOR PREVENTING FIRING SYSTEM ACTUATION UNLESS AN UNSPENT STAPLE CARTRIDGE IS PRESENT, now U.S. Pat. No. 10,639,034;

U.S. patent application Ser. No. 15/385,947, entitled STAPLE CARTRIDGES AND ARRANGEMENTS OF STAPLES AND STAPLE CAVITIES THEREIN, now U.S. Pat. No. 10,568,625;

U.S. patent application Ser. No. 15/385,896, entitled METHOD FOR RESETTING A FUSE OF A SURGICAL INSTRUMENT SHAFT, now U.S. Patent Application Publication No. 2018/0168597;

U.S. patent application Ser. No. 15/385,898, entitled STAPLE FORMING POCKET ARRANGEMENT TO ACCOMMODATE DIFFERENT TYPES OF STAPLES, now U.S. Pat. No. 10,537,325;

U.S. patent application Ser. No. 15/385,899, entitled SURGICAL INSTRUMENT COMPRISING IMPROVED JAW CONTROL, now U.S. Pat. No. 10,758,229;

U.S. patent application Ser. No. 15/385,901, entitled STAPLE CARTRIDGE AND STAPLE CARTRIDGE CHANNEL COMPRISING WINDOWS DEFINED THEREIN, now U.S. Pat. No. 10,667,809;

U.S. patent application Ser. No. 15/385,902, entitled SURGICAL INSTRUMENT COMPRISING A CUTTING MEMBER, now U.S. Pat. No. 10,888,322;

U.S. patent application Ser. No. 15/385,904, entitled STAPLE FIRING MEMBER COMPRISING A MISSING CARTRIDGE AND/OR SPENT CARTRIDGE LOCKOUT, now U.S. Pat. No. 10,881,401;

U.S. patent application Ser. No. 15/385,905, entitled FIRING ASSEMBLY COMPRISING A LOCKOUT, now U.S. Pat. No. 10,695,055;

U.S. patent application Ser. No. 15/385,907, entitled SURGICAL INSTRUMENT SYSTEM COMPRISING AN END EFFECTOR LOCKOUT AND A FIRING ASSEMBLY LOCKOUT, now U.S. Patent Application Publication No. 2018/0168608;

U.S. patent application Ser. No. 15/385,908, entitled FIRING ASSEMBLY COMPRISING A FUSE, now U.S. Patent Application Publication No. 2018/0168609;

U.S. patent application Ser. No. 15/385,909, entitled FIRING ASSEMBLY COMPRISING A MULTIPLE FAILED-STATE FUSE, now U.S. Patent Application Publication No. 2018/0168610;

U.S. patent application Ser. No. 15/385,920, entitled STAPLE FORMING POCKET ARRANGEMENTS, now U.S. Pat. No. 10,499,914;

U.S. patent application Ser. No. 15/385,913, entitled ANVIL ARRANGEMENTS FOR SURGICAL STAPLE/FASTENERS, now U.S. Patent Application Publication No. 2018/0168614;

U.S. patent application Ser. No. 15/385,914, entitled METHOD OF DEFORMING STAPLES FROM TWO DIFFERENT TYPES OF STAPLE CARTRIDGES WITH THE SAME SURGICAL STAPLING INSTRUMENT, now U.S. Patent Application Publication No. 2018/0168615;

U.S. patent application Ser. No. 15/385,893, entitled BILATERALLY ASYMMETRIC STAPLE FORMING POCKET PAIRS, now U.S. Pat. No. 10,682,138;

U.S. patent application Ser. No. 15/385,929, entitled CLOSURE MEMBERS WITH CAM SURFACE ARRANGEMENTS FOR SURGICAL INSTRUMENTS WITH SEPARATE AND DISTINCT CLOSURE AND FIRING SYSTEMS, now U.S. Pat. No. 10,667,810;

U.S. patent application Ser. No. 15/385,911, entitled SURGICAL STAPLE/FASTENERS WITH INDEPENDENTLY ACTUATABLE CLOSING AND FIRING SYSTEMS, now U.S. Pat. No. 10,448,950;

U.S. patent application Ser. No. 15/385,927, entitled SURGICAL STAPLING INSTRUMENTS WITH SMART STAPLE CARTRIDGES, now U.S. Patent Application Publication No. 2018/0168625;

U.S. patent application Ser. No. 15/385,917, entitled STAPLE CARTRIDGE COMPRISING STAPLES WITH DIFFERENT CLAMPING BREADTHS, now U.S. Pat. No. 10,993,715;

U.S. patent application Ser. No. 15/385,900, entitled STAPLE FORMING POCKET ARRANGEMENTS COMPRISING PRIMARY SIDEWALLS AND POCKET SIDEWALLS, now U.S. Pat. No. 10,898,186;

U.S. patent application Ser. No. 15/385,931, entitled NO-CARTRIDGE AND SPENT CARTRIDGE LOCKOUT ARRANGEMENTS FOR SURGICAL STAPLE/FASTENERS, now U.S. Pat. No. 10,980,536;

U.S. patent application Ser. No. 15/385,915, entitled FIRING MEMBER PIN ANGLE, now U.S. Pat. No. 10,779,823;

U.S. patent application Ser. No. 15/385,897, entitled STAPLE FORMING POCKET ARRANGEMENTS COMPRISING ZONED FORMING SURFACE GROOVES, now U.S. Patent Application Publication No. 2018/0168598;

U.S. patent application Ser. No. 15/385,922, entitled SURGICAL INSTRUMENT WITH MULTIPLE FAILURE RESPONSE MODES, now U.S. Pat. No. 10,426,471;

U.S. patent application Ser. No. 15/385,924, entitled SURGICAL INSTRUMENT WITH PRIMARY AND SAFETY PROCESSORS, now U.S. Pat. No. 10,758,230;

U.S. patent application Ser. No. 15/385,912, entitled SURGICAL INSTRUMENTS WITH JAWS THAT ARE PIVOTABLE ABOUT A FIXED AXIS AND INCLUDE SEPARATE AND DISTINCT CLOSURE AND FIRING SYSTEMS, now U.S. Pat. No. 10,568,624;

U.S. patent application Ser. No. 15/385,910, entitled ANVIL HAVING A KNIFE SLOT WIDTH, now U.S. Pat. No. 10,485,543;

U.S. patent application Ser. No. 15/385,906, entitled FIRING MEMBER PIN CONFIGURATIONS, now U.S. Pat. No. 10,856,868;

U.S. patent application Ser. No. 15/386,188, entitled STEPPED STAPLE CARTRIDGE WITH ASYMMETRICAL STAPLES, now U.S. Pat. No. 10,537,324;

U.S. patent application Ser. No. 15/386,192, entitled STEPPED STAPLE CARTRIDGE WITH TISSUE RETENTION AND GAP SETTING FEATURES, now U.S. Pat. No. 10,687,810;

U.S. patent application Ser. No. 15/386,206, entitled STAPLE CARTRIDGE WITH DEFORMABLE DRIVER RETENTION FEATURES, now U.S. Pat. No. 10,945,727;

U.S. patent application Ser. No. 15/386,226, entitled DURABILITY FEATURES FOR END EFFECTORS AND FIRING ASSEMBLIES OF SURGICAL STAPLING INSTRUMENTS, now U.S. Patent Application Publication No. 2018/0168648;

U.S. patent application Ser. No. 15/386,222, entitled SURGICAL STAPLING INSTRUMENTS HAVING END EFFECTORS WITH POSITIVE OPENING FEATURES, now U.S. Patent Application Publication No. 2018/0168647;

U.S. patent application Ser. No. 15/386,236, entitled CONNECTION PORTIONS FOR DEPOSABLE LOADING UNITS FOR SURGICAL STAPLING INSTRUMENTS, now U.S. Patent Application Publication No. 2018/0168650;

U.S. patent application Ser. No. 15/385,887, entitled METHOD FOR ATTACHING A SHAFT ASSEMBLY TO A SURGICAL INSTRUMENT AND, ALTERNATIVELY, TO A SURGICAL ROBOT, now U.S. Pat. No. 10,835,245;

U.S. patent application Ser. No. 15/385,889, entitled SHAFT ASSEMBLY COMPRISING A MANUALLY-OPERABLE RETRACTION SYSTEM FOR USE WITH A MOTORIZED SURGICAL INSTRUMENT SYSTEM, now U.S. Patent Application Publication No. 2018/0168590;

U.S. patent application Ser. No. 15/385,890, entitled SHAFT ASSEMBLY COMPRISING SEPARATELY ACTUATABLE AND RETRACTABLE SYSTEMS, now U.S. Pat. No. 10,675,025;

U.S. patent application Ser. No. 15/385,891, entitled SHAFT ASSEMBLY COMPRISING A CLUTCH CONFIGURED TO ADAPT THE OUTPUT OF A ROTARY FIRING MEMBER TO TWO DIFFERENT SYSTEMS, now U.S. Patent Application Publication No. 2018/0168592;

U.S. patent application Ser. No. 15/385,892, entitled SURGICAL SYSTEM COMPRISING A FIRING MEMBER ROTATABLE INTO AN ARTICULATION STATE TO ARTICULATE AN END EFFECTOR OF THE SURGICAL SYSTEM, now U.S. Pat. No. 10,918,385;

U.S. patent application Ser. No. 15/385,894, entitled SHAFT ASSEMBLY COMPRISING A LOCKOUT, now U.S. Pat. No. 10,492,785;

U.S. patent application Ser. No. 15/385,895, entitled SHAFT ASSEMBLY COMPRISING FIRST AND SECOND ARTICULATION LOCKOUTS, now U.S. Pat. No. 10,542,982;

U.S. patent application Ser. No. 15/385,916, entitled SURGICAL STAPLING SYSTEMS, now U.S. Patent Application Publication No. 2018/0168575;

U.S. patent application Ser. No. 15/385,918, entitled SURGICAL STAPLING SYSTEMS, now U.S. Patent Application Publication No. 2018/0168618;

U.S. patent application Ser. No. 15/385,919, entitled SURGICAL STAPLING SYSTEMS, now U.S. Patent Application Publication No. 2018/0168619;

U.S. patent application Ser. No. 15/385,921, entitled SURGICAL STAPLE/FASTENER CARTRIDGE WITH MOVABLE CAMMING MEMBER CONFIGURED TO DISENGAGE FIRING MEMBER LOCKOUT FEATURES, now U.S. Pat. No. 10,687,809;

U.S. patent application Ser. No. 15/385,923, entitled SURGICAL STAPLING SYSTEMS, now U.S. Patent Application Publication No. 2018/0168623;

U.S. patent application Ser. No. 15/385,925, entitled JAW ACTUATED LOCK ARRANGEMENTS FOR PREVENTING ADVANCEMENT OF A FIRING MEMBER IN A SURGICAL END EFFECTOR UNLESS AN UNFIRED CARTRIDGE IS INSTALLED IN THE END EFFECTOR, now U.S. Pat. No. 10,517,595;

U.S. patent application Ser. No. 15/385,926, entitled AXIALLY MOVABLE CLOSURE SYSTEM ARRANGEMENTS FOR APPLYING CLOSURE MOTIONS TO JAWS OF SURGICAL INSTRUMENTS, now U.S. Patent Application Publication No. 2018/0168577;

U.S. patent application Ser. No. 15/385,928, entitled PROTECTIVE COVER ARRANGEMENTS FOR A JOINT INTERFACE BETWEEN A MOVABLE JAW AND ACTUATOR SHAFT OF A SURGICAL INSTRUMENT, now U.S. Patent Application Publication No. 2018/0168578;

U.S. patent application Ser. No. 15/385,930, entitled SURGICAL END EFFECTOR WITH TWO SEPARATE COOPERATING OPENING FEATURES FOR OPENING AND CLOSING END EFFECTOR JAWS, now U.S. Patent Application Publication No. 2018/0168579;

U.S. patent application Ser. No. 15/385,932, entitled ARTICULATABLE SURGICAL END EFFECTOR WITH ASYMMETRIC SHAFT ARRANGEMENT, now U.S. Pat. No. 10,959,727;

U.S. patent application Ser. No. 15/385,933, entitled ARTICULATABLE SURGICAL INSTRUMENT WITH INDEPENDENT PIVOTABLE LINKAGE DISTAL OF AN ARTICULATION LOCK, now U.S. Pat. No. 10,603,036;

U.S. patent application Ser. No. 15/385,934, entitled ARTICULATION LOCK ARRANGEMENTS FOR LOCKING AN END EFFECTOR IN AN ARTICULATED POSITION IN RESPONSE TO ACTUATION OF A JAW CLOSURE SYSTEM, now U.S. Pat. No. 10,582,928;

U.S. patent application Ser. No. 15/385,935, entitled LATERALLY ACTUATABLE ARTICULATION LOCK ARRANGEMENTS FOR LOCKING AN END EFFECTOR OF A SURGICAL INSTRUMENT IN AN ARTICULATED CONFIGURATION, now U.S. Pat. No. 10,524,789; and U.S. patent application Ser. No. 15/385,936, entitled ARTICULATABLE SURGICAL INSTRUMENTS WITH ARTICULATION STROKE AMPLIFICATION FEATURES, now U.S. Pat. No. 10,517,596.

Applicant of the present application owns the following U.S. Patent Applications that were filed on Jun. 24, 2016 and which are each herein incorporated by reference in their respective entireties:

U.S. patent application Ser. No. 15/191,775, entitled STAPLE CARTRIDGE COMPRISING WIRE STAPLES AND STAMPED STAPLES, now U.S. Pat. No. 11,000,278;

U.S. patent application Ser. No. 15/191,807, entitled STAPLING SYSTEM FOR USE WITH WIRE STAPLES AND STAMPED STAPLES, now U.S. Pat. No. 10,702,270;

U.S. patent application Ser. No. 15/191,834, entitled STAMPED STAPLES AND STAPLE CARTRIDGES USING THE SAME, now U.S. Pat. No. 10,542,979;

U.S. patent application Ser. No. 15/191,788, entitled STAPLE CARTRIDGE COMPRISING OVER-DRIVEN STAPLES, now U.S. Pat. No. 10,675,024; and U.S. patent application Ser. No. 15/191,818, entitled STAPLE CARTRIDGE COMPRISING OFFSET LONGITUDINAL STAPLE ROWS, now U.S. Pat. No. 10,893,863.

Applicant of the present application owns the following U.S. Patent Applications that were filed on Jun. 24, 2016 and which are each herein incorporated by reference in their respective entireties:

U.S. Design patent application Ser. No. 29/569,218, entitled SURGICAL FASTENER, now U.S. Design Pat. No. D826,405;

U.S. Design patent application Ser. No. 29/569,227, entitled SURGICAL FASTENER, now U.S. Design Pat. No. D822,206;

U.S. Design patent application Ser. No. 29/569,259, entitled SURGICAL FASTENER CARTRIDGE, now U.S. Design Pat. No. D847,989; and U.S. Design patent application Ser. No. 29/569,264, entitled SURGICAL FASTENER CARTRIDGE, now U.S. Design Pat. No. D850,617.

Applicant of the present application owns the following patent applications that were filed on Apr. 1, 2016 and which are each herein incorporated by reference in their respective entirety:

U.S. patent application Ser. No. 15/089,325, entitled METHOD FOR OPERATING A SURGICAL STAPLING SYSTEM, now U.S. Patent Application Publication No. 2017/0281171;

U.S. patent application Ser. No. 15/089,321, entitled MODULAR SURGICAL STAPLING SYSTEM COMPRISING A DISPLAY, now U.S. Pat. No. 10,271,851;

U.S. patent application Ser. No. 15/089,326, entitled SURGICAL STAPLING SYSTEM COMPRISING A DISPLAY INCLUDING A RE-ORIENTABLE DISPLAY FIELD, now U.S. Pat. No. 10,433,849;

U.S. patent application Ser. No. 15/089,263, entitled SURGICAL INSTRUMENT HANDLE ASSEMBLY WITH RECONFIGURABLE GRIP PORTION, now U.S. Pat. No. 10,307,159;

U.S. patent application Ser. No. 15/089,262, entitled ROTARY POWERED SURGICAL INSTRUMENT WITH MANUALLY ACTUATABLE BAILOUT SYSTEM, now U.S. Pat. No. 10,357,246;

U.S. patent application Ser. No. 15/089,277, entitled SURGICAL CUTTING AND STAPLING END EFFECTOR WITH ANVIL CONCENTRIC DRIVE MEMBER, now U.S. Pat. No. 10,531,874;

U.S. patent application Ser. No. 15/089,296, entitled INTERCHANGEABLE SURGICAL TOOL ASSEMBLY WITH A SURGICAL END EFFECTOR THAT IS SELECTIVELY ROTATABLE ABOUT A SHAFT AXIS, now U.S. Pat. No. 10,413,293;

U.S. patent application Ser. No. 15/089,258, entitled SURGICAL STAPLING SYSTEM COMPRISING A SHIFTABLE TRANSMISSION, now U.S. Pat. No. 10,342,543;

U.S. patent application Ser. No. 15/089,278, entitled SURGICAL STAPLING SYSTEM CONFIGURED TO PROVIDE SELECTIVE CUTTING OF TISSUE, now U.S. Pat. No. 10,420,552;

U.S. patent application Ser. No. 15/089,284, entitled SURGICAL STAPLING SYSTEM COMPRISING A CONTOURABLE SHAFT, now U.S. Patent Application Publication No. 2017/0281186;

U.S. patent application Ser. No. 15/089,295, entitled SURGICAL STAPLING SYSTEM COMPRISING A TISSUE COMPRESSION LOCKOUT, now U.S. Pat. No. 10,856,867;

U.S. patent application Ser. No. 15/089,300, entitled SURGICAL STAPLING SYSTEM COMPRISING AN UNCLAMPING LOCKOUT, now U.S. Pat. No. 10,456,140;

U.S. patent application Ser. No. 15/089,196, entitled SURGICAL STAPLING SYSTEM COMPRISING A JAW CLOSURE LOCKOUT, now U.S. Pat. No. 10,568,632;

U.S. patent application Ser. No. 15/089,203, entitled SURGICAL STAPLING SYSTEM COMPRISING A JAW ATTACHMENT LOCKOUT, now U.S. Pat. No. 10,542,991;

U.S. patent application Ser. No. 15/089,210, entitled SURGICAL STAPLING SYSTEM COMPRISING A SPENT CARTRIDGE LOCKOUT, now U.S. Pat. No. 10,478,190;

U.S. patent application Ser. No. 15/089,324, entitled SURGICAL INSTRUMENT COMPRISING A SHIFTING MECHANISM, now U.S. Pat. No. 10,314,582;

U.S. patent application Ser. No. 15/089,335, entitled SURGICAL STAPLING INSTRUMENT COMPRISING MULTIPLE LOCKOUTS, now U.S. Pat. No. 10,485,542;

U.S. patent application Ser. No. 15/089,339, entitled SURGICAL STAPLING INSTRUMENT, now U.S. Patent Application Publication No. 2017/0281173;

U.S. patent application Ser. No. 15/089,253, entitled SURGICAL STAPLING SYSTEM CONFIGURED TO APPLY ANNULAR ROWS OF STAPLES HAVING DIFFERENT HEIGHTS, now U.S. Pat. No. 10,413,297;

U.S. patent application Ser. No. 15/089,304, entitled SURGICAL STAPLING SYSTEM COMPRISING A GROOVED FORMING POCKET, now U.S. Pat. No. 10,285,705;

U.S. patent application Ser. No. 15/089,331, entitled ANVIL MODIFICATION MEMBERS FOR SURGICAL STAPLE/FASTENERS, now U.S. Pat. No. 10,376,263;

U.S. patent application Ser. No. 15/089,336, entitled STAPLE CARTRIDGES WITH ATRAUMATIC FEATURES, now U.S. Pat. No. 10,709,446;

U.S. patent application Ser. No. 15/089,312, entitled CIRCULAR STAPLING SYSTEM COMPRISING AN INCISABLE TISSUE SUPPORT, now U.S. Patent Application Publication No. 2017/0281189;

U.S. patent application Ser. No. 15/089,309, entitled CIRCULAR STAPLING SYSTEM COMPRISING ROTARY FIRING SYSTEM, now U.S. Pat. No. 10,675,021; and U.S. patent application Ser. No. 15/089,349, entitled CIRCULAR STAPLING SYSTEM COMPRISING LOAD CONTROL, now U.S. Pat. No. 10,682,136.

Applicant of the present application also owns the U.S. Patent Applications identified below which were filed on Dec. 31, 2015 which are each herein incorporated by reference in their respective entirety:

U.S. patent application Ser. No. 14/984,488, entitled MECHANISMS FOR COMPENSATING FOR BATTERY PACK FAILURE IN POWERED SURGICAL INSTRUMENTS, now U.S. Pat. No. 10,292,704;

U.S. patent application Ser. No. 14/984,525, entitled MECHANISMS FOR COMPENSATING FOR DRIVETRAIN FAILURE IN POWERED SURGICAL INSTRUMENTS, now U.S. Pat. No. 10,368,865; and U.S. patent application Ser. No. 14/984,552, entitled SURGICAL INSTRUMENTS WITH SEPARABLE MOTORS AND MOTOR CONTROL CIRCUITS, now U.S. Pat. No. 10,265,068.

Applicant of the present application also owns the U.S. Patent Applications identified below which were filed on Feb. 9, 2016 which are each herein incorporated by reference in their respective entirety:

U.S. patent application Ser. No. 15/019,220, entitled SURGICAL INSTRUMENT WITH ARTICULATING AND AXIALLY TRANSLATABLE END EFFECTOR, now U.S. Pat. No. 10,245,029;

U.S. patent application Ser. No. 15/019,228, entitled SURGICAL INSTRUMENTS WITH MULTIPLE LINK ARTICULATION ARRANGEMENTS, now U.S. Pat. No. 10,433,837;

U.S. patent application Ser. No. 15/019,196, entitled SURGICAL INSTRUMENT ARTICULATION MECHANISM WITH SLOTTED SECONDARY CONSTRAINT, now U.S. Pat. No. 10,413,291;

U.S. patent application Ser. No. 15/019,206, entitled SURGICAL INSTRUMENTS WITH AN END EFFECTOR THAT IS HIGHLY ARTICULATABLE RELATIVE TO AN ELONGATE SHAFT ASSEMBLY, now U.S. Pat. No. 10,653,413;

U.S. patent application Ser. No. 15/019,215, entitled SURGICAL INSTRUMENTS WITH NON-SYMMETRICAL ARTICULATION ARRANGEMENTS, now U.S. Patent Application Publication No. 2017/0224332;

U.S. patent application Ser. No. 15/019,227, entitled ARTICULATABLE SURGICAL INSTRUMENTS WITH SINGLE ARTICULATION LINK ARRANGEMENTS, now U.S. Patent Application Publication No. 2017/0224334;

U.S. patent application Ser. No. 15/019,235, entitled SURGICAL INSTRUMENTS WITH TENSIONING ARRANGEMENTS FOR CABLE DRIVEN ARTICULATION SYSTEMS, now U.S. Pat. No. 10,245,030;

U.S. patent application Ser. No. 15/019,230, entitled ARTICULATABLE SURGICAL INSTRUMENTS WITH OFF-AXIS FIRING BEAM ARRANGEMENTS, now U.S. Pat. No. 10,588,625; and U.S. patent application Ser. No. 15/019,245, entitled SURGICAL INSTRUMENTS WITH CLOSURE STROKE REDUCTION ARRANGEMENTS, now U.S. Pat. No. 10,470,764.

Applicant of the present application also owns the U.S. Patent Applications identified below which were filed on Feb. 12, 2016 which are each herein incorporated by reference in their respective entirety:

U.S. patent application Ser. No. 15/043,254, entitled MECHANISMS FOR COMPENSATING FOR DRIVETRAIN FAILURE IN POWERED SURGICAL INSTRUMENTS, now U.S. Pat. No. 10,258,331;

U.S. patent application Ser. No. 15/043,259, entitled MECHANISMS FOR COMPENSATING FOR DRIVETRAIN FAILURE IN POWERED SURGICAL INSTRUMENTS, now U.S. Pat. No. 10,448,948;

U.S. patent application Ser. No. 15/043,275, entitled MECHANISMS FOR COMPENSATING FOR DRIVETRAIN FAILURE IN POWERED SURGICAL INSTRUMENTS, now U.S. Patent Application Publication No. 2017/0231627; and U.S. patent application Ser. No. 15/043,289, entitled MECHANISMS FOR COMPENSATING FOR DRIVETRAIN FAILURE IN POWERED SURGICAL INSTRUMENTS, now U.S. Patent Application Publication No. 2017/0231628.

Applicant of the present application owns the following patent applications that were filed on Jun. 18, 2015 and which are each herein incorporated by reference in their respective entirety:

U.S. patent application Ser. No. 14/742,925, entitled SURGICAL END EFFECTORS WITH POSITIVE JAW OPENING ARRANGEMENTS, now U.S. Pat. No. 10,182,818;

U.S. patent application Ser. No. 14/742,941, entitled SURGICAL END EFFECTORS WITH DUAL CAM ACTUATED JAW CLOSING FEATURES, now U.S. Pat. No. 10,052,102;

U.S. patent application Ser. No. 14/742,914, entitled MOVABLE FIRING BEAM SUPPORT ARRANGEMENTS FOR ARTICULATABLE SURGICAL INSTRUMENTS, now U.S. Pat. No. 10,405,863;

U.S. patent application Ser. No. 14/742,900, entitled ARTICULATABLE SURGICAL INSTRUMENTS WITH COMPOSITE FIRING BEAM STRUCTURES WITH CENTER FIRING SUPPORT MEMBER FOR ARTICULATION SUPPORT, now U.S. Pat. No. 10,335,149;

U.S. patent application Ser. No. 14/742,885, entitled DUAL ARTICULATION DRIVE SYSTEM ARRANGEMENTS FOR ARTICULATABLE SURGICAL INSTRUMENTS, now U.S. Pat. No. 10,368,861; and U.S. patent application Ser. No. 14/742,876, entitled PUSH/PULL ARTICULATION DRIVE SYSTEMS FOR ARTICULATABLE SURGICAL INSTRUMENTS, now U.S. Pat. No. 10,178,992.

Applicant of the present application owns the following patent applications that were filed on Mar. 6, 2015 and which are each herein incorporated by reference in their respective entirety:

U.S. patent application Ser. No. 14/640,746, entitled POWERED SURGICAL INSTRUMENT, now U.S. Pat. No. 9,808,246;

U.S. patent application Ser. No. 14/640,795, entitled MULTIPLE LEVEL THRESHOLDS TO MODIFY OPERATION OF POWERED SURGICAL INSTRUMENTS, now U.S. Pat. No. 10,441,279;

U.S. patent application Ser. No. 14/640,832, entitled ADAPTIVE TISSUE COMPRESSION TECHNIQUES TO ADJUST CLOSURE RATES FOR MULTIPLE TISSUE TYPES, now U.S. Pat. No. 10,687,806;

U.S. patent application Ser. No. 14/640,935, entitled OVERLAID MULTI SENSOR RADIO FREQUENCY (RF) ELECTRODE SYSTEM TO MEASURE TISSUE COMPRESSION, now U.S. Pat. No. 10,548,504;

U.S. patent application Ser. No. 14/640,831, entitled MONITORING SPEED CONTROL AND PRECISION INCREMENTING OF MOTOR FOR POWERED SURGICAL INSTRUMENTS, now U.S. Pat. No. 9,895,148;

U.S. patent application Ser. No. 14/640,859, entitled TIME DEPENDENT EVALUATION OF SENSOR DATA TO DETERMINE STABILITY, CREEP, AND VISCOELASTIC ELEMENTS OF MEASURES, now U.S. Pat. No. 10,052,044;

U.S. patent application Ser. No. 14/640,817, entitled INTERACTIVE FEEDBACK SYSTEM FOR POWERED SURGICAL INSTRUMENTS, now U.S. Pat. No. 9,924,961;

U.S. patent application Ser. No. 14/640,844, entitled CONTROL TECHNIQUES AND SUB-PROCESSOR CONTAINED WITHIN MODULAR SHAFT WITH SELECT CONTROL PROCESSING FROM HANDLE, now U.S. Pat. No. 10,045,776;

U.S. patent application Ser. No. 14/640,837, entitled SMART SENSORS WITH LOCAL SIGNAL PROCESSING, now U.S. Pat. No. 9,993,248;

U.S. patent application Ser. No. 14/640,765, entitled SYSTEM FOR DETECTING THE MIS-INSERTION OF A STAPLE CARTRIDGE INTO A SURGICAL STAPLE/FASTENER, now U.S. Pat. No. 10,617,412;

U.S. patent application Ser. No. 14/640,799, entitled SIGNAL AND POWER COMMUNICATION SYSTEM POSITIONED ON A ROTATABLE SHAFT, now U.S. Pat. No. 9,901,342; and U.S. patent application Ser. No. 14/640,780, entitled SURGICAL INSTRUMENT COMPRISING A LOCKABLE BATTERY HOUSING, now U.S. Pat. No. 10,245,033.

Applicant of the present application owns the following patent applications that were filed on Feb. 27, 2015, and which are each herein incorporated by reference in their respective entirety:

U.S. patent application Ser. No. 14/633,576, entitled SURGICAL INSTRUMENT SYSTEM COMPRISING AN INSPECTION STATION, now U.S. Pat. No. 10,045,779;

U.S. patent application Ser. No. 14/633,546, entitled SURGICAL APPARATUS CONFIGURED TO ASSESS WHETHER A PERFORMANCE PARAMETER OF THE SURGICAL APPARATUS IS WITHIN AN ACCEPTABLE PERFORMANCE BAND, now U.S. Pat. No. 10,180,463;

U.S. patent application Ser. No. 14/633,560, entitled SURGICAL CHARGING SYSTEM THAT CHARGES AND/OR CONDITIONS ONE OR MORE BATTERIES, now U.S. Patent Application Publication No. 2016/0249910;

U.S. patent application Ser. No. 14/633,566, entitled CHARGING SYSTEM THAT ENABLES EMERGENCY RESOLUTIONS FOR CHARGING A BATTERY, now U.S. Pat. No. 10,182,816;

U.S. patent application Ser. No. 14/633,555, entitled SYSTEM FOR MONITORING WHETHER A SURGICAL INSTRUMENT NEEDS TO BE SERVICED, now U.S. Pat. No. 10,321,907;

U.S. patent application Ser. No. 14/633,542, entitled REINFORCED BATTERY FOR A SURGICAL INSTRUMENT, now U.S. Pat. No. 9,931,118;

U.S. patent application Ser. No. 14/633,548, entitled POWER ADAPTER FOR A SURGICAL INSTRUMENT, now U.S. Pat. No. 10,245,028;

U.S. patent application Ser. No. 14/633,526, entitled ADAPTABLE SURGICAL INSTRUMENT HANDLE, now U.S. Pat. No. 9,993,258;

U.S. patent application Ser. No. 14/633,541, entitled MODULAR STAPLING ASSEMBLY, now U.S. Pat. No. 10,226,250; and U.S. patent application Ser. No. 14/633,562, entitled SURGICAL APPARATUS CONFIGURED TO TRACK AN END-OF-LIFE PARAMETER, now U.S. Pat. No. 10,159,483.

Applicant of the present application owns the following patent applications that were filed on Dec. 18, 2014 and which are each herein incorporated by reference in their respective entirety:

U.S. patent application Ser. No. 14/574,478, entitled SURGICAL INSTRUMENT SYSTEMS COMPRISING AN ARTICULATABLE END EFFECTOR AND MEANS FOR ADJUSTING THE FIRING STROKE OF A FIRING MEMBER, now U.S. Pat. No. 9,844,374;

U.S. patent application Ser. No. 14/574,483, entitled SURGICAL INSTRUMENT ASSEMBLY COMPRISING LOCKABLE SYSTEMS, now U.S. Pat. No. 10,188,385;

U.S. patent application Ser. No. 14/575,139, entitled DRIVE ARRANGEMENTS FOR ARTICULATABLE SURGICAL INSTRUMENTS, now U.S. Pat. No. 9,844,375;

U.S. patent application Ser. No. 14/575,148, entitled LOCKING ARRANGEMENTS FOR DETACHABLE SHAFT ASSEMBLIES WITH ARTICULATABLE SURGICAL END EFFECTORS, now U.S. Pat. No. 10,085,748;

U.S. patent application Ser. No. 14/575,130, entitled SURGICAL INSTRUMENT WITH AN ANVIL THAT IS SELECTIVELY MOVABLE ABOUT A DISCRETE NON-MOVABLE AXIS RELATIVE TO A STAPLE CARTRIDGE, now U.S. Pat. No. 10,245,027;

U.S. patent application Ser. No. 14/575,143, entitled SURGICAL INSTRUMENTS WITH IMPROVED CLOSURE ARRANGEMENTS, now U.S. Pat. No. 10,004,501;

U.S. patent application Ser. No. 14/575,117, entitled SURGICAL INSTRUMENTS WITH ARTICULATABLE END EFFECTORS AND MOVABLE FIRING BEAM SUPPORT ARRANGEMENTS, now U.S. Pat. No. 9,943,309;

U.S. patent application Ser. No. 14/575,154, entitled SURGICAL INSTRUMENTS WITH ARTICULATABLE END EFFECTORS AND IMPROVED FIRING BEAM SUPPORT ARRANGEMENTS, now U.S. Pat. No. 9,968,355;

U.S. patent application Ser. No. 14/574,493, entitled SURGICAL INSTRUMENT ASSEMBLY COMPRISING A FLEXIBLE ARTICULATION SYSTEM, now U.S. Pat. No. 9,987,000; and U.S. patent application Ser. No. 14/574,500, entitled SURGICAL INSTRUMENT ASSEMBLY COMPRISING A LOCKABLE ARTICULATION SYSTEM, now U.S. Pat. No. 10,117,649.

Applicant of the present application owns the following patent applications that were filed on Mar. 1, 2013 and which are each herein incorporated by reference in their respective entirety:

U.S. patent application Ser. No. 13/782,295, entitled ARTICULATABLE SURGICAL INSTRUMENTS WITH CONDUCTIVE PATHWAYS FOR SIGNAL COMMUNICATION, now U.S. Pat. No. 9,700,309;

U.S. patent application Ser. No. 13/782,323, entitled ROTARY POWERED ARTICULATION JOINTS FOR SURGICAL INSTRUMENTS, now U.S. Pat. No. 9,782,169;

U.S. patent application Ser. No. 13/782,338, entitled THUMBWHEEL SWITCH ARRANGEMENTS FOR SURGICAL INSTRUMENTS, now U.S. Patent Application Publication No. 2014/0249557;

U.S. patent application Ser. No. 13/782,499, entitled ELECTROMECHANICAL SURGICAL DEVICE WITH SIGNAL RELAY ARRANGEMENT, now U.S. Pat. No. 9,358,003;

U.S. patent application Ser. No. 13/782,460, entitled MULTIPLE PROCESSOR MOTOR CONTROL FOR MODULAR SURGICAL INSTRUMENTS, now U.S. Pat. No. 9,554,794;

U.S. patent application Ser. No. 13/782,358, entitled JOYSTICK SWITCH ASSEMBLIES FOR SURGICAL INSTRUMENTS, now U.S. Pat. No. 9,326,767;

U.S. patent application Ser. No. 13/782,481, entitled SENSOR STRAIGHTENED END EFFECTOR DURING REMOVAL THROUGH TROCAR, now U.S. Pat. No. 9,468,438;

U.S. patent application Ser. No. 13/782,518, entitled CONTROL METHODS FOR SURGICAL INSTRUMENTS WITH REMOVABLE IMPLEMENT PORTIONS, now U.S. Patent Application Publication No. 2014/0246475;

U.S. patent application Ser. No. 13/782,375, entitled ROTARY POWERED SURGICAL INSTRUMENTS WITH MULTIPLE DEGREES OF FREEDOM, now U.S. Pat. No. 9,398,911; and U.S. patent application Ser. No. 13/782,536, entitled SURGICAL INSTRUMENT SOFT STOP, now U.S. Pat. No. 9,307,986.

Applicant of the present application also owns the following patent applications that were filed on Mar. 14, 2013 and which are each herein incorporated by reference in their respective entirety:

U.S. patent application Ser. No. 13/803,097, entitled ARTICULATABLE SURGICAL INSTRUMENT COMPRISING A FIRING DRIVE, now U.S. Pat. No. 9,687,230;

U.S. patent application Ser. No. 13/803,193, entitled CONTROL ARRANGEMENTS FOR A DRIVE MEMBER OF A SURGICAL INSTRUMENT, now U.S. Pat. No. 9,332,987;

U.S. patent application Ser. No. 13/803,053, entitled INTERCHANGEABLE SHAFT ASSEMBLIES FOR USE WITH A SURGICAL INSTRUMENT, now U.S. Pat. No. 9,883,860;

U.S. patent application Ser. No. 13/803,086, entitled ARTICULATABLE SURGICAL INSTRUMENT COMPRISING AN ARTICULATION LOCK, now U.S. Patent Application Publication No. 2014/0263541;

U.S. patent application Ser. No. 13/803,210, entitled SENSOR ARRANGEMENTS FOR ABSOLUTE POSITIONING SYSTEM FOR SURGICAL INSTRUMENTS, now U.S. Pat. No. 9,808,244;

U.S. patent application Ser. No. 13/803,148, entitled MULTI-FUNCTION MOTOR FOR A SURGICAL INSTRUMENT, now U.S. Pat. No. 10,470,762;

U.S. patent application Ser. No. 13/803,066, entitled DRIVE SYSTEM LOCKOUT ARRANGEMENTS FOR MODULAR SURGICAL INSTRUMENTS, now U.S. Pat. No. 9,629,623;

U.S. patent application Ser. No. 13/803,117, entitled ARTICULATION CONTROL SYSTEM FOR ARTICULATABLE SURGICAL INSTRUMENTS, now U.S. Pat. No. 9,351,726;

U.S. patent application Ser. No. 13/803,130, entitled DRIVE TRAIN CONTROL ARRANGEMENTS FOR MODULAR SURGICAL INSTRUMENTS, now U.S. Pat. No. 9,351,727; and U.S. patent application Ser. No. 13/803,159, entitled METHOD AND SYSTEM FOR OPERATING A SURGICAL INSTRUMENT, now U.S. Pat. No. 9,888,919.

Applicant of the present application also owns the following patent application that was filed on Mar. 7, 2014 and is herein incorporated by reference in its entirety:

U.S. patent application Ser. No. 14/200,111, entitled CONTROL SYSTEMS FOR SURGICAL INSTRUMENTS, now U.S. Pat. No. 9,629,629.

Applicant of the present application also owns the following patent applications that were filed on Mar. 26, 2014 and are each herein incorporated by reference in their respective entirety:

U.S. patent application Ser. No. 14/226,106, entitled POWER MANAGEMENT CONTROL SYSTEMS FOR SURGICAL INSTRUMENTS, now U.S. Patent Application Publication No. 2015/0272582;

U.S. patent application Ser. No. 14/226,099, entitled STERILIZATION VERIFICATION CIRCUIT, now U.S. Pat. No. 9,826,977;

U.S. patent application Ser. No. 14/226,094, entitled VERIFICATION OF NUMBER OF BATTERY EXCHANGES/PROCEDURE COUNT, now U.S. Patent Application Publication No. 2015/0272580;

U.S. patent application Ser. No. 14/226,117, entitled POWER MANAGEMENT THROUGH SLEEP OPTIONS OF SEGMENTED CIRCUIT AND WAKE UP CONTROL, now U.S. Pat. No. 10,013,049;

U.S. patent application Ser. No. 14/226,075, entitled MODULAR POWERED SURGICAL INSTRUMENT WITH DETACHABLE SHAFT ASSEMBLIES, now U.S. Pat. No. 9,743,929;

U.S. patent application Ser. No. 14/226,093, entitled FEEDBACK ALGORITHMS FOR MANUAL BAILOUT SYSTEMS FOR SURGICAL INSTRUMENTS, now U.S. Pat. No. 10,028,761;

U.S. patent application Ser. No. 14/226,116, entitled SURGICAL INSTRUMENT UTILIZING SENSOR ADAPTATION, now U.S. Patent Application Publication No. 2015/0272571;

U.S. patent application Ser. No. 14/226,071, entitled SURGICAL INSTRUMENT CONTROL CIRCUIT HAVING A SAFETY PROCESSOR, now U.S. Pat. No. 9,690,362;

U.S. patent application Ser. No. 14/226,097, entitled SURGICAL INSTRUMENT COMPRISING INTERACTIVE SYSTEMS, now U.S. Pat. No. 9,820,738;

U.S. patent application Ser. No. 14/226,126, entitled INTERFACE SYSTEMS FOR USE WITH SURGICAL INSTRUMENTS, now U.S. Pat. No. 10,004,497;

U.S. patent application Ser. No. 14/226,133, entitled MODULAR SURGICAL INSTRUMENT SYSTEM, now U.S. Patent Application Publication No. 2015/0272557;

U.S. patent application Ser. No. 14/226,081, entitled SYSTEMS AND METHODS FOR CONTROLLING A SEGMENTED CIRCUIT, now U.S. Pat. No. 9,804,618;

U.S. patent application Ser. No. 14/226,076, entitled POWER MANAGEMENT THROUGH SEGMENTED CIRCUIT AND VARIABLE VOLTAGE PROTECTION, now U.S. Pat. No. 9,733,663;

U.S. patent application Ser. No. 14/226,111, entitled SURGICAL STAPLING INSTRUMENT SYSTEM, now U.S. Pat. No. 9,750,499; and U.S. patent application Ser. No. 14/226,125, entitled SURGICAL INSTRUMENT COMPRISING A ROTATABLE SHAFT, now U.S. Pat. No. 10,201,364.

Applicant of the present application also owns the following patent applications that were filed on Sep. 5, 2014 and which are each herein incorporated by reference in their respective entirety:

U.S. patent application Ser. No. 14/479,103, entitled CIRCUITRY AND SENSORS FOR POWERED MEDICAL DEVICE, now U.S. Pat. No. 10,111,679;

U.S. patent application Ser. No. 14/479,119, entitled ADJUNCT WITH INTEGRATED SENSORS TO QUANTIFY TISSUE COMPRESSION, now U.S. Pat. No. 9,724,094;

U.S. patent application Ser. No. 14/478,908, entitled MONITORING DEVICE DEGRADATION BASED ON COMPONENT EVALUATION, now U.S. Pat. No. 9,737,301;

U.S. patent application Ser. No. 14/478,895, entitled MULTIPLE SENSORS WITH ONE SENSOR AFFECTING A SECOND SENSOR'S OUTPUT OR INTERPRETATION, now U.S. Pat. No. 9,757,128;

U.S. patent application Ser. No. 14/479,110, entitled POLARITY OF HALL MAGNET TO DETECT MISLOADED CARTRIDGE, now U.S. Pat. No. 10,016,199;

U.S. patent application Ser. No. 14/479,098, entitled SMART CARTRIDGE WAKE UP OPERATION AND DATA RETENTION, now U.S. Pat. No. 10,135,242;

U.S. patent application Ser. No. 14/479,115, entitled MULTIPLE MOTOR CONTROL FOR POWERED MEDICAL DEVICE, now U.S. Pat. No. 9,788,836; and U.S. patent application Ser. No. 14/479,108, entitled LOCAL DISPLAY OF TISSUE PARAMETER STABILIZATION, now U.S. Patent Application Publication No. 2016/0066913.

Applicant of the present application also owns the following patent applications that were filed on Apr. 9, 2014 and which are each herein incorporated by reference in their respective entirety:

U.S. patent application Ser. No. 14/248,590, entitled MOTOR DRIVEN SURGICAL INSTRUMENTS WITH LOCKABLE DUAL DRIVE SHAFTS, now U.S. Pat. No. 9,826,976;

U.S. patent application Ser. No. 14/248,581, entitled SURGICAL INSTRUMENT COMPRISING A CLOSING DRIVE AND A FIRING DRIVE OPERATED FROM THE SAME ROTATABLE OUTPUT, now U.S. Pat. No. 9,649,110;

U.S. patent application Ser. No. 14/248,595, entitled SURGICAL INSTRUMENT SHAFT INCLUDING SWITCHES FOR CONTROLLING THE OPERATION OF THE SURGICAL INSTRUMENT, now U.S. Pat. No. 9,844,368;

U.S. patent application Ser. No. 14/248,588, entitled POWERED LINEAR SURGICAL STAPLE/FASTENER, now U.S. Pat. No. 10,405,857;

U.S. patent application Ser. No. 14/248,591, entitled TRANSMISSION ARRANGEMENT FOR A SURGICAL INSTRUMENT, now U.S. Pat. No. 10,149,680;

U.S. patent application Ser. No. 14/248,584, entitled MODULAR MOTOR DRIVEN SURGICAL INSTRUMENTS WITH ALIGNMENT FEATURES FOR ALIGNING ROTARY DRIVE SHAFTS WITH SURGICAL END EFFECTOR SHAFTS, now U.S. Pat. No. 9,801,626;

U.S. patent application Ser. No. 14/248,587, entitled POWERED SURGICAL STAPLE/FASTENER, now U.S. Pat. No. 9,867,612;

U.S. patent application Ser. No. 14/248,586, entitled DRIVE SYSTEM DECOUPLING ARRANGEMENT FORA SURGICAL INSTRUMENT, now U.S. Pat. No. 10,136,887; and U.S. patent application Ser. No. 14/248,607, entitled MODULAR MOTOR DRIVEN SURGICAL INSTRUMENTS WITH STATUS INDICATION ARRANGEMENTS, now U.S. Pat. No. 9,814,460.

Applicant of the present application also owns the following patent applications that were filed on Apr. 16, 2013 and which are each herein incorporated by reference in their respective entirety:

U.S. Provisional Patent Application Ser. No. 61/812,365, entitled SURGICAL INSTRUMENT WITH MULTIPLE FUNCTIONS PERFORMED BY A SINGLE MOTOR;

U.S. Provisional Patent Application Ser. No. 61/812,376, entitled LINEAR CUTTER WITH POWER;

U.S. Provisional Patent Application Ser. No. 61/812,382, entitled LINEAR CUTTER WITH MOTOR AND PISTOL GRIP;

U.S. Provisional Patent Application Ser. No. 61/812,385, entitled SURGICAL INSTRUMENT HANDLE WITH MULTIPLE ACTUATION MOTORS AND MOTOR CONTROL; and U.S. Provisional Patent Application Ser. No. 61/812,372, entitled SURGICAL INSTRUMENT WITH MULTIPLE FUNCTIONS PERFORMED BY A SINGLE MOTOR.

Numerous specific details are set forth to provide a thorough understanding of the overall structure, function, manufacture, and use of the embodiments as described in the specification and illustrated in the accompanying drawings. Well-known operations, components, and elements have not been described in detail so as not to obscure the embodiments described in the specification. The reader will understand that the embodiments described and illustrated herein are non-limiting examples, and thus it can be appreciated that the specific structural and functional details disclosed herein may be representative and illustrative. Variations and changes thereto may be made without departing from the scope of the claims.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a surgical system, device, or apparatus that "comprises," "has," "includes" or "contains" one or more elements possesses those one or more elements, but is not limited to possessing only those one or more elements. Likewise, an element of a system, device, or apparatus that "comprises," "has," "includes" or "contains" one or more features possesses those one or more features, but is not limited to possessing only those one or more features.

The terms "proximal" and "distal" are used herein with reference to a clinician manipulating the handle portion of the surgical instrument. The term "proximal" refers to the portion closest to the clinician and the term "distal" refers to the portion located away from the clinician. It will be further appreciated that, for convenience and clarity, spatial terms such as “vertical”, “horizontal”, “up”, and “down” may be used herein with respect to the drawings. However, surgical instruments are used in many orientations and positions, and these terms are not intended to be limiting and/or absolute.

Various exemplary devices and methods are provided for performing laparoscopic and minimally invasive surgical procedures. However, the reader will readily appreciate that the various methods and devices disclosed herein can be used in numerous surgical procedures and applications including, for example, in connection with open surgical procedures. As the present Detailed Description proceeds, the reader will further appreciate that the various instruments disclosed herein can be inserted into a body in any way, such as through a natural orifice, through an incision or puncture hole formed in tissue, etc. The working portions or end effector portions of the instruments can be inserted directly into a patient’s body or can be inserted through an access device that has a working channel through which the end effector and elongate shaft of a surgical instrument can be advanced.

A surgical stapling system can comprise a shaft and an end effector extending from the shaft. The end effector comprises a first jaw and a second jaw. The first jaw comprises a staple cartridge. The staple cartridge is insertable into and removable from the first jaw; however, other embodiments are envisioned in which a staple cartridge is not removable from, or at least readily replaceable from, the first jaw. The second jaw comprises an anvil configured to deform staples ejected from the staple cartridge. The second jaw is pivotable relative to the first jaw about a closure axis; however, other embodiments are envisioned in which the first jaw is pivotable relative to the second jaw. The surgical stapling system further comprises an articulation joint configured to permit the end effector to be rotated, or articulated, relative to the shaft. The end effector is rotatable about an articulation axis extending through the articulation joint. Other embodiments are envisioned which do not include an articulation joint.

The staple cartridge comprises a cartridge body. The cartridge body includes a proximal end, a distal end, and a deck extending between the proximal end and the distal end. In use, the staple cartridge is positioned on a first side of the tissue to be stapled and the anvil is positioned on a second side of the tissue. The anvil is moved toward the staple cartridge to compress and clamp the tissue against the deck. Thereafter, staples removably stored in the cartridge body can be deployed into the tissue. The cartridge body includes staple cavities defined therein wherein staples are removably stored in the staple cavities. The staple cavities are arranged in six longitudinal rows. Three rows of staple cavities are positioned on a first side of a longitudinal slot and three rows of staple cavities are positioned on a second side of the longitudinal slot. Other arrangements of staple cavities and staples may be possible.

The staples are supported by staple drivers in the cartridge body. The drivers are movable between a first, or unfired position, and a second, or fired, position to eject the staples from the staple cavities. The drivers are retained in the cartridge body by a retainer which extends around the bottom of the cartridge body and includes resilient members configured to grip the cartridge body and hold the retainer to the cartridge body. The drivers are movable between their unfired positions and their fired positions by a sled. The sled is movable between a proximal position adjacent the proximal end and a distal position adjacent the distal end. The sled comprises a plurality of ramped surfaces configured to slide under the drivers and lift the drivers, and the staples supported thereon, toward the anvil.

Further to the above, the sled is moved distally by a firing member. The firing member is configured to contact the sled and push the sled toward the distal end. The longitudinal slot defined in the cartridge body is configured to receive the firing member. The anvil also includes a slot configured to receive the firing member. The firing member further comprises a first cam which engages the first jaw and a second cam which engages the second jaw. As the firing member is advanced distally, the first cam and the second cam can control the distance, or tissue gap, between the deck of the staple cartridge and the anvil. The firing member also comprises a knife configured to incise the tissue captured intermediate the staple cartridge and the anvil. It is desirable for the knife to be positioned at least partially proximal to the ramped surfaces such that the staples are ejected ahead of the knife.

FIG. 1 depicts a motor-driven surgical system 10 that may be used to perform a variety of different surgical procedures. As can be seen in that Figure, one example of the surgical system 10 includes four interchangeable surgical tool assemblies 1000, 3000, 5000 and 7000 that are each adapted for interchangeable use with a handle assembly 500. Each interchangeable surgical tool assembly 1000, 3000, 5000 and 7000 may be designed for use in connection with the performance of one or more specific surgical procedures. In another surgical system embodiment, one or more of the interchangeable surgical tool assemblies 1000, 3000, 5000 and 7000 may also be effectively employed with a tool drive assembly of a robotically controlled or automated surgical system. For example, the surgical tool assemblies disclosed herein may be employed with various robotic systems, instruments, components and methods such as, but not limited to, those disclosed in U.S. Pat. No. 9,072,535, entitled SURGICAL STAPLING INSTRUMENTS WITH ROTATABLE STAPLE DEPLOYMENT ARRANGEMENTS, which is hereby incorporated by reference herein in its entirety.

Figure 2:
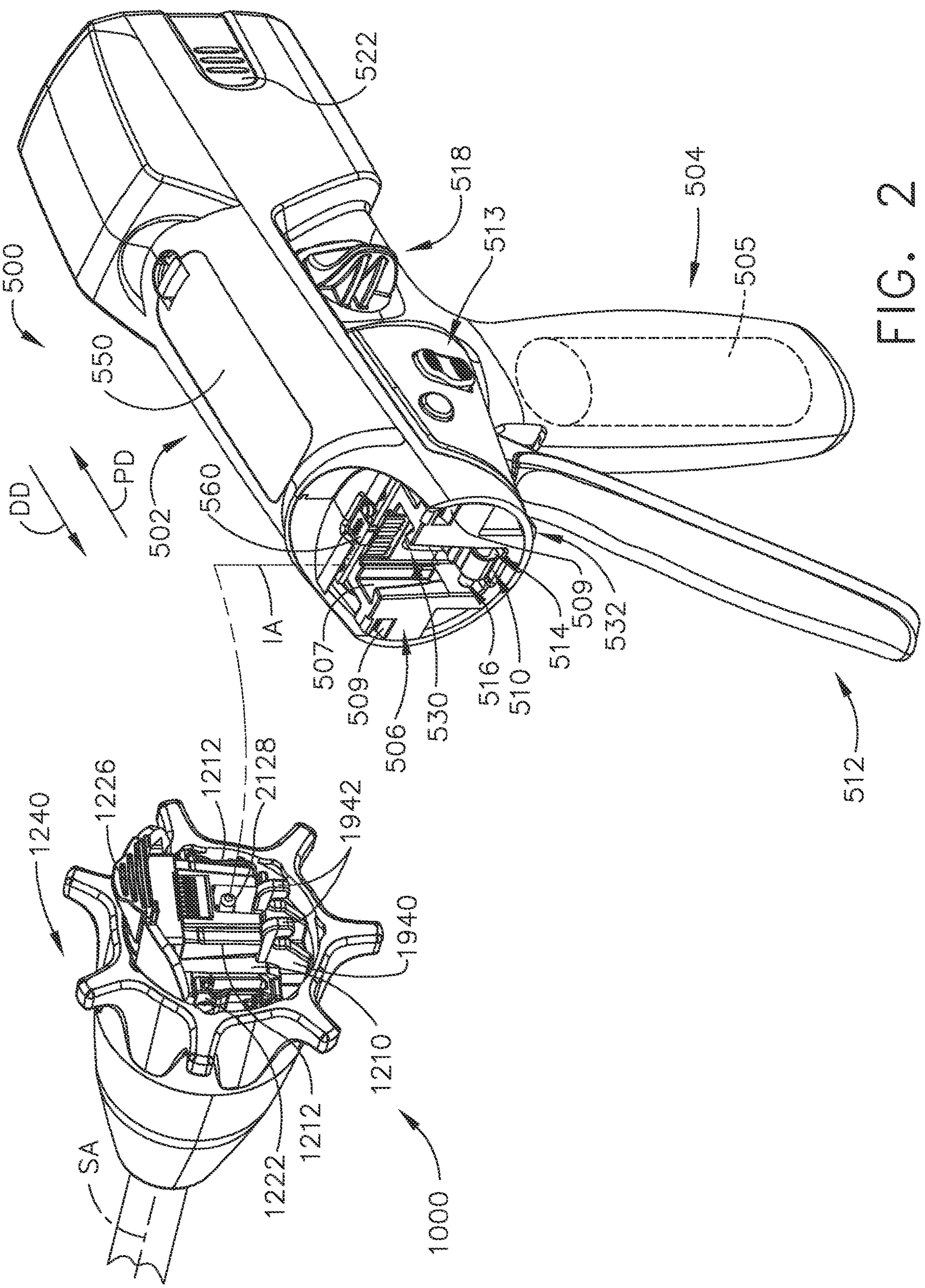
FIG. 2 is an exploded assembly view of portions of the handle assembly and one of the interchangeable surgical tool assemblies depicted in FIG. 1.

FIG. 2 illustrates attachment of an interchangeable surgical tool assembly 1000 to the handle assembly 500. It will be understood that any of the other interchangeable tool assemblies 3000, 5000, and 7000 may be coupled to the handle assembly 500 in a similar manner. The attachment arrangement and process depicted in FIG. 2 may also be employed in connection with attachment of any of the interchangeable surgical tool assemblies 1000, 3000, 5000 and 7000 to a tool drive portion or tool drive housing of a robotic system. The handle assembly 500 may comprise a handle housing 502 that includes a pistol grip portion 504 that can be gripped and manipulated by the clinician. As will be briefly discussed below, the handle assembly 500 operably supports a plurality of drive systems 510, 530 that are configured to generate and apply various control motions to corresponding portions of the interchangeable surgical tool assembly 1000, 3000, 5000 and/or 7000 that is operably attached thereto.

As can be seen in FIG. 2, the handle assembly 500 may further include a handle frame 506 that operably supports the plurality of drive systems. For example, the handle frame 506 can operably support a “first” or closure drive system, generally designated as 510, which may be employed to apply closing and opening motions to the interchangeable surgical tool assembly 1000, 3000, 5000 and 7000 that is operably attached or coupled to the handle assembly 500. In at least one form, the closure drive system 510 may include an actuator in the form of a closure trigger 512 that is pivotally supported by the handle frame 506. Such arrangement enables the closure trigger 512 to be manipulated by a clinician such that when the clinician grips the pistol grip portion 504 of the handle assembly 500, the closure trigger 512 may be easily pivoted from a starting or "unactuated" position to an "actuated" position and more particularly to a fully compressed or fully actuated position. In various forms, the closure drive system 510 further includes a closure linkage assembly 514 that is pivotally coupled to the closure trigger 512 or otherwise operably interfaces therewith. As will be discussed in further detail below, in the illustrated example, the closure linkage assembly 514 includes a transverse attachment pin 516 that facilitates attachment to a corresponding drive system on the surgical tool assembly. In use, to actuate the closure drive system 510, the clinician depresses the closure trigger 512 towards the pistol grip portion 504. As described in further detail in U.S. patent application Ser. No. 14/226,142, entitled SURGICAL INSTRUMENT COMPRISING A SENSOR SYSTEM, now U.S. Pat. No. 9,913,642, which is hereby incorporated by reference in its entirety herein, when the clinician fully depresses the closure trigger 512 to attain the full closure stroke, the closure drive system 510 is configured to lock the closure trigger 512 into the fully depressed or fully actuated position. When the clinician desires to unlock the closure trigger 512 to permit it to be biased to the unactuated position, the clinician simply activates a closure release button assembly 518 which enables the closure trigger to return to unactuated position. The closure release button assembly 518 may also be configured to interact with various sensors that communicate with a microprocessor 560 in the handle assembly 500 for tracking the position of the closure trigger 512. Further details concerning the configuration and operation of the closure release button assembly 518 may be found in U.S. Patent Application Publication No. 2015/0272575, now U.S. Pat. No. 9,913,642.

In at least one form, the handle assembly 500 and the handle frame 506 may operably support another drive system referred to herein as a firing drive system 530 that is configured to apply firing motions to corresponding portions of the interchangeable surgical tool assembly that is attached thereto. As was described in detail in U.S. Patent Application Publication No. 2015/0272575, now U.S. Pat. No. 9,913,642, the firing drive system 530 may employ an electric motor 505 that is located in the pistol grip portion 504 of the handle assembly 500. In various forms, the motor 505 may be a DC brushed driving motor having a maximum rotation of, approximately, 25,000 RPM, for example. In other arrangements, the motor 505 may include a brushless motor, a cordless motor, a synchronous motor, a stepper motor, or any other suitable electric motor. The motor 505 may be powered by a power source 522 that in one form may comprise a removable power pack. The power pack may support a plurality of Lithium Ion ("LI") or other suitable batteries therein. A number of batteries connected in series may be used as the power source 522 for the surgical system 10. In addition, the power source 522 may be replaceable and/or rechargeable.

The electric motor 505 is configured to axially drive a longitudinally movable drive member (not shown) in a distal and proximal directions depending upon the polarity of the motor. For example, when the motor is driven in one rotary direction, the longitudinally movable drive member will be axially driven in a distal direction "DD". When the motor 505 is driven in the opposite rotary direction, the longitudinally movable drive member will be axially driven in a proximal direction "PD". The handle assembly 500 can include a switch 513 which can be configured to reverse the polarity applied to the electric motor 505 by the power source 522 or otherwise control the motor 505. The handle assembly 500 can also include a sensor or sensors (not shown) that is configured to detect the position of the drive member and/or the direction in which the drive member is being moved. Actuation of the motor 505 can be controlled by a firing trigger 532 (FIG. 1) that is pivotally supported on the handle assembly 500. The firing trigger 532 may be pivoted between an unactuated position and an actuated position. The firing trigger 532 may be biased into the unactuated position by a spring or other biasing arrangement such that when the clinician releases the firing trigger 532, it may be pivoted or otherwise returned to the unactuated position by the spring or biasing arrangement. In at least one form, the firing trigger 532 can be positioned "outboard" of the closure trigger 512 as was discussed above. As discussed in U.S. Patent Application Publication No. 2015/0272575, now U.S. Pat. No. 9,913,642, the handle assembly 500 may be equipped with a firing trigger safety button (not shown) to prevent inadvertent actuation of the firing trigger 532. When the closure trigger 512 is in the unactuated position, the safety button is contained in the handle assembly 500 where the clinician cannot readily access it and move it between a safety position preventing actuation of the firing trigger 532 and a firing position wherein the firing trigger 532 may be fired. As the clinician depresses the closure trigger 512, the safety button and the firing trigger 532 pivot down wherein they can then be manipulated by the clinician.

In at least one form, the longitudinally movable drive member may have a rack of teeth (not shown) formed thereon for meshing engagement with a corresponding drive gear arrangement (not shown) that interfaces with the motor. Further details regarding those features may be found in U.S. Patent Application Publication No. 2015/0272575, now U.S. Pat. No. 9,913,642. At least one form also includes a manually-actuatable "bailout" assembly that is configured to enable the clinician to manually retract the longitudinally movable drive member should the motor 505 become disabled. The bailout assembly may include a lever or bailout handle assembly that is stored within the handle assembly 500 under a releasable door 550. See FIG. 2. The lever may be configured to be manually pivoted into ratcheting engagement with the teeth in the drive member. Thus, the clinician can manually retract the drive member by using the bailout handle assembly to ratchet the drive member in the proximal direction "PD". U.S. Pat. No. 8,608,045, entitled POWERED SURGICAL CUTTING AND STAPLING APPARATUS WITH MANUALLY RETRACTABLE FIRING SYSTEM, the entire disclosure of which is hereby incorporated by reference herein, discloses bailout arrangements and other components, arrangements and systems that may also be employed with any one of the various interchangeable surgical tool assemblies disclosed herein.

Figure 3:
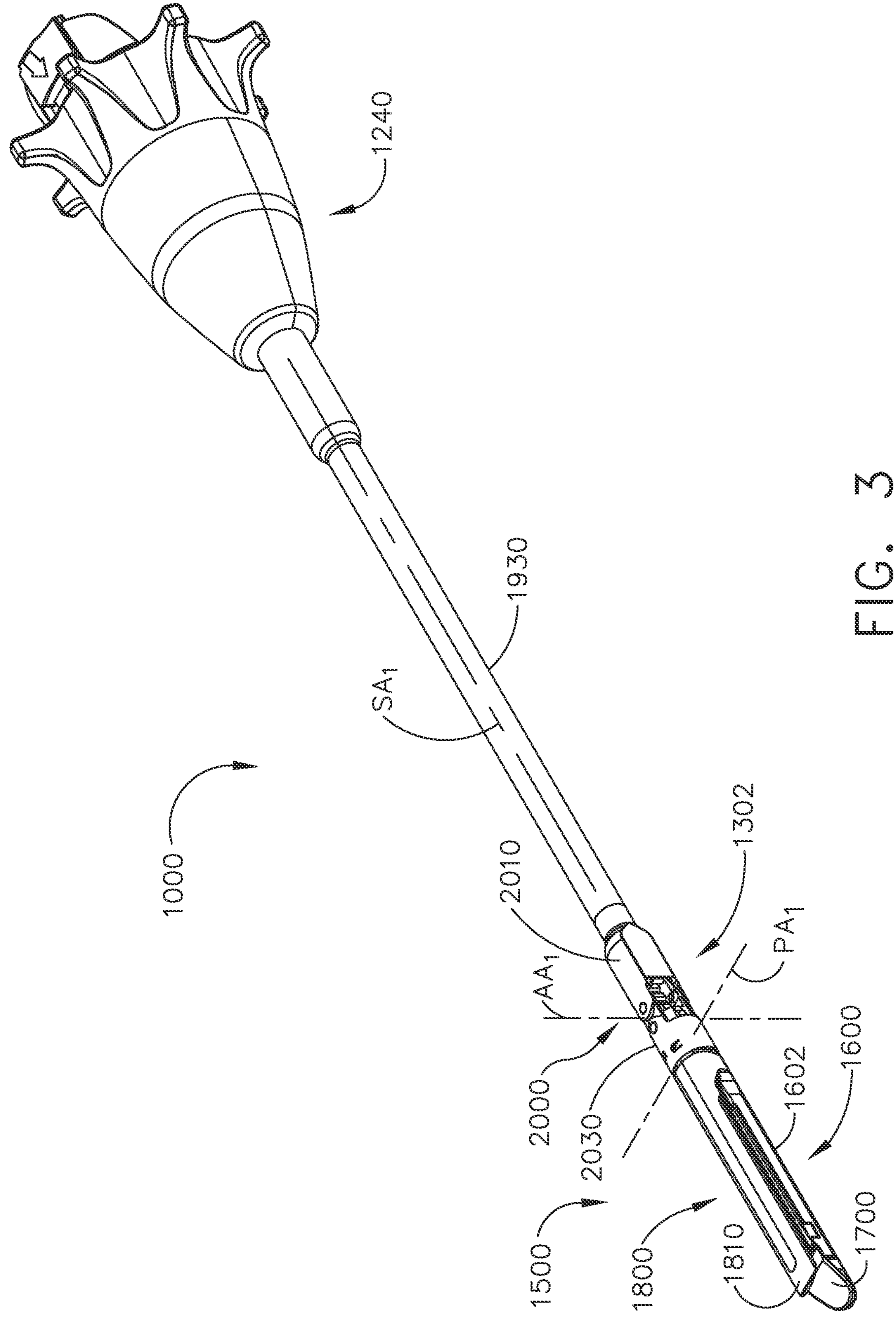
FIG. 3 is a perspective view of one of the interchangeable surgical tool assemblies depicted in FIG. 1.
Figure 4:
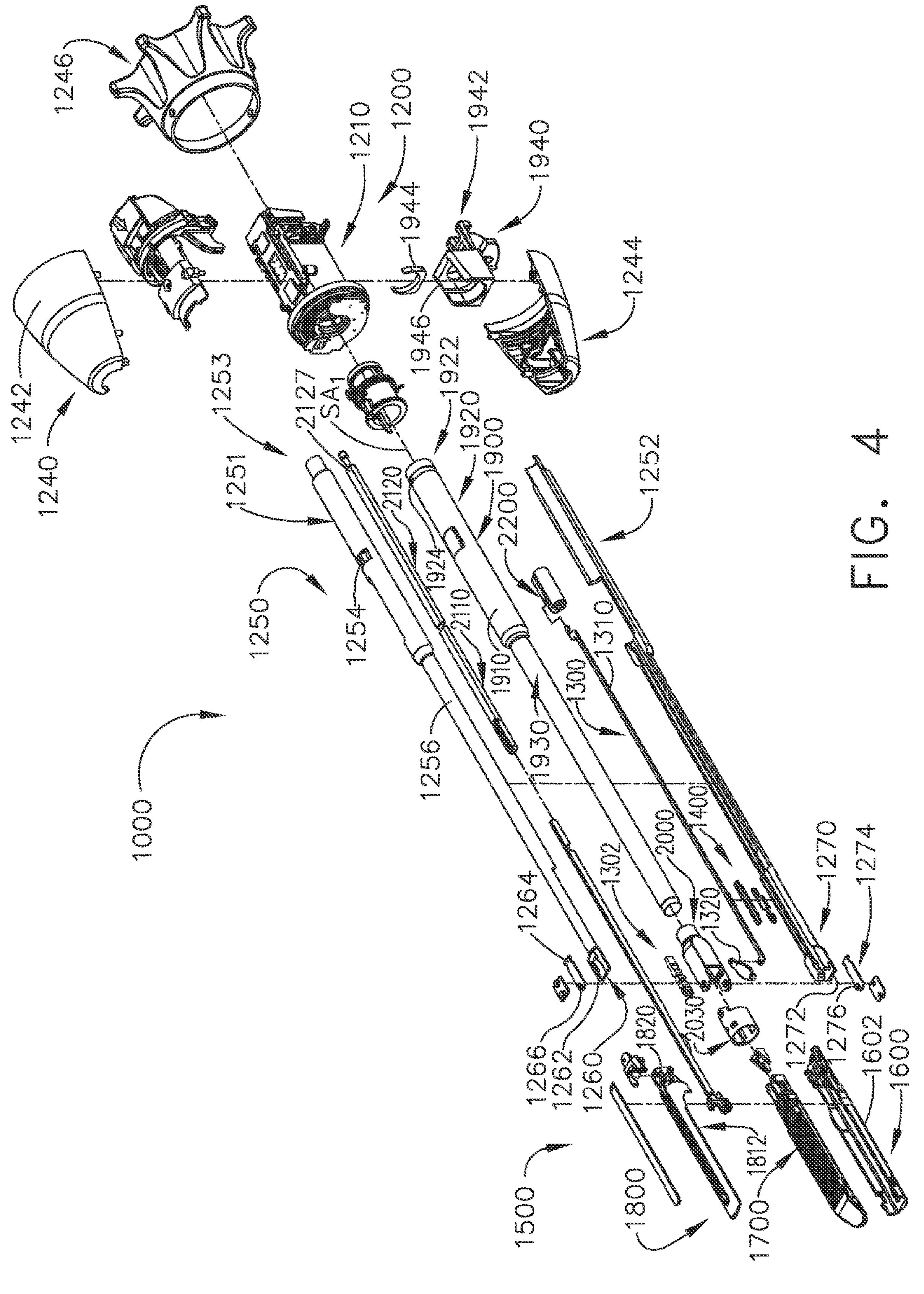
FIG. 4 is an exploded assembly view of the interchangeable surgical tool assembly of FIG. 3.

Turning now to FIGS. 3 and 4, the interchangeable surgical tool assembly 1000 includes a surgical end effector 1500 that comprises a first jaw 1600 and a second jaw 1800. In one arrangement, the first jaw comprises an elongate channel 1602 that is configured to operably support a surgical staple/fastener cartridge 1700 therein. The second jaw 1800 comprises an anvil 1810 that is pivotally supported relative to the elongate channel 1602. The interchangeable surgical tool assembly 1000 includes an articulation system 1300 that comprises an articulation joint 1302 and an articulation lock 1400 (FIGS. 4-6) which can be configured to releasably hold the surgical end effector 1500 in a desired articulated position relative to a shaft axis $SA_1$. Further details regarding the articulation system and articulation lock may be found in U.S. patent application Ser. No. 15/635,837, entitled SURGICAL INSTRUMENT COMPRISING AN ARTICULATION SYSTEM LOCKABLE TO A FRAME, filed on Jun. 28, 2017, now U.S. Patent Application Publication No. 2019/0000472, and hereby incorporated by reference herein in its entirety.

As can be further seen in FIGS. 4 and 7-9, the interchangeable surgical tool assembly 1000 includes a tool frame assembly 1200 that comprises a tool chassis 1210 that operably supports a nozzle assembly 1240 thereon. In one form, the nozzle assembly 1240 is comprised of nozzle portions 1242, 1244 as well as an actuator wheel portion 1246 that is configured to be coupled to the assembled nozzle portions 1242, 1244 by snaps, lugs, screws etc. The interchangeable surgical tool assembly 1000 includes a proximal closure assembly 1900 which is operably coupled to a distal closure assembly 2000 that is utilized to close and/or open the anvil 1810 of the surgical end effector 1500 as will be discussed in further detail below. In addition, the interchangeable surgical tool assembly 1000 includes a spine assembly 1250 that operably supports the proximal closure assembly 1900 and is coupled to the surgical end effector 1500. In various circumstances, for ease of assembly, the spine assembly 1250 may be fabricated from an upper spine segment 1251 and a lower spine segment 1252 that are interconnected together by snap features, adhesive, welding, etc. In assembled form, the spine assembly 1250 includes a proximal end 1253 that is rotatably supported in the tool chassis 1210. In one arrangement, for example, the proximal end 1253 of the spine assembly 1250 is attached to a spine bearing (not shown) that is configured to be supported within the tool chassis 1210. Such arrangement facilitates rotatable attachment of the spine assembly 1250 to the tool chassis 1210 such that the spine assembly 1250 may be selectively rotated about the shaft axis $SA_1$ relative to the tool chassis 1210. In particular, in one arrangement, for example, the proximal end 1253 of the spine assembly 1250 includes an upper lug seat 1254 (FIGS. 4, 5, 7, 8 and 10) and a lower lug seat (not shown) that are each configured to receive a corresponding nozzle lug 1245 extending inwardly from each of the nozzle portions 1242, 1244. Such arrangement facilitates rotation of the spine assembly 1250 about the shaft axis $SA_1$ by rotating the actuator wheel portion 1246 of the nozzle assembly 1240.

Figure 5:
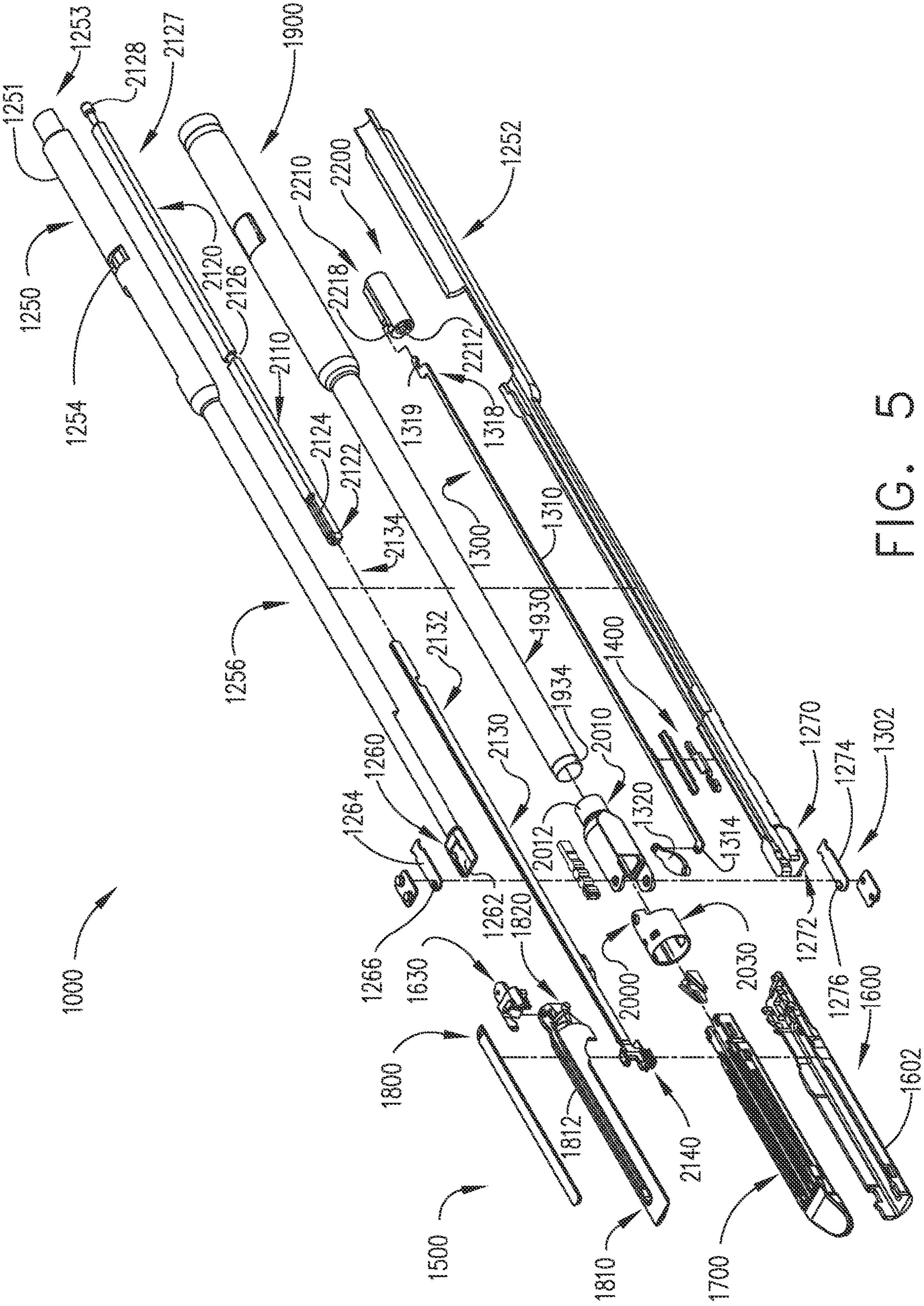
FIG. 5 is another exploded assembly view of a distal portion of the interchangeable surgical tool assembly of FIGS. 3 and 4.

As can be seen in FIGS. 4 and 5, spine assembly 1250 further includes an intermediate spine shaft segment 1256 that has a diameter that is less than the diameter of the proximal end 1253 of the spine assembly 1250. The intermediate spine shaft segment 1256 of the upper spine segment 1251 terminates in an upper lug mount feature 1260 and the intermediate spine shaft segment of the lower spine segment 1252 terminates in a lower lug mount feature 1270. As can be most particularly seen in FIG. 6, for example, the upper lug mount feature 1260 is formed with a lug slot 1262 therein that is adapted to mountingly support an upper mounting link 1264 therein. Similarly, the lower lug mount feature 1270 is formed with a lug slot 1272 therein that is adapted to mountingly support a lower mounting link 1274 therein. The upper mounting link 1264 includes a pivot socket 1266 therein that is offset from the shaft axis $SA_1$. The pivot socket 1266 is adapted to rotatably receive therein a pivot pin 1634 that is formed on a channel cap or anvil retainer 1630 that is attached to a proximal end portion 1610 of the elongate channel 1602. The lower mounting link 1274 includes lower pivot pin 1276 that adapted to be received within a pivot hole 1611 formed in the proximal end portion 1610 of the elongate channel 1602. See FIG. 6. The lower pivot pin 1276 as well as the pivot hole 1611 is offset from the shaft axis $SA_1$. The lower pivot pin 1276 is vertically aligned with the pivot socket 1266 to define an articulation axis $AA_1$ about which the surgical end effector 1500 may articulate relative to the shaft axis $SA_1$. Although the articulation axis $AA_1$ is transverse to the shaft axis $SA_1$, the articulation axis $AA_1$ is laterally offset therefrom and does not intersect the shaft axis $SA_1$.

Figure 6:
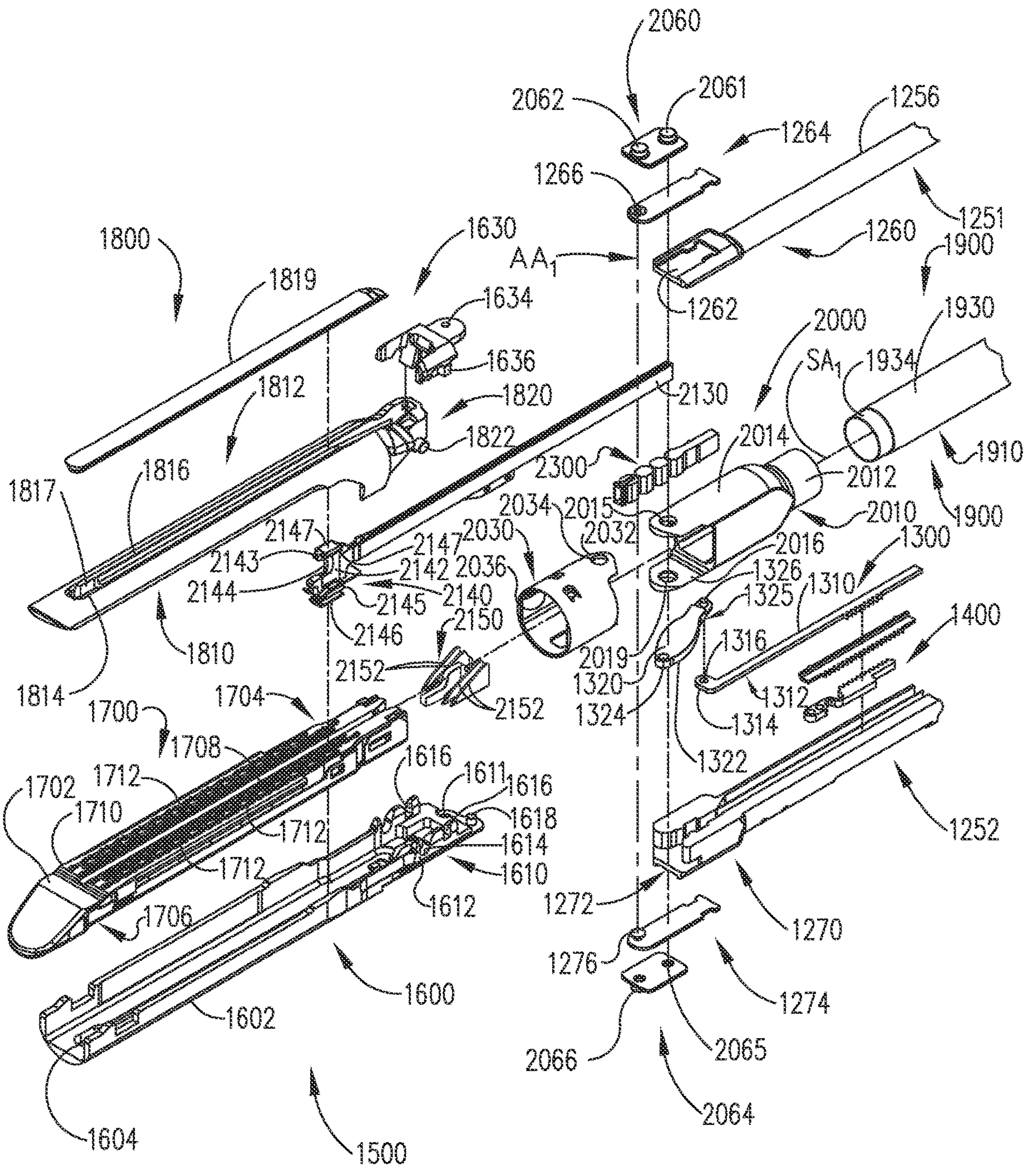
FIG. 6 is another exploded assembly view of a distal portion of the interchangeable surgical tool assembly of FIGS. 3-5.
Figure 15:
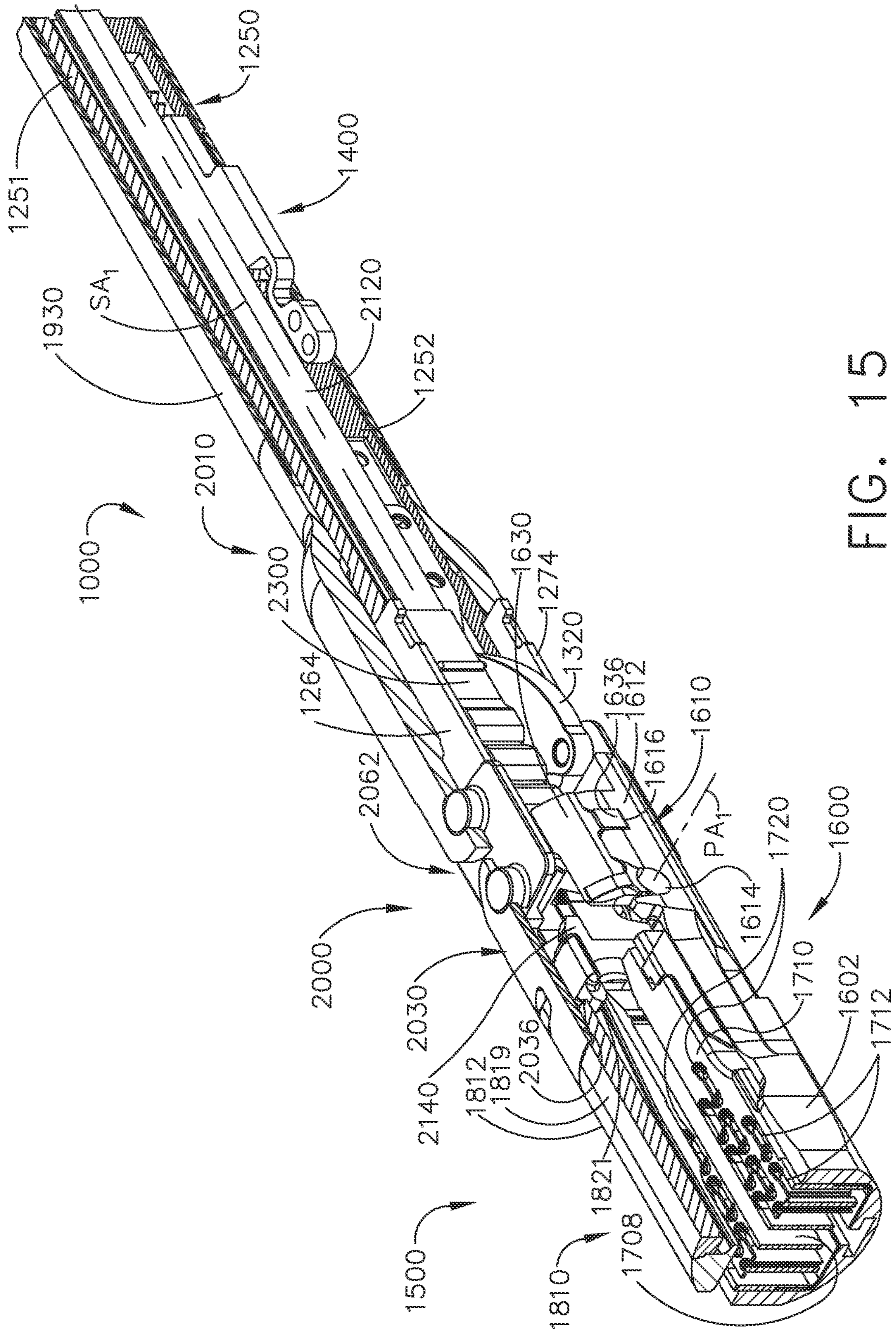
FIG. 15 is a cross-sectional perspective view of a distal portion of the interchangeable surgical tool assembly of FIGS. 3-14.

Referring now to FIGS. 6 and 15, the anvil 1810 in the illustrated example includes an anvil body 1812 that terminates in anvil mounting portion 1820. The anvil mounting portion 1820 is movably or pivotably supported on the elongate channel 1602 for selective pivotal travel relative thereto about a fixed anvil pivot axis $PA_1$ (FIG. 15) that is transverse to the shaft axis $SA_1$. In the illustrated arrangement, a pivot member or anvil trunnion 1822 extends laterally out of each lateral side of the anvil mounting portion 1820 to be received in a corresponding trunnion cradle 1614 formed in the upstanding walls 1612 of the proximal end portion 1610 of the elongate channel 1602. The anvil trunnions 1822 are pivotally retained in their corresponding trunnion cradle 1614 by the channel cap or anvil retainer 1630. The channel cap or anvil retainer 1630 includes a pair of attachment lugs 1636 that are configured to be retainingly received within corresponding lug grooves or notches 1616 formed in the upstanding walls 1612 of the proximal end portion 1610 of the elongate channel 1602.

In the illustrated example, the surgical end effector 1500 is selectively articulatable about the articulation axis $AA_1$ by the articulation system 1300. In one form, the articulation system 1300 includes proximal articulation driver 1310 that is pivotally coupled to an articulation link 1320. As can be most particularly seen in FIG. 6, an offset attachment lug 1314 is formed on a distal end 1312 of the proximal articulation driver 1310. A pivot hole 1316 is formed in the offset attachment lug 1314 and is configured to pivotally receive therein a proximal link pin 1326 formed on the proximal end 1325 of the articulation link 1320. A distal end 1322 of the articulation link 1320 includes a pivot hole 1324 that is configured to pivotally receive therein a channel pin 1618 formed on the proximal end portion 1610 of the elongate channel 1602. Thus, axial movement of proximal articulation driver 1310 will thereby apply articulation motions to the elongate channel 1602 to thereby cause the surgical end effector 1500 to articulate about the articulation axis $AA_1$ relative to the spine assembly 1250.

Figure 7:
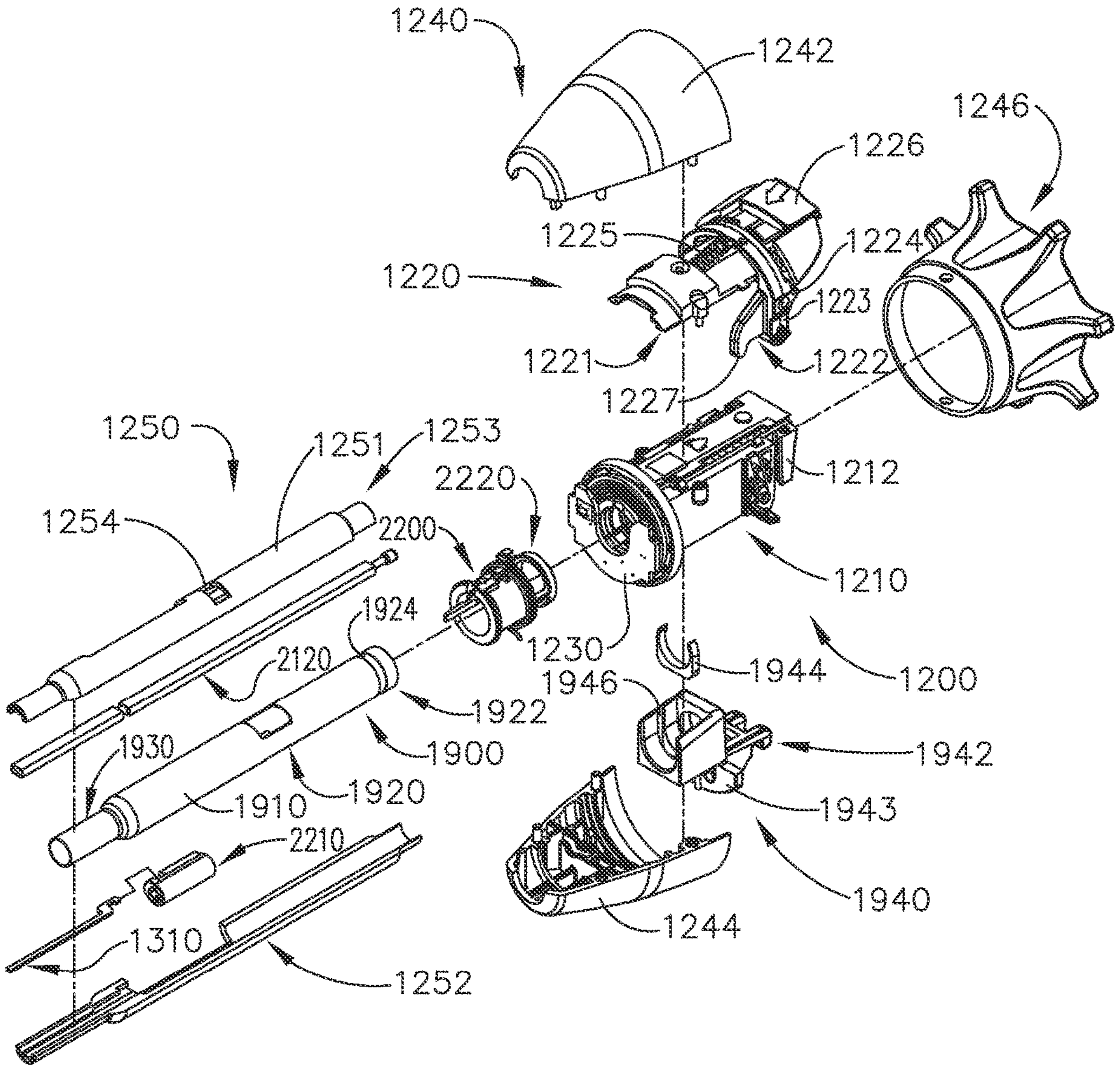
FIG. 7 is an exploded assembly view of a proximal portion of the interchangeable surgical tool assembly of FIGS. 3-6.
Figure 8:
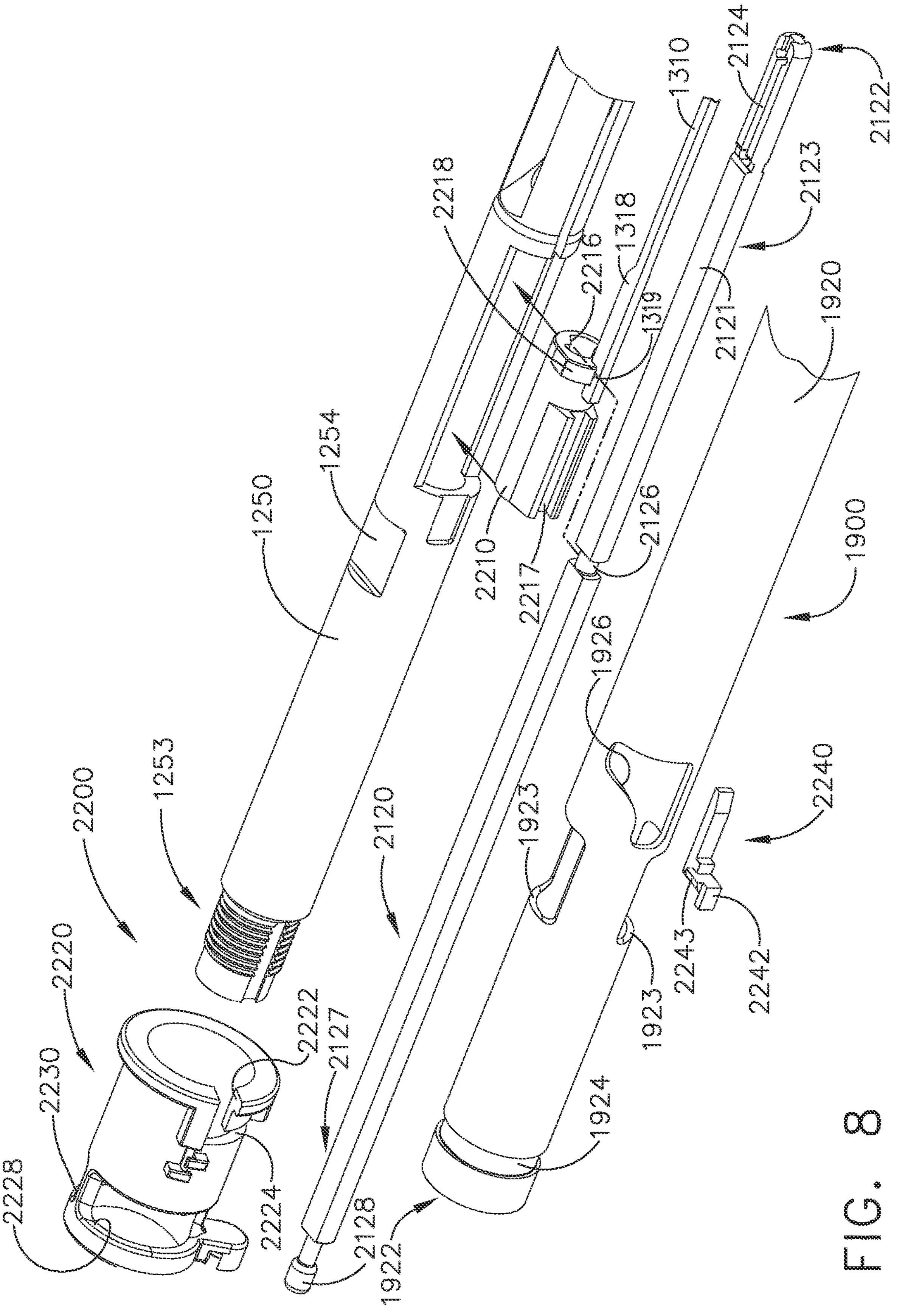
FIG. 8 is another exploded assembly view of a portion of the interchangeable surgical tool assembly of FIGS. 3-7.
Figure 9:
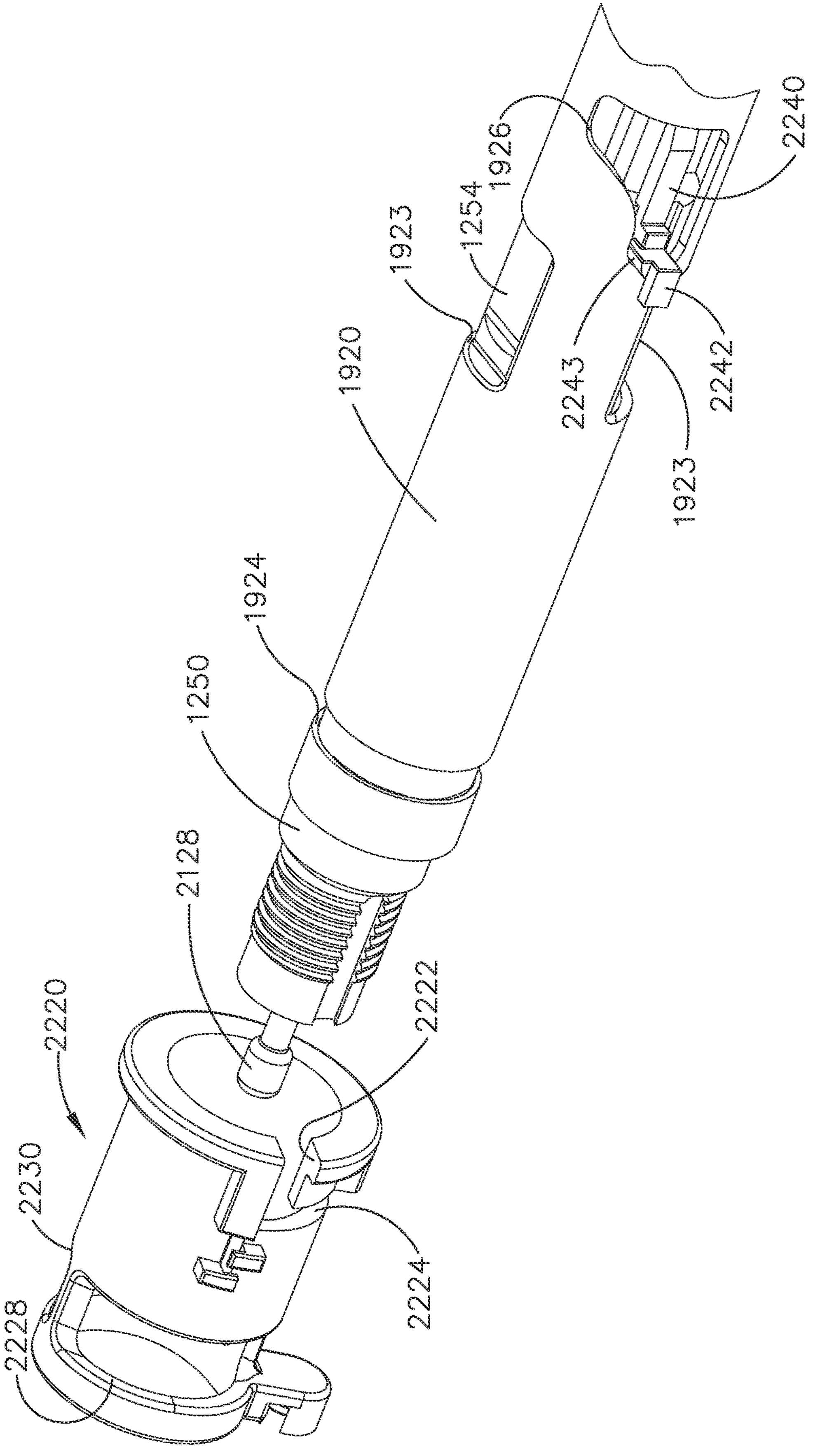
FIG. 9 is another exploded assembly view of a portion of the interchangeable surgical tool assembly of FIGS. 3-8.
Figure 10:
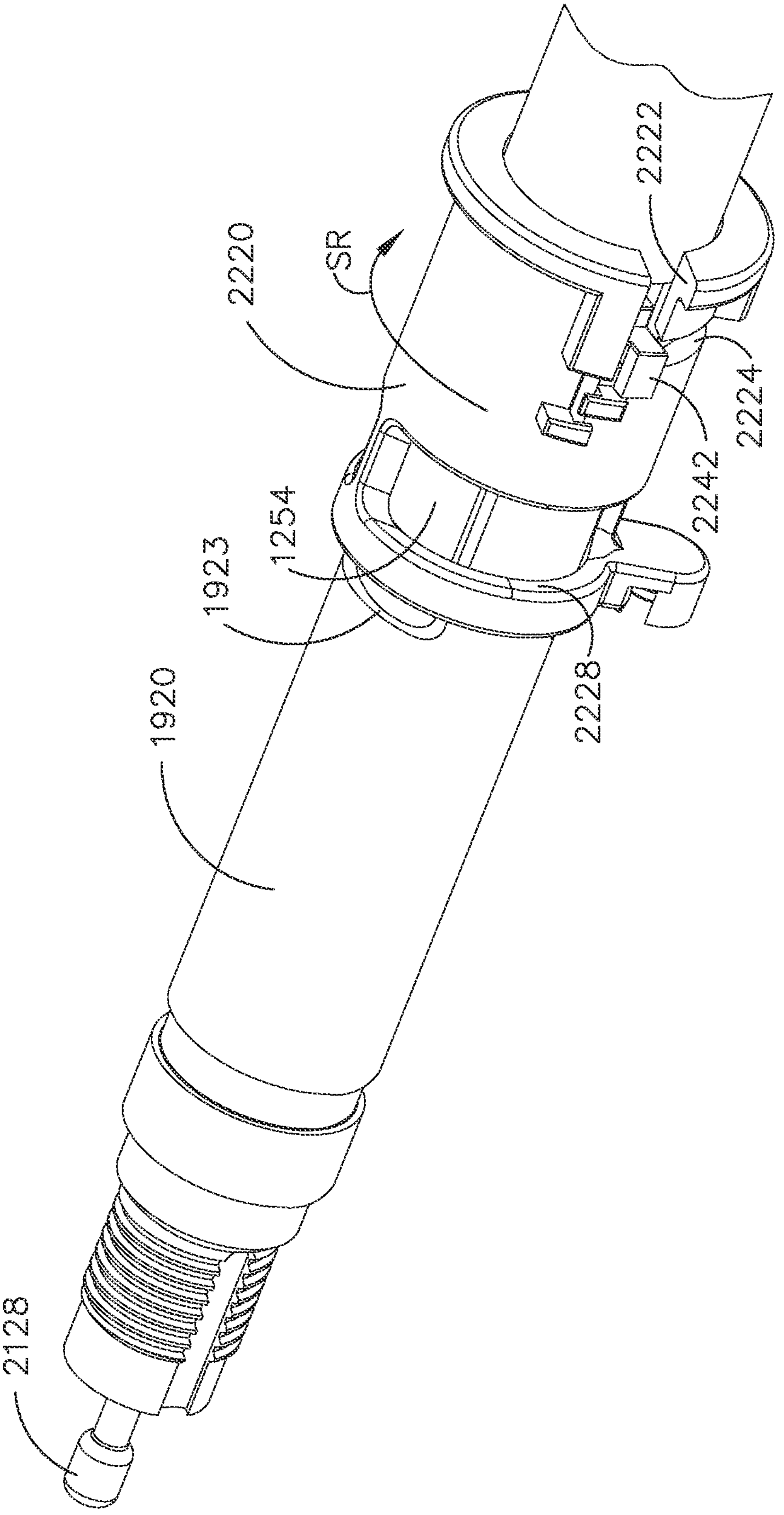
FIG. 10 is a perspective view of a proximal portion of the interchangeable surgical tool assembly of FIGS. 3-9.
Figure 11:
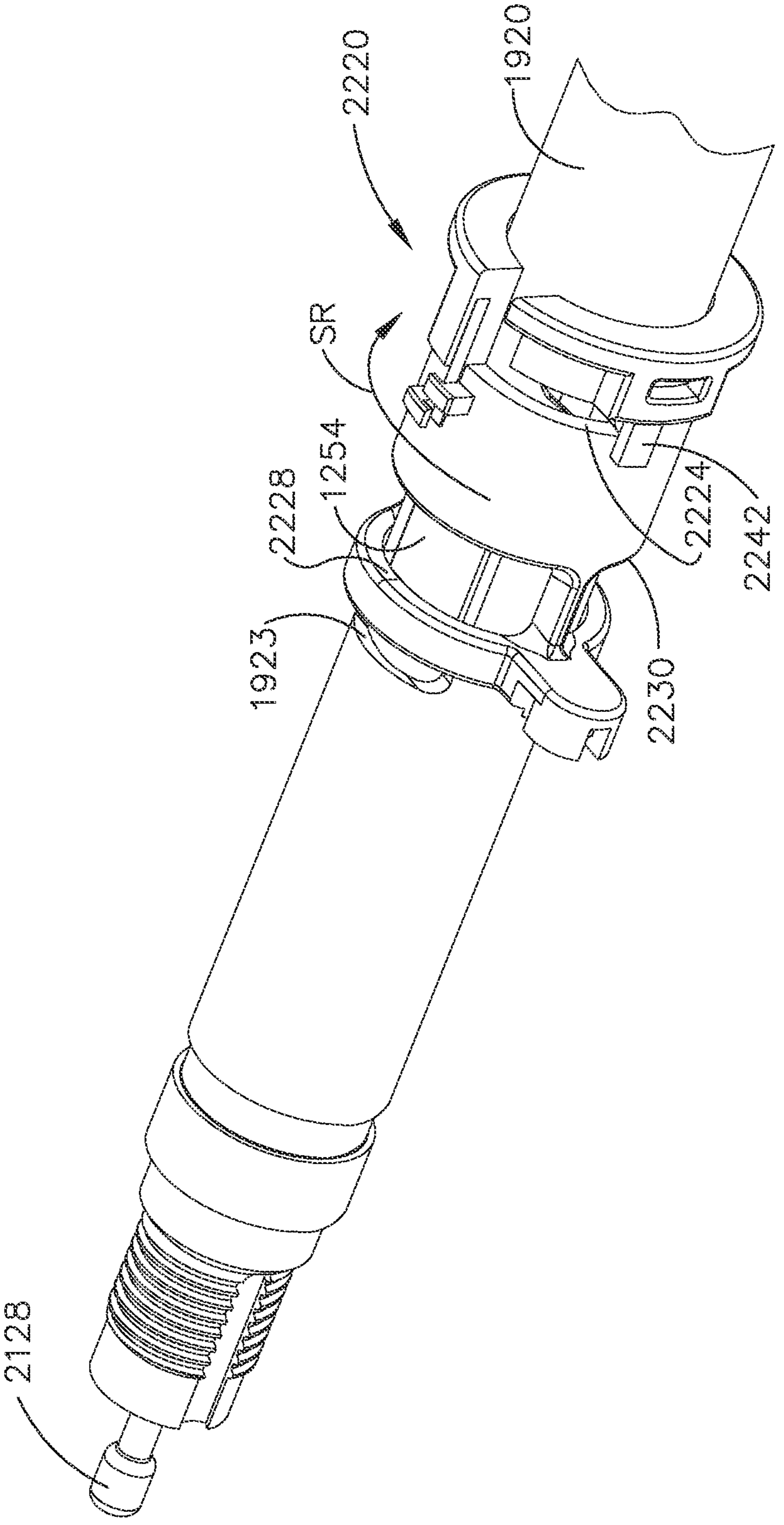
FIG. 11 is another perspective view of the proximal portion of the interchangeable surgical tool assembly of FIGS. 3-10.
Figure 12:
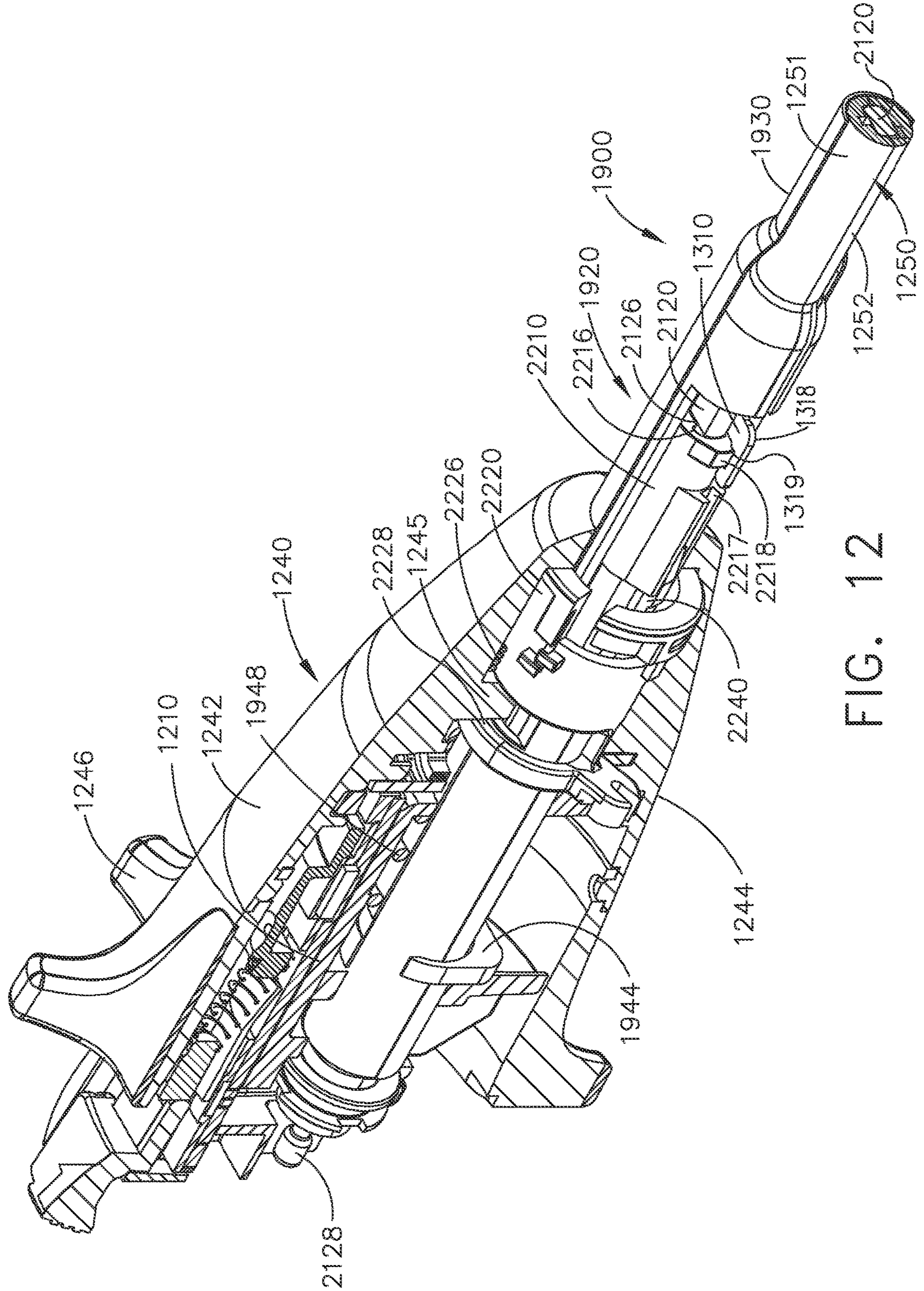
FIG. 12 is a cross-sectional perspective view of the proximal portion of the interchangeable surgical tool assembly of FIGS. 3-11.
Figure 13:
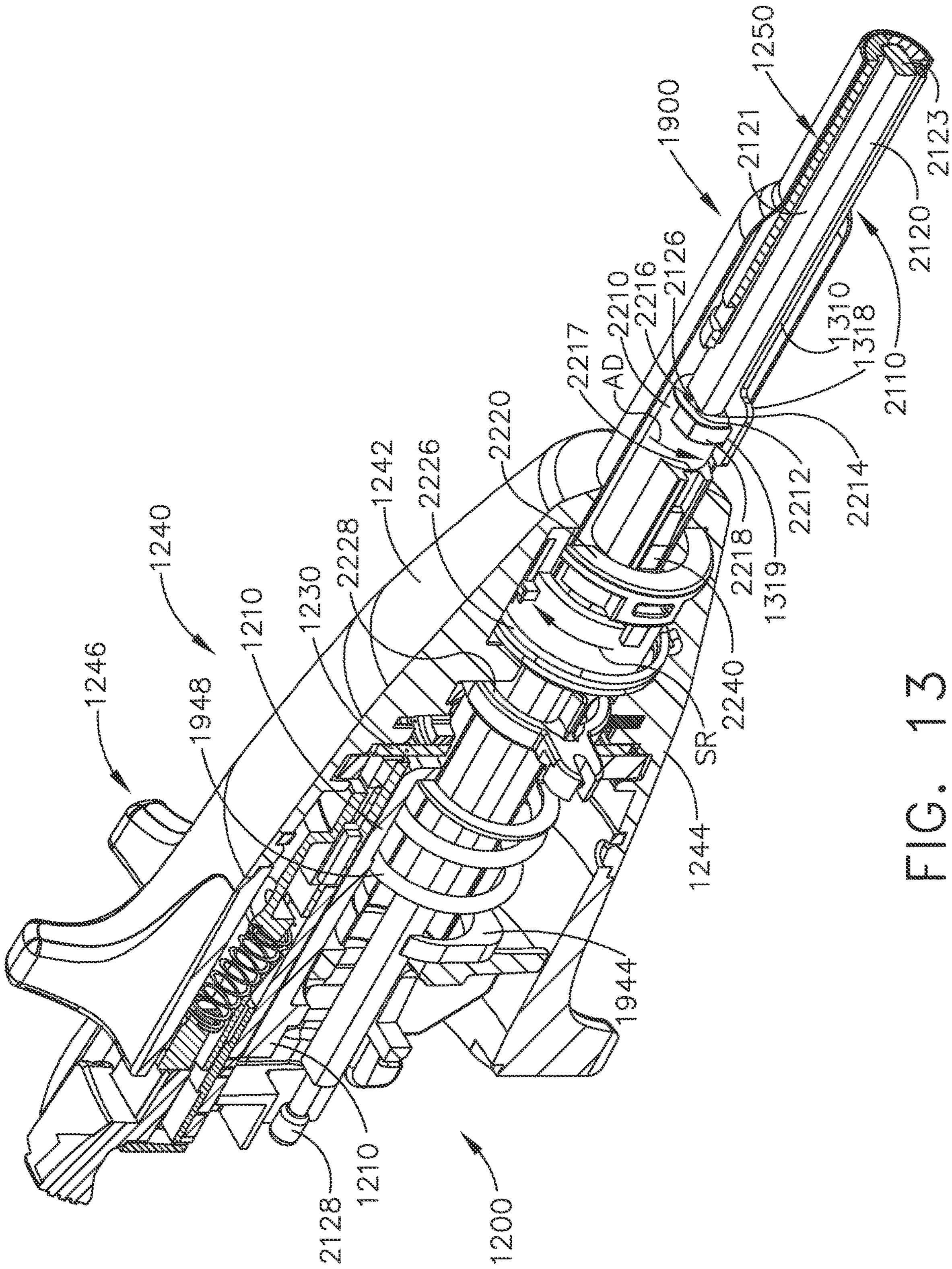
FIG. 13 is another cross-sectional perspective view of the proximal portion of the interchangeable surgical tool assembly of FIGS. 3-12.
Figure 14:
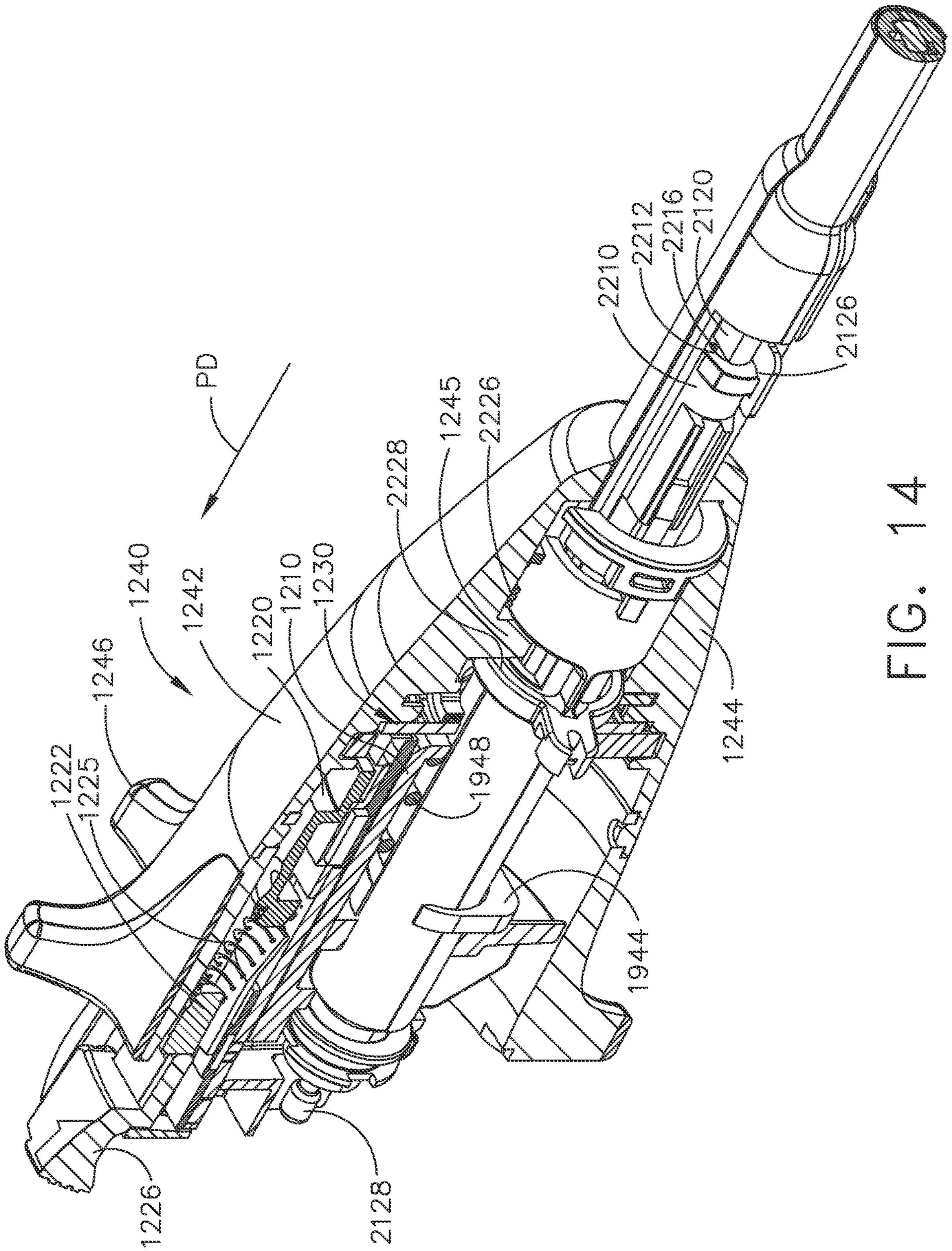
FIG. 14 is another cross-sectional perspective view of the proximal portion of the interchangeable surgical tool assembly of FIGS. 3-13.

Movement of the anvil 1810 relative to the elongate channel 1602 is effectuated by axial movement of the proximal closure assembly 1900 and the distal closure assembly 2000. Referring now to FIGS. 4 and 7, in the illustrated arrangement, the proximal closure assembly 1900 comprises a proximal closure tube 1910 that has a proximal closure tube portion 1920 and a distal portion 1930. The distal portion 1930 has a diameter that is less than the diameter of the proximal closure tube portion 1920. The proximal end 1922 of the proximal closure tube portion 1920 is rotatably supported in a closure shuttle 1940 that is slidably supported within the tool chassis 1210 such that it may be axially moved relative thereto. In one form, the closure shuttle 1940 includes a pair of proximally-protruding hooks 1942 that are configured for attachment to the attachment pin 516 that is attached to the closure linkage assembly 514 of the handle assembly 500. The proximal end 1922 of the proximal closure tube portion 1920 is coupled to the closure shuttle 1940 for relative rotation thereto. For example, a U-shaped connector 1944 is inserted into an annular slot 1924 in the proximal closure tube portion 1920 and is retained within vertical slots 1946 in the closure shuttle 1940. Such arrangement serves to attach the proximal closure assembly 1900 to the closure shuttle 1940 for axial travel therewith while enabling the proximal closure assembly 1900 to rotate relative to the closure shuttle 1940 about the shaft axis $SA_1$. A closure spring 1948 (FIGS. 12-14) extends over the proximal closure tube portion 1920 to bias the closure shuttle 1940 in the proximal direction PD which can serve to pivot the closure trigger 512 on the handle assembly 500 (FIG. 2) into the unactuated position when the interchangeable surgical tool assembly 1000 is operably coupled to the handle assembly 500.

Referring now to FIGS. 5 and 6, a distal portion 1930 of the proximal closure tube 1910 is attached to the distal closure assembly 2000. In the illustrated arrangement for example, the distal closure assembly 2000 includes an articulation connector 2010 that is coupled to a distal closure tube segment 2030. In the illustrated example, the distal closure tube segment 2030 has a diameter that is larger than the diameter of the distal portion 1930 of the proximal closure tube 1910. The articulation connector 2010 has a proximally extending end portion 2012 that is adapted to be received on a connection flange 1934 formed on the distal end of the distal portion 1930. The articulation connector 2010 may be retained on the connection flange 1934 by an appropriate fastener arrangement such as adhesive, welding, etc. The articulation connector 2010 includes upper and lower tangs 2014, 2016 protrude distally from a distal end of the articulation connector 2010 to be movably coupled to an end effector closure sleeve or distal closure tube segment 2030. The distal closure tube segment 2030 includes an upper tang 2032 and a lower tang (not shown) that protrude proximally from a proximal end thereof. An upper double pivot link 2060 includes proximal and distal pins 2061, 2062 that engage corresponding holes 2015, 2034 in the upper tangs 2014, 2032 of the articulation connector 2010 and distal closure tube segment 2030, respectively. Similarly, a lower double pivot link 2064 includes proximal and distal pins 2065, 2066 that engage corresponding holes 2019 in the lower tangs 2016 of the articulation connector 2010 and distal closure tube segment 2030, respectively. As will be discussed in further detail below, distal and proximal axial translation of the proximal closure assembly 1900 and distal closure assembly 2000 will result in the closing and opening of the anvil 1810 relative to the elongate channel 1602.

In at least one arrangement, the interchangeable surgical tool assembly 1000 further includes a firing system generally designated as 2100. In the illustrated example, the firing system 2100 includes a firing member assembly 2110 that is supported for axial travel within the spine assembly 1250. In the illustrated embodiment, the firing member assembly 2110 includes an intermediate firing shaft portion 2120 that is configured for attachment to a distal cutting portion or knife bar 2130. The firing member assembly 2110 may also be referred to herein as a "second shaft" and/or a "second shaft assembly". As can be seen in FIG. 5, the intermediate firing shaft portion 2120 may include a longitudinal slot 2124 in a distal end 2122 thereof which can be configured to receive a proximal end 2132 of the knife bar 2130. The longitudinal slot 2124 and the proximal end 2132 of the knife bar 2130 can be sized and configured to permit relative movement therebetween and can comprise a slip joint 2134. The slip joint 2134 can permit the intermediate firing shaft portion 2120 of the firing member assembly 2110 to be moved to articulate the end effector 1500 without moving, or at least substantially moving, the knife bar 2130. Once the end effector 1500 has been suitably oriented, the intermediate firing shaft portion 2120 can be advanced distally until a proximal sidewall of the longitudinal slot 2124 comes into contact with a portion of the knife bar 2130 to advance the knife bar 2130 and fire the surgical staple/fastener cartridge 1700 positioned within the elongate channel 1602. In the illustrated arrangement, a proximal end 2127 of the intermediate firing shaft portion 2120 has a firing shaft attachment lug 2128 formed thereon (FIG. 8) that is configured to be seated into an attachment cradle (not shown) that is on the distal end of the longitudinally movable drive member (not shown) of the firing drive system 530 within the handle assembly 500. Such arrangement facilitates the axial movement of the intermediate firing shaft portion 2120 upon actuation of the firing drive system 530.

Further to the above, the interchangeable tool assembly 1000 can include a shifter assembly 2200 which can be configured to selectively and releasably couple the proximal articulation driver 1310 to the firing system 2100. In one form, the shifter assembly 2200 includes a lock collar, or lock sleeve 2210, positioned around the intermediate firing shaft portion 2120 of the firing system 2100 wherein the lock sleeve 2210 can be rotated between an engaged position in which the lock sleeve 2210 couples the proximal articulation driver 1310 to the firing member assembly 2110 and a disengaged position in which the proximal articulation driver 1310 is not operably coupled to the firing member assembly 2110. When lock sleeve 2210 is in its engaged position, distal movement of the firing member assembly 2110 can move the proximal articulation driver 1310 distally and, correspondingly, proximal movement of the firing member assembly 2110 can move the proximal articulation driver 1310 proximally. When lock sleeve 2210 is in its disengaged position, movement of the firing member assembly 2110 is not transmitted to the proximal articulation driver 1310 and, as a result, the firing member assembly 2110 can move independently of the proximal articulation driver 1310. In various circumstances, the proximal articulation driver 1310 can be held in position by the articulation lock 1400 when the proximal articulation driver 1310 is not being moved in the proximal or distal directions by the firing member assembly 2110.

In the illustrated arrangement, the intermediate firing shaft portion 2120 of the firing member assembly 2110 is formed with two opposed flat sides 2121, 2123 with a drive notch 2126 formed therein. See FIG. 8. As can also be seen in FIG. 13, the lock sleeve 2210 comprises a cylindrical, or an at least substantially cylindrical, body that includes a longitudinal aperture 2212 that is configured to receive the intermediate firing shaft portion 2120 therethrough. The lock sleeve 2210 can comprise diametrically-opposed, inwardly-facing lock protrusions 2214, 2216 that, when the lock sleeve 2210 is in one position, are engagingly received within corresponding portions of the drive notch 2126 in the intermediate firing shaft portion 2120 and, when in another position, are not received within the drive notch 2126 to thereby permit relative axial motion between the lock sleeve 2210 and the intermediate firing shaft portion 2120.

Referring now to FIGS. 8 and 12-14, in the illustrated example, the lock sleeve 2210 further includes a lock member 2218 that is sized to be movably received within a notch 1319 in a proximal end 1318 of the proximal articulation driver 1310. Such arrangement permits the lock sleeve 2210 to slightly rotate into and out of engagement with the intermediate firing shaft portion 2120 while remaining in engagement with the notch 1319 in the proximal articulation driver 1310. For example, when the lock sleeve 2210 is in its engaged position, the lock protrusions 2214, 2216 are positioned within the drive notch 2126 in the intermediate firing shaft portion 2120 such that a distal pushing force and/or a proximal pulling force can be transmitted from the firing member assembly 2110 to the lock sleeve 2210. Such axial pushing or pulling motion is then transmitted from the lock sleeve 2210 to the proximal articulation driver 1310 to thereby articulate the surgical end effector 1500. In effect, the firing member assembly 2110, the lock sleeve 2210, and the proximal articulation driver 1310 will move together when the lock sleeve 2210 is in its engaged (articulation) position. On the other hand, when the lock sleeve 2210 is in its disengaged position, the lock protrusions 2214, 2216 are not received within the drive notch 2126 in the intermediate firing shaft portion 2120 and, as a result, a distal pushing force and/or a proximal pulling force may not be transmitted from the firing member assembly 2110 to the lock sleeve 2210 (and the proximal articulation driver 1310).

In the illustrated example, relative movement of the lock sleeve 2210 between its engaged and disengaged positions may be controlled by a shifter assembly 2200 that is interfaces with the proximal closure tube 1910 of the proximal closure assembly 1900. More specifically and with reference to FIGS. 8 and 9, the shifter assembly 2200 further includes a shifter key 2240 that is configured to be slidably received within a key groove 2217 formed in the outer perimeter of the lock sleeve 2210. Such arrangement enables the shifter key 2240 to move axially with respect to the lock sleeve 2210. Referring to FIGS. 8-11, the shifter key 2240 includes an actuator lug 2242 that extends through a cam slot or cam opening 1926 in the proximal closure tube portion 1920. See FIG. 9. A cam surface 2243 is also provided adjacent the actuator lug 2242 which is configured to cammingly interact with the cam opening 1926 so as to cause the shifter key 2240 to rotate in response to axial motion of the proximal closure tube portion 1920.

Also in the illustrated example, the shifter assembly 2200 further includes a switch drum 2220 that is rotatably received on a proximal end portion of the proximal closure tube portion 1920. As can be seen in FIGS. 10-14, the actuator lug 2242 extends through an axial slot segment 2222 in the switch drum 2220 and is movably received within an arcuate slot segment 2224 in the switch drum 2220. A switch drum torsion spring 2226 (FIGS. 12-14) is mounted on the switch drum 2220 and engages nozzle portion 1244 to apply a torsional bias or rotation (arrow SR in FIGS. 10 and 11) which serves to rotate the switch drum 2220 until the actuator lug 2242 reaches the end of the arcuate slot segment 2224. See FIGS. 11 and 12. When in this position, the switch drum 2220 may provide a torsional bias to the shifter key 2240 which thereby causes the lock sleeve 2210 to rotate into its engaged position with the intermediate firing shaft portion 2120. This position also corresponds to the unactuated configuration of the proximal closure assembly 1900. In one arrangement, for example, when the proximal closure assembly 1900 is in an unactuated configuration (anvil 1810 is in an open position spaced away from the surgical staple/fastener cartridge 1700) the actuator lug 2242 is located in the upper portion of the cam opening 1926 in the proximal closure tube portion 1920. When in that position, actuation of the intermediate firing shaft portion 2120 will result in the axial movement of the proximal articulation driver 1310. Once the user has articulated the surgical end effector 1500 to a desired orientation, the user may then actuate the proximal closure assembly 1900. Actuation of the proximal closure assembly 1900 will result in the distal travel of the proximal closure tube portion 1920 to ultimately apply a closing motion to the anvil 1810. This distal travel of the proximal closure tube portion 1920 will result in the cam opening 1926 cammingly interacting with the cam surface 2243 on the actuator lug 2242 to thereby cause the shifter key 2240 to rotate the lock sleeve 2210 in an actuation direction AD. Such rotation of the lock sleeve 2210 will result in the disengagement of the lock protrusions 2214, 2216 from the drive notch 2126 in the intermediate firing shaft portion 2120. When in such configuration, the firing drive system 530 may be actuated to actuate the intermediate firing shaft portion 2120 without actuating the proximal articulation driver 1310. Further details concerning the operation of the switch drum 2220 and lock sleeve 2210, as well as alternative articulation and firing drive arrangements that may be employed with the various interchangeable surgical tool assemblies described herein, may be found in U.S. patent application Ser. No. 13/803,086, now U.S. Patent Application Publication No. 2014/0263541, and U.S. patent application Ser. No. 15/019,196, now U.S. Pat. No. 10,413,291, the entire disclosures of which are hereby incorporated by reference herein.

Referring again to FIGS. 8-13, the switch drum 2220 can further comprise at least partially circumferential openings 2228, 2230 defined therein which can receive circumferential lugs/mounts 1245 that extend from the nozzle portions 1242, 1244 and permit relative rotation, but not translation, between the switch drum 2220 and the nozzle assembly 1240. The nozzle lugs 1245 extend through corresponding openings 1923 in the proximal closure tube portion 1920 to be seated in lug seats 1254 in the spine assembly 1250. See FIGS. 8 and 9. Such arrangement enables the user to rotate the spine assembly 1250 about the shaft axis by rotating the nozzle assembly 1240.

As also illustrated in FIGS. 7 and 12-14, the interchangeable tool assembly 1000 can comprise a slip ring assembly 1230 which can be configured to conduct electrical power to and/or from the surgical end effector 1500 and/or communicate signals to and/or from the surgical end effector 1500, back to a microprocessor 560 (FIG. 2) in the handle assembly 500 or robotic system controller, for example. Further details concerning the slip ring assembly 1230 and associated connectors may be found in U.S. patent application Ser. No. 13/803,086, now U.S. Patent Application Publication No. 2014/0263541, and U.S. patent application Ser. No. 15/019,196, now U.S. Pat. No. 10,413,291, which have each been herein incorporated by reference in their respective entirety as well as in U.S. patent application Ser. No. 13/800,067, entitled STAPLE CARTRIDGE TISSUE THICKNESS SENSOR SYSTEM, now U.S. Patent Application Publication No. 2014/0263552, which is hereby incorporated by reference herein in its entirety. As also described in further detail in the aforementioned patent applications that have been incorporated by reference herein, the interchangeable surgical tool assembly 1000 can also comprise at least one sensor that is configured to detect the position of the switch drum 2220.

Referring again to FIG. 2, the tool chassis 1210 includes at least one, and preferably two, tapered attachment portions 1212 formed thereon that are adapted to be received within corresponding dovetail slots 507 formed within the distal end portion of the handle frame 506 of the handle assembly 500. Various interchangeable surgical tool assemblies employ a latch system 1220 for removably coupling the interchangeable surgical tool assembly 1000 to the handle frame 506 of the handle assembly 500. As can be seen in FIG. 7, for example, in at least one form, the latch system 1220 includes a lock member or lock yoke 1222 that is movably coupled to the tool chassis 1210. In the illustrated embodiment, for example, the lock yoke 1222 has a U-shape with two spaced downwardly extending legs 1223. The legs 1223 each have a pivot lug (not shown) formed thereon that are adapted to be received in corresponding holes formed in the tool chassis 1210. Such arrangement facilitates pivotal attachment of the lock yoke 1222 to the tool chassis 1210. The lock yoke 1222 may include two proximally protruding lock lugs 1224 that are configured for releasable engagement with corresponding lock detents or grooves 509 in the distal end of the handle frame 506 of the handle assembly 500. See FIG. 2. In various forms, the lock yoke 1222 is biased in the proximal direction by a spring or biasing member 1225. Actuation of the lock yoke 1222 may be accomplished by a latch button 1226 that is slidably mounted on a latch actuator assembly 1221 that is mounted to the tool chassis 1210. The latch button 1226 may be biased in a proximal direction relative to the lock yoke 1222. The lock yoke 1222 may be moved to an unlocked position by biasing the latch button 1226 in the distal direction which also causes the lock yoke 1222 to pivot out of retaining engagement with the distal end of the handle frame 506. When the lock yoke 1222 is in "retaining engagement" with the distal end of the handle frame 506, the lock lugs 1224 are retainingly seated within the corresponding lock detents or grooves 509 in the distal end of the handle frame 506.

In the illustrated arrangement, the lock yoke 1222 includes at least one and preferably two lock hooks 1227 that are adapted to contact corresponding lock lug portions 1943 that are formed on the closure shuttle 1940. When the closure shuttle 1940 is in an unactuated position, the lock yoke 1222 may be pivoted in a distal direction to unlock the interchangeable surgical tool assembly 1000 from the handle assembly 500. When in that position, the lock hooks 1227 do not contact the lock lug portions 1943 on the closure shuttle 1940. However, when the closure shuttle 1940 is moved to an actuated position, the lock yoke 1222 is prevented from being pivoted to an unlocked position. Stated another way, if the clinician were to attempt to pivot the lock yoke 1222 to an unlocked position or, for example, the lock yoke 1222 was inadvertently bumped or contacted in a manner that might otherwise cause it to pivot distally, the lock hooks 1227 on the lock yoke 1222 will contact the lock lug portions 1943 on the closure shuttle 1940 and prevent movement of the lock yoke 1222 to an unlocked position.

Referring again to FIG. 6, the knife bar 2130 may comprise a laminated beam structure that includes at least two beam layers. Such beam layers may comprise, for example, stainless steel bands that are interconnected by, for example, welding or pinning together at their proximal ends and/or at other locations along their length. In alternative embodiments, the distal ends of the bands are not connected together to allow the laminates or bands to splay relative to each other when the end effector is articulated. Such arrangement permits the knife bar 2130 to be sufficiently flexible to accommodate articulation of the end effector. Various laminated knife bar arrangements are disclosed in U.S. patent application Ser. No. 15/019,245, entitled SURGICAL INSTRUMENTS WITH CLOSURE STROKE REDUCTION ARRANGEMENTS, now U.S. Pat. No. 10,470,764, which is hereby incorporated by reference in its entirety. As can also be seen in FIG. 6, a firing shaft support assembly 2300 is employed to provide lateral support to the knife bar 2130 as it flexes to accommodate articulation of the surgical end effector 1500. Further details concerning the operation of the firing shaft support assembly 2300 and alternative knife bar support arrangements may be found in U.S. patent application Ser. No. 15/019,245, entitled SURGICAL INSTRUMENTS WITH CLOSURE STROKE REDUCTION ARRANGEMENTS, now U.S. Pat. No. 10,470,764, and U.S. patent application Ser. No. 15/019,220, entitled SURGICAL INSTRUMENT WITH ARTICULATING AND AXIALLY TRANSLATABLE END EFFECTOR, now U.S. Pat. No. 10,245,029, which are each hereby incorporated by reference herein in their respective entireties.

As can also be seen in FIG. 6, a firing member or knife member 2140 is attached to the distal end of the knife bar 2130. In one exemplary form, the firing member 2140 comprises a body portion 2142 that supports a knife or tissue cutting portion 2144. The body portion 2142 protrudes through an elongate slot 1604 in the elongate channel 1602 and terminates in a foot member 2146 that extends laterally on each side of the body portion 2142. As the firing member 2140 is driven distally through the surgical staple/fastener cartridge 1700, the foot member 2146 rides within a passage 1622 (FIG. 48) in the elongate channel 1602 that is located under the surgical staple/fastener cartridge 1700. In one arrangement, the body portion 2142 includes two laterally protruding central tabs 2145 that may ride above the central passage within the surgical staple/fastener cartridge 1700. See FIG. 6. The tissue cutting portion 2144 is disposed between a distally protruding top nose portion 2143. As can be further seen in FIG. 6, the firing member 2140 may further include two laterally extending top tabs, pins or anvil engagement features 2147. As the firing member 2140 is driven distally, a top portion of the body portion 2142 extends through a centrally disposed anvil slot 1814 and the anvil engagement features 2147 ride on corresponding anvil ledges 1816 formed on each side of the anvil slot 1814. In one arrangement, to facilitate assembly of the anvil 1810 and firing member 2140 arrangement, the top of the anvil body 1812 has an opening 1817 therein. Once the anvil 1810 is assembled onto the elongate channel 1602 and the firing member 2140 is installed, the opening 1817 is covered by an anvil cap 1819 that is affixed to the anvil body 1812 by welding or other suitable fastening means.

Returning to FIG. 6, the firing member 2140 is configured to operably interface with a sled assembly 2150 that is operably supported within a body 1702 of the surgical staple/fastener cartridge 1700. The sled assembly 2150 is slidably displaceable within the surgical staple/fastener cartridge body 1702 from a proximal starting position adjacent the proximal end 1704 of the cartridge body 1702 to an ending position adjacent a distal end 1706 of the cartridge body 1702. The cartridge body 1702 operably supports therein a plurality of staple drivers (not shown) that are aligned in rows on each side of a centrally disposed slot 1708. The centrally disposed slot 1708 enables the firing member 2140 to pass therethrough and cut the tissue that is clamped between the anvil 1810 and the surgical staple/fastener cartridge 1700. The drivers are associated with corresponding staple/fastener pockets 1712 that open through an upper deck surface 1710 of the cartridge body 1702. Each of the staple drivers supports one or more surgical staple/fastener or fastener (not shown) thereon. The sled assembly 2150 includes a plurality of sloped or wedge-shaped cams 2152 wherein each cam 2152 corresponds to a particular line of fasteners or drivers located on a side of the slot 1708.

Attachment of the interchangeable surgical tool assembly 1000 to the handle assembly 500 will now be described with reference to FIG. 2. To commence the coupling process, the clinician may position the tool chassis 1210 of the interchangeable surgical tool assembly 1000 above or adjacent to the distal end of the handle frame 506 such that the tapered attachment portions 1212 formed on the tool chassis 1210 are aligned with the dovetail slots 507 in the handle frame 506. The clinician may then move the surgical tool assembly 1000 along an installation axis IA that is perpendicular to the shaft axis $SA_1$ to seat the tapered attachment portions 1212 in "operable engagement" with the corresponding dovetail receiving slots 507 in the distal end of the handle frame 506. In doing so, the firing shaft attachment lug 2128 on the intermediate firing shaft portion 2120 will also be seated in the attachment cradle (not shown) in the longitudinally movable drive member (not shown) within the handle assembly 500 and the portions of attachment pin 516 on the closure link 514 will be seated in the corresponding hooks 1942 in the closure shuttle 1940. As used herein, the term "operable engagement" in the context of two components means that the two components are sufficiently engaged with each other so that upon application of an actuation motion thereto, the components may carry out their intended action, function and/or procedure.

During a typical surgical procedure, the clinician may introduce the surgical end effector 1500 into the surgical site through a trocar or other opening in the patient to access the target tissue. When doing so, the clinician typically axially aligns the surgical end effector 1500 along the shaft axis (unarticulated state). Once the surgical end effector 1500 has passed through the trocar port, for example, the clinician may need to articulate the end effector 1500 to advantageously position it adjacent the target tissue. This is prior to closing the anvil onto the target tissue, so the closure drive system 510 would remain unactuated. When in this position, actuation of the firing drive system 530 will result in the application of articulation motions to the proximal articulation driver 1310. Once the end effector has attained the desired articulated position, the firing drive system 530 is deactivated and the articulation lock 1400 may retain the surgical end effector 1500 in the articulated position. The clinician may then actuate the closure drive system 510 to close the anvil 1810 onto the target tissue. Such actuation of the closure drive system 510 may also result in the shifter assembly 2200 delinking the proximal articulation driver from the intermediate firing shaft portion 2120. Thus, once the target tissue has been captured in the surgical end effector 1500, the clinician may once again actuate the firing drive system 530 to axially advance the firing member 2140 through the surgical staple/fastener cartridge 1700 to cut the clamped tissue and fire the staples into the cut tissue. Other closure and firing drive arrangements, actuator arrangements (both handheld, manual and automated or robotic) may also be employed to control the axial movement of the closure system components, the articulation system components and/or the firing system components of the surgical tool assembly 1000 without departing from the spirit and scope of the various inventions disclosed herein.

Figure 16:
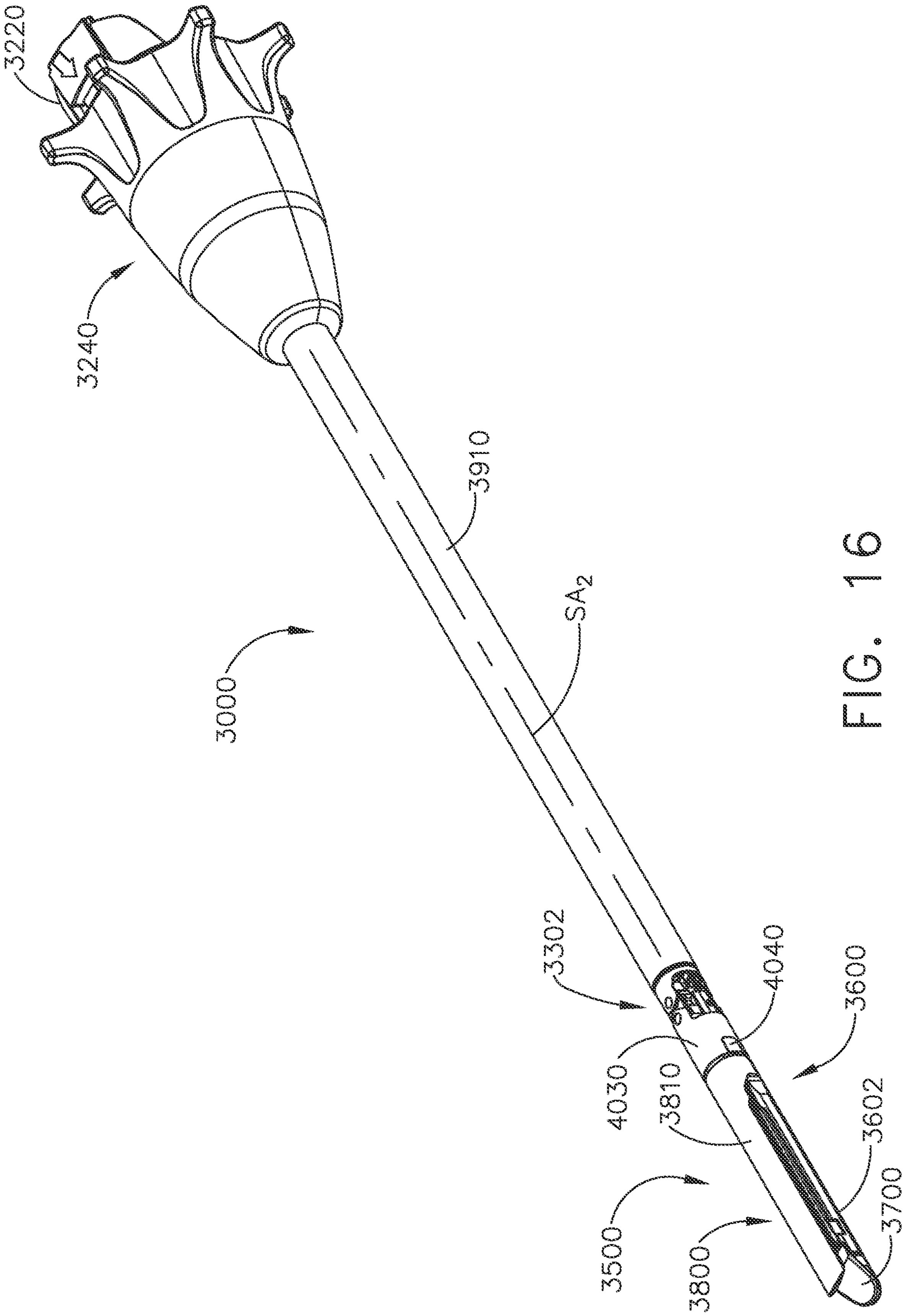
FIG. 16 is a perspective view of another one of the interchangeable surgical tool assemblies depicted in FIG. 1.
Figure 17:
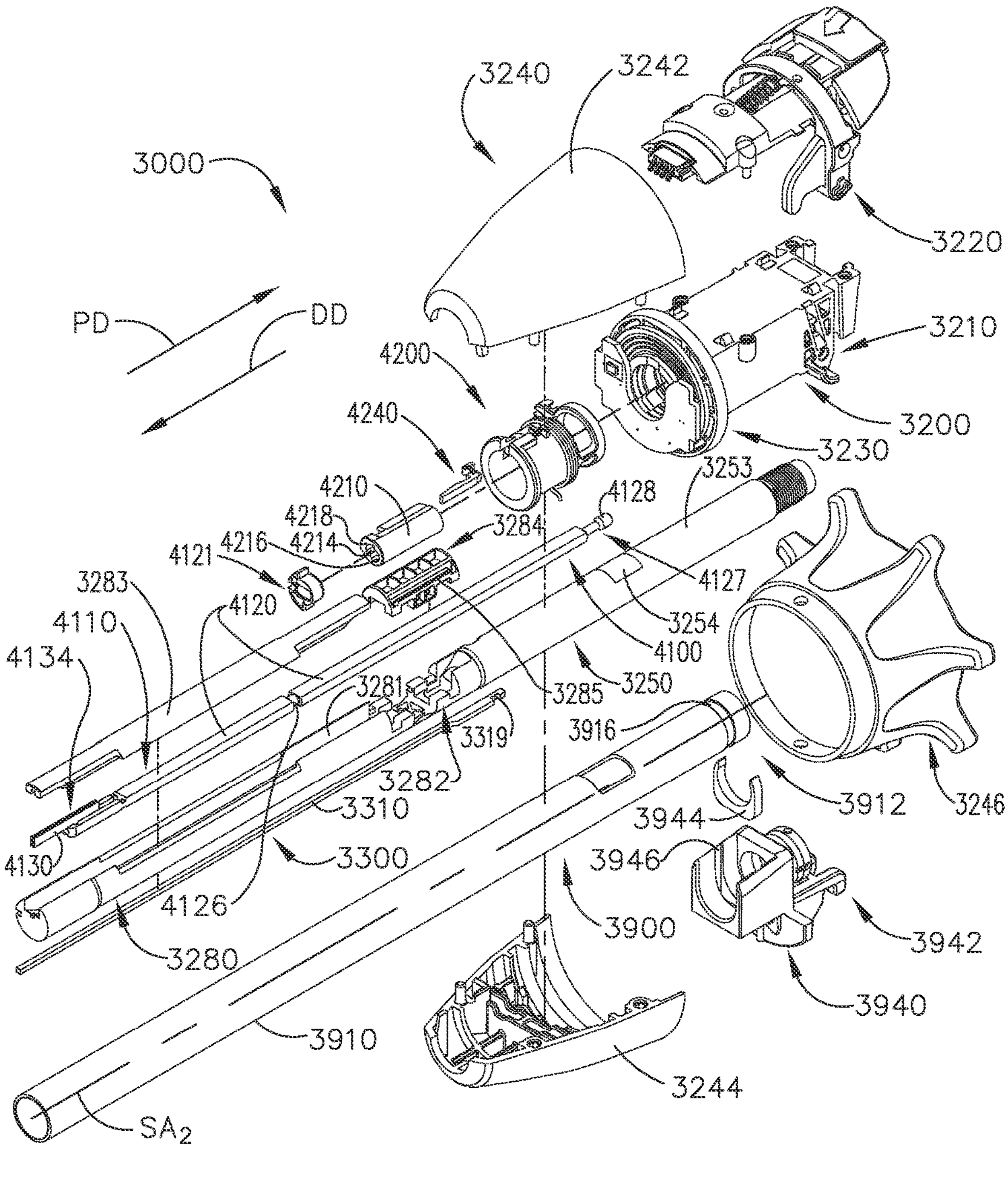
FIG. 17 is an exploded assembly view of a proximal portion of the interchangeable surgical tool assembly of FIG. 16.
Figure 18:
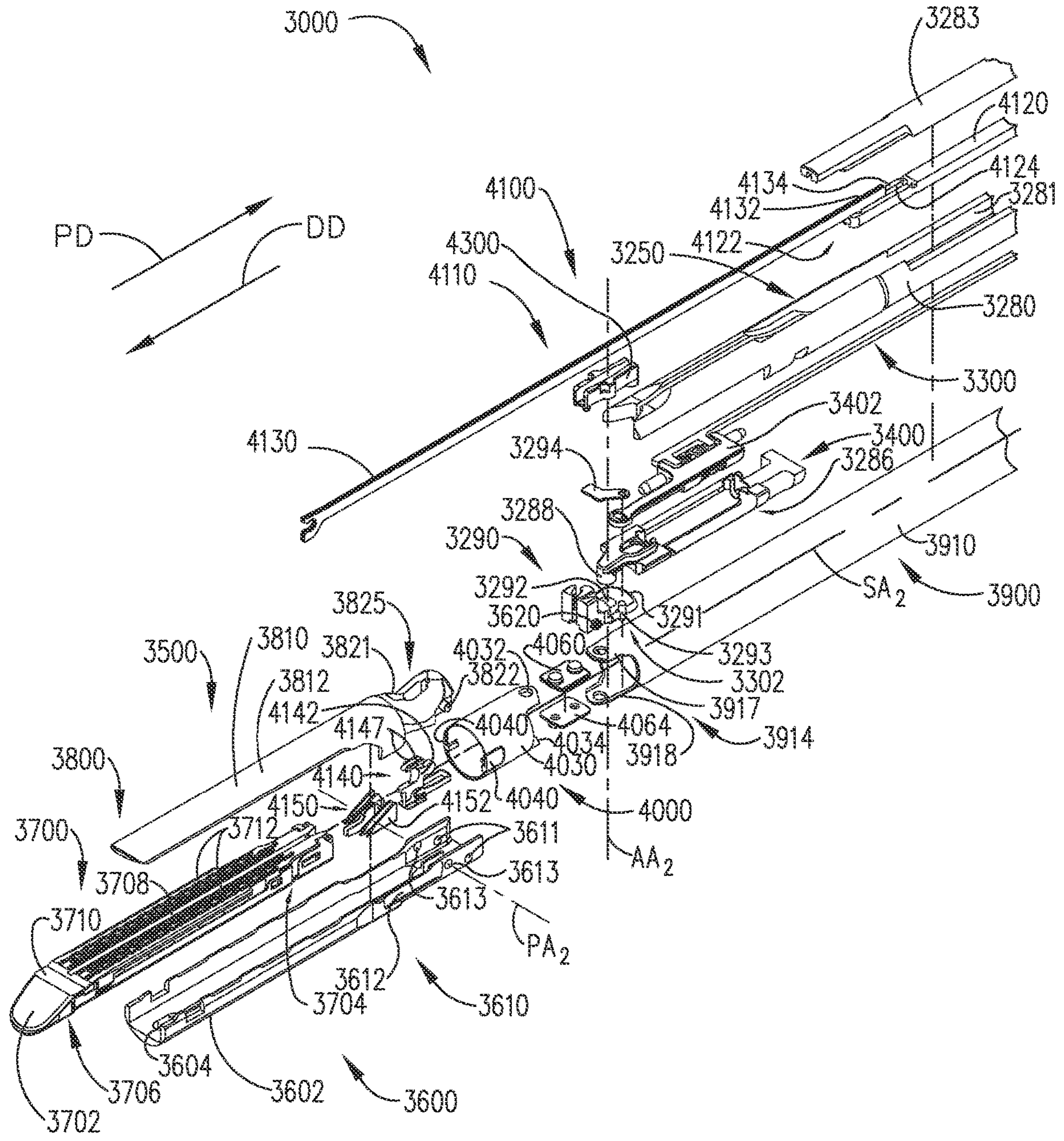
FIG. 18 is another exploded assembly view of a distal portion of the interchangeable surgical tool assembly of FIGS. 16 and 17.

Returning now to FIG. 1, the surgical system 10 illustrated in that Figure includes four interchangeable surgical tool assemblies 1000, 3000, 5000 and 7000 that may each be effectively employed with the same handle assembly 500 to perform different surgical procedures. Turning now to FIGS. 16-18, the interchangeable surgical tool assembly 3000 includes a surgical end effector 3500 that comprises a first jaw 3600 and a second jaw 3800. In one arrangement, the first jaw comprises an elongate channel 3602 that is configured to operably support a surgical staple/fastener cartridge 3700 therein. The second jaw 3800 comprises an anvil 3810 that is pivotally supported relative to the elongate channel 3602. The interchangeable surgical tool assembly 3000 includes an articulation system 3300 that comprises an articulation joint 3302 and an articulation lock 3400 which can be configured to releasably hold the surgical end effector 3500 in a desired articulated position relative to a shaft axis $SA_2$. Details regarding the construction and operation of the articulation lock 3400 as well as alternative lock configurations and operational details may be found in in U.S. patent application Ser. No. 13/803,086, entitled ARTICULATABLE SURGICAL INSTRUMENT COMPRISING AN ARTICULATION LOCK, now U.S. Patent Application Publication No. 2014/0263541, the entire disclosure of which is hereby incorporated by reference herein. Additional details concerning the articulation lock 3400 may also be found in U.S. patent application Ser. No. 15/019,196, filed Feb. 9, 2016, entitled SURGICAL INSTRUMENT ARTICULATION MECHANISM WITH SLOTTED SECONDARY CONSTRAINT, now U.S. Pat. No. 10,413,291, the entire disclosure of which is hereby incorporated by reference herein.

As can be seen in FIG. 17, the interchangeable surgical tool assembly 3000 includes a tool frame assembly 3200 that comprises a tool chassis 3210 that operably supports a nozzle assembly 3240 thereon. In one form, the nozzle assembly 3240 is comprised of nozzle portions 3242, 3244 as well as an actuator wheel portion 3246 that is configured to be coupled to the assembled nozzle portions 3242, 3244 by snaps, lugs, screws etc. The interchangeable surgical tool assembly 3000 includes a proximal closure assembly 3900 which is operably coupled to a distal closure assembly 4000 that is utilized to close and/or open the anvil 3810 of the surgical end effector 3500 as will be discussed in further detail below. In addition, the interchangeable surgical tool assembly 3000 includes an "elastic" spine assembly 3250 that operably supports the proximal closure assembly 3900 and is coupled to the surgical end effector 3500. One exemplary form of spine assembly 3250 is disclosed in U.S. patent application Ser. No. 15/385,911, entitled SURGICAL STAPLE/FASTENERS WITH INDEPENDENTLY ACTUATABLE CLOSING AND FIRING SYSTEMS, now U.S. Pat. No. 10,448,950, the entire disclosure of which is hereby incorporated by reference herein. For example, the spine assembly 3250 may comprise an elastic spine member that has a proximal end portion 3253 and a distal end portion 3280 that is separated from the proximal end portion 3253 of the elastic spine assembly 3250 by a stretch feature 3282 formed therebetween. In addition, a stretch limiting insert 3284 is retainingly supported between the distal end portion 3280 and the proximal end portion 3253. In various arrangements, the elastic spine assembly 3250 may be fabricated from, for example, suitable polymeric material, rubber, etc. which has a modulus of elasticity designated as $ME_1$ for reference purposes. The stretch limiting insert 3284 may have a modulus of elasticity designated as $ME_2$ for reference purposes. In various circumstances, the stretch limiting insert 3284 also includes a pair of stretch limiters 3285 (only one is shown in FIG. 17). The stretch limiter 3285 may have a modulus of elasticity for reference purposes of $ME_3$. In at least one arrangement, $ME_3<ME_2<ME_1$. Further details about at least one implementation of the elastic spine assembly 3250 and stretch limiting insert 3284 may be found in U.S. patent application Ser. No. 15/385,911, now U.S. Pat. No. 10,448,950.

In the illustrated arrangement, the distal end portion 3280 of the spine assembly 3250 has an opening 3281 therein for ease of assembly. A spine cap 3283 may be attached thereto to cover the opening 3281 after the various components have been assembled therein. In assembled form, the proximal end portion 3253 of the spine assembly 3250 is rotatably supported in the tool chassis 3210. In one arrangement, for example, the proximal end of the proximal end portion 3253 of the spine assembly 3250 is attached to a spine bearing (not shown) that is configured to be supported within the tool chassis 3210. Such arrangement facilitates rotatable attachment of the spine assembly 3250 to the tool chassis 3210 such that the spine assembly 3250 may be selectively rotated about a shaft axis $SA_2$ relative to the tool chassis 3210. In particular, in one arrangement, for example, the proximal end portion 3253 of the spine assembly 3250 includes two diametrically opposed lug seats 3254 (only one can be seen in FIG. 17) that are each configured to receive a corresponding nozzle lug (not shown) that extend inwardly from each of the nozzle portions 3242, 3244. Such arrangement facilitates rotation of the spine assembly 3250 about the shaft axis $SA_2$ by rotating the actuator wheel portion 3246 of the nozzle assembly 3240.

Referring now to FIG. 18, the distal end portion 3280 of the elastic spine assembly 3250 is attached to a distal frame segment 3286 that operably supports the articulation lock 3400 therein. The spine assembly 3250 is configured to, one, slidably support a firing member assembly 4110 therein and, two, slidably support the proximal closure tube 3910 which extends around the spine assembly 3250. The spine assembly 3250 can also be configured to slidably support a proximal articulation driver 3310. As can be seen in FIG. 18, the distal frame segment 3286 is pivotally coupled to the elongate channel 3602 by an end effector mounting assembly 3290. In one arrangement, for example, the distal end of the distal frame segment 3286 has a pivot pin 3288 formed thereon. The pivot pin 3288 is adapted to be pivotally received within a pivot hole 3292 formed in pivot base portion 3291 of the end effector mounting assembly 3290. The end effector mounting assembly 3290 is attached to a proximal end 3610 of the elongate channel 3602 by a spring pin 3620 or other suitable member that is received within mounting holes 3611 in the proximal end portion 3610. The pivot pin 3288 defines an articulation axis $AA_2$ that is transverse to the shaft axis $SA_2$. See FIG. 18. Such arrangement facilitates pivotal travel (i.e., articulation) of the surgical end effector 3500 about the articulation axis $AA_2$ relative to the elastic spine assembly 3250. The distal frame segment 3286 is further configured to support the articulation lock 3400 therein. Various articulation lock arrangements may be employed. At least one form of articulation lock 3400 is described in further detail in U.S. patent application Ser. No. 13/803,086, entitled ARTICULATABLE SURGICAL INSTRUMENT COMPRISING AN ARTICULATION LOCK, now U.S. Patent Application Publication No. 2014/0263541, the entire disclosure of which is hereby incorporated by reference herein. Additional details concerning the articulation lock may also be found in U.S. patent application Ser. No. 15/019,196, filed Feb. 9, 2016, entitled SURGICAL INSTRUMENT ARTICULATION MECHANISM WITH SLOTTED SECONDARY CONSTRAINT, now U.S. Pat. No. 10,413,291.

In the illustrated example, the surgical end effector 3500 is electively articulatable about the articulation axis $AA_2$ by the articulation system 3300. In one form, the articulation system 3300 includes the proximal articulation driver 3310 that operably interfaces with the articulation lock 3400. The articulation lock 3400 includes an articulation frame 3402 that is adapted to operably engage a drive pin 3293 on the pivot base portion 3291 of the end effector mounting assembly 3290. In addition, a cross link 3294 may be linked to the drive pin 3293 and articulation frame 3402 to assist articulation of the surgical end effector 3500. As indicated above, further details regarding the operation of the articulation lock 3400 and the articulation frame 3402 may be found in U.S. patent application Ser. No. 13/803,086, now U.S. Patent Application Publication No. 2014/0263541. Further details regarding the end effector mounting assembly and cross link 3294 may be found in U.S. patent application Ser. No. 15/019,245, filed Feb. 9, 2016, entitled SURGICAL INSTRUMENTS WITH CLOSURE STROKE REDUCTION ARRANGEMENTS, now U.S. Pat. No. 10,470,764, the entire disclosure of which is hereby incorporated by reference herein. As further described therein, as well as in other disclosures incorporated by reference herein, axial movement of proximal articulation driver 3310 will result in the engagement/disengagement of the articulation lock 3400 to thereby apply articulation motions to the elongate channel 3602 and thereby cause the surgical end effector 3500 to articulate about the articulation axis $AA_2$ relative to the spine assembly 3250.

The anvil 3810 in the illustrated example includes an anvil body 3812 that terminates in anvil mounting portion 3820. The anvil mounting portion 3820 is movably or pivotably supported on the elongate channel 3602 for selective pivotal travel relative thereto about a fixed anvil pivot axis $PA_2$ (FIG. 18) that is transverse to the shaft axis $SA_2$. In the illustrated arrangement, an anvil trunnion 3822 extends laterally out of each lateral side of the anvil mounting portion 3820 to be received in a corresponding trunnion pivot hole 3613 formed in the upstanding walls 3612 of the proximal end portion 3610 of the elongate channel 3602. Movement of the anvil 3810 relative to the elongate channel 3602 is effectuated by axial movement of the proximal closure assembly 3900 and the distal closure assembly 4000. In the illustrated arrangement, the proximal closure assembly 3900 comprises a proximal closure tube 3910 that has a proximal end 3912 and a distal end 3914. The proximal end 3912 is rotatably supported in a closure shuttle 3940 that is slidably supported within the tool chassis 3210 such that it may be axially moved relative thereto. In one form, the closure shuttle 3940 includes a pair of proximally-protruding hooks 3942 that are configured for attachment to the transverse attachment pin 516 that is attached to the closure linkage assembly 514 of the handle assembly 500. The proximal end 3912 is coupled to the closure shuttle 3940 for relative rotation thereto. For example, a U-shaped connector 3944 is inserted into an annular slot 3916 in the proximal end 3912 and is retained within vertical slots 3946 in the closure shuttle 3940. Such arrangement serves to attach the proximal closure assembly 3900 to the closure shuttle 3940 for axial travel therewith while enabling the proximal closure tube 3910 to rotate relative to the closure shuttle 3940 about the shaft axis $SA_2$. As was discussed above in connection with the interchangeable surgical tool assembly 1000, a closure spring (not shown) may extend over the proximal end 3912 of the proximal closure tube 3910 to bias the closure shuttle 3940 in the proximal direction PD which can serve to pivot the closure trigger 512 on the handle assembly 500 (FIG. 2) into the unactuated position when the interchangeable surgical tool assembly 3000 is operably coupled to the handle assembly 500 in the above described manner.

As can be seen in FIG. 18, the distal end 3914 of the proximal closure tube 3910 is attached to the distal closure assembly 4000. The distal end 3914 includes upper and lower tangs 3917, 3918 that are configured to be movably coupled to an end effector closure sleeve or distal closure tube segment 4030. The distal closure tube segment 4030 includes an upper tang 4032 and a lower tang 4034 that protrude proximally from a proximal end thereof. An upper double pivot link 4060 pivotally couples the upper tangs 3917 and 4032 and a lower double pivot link 4064 pivotally couples the lower tangs 3918 and 4034 together in the above-described manner. The distal advancement of the distal closure tube segment 4030 on the anvil mounting portion 3820 will result in closure or pivotal travel of the anvil 3810 towards the elongate channel 3602 about the fixed anvil pivot axis $PA_2$. In the illustrated arrangement, the distal closure tube segment 4030 also includes positive jaw or anvil opening features 4040 that are configured to coact with surfaces or ramp portions on the anvil mounting portion 3820 so as to cause the anvil 3810 to pivot from a closed position to an open position as the distal closure tube segment 4030 is moved proximally back to a starting position. Other embodiments may not employ the positive jaw opening features, but may rely on springs or other biasing arrangements to bias the anvil to the open position when the distal closure tube segment has been retracted to its proximal-most starting position. Further details regarding configurations and operation of the anvil opening features may be found in for example, U.S. patent application Ser. No. 15/385,911, entitled SURGICAL STAPLE/FASTENERS WITH INDEPENDENTLY ACTUATABLE CLOSING AND FIRING SYSTEMS, now U.S. Pat. No. 10,448,950.

In the illustrated arrangement, the interchangeable surgical tool assembly 3000 further includes a firing system generally designated as 4100. In various instances, the firing system 4100 includes a firing member assembly 4110 that is supported for axial travel within the spine assembly 3250. In the illustrated embodiment, the firing member assembly 4110 includes an intermediate firing shaft portion 4120 that is configured for attachment to a distal cutting portion or knife bar 4130. A support bushing arrangement 4121 may be employed to support the intermediate firing shaft portion 4120 within the spine assembly 3250. The firing member assembly 4110 may also be referred to herein as a "second shaft" and/or a "second shaft assembly". As can be seen in FIG. 18, the intermediate firing shaft portion 4120 may include a longitudinal slot 4124 in a distal end 4122 thereof which can be configured to receive a proximal end 4132 of the knife bar 4130. The longitudinal slot 4124 and the proximal end 4132 of the knife bar 4130 can be sized and configured to permit relative movement therebetween and can comprise a slip joint 4134. The slip joint 4134 can permit the intermediate firing shaft portion 4120 of the firing member assembly 4110 to be moved to articulate the end effector 3500 without moving, or at least substantially moving, the knife bar 4130 as was discussed above. In the illustrated arrangement, a proximal end 4127 of the intermediate firing shaft portion 4120 has a firing shaft attachment lug 4128 formed thereon that is configured to be seated into the attachment cradle (not shown) that is on the distal end of the longitudinally movable drive member (not shown) of the firing drive system 530 within the handle assembly 500 as was discussed above. Such arrangement facilitates the axial movement of the intermediate firing shaft portion 4120 upon actuation of the firing drive system 530. Other attachment configurations may also be employed to couple the intermediate firing shaft portion 4120 to other firing drive arrangements (e.g., manually actuated, robotic, etc.).

Further to the above, the interchangeable tool assembly 3000 can include a shifter assembly 4200 which can be configured to selectively and releasably couple the proximal articulation driver 3310 to the firing member assembly 4110 in the manner described above. In one form, the shifter assembly 4200 includes a lock collar, or lock sleeve 4210, positioned around the intermediate firing shaft portion 4120 of the firing member assembly 4110 wherein the lock sleeve 4210 can be rotated between an engaged position in which the lock sleeve 4210 couples the proximal articulation driver 3310 to the firing member assembly 4110 and a disengaged position in which the proximal articulation driver 3310 is not operably coupled to the firing member assembly 4110. As was discussed above, the intermediate firing shaft portion 4120 of the firing member assembly 4110 is formed with a drive notch 4126. The lock sleeve 4210 comprises a cylindrical, or an at least substantially cylindrical, body that includes a longitudinal aperture 4212 that is configured to receive the intermediate firing shaft portion 4120 therethrough. The lock sleeve 4210 can comprise diametrically-opposed, inwardly-facing lock protrusions 4214, 4216 that, when the lock sleeve 4210 is in one position, are engagingly received within corresponding portions of the drive notch 4126 in the intermediate firing shaft portion 4120 and, when in another position, are not received within the drive notch 4126 to thereby permit relative axial motion between the lock sleeve 4210 and the intermediate firing shaft 4120 as was discussed in further detail above. The lock sleeve 4210 further includes a lock member 4218 that is sized to be movably received within a notch 3319 in a proximal end of the proximal articulation driver 3310. When the lock sleeve 4210 is in its engaged position, the lock protrusions 4214, 4216 are positioned within the drive notch 4126 in the intermediate firing shaft portion 4120 such that a distal pushing force and/or a proximal pulling force can be transmitted from the firing member assembly 4110 to the lock sleeve 4210. Such axial pushing or pulling motion is then transmitted from the lock sleeve 4210 to the proximal articulation driver 3310 to thereby articulate the surgical end effector 3500.

As was discussed above, in the illustrated example, relative movement of the lock sleeve 4210 between its engaged and disengaged positions may be controlled by the shifter assembly 4200 that interfaces with the proximal closure tube 3910 of the proximal closure assembly 3900. The shifter assembly 4200 further includes a shifter key 4240 that is configured to be slidably received within a key groove (similar to the key groove 2217 illustrated in FIG. 8) formed in the outer perimeter of the lock sleeve 4210. Such arrangement enables the shifter key 4240 to move axially with respect to the lock sleeve 4210. Operation of the shifter assembly 4200 may be identical to the operation of the shifter assembly 2200 which was described in further detail above and which will not be repeated again for brevity. Further details, alternative arrangements and drive configurations that may be employed are disclosed in other arrangements that may be employed are disclosed in U.S. patent application Ser. No. 15/385,911, entitled SURGICAL STAPLE/FASTENERS WITH INDEPENDENTLY ACTUATABLE CLOSING AND FIRING SYSTEMS, now U.S. Pat. No. 10,448,950, U.S. patent application Ser. No. 13/803,086, now U.S. Patent Application Publication No. 2014/0263541, and U.S. patent application Ser. No. 15/019,196, now U.S. Pat. No. 10,413,291, the as well as other disclosures that have been incorporated herein.

The interchangeable tool assembly 3000 can comprise a slip ring assembly 3230 which can be configured to conduct electrical power to and/or from the surgical end effector 3500 and/or communicate signals to and/or from the surgical end effector 3500, back to a microprocessor 560 in the handle assembly 500 or robotic system controller, for example as was discussed above. Further details concerning the slip ring assembly 3230 and associated connectors may be found in U.S. patent application Ser. No. 13/803,086, now U.S. Patent Application Publication No. 2014/0263541, and U.S. patent application Ser. No. 15/019,196, now U.S. Pat. No. 10,413,291, which have each been herein incorporated by reference in their respective entirety as well as in U.S. patent application Ser. No. 13/800,067, entitled STAPLE CARTRIDGE TISSUE THICKNESS SENSOR SYSTEM, now U.S. Patent Application Publication No. 2014/0263552, which is hereby incorporated by reference herein in its entirety.

The illustrated interchangeable surgical tool assembly 3000 also employs a latch system 3220 for removably coupling the interchangeable surgical tool assembly 3000 to the handle frame 506 of the handle assembly 500, for example. The latch system 3220 may be identical to the latch system 1220 described in detail above. The knife bar 4130 may comprise a laminated beam structure that includes at least two beam layers. Such beam layers may comprise, for example, stainless steel bands that are interconnected by, for example, welding or pinning together at their proximal ends and/or at other locations along their length. In alternative embodiments, the distal ends of the bands are not connected together to allow the laminates or bands to splay relative to each other when the end effector is articulated. Such arrangement permits the knife bar 4130 to be sufficiently flexible to accommodate articulation of the end effector. Various laminated knife bar arrangements are disclosed in U.S. patent application Ser. No. 15/019,245, entitled SURGICAL INSTRUMENTS WITH CLOSURE STROKE REDUCTION ARRANGEMENTS, now U.S. Pat. No. 10,470,764, which is hereby incorporated by reference in its entirety. As can also be seen in FIG. 18, a firing shaft support assembly 4300 is employed to provide lateral support to the knife bar 4130 as it flexes to accommodate articulation of the surgical end effector 3500. Further details concerning the operation of the firing shaft support assembly 4300 and alternative knife bar support arrangements may be found in U.S. patent application Ser. No. 15/019,245, entitled SURGICAL INSTRUMENTS WITH CLOSURE STROKE REDUCTION ARRANGEMENTS, now U.S. Pat. No. 10,470,764, and U.S. patent application Ser. No. 15/019,220, entitled SURGICAL INSTRUMENT WITH ARTICULATING AND AXIALLY TRANSLATABLE END EFFECTOR, now U.S. Pat. No. 10,245,029, which are each hereby incorporated by reference herein in their respective entireties.

As can also be seen in FIG. 18, a firing member or knife member 4140 is attached to the distal end of the knife bar 4130. The firing member 4140 is configured to operably interface with a sled assembly 4150 that is operably supported within the body 3702 of the surgical staple/fastener cartridge 3700. The sled assembly 4150 is slidably displaceable within the surgical staple/fastener cartridge body 3702 from a proximal starting position adjacent the proximal end 3704 of the cartridge body 3702 to an ending position adjacent a distal end 3706 of the cartridge body 3702. The cartridge body 3702 operably supports therein a plurality of staple drivers (not shown) that are aligned in rows on each side of a centrally disposed slot 3708. The centrally disposed slot 3708 enables the firing member 4140 to pass therethrough and cut the tissue that is clamped between the anvil 3810 and the staple cartridge 3700. The drivers are associated with corresponding staple pockets 3712 that open through the deck surface 3710 of the cartridge body 3702. Each of the staple drivers supports one or more surgical staple/fastener or fastener (not shown) thereon. The sled assembly 4150 includes a plurality of sloped or wedge-shaped cams 4152 wherein each cam 4152 corresponds to a particular line of fasteners or drivers located on a side of the slot 3708.

Figure 49:
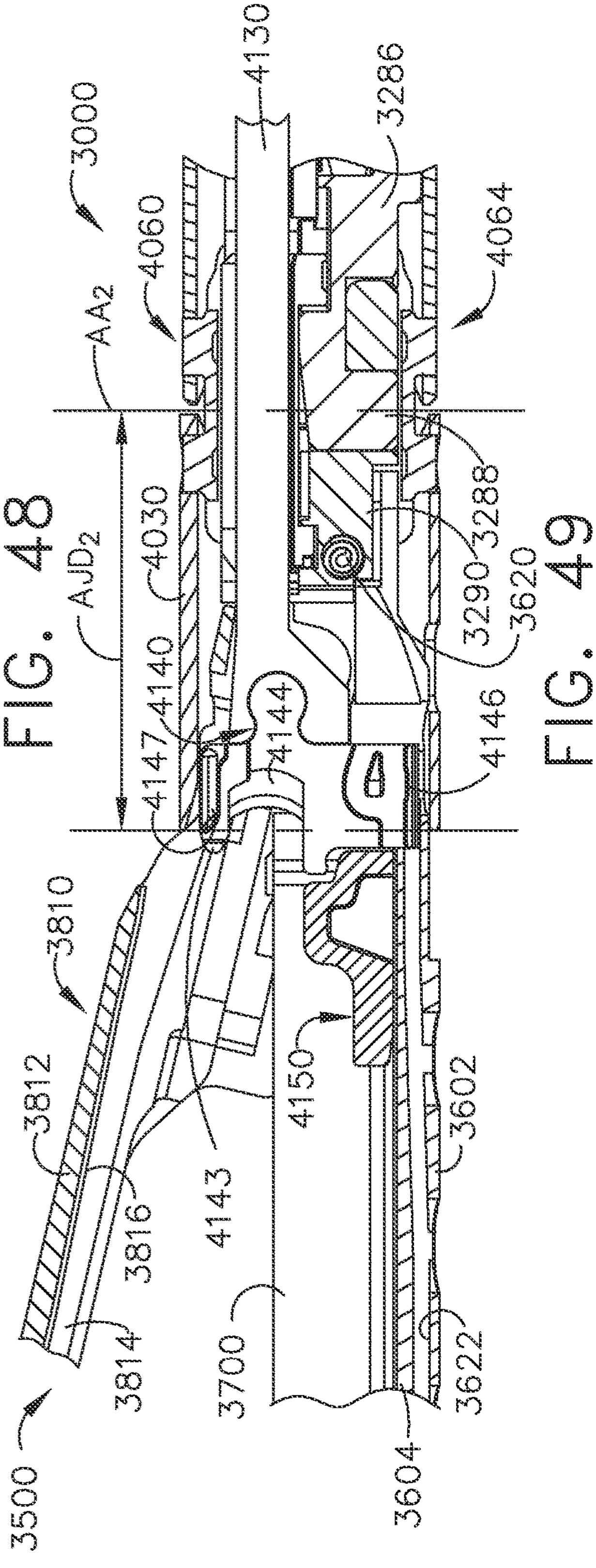
FIG. 49 is a partial cross-sectional view of the anvil mounting portion and elongate channel of the interchangeable surgical tool assembly of FIG. 16 with the anvil in a fully open position.

In one exemplary form, the firing member 4140 comprises a body portion 4142 that supports a knife or tissue cutting portion 4144. See FIG. 49. The body portion 4142 protrudes through an elongate slot 3604 in the elongate channel 3602 and terminates in a foot member 4146 that extends laterally on each side of the body portion 4142. As the firing member 4140 is driven distally through the surgical staple/fastener cartridge 3700, the foot member 4146 rides within a passage 3622 in the elongate channel 3602 that is located under the surgical staple/fastener cartridge 3700. The tissue cutting portion 4144 is disposed between a distally protruding top nose portion 4143. As can be further seen in FIG. 18, the firing member 4140 may further include two laterally extending top tabs, pins or anvil engagement features 4147. As the firing member 4140 is driven distally, a top portion of the body portion 4142 extends through a centrally disposed anvil slot 3814 and the anvil engagement features 4147 ride on corresponding ledges 3816 formed on each side of the anvil slot 3814. Further details concerning the firing member 4140, sled assembly 4150 and their various alternatives as well as examples of their operation will be discussed in further detail below and may also be found in U.S. patent application Ser. No. 15/385,911, entitled SURGICAL STAPLE/FASTENERS WITH INDEPENDENTLY ACTUATABLE CLOSING AND FIRING SYSTEMS, now U.S. Pat. No. 10,448,950. The interchangeable surgical tool assembly 3000 may be to the handle assembly 500 in the manner as described above with respect to the interchangeable surgical tool assembly 1000.

Figure 19:
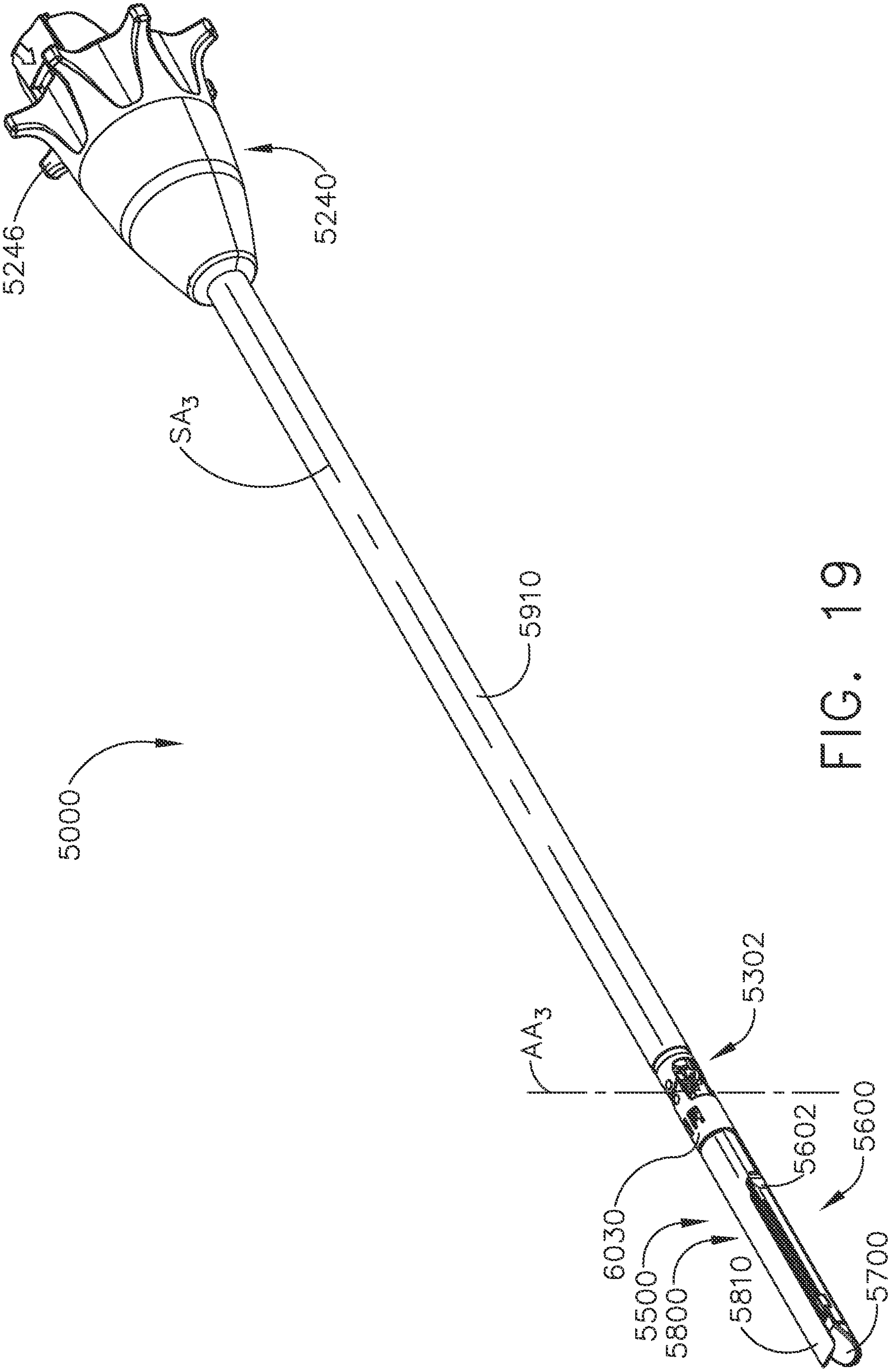
FIG. 19 is a perspective view of another one of the interchangeable surgical tool assemblies depicted in FIG. 1.
Figure 20:
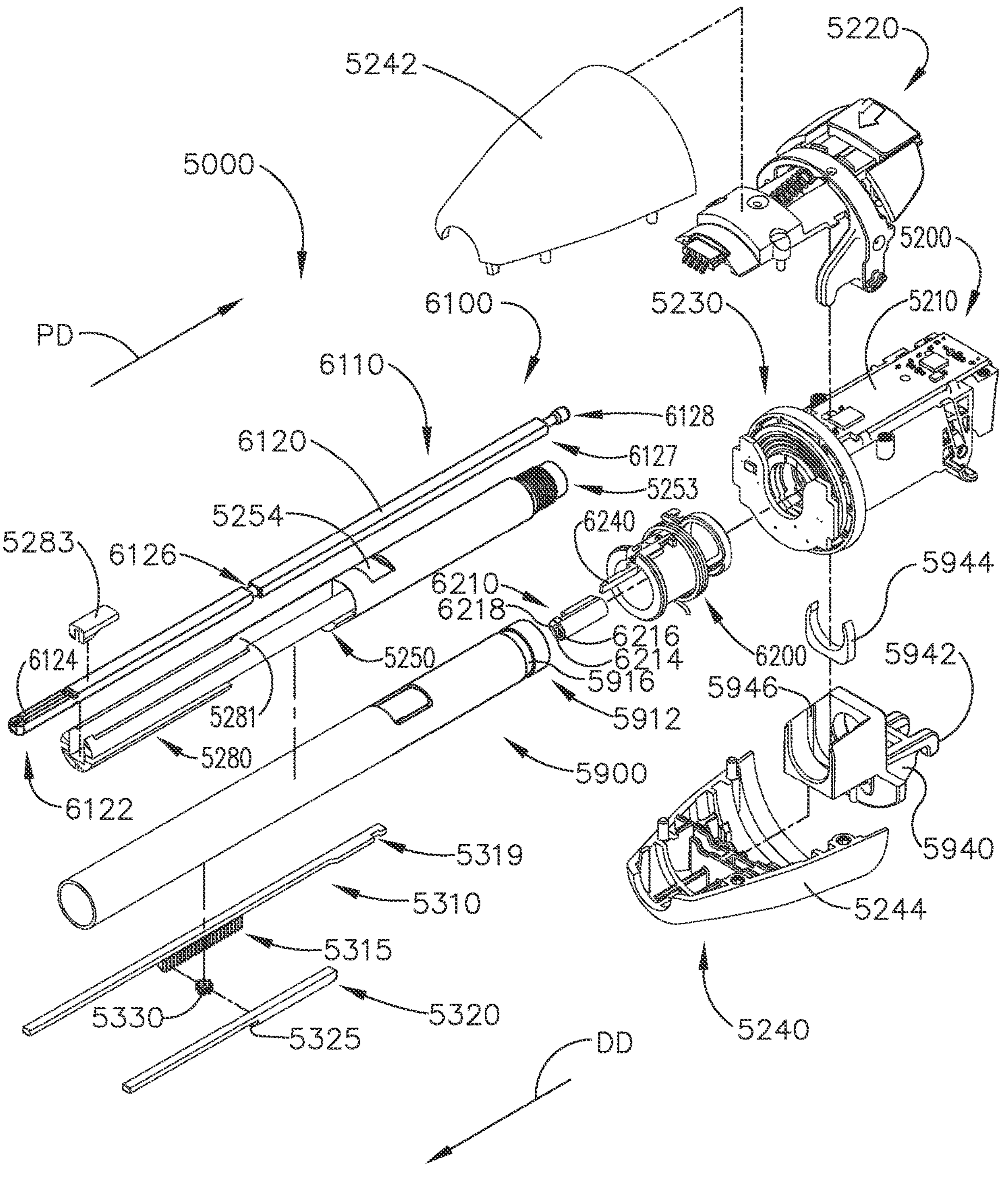
FIG. 20 is an exploded assembly view of a proximal portion of the interchangeable surgical tool assembly of FIG. 19.
Figure 21:
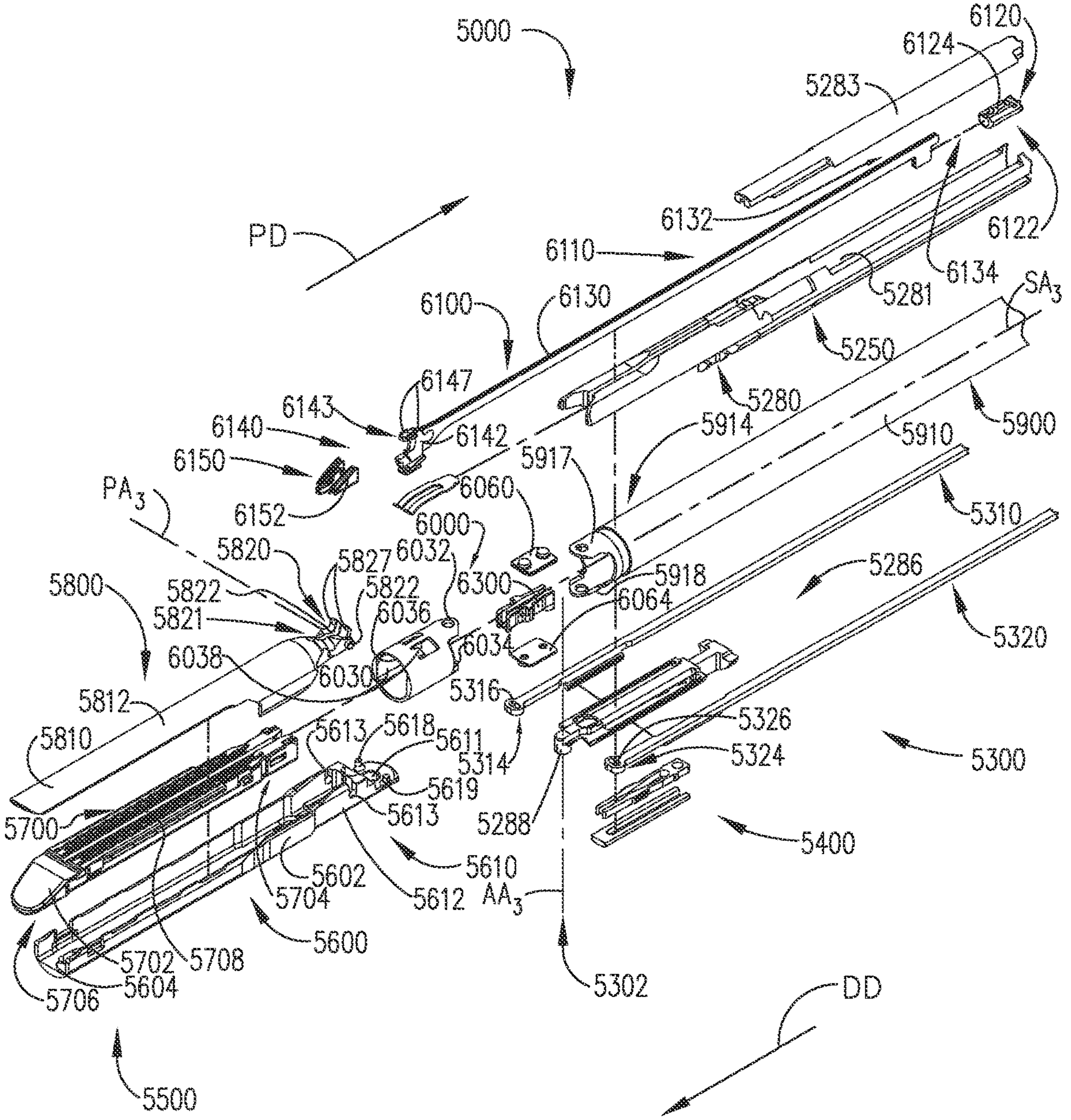
FIG. 21 is another exploded assembly view of a distal portion of the interchangeable surgical tool assembly of FIGS. 19 and 20.

Returning again to FIG. 1, as was discussed above, the surgical system 10 illustrated in that Figure includes four interchangeable surgical tool assemblies 1000, 3000, 5000 and 7000 that may each be effectively employed with the same handle assembly 500 to perform different surgical procedures. Turning now to FIGS. 19-21, the interchangeable surgical tool assembly 5000 includes a surgical end effector 5500 that comprises a first jaw 5600 and a second jaw 5800. In one arrangement, the first jaw comprises an elongate channel 5602 that is configured to operably support a surgical staple/fastener cartridge 5700 therein. The second jaw 5800 comprises an anvil 5810 that is movably supported relative to the elongate channel 5602. The interchangeable surgical tool assembly 5000 includes an articulation system 5300 that comprises an articulation joint 5302 and an articulation lock 5400 which can be configured to releasably hold the surgical end effector 5500 in a desired articulated position relative to a shaft axis $SA_3$. Details regarding the construction and operation of the articulation lock 5400 as well as alternative lock configurations and operational details may be found in in U.S. patent application Ser. No. 15/385,894, entitled SHAFT ASSEMBLY COMPRISING A LOCKOUT, now U.S. Pat. No. 10,492,785, the entire disclosure of which is hereby incorporated by reference herein. Alternative articulation lock arrangements may also be found in U.S. patent application Ser. No. 13/803,086, entitled ARTICULATABLE SURGICAL INSTRUMENT COMPRISING AN ARTICULATION LOCK, now U.S. Patent Application Publication No. 2014/0263541 and U.S. patent application Ser. No. 15/019,196, filed Feb. 9, 2016, entitled SURGICAL INSTRUMENT ARTICULATION MECHANISM WITH SLOTTED SECONDARY CONSTRAINT, now U.S. Pat. No. 10,413,291, the entire disclosures of each such reference being hereby incorporated by reference herein.

As can be seen in FIG. 20, the interchangeable surgical tool assembly 5000 includes a tool frame assembly 5200 that comprises a tool chassis 5210 that operably supports a nozzle assembly 5240 thereon. In one form, the nozzle assembly 5240 is comprised of nozzle portions 5242, 5244 as well as an actuator wheel portion 5246 that is configured to be coupled to the assembled nozzle portions 5242, 5244 by snaps, lugs, screws etc. The interchangeable surgical tool assembly 5000 includes a proximal closure assembly 5900 which is operably coupled to a distal closure assembly 6000 that is utilized to close and/or open the anvil 5810 of the surgical end effector 5500 as will be discussed in further detail below. In addition, the interchangeable surgical tool assembly 5000 includes a spine assembly 5250 that operably supports the proximal closure assembly 5900 and is coupled to the surgical end effector 5500. In the illustrated arrangement, the spine assembly 5250 includes a distal end portion 5280 that has an opening 5281 therein for ease of assembly. A spine cap 5283 may be attached thereto to cover the opening 5281 after the various components have been assembled therein. In assembled form, a proximal end portion 5253 of the spine assembly 5250 is rotatably supported in the tool chassis 5210. In one arrangement, for example, the proximal end of the proximal end portion 5253 of the spine assembly 5250 is attached to a spine bearing (not shown) that is configured to be supported within the tool chassis 5210. Such arrangement facilitates rotatable attachment of the spine assembly 5250 to the tool chassis 5210 such that the spine assembly 5250 may be selectively rotated about the shaft axis $SA_3$ relative to the tool chassis 5210. In particular, in one arrangement, for example, the proximal end portion 5253 of the spine assembly 5250 includes two diametrically opposed lug seats 5254 (only one can be seen in FIG. 20) that are each configured to receive a corresponding nozzle lug (not shown) that extend inwardly from each of the nozzle portions 5242, 5244. Such arrangement facilitates rotation of the spine assembly 5250 about the shaft axis $SA_3$ by rotating the actuator wheel portion 5246 of the nozzle assembly 5240.

Referring now to FIG. 21, the distal end portion 5280 of the spine assembly 5250 is attached to a distal frame segment 5286 that operably supports the articulation lock 5400 therein. The spine assembly 5250 is configured to, one, slidably support a firing member assembly 6110 therein and, two, slidably support a proximal closure tube 5910 which extends around the spine assembly 5250. The spine assembly 5250 can also be configured to slidably support a first articulation driver 5310 and a second articulation driver 5320. As can be seen in FIG. 21, the distal frame segment 5286 is pivotally coupled to a proximal end 5610 of the elongate channel 5602. In one arrangement, for example, the distal end of the distal frame segment 5286 has a pivot pin 5288 formed thereon. The pivot pin 5288 is adapted to be pivotally received within a pivot hole 5611 formed in the proximal end portion 5610 of the elongate channel 5602. The pivot pin 5288 defines an articulation axis $AA_3$ that is transverse to the shaft axis $SA_3$. See FIG. 21. Such arrangement facilitates pivotal travel (i.e., articulation) of the surgical end effector 5500 about the articulation axis $AA_3$ relative to the spine assembly 5250. The distal frame segment 5286 is further configured to support the articulation lock 5400 therein.

In the illustrated arrangement, a distal end 5314 of the first articulation driver 5310 is formed with a loop 5316 that is adapted to receive a first articulation pin 5618 therein that is formed on the proximal end portion 5610 of the elongate channel 5602. Similarly, a distal end 5324 of the second articulation driver 5320 has a loop 5326 that is adapted to receive a second articulation pin 5619 therein that is formed on the proximal end portion 5610 of the elongate channel 5602. In one arrangement, for example, the first articulation driver 5310 further comprises a proximal rack of teeth 5315 that is in meshing engagement with an idler gear 5330 rotatably supported in the spine assembly 5250. Similarly the second articulation driver 5320 further comprises a proximal rack of teeth 5325 that is in meshing engagement with the idler gear 5330. Thus, in such arrangement, movement of the first articulation driver 5310 in the distal direction DD will result in movement of the second articulation driver 5320 in the proximal direction PD. Movement of the first articulation driver 5310 in the proximal direction PD will result in the movement of the second articulation driver 5320 in the distal direction DD. Thus, such movement of the first and second articulation drivers 5310, 5320 will provide simultaneously pushing and pulling motions to the surgical end effector 5500 to articulate the surgical end effector about the articulation axis $AA_3$.

The anvil 5810 in the illustrated example includes an anvil body 5812 that terminates in anvil mounting portion 5820. The anvil mounting portion 5820 is movably supported on the elongate channel 5602 for selective pivotal and vertical travel relative thereto. In the illustrated arrangement, an anvil trunnion 5822 extends laterally out of each lateral side of the anvil mounting portion 5820 to be received in a corresponding "open-ended" vertical cradle 5613 formed in upstanding walls 5612 of the proximal end portion 5610 of the elongate channel 5602. Movement of the anvil 5810 relative to the elongate channel 5602 is effectuated by axial movement of the proximal closure assembly 5900 and the distal closure assembly 6000. In the illustrated arrangement, the proximal closure assembly 5900 comprises the proximal closure tube 5910 that has a proximal end 5912 and a distal end 5914. The proximal end 5912 is rotatably supported in a closure shuttle 5940 that is slidably supported within the tool chassis 5210 such that it may be axially moved relative thereto. In one form, the closure shuttle 5940 includes a pair of proximally-protruding hooks 5942 that are configured for attachment to the transverse attachment pin 516 that is attached to the closure linkage assembly 514 of the handle assembly 500. The proximal end 5912 of the proximal closure tube 5910 is coupled to the closure shuttle 5940 for relative rotation thereto. For example, a U-shaped connector 5944 is inserted into an annular slot 5916 in the proximal end 5912 and is retained within vertical slots 5946 in the closure shuttle 5940. Such arrangement serves to attach the proximal closure assembly 5900 to the closure shuttle 5940 for axial travel therewith while enabling the proximal closure tube 5910 to rotate relative to the closure shuttle 5940 about the shaft axis $SA_3$. As was discussed above in connection with the interchangeable surgical tool assembly 1000, a closure spring (not shown) may extend over the proximal end 5912 of the proximal closure tube 5910 to bias the closure shuttle 5940 in the proximal direction PD which can serve to pivot the closure trigger 512 on the handle assembly 500 (FIG. 2) into the unactuated position when the interchangeable surgical tool assembly 5000 is operably coupled to the handle assembly 500 in the above described manner.

As can be seen in FIG. 21, the distal end 5914 of the proximal closure tube 5910 is attached to the distal closure assembly 6000. The distal end 5914 includes upper and lower tangs 5917, 7918 that are configured to be movably coupled to an end effector closure sleeve or distal closure tube segment 6030. The distal closure tube segment 6030 includes an upper tang 6032 and a lower tang 6034 that protrude proximally from a proximal end thereof. An upper double pivot link 6060 pivotally couples the upper tangs 5917 and 6032 and a lower double pivot link 6064 pivotally couples the lower tangs 5918 and 6034 together in the above-described manner. The distal closure tube segment 6030 includes an internal cam surface 6036 that is configured to cammingly engage an anvil cam surface 5821 on the anvil mounting portion 5820. The distal advancement of the distal closure tube segment 6030 on the anvil mounting portion 5820 will result in closure or pivotal travel of the anvil 5810 towards the elongate channel 5602. In the illustrated arrangement, upstanding anvil tabs 5827 are formed on the anvil mounting portion 5820 and are configured to be contacted by two positive jaw opening tabs 6038 that extend inwardly within the distal closure tube segment 6030. Each positive jaw opening tab 6038 is configured to engage a corresponding one of the anvil tabs 5827 to pivot the anvil 5810 to an open position when the distal closure tube segment 6030 is axially moved in the proximal direction PD.

In the illustrated arrangement, the interchangeable surgical tool assembly 5000 further includes a firing system generally designated as 6100. In various instances, the firing system 6100 includes the firing member assembly 6110 that is supported for axial travel within the spine assembly 5250. In the illustrated embodiment, the firing member assembly 6110 includes an intermediate firing shaft portion 6120 that is configured for attachment to a distal cutting portion or knife bar 6130. The firing member assembly 6110 may also be referred to herein as a "second shaft" and/or a "second shaft assembly". As can be seen in FIG. 21, the intermediate firing shaft portion 6120 may include a longitudinal slot 6124 in a distal end 6122 thereof which can be configured to receive a proximal end 6132 of the knife bar 6130. The longitudinal slot 6124 and the proximal end 6132 of the knife bar 6130 can be sized and configured to permit relative movement therebetween and can comprise a slip joint 6134. The slip joint 6134 can permit the intermediate firing shaft portion 6120 of the firing member assembly 6110 to be moved to articulate the end effector 5500 without moving, or at least substantially moving, the knife bar 6130 as was discussed above. In the illustrated arrangement, a proximal end 6127 of the intermediate firing shaft portion 6120 has a firing shaft attachment lug 6128 formed thereon that is configured to be seated into an attachment cradle (not shown) that is on the distal end of the longitudinally movable drive member (not shown) of the firing drive system 530 within the handle assembly 500 as was discussed above. Such arrangement facilitates the axial movement of the intermediate firing shaft portion 6120 upon actuation of the firing drive system 530. Other attachment configurations may also be employed to couple the intermediate firing shaft portion to other firing drive arrangements (e.g., manually actuated, robotic, etc.).

Further to the above, the interchangeable tool assembly 5000 can include a shifter assembly 6200 which can be configured to selectively and releasably couple the first articulation driver 5310 to the firing member assembly 6110 in the manner described above. In one form, the shifter assembly 6200 includes a lock collar, or lock sleeve 6210, positioned around the intermediate firing shaft portion 6120 of the firing member assembly 6110 wherein the lock sleeve 6210 can be rotated between an engaged position in which the lock sleeve 6210 couples the first articulation driver 5310 to the firing member assembly 6110 and a disengaged position in which the first articulation driver 5310 is not operably coupled to the firing member assembly 6110. As was discussed above, the intermediate firing shaft portion 6120 of the firing member assembly 6110 is formed with a drive notch 6126. The lock sleeve 6210 comprises a cylindrical, or an at least substantially cylindrical, body that includes a longitudinal aperture that is configured to receive the intermediate firing shaft portion 6120 therethrough. The lock sleeve 6210 can comprise diametrically-opposed, inwardly-facing lock protrusions 6214, 6216 that, when the lock sleeve 6210 is in one position, are engagingly received within corresponding portions of the drive notch 6126 in the intermediate firing shaft portion 6120 and, when in another position, are not received within the drive notch 6126 to thereby permit relative axial motion between the lock sleeve 6210 and the intermediate firing shaft 6120 as was discussed in further detail above. The lock sleeve 6210 further includes a lock member 6218 that is sized to be movably received within a notch 5319 in a proximal end of the first articulation driver 5310. When the lock sleeve 6210 is in its engaged position, the lock protrusions 6214, 6216 are positioned within the drive notch 6126 in the intermediate firing shaft portion 6120 such that a distal pushing force and/or a proximal pulling force can be transmitted from the firing member assembly 6110 to the lock sleeve 6210. Such axial pushing or pulling motion is then transmitted from the lock sleeve 6210 to the first articulation driver 5310. Axial movement of the first articulation driver 5310 results in the axial movement of the second articulation driver 5320 in an opposite direction to thereby articulate the surgical end effector 5500.

As was discussed above, in the illustrated example, relative movement of the lock sleeve 6210 between its engaged and disengaged positions may be controlled by the shifter assembly 6200 that interfaces with the proximal closure tube 5910 of the proximal closure assembly 5900. The shifter assembly 6200 further includes a shifter key 6240 that is configured to be slidably received within a key groove (similar to the key groove 2217 illustrated in FIG. 8) formed in the outer perimeter of the lock sleeve 6210. Such arrangement enables the shifter key 6240 to move axially with respect to the lock sleeve 6210. Operation of the shifter assembly 6200 may be identical to the operation of the shifter assembly 2200 which was described in further detail above and which will not be repeated again for brevity. Further details, alternative arrangements and drive configurations that may be employed are disclosed in Other arrangements that may be employed are disclosed in U.S. patent application Ser. No. 15/385,911, entitled SURGICAL STAPLE/FASTENERS WITH INDEPENDENTLY ACTUATABLE CLOSING AND FIRING SYSTEMS, now U.S. Pat. No. 10,448,950, U.S. patent application Ser. No. 13/803,086, now U.S. Patent Application Publication No. 2014/0263541, and U.S. patent application Ser. No. 15/019,196, now U.S. Pat. No. 10,413,291, the as well as other disclosures that have been incorporated herein.

The interchangeable tool assembly 5000 can comprise a slip ring assembly 5230 which can be configured to conduct electrical power to and/or from the surgical end effector 5500 and/or communicate signals to and/or from the surgical end effector 5500, back to a microprocessor 560 in the handle assembly 500 or robotic system controller, for example as was discussed above. Further details concerning the slip ring assembly 5230 and associated connectors may be found in U.S. patent application Ser. No. 13/803,086, now U.S. Patent Application Publication No. 2014/0263541, and U.S. patent application Ser. No. 15/019,196, now U.S. Pat. No. 10,413,291, which have each been herein incorporated by reference in their respective entirety as well as in U.S. patent application Ser. No. 13/800,067, entitled STAPLE CARTRIDGE TISSUE THICKNESS SENSOR SYSTEM, now U.S. Patent Application Publication No. 2014/0263552, which is hereby incorporated by reference herein in its entirety.

The illustrated interchangeable surgical tool assembly 5000 also employs a latch system 5220 for removably coupling the interchangeable surgical tool assembly 5000 to the handle frame 506 of the handle assembly 500, for example. The latch system 5220 may be identical to the latch system 1220 described in detail above. The knife bar 6130 may comprise a laminated beam structure that includes at least two beam layers. Such beam layers may comprise, for example, stainless steel bands that are interconnected by, for example, welding or pinning together at their proximal ends and/or at other locations along their length. In alternative embodiments, the distal ends of the bands are not connected together to allow the laminates or bands to splay relative to each other when the end effector is articulated. Such arrangement permits the knife bar 6130 to be sufficiently flexible to accommodate articulation of the end effector. Various laminated knife bar arrangements are disclosed in U.S. patent application Ser. No. 15/019,245, entitled SURGICAL INSTRUMENTS WITH CLOSURE STROKE REDUCTION ARRANGEMENTS, now U.S. Pat. No. 10,470,764, which is hereby incorporated by reference in its entirety. As can also be seen in FIG. 21, a firing shaft support assembly 6300 is employed to provide lateral support to the knife bar 6130 as it flexes to accommodate articulation of the surgical end effector 5500. Further details concerning the operation of the firing shaft support assembly 6300 and alternative knife bar support arrangements may be found in U.S. patent application Ser. No. 15/019,245, entitled SURGICAL INSTRUMENTS WITH CLOSURE STROKE REDUCTION ARRANGEMENTS, now U.S. Pat. No. 10,470,764, and U.S. patent application Ser. No. 15/019,220, entitled SURGICAL INSTRUMENT WITH ARTICULATING AND AXIALLY TRANSLATABLE END EFFECTOR, now U.S. Pat. No. 10,245,029, which are each hereby incorporated by reference herein in their respective entireties.

Figure 50:
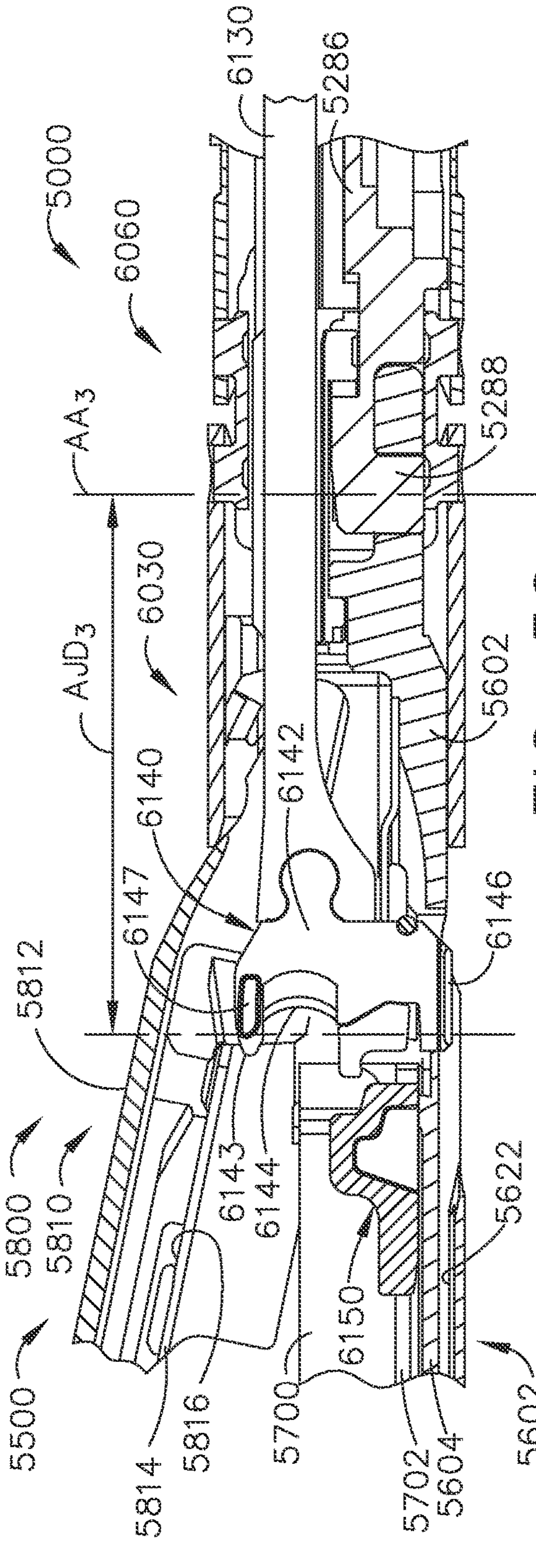
FIG. 50 is a partial cross-sectional view of the anvil mounting portion and elongate channel of the interchangeable surgical tool assembly of FIG. 19 with the anvil in a fully open position.

As can also be seen in FIGS. 21 and 50, a firing member or knife member 6140 is attached to the distal end of the knife bar 6130. The firing member 6140 is configured to operably interface with a sled assembly 6150 that is operably supported within the body 5702 of the surgical staple/fastener cartridge 5700. The sled assembly 6150 is slidably displaceable within the surgical staple/fastener cartridge body 5702 from a proximal starting position adjacent a proximal end 5704 of the cartridge body 5702 to an ending position adjacent a distal end 5706 of the cartridge body 5702. The cartridge body 5702 operably supports therein a plurality of staple drivers (not shown) that are aligned in rows on each side of a centrally disposed slot 5708. The centrally disposed slot 5708 enables the firing member 6140 to pass therethrough and cut the tissue that is clamped between the anvil 5810 and the staple cartridge 5700. The drivers are associated with corresponding staple pockets that open through the upper deck surface of the cartridge body 5702. Each of the staple drivers supports one or more surgical staple/fastener or fastener (not shown) thereon. The sled assembly includes a plurality of sloped or wedge-shaped cams 6152 wherein each cam corresponds to a particular line of fasteners or drivers located on a side of the slot 5708.

In one exemplary form, the firing member 6140 comprises a body portion 6142 that supports a knife or tissue cutting portion 6144. See FIG. 50. The body portion 6142 protrudes through an elongate slot 5604 in the elongate channel 5602 and terminates in a foot member 6146 that extends laterally on each side of the body portion 6142. As the firing member 6140 is driven distally through the surgical staple/fastener cartridge 5700, the foot member 6146 rides within a passage 5622 in the elongate channel 5602 that is located under the surgical staple/fastener cartridge 5700. The tissue cutting portion 6144 is disposed between a distally protruding top nose portion 6143. As can be further seen in FIGS. 21 and 50, the firing member 6140 may further include two laterally extending top tabs, pins or anvil engagement features 6147. As the firing member 6140 is driven distally, a top portion of the body portion 6142 extends through a centrally disposed anvil slot 5814 and the anvil engagement features 6147 ride on corresponding ledges 5816 formed on each side of the anvil slot 5814. Further details concerning the firing member 6140, sled assembly 6150, and their various alternatives as well as examples of their operation will be discussed in further detail below and may also be found in U.S. patent application Ser. No. 15/385,911, entitled SURGICAL STAPLE/FASTENERS WITH INDEPENDENTLY ACTUATABLE CLOSING AND FIRING SYSTEMS, now U.S. Pat. No. 10,448,950. The interchangeable surgical tool assembly 5000 may be operably coupled to the handle assembly 500 in the manner as described above with respect to the interchangeable surgical tool assembly 1000.

Figure 22:
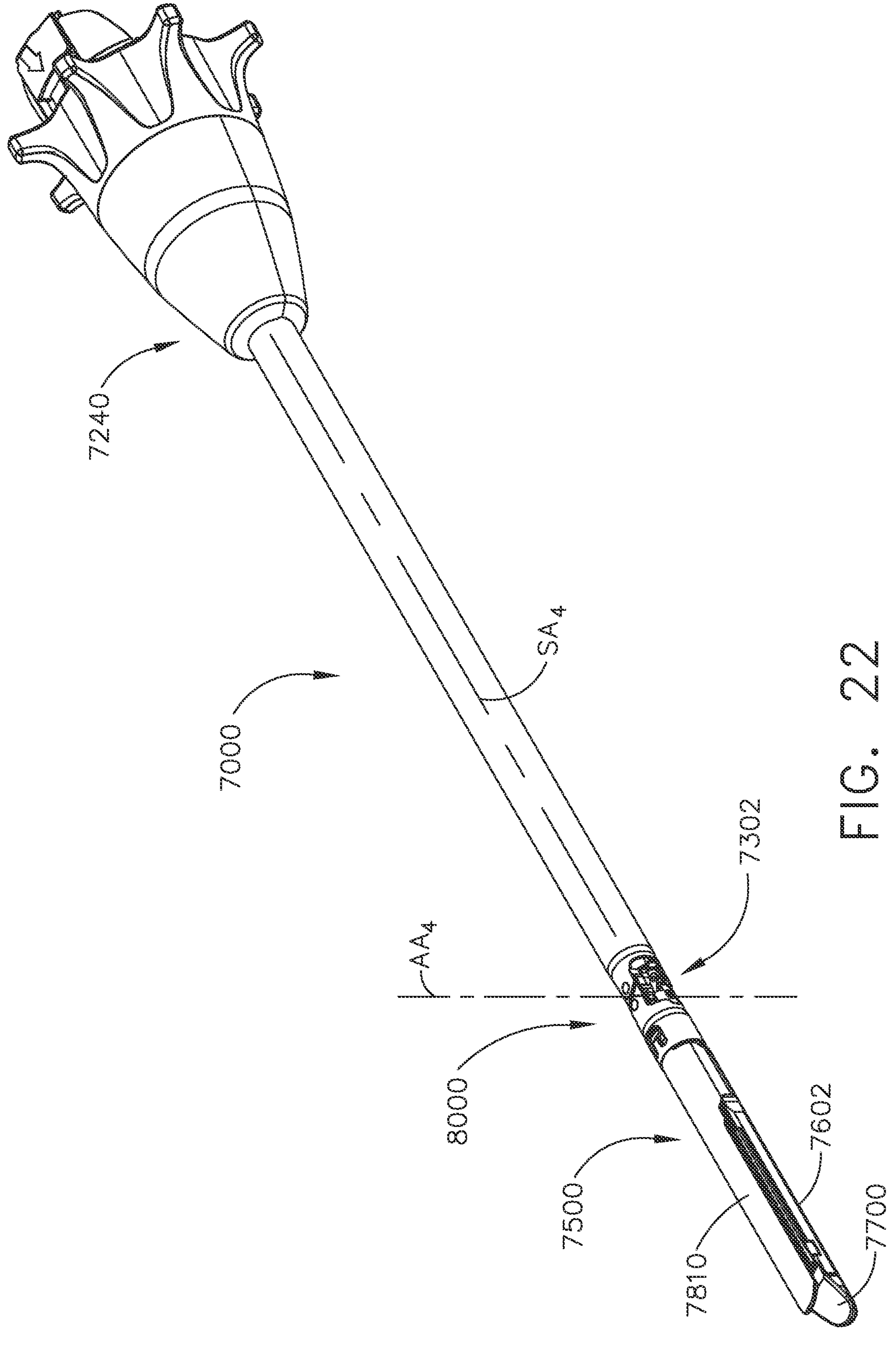
FIG. 22 is a perspective view of another one of the interchangeable surgical tool assemblies depicted in FIG. 1.
Figure 23:
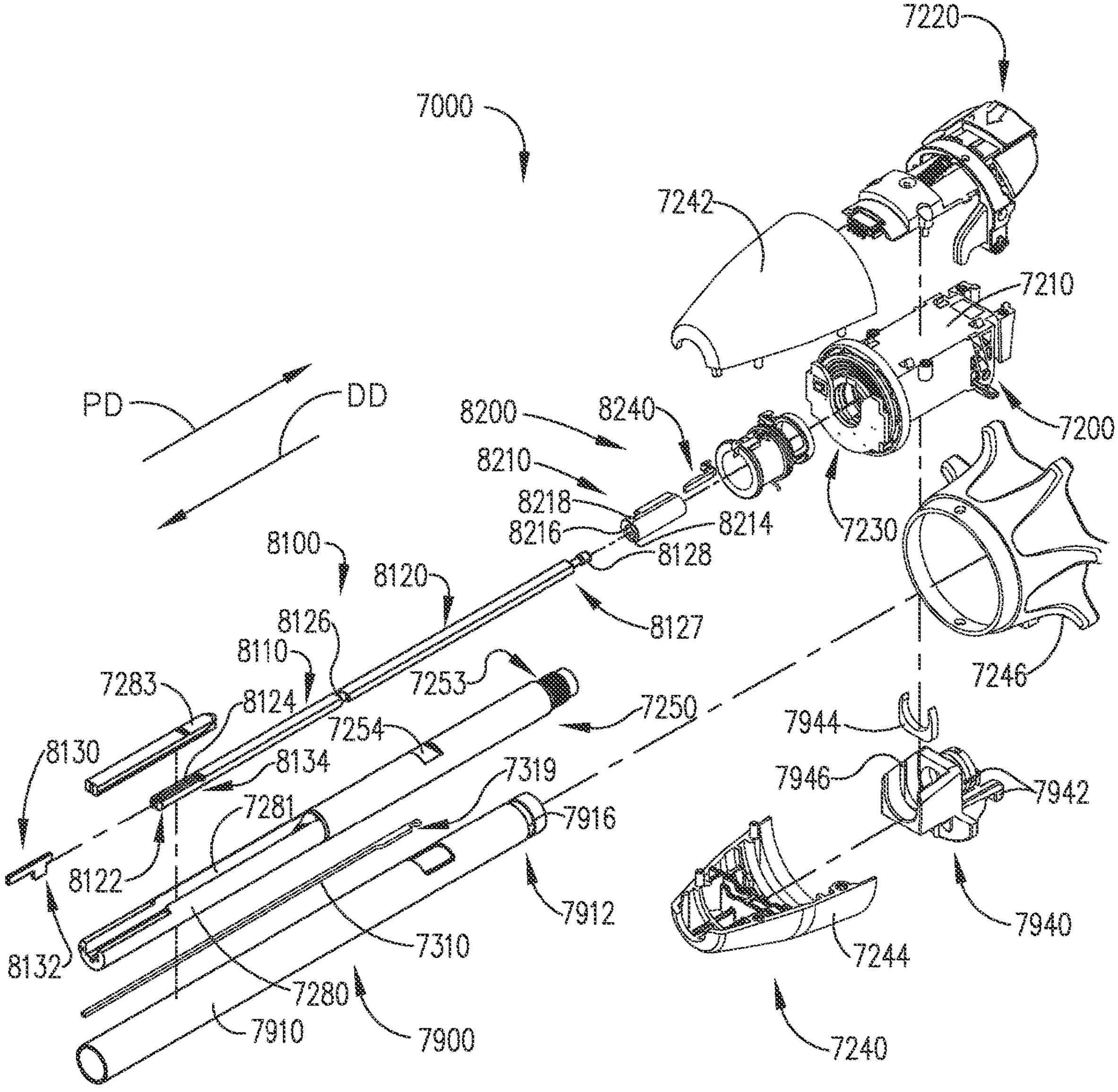
FIG. 23 is an exploded assembly view of a proximal portion of the interchangeable surgical tool assembly of FIG. 22.
Figure 24:
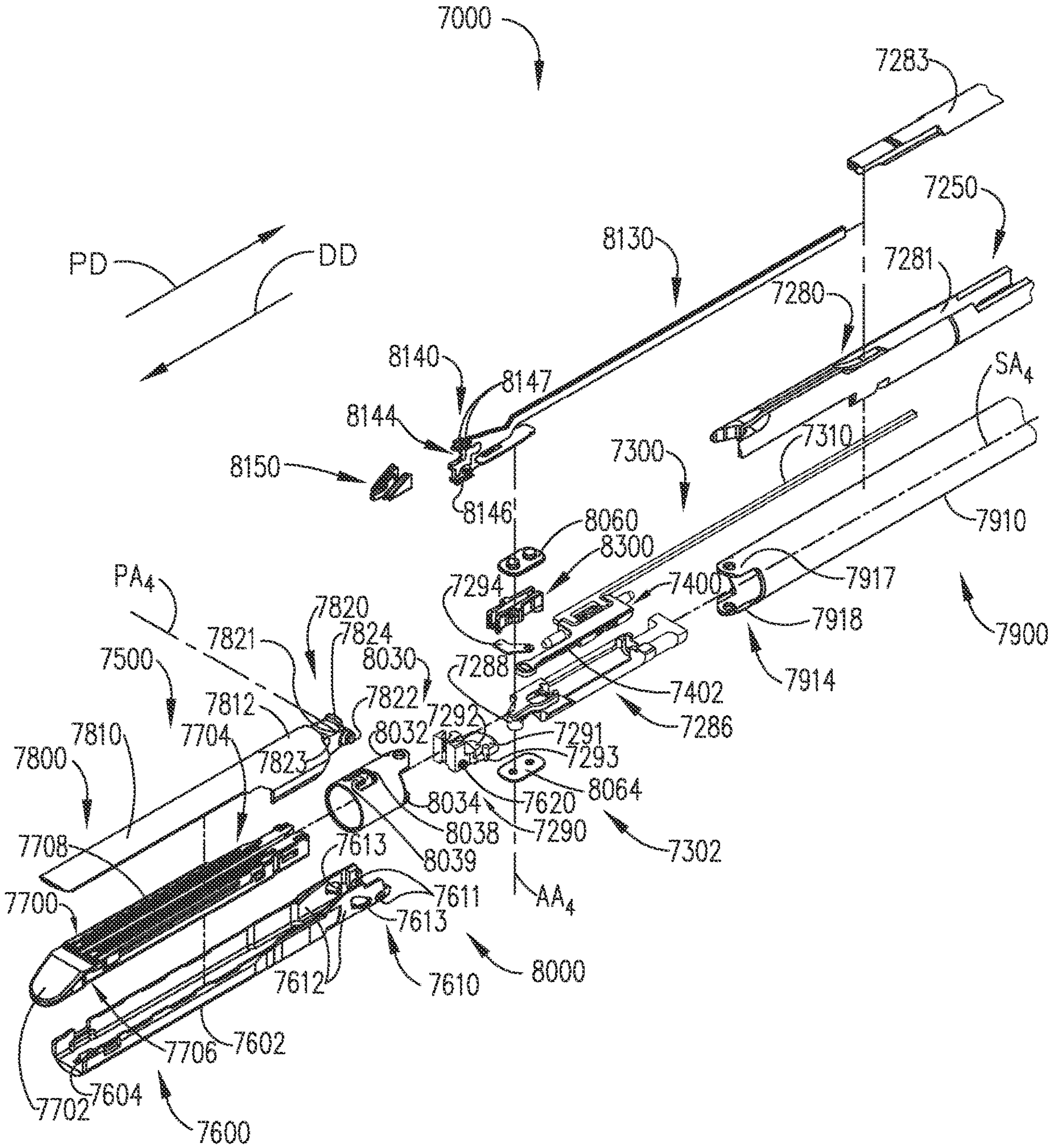
FIG. 24 is another exploded assembly view of a distal portion of the interchangeable surgical tool assembly of FIGS. 22 and 23.

Returning again to FIG. 1, as was discussed above, the surgical system 10 illustrated in that Figure includes four interchangeable surgical tool assemblies 1000, 3000, 5000 and 7000 that may each be effectively employed with the same handle assembly 500 to perform different surgical procedures. Turning now to FIGS. 22-24, the interchangeable surgical tool assembly 7000 includes a surgical end effector 7500 that comprises a first jaw 7600 and a second jaw 7800. In one arrangement, the first jaw comprises an elongate channel 7602 that is configured to operably support a surgical staple/fastener cartridge 7700 therein. The second jaw 7800 comprises an anvil 7810 that is movably supported relative to the elongate channel 7602. The interchangeable surgical tool assembly 7000 includes an articulation system 7300 that comprises an articulation joint 7302 and an articulation lock 7400 which can be configured to releasably hold the surgical end effector 7500 in a desired articulated position relative to a shaft axis $SA_4$. Details regarding the construction and operation of the articulation lock 7400 as well as alternative lock configurations and operational details may be found in in U.S. patent application Ser. No. 13/803,086, entitled ARTICULATABLE SURGICAL INSTRUMENT COMPRISING AN ARTICULATION LOCK, now U.S. Patent Application Publication No. 2014/0263541, the entire disclosure of which is hereby incorporated by reference herein. Additional details concerning the articulation lock 7400 and/or alternative articulation lock arrangements may also be found in U.S. patent application Ser. No. 15/019,196, filed Feb. 9, 2016, entitled SURGICAL INSTRUMENT ARTICULATION MECHANISM WITH SLOTTED SECONDARY CONSTRAINT, now U.S. Pat. No. 10,413,291, the entire disclosure of which is hereby incorporated by reference herein.

As can be seen in FIG. 24, the interchangeable surgical tool assembly 7000 includes a tool frame assembly 7200 that comprises a tool chassis 7210 that operably supports a nozzle assembly 7240 thereon. In one form, the nozzle assembly 7240 is comprised of nozzle portions 7242, 7244 as well as an actuator wheel portion 7246 that is configured to be coupled to the assembled nozzle portions 7242, 7244 by snaps, lugs, screws etc. The interchangeable surgical tool assembly 7000 includes a proximal closure assembly 7900 which is operably coupled to a distal closure assembly 8000 that is utilized to close and/or open the anvil 7810 of the surgical end effector 7500 as will be discussed in further detail below. In addition, the interchangeable surgical tool assembly 7000 includes a spine assembly 7250 that operably supports the proximal closure assembly 7900 and is coupled to the surgical end effector 3500. In the illustrated arrangement, the spine assembly 7250 includes a distal end portion 7280 that has an opening 7281 therein for ease of assembly. A spine cap 7283 may be attached thereto to cover the opening 7281 after the various components have been assembled therein. In assembled form, a proximal end portion 7253 of the spine assembly 7250 is rotatably supported in the tool chassis 7210. In one arrangement, for example, the proximal end of the proximal end portion 7253 of the spine assembly 7250 is attached to a spine bearing (not shown) that is configured to be supported within the tool chassis 7210. Such arrangement facilitates rotatable attachment of the spine assembly 7250 to the tool chassis 7210 such that the spine assembly 7250 may be selectively rotated about the shaft axis $SA_4$ relative to the tool chassis 7210. In particular, in one arrangement, for example, the proximal end portion 7253 of the spine assembly 7250 includes two diametrically opposed lug seats 7254 (only one can be seen in FIG. 23) that are each configured to receive a corresponding nozzle lug (not shown) that extend inwardly from each of the nozzle portions 7242, 7244. Such arrangement facilitates rotation of the spine assembly 7250 about the shaft axis $SA_4$ by rotating the actuator wheel portion 7246 of the nozzle assembly 7240.

Referring now to FIG. 24, the distal end portion 7280 of the spine assembly 7250 is attached to a distal frame segment 7286 that operably supports the articulation lock 7400 therein. The spine assembly 7250 is configured to, one, slidably support a firing member assembly 8110 therein and, two, slidably support a proximal closure tube 7910 which extends around the spine assembly 7250. The spine assembly 7250 can also be configured to slidably support a proximal articulation driver 7310. As can be seen in FIG. 24, the distal frame segment 7286 is pivotally coupled to the elongate channel 7602 by an end effector mounting assembly 7290. In one arrangement, for example, the distal end of the distal frame segment 7286 has a pivot pin 7288 formed thereon. The pivot pin 7288 is adapted to be pivotally received within a pivot hole 7292 formed in pivot base portion 7291 of the end effector mounting assembly 7290. The end effector mounting assembly 7290 is attached to a proximal end portion 7610 of the elongate channel 7602 by a spring pin 7620 or other suitable member that is received within mounting holes 7611 in the proximal end portion 7610. The pivot pin 7288 defines an articulation axis $AA_4$ that is transverse to the shaft axis $SA_4$. See FIG. 24. Such arrangement facilitates pivotal travel (i.e., articulation) of the surgical end effector 7500 about the articulation axis $AA_4$ relative to the spine assembly 7250. The distal frame segment 7286 is further configured to support the articulation lock 7400 therein. Various articulation lock arrangements may be employed. At least one form of articulation lock 7400 is described in further detail in U.S. patent application Ser. No. 13/803,086, entitled ARTICULATABLE SURGICAL INSTRUMENT COMPRISING AN ARTICULATION LOCK, now U.S. Patent Application Publication No. 2014/0263541, the entire disclosure of which is hereby incorporated by reference herein. Additional details concerning the articulation lock may also be found in U.S. patent application Ser. No. 15/019,196, filed Feb. 9, 2016, entitled SURGICAL INSTRUMENT ARTICULATION MECHANISM WITH SLOTTED SECONDARY CONSTRAINT, now U.S. Pat. No. 10,413,291.

In the illustrated example, the surgical end effector 7500 is electively articulatable about the articulation axis $AA_4$ by the articulation system 7300. In one form, the articulation system 7300 includes the proximal articulation driver 7310 that operably interfaces with the articulation lock 7400. The articulation lock 7400 includes an articulation frame 7402 that is adapted to operably engage a drive pin 7293 on the pivot base portion 7291 of the end effector mounting assembly 7290. In addition, a cross link 7294 may be linked to the drive pin 7293 and articulation frame 7402 to assist articulation of the surgical end effector 7500. As indicated above, further details regarding the operation of the articulation lock 7400 and the articulation frame 7402 may be found in U.S. patent application Ser. No. 13/803,086, now U.S. Patent Application Publication No. 2014/0263541. Further details regarding the end effector mounting assembly and cross link 7294 may be found in U.S. patent application Ser. No. 15/019,245, filed Feb. 9, 2016, entitled SURGICAL INSTRUMENTS WITH CLOSURE STROKE REDUCTION ARRANGEMENTS, now U.S. Pat. No. 10,470,764, the entire disclosure of which is hereby incorporated by reference herein. As further described therein, as well as in other disclosures incorporated by reference herein, axial movement of proximal articulation driver 7310 will result in the engagement/disengagement of the articulation lock 7400 to thereby apply articulation motions to the elongate channel 7602 and thereby cause the surgical end effector 7500 to articulate about the articulation axis $AA_4$ relative to the spine assembly 7250.

The anvil 7810 in the illustrated example includes an anvil body 7812 that terminates in anvil mounting portion 7820. The anvil mounting portion 7820 is movably supported on the elongate channel 7602 for selective pivotal and axial travel relative thereto. In the illustrated arrangement, an anvil trunnion 7822 extends laterally out of each lateral side of the anvil mounting portion 7820 to be received in a corresponding "kidney-shaped" opening 7613 formed in upstanding walls 7612 of the proximal end portion 7610 of the elongate channel 7602. Movement of the anvil 7810 relative to the elongate channel 7602 is effectuated by axial movement of the proximal closure assembly 7900 and the distal closure assembly 8000. In the illustrated arrangement, the proximal closure assembly 7900 comprises the proximal closure tube 7910 that has a proximal end 7912 and a distal end 7914. The proximal end 7912 is rotatably supported in a closure shuttle 7940 that is slidably supported within the tool chassis 7210 such that it may be axially moved relative thereto. In one form, the closure shuttle 7940 includes a pair of proximally-protruding hooks 7942 that are configured for attachment to the transverse attachment pin 516 that is attached to the closure linkage assembly 514 of the handle assembly 500. The proximal end 7912 of the proximal closure tube 7910 is coupled to the closure shuttle 7940 for relative rotation thereto. For example, a U-shaped connector 7944 is inserted into an annular slot 7916 in the proximal end 7912 of the proximal closure tube 7910 and is retained within vertical slots 7946 in the closure shuttle 7940. Such arrangement serves to attach the proximal closure assembly 7900 to the closure shuttle 7940 for axial travel therewith while enabling the proximal closure tube 7910 to rotate relative to the closure shuttle 7940 about the shaft axis $SA_4$. As was discussed above in connection with the interchangeable surgical tool assembly 1000, a closure spring (not shown) may extend over the proximal end 7912 of the proximal closure tube 7910 to bias the closure shuttle 7940 in the proximal direction PD which can serve to pivot the closure trigger 512 on the handle assembly 500 (FIG. 2) into the unactuated position when the interchangeable surgical tool assembly 7000 is operably coupled to the handle assembly 500 in the above described manner.

As can be seen in FIG. 24, the distal end 7914 of the proximal closure tube 3910 is attached to the distal closure assembly 8000. The distal end 7914 includes upper and lower tangs 7917, 7918 that are configured to be movably coupled to an end effector closure sleeve or distal closure tube segment 8030. The distal closure tube segment 8030 includes an upper tang 8032 and a lower tang 8034 that protrude proximally from a proximal end thereof. An upper double pivot link 8060 pivotally couples the upper tangs 7917 and 8032 and a lower double pivot link 8064 pivotally couples the lower tangs 7918 and 8034 together in the above-described manner. The distal advancement of the distal closure tube segment 8030 on the anvil mounting portion 7820 will result in closure or pivotal travel of the anvil 7810 towards the elongate channel 7602. In the illustrated arrangement, an upstanding anvil tab 7824 is formed on the anvil mounting portion 7820 and extends into a horseshoe-shaped opening 8038. Opening 8038 defines an opening tab 8039 configured to operably interface with the anvil tab 7824 as the distal closure tube is retracted in the distal direction. Such interaction between the opening tab 8039 and the anvil tab 7824 applies an opening motion to the anvil 7810 to thereby cause the anvil 7810 to move to an open position.

In the illustrated arrangement, the interchangeable surgical tool assembly 7000 further includes a firing system generally designated as 8100. In various instances, the firing system 8100 includes the firing member assembly 8110 that is supported for axial travel within the spine assembly 7250. In the illustrated embodiment, the firing member assembly 8110 includes an intermediate firing shaft portion 8120 that is configured for attachment to a distal cutting portion or knife bar 8130. The firing member assembly 8110 may also be referred to herein as a "second shaft" and/or a "second shaft assembly". As can be seen in FIG. 24, the intermediate firing shaft portion 8120 may include a longitudinal slot 8124 in a distal end 8122 thereof which can be configured to receive a proximal end 8132 of the knife bar 8130. The longitudinal slot 8124 and the proximal end 8132 of the knife bar 8130 can be sized and configured to permit relative movement therebetween and can comprise a slip joint 8134. The slip joint 8134 can permit the intermediate firing shaft portion 8120 of the firing member assembly 8110 to be moved to articulate the end effector 7500 without moving, or at least substantially moving, the knife bar 8130 as was discussed above. In the illustrated arrangement, a proximal end 8127 of the intermediate firing shaft portion 8120 has a firing shaft attachment lug 8128 formed thereon that is configured to be seated into an attachment cradle (not shown) that is on the distal end of the longitudinally movable drive member (not shown) of the firing drive system 530 within the handle assembly 500 as was discussed above. Such arrangement facilitates the axial movement of the intermediate firing shaft portion 8120 upon actuation of the firing drive system 530. Other attachment configurations may also be employed to couple the intermediate firing shaft portion to other firing drive arrangements (e.g., manually actuated, robotic, etc.).

Further to the above, the interchangeable tool assembly 7000 can include a shifter assembly 8200 which can be configured to selectively and releasably couple the proximal articulation driver 7310 to the firing member assembly 8110 in the manner described above. In one form, the shifter assembly 8200 includes a lock collar, or lock sleeve 8210, positioned around the intermediate firing shaft portion 8120 of the firing member assembly 8110 wherein the lock sleeve 8210 can be rotated between an engaged position in which the lock sleeve 8210 couples the proximal articulation driver 7310 to the firing member assembly 8110 and a disengaged position in which the proximal articulation driver 7310 is not operably coupled to the firing member assembly 8110. As was discussed above, the intermediate firing shaft portion 8120 of the firing member assembly 8110 is formed with a drive notch 8126. The lock sleeve 8210 comprises a cylindrical, or an at least substantially cylindrical, body that includes a longitudinal aperture that is configured to receive the intermediate firing shaft portion 8120 therethrough. The lock sleeve 8210 can comprise diametrically-opposed, inwardly-facing lock protrusions 8214, 8216 that, when the lock sleeve 8210 is in one position, are engagingly received within corresponding portions of the drive notch 8126 in the intermediate firing shaft portion 8120 and, when in another position, are not received within the drive notch 8126 to thereby permit relative axial motion between the lock sleeve 8210 and the intermediate firing shaft 8120 as was discussed in further detail above. The lock sleeve 8210 further includes a lock member 8218 that is sized to be movably received within a notch 7319 in a proximal end of the proximal articulation driver 7310. When the lock sleeve 8210 is in its engaged position, the lock protrusions 8214, 8216 are positioned within the drive notch 7126 in the intermediate firing shaft portion 8120 such that a distal pushing force and/or a proximal pulling force can be transmitted from the firing member assembly 8110 to the lock sleeve 8210. Such axial pushing or pulling motion is then transmitted from the lock sleeve 8210 to the proximal articulation driver 7310 to thereby articulate the surgical end effector 7500.

As was discussed above, in the illustrated example, relative movement of the lock sleeve 8210 between its engaged and disengaged positions may be controlled by the shifter assembly 8200 that interfaces with the proximal closure tube 7910 of the proximal closure assembly 7900. The shifter assembly 8200 further includes a shifter key 8240 that is configured to be slidably received within a key groove (similar to the key groove 2217 illustrated in FIG. 8) formed in the outer perimeter of the lock sleeve 8210. Such arrangement enables the shifter key 8240 to move axially with respect to the lock sleeve 8210. Operation of the shifter assembly 8200 may be identical to the operation of the shifter assembly 2200 which was described in further detail above and which will not be repeated again for brevity. Further details, alternative arrangements and drive configurations that may be employed are disclosed in Other arrangements that may be employed are disclosed in U.S. patent application Ser. No. 15/385,911, entitled SURGICAL STAPLE/FASTENERS WITH INDEPENDENTLY ACTUATABLE CLOSING AND FIRING SYSTEMS, now U.S. Pat. No. 10,448,950, U.S. patent application Ser. No. 13/803,086, now U.S. Patent Application Publication No. 2014/0263541, and U.S. patent application Ser. No. 15/019, 196, now U.S. Pat. No. 10,413,291, the as well as other disclosures that have been incorporated herein.

The interchangeable tool assembly 7000 can comprise a slip ring assembly 7230 which can be configured to conduct electrical power to and/or from the surgical end effector 7500 and/or communicate signals to and/or from the surgical end effector 7500, back to a microprocessor 560 in the handle assembly 500 or robotic system controller, for example as was discussed above. Further details concerning the slip ring assembly 7230 and associated connectors may be found in U.S. patent application Ser. No. 13/803,086, now U.S. Patent Application Publication No. 2014/0263541, and U.S. patent application Ser. No. 15/019,196, now U.S. Pat. No. 10,413,291, which have each been herein incorporated by reference in their respective entirety as well as in U.S. patent application Ser. No. 13/800,067, entitled STAPLE CARTRIDGE TISSUE THICKNESS SENSOR SYSTEM, now U.S. Patent Application Publication No. 2014/0263552, which is hereby incorporated by reference herein in its entirety.

The illustrated interchangeable surgical tool assembly 7000 also employs a latch system 7220 for removably coupling the interchangeable surgical tool assembly 7000 to the handle frame 506 of the handle assembly 500, for example. The latch system 7220 may be identical to the latch system 1220 described in detail above. The knife bar 8130 may comprise a laminated beam structure that includes at least two beam layers. Such beam layers may comprise, for example, stainless steel bands that are interconnected by, for example, welding or pinning together at their proximal ends and/or at other locations along their length. In alternative embodiments, the distal ends of the bands are not connected together to allow the laminates or bands to splay relative to each other when the end effector is articulated. Such arrangement permits the knife bar 8130 to be sufficiently flexible to accommodate articulation of the end effector. Various laminated knife bar arrangements are disclosed in U.S. patent application Ser. No. 15/019,245, entitled SURGICAL INSTRUMENTS WITH CLOSURE STROKE REDUCTION ARRANGEMENTS, now U.S. Pat. No. 10,470,764, which is hereby incorporated by reference in its entirety. As can also be seen in FIG. 24, a firing shaft support assembly 8300 is employed to provide lateral support to the knife bar 8130 as it flexes to accommodate articulation of the surgical end effector 7500. Further details concerning the operation of the firing shaft support assembly 8300 and alternative knife bar support arrangements may be found in U.S. patent application Ser. No. 15/019,245, entitled SURGICAL INSTRUMENTS WITH CLOSURE STROKE REDUCTION ARRANGEMENTS, now U.S. Pat. No. 10,470,764 and U.S. patent application Ser. No. 15/019,220, entitled SURGICAL INSTRUMENT WITH ARTICULATING AND AXIALLY TRANSLATABLE END EFFECTOR, now U.S. Pat. No. 10,245,029, which are each hereby incorporated by reference herein in their respective entireties.

As can also be seen in FIG. 24, a firing member or knife member 8140 is attached to the distal end of the knife bar 8130. The firing member 8140 is configured to operably interface with a sled assembly 8150 that is operably supported within the body 7702 of the surgical staple/fastener cartridge 7700. See FIG. 51. The sled assembly 8150 is slidably displaceable within the surgical staple/fastener cartridge body 7702 from a proximal starting position adjacent a proximal end 7704 of the cartridge body 7702 to an ending position adjacent a distal end 7706 of the cartridge body 7702. The cartridge body 7702 operably supports therein a plurality of staple drivers (not shown) that are aligned in rows on each side of a centrally disposed slot 7708. The centrally disposed slot 7708 enables the firing member 8140 to pass therethrough and cut the tissue that is clamped between the anvil 7810 and the staple cartridge 7700. The drivers are associated with corresponding staple pockets that open through the upper deck surface of the cartridge body 7702. Each of the staple drivers supports one or more surgical staple/fastener or fastener (not shown) thereon. The sled assembly includes a plurality of sloped or wedge-shaped cams wherein each cam corresponds to a particular line of fasteners or drivers located on a side of the slot 7708.

In one exemplary form, the firing member 8140 comprises a body portion 8142 that supports a knife or tissue cutting portion 8144. See FIG. 51. The body portion 8142 protrudes through an elongate slot 7604 in the elongate channel 7602 and terminates in a foot member 8146 that extends laterally on each side of the body portion 8142. As the firing member 8140 is driven distally through the surgical staple/fastener cartridge 7700, the foot member 8146 rides within a passage 7622 in the elongate channel 7602 that is below the staple cartridge 7700. The tissue cutting portion 8144 is disposed between a distally protruding top nose portion 8143. As can be further seen in FIG. 24, the firing member 8140 may further include two laterally extending top tabs, pins or anvil engagement features 8147. As the firing member 8140 is driven distally, a top portion of the body portion 8142 extends through a centrally disposed anvil slot 7814 and the anvil engagement features 8147 ride on corresponding ledges 7816 formed on each side of the anvil slot 7814. Further details concerning the firing member 8140, sled assembly 8150, and their various alternatives as well as examples of their operation will be discussed in further detail below and may also be found in U.S. patent application Ser. No. 15/385,911, entitled SURGICAL STAPLE/FASTENERS WITH INDEPENDENTLY ACTUATABLE CLOSING AND FIRING SYSTEMS, now U.S. Pat. No. 10,448,950. The interchangeable surgical tool assembly 7000 may be operably coupled to the handle assembly 500 in the manner as described above with respect to the interchangeable surgical tool assembly 1000.

As can be appreciated from the foregoing descriptions, the interchangeable surgical tool assemblies described herein may be actuated by the same handle assembly, robotic system or other automated actuation system. All of the above described interchangeable surgical tool assemblies comprise surgical cutting and fastening instruments that have somewhat similar closure and firing components. However, the closure and firing systems and components of each of these tool assemblies have differences that may seem somewhat subtle at first blush, but, as will be further discussed below, such differences can result in significant improvements in the material composition, design, construction, manufacture and use of such tools. As will become apparent as the present Detailed Description proceeds, the interchangeable surgical tool assembly 1000 contains subtle design differences when compared to the other interchangeable surgical tool assemblies 3000, 5000, 7000 described herein that can result in significant improvements in the overall functionality, reliability, and cost of the tool assembly. Moreover, we have discovered that, in some cases, a synergistic effect exists between certain component arrangements employed by the tool assembly 1000 which can further enhance the overall efficiency and functionality of the tool assembly 1000. In order to better understand these differences and improvements, certain components and systems of each of the tool assemblies 1000, 3000, 5000, 7000 will now be further described and compared to each other below.

For example, each of the interchangeable surgical tool assemblies 1000, 3000, 5000, 7000 must be able to apply a sufficient amount of closure force to cause the jaws to sufficiently clamp the target tissue so as to permit the firing member to properly treat the clamped tissue upon actuation of the firing drive system. For example, in the illustrated assemblies, the respective closure system components must be able to clamp the anvil and surgical staple/fastener cartridge onto the target tissue to enable the firing member to properly sever the clamped tissue and eject lines of staples or fasteners on each side of the tissue cut line. Depending upon the thickness and composition of the target tissue, significant closure forces and firing forces are often required. Thus, the closure and firing drive systems in the handle assembly housing, robotic housing, etc. must be able to generate such forces of sufficient magnitude (through the use of a motor or manually generated motion, for example) to sufficiently close the jaws and fire the firing member through the clamped tissue. Such procedures further require that the components within the interchangeable shaft assemblies to be sufficiently robust to accommodate the magnitudes of the forces being transmitted therethrough. In the past, the magnitudes of such forces often dictated that the closure system components, as well as the firing system components, be fabricated from metal or other suitable materials with relatively large cross-sectional thicknesses and of substantial reinforced configurations.

The tissue loads encountered during the clamping process typically create a large "moment" about the anvil pivot axis PA. The closure system components must be designed to counteract such moment. In various circumstances, for example, a moment about the anvil pivot axis PA in the opposite direction is needed. To maximize the efficiency of the system (e.g., minimize the magnitude of the force applied), the largest practical moment arm is desired. However, as will be further discussed below, there are trade-offs with other design variables when seeking to establish a large counter moment. For example, there is a balance between the distance from the articulation joint to the first staple and the length of the moment arm for a closure system where the firing and closing systems are separate and distinct. The larger the moment arm of the closure system, the more efficiently it handles clamp loads and tissue compression. However, the distance between the articulation joint and the first staple may have a large impact on the access of the surgical end effector as it is positioned into tight spaces within a laparoscopic environment.

Figure 25:
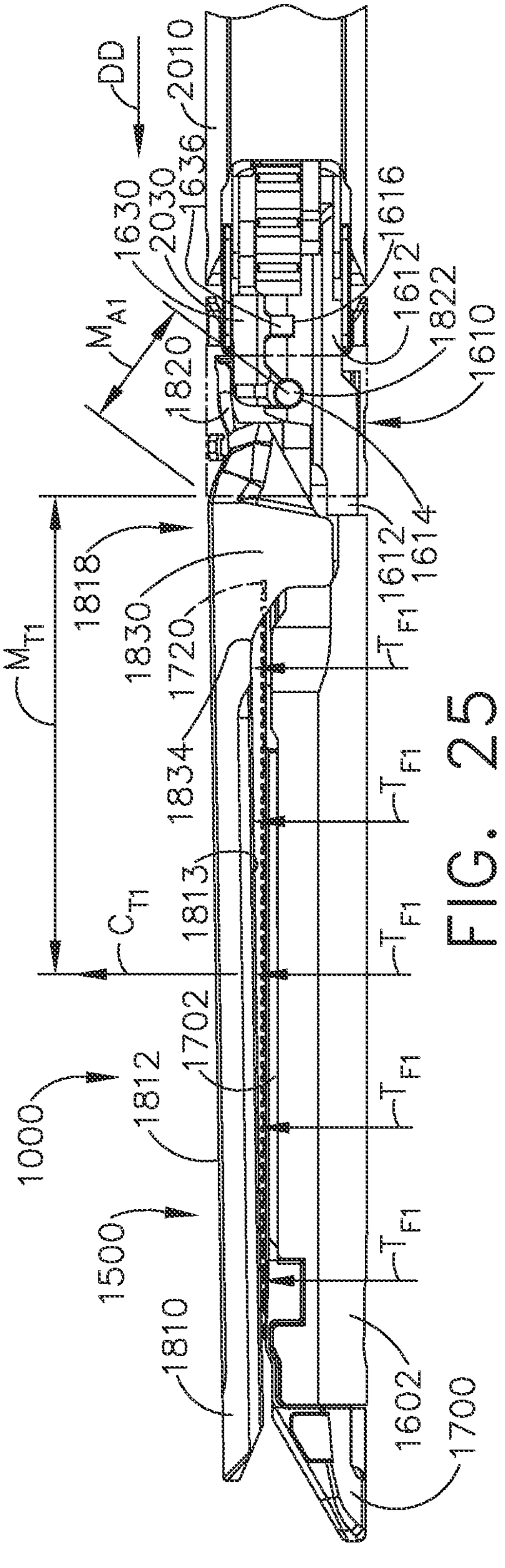
FIG. 25 is a side elevational view of a distal portion of the interchangeable surgical tool assembly of FIG. 3 with the anvil thereof in a fully closed position.

FIGS. 25-32 illustrate exemplary moment arms for each of the surgical end effectors 1500, 3500, 5500, 7500. Turning first to FIG. 25, as was described above, the anvil trunnions 1822 extend laterally out of each lateral side of the anvil mounting portion 1820 to be received in a corresponding trunnion cradle 1614 formed in the upstanding walls 1612 of the proximal end portion 1610 of the elongate channel 1602. The anvil trunnions 1822 are pivotally retained in their corresponding trunnion cradle 1614 by the channel cap or anvil retainer 1630. The channel cap 1630 includes a pair of attachment lugs 1636 that are configured to be retainingly received within corresponding lug grooves or notches 1616 formed in the upstanding walls 1612 of the proximal end portion 1610 of the elongate channel 1602. Such arrangement constrains the anvil 1810 to only pivot about the pivot axis $PA_1$ (see FIG. 3). Under such arrangement, the anvil mounting portion 1820 does not move axially or vertically. As the distal closure tube segment 2030 is advanced in the distal direction DD under a horizontal closure force $F_{H1}$ (FIG. 26), the interaction between an internal cam surface 2036 on the distal closure tube segment 2030 and an anvil cam surface 1821 on the anvil mounting portion 1820 results in the application of a closure force $F_{C1}$ to the anvil cam surface 1821. The closure force $F_{C1}$ comprises the resultant force of the horizontal closure force $F_{H1}$ and a vertical closure force $F_{V1}$ and is essentially "normal to" or perpendicular to the cam surface 1821 on the anvil mounting portion 1820. See FIG. 26. $M_{A1}$ represents a closure moment arm from the anvil pivot axis $PA_1$ (coincident with the center of anvil trunnions 1822) to the point of contact between the internal cam surface 2036 on the distal closure tube segment 2030 and the anvil cam surface 1821 on the anvil mounting portion 1820 when the anvil 1810 has been pivoted to the fully closed position. In one example, the closure moment arm $M_{A1}$ may be approximately 0.415 inches, for example. $M_{A1} \times F_{C1}$=a closure moment $C_{M1}$ that is applied to the anvil mounting portion 1820.

Figure 26:
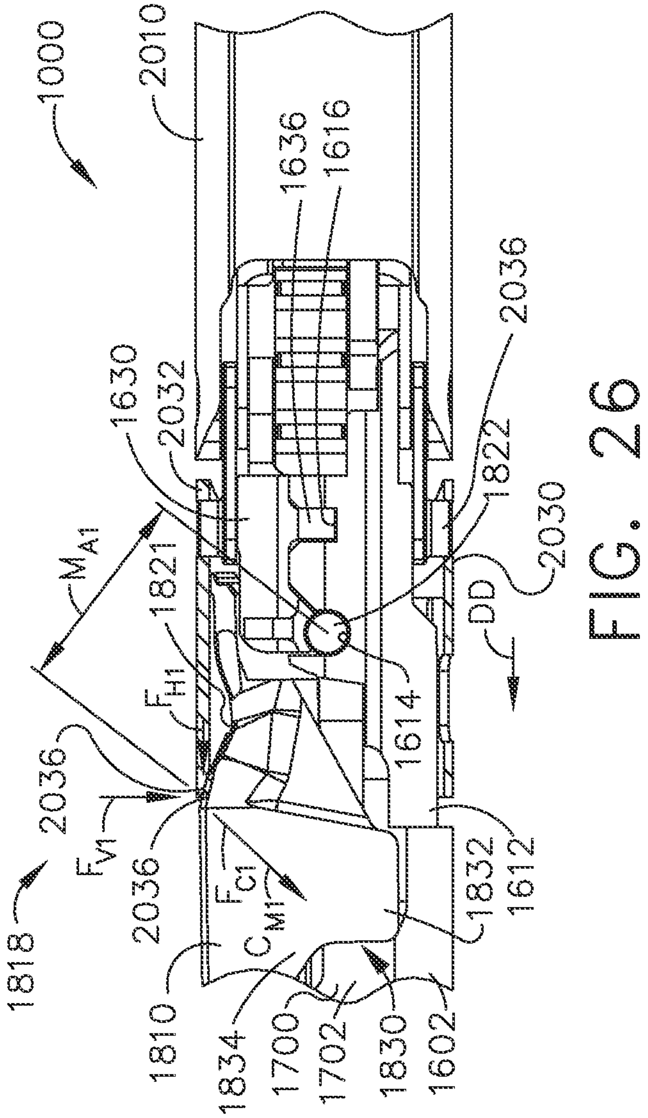
FIG. 26 is an enlarged side elevational view of the anvil mounting portion and elongate channel of the interchangeable surgical tool assembly of FIG. 25.

To ensure that the each side of the tissue cut line is fastened with staples or fasteners extending from the proximal end to the distal end of the tissue cutline, a proximal end portion 1818 of the anvil body 1812 is formed with two tissue stop formations or tissue locating features 1830 that extend downwardly from each lateral side of the anvil body 1812 (only one tissue stop formation 1830 may be seen in FIGS. 25 and 26). When the anvil 1810 is opened to receive the target tissue between the underside of the anvil and the cartridge deck surface, the downwardly extending tissue stop 1830 serve to prevent the target tissue from extending proximally past the proximal most staples/fasteners in the surgical staple/fastener cartridge 1700. If the tissue were to extend proximally beyond the proximal most staples/fasteners, that portion of tissue may be severed by the firing member during the firing process and may not be fastened which may lead to catastrophic results. The downwardly extending tissue stops 1830 may prevent this from happening. In the embodiment depicted in FIG. 26, for example, the proximal-most staple/fastener pockets 1720 are shown in phantom lines relative to the tissue stops 1830. As can be seen in that Figure, the tissue stop 1830 has a downwardly extending portion 1832 and a chamfered portion 1834. The target tissue is contacted by the portions 1832, 1834 to prevent the target tissue from extending proximally beyond the proximal most staples/fasteners that are supported in the proximal most staple/fastener pockets 1720 in the staple/fastener cartridge body 1702.

Returning again to FIG. 25, as the anvil 1810 is pivoted closed onto the target tissue (not shown) that is positioned between the underside or tissue contacting surface 1813 of the anvil body 1812, the tissue applies tissue forces $T_{F1}$ to the underside 1813 of the anvil body 1812 which cause the anvil 1810 to experience a tissue counter moment $C_{T1}$ that must be overcome by the closure moment $C_{M1}$ established by the closure system components. The example depicted in FIG. 25 illustrates equally distributed tissue forces $T_{F1}$ on the anvil 1810 and a tissue moment arm $M_{T1}$ established by the clamped tissue (the clamped tissue is not shown in FIG. 25 for clarity purposes). As can be seen in that Figure, in that example, the tissue moment arm $M_{T1}$ is considerably longer than the closure moment arm $M_{A1}$ (i.e., $M_{T1}>M_{A1}$).

Figure 27:
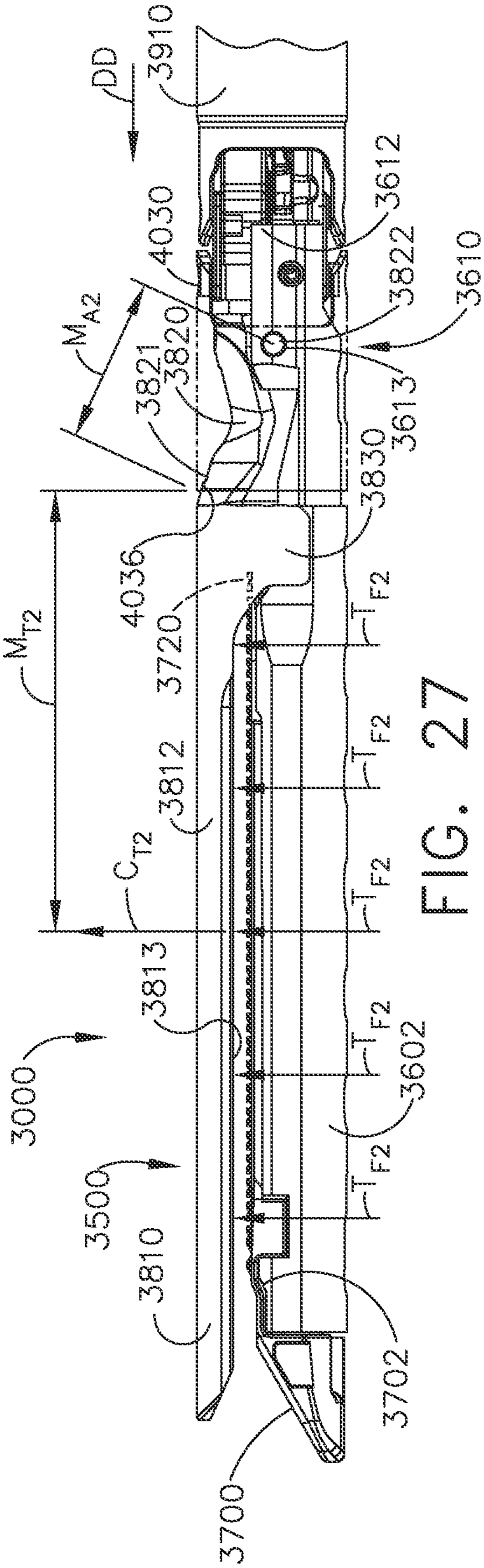
FIG. 27 is a side elevational view of a distal portion of the interchangeable surgical tool assembly of FIG. 16 with the anvil thereof in a fully closed position.
Figure 28:
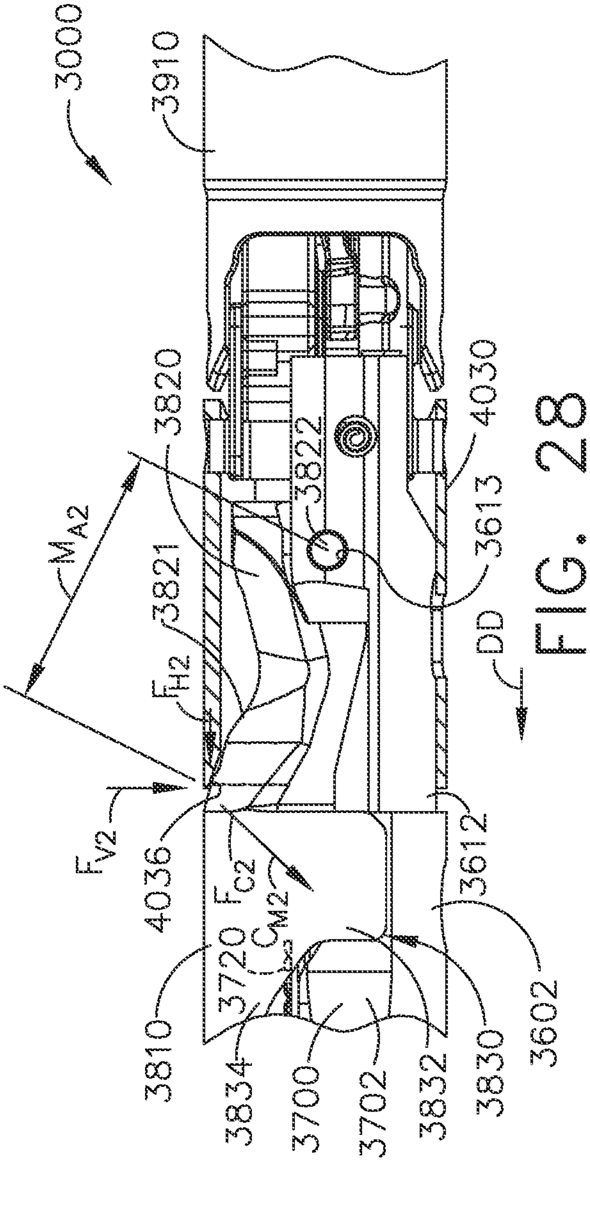
FIG. 28 is an enlarged side elevational view of the anvil mounting portion and elongate channel of the interchangeable surgical tool assembly of FIG. 27.

Turning next to FIGS. 27 and 28, as was described above, the anvil trunnions 3822 of the anvil 3810 of the interchangeable surgical tool assembly 3000 extend laterally out of each lateral side of the anvil mounting portion 3820 to be received in corresponding trunnion holes 3613 formed in the upstanding walls 3612 of the proximal end portion 3610 of the elongate channel 3602. Such arrangement constrains the anvil 3810 to only pivot about the anvil pivot axis $PA_2$ (see FIG. 18). Under such arrangement, the anvil mounting portion 3820 does not move axially or vertically. As the distal closure tube segment 4030 is advanced in the distal direction DD under a horizontal closure force $F_{H2}$ (FIG. 28), the interaction between an internal cam surface 4036 on the distal closure tube segment 4030 and an anvil cam surface 3821 on the anvil mounting portion 3820 results in the application of a closure force $F_{C2}$ to the anvil cam surface 3821. The closure force $F_{C2}$ comprises the resultant force of the horizontal closure force $F_{H2}$ and a vertical closure force $F_{V2}$ and is essentially "normal to" or perpendicular to the anvil cam surface 3821 on the anvil mounting portion 3820. See FIG. 28. $M_{A2}$ represents the closure moment arm from the anvil pivot axis $PA_2$ (center of anvil trunnions 3822) to the point of contact between the internal cam surface 4036 on the distal closure tube 4030 and the anvil cam surface 3821 on the anvil mounting portion 3820 when the anvil 3810 has been pivoted to the fully closed position. In one example, closure moment arm $M_{A2}$ may be approximately 0.539 inches, for example. $M_{A2} \times F_{C2}$=a closure moment $C_{M2}$ that is applied to the anvil mounting portion 3820.

In the example depicted in FIGS. 27 and 28, the anvil body 3812 is formed with two tissue stop formations or tissue locating features 3830 that extend downwardly from each lateral side of the anvil body 3812 (only one tissue stop formation 3830 may be seen in FIGS. 27 and 28). When the anvil 3810 is opened to receive the target tissue between the underside of the anvil and the cartridge deck surface, the downwardly extending tissue stop formations 3830 serve to prevent the target tissue from extending proximally past the proximal most staples/fasteners in the surgical staple/fastener/fastener cartridge 3700. In the embodiment depicted in FIG. 28, for example, the proximal-most staple pockets 3720 are shown in phantom lines relative to the tissue stop formations 3830. As can be seen in that Figure, the tissue stop formation 3830 has a downwardly extending portion 3832 and a chamfered portion 3834. The target tissue is contacted by the portions 3832, 3834 to prevent the target tissue from extending proximally beyond the proximal most staples/fasteners that are supported in the proximal-most staple/fastener pockets 3720 in the staple/fastener cartridge body 3702.

Returning again to FIG. 27, as the anvil 3810 is pivoted closed onto the target tissue (not shown) that is positioned between the underside or tissue contacting surface 3813 of the anvil body 3812, the tissue applies tissue forces $T_{F2}$ to the underside 3813 of the anvil body 3812 which cause the anvil 3810 to experience a tissue counter moment $C_{T2}$ that must be overcome by the closure moment $C_{M2}$ established by the closure system components. The example depicted FIG. 27 illustrates equally distributed tissue forces $T_{F2}$ on the anvil 3810 and a tissue moment arm $M_{T2}$ established by the clamped tissue (the clamped tissue is not shown in FIG. 27 for clarity purposes). As can be seen in that Figure, in that example, the tissue moment arm $M_{T2}$ is considerably longer than the closure moment arm $M_{A2}$ (i.e., $M_{T2}>M_{A2}$).

Figure 29:
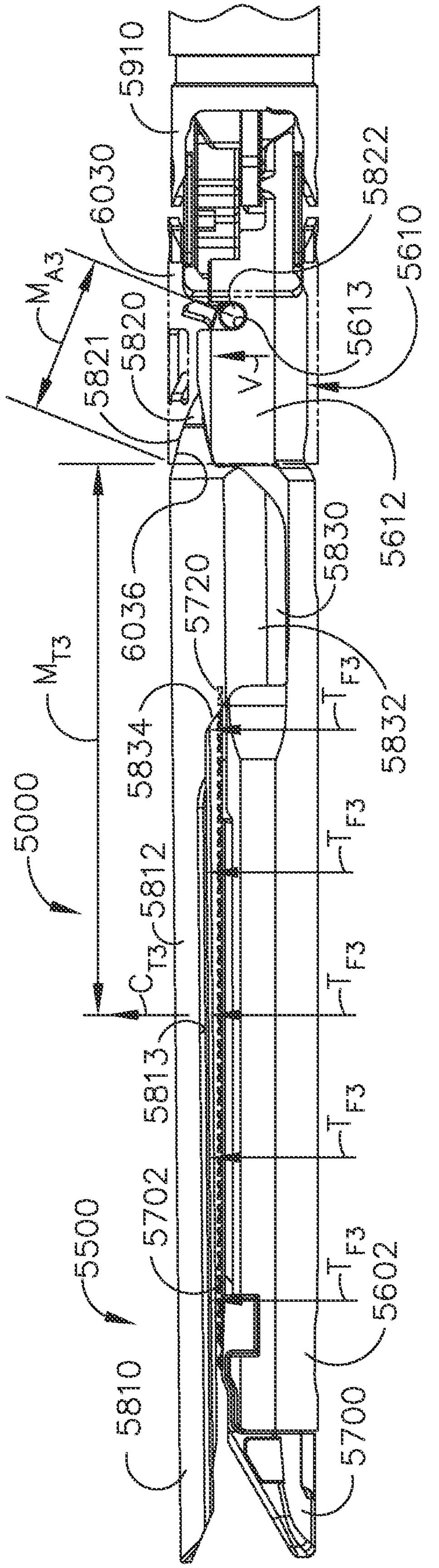
FIG. 29 is a side elevational view of a distal portion of the interchangeable surgical tool assembly of FIG. 19 with the anvil thereof in a fully closed position.
Figure 30:
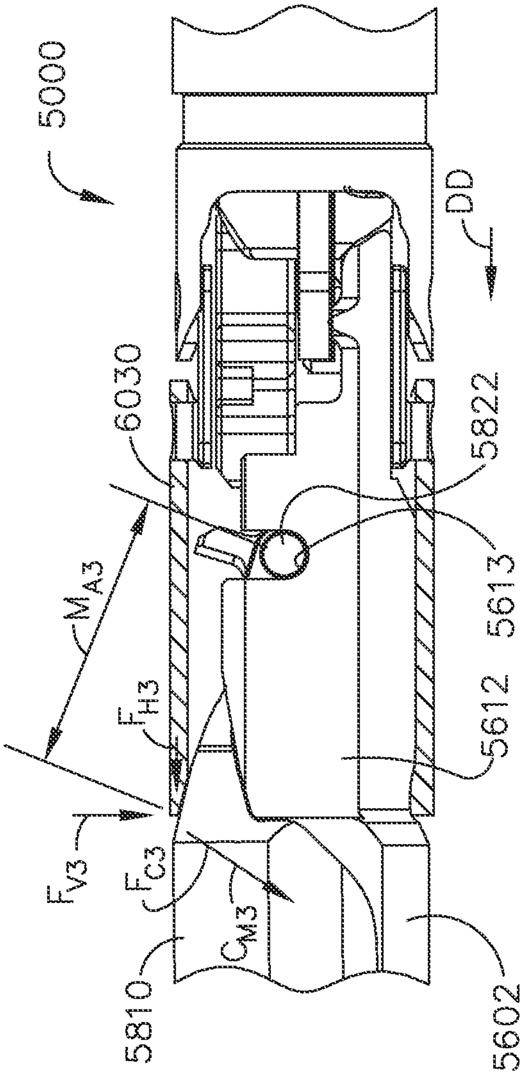
FIG. 30 is an enlarged side elevational view of the anvil mounting portion and elongate channel of the interchangeable surgical tool assembly of FIG. 29.

Turning next to FIGS. 29 and 30, as was described above, the anvil trunnions 5822 of the anvil 5810 of the interchangeable surgical tool assembly 5000 extend laterally out of each lateral side of the anvil mounting portion 5820 to be received in the corresponding "open-ended" vertical cradle 5613 formed in the upstanding walls 5612 of the proximal end portion 5610 of the elongate channel 5602. In this arrangement, the anvil trunnions 5822 are free to pivot within their respective cradles 5613 as the distal closure tube segment 6030 cammingly contacts the anvil cam surface 5821 on the anvil mounting portion 5820. Under such arrangement, the anvil 5810 does not move axially, but the anvil trunnions 5822 are free to move vertically (arrow V) within their respective cradles 5613. As the distal closure tube segment 6030 is advanced in the distal direction DD under the horizontal closure force $F_{H3}$ (FIG. 30), the interaction between an internal cam surface 6036 on the distal closure tube segment 6030 and the anvil cam surface 5821 on the anvil mounting portion 5820 results in the application of a closure force $F_{C3}$ to the anvil cam surface 5821. The closure force $F_{C3}$ comprises the resultant force of the horizontal closure force $F_{H3}$ and a vertical closure force $F_{V3}$ and is essentially "normal to" or perpendicular to the anvil cam surface 5821 on the anvil mounting portion 5820. See FIG. 30. $M_{A3}$ represents the closure moment arm from the anvil pivot axis $P_{A3}$ (coincident with the center of anvil trunnions 5822) to the point of contact between the internal cam surface 6036 on the distal closure tube 6030 and the anvil cam surface 5821 on the anvil mounting portion 5820 when the anvil 5810 has been pivoted to the closed position. In one example, closure moment arm $M_{A3}$ may be approximately 0.502 inches, for example. $M_{A3} \times F_{C3}$=a closure moment $C_{M3}$ that is applied to the anvil mounting portion 5820.

In the example depicted in FIGS. 29 and 30, the anvil body 5812 is formed with two tissue stop formations or tissue locator features 5830 that extend downwardly from each lateral side of the anvil body 5812 (only one tissue stop formation 5830 may be seen in FIGS. 29 and 30). When the anvil 5810 is opened to receive the target tissue between the underside of the anvil and the cartridge deck surface, the downwardly extending tissue stop formations 5830 serve to prevent the target tissue from extending proximally past the proximal most staples/fasteners in the surgical staple/fastener cartridge 5700. In the embodiment depicted in FIG. 29, for example, the proximal-most staple/fastener pockets 5720 are shown in phantom lines relative to the tissue stop formations 5830. As can be seen in that Figure, the tissue stop formation 5830 has a downwardly extending portion 5832 and a chamfered portion 5834. The target tissue is contacted by the portions 5832, 5834 to prevent the target tissue from extending proximally beyond the proximal most staples/fasteners that are supported in the proximal-most staple/fastener pockets 5720 in the staple/fastener cartridge body 5702.

Returning again to FIG. 29, as the anvil 5810 is pivoted closed onto the target tissue (not shown) that is positioned between the underside 5813 of the anvil body 5812, the tissue applies tissue forces $T_{F3}$ to the underside or tissue contacting surface 5813 of the anvil body 5812 which cause the anvil 5810 to experience a tissue counter moment $C_{T3}$ that must be overcome by the closure moment $C_{M3}$ established by the closure system components. The example depicted in FIG. 29 illustrates equally distributed tissue forces $T_{F3}$ on the anvil 5810 and a tissue moment arm $M_{T3}$ established by the clamped tissue (the clamped tissue is not shown in FIG. 29 for clarity purposes). As can be seen in that Figure, in that example, the tissue moment arm $M_{T3}$ is considerably longer than the closure moment arm $M_{A3}$ (i.e., $M_{T3}>M_{A3}$).

Figure 31:
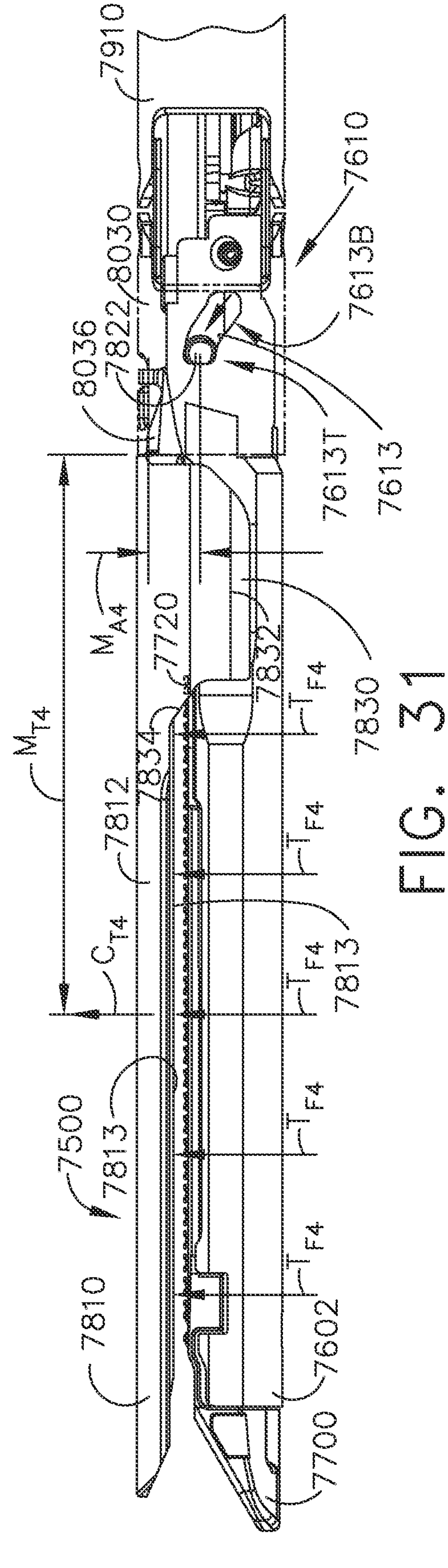
FIG. 31 is a side elevational view of a distal portion of the interchangeable surgical tool assembly of FIG. 22 with the anvil thereof in a fully closed position.
Figure 32:
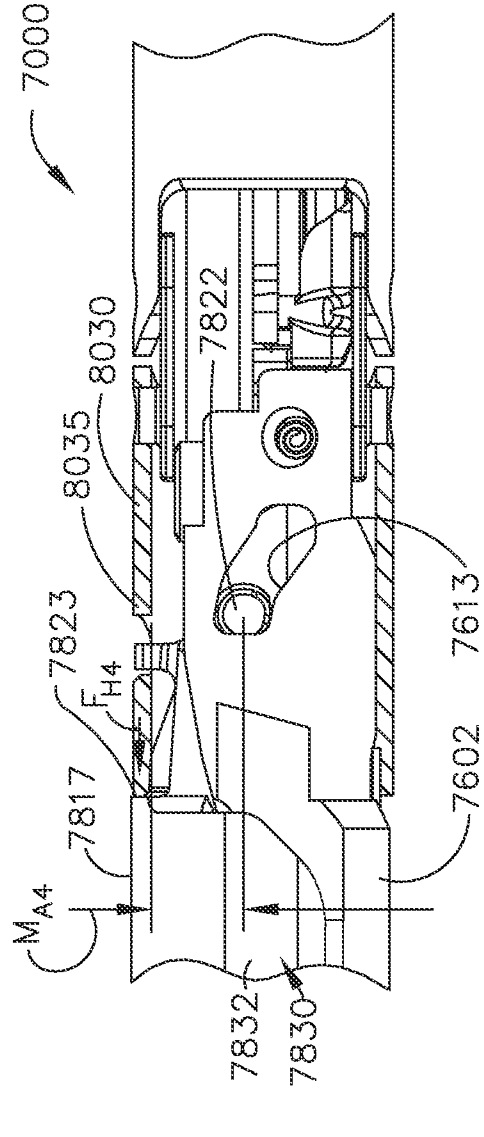
FIG. 32 is an enlarged side elevational view of the anvil mounting portion and elongate channel of the interchangeable surgical tool assembly of FIG. 31.

Turning now to FIGS. 31 and 32, as was described above, the anvil trunnions 7822 of the anvil 7810 of the interchangeable surgical tool assembly 7000 extend laterally out of each lateral side of the anvil mounting portion 7820 to be received in the corresponding "kidney-shaped" opening 7613 formed in the upstanding walls 7612 of the proximal end portion 7610 of the elongate channel 7602. When the anvil 7810 is in a "fully" open position, the anvil trunnions 7822 may generally be located in the bottom portion 7613B of the kidney slot 7613. The anvil 7810 can be moved to a closed position by distally advancing the distal closure tube segment 8030 in the distal direction DD so that the internal cam surface 8036 on the distal end 8035 of the distal closure tube segment 8030 rides up an anvil cam surface 7821 that is formed on the anvil mounting portion 7820 of the anvil 7810. As the internal cam surface 8036 on the distal end 8035 of the distal closure tube segment 8030 is distally advanced along the anvil cam surface 7821 on the anvil mounting portion 7820 under the horizontal closure force $F_{H4}$ (FIG. 32), the distal closure tube segment 8030 causes the body portion 7812 of the anvil 7810 to pivot and move axially relative to the surgical staple/fastener cartridge 7700 as the anvil trunnions 7822 move upwardly and distally in the kidney slots 7613. When the distal closure tube segment 8030 reaches the end of its closure stroke, the distal end 8035 of the distal closure tube segment 8030 abuts/contacts an abrupt anvil ledge 7823 and serves to position the anvil 7810 so that the forming pockets (not shown) in the underside or tissue contacting surface 7813 of the body portion 7812 are properly aligned with the staples/fasteners in the staple/fastener cartridge 7700. The anvil ledge 7823 is defined between the anvil cam surface 7821 on the anvil mounting portion 7820 and the anvil body portion 7812. Stated another way, in this arrangement, the anvil cam surface 7821 does not extend to an outermost surface 7817 of the anvil body 7812. When in that position, the anvil trunnions 7822 are located at top portions 7613T of the kidney slots 7613. $M_{A4}$ represents the moment arm from the anvil pivot axis $P_{A4}$ (coincident with the center of the anvil trunnions 7822) when the trunnions 7822 are located in the top portions 7613T of the kidney slots 7613 as shown. In one example, the moment arm $M_{A4}$ may be approximately 0.184 inches, for example. $M_{A4} \times F_{H4}$=a closure moment $C_{M4}$ that is applied to the anvil mounting portion 7820.

In the example depicted in FIGS. 31 and 32, the anvil body 7812 is formed with two tissue stop formations or tissue locator formations 7830 that extend downwardly from each lateral side of the anvil body 7812 (only one tissue stop formation 7830 may be seen in FIGS. 31 and 32). When the anvil 7810 is opened to receive the target tissue between the underside of the anvil and the cartridge deck surface, the downwardly extending tissue stop formations 7830 serve to prevent the target tissue from extending proximally past the proximal most staples/fasteners in the surgical staple/fastener cartridge 7700. In the embodiment depicted in FIG. 31, for example, the proximal most staple/fastener pockets 7720 are shown in phantom lines relative to the tissue stop formations 7830. As can be seen in that Figure, the tissue stop formation 7830 has a downwardly extending portion 7832 and a chamfered portion 7834. The target tissue is contacted by the portions 7832, 7834 to prevent the target tissue from extending proximally beyond the proximal most staples/fasteners that are supported in the proximal most staple/fastener pockets 7720 in the staple/fastener cartridge body 7702.

Returning again to FIG. 31, as the anvil 7810 is pivoted closed onto the target tissue (not shown) that is positioned between the underside or tissue contacting surface 7813 of the anvil body portion 7812, the tissue applies tissue forces $T_{F4}$ to the underside 7813 of the anvil body 7812 which cause the anvil 7810 to experience a tissue counter moment $C_{T4}$ that must be overcome by a closure moment $C_{M4}$ established by the closure system components. The example depicted FIG. 31 illustrates equally distributed tissue forces $T_{F4}$ on the anvil 7810 and a tissue moment arm $M_{T4}$ established by the clamped tissue (the clamped tissue is not shown in FIG. 31 for clarity purposes). As can be seen in that Figure, in that example, the tissue moment arm $M_{T4}$ is considerably longer than the closure moment arm $M_{A4}$ (i.e., $M_{T4}>M_{A4}$).

The illustrated exemplary interchangeable surgical tool assemblies 1000, 3000, 5000, 7000 comprise surgical stapling devices that employ "separate and distinct" closure and firing systems. That is, the closure system employed to close the jaws is separately actuatable from the firing system used to drive the firing member through the surgical staple/fastener cartridge to cut and fasten tissue. These separate and distinct closure and firing systems may be distinguishable from those surgical stapling instruments wherein actuation of the firing system to advance the firing member is required to move the jaws from an open position to a closed position. As will be discussed in further detail below, however, the firing members of some of the interchangeable surgical tool assemblies disclosed herein may also apply additional closure motions to the anvil as the firing member is fired (i.e., distally advanced through the surgical end effector). As can be seen from reference to FIGS. 25-32, in the illustrated examples, $M_{A2}>M_{A3}>M_{A1}>M_{A4}$. FIGS. 25, 27, 29 and 31 also illustrate the resistive forces established by the tissue during the closure process. $T_F$ represents the force generated by the tissue when the tissue is clamped between the anvil and the staple cartridge. These forces establish a "counter" moment $C_T$ that is applied to the anvil about the point/area where the distal closure tube segment is in camming contact with the anvil cam surface on the anvil mounting portion. In these illustrated examples, the tissue moment arm for each surgical instrument (tool assembly) is generally larger than the closure moment arm for that instrument. It may be appreciated from the difference between a typical tissue moment arm encountered when clamping tissue between the anvil and the surgical staple/fastener cartridge and the closure moment arm of the instrument results in the need for sufficient closure forces to be applied by the distal closure tube segment to the anvil in order to sufficiently close the anvil onto the tissue. Thus, the distal closure tube segment must be sufficiently strong and robust to handle the considerable stresses formed therein during the closure process. To establish a stress state in the distal closure tube segment that more closely resembles a "hoop stress" state instead of a "ring stress" state, the sidewalls of the distal closure tube segment may be thickened so as to contact the side walls and anvil mounting portions of the corresponding elongate channel. Such arrangement may also add strength to the overall hoop-like structure of the tube. Maximizing the thickness on the anvil side of the distal closure tube segment may also improve the strength of the tube segment (hoop) while allowing room for a large bearing or cam surface to cam the anvil downward towards the cartridge. U.S. patent application Ser. No. 15/385,911, entitled SURGICAL STAPLE/FASTENERS WITH INDEPENDENTLY ACTUATABLE CLOSING AND FIRING SYSTEMS, now U.S. Pat. No. 10,448,950, discloses several distal closure tube segment configurations which may be employed in the various interchangeable surgical tool assemblies disclosed herein.

Figures 33, 34:
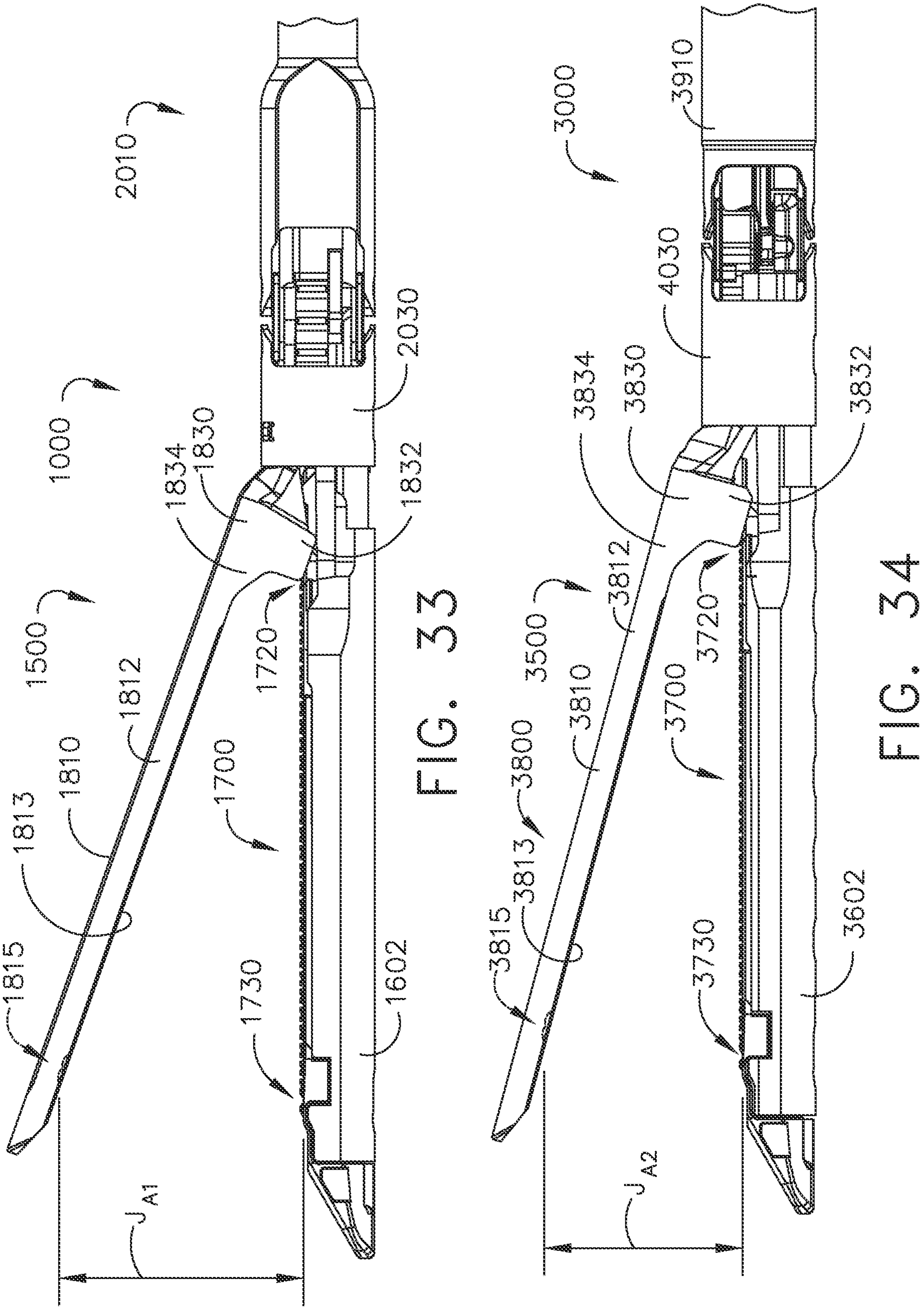
FIG. 33 is a side elevational view of a distal portion of the interchangeable surgical tool assembly of FIG. 3 with the anvil thereof in a fully open position.
FIG. 34 is a side elevational view of a distal portion of the interchangeable surgical tool assembly of FIG. 16 with the anvil thereof in a fully open position.
Figure 35:
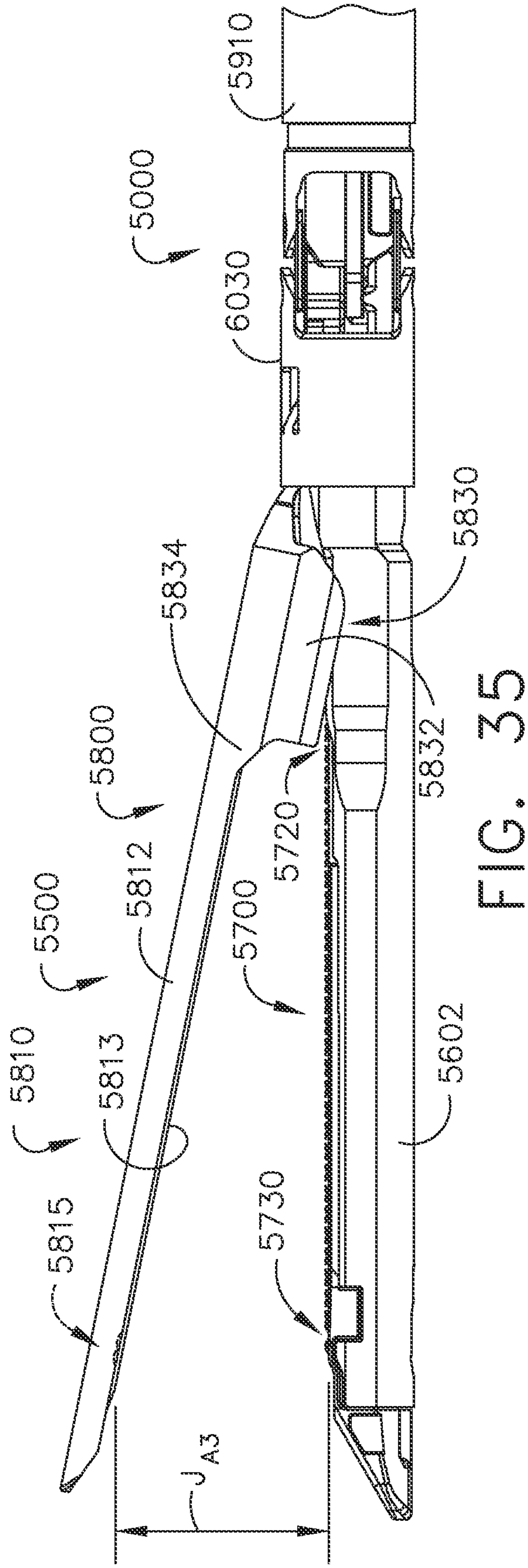
FIG. 35 is a side elevational view of a distal portion of the interchangeable surgical tool assembly of FIG. 19 with the anvil thereof in a fully open position.
Figure 36:
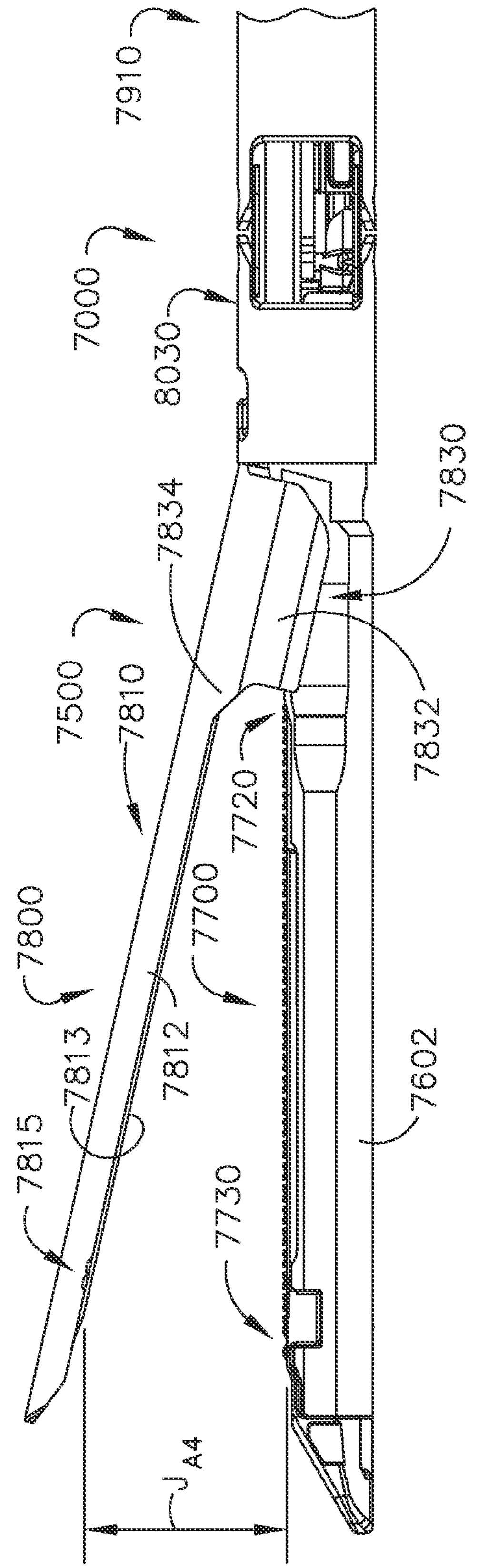
FIG. 36 is a side elevational view of a distal portion of the interchangeable surgical tool assembly of FIG. 22 with the anvil thereof in a fully open position.

The forgoing discussion and comparisons may illustrate that closure system designs that have large closure moment arms may lead to improved efficiencies of the closure system components and can reduce the amount of closure forces that are required to achieve full anvil closure onto the tissue. However, as noted above, there may be tradeoffs with other design variables when attempting to maximize the closure moment arm. For example, another desirable attribute relates to "jaw aperture". "Jaw aperture" may refer to a distance $J_A$ which is measured from the middle of a distalmost staple or fastener center along a line that is perpendicular to the corresponding distalmost staple forming pocket on the underside or tissue contact surface of the anvil body portion. FIG. 33 illustrates the jaw aperture $J_{A1}$ for the surgical end effector 1500. In the illustrated example, the distalmost staple/fastener pockets 1730 contain the distalmost staples or fasteners (not shown) therein. Each distalmost staple or fastener corresponds to a distalmost staple/fastener forming pocket 1815 (shown in phantom in FIG. 33) that is formed in the underside or tissue contacting surface 1813 of the anvil body 1812. The distance $J_{A1}$ between the distalmost staple/fastener pocket 1730 and the corresponding distalmost staple/fastener forming pocket 1815 is the "jaw aperture" for the surgical end effector 1500. In at least one embodiment, for example, $J_{A1}$ is approximately 1.207 inches. FIG. 34 illustrates the jaw aperture $J_{A2}$ for the surgical end effector 3500. In the illustrated example, the distalmost staple/fastener pockets 3730 contain the distalmost staples or fasteners (not shown) therein. Each distalmost staple or fastener corresponds to a distalmost staple/fastener forming pocket 3815 that is formed in the underside or tissue contact surface 3813 of the anvil body 3812. The distance $J_{A2}$ between the distalmost staple/fastener pocket 3730 and the corresponding distalmost staple/fastener forming pocket 3815 is the "jaw aperture" for the surgical end effector 3500. In at least one embodiment, for example, $J_{A2}$ is approximately 0.781 inches. FIG. 35 illustrates the jaw aperture $J_{A3}$ for the surgical end effector 5500. In the illustrated example, the distalmost staple/fastener pockets 5730 contain the distalmost staples/fasteners (not shown therein). Each distalmost staple/fastener corresponds to a distalmost staple/fastener forming pocket 5815 that is formed in the underside or tissue contact surface 5813 of the anvil body 5812. The distance $J_{A3}$ between the distalmost staple/fastener pocket 5730 and the corresponding distalmost staple/fastener forming pocket 5815 is the "jaw aperture" for the surgical end effector 5500. In at least one embodiment, for example, $J_{A3}$ is approximately 0.793 inches. FIG. 36 illustrates the jaw aperture $J_{A4}$ for the surgical end effector 7500. In the illustrated example, the distalmost staple/fastener pockets 7730 contain the distalmost staples or fasteners (not shown) therein. Each distalmost staple or fastener corresponds to a distalmost staple/fastener forming pocket 7815 that is formed in the underside or tissue contact surface 7813 of the anvil body 7812. The distance $J_{A4}$ between the distalmost staple/fastener pocket 7730 and the corresponding distalmost staple/fastener forming pocket 7815 is the "jaw aperture" for the surgical end effector 7500. In at least one embodiment, for example, $J_{A4}$ is approximately 0.717 inches. Thus, for these examples, $J_{A1}>J_{A3}>J_{A2}>J_{A4}$. As such, comparatively, surgical end effector 1500 has the greatest jaw aperture.

Figure 37:
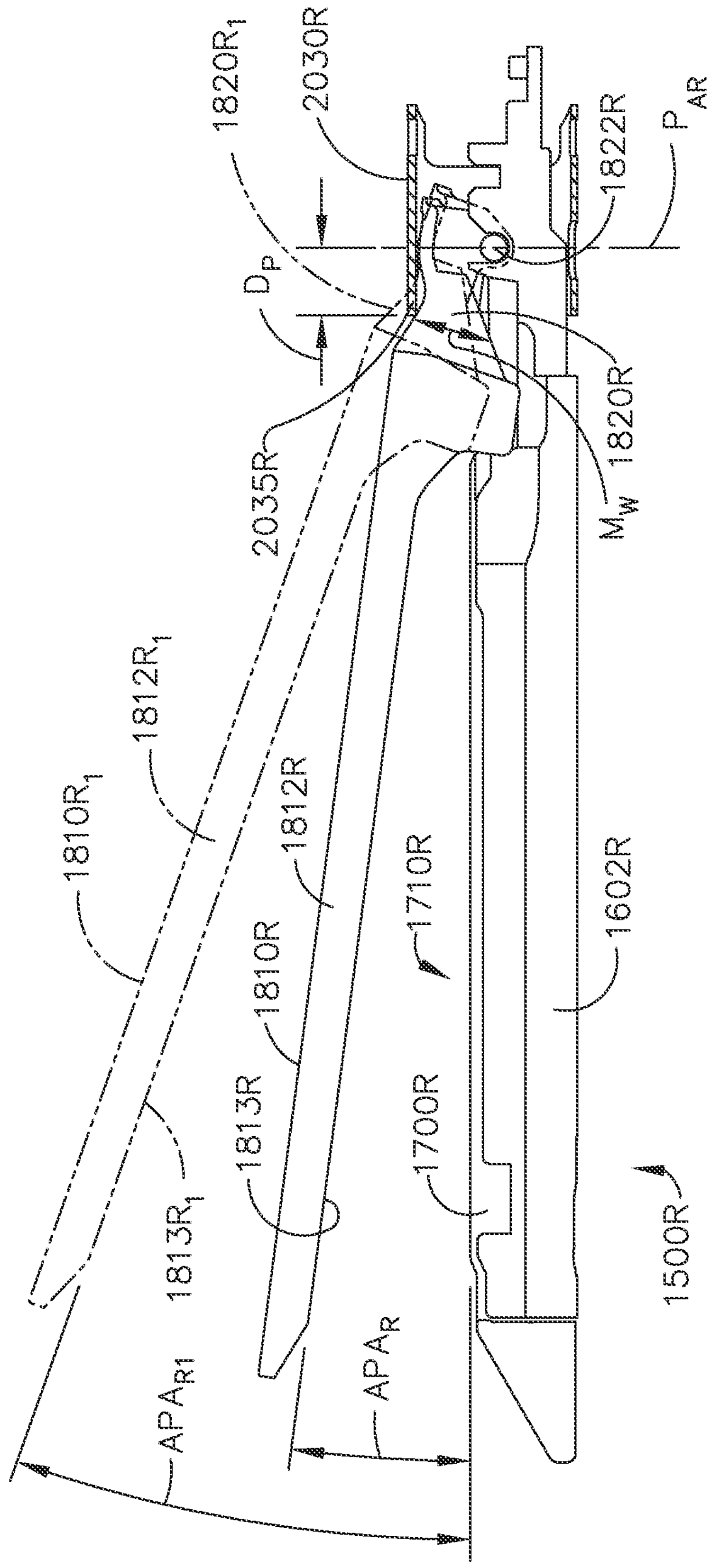
FIG. 37 is a side elevational view of a distal portion of another interchangeable surgical tool assembly with the anvil thereof shown in one open position in solid lines and another open position in phantom lines.

In those surgical end effector designs that employ separate and distinct closure and firing systems that utilize an axially movable closure ring or distal closure tube segment such as the examples described above, the interrelationships between the anvil or jaw pivot axis $P_A$ and the distal end of the distal closure tube segment as well as the robustness of the anvil mounting portion may determine the magnitude of the jaw aperture that is attainable for each specific end effector design. These interrelationships may be better appreciated from reference to FIG. 37, for example. FIG. 37 depicts a surgical end effector 1500R that employs an anvil 1810R that has an anvil mounting portion 1820R that is shown in solid lines. The anvil mounting portion 1820R includes anvil trunnions 1822R that define a reference pivot axis $P_{AR}$ about which the anvil mounting portion 1820R may pivot relative to an elongate channel 1602R. The surgical end effector 1500R also employs a distal closure tube segment 2030R that has a distal end 2035R that is configured to cammingly contact the anvil mounting portion 1820R in the various manners discussed above. A surgical staple/fastener cartridge 1700R is supported in the elongate channel 1602R and has a cartridge deck surface or tissue contact surface 1710R. FIG. 37 depicts a distance $D_P$ between the reference pivot axis $P_{AR}$ and the distal end 2035R of the distal closure tube segment 2030R. FIG. 37 illustrates the anvil 1810R in solid lines. The anvil body 1812R is in its maximum open position when the distal closure tube segment 2030R is in its proximal most starting position relative to the anvil mounting portion 1820R. The maximum aperture angle $APA_R$ for that configuration is approximately ten degrees, for example. This aperture angle $APA_R$ is typical for many end effector arrangements. In another end effector arrangement, the aperture angle is 12.25 degrees. In one arrangement, for example, $D_P$ may be approximately 0.200 inches. To attain a larger aperture angle $APA_{R1}$ of, for example, twenty-two degrees, if the relationship between the distal end 2035R of the distal closure tube segment 2030R and the reference pivot axis $P_{AR}$ remains unchanged, then a cross-sectional width Mw of an anvil mounting portion 1820$R_1$ must undesirably be decreased. The anvil 1810$R_1$ is illustrated in phantom lines. As can be seen in that Figure, an abrupt ledge must be formed between the anvil body 1812$R_1$ and the anvil mounting portion 1820$R_1$ such that the cross-sectional width thereof is reduced. The aperture angle $APA_{R1}$ is measured from the underside 1813$R_1$ of the anvil body 1812$R_1$ and the deck surface 1710R of the surgical staple/fastener cartridge 1700R. Such reduction in robustness of the anvil mounting portion of the anvil may lead to reduced anvil reliability and is less desirable than anvils that have anvil mounting portions with larger cross-sectional profiles.

Figure 38:
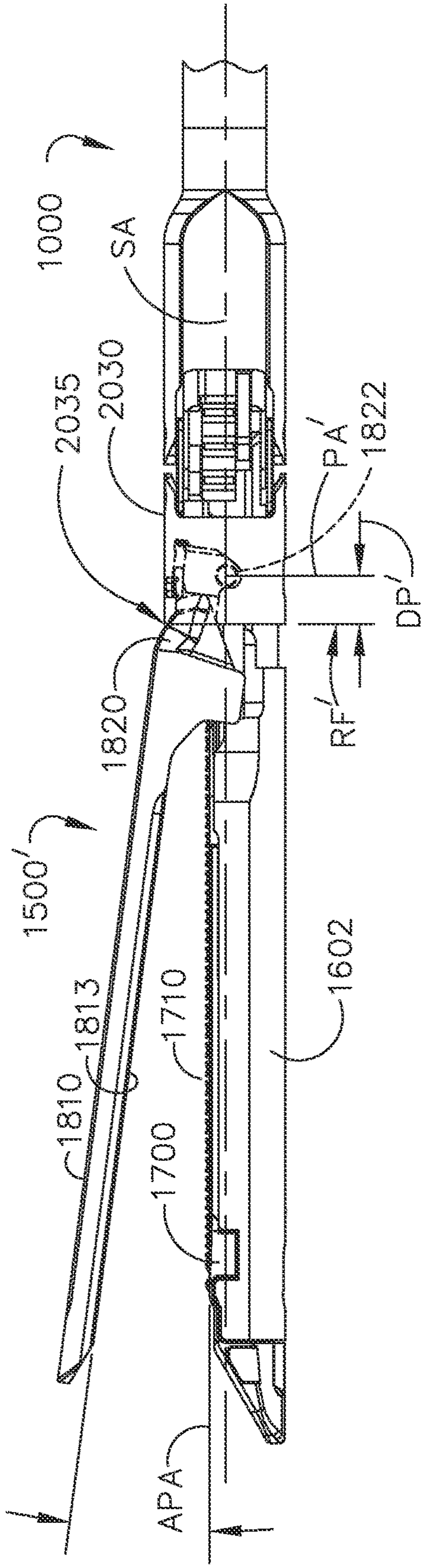
FIG. 38 is a side elevational view of a distal portion of another interchangeable surgical tool assembly with the anvil thereof in an open position.
Figure 39:
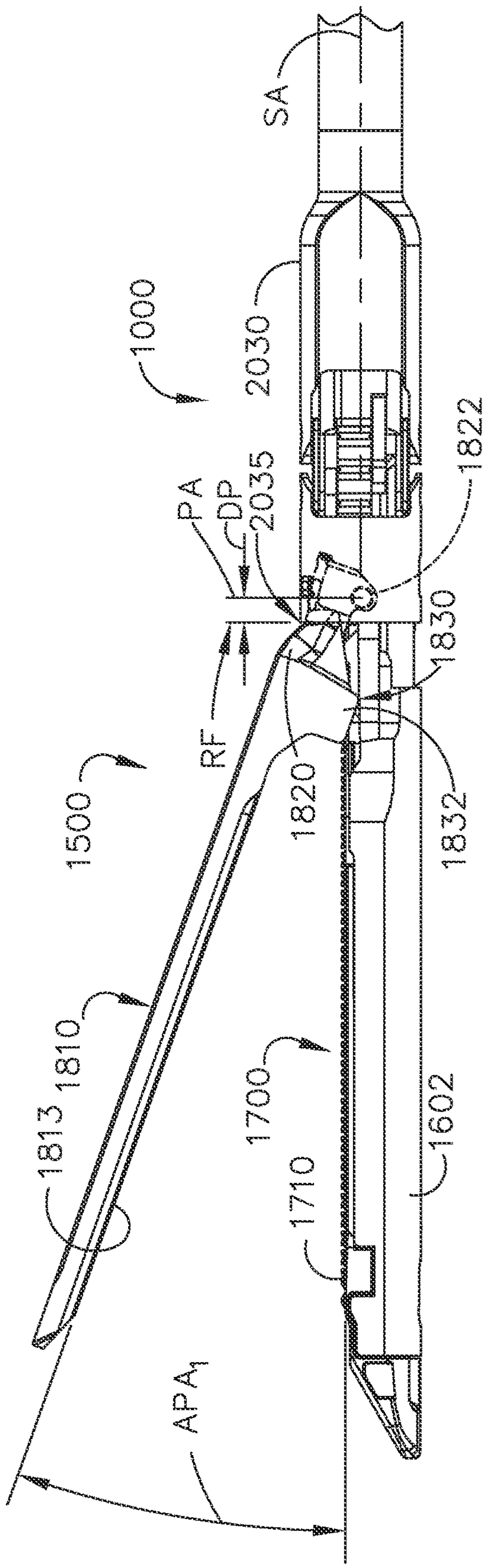
FIG. 39 is a side elevational view of a distal portion of the interchangeable surgical tool assembly of FIG. 3 with the anvil thereof in a fully open position.

Referring now to FIGS. 38 and 39, increases in jaw aperture (or aperture angle) may be more easily achieved as the pivot or pivot axis PA moves closer to the distal end of the starting or proximal position of the distal closure tube segment. FIG. 38 illustrates a surgical end effector 1500' that is substantially similar to surgical end effector 1500, except for the location of the pivot axis PA' relative to the distal end 2035 of the distal closure tube segment 2030. As can be seen in that Figure, the distance between the pivot axis PA' and the distal end 2035 of the distal closure tube segment 2030 when the distal closure tube segment 2030 is in its proximalmost starting position is represented by DP' and the aperture angle is APA. Stated another way, when the distal closure tube segment 2030 is in its starting position that corresponds with the fully open position of the anvil 1810, the distal end 2035 thereof is on a reference plane RF that is perpendicular to said shaft axis SA. The distance between the pivot axis PA' and the reference plane RF' measured along a line that is perpendicular to the reference plane RF' and extends through the pivot axis PA' is DP'. In at least one arrangement, DP' is approximately 0.200 inches and the aperture angle APA may be approximately 10°.

FIG. 38 illustrates the aperture angle APA of a surgical end effector 1500' with a distance DP' between the reference pivot axis PA' and the distal end 2035 of the distal closure tube segment 2030. Turning next to FIG. 39, as can be seen in that Figure, the distance DP between the pivot axis PA and the reference plane RF upon which the distal end 2035 of the distal closure tube segment 2030 is located when the distal closure tube segment 2030 is in its proximal most starting position is less than distance DP' and the aperture angle $APA_1$ is greater than APA. For example, in at least one embodiment, the distance DP is approximately 0.090 inches and the aperture angle $APA_1$ is approximately twenty two degrees. Thus, by moving the pivot axis PA closer to the distal end of the distal closure tube segment when the distal closure tube segment is in its proximal most starting position, the jaw aperture may be significantly increased without the need to reduce the cross-sectional width of the anvil mounting position. This may represent a significant improvement over other surgical end effector arrangements. In various circumstances, the center of the anvil trunnions 1822 may ideally be located between 0.010-0.060 inches from the distal end 2035 of the distal closure tube segment 2030 when the distal closure tube segment is in the starting (proximal most) position. A maximum distance for large jaw aperture applications may be, for example, 0.090 inches. As can also be seen in FIG. 39, when the anvil 1810 is in its fully open position as shown, the downwardly extending portion 1832 of the tissue stop 1830 generally stops at the staple cartridge deck surface 1710 to prevent any proximal movement of the target tissue during clamping.

Figure 40:
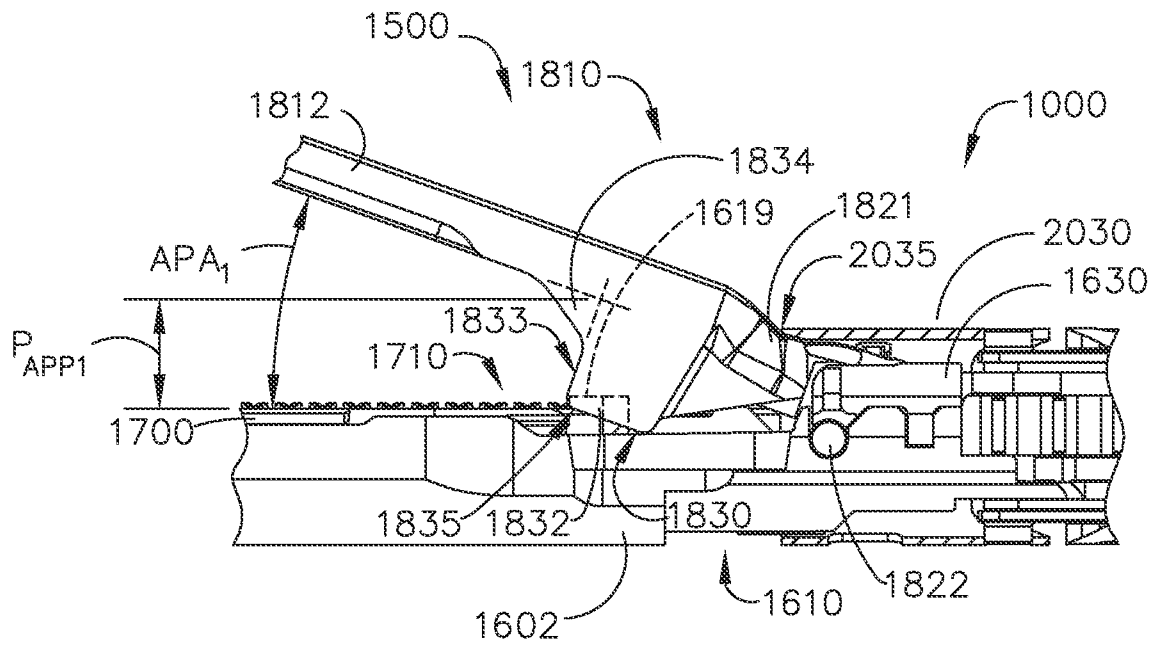
FIG. 40 is an enlarged side elevational view of the anvil mounting portion and elongate channel of the interchangeable surgical tool assembly of FIG. 39.
Figure 41:
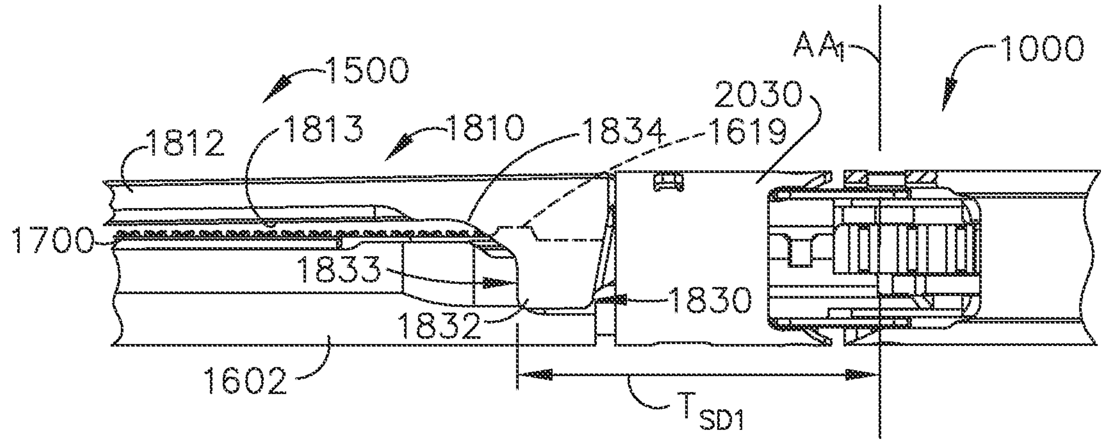
FIG. 41 is a side elevational view of a distal portion of the interchangeable surgical tool assembly of FIGS. 39 and 40 with the anvil thereof in a fully closed position.

FIGS. 40 and 41 illustrate tissue stop or tissue locator arrangements 1830 employed on one form of the surgical end effector 1500. As indicated above, the tissue stops 1830 comprise a downwardly extending portion 1832 and a chamfered portion 1834. The downwardly extending portion 1832 comprises a distal edge 1833 that terminates in a distal corner portion 1835. FIG. 40 illustrates the anvil 1810 in its fully open position. The underside 1813 of the anvil body 1812 is positioned at an aperture angle $APA_1$. In at least one arrangement, the aperture angle $APA_1$ is greater than 12.25 degrees (12.25°) and may be as large as eighteen degrees (18°). When in that fully open position, the surgical end effector 1500 may further have a proximal aperture $P_{APP1}$ that in at least one arrangement may be approximately 0.254 inches, for example. The proximal aperture defines how much tissue can be positioned between the proximal portions of the jaws (anvil and cartridge). A large proximal aperture may be most advantageous, for example, when cutting and fastening lung tissue which may be partially inflated when being introduced between the anvil and cartridge. The proximal aperture may be measured from the center of the proximal most fastener pocket or pocket pair directly vertical to the underside or tissue contact surface on the anvil body.

When the anvil 1810 is in the fully opened position as shown in FIG. 40, the distal corner 1835 does not extend above the cartridge deck surface 1710 so as to prevent tissue from moving proximal to the proximal most staples in the proximal most staple pockets 1720. In at least one embodiment, an upstanding channel stop portion 1619 may extend upwardly from the side walls of the elongate channel 1602 so as to coincide with each corresponding tissue stop 1830 to further prevent any proximal infiltration of tissue between the tissue stop 1830 and the channel stop portion 1619. FIG. 41 illustrates the anvil 1810 in a fully closed position. When in that position, the distal edges 1833 of the tissue stops 1830 are approximately aligned or coincident with the locations of the proximal most staples/fasteners in the staple/fastener cartridge 1700. The distance from the articulation axis $AA_1$ to the proximal most staples/fasteners is identified as Tam. In one arrangement, Tam is approximately 1.044 inches, for example. When the anvil 1810 is fully closed, the tissue stops 1830 may be sized and shaped relative to the proximal end portion 1610 of the elongate channel 1602 so as to facilitate easy insertion through a correspondingly sized standard trocar. In at least one example, the tissue stops 1830 of the anvil 1810 are sized and shaped relative to the elongate channel 1602 so as to permit the surgical end effector 1500 to be inserted through a conventional 12 mm trocar.

Figure 42:
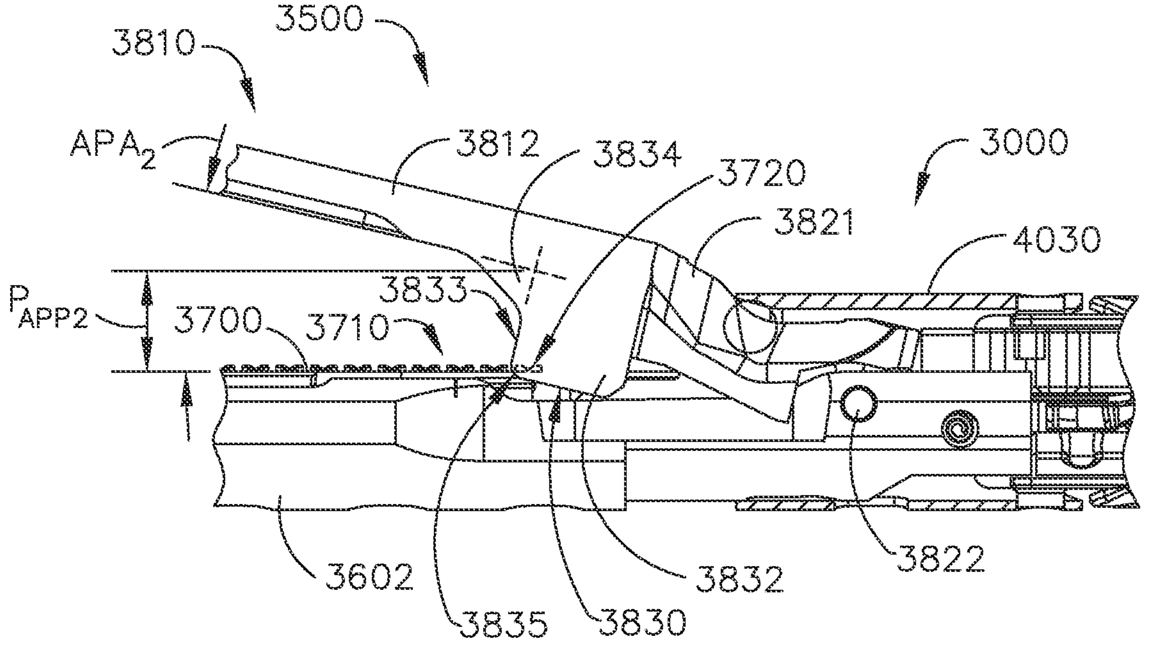
FIG. 42 is an enlarged side elevational view of the anvil mounting portion and elongate channel of the interchangeable surgical tool assembly of FIG. 16 with the anvil thereof in a fully open position.
Figure 43:
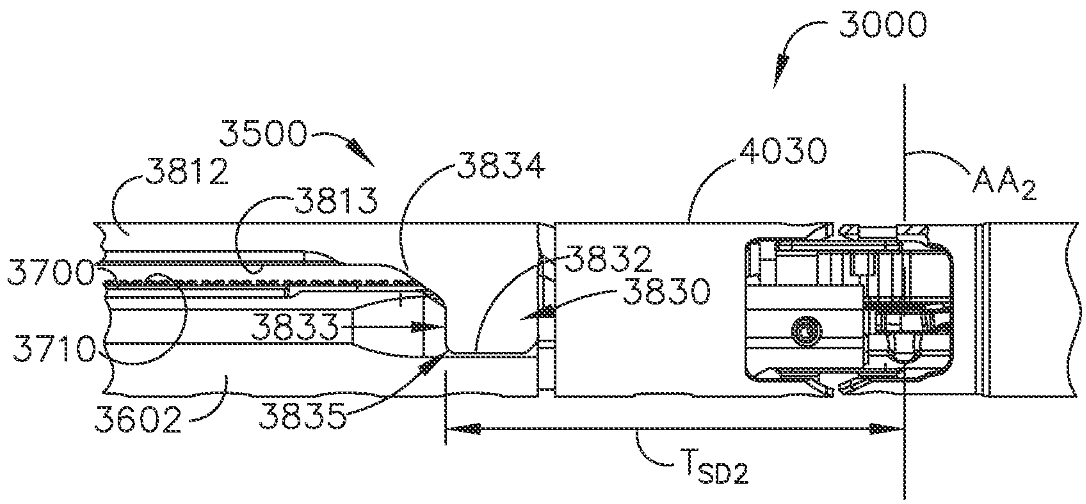
FIG. 43 is a side elevational view of a distal portion of the interchangeable surgical tool assembly of FIG. 42 with the anvil thereof in a fully closed position.

FIGS. 42 and 43 illustrate tissue stop arrangements 3830 employed on one form of the surgical end effector 3500. As indicated above, the tissue stops 3830 comprise a downwardly extending portion 3832 and a chamfered portion 3834. The downwardly extending portion 3832 comprises a distal edge 3833 that terminates in a distal corner portion 3835. FIG. 42 illustrates the anvil 3810 in its fully open position. The underside 3813 of the anvil body 3812 is positioned at an aperture angle $APA_2$. In at least one arrangement, the aperture angle $APA_2$ is approximately thirteen and one half degrees (13.5°). When in that fully open position, the surgical end effector 3500 may further have a proximal aperture $P_{APP2}$ that in at least one arrangement may be approximately 0.242 inches, for example. When the anvil 3810 is in the fully opened position as shown in FIG. 42, the distal corner 3835 does not extend above the cartridge deck surface 3710 so as to prevent tissue from moving proximal to the proximal most staples/fasteners in the proximal most staple/fastener pockets 3720. FIG. 43 illustrates the anvil 3810 in a fully closed position. When in that position, the distal edges 3833 of the tissue stops 3830 are approximately aligned or coincident with the locations of the proximal most staples/fasteners in the staple/fastener cartridge 3700. The distance from the articulation axis $AA_2$ to the proximal most staples/fasteners is identified as $T_{SD2}$. In one arrangement, $T_{SD2}$ is approximately 1.318 inches, for example.

Figure 44:
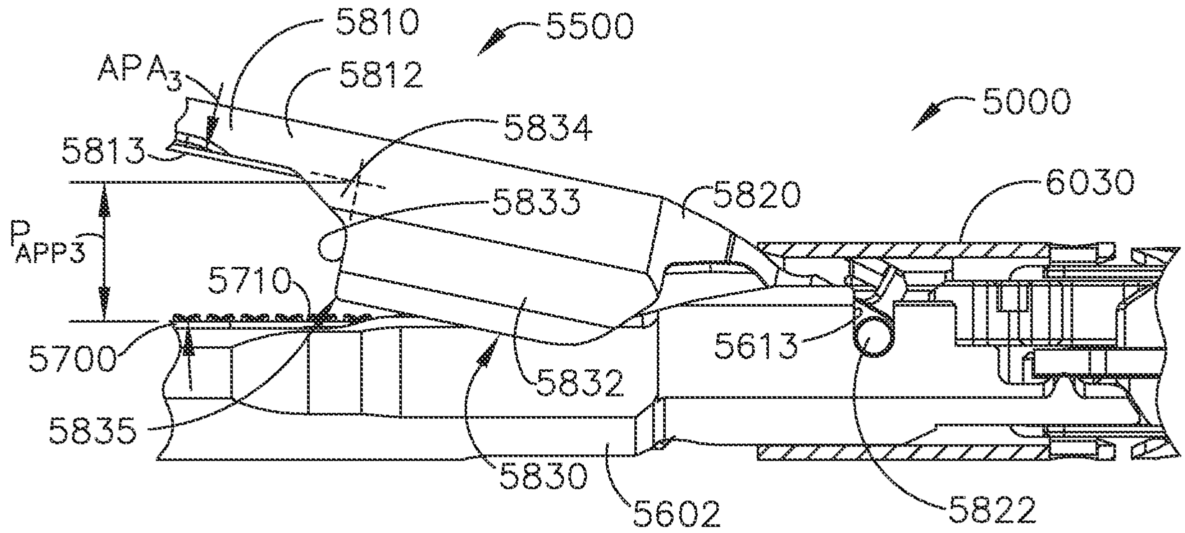
FIG. 44 is an enlarged side elevational view of the anvil mounting portion and elongate channel of the interchangeable surgical tool assembly of FIG. 19 with the anvil thereof in a fully open position.
Figure 45:
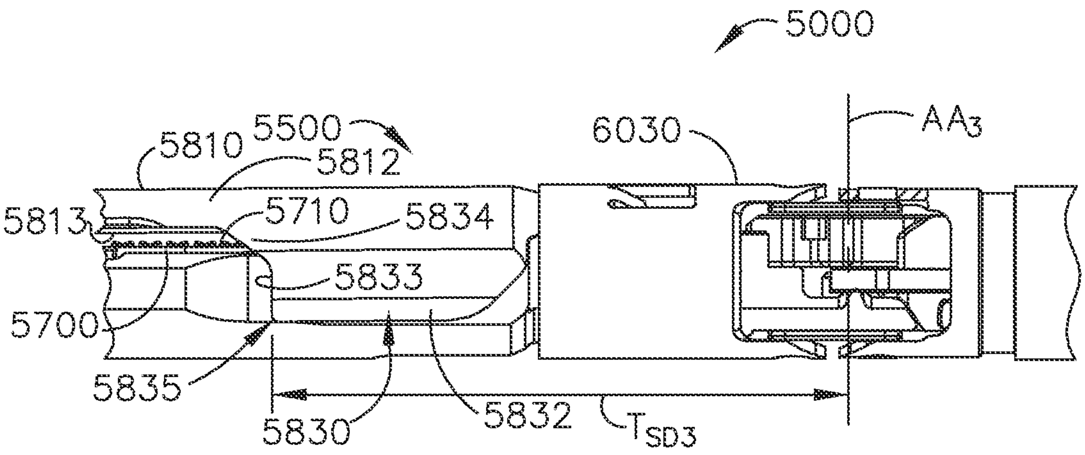
FIG. 45 is a side elevational view of a distal portion of the interchangeable surgical tool assembly of FIG. 44 with the anvil thereof in a fully closed position.

FIGS. 44 and 45 illustrate tissue stop arrangements 5830 employed on one form of the surgical end effector 5500. As indicated above, the tissue stops 5830 comprise a downwardly extending portion 5832 and a chamfered portion 5834. The downwardly extending portion 5832 comprises a distal edge 5833 that terminates in a distal corner portion 5835. FIG. 44 illustrates the anvil 5810 in its fully open position. The underside 5813 of the anvil body 5812 is positioned at an aperture angle $APA_3$. In at least one arrangement, the aperture angle $APA_3$ is approximately eight degrees (8°). When in that fully open position, the surgical end effector 5500 may further have a proximal aperture $P_{APP3}$ that in at least one arrangement may be approximately 0.226 inches, for example. When the anvil 5810 is in the fully opened position as shown in FIG. 44, the distal corner 3835 extends slightly above the cartridge deck surface 5710. FIG. 45 illustrates the anvil 5810 in a fully closed position. When in that position, the distal edges 5833 of the tissue stops 5830 are approximately aligned or coincident with the locations of the proximal most staples/fasteners in the staple/fastener cartridge 5700. The distance from the articulation axis $AA_3$ to the proximal most staples/fasteners is identified as $T_{SD3}$. In one arrangement, Tan is approximately 1.664 inches, for example.

Figure 46:
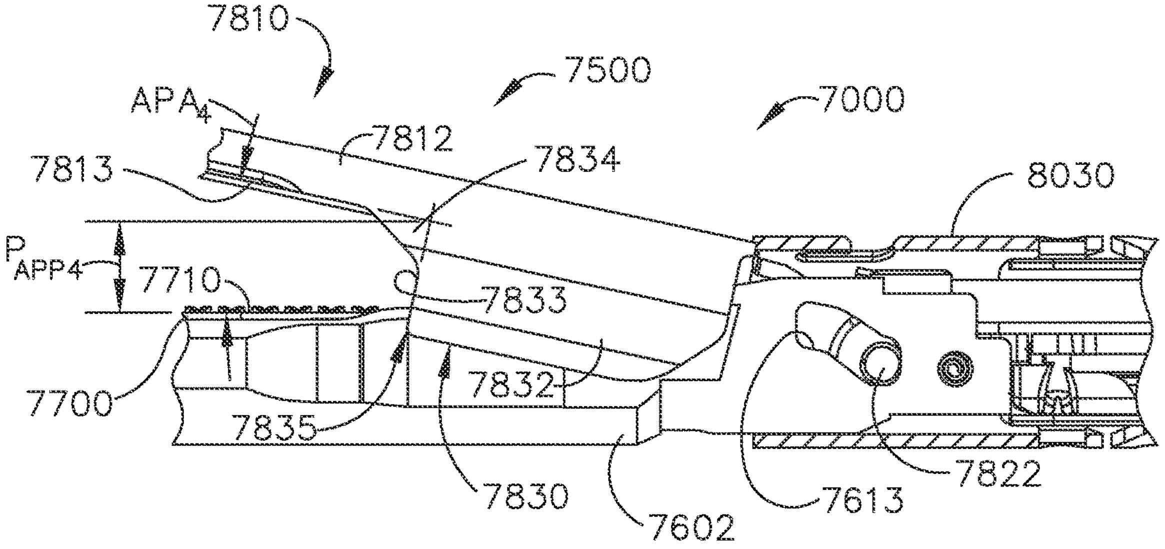
FIG. 46 is an enlarged side elevational view of the anvil mounting portion and elongate channel of the interchangeable surgical tool assembly of FIG. 22 with the anvil thereof in a fully open position.
Figure 47:
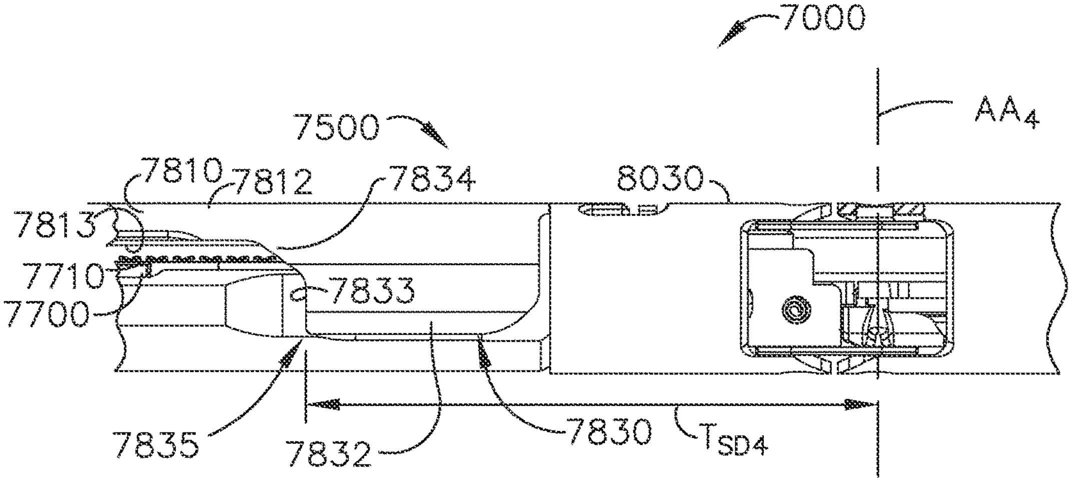
FIG. 47 is a side elevational view of a distal portion of the interchangeable surgical tool assembly of FIG. 46 with the anvil thereof in a fully closed position.

FIGS. 46 and 47 illustrate tissue stop arrangements 7830 employed on one form of the surgical end effector 7500. As indicated above, the tissue stops 7830 comprise a downwardly extending portion 7832 and a chamfered portion 7834. The downwardly extending portion 7832 comprises a distal edge 7833 that terminates in a distal corner portion 7835. FIG. 46 illustrates the anvil 7810 in its fully open position. The underside 7813 of the anvil body portion 7812 is positioned at an aperture angle $APA_4$. In at least one arrangement, the aperture angle $APA_4$ is approximately ten degrees (10°). When in that fully open position, the surgical end effector 7500 may further have a proximal aperture $P_{APP4}$ that in at least one arrangement may be approximately 0.188 inches, for example. When the anvil 7810 is in the fully opened position as shown in FIG. 46, the distal corner portion 7835 extends slightly below the cartridge deck surface 7710 so as to prevent tissue from getting proximal to the proximal most staples/fasteners in the proximal most staple pockets 7720. FIG. 47 illustrates the anvil 7810 in a fully closed position. When in that position, the distal edges 7833 of the tissue stops 7830 is approximately aligned or coincident with the locations of the proximal most staples/fasteners in the staple/fastener cartridge 7700. The distance from the articulation axis $AA_4$ to the proximal most staples/fasteners is identified as $T_{SD4}$. In one arrangement, $T_{SD4}$ is approximately 1.686 inches, for example.

Figure 48:
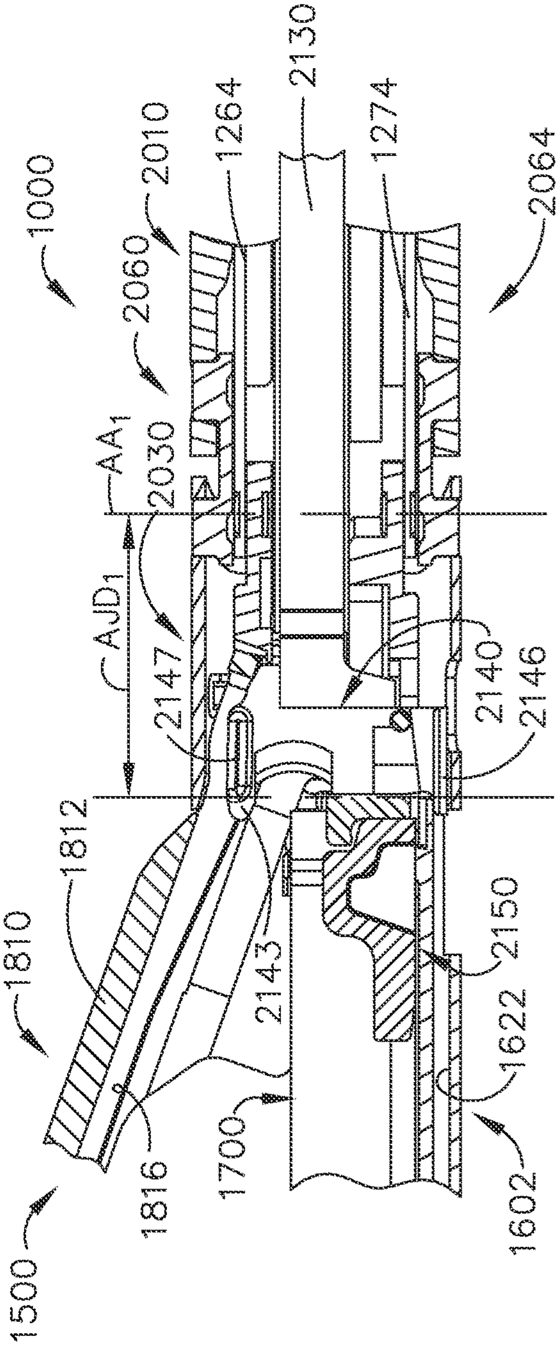
FIG. 48 is a partial cross-sectional view of the anvil mounting portion and elongate channel of the interchangeable surgical tool assembly of FIG. 3 with the anvil in a fully open position.
Figure 51:
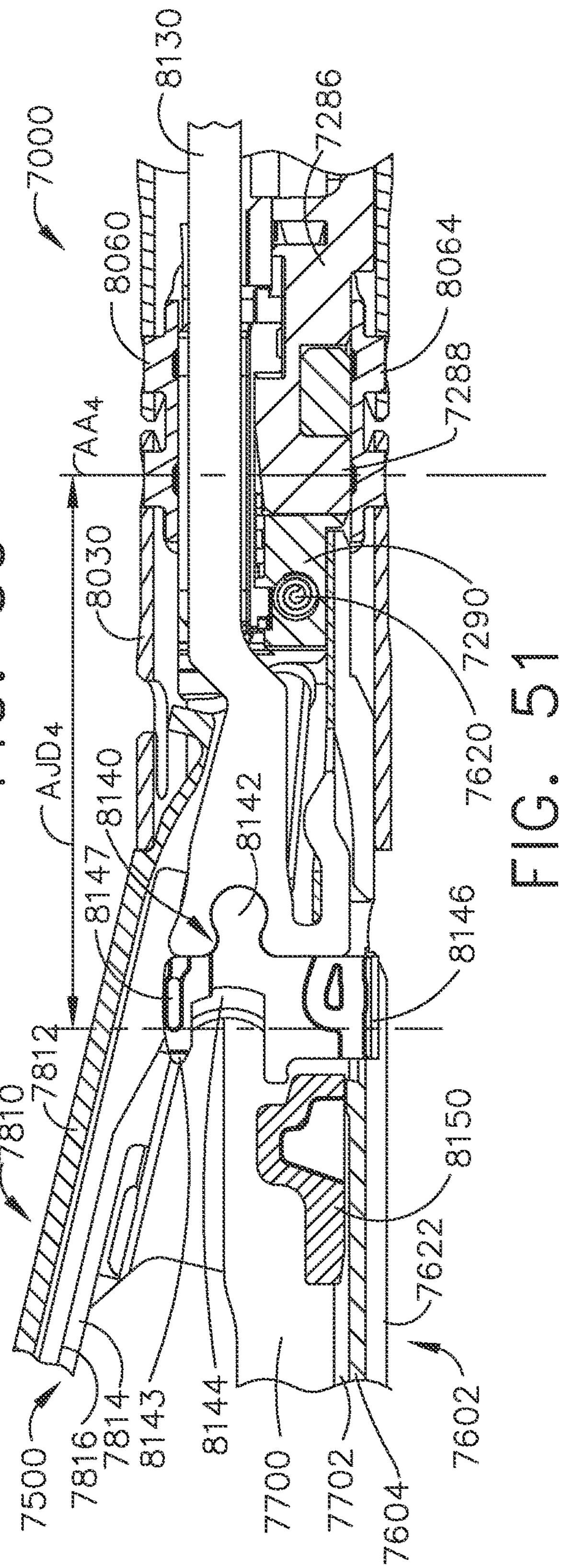
FIG. 51 is a partial cross-sectional view of the anvil mounting portion and elongate channel of the interchangeable surgical tool assembly of FIG. 22 with the anvil in a fully open position.

In various circumstances, the relationships of the firing member to the articulation axis AA as well as to the jaw pivot axis PA about which the anvil pivots may bear upon the length of the articulation joint arrangement. Of course, longer articulation joint arrangements may detrimentally affect the end effector's maneuverability within tight spaces and also limit the magnitude of the jaw aperture that may ultimately be obtained by the end effector. FIG. 48 illustrates the surgical end effector 1500 in a fully open position. That is, the anvil 1810 has been pivoted to its fully open position and the firing member 2140 is in its home or starting position. The distance between the distal end of each of the anvil engagement features 2147 and the articulation axis $AA_1$ is represented by $AJD_1$. In at least one example, $AJD_1$ is approximately 0.517 inches. By way of comparison and turning to FIG. 49, the distance $AJD_2$ from the distal end of each of the anvil engagement features 4147 and the articulation axis $AA_2$ is, in at least one example, is approximately 0.744 inches. Referring to FIG. 50, the distance $AJD_3$ from the distal end of each of the anvil engagement features 6147 and the articulation axis $AA_3$ is, in at least one example, is approximately 1.045 inches. Turning to FIG. 51, the distance $AJD_4$ from the distal end of each of the anvil engagement features 8147 and the articulation axis $AA_4$ is, in at least one example, is approximately 1.096 inches. Thus, as can be seen from this comparison, the articulation joint arrangement (as measured by distances $AJD_1$, $AJD_2$, $AJD_3$, $AJD_4$) of the surgical end effector 1500 is more compact and thus may be more maneuverable than the surgical end effectors 3500, 5500 and 7500 in at least some surgical applications.

Figure 52:
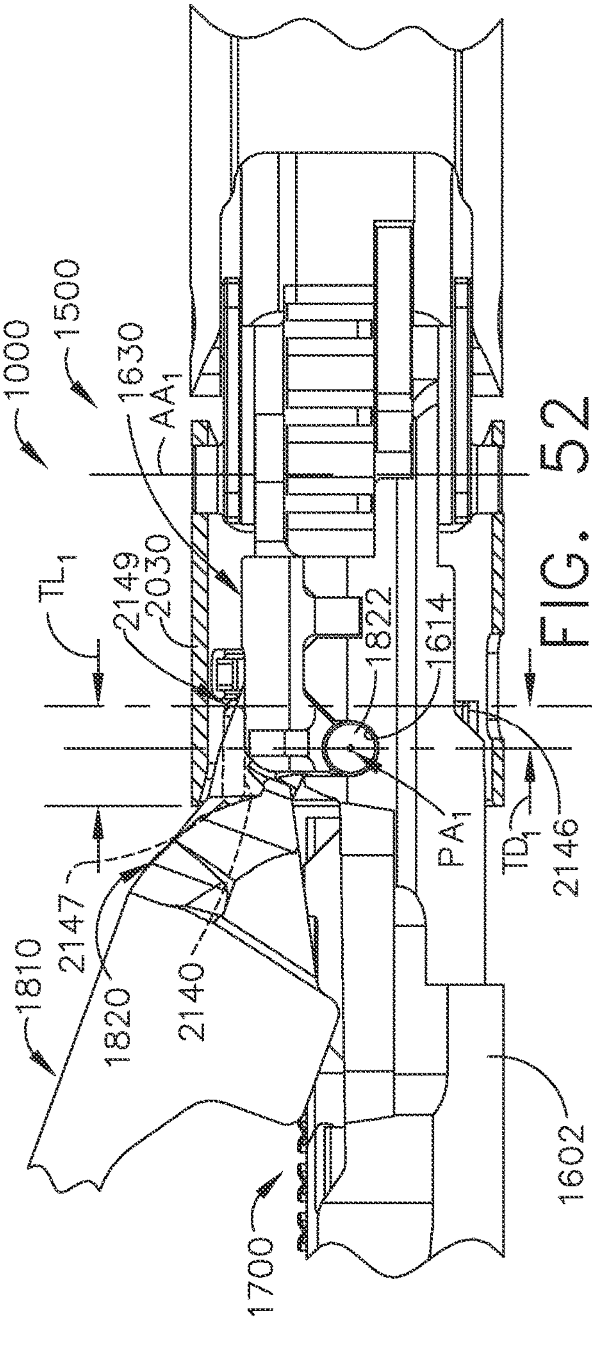
FIG. 52 is another partial cross-sectional view of a portion of the interchangeable surgical tool assembly of FIG. 3 with the anvil of the surgical end effector thereof in a fully open position.
Figure 53:
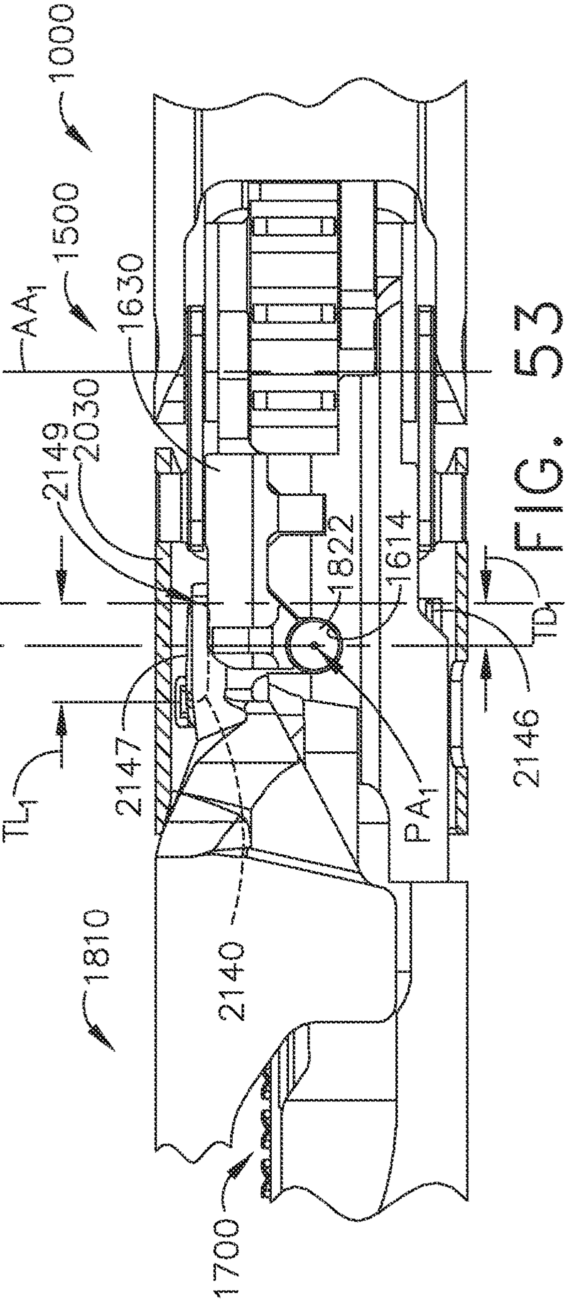
FIG. 53 is another partial cross-sectional view of a portion of the interchangeable surgical tool assembly of FIG. 52 with the anvil in a fully closed position.

Another factor that may affect the length of the joint arrangement relates to the location of the firing member relative to the anvil pivot axis PA about which the anvil pivots. For example, FIG. 52 illustrates the anvil 1810 of surgical end effector 1500 in its fully open position. When in that position, the firing member 2140 is in its parked or "starting position". As can be seen in that Figure, one useful metric for comparing the "compactness" of the articulation joint arrangement is the proximal tab distance $TD_1$ between the proximal end 2149 of each of the top anvil engagement features 2147 and the anvil pivot axis $PA_1$. In at least one preferred arrangement, the proximal tab distance $TD_1$ is approximately greater than thirty-five percent (35%) of the overall length $TL_1$ of each of the anvil engagement features 2147 when the anvil 1810 is in a fully open position and the firing member 2140 is in its proximal most or starting position. Stated another way, when the anvil 1810 and the firing member 2140 are in the above described positions, at least 35% of each of the anvil engagement features 2147 extends proximally past the anvil pivot axis $PA_1$. FIG. 53 illustrates the end effector 1500 with the anvil 1810 in the closed position and the firing member 2140 in its proximal most or starting position. As can be seen in that Figure, at least 35% of each of the anvil engagement features 2147 extends proximally past the anvil pivot axis $PA_1$.

Figure 54:
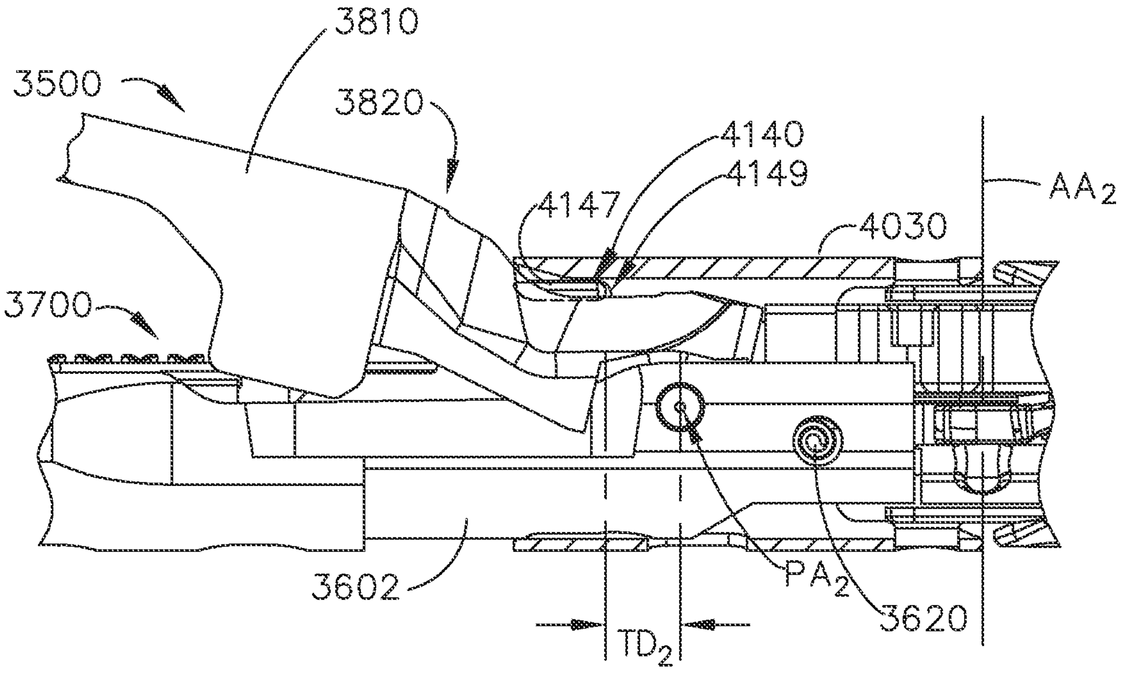
FIG. 54 is another partial cross-sectional view of a portion of the interchangeable surgical tool assembly of FIG. 16 wherein the anvil is in a fully open position.
Figure 55:
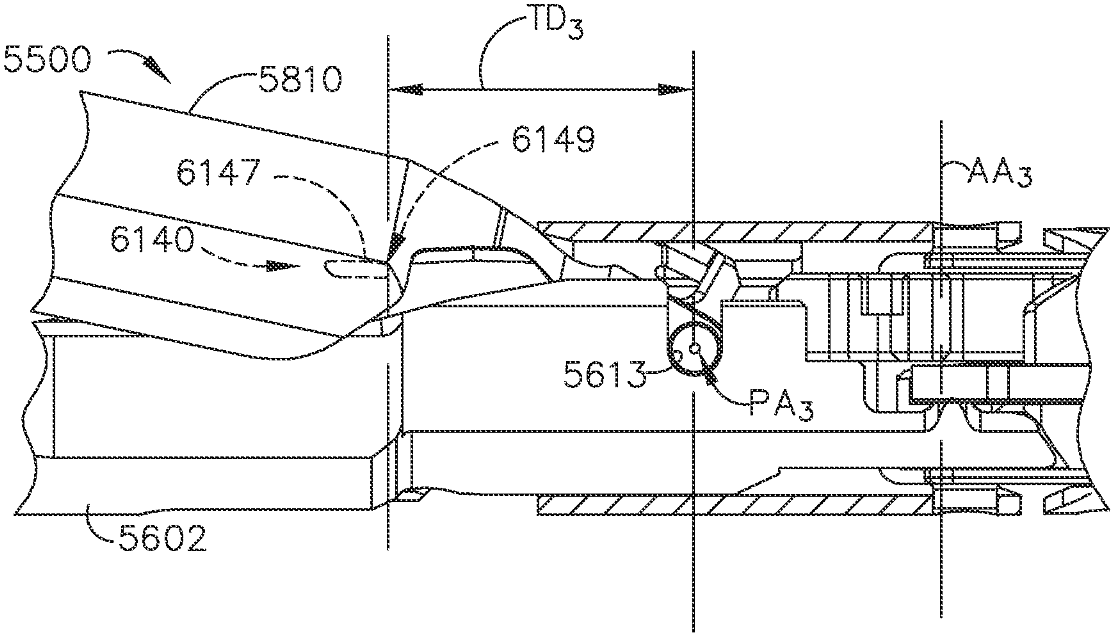
FIG. 55 is another partial cross-sectional view of a portion of the interchangeable surgical tool assembly of FIG. 19 wherein the anvil is in a fully open position.
Figure 56:
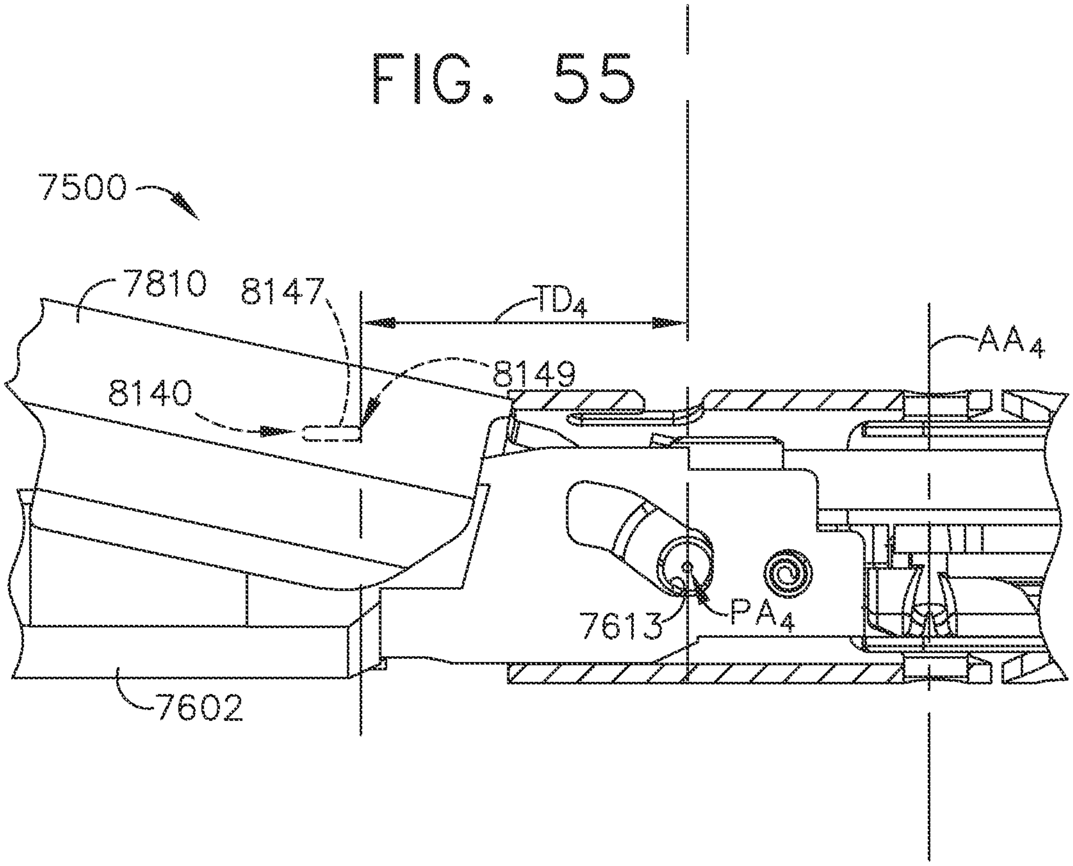
FIG. 56 is another partial cross-sectional view of a portion of the interchangeable surgical tool assembly of FIG. 22 wherein the anvil is in a fully open position.

FIG. 54 illustrates the position of the firing member 4140 of the surgical end effector 3500 when the anvil 3810 is in its fully open position and the firing member 4140 is in its proximal most or starting position. As can be seen in that Figure, each of the anvil engagement features 4147 are completely distal to the anvil pivot axis $PA_2$ thereby resulting in a longer articulation joint arrangement. Thus, the distance $TD_2$, is the distal distance between the proximal ends 4149 of the anvil engagement features 4147 and the anvil pivot axis $PA_2$. FIG. 55 illustrates the position of the firing member 6140 of the surgical end effector 5500 when the anvil 5810 is in its fully open position and the firing member 6140 is in its proximal most or starting position. As can be seen in that Figure, each of the anvil engagement features 6147 are completely distal to the anvil pivot axis $P_{A3}$ thereby resulting in a longer articulation joint arrangement. Thus, the distance $TD_3$, is the distal distance between the proximal ends 6149 of the anvil engagement features 6147 and the anvil pivot axis $P_{A3}$. FIG. 56 illustrates the position of the firing member 8140 of the surgical end effector 7500 when the anvil 7810 is in its fully open position and the firing member 8140 is in its proximal-most or starting position. As can be seen in that Figure, each of the anvil engagement features 8147 are completely distal to the anvil pivot axis $P_{A4}$ thereby resulting in a longer articulation joint arrangement. Thus, the distance $TD_4$, is the distal distance between the proximal ends 8149 of the anvil engagement features 8147 and the anvil pivot axis $P_{A4}$. For comparison purposes, the surgical end effector 1500 is the only surgical end effector wherein a portion of the anvil engagement features on the firing member extend proximally past the anvil pivot axis when the firing member is in its proximal most or starting position. The anvil engagement features of each of the firing members of the surgical end effectors 3500, 5500 and 7500 are completely distal to their respective anvil pivot axes when the firing members are in their proximal most or starting position. Taking this comparison further, for example, the surgical end effector 1500 is the only surgical end effector wherein at least thirty-five percent (35%) of the anvil engagement features reside between the anvil pivot axis and the articulation axis when the firing member is in its starting position and the anvil is fully opened. Similar comparisons may be drawn from comparing the same distances between the location of the lower channel engagement features on the firing member to the jaw pivot axis when the firing member is in its proximal most starting position.

Another metric that may be used to assess the compactness of the articulation joint arrangement may comprise comparing the ratio between the distance from the articulation axis to the distal end of the anvil engagement features on the firing member (distances $AJD_1$, $AJD_2$, $AJD_3$, $AJD_4$—FIGS. 48-51) relative to the distance from the articulation axis to the distal edge of the tissue stops or the proximal most staple/fastener (distances $TSD_1$, $TSD_2$, $TSD_3$, $TSD_4$—FIGS. 41, 43, 45, 47) for each end effector. For example, in a preferred arrangement, $AJD/TSD<0.500$. The ratio of AJD/TSD may be referred to herein as the "compactness ratio" of that particular surgical end effector. In one arrangement, for example, for end effector 1500, $AJD_1/TSD_1=0.517$ inches/1.044 inches=0.495. In one illustrated example for end effector 3500, $AJD_2/TSD_2=0.744$ inches/1.318 inches=0.564. In one illustrated example for end effector 5500, $AJD_3/TSD_3$=1.045 inches/1.664 inches=0.628. In one illustrated arrangement, $AJD_4/TSD_4$=1.096 inches/1.686 inches=0.650. Thus, in at least one preferred arrangement wherein the articulation joint arrangement is the most compact, has the largest jaw aperture and is the most maneuverable, the ratio between the distance from the articulation axis to the proximal end of the anvil engagement features on the firing member and the distance from the articulation axis to the distal edge of the tissue stops or the proximal most staple/fastener is approximately less than 0.500.

Figure 57:
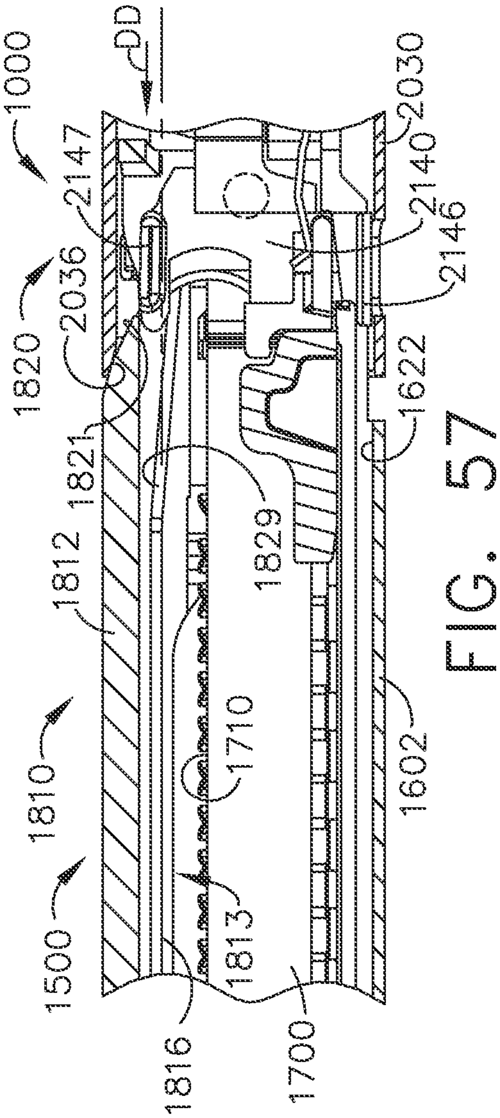
FIG. 57 is another partial cross-sectional view of a portion of the interchangeable surgical tool assembly of FIG. 3 wherein the firing member thereof is in a starting position.
Figure 58:
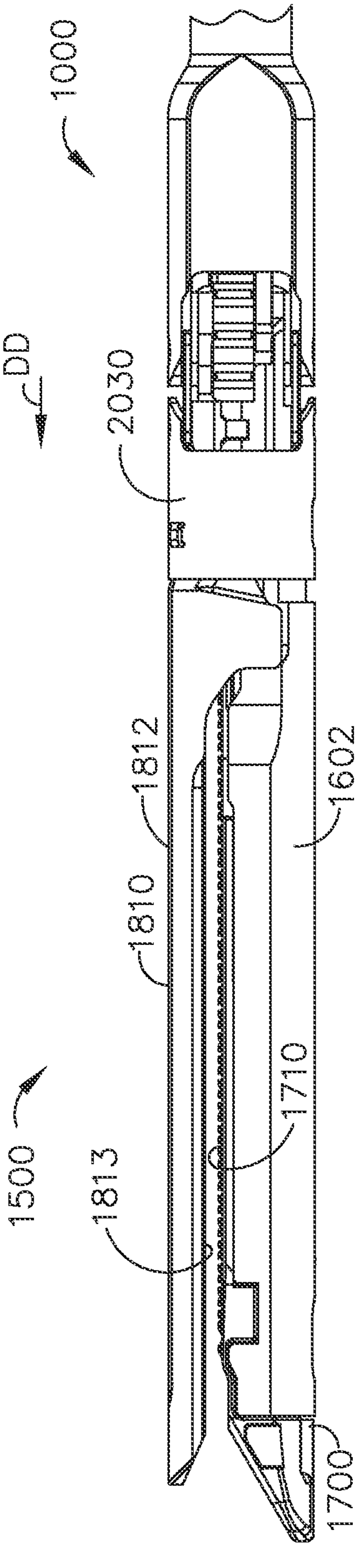
FIG. 58 is a side elevational view of the surgical end effector of FIG. 57 with the anvil in a fully closed position.
Figure 59:
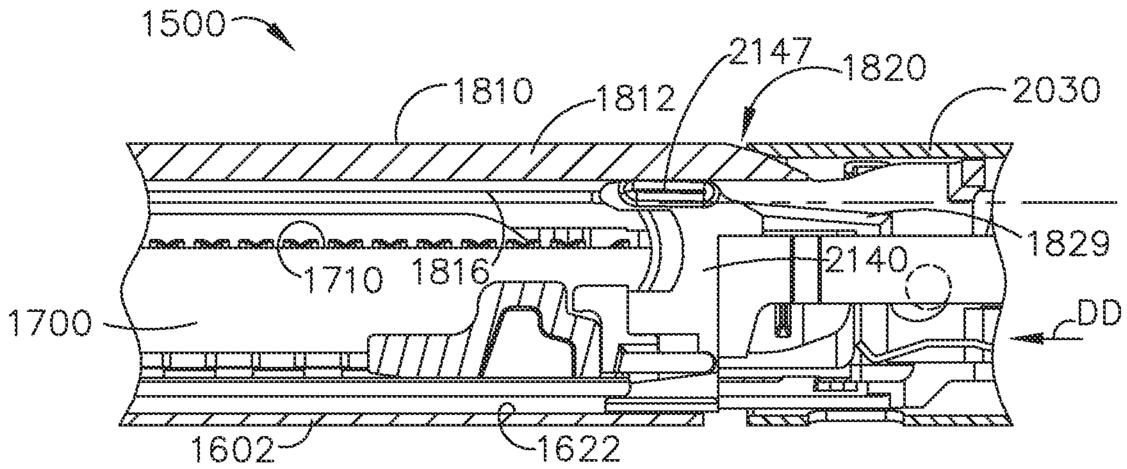
FIG. 59 is another partial cross-sectional view of the portion of the surgical end effector of FIGS. 57 and 58 wherein the firing member is in initial engagement with the anvil thereof.
Figure 61:
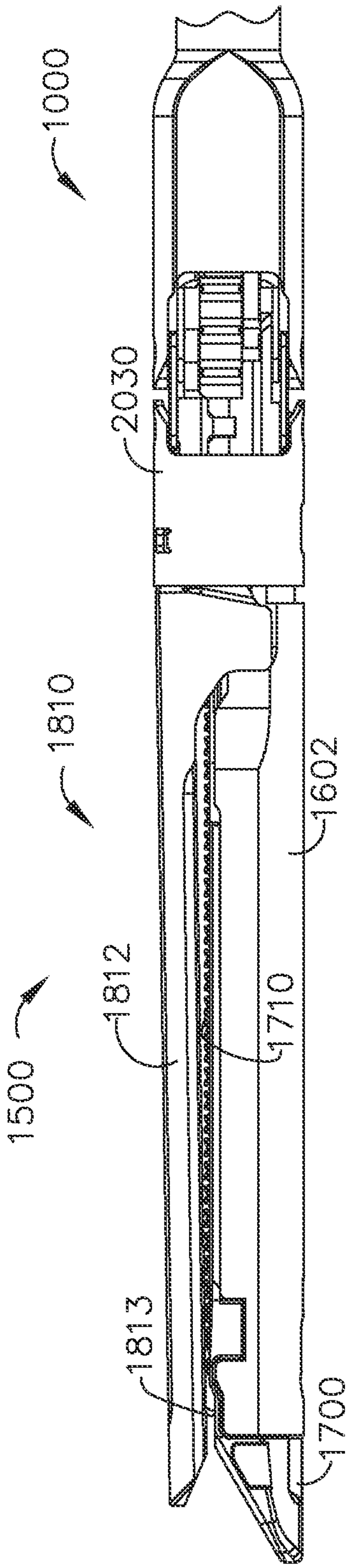
FIG. 61 is another side elevational view of the surgical end effector of FIGS. 57-60 with the anvil in an over closed position.

FIGS. 57-61 illustrate a progressive closure arrangement for moving the anvil 1810 of the surgical end effector 1500 from a fully open position to a closed position and then to an over closed position. FIGS. 57 and 58 illustrate the anvil 1810 in a closed position. In both of those Figures, the distal closure tube segment 2030 has been advanced in the distal direction DD to its fully closed position. As was discussed above, the interaction between an internal cam surface 2036 on the distal closure tube segment 2030 and an anvil cam surface 1821 on the anvil mounting portion 1820 causes the anvil 1810 to pivot to the closed position. As can be seen in FIG. 58, the staple forming underside or tissue contacting surface 1813 of the anvil body 1812 may be relatively parallel and spaced relative to the cartridge deck surface 1710 of the surgical staple/fastener cartridge. When in that initial closed position, the firing member 2140 is in its starting position as can be seen in FIG. 57. When in that position, the anvil engagement features 2147 of the firing member 2140 have not engaged the anvil 1810 but are in substantial horizontal alignment with the ledges 1816 formed in the anvil 1810. In at least one arrangement, a ramp segment 1829 is formed proximal to each of the horizontal anvil ledges 1816. FIG. 59 illustrates the position of the firing member 2140 after it has been distally advanced to a point wherein the anvil engagement features 2147 have initially engaged the horizontal anvil ledges 1816 on the anvil 1810 and FIG. 61 illustrates the position of the firing member 2140 and the anvil 1810 such that the anvil engagement features are in full engagement with the anvil ledges 1816 to apply an "overclosure" force to the anvil 1810 as the firing member 2140 continues to be distally advanced. In at least one arrangement as illustrated in FIG. 61, for example, when the anvil 1810 is in the over closed position (with no tissue being clamped between the anvil and the cartridge), the distal portion of the anvil 1810 will contact with the cartridge deck surface 1710. As a result of such configuration, the force required to distally advance the firing member from its starting position to its ending position within the end effector may generally be less than other surgical end effector arrangements that do not employ such progressive closure arrangements.

Figure 62:
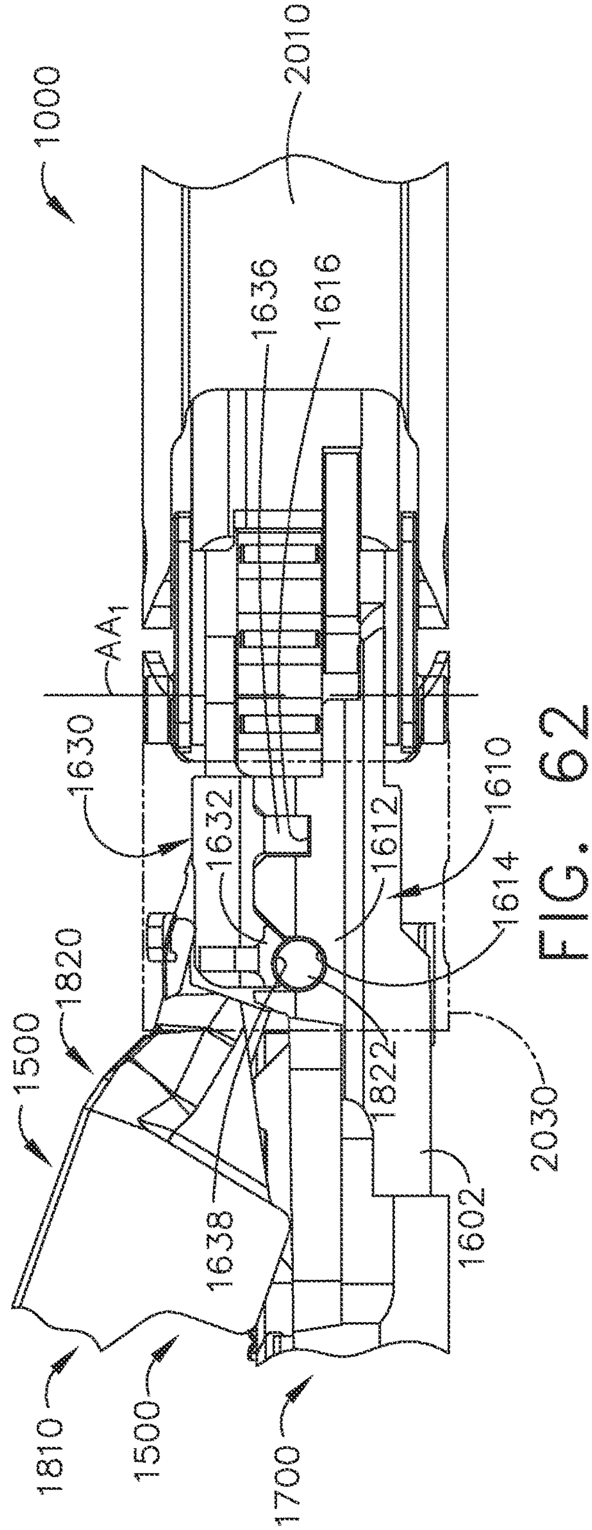
FIG. 62 is a partial side elevational view of the surgical end effector of the interchangeable surgical tool assembly of FIG. 3 in a fully open position with the distal closure tube segment shown in phantom to illustrate the anvil retaining member.
Figure 63:
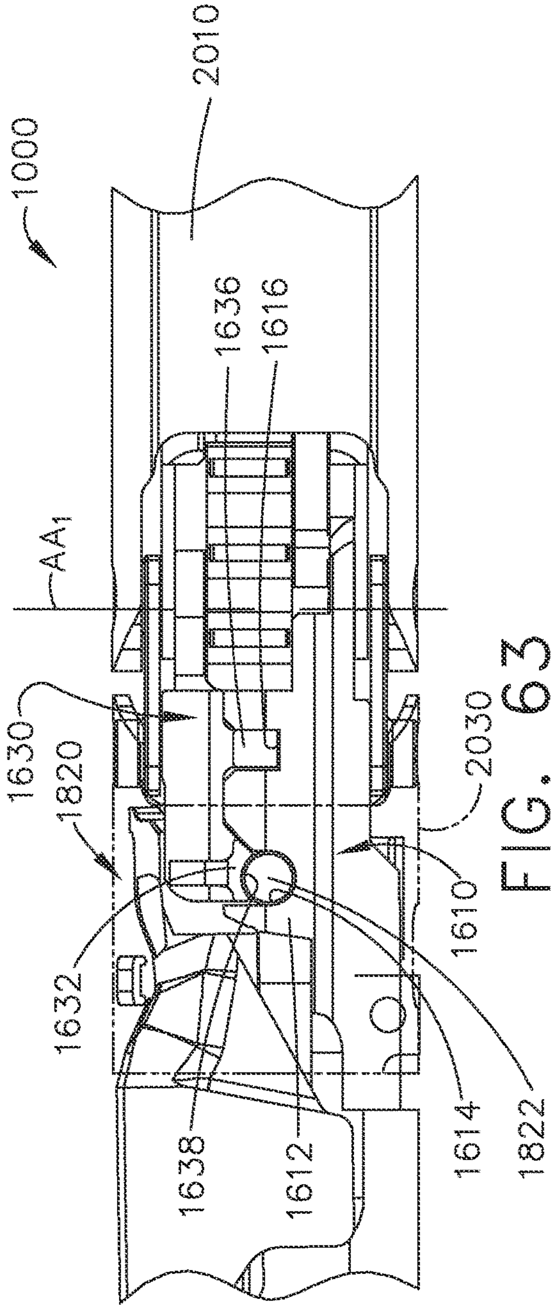
FIG. 63 is another partial side elevational view of the surgical end effector of FIG. 62 with the anvil in a fully closed position.

FIG. 62 illustrates the anvil 1810 of the surgical end effector 1500 in a fully opened position. As was discussed above, each of the anvil trunnions 1822 are received in a corresponding trunnion cradle 1614 that is formed in the upstanding walls 1612 of the proximal end portion 1610 of the elongate channel 1602. The anvil trunnions 1822 are pivotally retained in their corresponding trunnion cradle 1614 by the channel cap or anvil retainer 1630. The channel cap 1630 includes a pair of attachment lugs 1636 that are configured to be retainingly received within corresponding lug grooves or notches 1616 formed in the upstanding walls 1612 of the proximal end portion 1610 of the elongate channel 1602. During a portion of the closure stroke for the anvil 1810 on thick tissue, counterforces established during the tissue clamping process seek to push the anvil trunnions 1822 out of their respective trunnion cradles 1614. The channel cap 1630 includes a pair of slot cap portions 1632 that correspond to each trunnion cradle 1614. When the channel cap 1630 is installed onto the proximal end portion 1610 of the elongate channel 1602, each slot cap portion 1632 serves to retain the anvil trunnions 1822 within their respective trunnion cradles 1614 during the closure process. As can be seen in FIGS. 62 and 63, each slot cap portion 1632 may have an arcuate bottom portion 1638 that is configured to pivotally receive the corresponding anvil trunnion 1822. Each slot cap 1632 may have a wedge shape to completely block the open end of the trunnion cradles 1614. Such channel cap arrangement 1630 may facilitate ease of assembly of the anvil 1810 to the elongate channel 1602. Once the anvil trunnions 1822 have been placed into their respective trunnion cradles 1614, the channel cap 1630 may then be installed as shown. In at least one arrangement, the distal closure tube segment 2030 serves to retain the channel cap 1630 in position which serves to prevent the anvil trunnions 1822 from moving vertically in their respective trunnion cradles 1614 during closure as shown in FIG. 63. In another arrangement, the attachment lugs 1636 may be frictionally retained within their respective notches 1616 or otherwise be retained therein by adhesive or other fastening means.

The four interchangeable tool assemblies 1000, 3000, 5000 and 7000 employ different jaw opening configurations to facilitate moving the anvil from a closed position to a fully open position. For example, the distal closure tube segment 4030 of the interchangeable tool assembly 3000 includes positive jaw or anvil opening features 4040 that correspond to each of the sidewalls of the distal closure tube segment 4030 and protrude inwardly therefrom. The positive anvil opening features 4040 extend inwardly through corresponding openings in the transitional sidewalls and may be welded to the distal closure tube segment 4030. In this arrangement, the positive anvil opening features are axially aligned with each other and are configured to operably interface with corresponding opening ramps formed on the undersides of the anvil mounting portion 3820. When the anvil 3810 and the distal closure tube segment 4030 are in their fully closed positions, each of the positive anvil opening features 4040 is located in a cavity that is established between the anvil opening ramps and the bottom portion of the elongate channel 3602. When in that position, the positive anvil opening features 4040 do not contact the anvil mounting portion 3820 or at least may not apply any significant opening motions or forces thereto. When the distal closure tube segment 4030 is moved in the proximal direction, the anvil opening features 4040 are brought into contact with the anvil opening ramps to cause the anvil 3810 to pivot to an open position. Further details regarding the positive anvil opening features 4040 may be found in U.S. patent application Ser. No. 15/385,911, entitled SURGICAL STAPLE/FASTENERS WITH INDEPENDENTLY ACTUATABLE CLOSING AND FIRING SYSTEMS, now U.S. Pat. No. 10,448,950.

With regard to the surgical end effector 5500 of tool assembly 5000, the distal closure tube segment 6030 includes two inwardly extending positive anvil opening tabs 6038 that may be punched into the wall of the distal closure tube segment 6030. See FIG. 21. In the illustrated arrangement, the tabs 6038 are axially aligned with each other and are configured to contact corresponding upstanding anvil tails 5827 formed on the anvil mounting portion 5820. When the distal closure tube segment 6030 is moved in the proximal direction, the anvil opening features 6038 are brought into contact with the anvil tails 5827 to cause the anvil 5810 to pivot to an open position.

With regard to the surgical end effector 7500 of the tool assembly 7000, a positive anvil opening motion is applied to the anvil 7810 by the distal closure tube segment 8030 when the distal closure tube segment 8030 is moved proximally. As was discussed above, an upstanding anvil tab 7824 is formed on the anvil mounting portion 7820 and extends into the horseshoe-shaped opening 8038 in the distal closure tube segment 8030. See FIG. 24. Opening 8038 defines an opening tab 8039 that is configured to operably interface with the anvil tab 7824 as the distal closure tube segment 8030 is retracted in the distal direction. Such interaction between the opening tab 8039 and the anvil tab 7824 applies an opening motion to the anvil 7810 to thereby cause the anvil 7810 to move to an open position.

Figure 64:
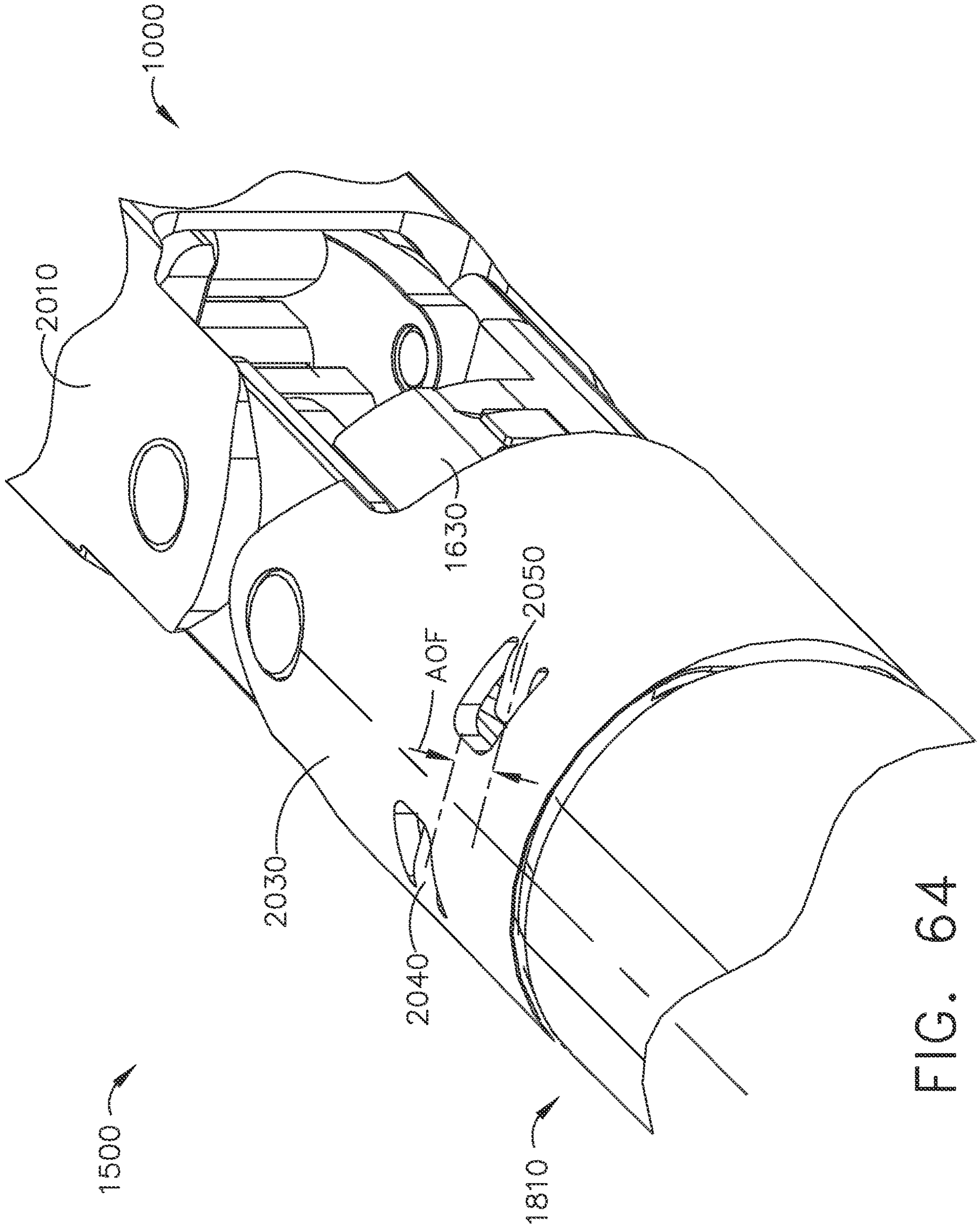
FIG. 64 is a partial perspective view of a distal closure tube segment of the interchangeable surgical tool assembly of FIG. 3 with the anvil in a fully closed position.
Figure 65:
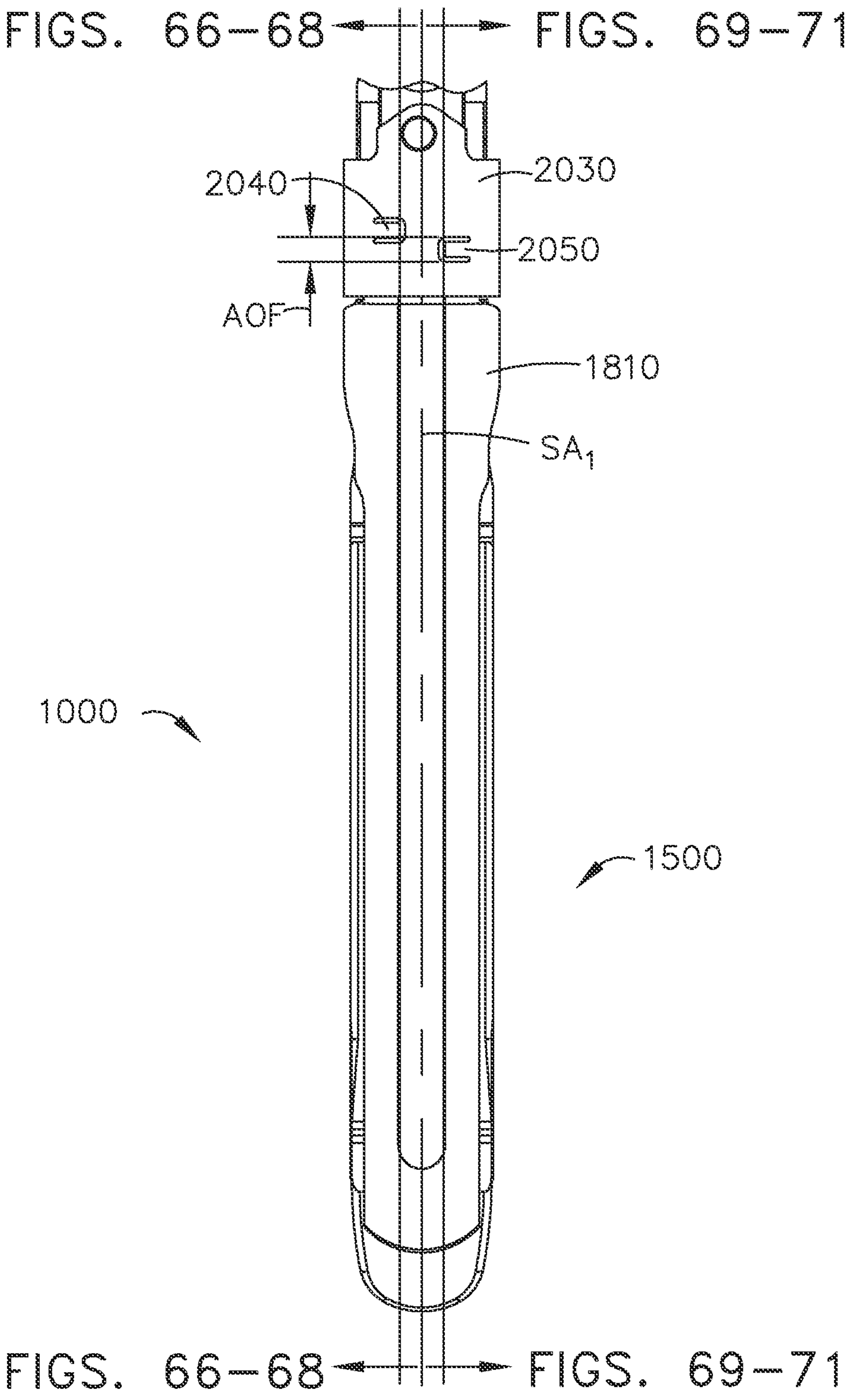
FIG. 65 is a top plan view of the distal closure tube segment and anvil of FIG. 64.
Figure 66:
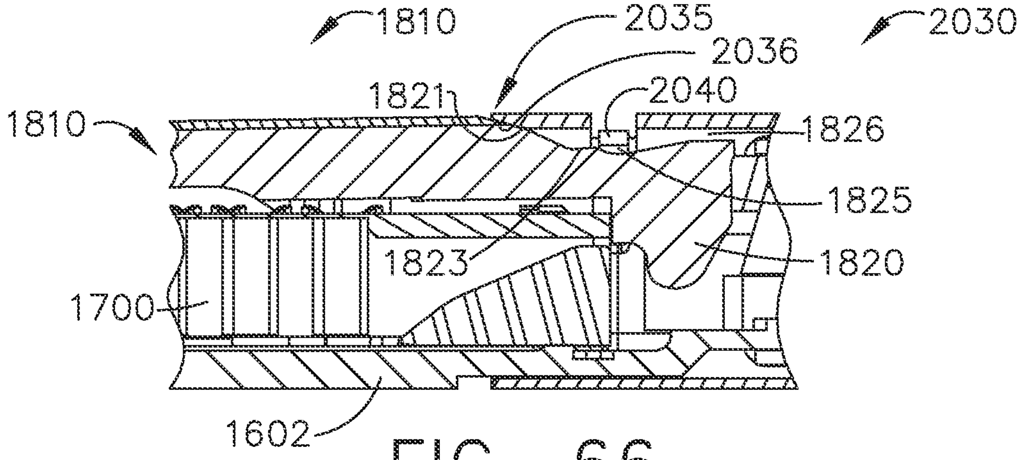
FIG. 66 is a partial cross-sectional view of the anvil and distal closure tube segment of FIGS. 64 and 65 illustrating the position of a proximal jaw opening feature when the anvil is in a fully closed position.
Figure 67:
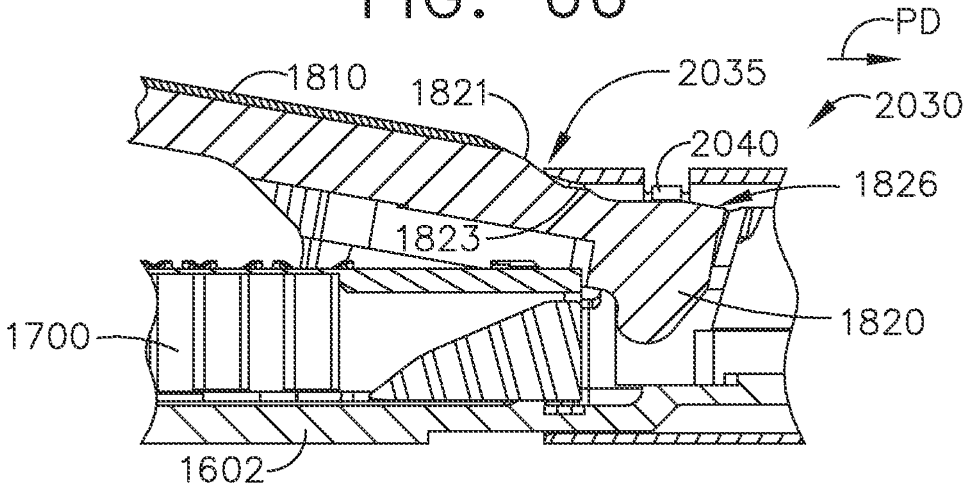
FIG. 67 is another partial cross-sectional view of a portion of the anvil and distal closure tube segment of FIGS. 64-66 illustrating the position of the proximal jaw opening feature when the anvil is between the fully open and fully closed positions.

With regard to surgical end effector 1500 of the interchangeable tool assembly 1000, in the illustrated example, the distal closure tube segment 2030 employs two axially offset, proximal and distal positive jaw opening features 2040 and 2050 as illustrated in FIGS. 64-77. As can be seen in FIGS. 64 and 65, the proximal positive jaw opening feature 2040 is axially proximal to the distal positive jaw opening feature 2050 by an axial offset distance AOF. In FIG. 65, the proximal positive jaw opening feature 2040 is located on the right side (as viewed by a user of the tool assembly) of the shaft axis $SA_1$. FIGS. 66, 72 and 73 illustrate the position of the proximal positive jaw opening feature 2040 when the anvil 1810 is in the closed position. As can be most particularly seen in FIG. 66, when in that position, the proximal positive jaw opening feature 2040 is in a right side or first relieved area 1825 formed in the anvil mounting portion 1820. FIGS. 69, 72 and 73 illustrate the position of the distal positive jaw opening feature 2050 when the anvil 1810 is in the closed position. As can be most particularly seen in FIG. 69, when in that position, the distal positive jaw opening feature is in contact with a stepped portion 1823 of the anvil cam surface 1821.

Figure 70:
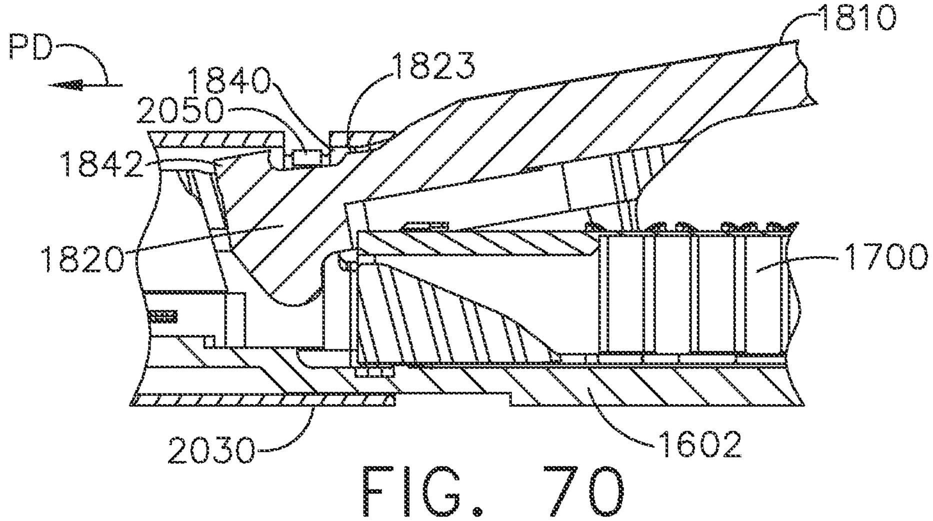
FIG. 70 is a partial cross-sectional view of the anvil and distal closure tube segment of FIGS. 64-69 illustrating the position of the distal jaw opening feature when the anvil is between the fully open and fully closed positions.
Figure 74:
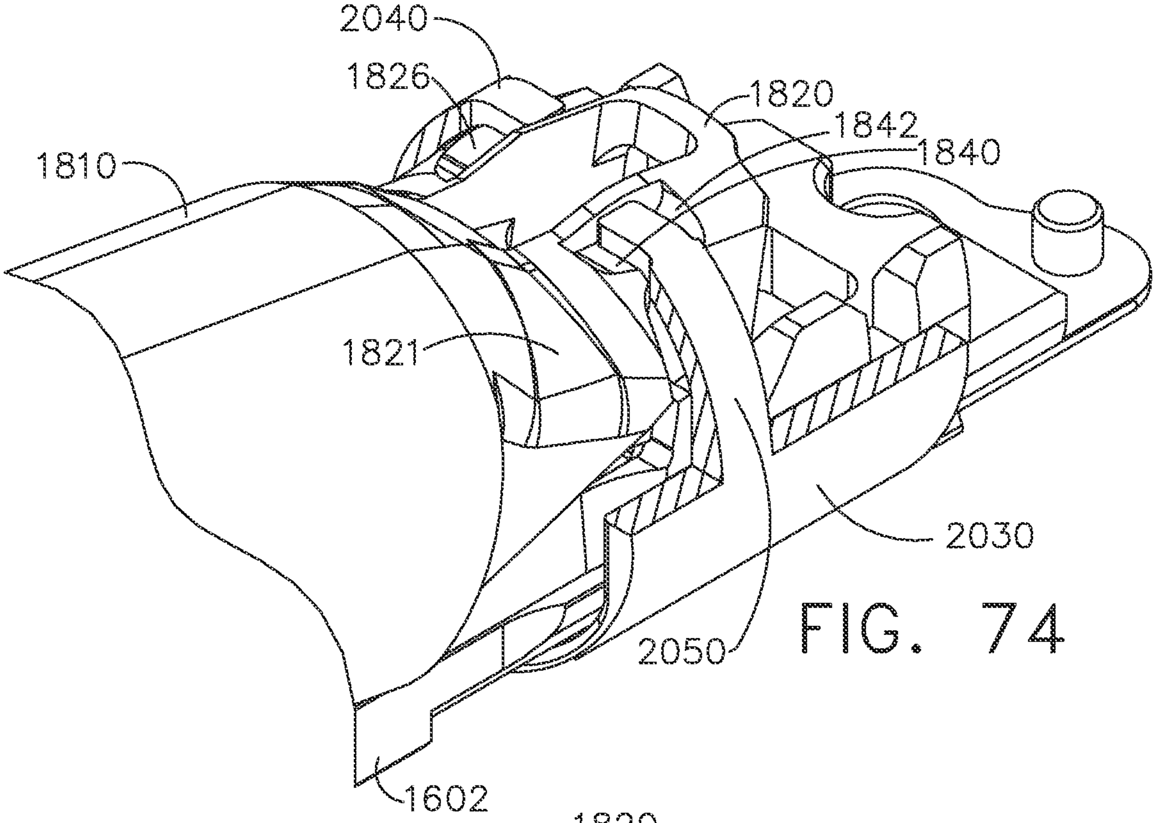
FIG. 74 is a partial left side perspective view of the anvil and distal closure tube segment of FIGS. 64-73 with the anvil in a partially open position.
Figure 75:
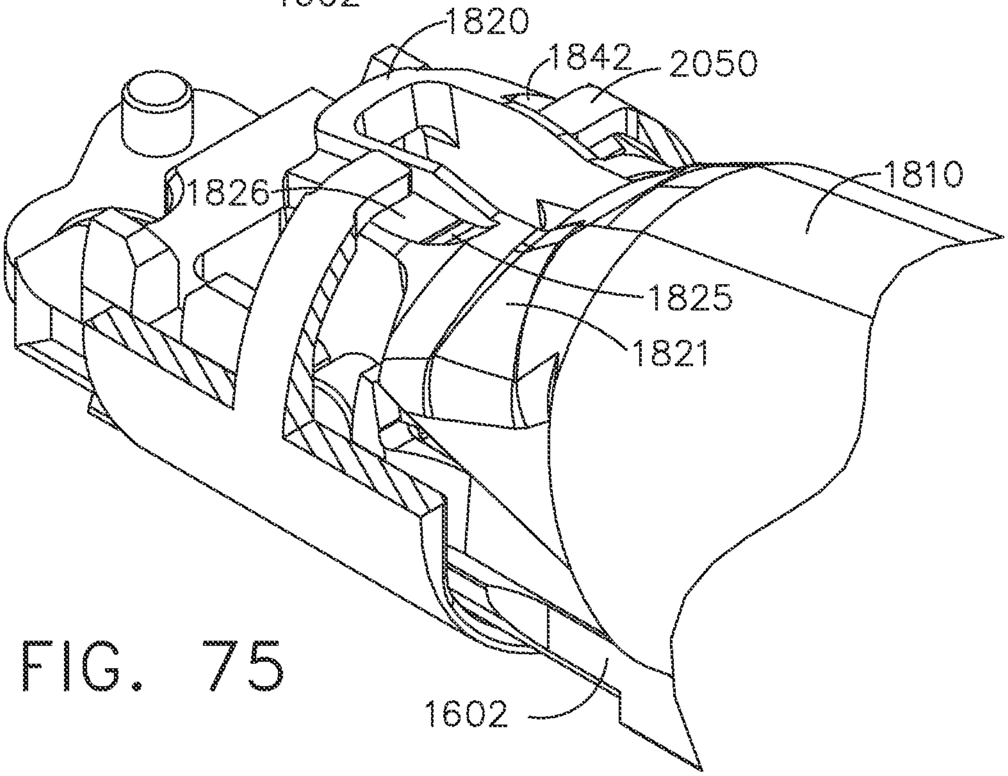
FIG. 75 is a partial right side perspective view of the anvil and distal closure tube segment of FIGS. 64-74 with the anvil in a partially open position.
Figure 76:
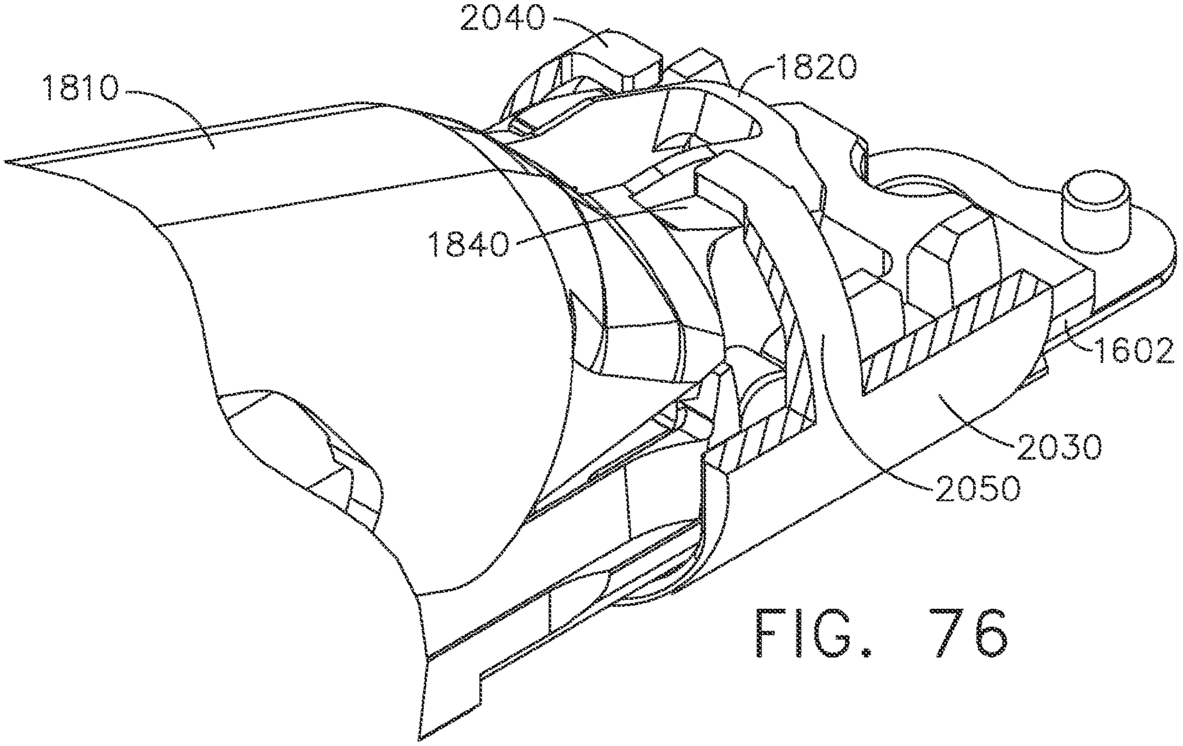
FIG. 76 is a partial left side perspective view of the anvil and distal closure tube segment of FIGS. 64-75 with the anvil in a fully open position.
Figure 77:
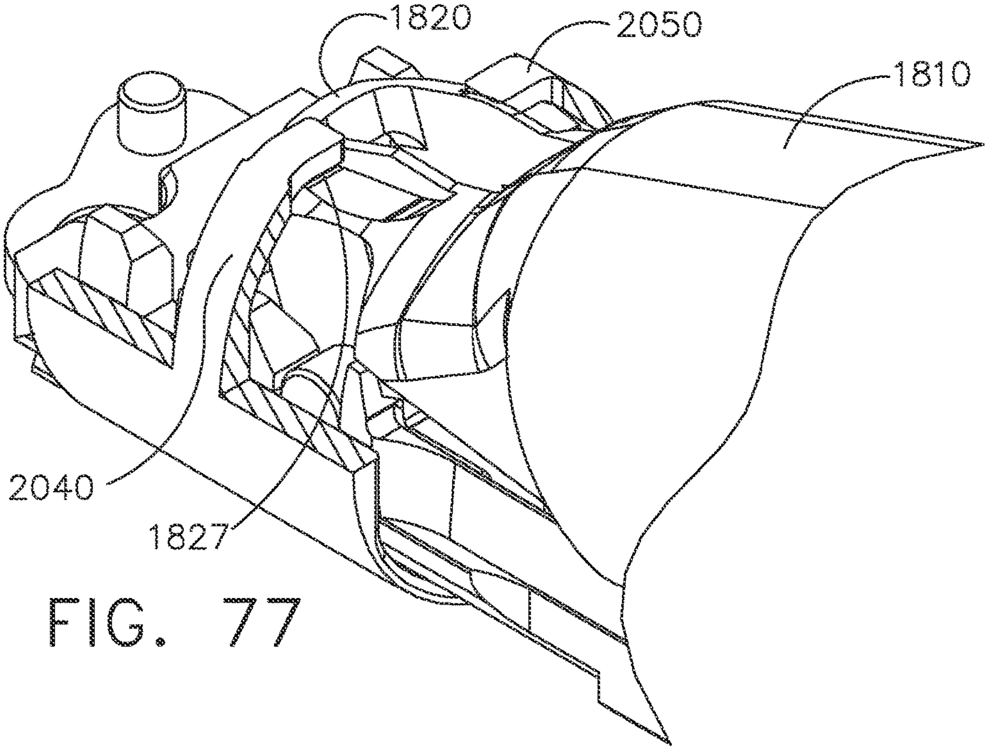
FIG. 77 is a partial right side perspective view of the anvil and distal closure tube segment of FIGS. 64-76 with the anvil in a fully open position.

To commence the opening process, the jaw closure system is actuated to move the distal closure tube segment 2030 in the proximal direction PD. As the distal closure tube segment 2030 is moved in the proximal direction PD, the proximal positive jaw opening feature 2040 contacts a first or right side jaw opening cam surface 1826 and begins to apply a jaw opening motion to the anvil 1810. See FIGS. 67, 74 and 75. As can be seen in FIGS. 70, 74 and 75, during this proximal movement of the distal closure tube segment 2030, the distal positive jaw opening feature 2050 is axially movable within a second or left relief area 1840 formed in the anvil mounting portion 1820. Thus, while the proximal positive jaw opening feature 2040 is applying a first or initial opening motion to the anvil mounting portion 1820, the distal positive jaw opening feature 2050 is not applying any significant opening motion to the anvil 1810. Further proximal motion of the distal closure tube segment 2030 will result in the distal positive jaw opening feature 2050 contacting a left anvil open tab 1842 and the proximal positive jaw opening feature 2040 disengaging the jaw opening cam surface 1826. Thus, the proximal positive jaw opening feature 2040 has disengaged the anvil mounting portion 1820 and is not applying any further opening motion thereto while the distal positive jaw opening feature 2050 is applying a second jaw opening motion to the anvil mounting portion 1820 to pivot the anvil 1810 to a fully open position illustrated in FIGS. 68, 71, 76 and 77.

Figure 78:
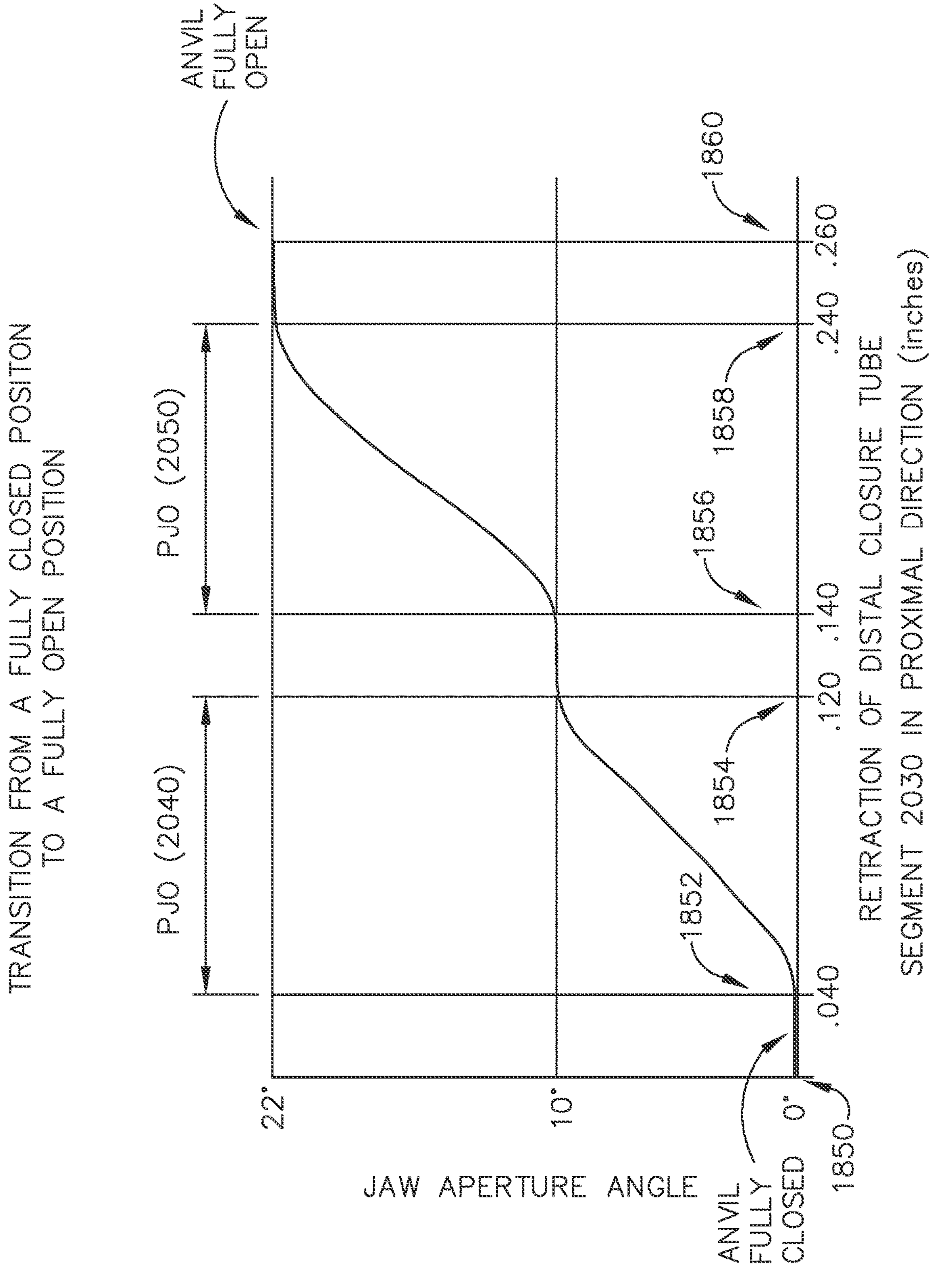
FIG. 78 is a graphical comparison between the jaw aperture angle and retraction of the distal closure tube segment of FIGS. 64-77.

FIG. 78 depicts the anvil or jaw opening process employed by the interchangeable tool assembly 1000 in graphical form. As can be seen in that Figure, the left or vertical axis of the graph represents the amount of jaw aperture from about 0° to about 22° ("anvil aperture angle") and the bottom or horizontal axis represents the approximate proximal axial travel of the distal closure tube segment 2030 from a position wherein the anvil is fully closed to a position wherein the anvil is fully open. As indicated above, the "anvil aperture angle" or "jaw aperture angle" may represent the angle between the cartridge deck surface or tissue contacting surface on the surgical fastener cartridge or "first jaw" and the fastener forming surface or tissue contacting surface on the anvil or "second jaw". When the anvil is fully closed, the anvil aperture angle may be approximately 0°, for example. In the illustrated arrangement, the distal closure tube segment 2030 can move proximally from a first position (1850 on the graph) that corresponds to the fully closed position a proximal distance of, for example, about 0.040 inches to a first intermediate position (1852 on the graph) before the proximal positive jaw opening feature 2040 begins to apply a first jaw opening motion to the anvil 1810. As the distal closure tube segment 2030 continues to move proximally from the first intermediate position 1852 to a second intermediate position (1854 on the graph) a further proximal distance of, for example, about 0.040 inches to about 0.120 inches, the proximal positive jaw opening feature 2040 moves the anvil 1810 through an anvil aperture angle from 0° to about 10°. While the distal closure tube segment 2030 continues to travel proximally from the second intermediate position 1854 to a third intermediate position (1856 on the graph) a further proximal distance (from about 0.120 inches to about 0.140 inches), the anvil remains at about a 10° anvil aperture angle. Further proximal movement of the distal closure tube segment 2030 from the third intermediate position 1856 to a fourth intermediate position (1858 on the graph) a proximal distance (from about 0.140 inches to about 0.240 inches), the distal positive jaw opening feature 2050 begins to apply a second jaw opening motion to the anvil 1810. As the distal closure tube segment 2030 continues to move proximally from the third intermediate position 1856 to a fourth intermediate position (1858 on the graph) a further proximal distance (from, for example, about 0.140 inches to about 0.240 inches), the distal positive jaw opening feature 2050 moves the anvil 1810 relative to the elongate channel 1602 such that the anvil aperture angle increases from about 10° to about 22°, for example. While the distal closure tube segment 2030 continues to travel proximally from the fourth intermediate position 1858 to a final proximal position (1860 on the graph) a further proximal distance (from about 0.240 inches to about 0.260 inches, for example), the anvil 1810 remains at a fully open position with an anvil aperture angle of approximately 22°.

Figure 68:
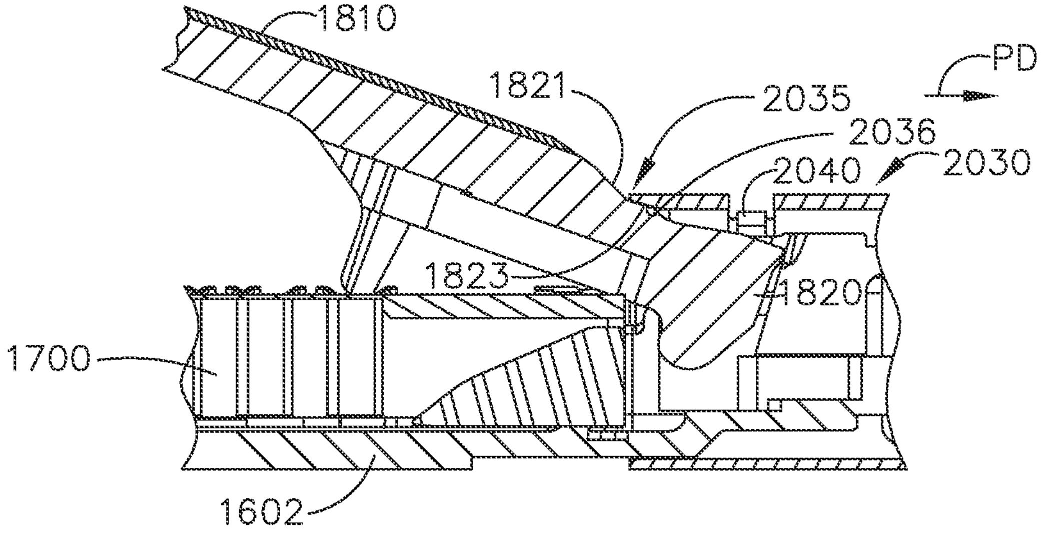
FIG. 68 is another partial cross-sectional view of a portion of the anvil and distal closure tube segment of FIGS. 64-67 illustrating the position of the proximal jaw opening feature when the anvil is in the fully open position.
Figure 69:
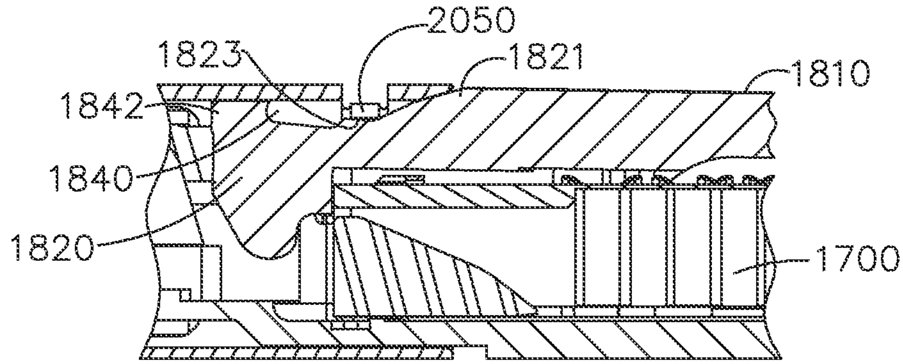
FIG. 69 is a partial cross-sectional view of the anvil and distal closure tube segment of FIGS. 64-68 illustrating the position of a distal jaw opening feature when the anvil is in a fully closed position.
Figure 71:
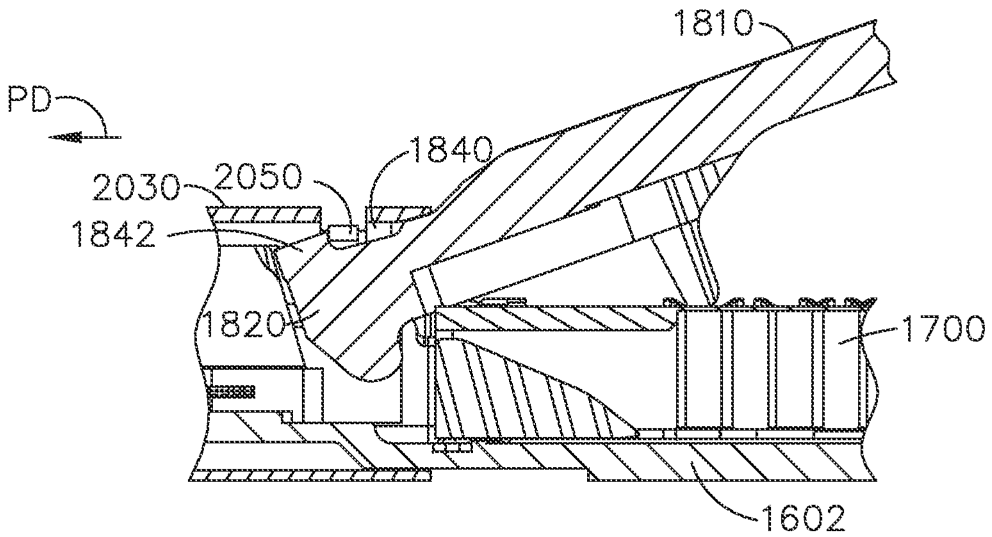
FIG. 71 is another partial cross-sectional view of a portion of the anvil and distal closure tube segment of FIGS. 64-70 illustrating the position of the distal jaw opening feature when the anvil is in the fully open position.
Figure 72:
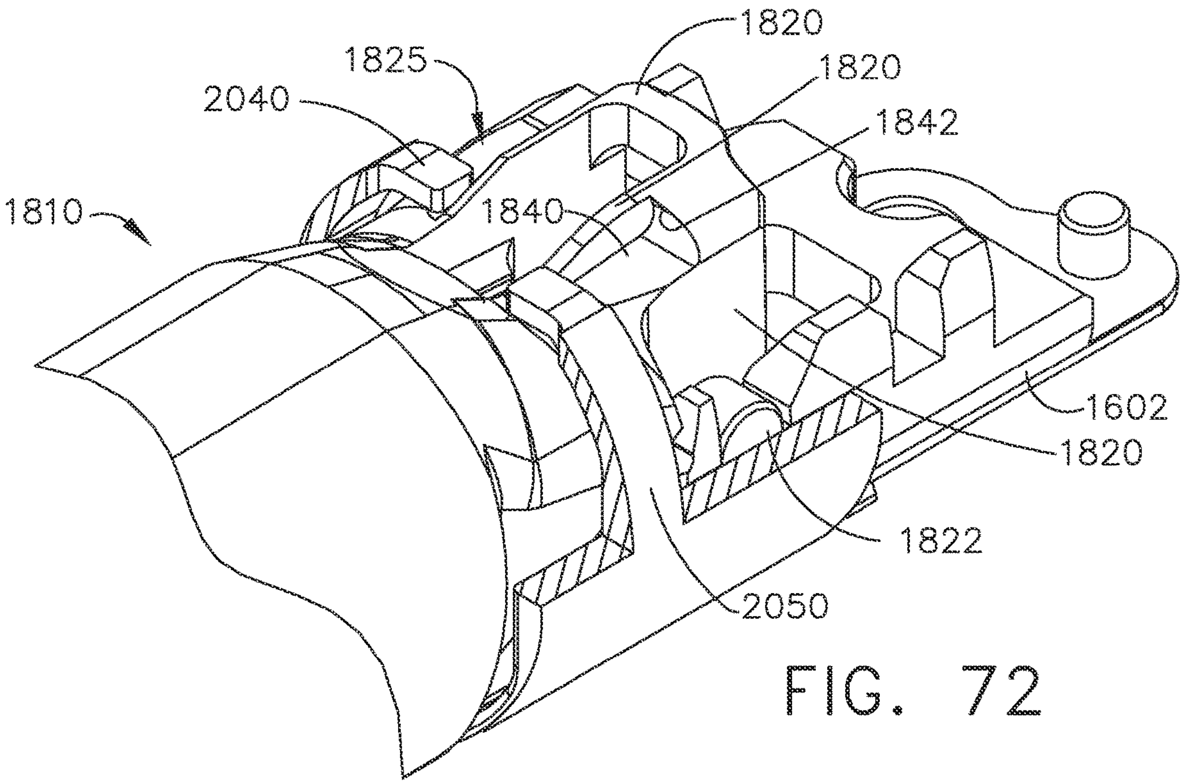
FIG. 72 is a partial left side perspective view of the anvil and distal closure tube segment of FIGS. 64-71 with the anvil in a fully closed position.
Figure 73:
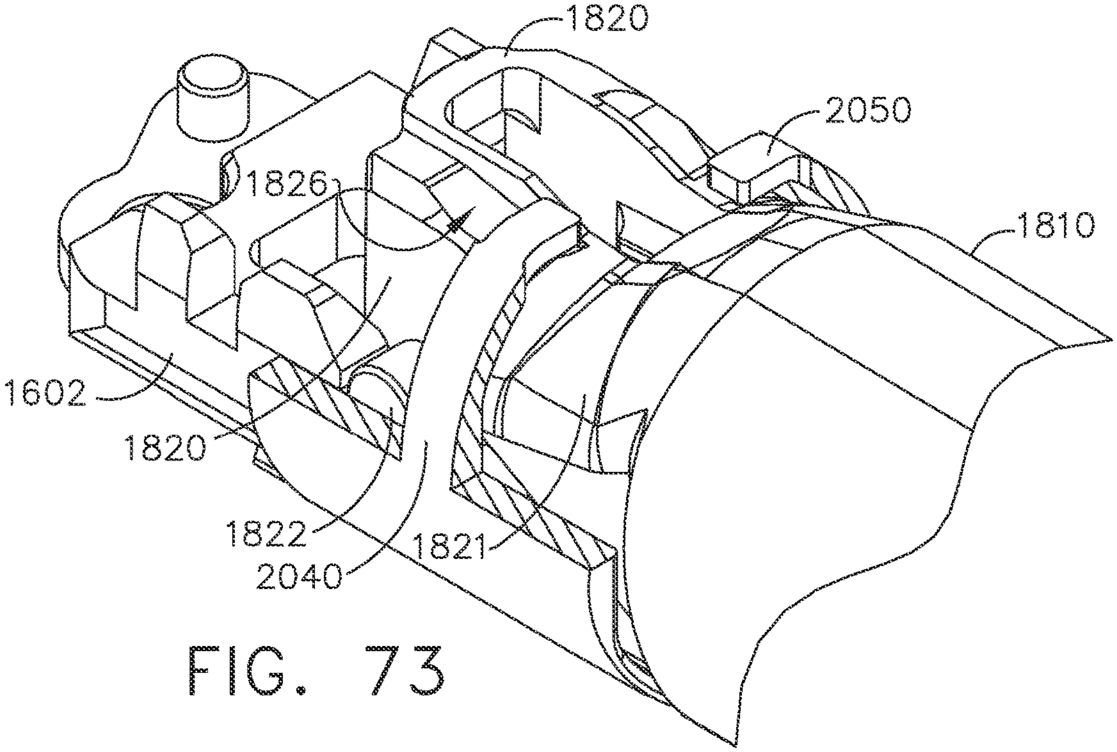
FIG. 73 is a partial right side perspective view of the anvil and distal closure tube segment of FIGS. 64-72 with the anvil in a fully closed position.

The closure process of the illustrated example of the interchangeable tool assembly 1000 may be understood from reference to FIGS. 67-69 and 70-72, as well as FIG. 78. FIGS. 68 and 71 illustrate the anvil 1810 in its fully open position. As can be seen in those Figures, the proximal positive jaw opening feature 2040 is out of contact with the anvil mounting portion 1820 and the distal positive jaw opening feature 2050 is in contact with the left anvil open tab 1842. When the anvil closure process is commenced, the closure drive system is actuated to move the distal closure tube segment 2030 in the distal direction DD. As the distal closure tube segment moves from the final proximal position 1860 to the fourth intermediate position 1858 (FIG. 78), the anvil 1810 remains in its fully open position. Thus, once the closure process is commenced, in at least one example, the distal closure tube segment 2030 may move distally a first or initial predetermined axial closure distance before the anvil 1810 begins to move. Stated another way, the distal closure tube segment may move the first predetermined axial closure distance before any closure motion is applied to the anvil 1810. In at least one example, the first or initial predetermined closure distance may be approximately 0.020 inches. As the distal closure tube segment 2030 continues to move distally through an intermediate axial closure distance, the distal end 2035 of the distal closure tube segment 2030 begins to contact the anvil cam surface 1821 on the anvil mounting portion 1820 (FIGS. 67 and 70) until the internal cam surface 2036 on the distal closure tube segment 2030 begins to cammingly contact the anvil cam surface 1821. As the internal cam surface 2036 travels up the anvil cam surface 1821, the anvil 1810 is pivoted to the fully closed position. The anvil cam surface 1821 and the internal cam surface 2036 may be configured to permit further distal travel of the distal closure tube segment 2030 from, for example, first intermediate point or position 1852 to the first position 1850 (FIG. 78). Thus, in at least one example, the distal closure tube segment 2030 may move distally a final predetermined axial closure distance during the closing process after the anvil 1810 has attained its fully closed position. In at least one example, the final predetermined axial closure distance may be approximately 0.040 inches.

In those surgical stapling devices that employ a firing member assembly that comprises a firing member that has a tissue cutting surface, it may be desirable for the firing system and portions of the end effector to be configured in such a way so as to prevent the inadvertent advancement of the firing member unless an unspent staple cartridge is properly supported in the end effector. If, for example, no staple cartridge is present at all and the firing member is distally advanced through the end effector, the tissue would be severed, but not stapled. Similarly, if a spent staple cartridge (i.e., a staple cartridge wherein at least some of the staples have already been fired therefrom) is present in the end effector and the firing member is advanced, the tissue would be severed, but may not be completely stapled, if at all. It will be appreciated that such occurrences could lead to undesirable catastrophic results during the surgical procedure. U.S. Pat. No. 6,988,649 entitled SURGICAL STAPLING INSTRUMENT HAVING A SPENT CARTRIDGE LOCKOUT, U.S. Pat. No. 7,044,352 entitled SURGICAL STAPLING INSTRUMENT HAVING A SINGLE LOCKOUT MECHANISM FOR PREVENTION OF FIRING, U.S. Pat. No. 7,380,695 entitled SURGICAL STAPLING INSTRUMENT HAVING A SINGLE LOCKOUT MECHANISM FOR PREVENTION OF FIRING, U.S. Patent Application Publication No. 2016/0367247, entitled SURGICAL STAPLING INSTRUMENTS WITH LOCKOUT ARRANGEMENTS FOR PREVENTING FIRING SYSTEM ACTUATION WHEN A CARTRIDGE IS SPENT OR MISSING, now U.S. Pat. No. 10,154,841 and U.S. patent application Ser. No. 15/385,958, entitled SURGICAL INSTRUMENTS WITH LOCKOUT ARRANGEMENTS FOR PREVENTING FIRING SYSTEM ACTUATION UNLESS AN UNSPENT STAPLE CARTRIDGE IS PRESENT, now U.S. Pat. No. 10,639,034, each disclose various firing member lockout arrangements. Each of those references is hereby incorporated by reference in its entirety herein.

Referring to FIGS. 60A-60I, there is shown a surgical end effector 9010 that comprises a portion of a surgical tool assembly 9000 that comprises a first jaw 9020 and a second jaw 9120. In the illustrated arrangement, for example, the first jaw 9020 comprises an elongate channel 9022 that is configured to removably and operably support a surgical staple cartridge 9600 therein. The elongate channel 9022 is attached to an elongate shaft assembly 9300 of the surgical tool assembly. In the arrangement depicted in FIGS. 60C and 60D, for example, the elongate channel 9022 is pivotally coupled to a spine assembly 9310 of the elongate shaft assembly 9300 for selective articulation relative thereto. See FIGS. 60D, 60E, 60H and 60I. The elongate shaft assembly 9300 may define a shaft axis SA. The second jaw 9120 comprises an anvil 9122 that is movably supported on the elongate channel 9022 and which is movable between open and closed positions by the closure system 9400. The anvil 9122 includes an anvil body 9124 and an anvil mounting portion 9126 that is pivotally supported for pivotal travel relative to the proximal end 9024 of the elongate channel 9022. The closure system 9400 may include, for example, an axially movable distal closure tube segment 9410 that is configured to cammingly engage a cam surface 9128 on the anvil mounting portion 9126 when the distal closure tube segment 9410 is axially advanced in the distal direction DD. The distal closure tube segment 9410 may also be configured to apply opening motions to the anvil mounting portion 9126 when the distal closure tube segment 9410 is moved in the proximal direction PD. See FIGS. 60C and 60D.

The surgical tool assembly 9000 further includes a firing system 9500 that, in the illustrated arrangement, comprises a firing member assembly 9510 that is configured to receive firing motions from a firing control system supported in a housing of a handheld control system or a robotic control system, for example. In the illustrated embodiment, one form of firing member assembly 9510 comprises a first firing member element 9520 that consists of a firing member body 9522 that supports a tissue cutting surface or blade 9524 thereon. The firing member body 9522 is coupled to a firing bar or knife bar 9530 that operably interfaces with corresponding portions of the firing system 9500 to receive the firing motions from the firing control system. The firing member body 9522 may include second jaw or anvil engagement features 9526 that may comprise laterally extending tab features configured to be received within corresponding second jaw passages or slots 9125 in the anvil body 9124. In addition, the firing member body 9522 may further include first jaw or channel engagement features or a foot 9528 that is configured to be received in corresponding first jaw passages or slots or openings 9023 in the elongate channel 9022.

The staple cartridge 9600 comprises a cartridge body 9602. See FIGS. 60H and 60I. The cartridge body 9602 includes a proximal end 9604, a distal end (not shown), and a deck 9606 extending between the proximal end and the distal end. In use, the staple cartridge 9600 is positioned on a first side of the tissue to be stapled and the anvil 9122 is positioned on a second side of the tissue. The anvil 9122 is moved toward the staple cartridge 9600 to compress and clamp the tissue against the deck 9606. Thereafter, staples or fasteners removably stored in the cartridge body 9602 can be deployed into the tissue. The cartridge body 9602 includes staple or fastener cavities (not shown) defined therein wherein staples or fasteners (not shown) are removably stored in the staple cavities. The staple cavities may be arranged in longitudinal rows. In one arrangement, for example, three rows of staple cavities are positioned on a first side of a longitudinal slot and three rows of staple cavities are positioned on a second side of the longitudinal slot. The longitudinal slot is configured to axially receive the first firing member element 9520 therethrough. Other arrangements of staple/fastener cavities and staples or fasteners may be possible.

Figure 60:
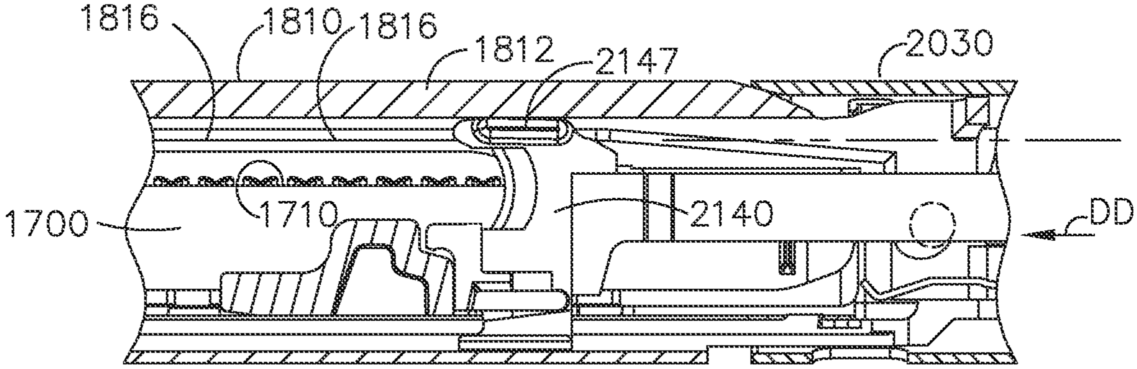
FIG. 60 is another partial cross-sectional view of the surgical end effector of FIGS. 57 and 58 after the firing member thereof has been distally advanced during the firing process.
Figure 60A:
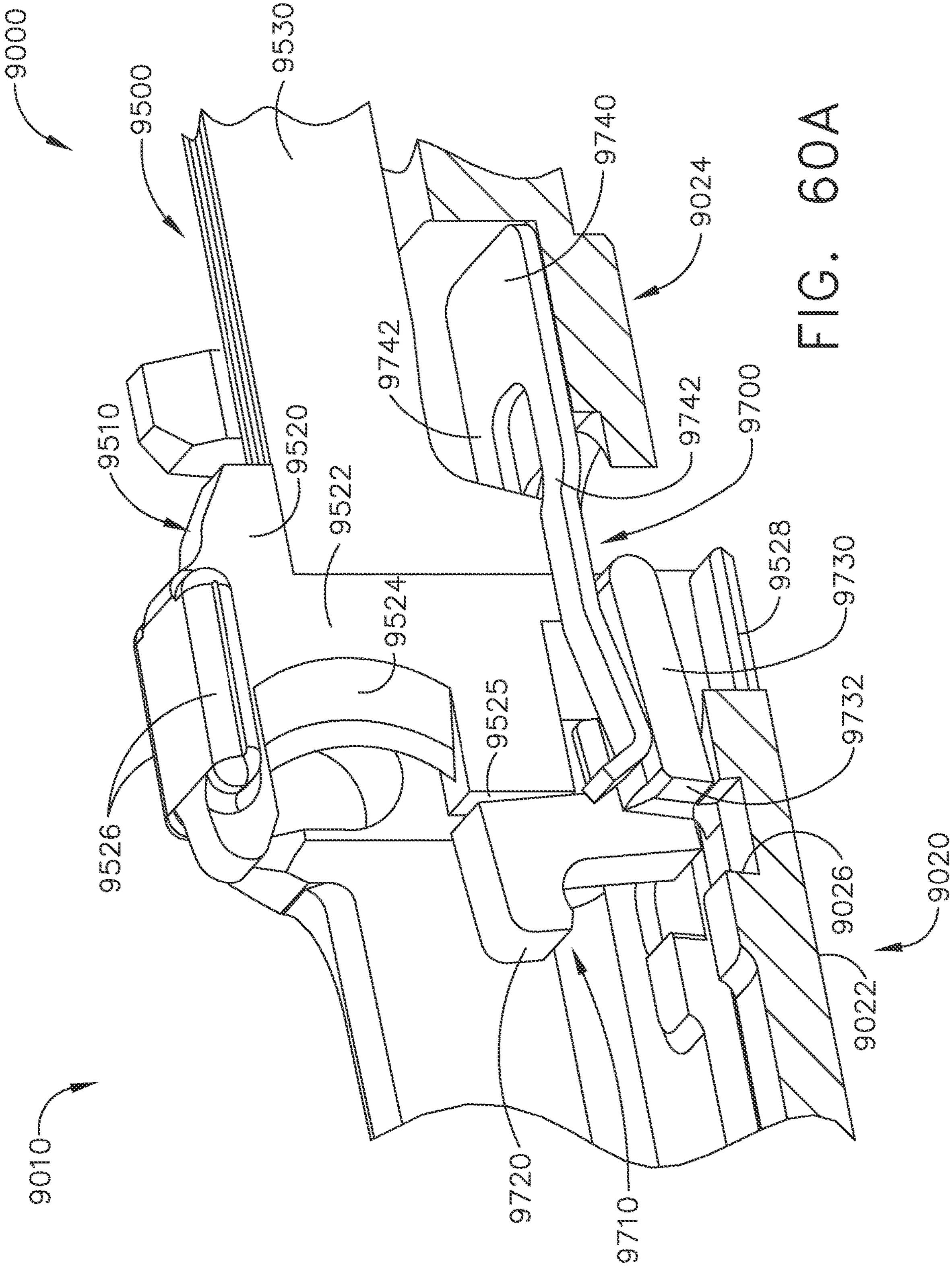
FIG. 60A is a perspective view of a portion of a firing member assembly of surgical stapling instrument that includes a first firing member element and a second firing member element that is movable relative to the first firing member element between a locked and an unlocked position.
Figure 60B:
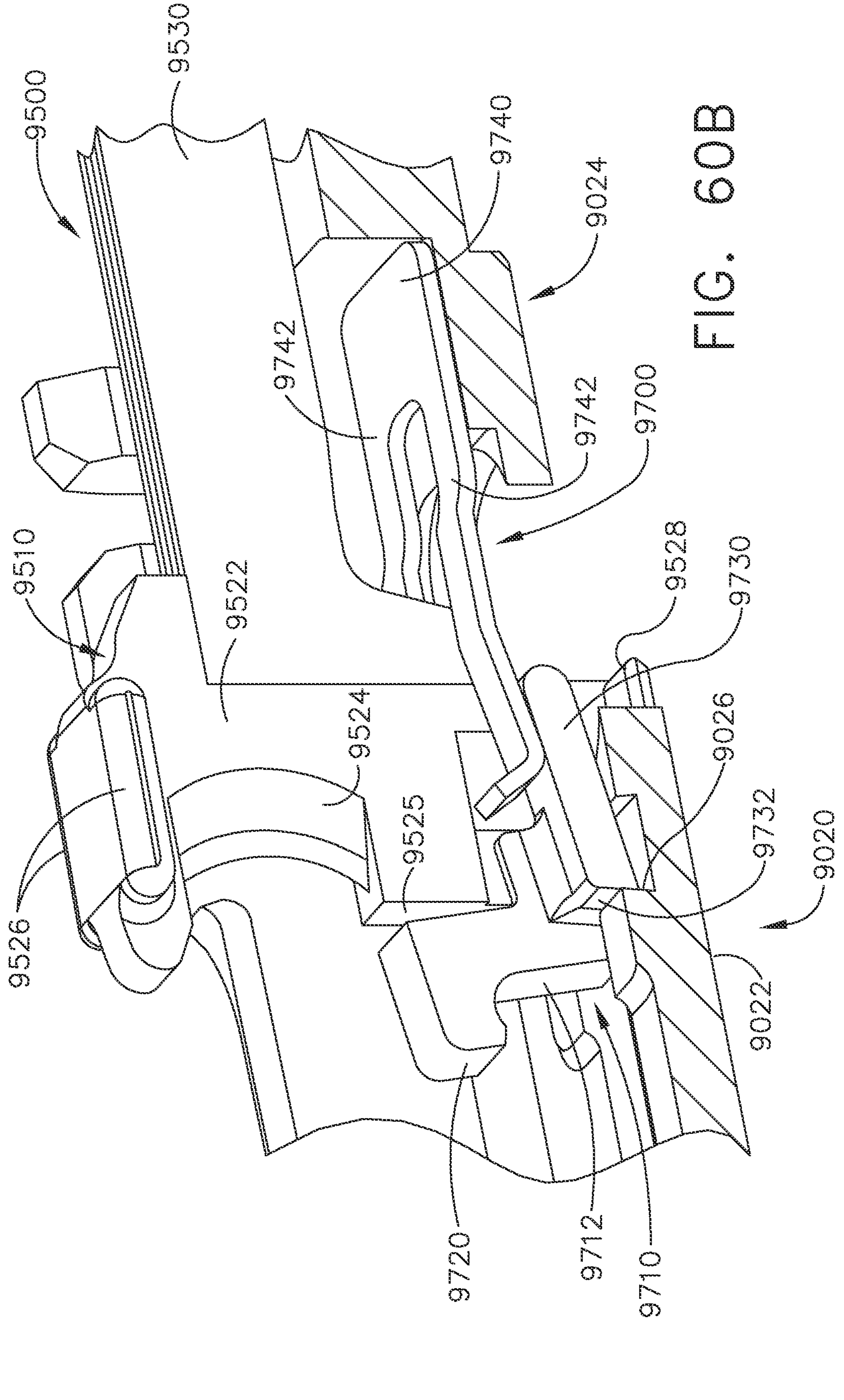
FIG. 60B is another perspective view of the firing member assembly of FIG. 60A with the second firing member element in the locked position.
Figure 60C:
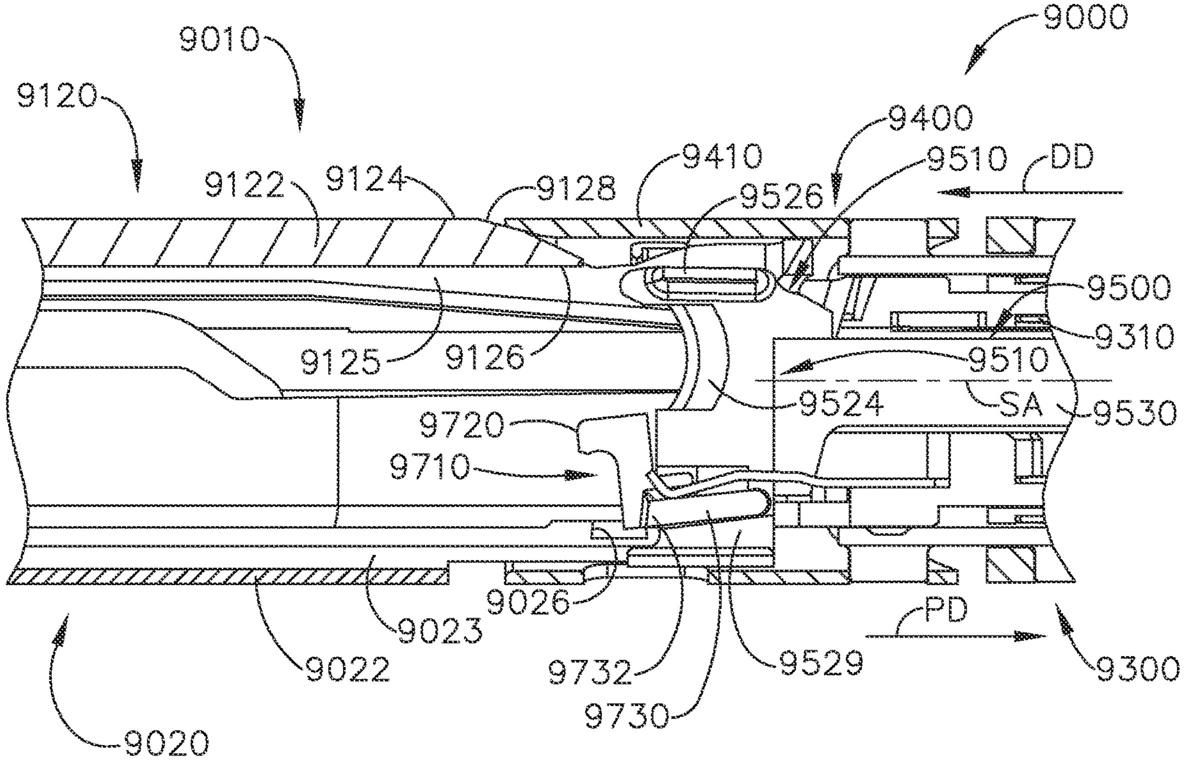
FIG. 60C is a cross-sectional elevational view of the surgical stapling instrument of FIG. 60A with the firing member assembly in a starting position.
Figure 60D:
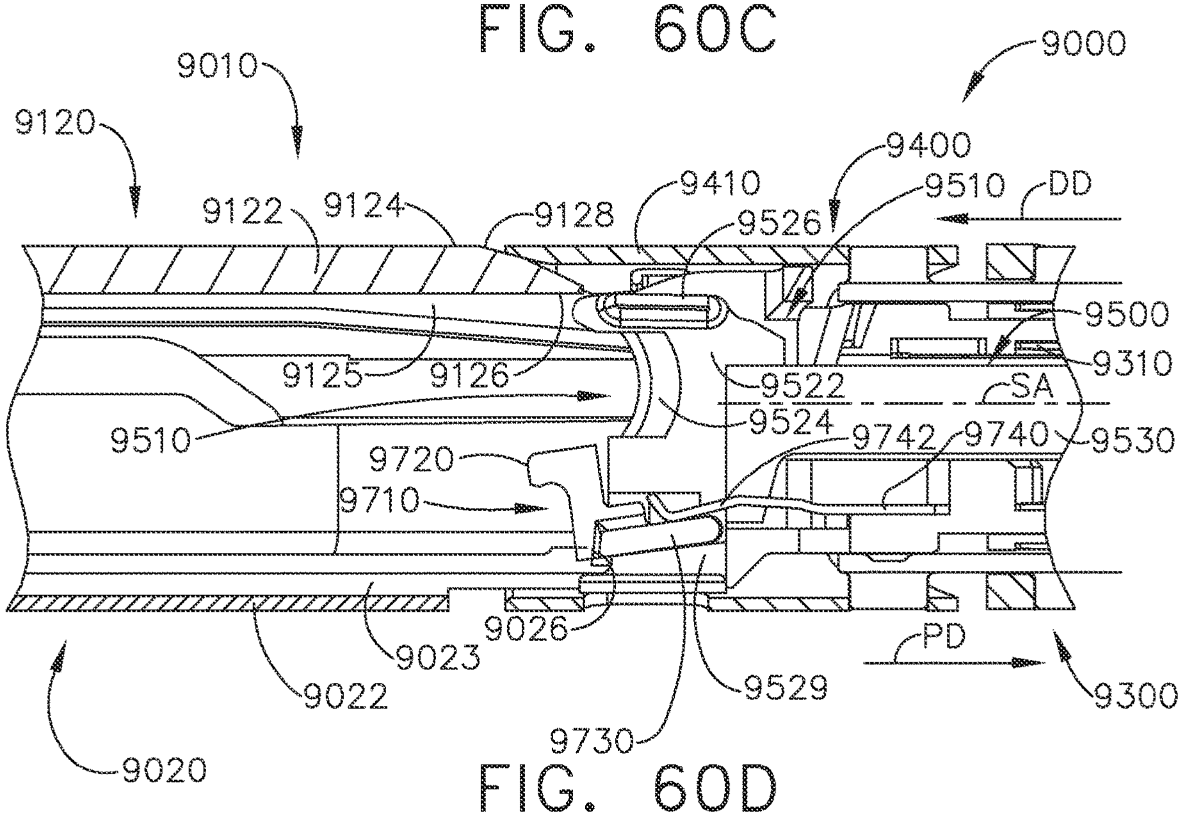
FIG. 60D is another cross-sectional view of the surgical stapling instrument of FIG. 60C illustrated in a locked out configuration.

The staples or fasteners are supported by staple drivers (not shown) that are movably supported in the cartridge body 9602. The drivers are movable between a first, or unfired position, and a second, or fired, position to eject the staples or fasteners from the cavities. The drivers are retained in the cartridge body 9602 by a retainer (not shown) which extends around the bottom of the cartridge body 9602 and includes resilient members configured to grip the cartridge body and hold the retainer to the cartridge body. The drivers are movable between their unfired positions and their fired positions by a sled 9610. The sled 9610 is movable between a proximal, or "unfired" position adjacent the proximal end 9604 and a distal or "fired" position adjacent the distal end (after firing). As can be seen in FIG. 60G, the sled 9610 comprises a plurality of ramped or cam surfaces 9620 that are configured to slide under the drivers and lift the drivers, and the staples or fasteners supported thereon, toward the anvil. An "unfired", "unspent", "fresh" or "new" staple cartridge 9600 means herein that the staple cartridge 9600 has all of its staples or fasteners in their "ready-to-be-fired positions". When in that position, the sled assembly 9610 is located in its starting or "unfired" position. The new staple cartridge 9600 is seated within the elongate channel 9022 and may be retained therein by snap features on the cartridge body 9602 that are configured to retainingly engage corresponding portions of the elongate channel 9022. FIGS. 60G and 60H illustrate a portion of the surgical end effector 9010 with a new or unfired surgical staple cartridge 9600 seated therein. As can be seen in FIGS. 60G and 60H, the sled 9610 is in the unfired position. To prevent the firing system 9500 from being activated and, more precisely, to prevent the first firing member element 9520 from being distally driven through the surgical end effector 9010 unless an unfired or new surgical staple cartridge 9600 has been properly seated within the elongate channel 9022, the illustrated surgical tool assembly 9000 employs a firing member lockout system generally designated as 9700.

Figure 60E:
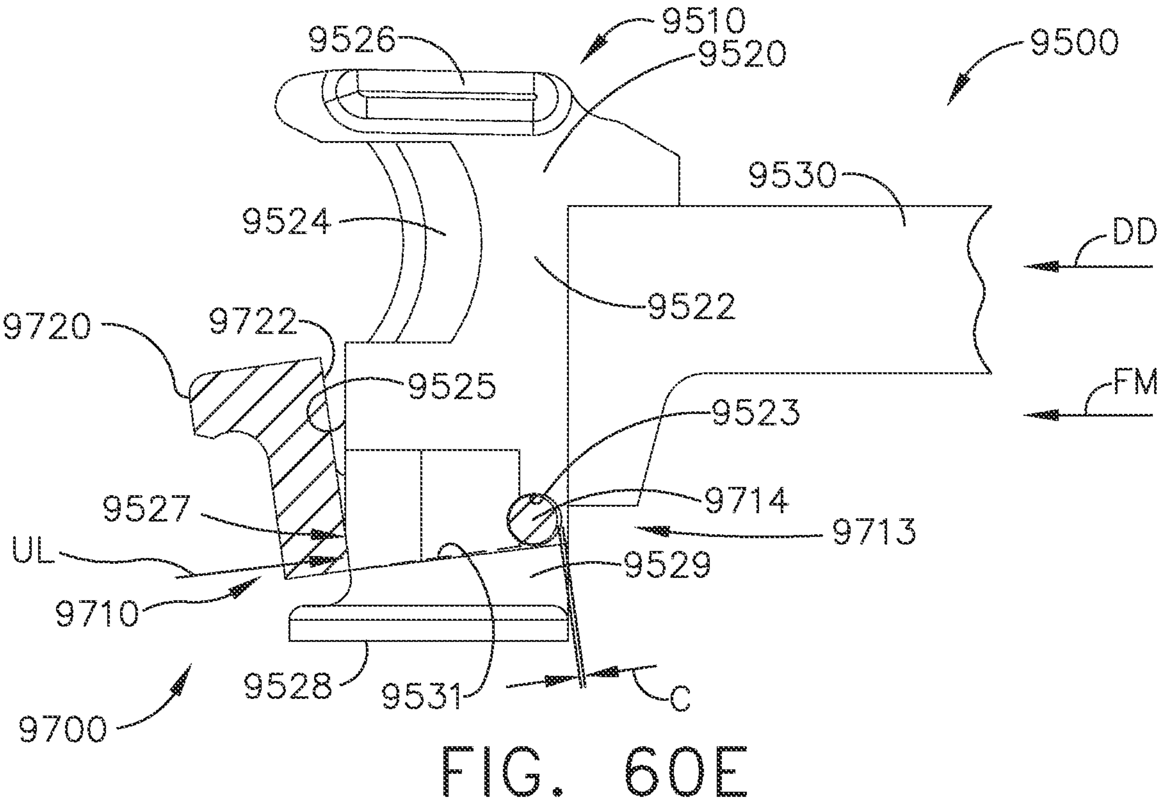
FIG. 60E is a side view of a firing member assembly with the second firing member element in a lockout orientation.
Figure 60F:
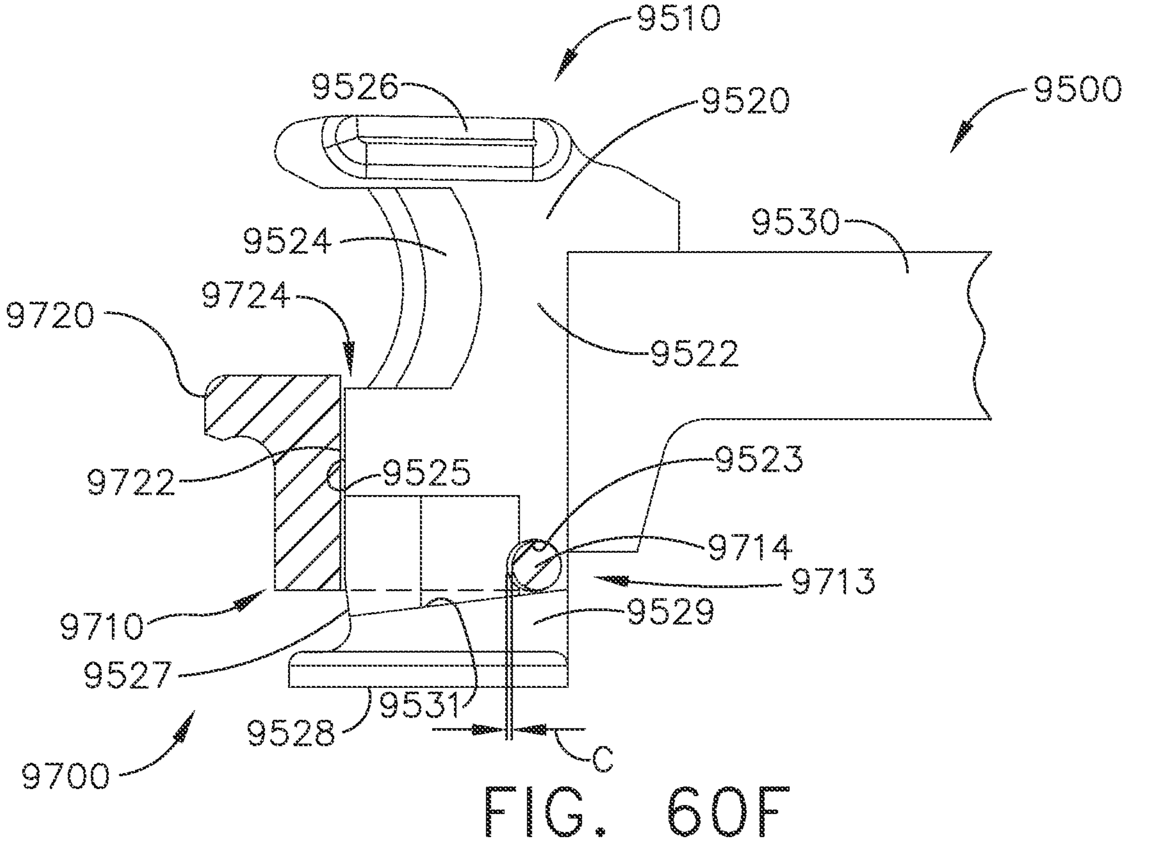
FIG. 60F is another side view of the firing member assembly of FIG. 60E with the second firing member element illustrated in an unlocked or firing orientation.
Figure 60G:
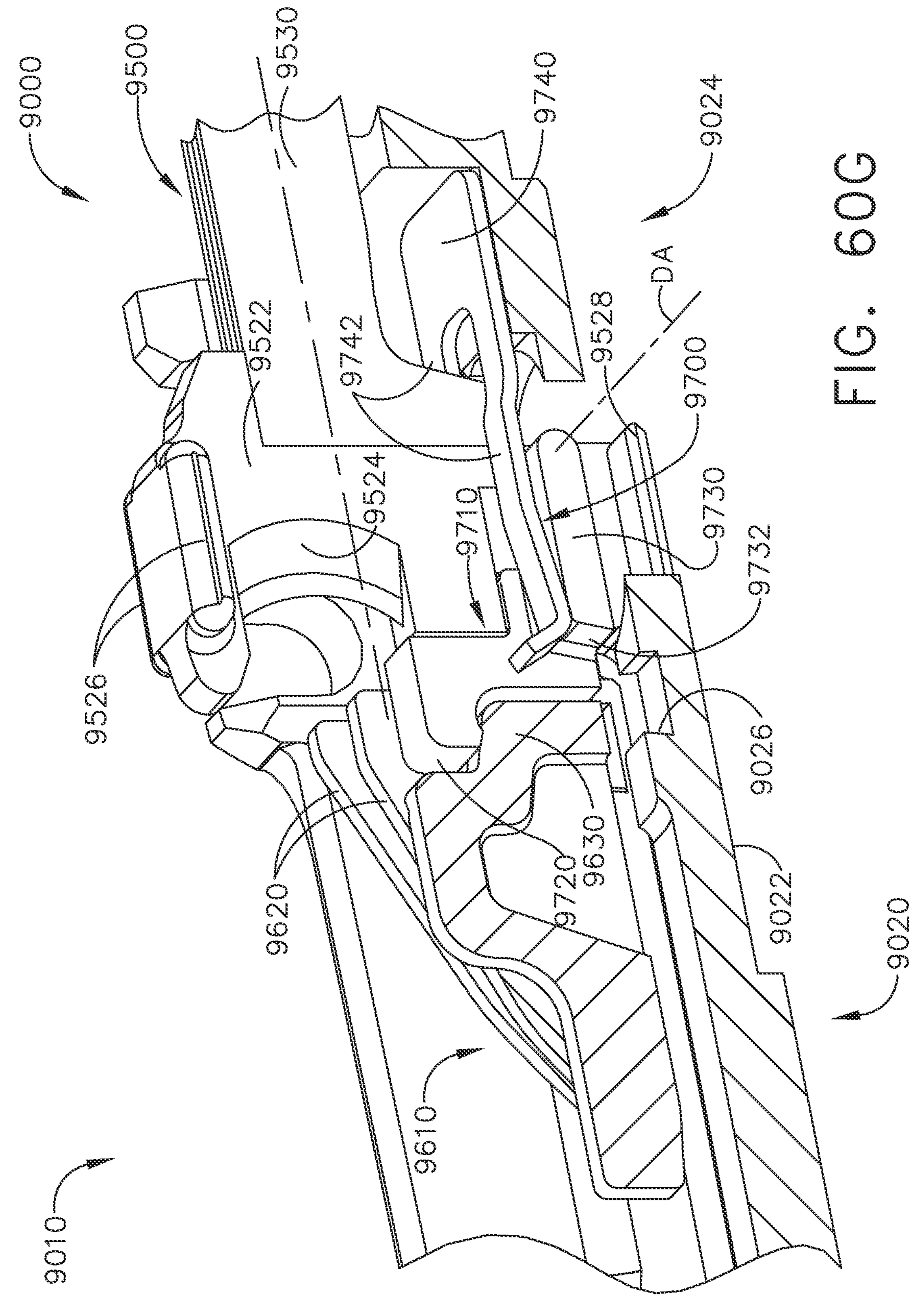
FIG. 60G is another partial perspective view of the surgical stapling instrument of FIG. 60A illustrated in an unlocked configuration.
Figure 60H:
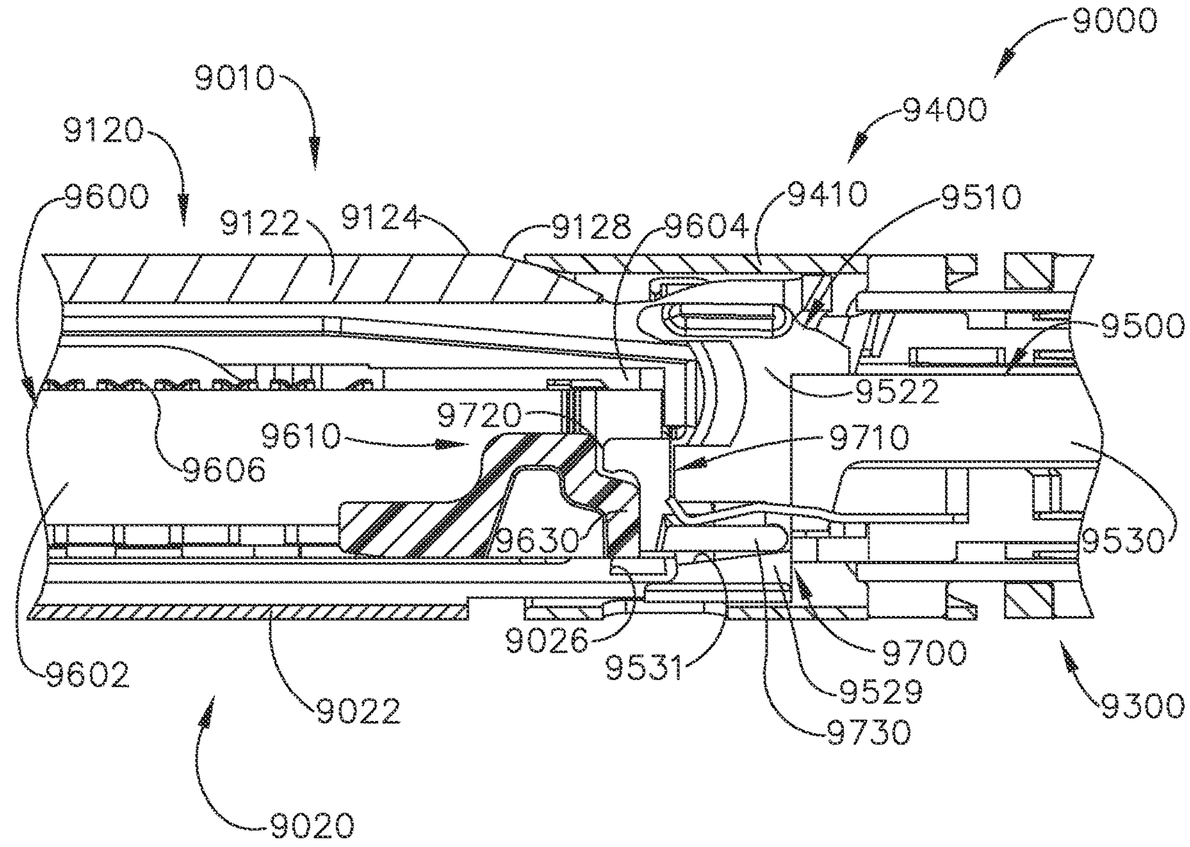
FIG. 60H is a cross-sectional view of the surgical stapling instrument of FIG. 60A with an unfired surgical fastener cartridge operably supported in an elongate channel thereof and with the firing member assembly illustrated in a starting position.

Referring now to FIGS. 60E and 60F, in one form, the firing member lockout system 9700 comprises a second firing member element or tippable element 9710 that comprises a sled engaging portion 9720. In the illustrated arrangement, the second firing member element 9710 is pivotally coupled to the firing member body 9522 by an attachment joint 9713 in the form of, for example, a pivot member or members 9714 that are pivotally received in corresponding pivot holes 9523 provided in the firing member body 9522 for pivotal travel relative thereto about a pivot axis PA that is transverse to the shaft axis SA. Such arrangement facilitates pivotal travel of the second firing member element 9710 relative to the firing member body 9522 between a locked position (FIG. 60E) and an unlocked position (FIG. 60F). In the illustrated example, the firing member body 9522 comprises a distal surface 9525 that is approximately perpendicular to the channel engagement features 9528 and a lockout surface 9527 that is angled relative to the distal surface 9525. In addition, one or more support ramps 9529 are formed on the firing member body 9522 that serve to define corresponding landing surfaces 9531 for receiving the second firing member element 9710 when in the locked configuration. See FIG. 60E.

As can be seen in FIG. 60F, when the second firing member element 9710 is in the unlocked position, a space, generally indicated as 9724, is provided between a proximal surface 9722 of the second firing member element 9710 and the distal surface 9525 of the firing member body 9522. Thus, when in the unlocked position, the proximal surface 9722 of the second firing member element 9710 is not in contact with the distal surface 9525 of the firing member body 9522. Referring now to FIGS. 60A-60D, the second firing member element 9710 further comprises at least one lockout-engaging portion 9730 that includes an angled lock end 9732 that is configured to engage a corresponding lock-out notch 9026 that is formed in the elongate channel 9022 when the second firing member element 9710 is in the locked position. In one embodiment, for example, the second firing member element 9710 includes two lockout-engaging portions 9730. As can also be seen in FIGS. 60A-60D, a lockout spring or biasing member 9740 is mounted in the proximal end 9024 of the elongate channel 9022 and includes two spring arms 9742 that each correspond to a lockout-engaging portion 9730. The spring arms 9742 serve to bias the second firing member element 9710 into the locked position as shown in FIGS. 60B-60D.

Figure 60I:
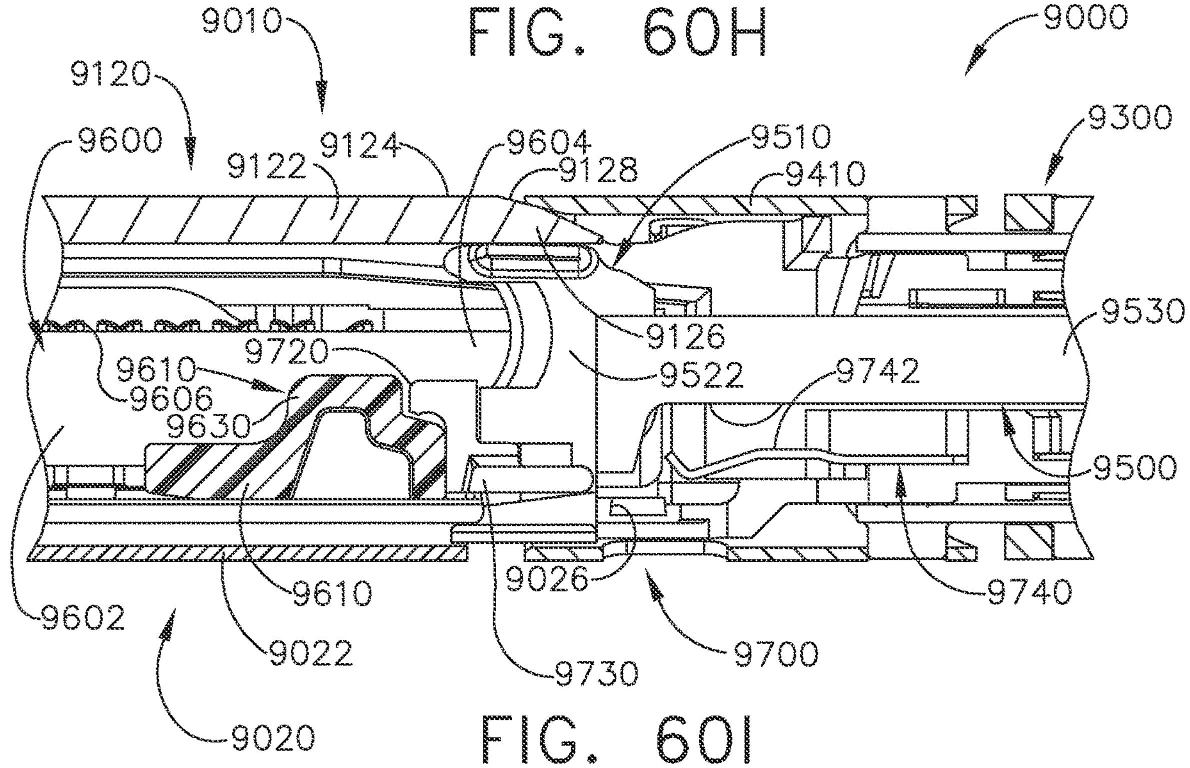
FIG. 60I is another cross-sectional view of the surgical stapling instrument of FIG. 60H with the firing member assembly illustrated in a partially-fired configuration.

Turning now to FIGS. 60G-60I, the sled 9610 comprises an unlocking portion 9630 that is configured to engage the sled engaging portion 9720 on the second firing member element 9710 when the sled 9610 is in the unfired position. Such arrangement serves to pivot the second firing member element 9710 into the unlocked position. When in the unlocked position, the angled lock end 9732 of each lockout-engaging portion 9730 is pivoted out of the corresponding lock-out notch 9026 in the elongate channel 9022 so that the firing member assembly 9510 may be fired or distally advanced through the staple cartridge. If the staple cartridge that has been loaded into the elongate channel 9022 was previously fired or even partially fired, the sled 9610 will not be in the unfired position so as to pivot the second firing member element 9710 into the unlocked position. In such instance therefor, the clinician will be unable to distally advance or fire the firing member assembly 9510. When in the unlocked position, actuation of the firing system 9500 will result in the distal travel of the firing member assembly 9510. As indicated above, when the firing member assembly 9510 is driven distally, the second firing member element 9710 is in contact with the firing member body 9522 through the pivot members 9714. However, when the second firing member element 9710 is pivoted into the locked position (FIG. 60E), a portion of the proximal surface 9722 is in abutting contact with the angled lockout surface 9527 on the firing member body 9522. In addition, as can be most particularly seen in FIGS. 60E and 60F, the pivot hole 9523 in the firing member body 9522 is sized relative to the corresponding pivot member 9714 to provide clearance C therebetween so that the load is transferred through the second firing member element directly to the firing member body 9522 and not through the pivot members 9714. As can be seen in FIG. 60E, the angled lockout surface 9527 facilitates pivotal travel of the sled engaging portion 9720 into the locked position. When the second firing member element 9720 is in the locked position, should the clinician inadvertently apply a firing motion FM to the firing member assembly 9510 in the distal direction DD, the engagement between the second firing member element 9720 and the lock-out notch 9026 in the elongate channel 9022 will prevent the distal advancement of the firing member assembly 9510 and cause a resultant unlocking load force UL to be applied to the second firing member element 9720. This unlocking load force UL will be applied to the angled lockout surface 9527 on the firing member body 9522 and will not be applied to the pivot members 9714. Such arrangement avoids loading or stressing the pivot members 9714 should the clinician inadvertently attempt to advance the firing member assembly 9510 when in the locked position. Thus, this configuration may prevent the pivot members 9714 from shearing off during such attempted advancement of the firing member assembly 9510.

Thus, the foregoing firing member assembly 9510 and firing member lockout assembly 9700 may provide several advantages. For example, as was discussed above, the distal surface 9525 on the firing member body 9522 carries the load during firing and avoids transferring such load to the pivot members that attach the second firing member element 9710 to the first firing member element 9520. When in the lockout state or locked position, the load is carried by the angled lock ends 9732 on the lockout engaging portions 9730. Such arrangement also avoids the need for the firing member assembly 9510 or more precisely the first firing member element 9520 from moving vertically which may inadvertently lead to misalignment with the anvil and elongate channel when moved into an unlocked state for firing. Moreover, because the first firing member element 9520 does not move vertically, the anvil engagement features as well as the channel engagement features may be advantageously shaped and designed to obtain desirable engagement with the anvil and channel during firing. The design and shape of the firing member body may also afford a large surface area for attachment to the knife bar by, for example, welding. For example, the distal end of the knife bar may be attached to the firing member body by a butt weld and a laser weld from both sides to interconnect the laminates forming the knife bar at the distal end. Such weld configuration may be more longitudinally compact than prior weld configurations and can lead to superior joint length. Other advantages may also be enjoyed from the foregoing firing member and lockout system arrangements.

Many of the surgical instrument systems described herein are motivated by an electric motor; however, the surgical instrument systems described herein can be motivated in any suitable manner. In various instances, the surgical instrument systems described herein can be motivated by a manually-operated trigger, for example. In certain instances, the motors disclosed herein may comprise a portion or portions of a robotically controlled system. Moreover, any of the end effectors and/or tool assemblies disclosed herein can be utilized with a robotic surgical instrument system. U.S. patent application Ser. No. 13/118,241, entitled SURGICAL STAPLING INSTRUMENTS WITH ROTATABLE STAPLE DEPLOYMENT ARRANGEMENTS, now U.S. Pat. No. 9,072,535, for example, discloses several examples of a robotic surgical instrument system in greater detail.

The surgical instrument systems described herein have been described in connection with the deployment and deformation of staples; however, the embodiments described herein are not so limited. Various embodiments are envisioned which deploy fasteners other than staples, such as clamps or tacks, for example. Moreover, various embodiments are envisioned which utilize any suitable means for sealing tissue. For instance, an end effector in accordance with various embodiments can comprise electrodes configured to heat and seal the tissue. Also, for instance, an end effector in accordance with certain embodiments can apply vibrational energy to seal the tissue.

EXAMPLES

Example 1—A surgical instrument that comprises an elongate shaft assembly that defines a shaft axis. A surgical end effector is operably coupled to the elongate shaft assembly for selective articulation relative thereto about an articulation axis that is transverse to the shaft axis. The surgical end effector comprises a first end effector jaw that is coupled to an articulation joint that is coupled to the elongate shaft assembly. A second end effector jaw is coupled to the first end effector jaw for selective pivotal travel relative thereto about a jaw pivot axis that is transverse to the shaft axis. One of the first and second end effector jaws is configured to operably support therein a surgical fastener cartridge that comprises a proximal most fastener location. One of the first and second end effector jaws is movable between an open position and a fully closed position by an axially movable closure member that comprises a closure member cam surface that is configured for camming contact with a jaw cam surface on one of the first and second effector jaws. A first distance between the articulation axis and an area of camming contact between the closure member cam surface and the jaw cam surface divided by a second distance from the articulation axis to the proximal most fastener location is less than 0.5.

Example 2—The surgical instrument of Example 1, wherein the first distance between the jaw pivot axis and the area of camming contact between the closure cam member surface and the jaw cam surface divided by the second distance from the articulation axis to the proximal fastener location is greater than 0.2 and less than 0.5.

Example 3—The surgical instrument of Examples 1 or 2, wherein the surgical fastener cartridge is supported in the first end effector jaw and wherein the second end effector jaw comprises an anvil comprising the jaw cam surface.

Example 4—The surgical instrument of Examples 1, 2 or 3, wherein the jaw pivot axis is fixed.

Example 5—The surgical instrument of Example 3, wherein the anvil comprises at least one tissue stop member comprising a distal tissue contact surface that corresponds to the proximal most fastener location when the anvil is in the fully closed position.

Example 6—The surgical instrument of Examples 3 or 5, wherein the anvil comprises an anvil body and an anvil mounting portion that comprises the jaw cam surface and a pair of laterally extending anvil trunnions that are configured to be pivotally supported in corresponding openings in the first end effector jaw.

Example 7—The surgical instrument of Examples 1, 2, 3, 4, 5 or 6, wherein the closure member comprises an axially movable distal closure tube segment comprising the closure member cam surface.

Example 8—The surgical instrument of Example 7, wherein the elongate shaft assembly comprises a spine assembly that is operably coupled to the first end effector jaw and a proximal closure tube assembly that is movably supported for axial travel relative to the spine assembly and is pivotally coupled to the axially movable distal closure tube segment.

Example 9—The surgical instrument of Example 8, wherein the proximal closure tube assembly operably interfaces with a closure system that is configured to selectively apply axial closure and opening motions to the proximal closure tube assembly.

Example 10—The surgical instrument of Example 9, wherein the closure system is supported by a handheld housing.

Example 11—The surgical instrument of Example 10, wherein the closure system is supported by a housing that operably interfaces with a robotic controlled actuator.

Example 12—A surgical instrument that comprises an elongate shaft assembly that defines a shaft axis and further comprises a surgical end effector that is operably coupled to the elongate shaft assembly for selective articulation relative thereto about an articulation axis that is transverse to the shaft axis. The surgical end effector comprises an elongate channel that is coupled to an articulation joint that is coupled to the elongate shaft assembly. The elongate channel is configured to operably support a surgical fastener cartridge. The surgical fastener cartridge comprises a proximal most fastener location. The surgical end effector further comprises an anvil that is pivotally coupled to the elongate channel for selective pivotal travel relative thereto about a fixed anvil pivot axis that is transverse to the shaft axis. The anvil is movable between an open position and a fully closed position by an axially movable closure member that comprises a closure member cam surface that is configured for camming contact with an anvil cam surface on the anvil. A first distance between the articulation axis and an area of camming contact between the closure member cam surface and the cam surface divided by a second distance from the articulation axis to the proximal most fastener location is less than 0.5.

Example 13—The surgical instrument of Example 12, wherein the first distance between the anvil pivot axis and the area of camming contact between the closure member cam surface and the anvil cam surface divided by the second distance from the articulation axis to the proximal most fastener location is greater than 0.2 and less than 0.5.

Example 14—The surgical instrument of Examples 12 or 13, wherein the anvil comprises at least one tissue stop member that comprises a distal tissue contact surface that corresponds to the proximal most fastener location when the anvil is in the fully closed position.

Example 15—The surgical instrument of Examples 12, 13 or 14, wherein the anvil comprises an anvil body and an anvil mounting portion that comprises the anvil cam surface and a pair of laterally extending anvil trunnions that are configured to be pivotally supported in corresponding openings in the elongate channel.

Example 16—The surgical instrument of Examples 12, 13, 14 or 15, wherein the closure member comprises an axially movable distal closure tube segment that comprises the closure member cam surface.

Example 17—The surgical instrument of Example 16, wherein the elongate shaft assembly comprises a spine assembly that is operably coupled to the elongate channel. A proximal closure tube assembly is movably supported for axial travel relative to the spine assembly and is pivotally coupled to the axially movable distal closure tube segment.

Example 18—The surgical instrument of Example 17, wherein the proximal closure tube assembly operably interfaces with a closure system that is configured to selectively apply axial closure and opening motions to the proximal closure tube assembly.

Example 19—The surgical instrument of Example 18, further comprising a firing member that is operably supported for axial travel through the surgical fastener cartridge upon application of axial firing motions thereto.

Example 20—A surgical system that comprises a housing that operably supports a closure system therein. The surgical system further comprises an interchangeable surgical tool assembly that comprises an elongate shaft assembly that is operably and removably couplable to the housing such that a proximal closure portion thereof is configured to receive axial closure motions from the closure system. The elongate shaft assembly defines a shaft axis. A surgical end effector is operably coupled to the elongate shaft assembly for selective articulation relative thereto about an articulation axis that is transverse to the shaft axis. The surgical end effector comprises a first end effector jaw that is coupled to an articulation joint that is coupled to the elongate shaft assembly. A second end effector jaw is coupled to the first end effector jaw for selective pivotal travel relative thereto about a jaw pivot axis that is transverse to the shaft axis. One of the first and second end effector jaws is configured to operably support a surgical fastener cartridge that includes a proximal most fastener location. One of the first and second end effector jaws is movable between an open position and a fully closed position by an axially movable distal closure member that is operably coupled to the proximal closure portion of the elongate shaft assembly. The distal closure member comprises a closure member cam surface that is configured for camming contact with a jaw cam surface on one of the first and second end effector jaws. A first distance between the articulation axis and an area of camming contact between the closure member cam surface and the jaw cam surface divided by a second distance from the articulation axis to the proximal most fastener location is less than 0.5.

Example 21—A surgical instrument comprising an elongate shaft assembly that defines a shaft axis. A surgical end effector is operably coupled to the elongate shaft assembly for selective articulation relative thereto about an articulation axis that is transverse to the shaft axis. The surgical end effector also comprises a first end effector jaw that is coupled to an articulation joint that is coupled to the elongate shaft assembly. A second end effector jaw is coupled to the first end effector jaw for selective pivotal travel relative thereto about a jaw pivot axis that is transverse to the shaft axis. The surgical instrument further comprises an axially movable firing member that comprises at least one jaw engagement feature that is configured to apply a closure motion to the second end effector jaw as the axially movable firing member is moved from a starting position to an end position within the first end effector jaw. At least one jaw engagement feature is configured such that a portion thereof is positioned between the jaw pivot axis and the articulation axis when the axially movable firing member is in the starting position.

Example 22—The surgical instrument of Example 21, wherein the portion of at least one jaw engagement feature is positioned between the jaw pivot axis and the articulation axis when the axially movable firing member is in the starting position and the second end effector jaw is in a fully opened position.

Example 23—The surgical instrument of Examples 21 or 22, wherein at least thirty five percent of each jaw engagement feature is located between the jaw pivot axis and the articulation axis when the axially movable firing member is in the starting position.

Example 24—The surgical instrument of Example 22, wherein at least thirty-five percent of each jaw engagement feature is between the jaw pivot axis and the articulation axis when the axially movable firing member is in the starting position and the end effector second jaw is in a fully opened position.

Example 25—The surgical instrument of Examples 21, 22, 23 or 24, further comprising an axially movable closure member that is independently movable relative to the axially movable firing member and is configured to selectively apply additional closure motions to the second end effector jaw.

Example 26—The surgical instrument of Example 25, wherein the axially movable closure member comprises a closure member cam surface that is configured for camming contact with a jaw cam surface on the second end effector jaw.

Example 27—The surgical instrument of Examples 21, 22, 23, 24, 25 or 26, wherein the axially movable firing member comprises a tissue cutting surface.

Example 28—The surgical instrument of Examples 21, 22, 23, 24, 25, 26 or 27, wherein the first end effector jaw comprises an elongate channel that is configured to operably support a surgical fastener cartridge therein and wherein the second end effector jaw comprises an anvil.

Example 29—The surgical instrument of Examples 21, 22, 23, 24, 25, 26, 27 or 28, wherein the jaw pivot axis is fixed.

Example 30—A surgical instrument comprising an elongate shaft assembly that defines a shaft axis. A surgical end effector is operably coupled to the elongate shaft assembly for selective articulation relative thereto about an articulation axis that is transverse to the shaft axis. The surgical end effector comprises an elongate channel that is coupled to the elongate shaft assembly and is configured to operably support a surgical fastener cartridge therein. An anvil is coupled to the elongate channel for selective pivotal travel relative thereto about a fixed jaw pivot axis that is transverse to the shaft axis. The surgical instrument further comprises an axially movable firing member that comprises at least one anvil engagement feature that is configured to apply a closure motion to the anvil as the axially movable firing member is moved from a starting position to an end position within the elongate channel. At least one anvil engagement feature is configured such that a portion thereof is positioned between the fixed jaw pivot axis and the articulation axis when the axially movable firing member is in the starting position.

Example 31—The surgical instrument of Example 30, wherein the portion of the at least one anvil engagement feature is positioned between the fixed jaw pivot axis and the articulation axis when the axially movable firing member is in the starting position and the anvil is in a fully opened position.

Example 32—The surgical instrument of Examples 30 or 31, wherein at least thirty-five percent of each anvil engagement feature is located between the fixed jaw pivot axis and the articulation axis when the axially movable firing member is in the starting position.

Example 33—The surgical instrument of Examples 30, 31 or 32, wherein at least thirty-five percent of each anvil engagement feature is located between the fixed jaw pivot axis and the articulation axis when the axially movable firing member is in the starting position.

Example 34—The surgical instrument of Example 30, wherein at least thirty-five percent of each anvil engagement feature is located between the jaw pivot axis and the articulation axis when the axially movable firing member is in the starting position and the anvil is in a fully opened position.

Example 35—The surgical instrument of Examples 30, 31, 32, 33 or 34, further comprising an axially movable closure member that is independently movable relative to the axially movable firing member and is configured to selectively apply additional closure motions to the anvil.

Example 36—The surgical instrument of Example 35, wherein the axially movable closure member comprises a closure member cam surface that is configured for camming contact with an anvil cam surface on the anvil.

Example 37—The surgical instrument of Examples 30, 31, 32, 33, 34, 35 or 36, wherein the firing member comprises a tissue cutting surface.

Example 38—The surgical instrument of Examples 30, 31, 32, 33, 34, 35 or 36, wherein the firing member comprises a firing member body comprising a tissue cutting surface thereon and wherein at least one anvil engagement feature comprises a first anvil engagement tab that protrudes from a first lateral side of a top portion of the firing member body and a second anvil engagement tab that protrudes from a second lateral side of the top portion of the firing member body.

Example 39—The surgical instrument of Example 38, wherein the firing member body extends through a slot in an anvil mounting portion of the anvil when the firing member is in the starting position.

Example 40—A surgical system comprising a housing that operably supports a closure system and a firing system. The closure system and the firing system are independently actuatable relative to each other. The surgical system further comprises an interchangeable surgical tool assembly that comprises an elongate shaft assembly that is operably and removably couplable to the housing such that a proximal closure portion thereof is configured to receive axial closure motions from the closure system and a proximal firing member thereof is configured to receive firing motions from the firing system. The elongate shaft assembly defines a shaft axis. A surgical end effector is operably coupled to the elongate shaft assembly for selective articulation relative thereto about an articulation axis that is transverse to the shaft axis. The surgical end effector comprises an elongate channel that is coupled to the elongate shaft assembly and is configured to operably support a surgical fastener cartridge therein. An anvil is coupled to the elongate channel for selective pivotal travel relative thereto about a jaw pivot axis that is transverse to the shaft axis. An axially movable firing member is operably coupled to the proximal firing member and comprises at least one anvil engagement feature that is configured to apply a closure motion to the anvil as the axially movable firing member is moved from a starting position to an end position within the elongate channel. At least one anvil engagement feature is configured such that a portion thereof is positioned between the jaw pivot axis and the articulation axis when the axially movable firing member is in the starting position.

Example 41—The surgical system of Example 40, wherein the housing comprises a portion of a robotic system.

Example 42—A surgical instrument comprising an elongate shaft assembly that defines a shaft axis. A first end effector jaw is coupled to the elongate shaft assembly and a second end effector jaw is coupled to the first end effector jaw for selective pivotal travel relative thereto between a fully open position and a fully closed position about a fixed jaw pivot axis that is transverse to the shaft axis and extends therethrough. The elongate shaft assembly comprises a closure member that is axially movable between a starting position that corresponds to the fully open position of the second end effector jaw and an ending position that corresponds to a fully closed position of the second end effector jaw relative to the first end effector jaw. When the closure member is in the starting position, a distal end thereof is located on a plane that is spaced distally from the jaw pivot axis a distance that is measured along the shaft axis that is no more than 0.090 inches.

Example 43—The surgical instrument of Example 42, wherein when the closure member is in the starting position, the distal end of the closure member is located on the plane and the plane intersects the jaw pivot axis.

Example 44—The surgical instrument of Examples 42 or 43, wherein the distance is within 0.010-0.060 inches.

Example 45—The surgical instrument of Examples 42, 43 or 44, wherein the closure member comprises an axially movable distal closure tube segment that comprises a closure cam surface that is configured to cammingly engage a jaw cam surface on the second end effector jaw as the axially movable distal closure tube segment is moved from the starting position to the ending position.

Example 46—The surgical instrument of Examples 42, 43, 44 or 45, wherein the first end effector jaw comprises an elongate channel that is configured to operably support a surgical fastener cartridge therein and wherein the second end effector jaw comprises an anvil.

Example 47—The surgical instrument of Example 46, wherein the anvil comprises an anvil body and an anvil mounting portion that comprises an anvil cam surface and a pair of laterally extending anvil trunnions that are configured to be pivotally supported in corresponding openings in the elongate channel.

Example 48—The surgical instrument of Examples 46 or 47, wherein the closure member comprises an axially movable distal closure tube segment that comprises a closure cam surface that is configured to cammingly engage the anvil cam surface on the anvil as the axially movable distal closure tube segment is moved from the starting position to the ending position.

Example 49—The surgical instrument of Example 48, wherein the elongate shaft assembly comprises a spine assembly that is operably coupled to the elongate channel and a proximal closure tube assembly that is movably supported for axial travel relative to the spine assembly and is pivotally coupled to the axially movable distal closure tube segment.

Example 50—The surgical instrument of Example 49, wherein proximal closure tube assembly operably interfaces with a closure system that is configured to selectively apply axial closure and opening motions to the proximal closure tube assembly.

Example 51—The surgical instrument of Example 50, wherein closure system is supported by a handheld housing.

Example 52—The surgical instrument of Example 50, wherein the closure system is supported by a housing that operably interfaces with a robotic controlled actuator.

Example 53—A surgical instrument comprising an elongate shaft assembly that defines a shaft axis. An elongate channel is configured to operably support a surgical fastener cartridge therein and is operably coupled to the elongate shaft assembly for selective articulation relative thereto about an articulation axis that is transverse to the shaft axis. An anvil is pivotally coupled to the elongate channel for selective pivotal travel relative thereto between a fully open position and a fully closed position about a fixed jaw pivot axis that transversely intersects the shaft axis. The elongate shaft assembly comprises a closure member that is axially movable between a starting position that corresponds to the fully open position of the anvil and an ending position that corresponds to a fully closed position of the anvil. When the closure member is in the starting position, a distal end thereof is located on a plane that is spaced distally from the jaw pivot axis a distance that is measured along the shaft axis that is no more than 0.090 inches.

Example 54—The surgical instrument of Example 53, wherein when the closure member is in the starting position, the distal end of the closure member is located on the plane and the plane intersects the jaw pivot axis.

Example 55—The surgical instrument of Examples 53 or 54, wherein the distance is within 0.010-0.060 inches.

Example 56—The surgical instrument of Examples 53, 54 or 55, wherein the anvil comprises an anvil body and an anvil mounting portion that comprises an anvil cam surface and a pair of laterally extending anvil trunnions that are configured to be pivotally supported in corresponding openings in the elongate channel.

Example 57—The surgical instrument of Examples 53, 54, 55 or 56, wherein the closure member comprises an axially movable distal closure tube segment that comprises a closure cam surface that is configured to cammingly engage the anvil cam surface on the anvil as the axially movable distal closure tube segment is moved from the starting position and to the ending position.

Example 58—The surgical instrument of Example 57, wherein the elongate shaft assembly comprises a spine assembly that is operably coupled to the elongate channel and a proximal closure tube assembly that is movably supported for axial travel relative to the spine assembly and is pivotally coupled to the axially movable distal closure tube segment.

Example 59—The surgical instrument of Example 58, wherein the proximal closure tube assembly operably interfaces with a closure system that is supported by a handheld housing and is configured to selectively apply axial closure and opening motions to the proximal closure tube assembly.

Example 60—The surgical instrument of Example 58, wherein the proximal closure tube assembly operably interfaces with a closure system that is supported by a housing that is configured to interface with a robotic system. The closure system is configured to selectively apply axial closure and opening motions to the proximal closure tube assembly.

Example 61—A surgical system that comprises a housing that operably supports a closure system. The surgical system further comprises an interchangeable surgical tool assembly that comprises an elongate shaft assembly that is operably and removably couplable to the housing such that a proximal closure portion thereof is configured to receive axial closure motions from the closure system. The elongate shaft assembly defines a shaft axis. A surgical end effector is operably coupled to the elongate shaft assembly for selective articulation relative thereto about an articulation axis that is transverse to the shaft axis. The surgical end effector comprises an elongate channel that is coupled to the elongate shaft assembly and is configured to operably support a surgical fastener cartridge therein. An anvil is coupled to the elongate channel for selective pivotal travel relative thereto about a jaw pivot axis that transversely intersects the shaft axis. The elongate shaft assembly comprises a closure member that is axially movable between a starting position that corresponds to a fully open position of the anvil and an ending position that corresponds to a fully closed position of the anvil. When the closure member is in the starting position, a distal end thereof is located on a plane that is spaced distally from the jaw pivot axis a distance that is measured along the shaft axis that is no more than 0.090 inches.

Example 62—A surgical stapling device that comprises an elongate shaft assembly that defines a shaft axis. A surgical end effector is operably coupled to the elongate shaft assembly by an articulation joint that is configured to facilitate selective articulation of the surgical end effector about an articulation axis that is transverse to the shaft axis.

The surgical end effector comprises a surgical staple cartridge that operably supports a plurality of surgical staples therein. An anvil is supported for selective pivotal travel relative to the surgical staple cartridge between a fully open position and a closed position. The anvil comprises a plurality of staple forming pockets that correspond to the surgical staples in the surgical staple cartridge. The surgical stapling device further comprises an axially movable firing member that comprises at least one anvil engagement feature thereon that is configured to engage the anvil when the anvil is in the closed position as the axially movable firing member is moved from a proximal most position to a distalmost position. The surgical stapling device also comprises means for increasing a jaw aperture distance between a distalmost staple in the surgical staple cartridge and a corresponding one of the staple forming pockets in the anvil while minimizing a joint distance between the articulation axis and a distal end of the anvil engagement feature on the axially movable firing member when the axially movable firing member is in the proximal most position.

Example 63—The surgical stapling device of Example 62, wherein the means for increasing comprises a closure member that is configured to apply closure motions to the anvil, wherein the closure member is axially movable between a starting position corresponding to the fully open position of the second end effector jaw and an ending position corresponding to a fully closed position of the anvil. When the closure member is in the starting position and the axially movable firing member is in the proximal most position, the distal end of the closure member is distally spaced from the distal end of the anvil engagement feature a horizontal distance that is within a range of 0.4-0.9 inches.

Example 64—The surgical stapling device of Example 63, wherein the horizontal distance is measured along a horizontal line that is parallel to or coincident with the shaft axis.

Example 65—The surgical stapling device of Examples 62, 63 or 64, wherein the closure member comprises an axially movable distal closure tube segment that comprises a closure cam surface that is configured to cammingly engage a cam surface on the anvil as the axially movable distal closure tube segment is moved from the starting position to the ending position.

Example 66—The surgical stapling device of Examples 62, 63, 64 or 65, wherein the surgical fastener cartridge is removably supported in an elongate channel that is operably coupled to the elongate shaft assembly by the articulation joint.

Example 67—The surgical stapling device of Example 66, wherein the anvil comprises an anvil body and an anvil mounting portion that comprises an anvil cam surface and a pair of laterally extending anvil trunnions that are configured to be pivotally supported in corresponding openings in the elongate channel.

Example 68—The surgical stapling device of Examples 63, 64, 65, 66 or 67, wherein the elongate shaft assembly comprises an axially movable proximal closure tube assembly and wherein the closure member comprises an axially movable distal closure tube segment that is operably coupled to the axially movable proximal closure tube assembly.

Example 69—The surgical stapling device of Example 68, wherein the axially movable distal closure tube segment comprises a closure cam surface that is configured to cammingly engage the anvil cam surface on the anvil as the axially movable distal closure tube segment is moved from the starting position to the ending position.

Example 70—The surgical stapling device of Examples 68 or 69, wherein the elongate shaft assembly comprises a spine assembly that is operably coupled to the elongate channel and movably supports at least a portion of the proximal closure tube assembly thereon and wherein the proximal closure tube assembly operably interfaces with a closure system that is configured to selectively apply axial closure and opening motions to the proximal closure tube assembly.

Example 71—The surgical stapling device of Example 70, wherein the closure system is supported by a handheld housing.

Example 72—The surgical stapling device of Example 70, wherein the closure system is supported by a housing that operably interfaces with a robotic controlled actuator.

Example 73—A surgical instrument that comprises an elongate shaft assembly that has an elongate channel coupled thereto that is configured to operably support a surgical fastener cartridge therein. An anvil is pivotally coupled to the elongate channel for selective pivotal travel relative thereto between a fully open position and a fully closed position about a fixed jaw pivot axis. A closure member is configured to apply closure motions to the anvil to move the anvil between the fully open position and the fully closed position as the closure member is moved from a starting position to an ending position. The surgical instrument further comprises an axially movably firing member that has at least one anvil engagement feature thereon that is configured to apply additional closure motions to the anvil as the axially movable firing member is moved from a proximal most position to a distalmost position within the elongate channel. When the closure member is in the starting position and the axially movable firing member is in the proximal most position, a distal end of the closure member is distal to a distal end of the anvil engagement feature.

Example 74—The surgical instrument of Example 73, wherein when the closure member is in the starting position and the axially movable firing member is in the proximal most position, the distal end of the closure member is distally spaced from the distal end of the anvil engagement feature a horizontal distance within a range of 0.4-0.9 inches.

Example 75—The surgical instrument of Example 74, wherein the elongate shaft assembly defines a shaft axis and wherein the horizontal distance is measured along a horizontal line that is parallel to or coincident with the shaft axis.

Example 76—The surgical instrument of Examples 73, 74 or 75, wherein the closure member comprises an axially movable distal closure tube segment that comprises a closure cam surface that is configured to cammingly engage an anvil cam surface on the anvil as the axially movable distal closure tube segment is moved from the starting position to the ending position.

Example 77—The surgical instrument of Example 76, wherein the elongate shaft assembly comprises a spine assembly that is operably coupled to the elongate channel. A proximal closure tube assembly is movably supported for axial travel relative to the spine assembly and is pivotally coupled to the axially movable distal closure tube segment.

Example 78—The surgical instrument of Example 77, wherein the proximal closure tube assembly operably interfaces with a closure system that is configured to selectively apply axial closure and opening motions to the proximal closure tube assembly.

Example 79—The surgical instrument of Example 78, wherein the closure system is supported by a handheld housing.

Example 80—The surgical instrument of Example 78, wherein the closure system is supported by a housing that operably interfaces with a robotic controlled actuator.

Example 81—A surgical system comprising a housing that operably supports a closure system. The surgical system further comprises an interchangeable surgical tool assembly that comprises an elongate shaft assembly that is operably and removably couplable to the housing such that a proximal closure portion thereof is configured to receive axial closure motions from the closure system. The elongate shaft assembly defines a shaft axis. The surgical tool assembly further comprises a surgical end effector that is operably coupled to the elongate shaft assembly for selective articulation relative thereto about an articulation axis that is transverse to the shaft axis. The surgical end effector comprises an elongate channel that is coupled to the elongate shaft assembly and is configured to operably support a surgical fastener cartridge therein. An anvil is coupled to the elongate channel for selective pivotal travel relative thereto between a fully open position and a fully closed position about a jaw pivot axis that is transverse to the shaft axis. The elongate shaft assembly comprises a distal closure member that is operably coupled to the proximal closure portion and is configured to apply closure motions to the anvil to move the anvil between the fully open position and the fully closed position as the distal closure member is moved from a starting position to an ending position. An axially movable firing member comprises at least one anvil engagement feature that is configured to apply additional closure motions to the anvil as the axially movable firing member is moved from a proximal most position to a distalmost position within the elongate channel. When the distal closure member is in the starting position and the axially movable firing member is in the proximal most position, a distal end of the distal closure member is distal to a distal end of the anvil engagement feature.

Example 82—A surgical instrument comprising a surgical end effector that comprises a first jaw that defines a first tissue contacting surface and a second jaw that is pivotally coupled to the first jaw. The second jaw is selectively movable between a fully open position and a fully closed position about a fixed jaw pivot axis. The second jaw comprises a second tissue contacting surface that faces the first tissue contacting surface. At least one tissue locating feature is on the second jaw and extends downward beyond the second tissue contacting surface and is configured to prevent tissue received between the first and second tissue contacting surfaces from extending proximally beyond a distal end portion of the at least one tissue locating feature when the second jaw is in the fully closed position. When the second jaw is in the fully open position, the distal end portion of each tissue locating feature is positioned relative to a corresponding portion of the first tissue contacting surface to prevent a gap therebetween. A jaw aperture angle between the first and second tissue contacting surfaces when the second jaw is in the fully open position is greater than 12.25 degrees.

Example 83—The surgical instrument of Example 82, wherein the distal end portion of each tissue locating feature is located a distance that is less than 0.750 inches from the fixed jaw pivot axis when the second jaw is in the fully closed position.

Example 84—The surgical instrument of Examples 82 or 83, wherein the first jaw comprises an elongate channel that is configured to operably support a surgical fastener cartridge therein and wherein the first tissue contacting surface comprises a deck surface of the surgical fastener cartridge.

Example 85—The surgical instrument of Examples 82, 83 or 84, wherein the second jaw comprises an anvil and wherein the second tissue contacting surface comprises a fastener forming undersurface of a portion of the anvil.

Example 86—The surgical instrument of Example 85, wherein the anvil comprises an anvil body portion and wherein the at least one tissue locating feature is formed on a proximal portion of the anvil body portion.

Example 87—The surgical instrument of Examples 82, 83, 84, 85 or 86, wherein the surgical end effector is sized to pass through a trocar cannula when the second jaw is in the fully closed position.

Example 88—The surgical instrument of Examples 82, 83, 84, 85, 86 or 87, further comprising means for applying closing and opening motions to the second jaw.

Example 89—The surgical instrument of Example 88, wherein the means for applying closing and opening motions comprises an axially movable closure tube. The closure tube comprises a closure cam surface on a distal end thereof that is configured to cammingly engage a jaw cam surface on the second jaw to apply closure motions thereto and at least one jaw opening feature that is configured to apply jaw opening motions to the second jaw when the axially movable closure tube is moved in a proximal direction.

Example 90—A surgical instrument comprising a surgical end effector that comprises a surgical fastener cartridge that comprises a cartridge body that operably supports a plurality of surgical fasteners therein. The cartridge body defines a tissue contacting surface through which the surgical fasteners are ejected. An anvil is pivotally supported relative to the surgical fastener cartridge for selective pivotal travel relative thereto between a fully open position and a fully closed position about a fixed jaw pivot axis. The anvil comprises an anvil body that defines a fastener forming surface that comprises a plurality of fastener forming formations, wherein each fastener forming formation corresponds to one of the surgical fasteners in the surgical fastener cartridge. The fastener forming surface faces the tissue contacting surface on the surgical fastener cartridge. At least one tissue stop protrudes from the anvil body and extends downward beyond the fastener forming surface and is configured to prevent tissue received between the tissue contacting surface and the fastener forming surface from extending proximally beyond a distal end portion of the tissue stop when the anvil is in the fully closed position. When the anvil is in the fully closed position, the distal end portion of each tissue stop is spaced from the fixed jaw pivot axis an axial distance that is less than 0.750 inches and wherein a vertical distance between a distalmost one of the fasteners in the surgical cartridge and a corresponding one of the fastener forming formations on the fastener forming surface when the anvil is in the fully open position is at least 0.900 inches.

Example 91—The surgical instrument of Example 90, wherein when the anvil is in the fully open position, a jaw aperture angle between the fastener forming surface and the tissue contacting surface is greater than 12.25 degrees.

Example 92—The surgical instrument of Examples 90 or 91, wherein the surgical end effector is sized to pass through a trocar cannula when the anvil is in the fully closed position.

Example 93—The surgical instrument of Examples 90, 91 or 92, further comprising means for applying closing and opening motions to the anvil.

Example 94—The surgical instrument of Example 93, wherein the means for applying closing and opening motions comprises an axially movable closure tube. The axially movable closure tube comprises a closure cam surface on a distal end thereof that is configured to cammingly engage an anvil cam surface on the anvil to apply closure motions thereto. At least one jaw opening feature is configured to apply jaw opening motions to the anvil when the axially movable closure tube is moved in a proximal direction.

Example 95—The surgical instrument of Examples 90, 91, 92, 93 or 94, wherein the surgical end effector is operably coupled to an elongate shaft assembly that defines a shaft axis.

Example 96—The surgical instrument of Example 95, wherein the tissue contacting surface of the cartridge body is parallel to the shaft axis and wherein the vertical distance is measured along a line extending from a distal most fastener and the corresponding fastener forming formation and perpendicular to the shaft axis.

Example 97—The surgical instrument of Example 90, 91, 92, 93, 94, 95 or 96, wherein the when the anvil is in the fully open position, the distal end portion of each tissue stop is positioned relative to a corresponding portion of the tissue contacting surface to prevent a gap therebetween.

Example 98—The surgical instrument of Example 97, wherein when the anvil is in the fully open position, a portion of each tissue stop is even with or extends below the tissue contacting surface to prevent tissue on the tissue contacting surface from extending proximally past the tissue stops.

Example 99—The surgical instrument of Examples 90, 91, 92, 93, 94, 95, 96, 97 or 98, wherein when the anvil is in the fully open position, a portion of each tissue stop is even with or extends below the tissue contacting surface to prevent tissue on the tissue contacting surface from extending proximally past the tissue stops.

Example 100—A surgical system comprising a housing that operably supports a closure system. An interchangeable surgical tool assembly comprises an elongate shaft assembly that is operably and removably couplable to the housing such that a proximal closure portion thereof is configured to receive axial closure motions from the closure system and defines a shaft axis. A surgical end effector is operably coupled to the elongate shaft assembly for selective articulation relative thereto about an articulation axis that is transverse to the shaft axis. The surgical end effector comprises a surgical fastener cartridge that comprises a cartridge body that operably supports a plurality of surgical fasteners therein and defines a tissue contacting surface through which the surgical fasteners are ejected. An anvil is pivotally supported relative to the surgical fastener cartridge for selective pivotal travel relative thereto between a fully open position and a fully closed position about a fixed jaw pivot axis. The anvil comprises an anvil body that defines a fastener forming surface that comprises a plurality of fastener forming formations, wherein each fastener forming formation corresponds to one of the surgical fasteners in the surgical fastener cartridge. The fastener forming surface faces the tissue contacting surface on the surgical fastener cartridge. At least one tissue stop protrudes from the anvil body and extends downward beyond the fastener forming surface and is configured to prevent tissue that is received between the tissue contacting surface and the fastener forming surface from extending proximally beyond a distal end portion of at least one tissue stop when the anvil is in the fully closed position. When the anvil is in the fully closed position, the distal end portion of each tissue stop is spaced from the fixed jaw pivot axis an axial distance that is less than 0.750 inches and wherein a vertical distance between a distalmost one of the fasteners in the surgical cartridge and a corresponding one of the fastener forming formations on the fastener forming surface when the anvil is in the fully open position is at least 0.900 inches.

Example 101—The surgical instrument of Example 100, wherein, when the anvil is in the fully open position, a jaw aperture angle between the fastener forming surface the tissue contacting surface is greater than 12.25 degrees.

Example 102—The surgical instrument of Examples 100 or 101, wherein the surgical end effector is sized to pass through a trocar cannula when the anvil is in the fully closed position.

Example 103—A surgical instrument that comprises a first jaw that includes a pair of laterally aligned vertical slots that are formed in a proximal end portion of the first jaw. Each vertical slot has an open upper end. A second jaw is movably supported for selective pivotal travel relative to the first jaw between a fully open and a fully closed position. The second jaw comprises a second jaw body and a pair of pivot members that protrude laterally from a proximal end of the second jaw body. Each pivot member is pivotally received in a corresponding one of the vertical slots in the first jaw such that the pivot members may pivot therein to facilitate pivotal travel of the second jaw relative to the first jaw. The surgical instrument further comprises a retainer member that is configured to operably engage the proximal end portion of the first jaw and retain the pivot members in the corresponding vertical slots as the second jaw moves between the fully open and the fully closed positions. An axially movable closure member is configured to apply closing and opening motions to the second jaw and retain the retainer member in retaining engagement with the proximal end portion of the first jaw.

Example 104—The surgical instrument of Example 103, wherein each pivot member has a circular cross-sectional shape and wherein the retainer member comprises a slot cap that corresponds to each vertical slot and is sized to extend therein through the open end. Each slot cap has an arcuate bottom portion that is configured to pivotally receive the corresponding pivot pin therein.

Example 105—The surgical instrument of Example 103, wherein each vertical slot is formed in a corresponding upstanding vertical wall portion of the first jaw and wherein the retainer member comprises a retainer body that is sized to span between the vertical wall portions. The retainer member further comprises a slot cap that corresponds to each vertical slot and is sized to extend therein through the open end. A mounting formation is on the retainer body and corresponds to each upstanding vertical wall portion and is configured to be seated in a correspondingly shaped mounting opening therein.

Example 106—The surgical instrument of Example 105, wherein the mounting formations are located proximal to the slot caps.

Example 107—The surgical instrument of Examples 103, 104, 105 or 106, wherein the axially movable closure member comprises an axially movable distal closure tube segment that is sized to slidably move over the retainer member to provide opening and closing motions to the second jaw and retain the retainer member in retaining engagement with the proximal end portion of the first jaw.

Example 108—The surgical instrument of Example 107, wherein the first jaw is operably coupled to an elongate shaft assembly.

Example 109—The surgical instrument of Example 108, wherein the elongate shaft assembly comprises a spine assembly that is operably coupled to the first jaw. A proximal closure tube assembly is movably supported for axial travel relative to the spine assembly and is pivotally coupled to the axially movable distal closure tube segment.

Example 110—The surgical instrument of Example 109, wherein the proximal closure tube assembly operably interfaces with a closure system that is configured to selectively apply axial closure and opening motions to the proximal closure tube assembly.

Example 111—The surgical instrument of Example 110, wherein the closure system is supported by a handheld housing.

Example 112—The surgical instrument of Example 110, wherein the closure system is supported by a housing that operably interfaces with a robotic controlled actuator.

Example 113—A surgical instrument comprising an elongate channel that is configured to operably support a surgical fastener cartridge therein. The elongate channel includes a pair of laterally aligned vertical slots that are formed in a proximal end portion of the elongate channel wherein each vertical slot includes an open upper end. An anvil is movably supported for selective pivotal travel relative to the elongate channel between a fully open and a fully closed position. The anvil comprises an anvil body and a pair of anvil trunnions that protrude laterally from an anvil mounting portion of the anvil body. Each anvil trunnion is pivotally received in a corresponding vertical slot in the elongate channel such that the anvil trunnions may pivot therein to facilitate pivotal travel of the anvil relative to the elongate channel. The surgical instrument further comprises a retainer member that is configured to be supported on the proximal end portion of the elongate channel and pivotally retain each anvil trunnion in the corresponding vertical slots as the anvil moves between the fully open and fully closed positions. An axially movable closure member is configured to apply closing and opening motions to the anvil and retain the retainer member in retaining engagement with the proximal end portion of the elongate channel.

Example 114—The surgical instrument of Example 113, wherein each anvil trunnion comprises a circular cross-sectional shape and wherein the retainer member comprises a slot cap that corresponds to each vertical slot and is sized to extend therein through the open end. Each slot cap has an arcuate bottom portion that is configured to pivotally receive the corresponding anvil trunnion therein.

Example 115—The surgical instrument of Example 113, wherein each vertical slot is formed in a corresponding upstanding vertical wall portion of the elongate channel and wherein the retainer member comprises a retainer body that is sized to span between the vertical wall portions. The retainer member further comprises a slot cap that corresponds to each vertical slot and is sized to extend therein through the open end. The retainer member also comprises mounting formations on the retainer body that correspond to each upstanding vertical wall portion and are configured to be seated in a correspondingly shaped mounting opening therein.

Example 116—The surgical instrument of Example 115, wherein the slot cap has a wedge shape that is configured to be inserted into the open end of the corresponding vertical slot.

Example 117—The surgical instrument of Examples 113, 114, 115 or 116, wherein the retainer member is affixed to the elongate channel by at least one of frictional engagement with the elongate channel, adhesive and welding.

Example 118—The surgical instrument of Examples 113, 114, 115, 116 or 117, wherein the axially movable closure member comprises an axially movable distal closure tube segment that is sized to slidably move over the retainer member to provide opening and closing motions to the anvil and retain the retainer member in retaining engagement with the proximal end portion of the elongate channel.

Example 119—The surgical instrument of Examples 113, 114, 115, 116, 117 or 118, wherein the elongate channel is operably coupled to an elongate shaft assembly.

Example 120—The surgical instrument of Example 119, wherein the elongate shaft assembly comprises a spine assembly that is operably coupled to the elongate channel and a proximal closure tube assembly that is movably supported for axial travel relative to the spine assembly and is pivotally coupled to the axially movable closure member.

Example 121—A surgical system comprising a housing that operably supports a closure system. The surgical system further comprises an interchangeable surgical tool assembly that includes an elongate shaft assembly that is operably and removably couplable to the housing such that a proximal closure portion thereof is configured to receive axial closure motions from the closure system. The interchangeable surgical tool assembly further comprises a surgical end effector that comprises an elongate channel that is configured to operably support a surgical fastener cartridge therein and includes a pair of laterally aligned vertical slots that are formed in a proximal end portion of the elongate channel. Each vertical slot includes an open upper end. An anvil is movably supported for selective pivotal travel relative to the elongate channel between a fully open and a fully closed position. The anvil comprises an anvil body and a pair of anvil trunnions that protrude laterally from an anvil mounting portion of the anvil body. Each anvil trunnion is pivotally received in a corresponding vertical slot in the elongate channel such that the anvil trunnions may pivot therein to facilitate pivotal travel of the anvil relative to elongate channel. The surgical system further comprises a retainer member that is configured to be supported on the proximal end portion of the elongate channel and pivotally retain each anvil trunnion in the corresponding vertical slots as the anvil moves between the fully open and the fully closed positions. An axially movable closure member is configured to apply closing and opening motions to the anvil and retain the retainer member in retaining engagement with the proximal end portion of the elongate channel.

Example 122—The surgical system of Example 121, wherein the axially movable closure member comprises an axially movable distal closure tube segment that is sized to slidably move over the retainer member to provide opening and closing motions to the anvil and retain the retainer member in retaining engagement with the proximal end portion of the elongate channel. The elongate shaft assembly further comprises a spine assembly that is operably coupled to the elongate channel; and a proximal closure tube assembly that is movably supported for axial travel relative to the spine assembly and is pivotally coupled to the axially movable distal closure tube segment.

Example 123—A surgical instrument comprising a first jaw and a second jaw that is coupled to the first jaw for selective pivotal travel relative thereto between a fully open position and a fully closed position. An axially movable closure member is selectively axially movable in a closure direction to move the second jaw from the fully open position to the fully closed position and in an axial opening direction to move the second jaw from the fully closed position to the fully open position. The axially movable closure member comprises a first jaw opening feature that is configured to apply a first jaw opening motion to the second jaw. A second jaw opening feature is axially spaced from the first jaw opening feature such that, when the closure member is moved in the axial opening direction, the first jaw opening feature applies the first jaw opening motion to the second jaw and when the closure member has axially moved a predetermined axial distance in the axial opening direction, the first jaw opening feature discontinues application of the first jaw opening motion and the second jaw opening feature applies a second jaw opening motion to the second jaw to move the second jaw to the fully open position.

Example 124—The surgical instrument of Example 123, wherein the first jaw opening feature is axially proximal to the second jaw opening feature.

Example 125—The surgical instrument of Examples 123 or 124, wherein the first jaw defines a central jaw axis wherein the first jaw opening feature is axially spaced from the central jaw axis on a first lateral side thereof on the closure member and wherein the second jaw opening feature is spaced from the central jaw axis on a second lateral side thereof that is opposite to the first lateral side on the closure member.

Example 126—The surgical instrument of Examples 123, 124 or 125, wherein the second jaw comprises a second jaw mounting portion that is pivotally supported on the first jaw. The second jaw mounting portion comprises a second jaw cam surface on the second jaw mounting portion and is configured to be axially cammingly contacted by the first jaw opening feature as the closure member is axially moved in the axial opening direction through the predetermined axial distance. The second jaw cam surface is configured to disengage the first jaw opening feature as the closure member continues to move in the axial opening direction beyond the predetermined axial distance. The second jaw mounting portion further comprises a second jaw cam surface that is configured to be axially camming contacted by the second jaw opening feature as the closure member continues to move in the axial opening direction beyond the predetermined axial distance.

Example 127—The surgical instrument of Example 126, wherein the closure member is axially movable in the axial opening direction from a first position corresponding to the fully closed position of the second jaw to a first intermediate axial position without applying the first jaw opening motion thereto.

Example 128—The surgical instrument of Example 127, wherein when the closure member is axially moved in the axial opening direction from the first intermediate axial position to a second intermediate axial position, the first jaw opening feature applies the first jaw opening motion to the second jaw to cause the second jaw to move relative to the first jaw through a second jaw aperture angle.

Example 129—The surgical instrument of Example 128, wherein the second jaw aperture angle is 10°.

Example 130—The surgical instrument of Examples 128 or 129, wherein when the closure member is axially moved in the axial opening direction between the second intermediate axial position and a third intermediate axial position, the first jaw opening feature does not move the second jaw relative to the first jaw beyond the second jaw aperture angle.

Example 131—The surgical instrument of Example 130, wherein axial movement of the closure member in the axial opening direction from the third intermediate axial position to a fourth intermediate axial position, causes the second jaw opening feature to apply the second jaw opening motion to the second jaw.

Example 132—The surgical instrument of Example 131, wherein axial movement of the closure member in the axial opening direction between the third intermediate axial position and the fourth intermediate axial position causes the second jaw to move relative to the first jaw to a second jaw aperture angle.

Example 133—The surgical instrument of Example 132, wherein the second jaw aperture angle is 22°.

Example 134—The surgical instrument of Examples 131, 132 or 133, wherein axial movement of the closure member in the axial opening direction from the third intermediate axial position to the fourth intermediate axial position causes the first jaw opening feature to discontinue application of the first jaw opening motion to the second jaw.

Example 135—The surgical instrument of Example 134, wherein axial movement of the closure member in the axial opening direction from the fourth intermediate axial position to a final axial position causes the second jaw opening feature to discontinue application of the second jaw opening motion to the second jaw.

Example 136—The surgical instrument of Examples 123, 124, 125, 126, 127, 128, 129, 130, 131, 132, 133, 134 or 135, wherein the first jaw comprises a surgical fastener cartridge and wherein the second jaw comprises an anvil.

Example 137—A surgical instrument comprising an elongate channel that is configured to operably support a surgical fastener cartridge therein. An anvil is pivotally supported on the elongate channel for selective pivotal travel relative thereto between a fully open position and a fully closed position. An axially movable closure member is selectively axially movable in a closure direction to move the anvil from the fully open position to the fully closed position and in an axial opening direction to move the anvil from the fully closed to the fully open position. The axially movable closure member comprises a proximal jaw opening feature that is configured to apply a first jaw opening motion to the anvil. A distal jaw opening feature is axially spaced from the proximal jaw opening feature such that, when the closure member is moved in the axial opening direction, the proximal jaw opening feature applies the first jaw opening motion to the anvil and when the closure member has axially moved a predetermined axial distance in the axial opening direction, the proximal jaw opening feature discontinues application of the first jaw opening motion and the distal jaw opening feature applies a second jaw opening motion to the anvil to move the anvil to the fully open position.

Example 138—The surgical instrument of Example 137, wherein when the closure member is axially moved in the axial opening direction from a first intermediate axial position to a second intermediate axial position, the first jaw opening feature causes the anvil to move through a first jaw aperture angle that is measured between a deck surface of the surgical fastener cartridge that is supported in the elongate channel and a fastener forming underside of the anvil.

Example 139—The surgical instrument of Example 138, wherein the first jaw aperture angle is 10°.

Example 140—The surgical instrument of Examples 138 or 139, wherein when the closure member is axially moved in the axial opening direction between the second intermediate axial position and a third intermediate axial position, the first jaw opening feature does not move the anvil relative to the elongate channel beyond the first jaw aperture angle.

Example 141—The surgical instrument of Example 140, wherein axial movement of the closure member in the axial opening direction from the third intermediate axial position to a fourth intermediate axial position, causes the second jaw opening feature to move the anvil through a second jaw aperture angle that is greater than the first jaw aperture angle.

Example 142—A surgical instrument comprising an elongate channel that is configured to operably support a surgical fastener cartridge therein. An anvil is pivotally supported on the elongate channel for selective pivotal travel relative thereto between a fully open position and a fully closed position. An axially movable distal closure tube segment is selectively axially movable in a closure direction to move the anvil from the fully open position to the fully closed position and in an axial opening direction to move the anvil from the fully closed position to the fully open position. The axially movable distal closure tube segment comprises a proximal jaw opening feature that is formed on the distal closure tube segment and is configured to apply a first jaw opening motion to the anvil. A distal jaw opening feature is formed on the distal closure tube segment and is axially spaced from the proximal jaw opening feature such that, when the distal closure tube segment is moved in the axial opening direction, the proximal jaw opening feature applies the first jaw opening motion to the anvil and when the distal closure tube segment has axially moved a predetermined axial distance in the opening direction, the proximal jaw opening feature discontinues application of the first jaw opening motion and the distal jaw opening feature applies a second jaw opening motion to the anvil to move the anvil to the fully open position.

Example 143—A surgical instrument comprising a first jaw and a second jaw that is coupled to the first jaw for selective pivotal travel relative thereto between a fully open position and a fully closed position. A closure member is configured to apply closure motions to the second jaw as the closure member is axially movable in a distal direction from a starting position corresponding to the fully open position of the second jaw to an ending position corresponding to the fully closed position of the second jaw. The closure member is further configured to move distally from the starting position an initial predetermined axial closure distance before applying the closure motion to the second jaw.

Example 144—The surgical instrument of Example 143, wherein the initial predetermined axial closure distance is 0.020 inches.

Example 145—The surgical instrument of Examples 143 or 144, wherein closure member is configured to distally move through a final predetermined axial closure distance after the second jaw has been moved to the fully closed position.

Example 146—The surgical instrument of Example 145, wherein the final predetermined axial closure distance is 0.040 inches.

Example 147—The surgical instrument of Examples 143, 144, 145 or 146, wherein the closure member comprises a closure camming surface that is configured to cammingly engage a jaw camming surface on the second jaw to apply the closure motions thereto.

Example 148—The surgical instrument of Examples 143, 144, 145, 146 or 147, wherein the closure member further comprises means for applying opening motions to the second jaw when the closure member axially moves in a proximal direction from the ending position to the starting position.

Example 149—The surgical instrument of Example 148, wherein the means for applying opening motions comprises a first jaw opening feature on the closure member that is configured to apply a first amount of jaw opening motion to the second jaw as the closure member is axially moved from the ending position to an intermediate axial position between the ending and starting position. The means further comprises a second jaw opening feature on the closure member that is axially spaced from the first jaw opening feature and is configured to apply a second amount of jaw opening motion to the second jaw as the closure member is axially moved from the intermediate position to the starting position.

Example 150—A surgical instrument comprising an elongate channel that is configured to operably support a surgical staple/fastener cartridge therein. An anvil is pivotally supported on the elongated channel for selective pivotal travel relative thereto between a fully open position and a fully closed position. A closure member is configured to apply closure motions to the anvil as the closure member is axially movable in a distal direction from a starting position corresponding to the fully open position of the anvil to an ending position corresponding to the fully closed position of the anvil. The closure member is configured to move distally from the starting position an initial predetermined axial closure distance before applying the closure motion to the anvil.

Example 151—The surgical instrument of Example 150, wherein the initial predetermined axial closure distance is 0.020 inches.

Example 152—The surgical instrument of Examples 150 or 151, wherein the closure member is configured to distally move through a final predetermined axial closure distance after the anvil has been moved to the fully closed position.

Example 153—The surgical instrument of Example 152, wherein the final predetermined axial closure distance is 0.040 inches.

Example 154—The surgical instrument of Examples 152 or 153, wherein the closure member is configured to apply the closure motion to the anvil as the closure member moves distally through an intermediate predetermined axial closure distance after the closure member traveled the initial predetermined axial closure distance and prior to traveling the final predetermined axial closure distance.

Example 155—The surgical instrument of Example 154, wherein the intermediate predetermined axial closure distance is 0.200 inches.

Example 156—The surgical instrument of Examples 150, 151, 152, 153, 154 or 155, wherein the closure member comprises a closure camming surface configured to cammingly engage an anvil camming surface on an anvil mounting portion of the anvil to apply the closure motion thereto.

Example 157—The surgical instrument of Examples 150, 151, 152, 153, 154, 155, 156 or 157, wherein the closure member further comprises means for applying opening motions to the anvil when the closure member axially moves in a proximal direction from the ending position to the starting position.

Example 158—The surgical instrument of Example 157, wherein the means for applying opening motions comprises a first jaw opening feature on the closure member that is configured to apply a first amount of jaw opening motion to the anvil as the closure member is axially moved from the ending position to an intermediate axial position between the ending position and starting position. The means further comprises a second jaw opening feature on the closure member that is axially spaced from the first jaw opening feature and is configured to apply a second amount of jaw opening motion to the anvil as the closure member is axially moved from the intermediate axial position to the starting position.

Example 159—A surgical system comprising a housing that operably supports a closure system. The surgical system further comprises an interchangeable surgical tool assembly that comprises an elongate shaft assembly that is operably and removably couplable to the housing such that a proximal closure portion of the elongate shaft assembly is configured to receive axial closure motions from the closure system. The interchangeable surgical tool assembly further comprises a surgical end effector that is operably coupled to the elongate shaft assembly. The surgical end effector comprises an elongate channel that is coupled to the elongate shaft assembly and is configured to operably support a surgical fastener cartridge therein. An anvil is coupled to the elongate channel for selective pivotal travel relative thereto between a fully open position and a fully closed position. The elongate shaft assembly comprises an axially movable proximal closure member that is configured to receive the axial closure motions. A distal closure member is operably coupled to the proximal closure member and is configured to apply the axial closure motions to the anvil as the distal closure member is axially movable in a distal direction from a starting position corresponding to the fully open position of the anvil to an ending position corresponding to the fully closed position of the anvil. The distal closure member is configured to move distally from the starting position an initial predetermined axial closure distance before applying the closure motions to the anvil.

Example 160—The surgical instrument of Example 159, wherein the distal closure member is configured to distally move through a final predetermined axial closure distance after the anvil has been moved to the fully closed position.

Example 161—A surgical tool assembly that comprises a first jaw and a second jaw that is movable relative to the first jaw. The surgical tool assembly further comprises a firing system that comprises a firing member assembly that is configured to move distally from a starting position upon application of a firing motion thereto. The firing member assembly comprises a first firing member element and a second firing member element that is pivotally coupled to the first firing member element at an attachment joint. The second firing member element is configured to move between a locked position wherein the second firing member element is in locking engagement with a lockout portion of the first jaw to prevent the firing member assembly from moving distally from the starting position upon application of the firing motion thereto and an unlocked position wherein the firing member assembly is distally advanceable from the starting position upon the application of the firing motion to the firing member assembly. The surgical tool assembly further comprises means for preventing an unlocking load from being applied to the attachment joint when the second firing member is in the locked position and the firing motion is applied to the first firing member element.

Example 162—The surgical tool assembly of Example 161, wherein the lockout portion comprises at least one lockout notch in the first jaw that is configured to retainingly engage the second firing member element when the second firing member element is in the locked position.

Example 163—The surgical tool assembly of Examples 161 or 162, further comprising a biasing member in the first jaw that is configured to bias the second firing member element into the locked position.

Example 164—The surgical tool assembly of Examples 161, 162 or 163, wherein the first firing member element comprises at least one first jaw engaging feature that is configured to be movably received within a corresponding first jaw passage and at least one second jaw engaging feature that is configured to be movably received within a corresponding second jaw passage.

Example 165—The surgical tool assembly of Example 164, wherein when the firing member assembly is in the starting position, each first jaw engaging feature is in axial alignment with the corresponding first jaw passage and each second jaw engaging feature is in axial alignment with the corresponding second jaw passage regardless of a position of the second firing member element.

Example 166—The surgical tool assembly of Example 165, wherein when the firing member assembly is in the starting position and the second firing member element is in the locked position, each first jaw engaging feature is in axial alignment with the corresponding first jaw passage and each said second jaw engaging feature is in axial alignment with the corresponding second jaw passage.

Example 167—The surgical tool assembly of Examples 161, 162, 163, 164, 165 or 166, wherein the first jaw is configured to operably support a removable surgical component therein that operably supports a movable component element therein. The movable component element is movable between an unfired and fired positions. The second firing member element is configured to be moved from the locked position by the movable component element when the removable surgical component is supported in the first jaw and the movable component element is in the unfired position.

Example 168—The surgical tool assembly of Examples 161, 162, 163, 164, 165, 166 or 167, wherein the first jaw is operably coupled to an elongate shaft that defines a shaft axis and wherein the second firing member element is pivotable relative to the first firing member element about a pivot axis that is transverse to the shaft axis.

Example 169—The surgical tool assembly of Claim Examples 161, 162, 163, 164, 165, 166, 167 or 168, wherein the first firing member element comprises a tissue cutting surface.

Example 170—The surgical tool assembly of Examples 161, 162, 163, 164, 165, 166, 168 or 169, wherein the first jaw is configured to operably support a surgical staple cartridge that operably supports a sled therein. The sled is movable between an unfired position and fired positions. The second firing member element is configured to be moved from the locked position by the sled when the surgical staple cartridge is supported in the first jaw and the sled is in the unfired position.

Example 171—The surgical tool assembly of Examples 161, 162, 163, 164, 165, 166, 167, 168, 169 or 170, wherein the means for preventing comprises a distal surface and a lockout surface on the first firing member element. The distal surface is configured relative to a proximal surface on the second firing member element such that a space is provided therebetween when the second firing member is in the unlocked position. The proximal surface abuts the lockout surface when the second firing member element is in the locked position.

Example 172—The surgical tool assembly of Examples 161, 162, 163, 164, 165, 166, 167, 168, 169, 170 or 171, wherein the attachment joint comprises at least one pivot member on the second firing member element and pivotally received within a corresponding pivot hole in the first firing member element.

Example 173—The surgical tool assembly of Example 172, further comprising a clearance between each pivot member and its corresponding pivot hole such that the unlocking load is not transferred to the at least one pivot member when the second firing member is in the locked position and the firing motion is applied to the first firing member element.

Example 174—A stapling assembly comprising an anvil jaw and a staple cartridge jaw comprising a lockout surface. A firing member includes a distal end that comprises anvil-camming portions and channel-camming portions. The firing member further comprises a distal edge that comprises a cutting member and a lockout force-receiving surface. A lockout member is pivotally coupled to the distal end of the firing member by at least one pivot member. The lockout member is configured to engage the lockout surface of the staple cartridge jaw to block the advancement of the firing member when a staple cartridge is not installed within the staple cartridge jaw or when a partially-spent staple cartridge is installed within the staple cartridge jaw and a firing motion is applied to the firing member. The firing member and the lockout member are configured to prevent an unlocking load from being applied to the pivot members when the lockout member is in engagement with the lockout surface and the firing motion is applied to the firing member.

Example 175—The stapling assembly of Example 174, wherein the staple cartridge jaw comprises a staple cartridge that includes a sled that is movable between an unfired position and a fired position. The sled is configured to engage the lockout member to prevent the lockout member from moving relative to the firing member to engage the lockout surface when the sled is in the unfired position.

Example 176—The stapling assembly of Examples 174 or 175, further comprising a spring that is configured to bias the lockout member relative to the firing member into a locked configuration when a partially-spent staple cartridge is present and when a staple cartridge is not present.

Example 177—The stapling assembly of Examples 174, 175 or 176, wherein the firing member is configured to not move substantially vertically.

Example 178—A surgical fastening instrument that comprises a first jaw that is configured to operably support an unfired surgical fastener cartridge therein. An anvil is movably supported relative to the first jaw. The surgical fastening instrument further includes a firing system that comprises a firing member assembly that is configured to axially move between a starting position and an ending position. The firing member assembly comprises a firing member that comprises a cutting surface and a tippable element that is pivotally coupled to the firing member by an attachment joint. The tippable element is configured to move relative to the firing member between a locked position wherein the tippable element is in locking engagement with a lockout portion of the first jaw to prevent the firing member assembly from moving distally from the starting position upon application of a firing motion thereto and an unlocked position wherein the firing member assembly is distally advanceable from the starting position upon the application of the firing motion to the firing member assembly. The firing member and tippable element are configured to prevent an unlocking load from being applied to the attachment joint when the tippable element is the locked position and the firing motion is applied to the firing member assembly. The surgical fastening instrument further comprises means for biasing the tippable element into the locking engagement unless an unfired surgical fastener cartridge is operably supported in the first jaw.

Example 179—The surgical fastening instrument of Example 178, wherein the attachment joint comprises at least one pivot member that is on the tippable element and is pivotally received within a corresponding pivot hole in the firing member.

Example 180—The surgical fastening instrument of Example 179, further comprising a clearance between each pivot member and its corresponding pivot hole such that the unlocking load is not transferred to each pivot member when the tippable element is in the locked position and the firing motion is applied to the firing member assembly.

Many of the surgical instrument systems described herein are motivated by an electric motor; however, the surgical instrument systems described herein can be motivated in any suitable manner. In various instances, the surgical instrument systems described herein can be motivated by a manually-operated trigger, for example. In certain instances, the motors disclosed herein may comprise a portion or portions of a robotically controlled system. Moreover, any of the end effectors and/or tool assemblies disclosed herein can be utilized with a robotic surgical instrument system. U.S. patent application Ser. No. 13/118,241, entitled SURGICAL STAPLING INSTRUMENTS WITH ROTATABLE STAPLE DEPLOYMENT ARRANGEMENTS, now U.S. Pat. No. 9,072,535, for example, discloses several examples of a robotic surgical instrument system in greater detail.

The surgical instrument systems described herein have been described in connection with the deployment and deformation of staples; however, the embodiments described herein are not so limited. Various embodiments are envisioned which deploy fasteners other than staples, such as clamps or tacks, for example. Moreover, various embodiments are envisioned which utilize any suitable means for sealing tissue. For instance, an end effector in accordance with various embodiments can comprise electrodes configured to heat and seal the tissue. Also, for instance, an end effector in accordance with certain embodiments can apply vibrational energy to seal the tissue.

The entire disclosures of:

U.S. Pat. No. 5,403,312, entitled ELECTROSURGICAL HEMOSTATIC DEVICE, which issued on Apr. 4, 1995;

U.S. Pat. No. 7,000,818, entitled SURGICAL STAPLING INSTRUMENT HAVING SEPARATE DISTINCT CLOSING AND FIRING SYSTEMS, which issued on Feb. 21, 2006;

U.S. Pat. No. 7,422,139, entitled MOTOR-DRIVEN SURGICAL CUTTING AND FASTENING INSTRUMENT WITH TACTILE POSITION FEEDBACK, which issued on Sep. 9, 2008;

U.S. Pat. No. 7,464,849, entitled ELECTRO-MECHANICAL SURGICAL INSTRUMENT WITH CLOSURE SYSTEM AND ANVIL ALIGNMENT COMPONENTS, which issued on Dec. 16, 2008;

U.S. Pat. No. 7,670,334, entitled SURGICAL INSTRUMENT HAVING AN ARTICULATING END EFFECTOR, which issued on Mar. 2, 2010;

U.S. Pat. No. 7,753,245, entitled SURGICAL STAPLING INSTRUMENTS, which issued on Jul. 13, 2010;

U.S. Pat. No. 8,393,514, entitled SELECTIVELY ORIENTABLE IMPLANTABLE FASTENER CARTRIDGE, which issued on Mar. 12, 2013;

U.S. patent application Ser. No. 11/343,803, entitled SURGICAL INSTRUMENT HAVING RECORDING CAPABILITIES, now U.S. Pat. No. 7,845,537;

U.S. patent application Ser. No. 12/031,573, entitled SURGICAL CUTTING AND FASTENING INSTRUMENT HAVING RF ELECTRODES, filed Feb. 14, 2008;

U.S. patent application Ser. No. 12/031,873, entitled END EFFECTORS FOR A SURGICAL CUTTING AND STAPLING INSTRUMENT, filed Feb. 15, 2008, now U.S. Pat. No. 7,980,443;

U.S. patent application Ser. No. 12/235,782, entitled MOTOR-DRIVEN SURGICAL CUTTING INSTRUMENT, now U.S. Pat. No. 8,210,411;

U.S. patent application Ser. No. 12/249,117, entitled POWERED SURGICAL CUTTING AND STAPLING APPARATUS WITH MANUALLY RETRACTABLE FIRING SYSTEM, now U.S. Pat. No. 8,608,045;

U.S. patent application Ser. No. 12/647,100, entitled MOTOR-DRIVEN SURGICAL CUTTING INSTRUMENT WITH ELECTRIC ACTUATOR DIRECTIONAL CONTROL ASSEMBLY, filed Dec. 24, 2009, now U.S. Pat. No. 8,220,688;

U.S. patent application Ser. No. 12/893,461, entitled STAPLE CARTRIDGE, filed Sep. 29, 2012, now U.S. Pat. No. 8,733,613;

U.S. patent application Ser. No. 13/036,647, entitled SURGICAL STAPLING INSTRUMENT, filed Feb. 28, 2011, now U.S. Pat. No. 8,561,870;

U.S. patent application Ser. No. 13/118,241, entitled SURGICAL STAPLING INSTRUMENTS WITH ROTATABLE STAPLE DEPLOYMENT ARRANGEMENTS, now U.S. Pat. No. 9,072,535;

U.S. patent application Ser. No. 13/524,049, entitled ARTICULATABLE SURGICAL INSTRUMENT COMPRISING A FIRING DRIVE, filed on Jun. 15, 2012, now U.S. Pat. No. 9,101,358;

U.S. patent application Ser. No. 13/800,025, entitled STAPLE CARTRIDGE TISSUE THICKNESS SENSOR SYSTEM, filed on Mar. 13, 2013, now U.S. Pat. No. 9,345,481;

U.S. patent application Ser. No. 13/800,067, entitled STAPLE CARTRIDGE TISSUE THICKNESS SENSOR SYSTEM, filed on Mar. 13, 2013, now U.S. Patent Application Publication No. 2014/0263552;

U.S. Patent Application Publication No. 2007/0175955, entitled SURGICAL CUTTING AND FASTENING INSTRUMENT WITH CLOSURE TRIGGER LOCKING MECHANISM, filed Jan. 31, 2006; and U.S. Patent Application Publication No. 2010/0264194, entitled SURGICAL STAPLING INSTRUMENT WITH AN ARTICULATABLE END EFFECTOR, filed Apr. 22, 2010, now U.S. Pat. No. 8,308,040, are hereby incorporated by reference herein.

Although various devices have been described herein in connection with certain embodiments, modifications and variations to those embodiments may be implemented. Particular features, structures, or characteristics may be combined in any suitable manner in one or more embodiments. Thus, the particular features, structures, or characteristics illustrated or described in connection with one embodiment may be combined in whole or in part, with the features, structures or characteristics of one ore more other embodiments without limitation. Also, where materials are disclosed for certain components, other materials may be used. Furthermore, according to various embodiments, a single component may be replaced by multiple components, and multiple components may be replaced by a single component, to perform a given function or functions. The foregoing description and following claims are intended to cover all such modification and variations.

The devices disclosed herein can be designed to be disposed of after a single use, or they can be designed to be used multiple times. In either case, however, a device can be reconditioned for reuse after at least one use. Reconditioning can include any combination of the steps including, but not limited to, the disassembly of the device, followed by cleaning or replacement of particular pieces of the device, and subsequent reassembly of the device. In particular, a reconditioning facility and/or surgical team can disassemble a device and, after cleaning and/or replacing particular parts of the device, the device can be reassembled for subsequent use. Those skilled in the art will appreciate that reconditioning of a device can utilize a variety of techniques for disassembly, cleaning/replacement, and reassembly. Use of such techniques, and the resulting reconditioned device, are all within the scope of the present application.

The devices disclosed herein may be processed before surgery. First, a new or used instrument may be obtained and, when necessary, cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, and/or high-energy electrons. The radiation may kill bacteria on the instrument and in the container. The sterilized instrument may then be stored in the sterile container. The sealed container may keep the instrument sterile until it is opened in a medical facility. A device may also be sterilized using any other technique known in the art, including but not limited to beta radiation, gamma radiation, ethylene oxide, plasma peroxide, and/or steam.

While this invention has been described as having exemplary designs, the present invention may be further modified within the spirit and scope of the disclosure. This application is therefore intended to cover any variations, uses, or adaptations of the invention using its general principles.

Any patent, publication, or other disclosure material, in whole or in part, that is said to be incorporated by reference herein is incorporated herein only to the extent that the incorporated materials do not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A surgical instrument, comprising:

a shaft assembly;

a surgical end effector movably coupled to said shaft assembly for selective articulation relative thereto about an articulation axis, wherein said surgical end effector comprises:

a first jaw; and a second jaw pivotably coupled to said first jaw for selective pivotable and non-translatable movement relative thereto about a non-moving pivot axis between a fully open position and a closed position, and wherein said shaft assembly further comprises:

an axially movable firing member configured to selectively move between a proximal-most starting position corresponding to said fully open position of said second jaw and a fired position, wherein said axially movable firing member comprises at least one second jaw engagement feature configured to slidably engage said second jaw, wherein each said at least one second jaw engagement feature comprises a total axial length and protrudes proximally beyond said non-moving pivot axis a distance that is less than said total axial length when said axially movable firing member is in said proximal-most starting position; and an axially movable closure member selectively movable between a proximal-most beginning position corresponding to said fully open position of said second jaw and an ending position, wherein said axially movable closure member is configured to move said second jaw from said fully open position to said closed position, wherein said axially movable closure member protrudes distally over at least a portion of said at least one second jaw engagement feature when said axially movable closure member is in said proximal-most beginning position and said axially movable firing member is in said proximal-most starting position.

2. The surgical instrument of claim 1, further comprising at least one positive jaw opening feature on said axially movable closure member, wherein each said at least one positive jaw opening feature is configured to contact a corresponding portion of said second jaw when said axially movable closure member is moved from said ending position to said proximal-most beginning position to apply jaw opening motions to said second jaw.

3. The surgical instrument of claim 2, wherein said at least one positive jaw opening feature comprises two positive jaw opening features.

4. The surgical instrument of claim 3, wherein said shaft assembly defines a shaft axis, wherein one said positive jaw opening feature is located on a first side of said shaft axis, and wherein the other said positive jaw opening feature is located on a second side of said shaft axis.

5. The surgical instrument of claim 4 wherein said other positive jaw opening feature is axially offset from said one positive jaw opening feature.

6. The surgical instrument of claim 1, wherein said distance is greater than thirty-five percent of said total axial length and less than said total axial length.

7. The surgical instrument of claim 1, wherein said axially movable closure member comprises a closure member distal end, wherein said closure member distal end is located an axial closure distance from said non-moving pivot axis that is approximately 0.090 inches.

8. The surgical instrument of claim 7, wherein said closure member comprises a closure tube.

9. The surgical instrument of claim 1, wherein said first jaw comprises an elongate channel to support a surgical staple cartridge therein, and wherein said second jaw comprises an anvil.

10. The surgical instrument of claim 9, wherein each said second jaw engagement feature comprises an anvil engagement feature that comprises an anvil engagement feature distal end, wherein said anvil engagement feature distal end is located an anvil engagement feature distance from said articulation axis when said anvil is in said fully open position, wherein said anvil comprises at least one tissue stop, wherein each said tissue stop comprises a tissue stop distal end, wherein when said anvil is in said closed position, said tissue stop distal end is located a tissue stop axial distance from said articulation axis, and wherein a ratio between said anvil engagement distance relative to said tissue stop axial distance is less than 0.5.

11. The surgical instrument of claim 10, wherein said tissue stop distal end is located another tissue stop axial distance from said non-moving pivot axis that is less than 0.75 inches.

12. The surgical instrument of claim 9, wherein said second jaw comprises a pair of laterally extending anvil trunnions configured to be pivotally received in corresponding anvil cradles in said elongate channel, and wherein said surgical instrument further comprises an anvil retainer attached to said elongate channel and configured to retain each said laterally extending anvil trunnion in said corresponding trunnion cradle such that said anvil trunnions define said non-moving pivot axis.

13. A surgical stapling device, comprising:

a shaft assembly;

a surgical end effector, comprising:

an elongate channel movably coupled to said shaft assembly for selective articulation relative thereto about an articulation axis;

an anvil comprising an anvil mounting portion pivotably coupled to said elongate channel for selective pivotable and non-translatable movement relative thereto about a non-moving pivot axis between a fully open position and a closed position, and wherein said shaft assembly further comprises:

an axially movable firing member configured to selectively move between a proximal-most starting position corresponding to said fully open position of said anvil and a fired position adjacent a distal end portion of said surgical end effector, wherein said axially movable firing member comprises a pair of anvil engagement features configured to slidably engage a corresponding anvil ledge in said anvil, wherein each said anvil engagement feature comprises an anvil engagement feature total axial length, wherein each said anvil engagement feature protrudes proximally beyond said non-moving pivot axis an anvil engagement feature distance that is less than said engagement feature total axial length when said axially movable firing member is in said proximal-most starting position; and an axially movable closure tube selectively movable between a proximal-most beginning position corresponding to said fully open position of said anvil and an ending position, wherein said axially movable closure tube is configured to move said anvil from said fully open position to said closed position when said axially movable closure tube is moved from said proximal-most beginning position to said ending position, and wherein said axially movable closure tube protrudes distally over at least a portion of each of said anvil engagement features when said axially movable closure tube is in said proximal-most beginning position and said axially movable firing member is in said proximal-most starting position.

14. The surgical stapling device of claim 13, wherein said anvil comprises a pair of laterally extending anvil trunnions configured to be pivotally received in corresponding anvil cradles in said elongate channel, and wherein said surgical instrument further comprises an anvil retainer attached to said elongate channel and configured to retain each said laterally extending anvil trunnion in said corresponding trunnion cradle such that said anvil trunnions define said non-moving pivot axis.

15. The surgical stapling device of claim 14, wherein said anvil engagement feature distance is greater than thirty-five percent of said anvil engagement feature total axial length and less than said anvil engagement feature total axial length.

16. The surgical stapling device of claim 15, wherein said axially movable closure tube comprises a closure tube distal end, wherein said closure tube distal end is located an axial closure distance from said non-moving pivot axis that is approximately 0.090 inches.

17. The surgical stapling device of claim 16, wherein each said anvil engagement feature comprises an anvil engagement feature distal end, wherein said anvil engagement feature distal end is located an anvil engagement feature distance from said articulation axis when said anvil is in said fully open position, wherein said anvil comprises at least one tissue stop, wherein each said tissue stop comprises a tissue stop distal end, wherein when said anvil is in said closed position, said tissue stop distal end is located a tissue stop axial distance from said articulation axis, and wherein a ratio between said anvil engagement distance relative to said tissue stop axial distance is less than 0.5.

18. The surgical stapling device of claim 17, wherein said tissue stop distal end is located another tissue stop axial distance from said non-moving pivot axis that is less than 0.75 inches.

* * * * *